US009551014B2

(12) United States Patent
Dühring et al.

(10) Patent No.: US 9,551,014 B2
(45) Date of Patent: *Jan. 24, 2017

(54) GENETICALLY ENHANCED CYANOBACTERIA FOR THE PRODUCTION OF A FIRST CHEMICAL COMPOUND HARBOURING $ZN^{2+}$, $CO^{2+}$ OR $NI^{2+}$ -INDUCIBLE PROMOTERS

(71) Applicant: Algenol Biofuels Inc., Ft. Myers, FL (US)

(72) Inventors: Ulf Dühring, Berlin (DE); Kerstin Baier, Kleinmachnow (DE); Frauke Germer, Berlin (DE); Tuo Shi, San Diego, CA (US)

(73) Assignee: Algenol Biotech LLC, Fort Meyers, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/320,569

(22) Filed: Jun. 30, 2014

(65) Prior Publication Data

US 2014/0370575 A1 Dec. 18, 2014

Related U.S. Application Data

(63) Continuation of application No. PCT/EP2012/076790, filed on Dec. 21, 2012.

(60) Provisional application No. 61/581,928, filed on Dec. 30, 2011.

(51) Int. Cl.

| | |
|---|---|
| ***C12N 1/13*** | (2006.01) |
| ***C12P 7/06*** | (2006.01) |
| ***C12N 1/12*** | (2006.01) |
| ***C12N 15/74*** | (2006.01) |

(52) U.S. Cl.

CPC . *C12P 7/06* (2013.01); *C12N 1/12* (2013.01); *C12N 15/74* (2013.01); *Y02E 50/17* (2013.01)

(58) Field of Classification Search

None

See application file for complete search history.

(56) References Cited

U.S. PATENT DOCUMENTS

| | | | |
|---|---|---|---|
| 6,306,639 | B1 | 10/2001 | Woods et al. |
| 6,699,696 | B2 | 3/2004 | Woods et al. |
| 7,785,861 | B2 | 8/2010 | Devroe et al. |
| 7,794,969 | B1 | 9/2010 | Reppas et al. |
| 7,968,321 | B1 | 6/2011 | Green et al. |
| 7,981,647 | B2 | 7/2011 | Berry et al. |
| 8,048,666 | B1 | 11/2011 | Green et al. |
| 8,163,516 | B2 | 4/2012 | Dehring et al. |
| 8,216,816 | B2 | 7/2012 | Green et al. |
| 8,465,954 | B2 | 6/2013 | Green et al. |
| 8,753,837 | B2 | 6/2014 | Lee et al. |
| 8,846,369 | B2 | 9/2014 | Piven et al. |
| 2011/0177571 | A1 | 7/2011 | Lee |
| 2014/0178958 | A1 | 6/2014 | Piven et al. |
| 2014/0322799 | A1 | 10/2014 | Dühring et al. |

FOREIGN PATENT DOCUMENTS

| | | |
|---|---|---|
| WO | WO2007084477 | 7/2007 |
| WO | WO2009078712 | 6/2009 |
| WO | WO2009098089 | 8/2009 |
| WO | WO2009105714 | 8/2009 |
| WO | WO2010078584 | 7/2010 |
| WO | WO2011018116 | 2/2011 |
| WO | WO2013098267 | 7/2013 |
| WO | WO2014100799 | 6/2014 |

OTHER PUBLICATIONS

Cavet et al., (2002), "A Nickel-Cobalt-sensing ArsR-SmtB Family Repressor," Jour. Biol. Chem., 277:38441-38448.
Cavet et al., (2003), "Zn, Cu and Co in cyanobacteria: selective control of metal availability," FEMS Microbiol. Rev., 27:165-181.
Garcia-Dominguez et al., (2000), "A Gene Cluster Involved in Metal Homeostasis in the Cyanobacterium Synechocystis sp. Strain PCC 6803," Jour. Bacteriol., 182:1507-1514.
Liu et al., (2004), "A novel Cyanobacterial SmtB/ArsR Family Repressor Regulates the Expression of a CPx-ATPase and a Metallothionein in Response to Both Cu(I)/Ag(I) and Zn(II)/Cd(II)," Jour. Biol. Chem., 279:17810-17818.
Lopez-Maury et al., (2002), "A two-component signal transduction system involved in nickel sensing in the cyanobacterium Synechocystis PCC 6803," Mol. Microbiol., 43:247-256.
Peca et al., (2008), "Construction of bioluminescent cyanobacterial reporter strains for detection of nickel, cobalt and zinc," FEMS Microbiol. Lett., 289:258-264.
Rutherford et al., (1999), "Cobalt-dependent Transcriptional Switching by a Dual-effector MerR-like Protein Regulates a Cobalt-exporting Variant CPx-type ATPase," Jour. Biol. Chem., 274:25827-25832.
Silver, S., (1996), "Bacterial Heavy Metal Resistance: New Surprises," Annu. Rev. Microbiol., 50:753-789.
Thelwell et al., (1998), "An SmtB-like repressor from Synechocystis PCC 6803 regulates a zinc exporter," Proc. Natl. Acad. Sci. USA, 95:10728-10733.
Deng et al, (1999), "Ethanol synthesis by genetic engineering in cyanobacteria," Applied and Environmental Microbiology, 65:523-528.
Wang et al., (2012), "Application of synthetic biology in cyanobacteria and algae," Frontiers in Microbiology, 3(344): 1-15.

(Continued)

*Primary Examiner* — Brian J Gangle

(74) *Attorney, Agent, or Firm* — Lawrence B. Ebert; Suzanne G. Jepson; David J. Lorenz

(57) ABSTRACT

One embodiment of the invention is directed to a genetically enhanced cyanobacterium for the production of a first chemical compound, comprising at least one first recombinant gene encoding a first biocatalyst for the production of the first chemical compound, wherein the gene is under the transcriptional control of a $Co^{2+}$ or $Zn^{2+}$-inducible promoter. Such a cyanobacterium can provide a tighter control of the production of the first chemical compound.

18 Claims, 87 Drawing Sheets

(56) References Cited

OTHER PUBLICATIONS

Gao et al., (2012) "Photosynthetic production of ethanol from carbon dioxide in genetically engineered cyanobacteria," Energy & Environmental Science 5:9857-9865.
Nakamura, et al. (2000), "CyanoBase, the genome database for Synechocystis, sp. strain PCC6803: Status for the year 2000," Nucleic Acids Research, 28:72.
Xu, et al. (2011), "Expression of genes in cyanobacteria: adaptation of endogenous plasmids as platforms for high-level gene expression in *Synechococcus* sp. PCC 7002," Methods in Molecular Biology, 684:273-293.
International Search Report (ISR) and Written Opinion for PCT/EP2012/076790, dated Apr. 10, 2013.
International Preliminary Report on Patentability (IPRP) for PCT/EP2012/076790, dated Jul. 1, 2014.
Holland-Staley et al. (2000), "Aerobic activity of *Escherichia coli* alcohol dehydrogenase is determined by a single amino acid," Jour. Bacteriol., 182:6049-6054.

FIG. 2A

PziaA-SalI-fw

5'-AGGTCGACGTTAGGAGCTAGG-3' (SEQ ID NO. 49)

ziaR/PziaA-SalI-fw

5'-ATCGTCGACCTCCTTAATCCG-3' (SEQ ID NO. 50)

PziaA-EcoRI-rev

5'-AAGAATTCATGGCGGCCAACG-3' (SEQ ID NO. 51)

FIG. 2B (SEQ ID NO. 1)

*ziaR-PziaA nucleotide sequence:*

```
1   gtcgacctccttaatccgattcctgcaaatggtctgcaac
41  ttccgatacaaattcatcacatgattatccgccaagctg
81  tagtaaacattacggccgacccggcgatactttaccaggc
121 gctgcgatcgtaaaattcgtaattgatgggaaactgccga
161 ttcactcactttcatcgcgctgctaaatcacagacacag
201 agttcttggcgggccaatgccgacattaaacgcaaccgac
241 tcggatcagctagtgcactgaaaaactccgccatttgctg
281 ggcctggtccaatgacatcacctctggttgaacctgtcgt
321 acctgctcaagatgaacaagaggttgatcacaaaggggca
361 tctcttcgttctggcaggattgtgactttgacaacgagga
401 cttattcatagaggttggcgttaggagctagggaaaaatt
441 taaactggatttagaaaatgattttcatcctaacatcttt
481 aatatctgagcatatcttcaggtgtttcaagatttgtgct
521 acggttcaaggaggtttttctttaaatcacgttggccgcc
561 atggaattc
```

| | |
|---|---|
| tta | *ziaR stop codon (anti-sense)* |
| cat | *ziaR start codon (anti-sense)* |
| gtcgac | *introduced SalI restriction site* |
| atggaattc | *PziaA-start codon/EcoRI restriction site* |

PCC6803

SEQ ID No.

85

86

GENETICALLY ENHANCED CYANOBACTERIA FOR THE PRODUCTION OF A FIRST CHEMICAL COMPOUND HARBOURING $ZN^{2+}$, $CO^{2+}$ OR $NI^{2+}$ -INDUCIBLE PROMOTERS

CROSS-REFERENCE TO RELATED APPLICATION

This application claims priority to PCT/EP2012/076790 having an international filing date of Dec. 21, 2012 which claims priority to U.S. provisional application 61/581,928 filed on Dec. 30, 2011, each of which are herein incorporated by reference in their entirety and for all purposes.

REFERENCE TO SEQUENCE LISTING

This application contains a sequence listing submitted by EFS-Web, thereby satisfying the requirements of 37 C.F.R. §1.821-1.825.

FIELD OF THE INVENTION

This invention is related to the field of production of chemical compounds of interest by using genetically enhanced cyanobacterial cells.

BACKGROUND OF THE INVENTION

Various products of interest, such as biofuels like fatty acid esters or alcohols, functional foods, vitamins, pharmaceuticals such as lactams, peptides and polyketides or terpenes and terpenoids and also biopolymers such as polyhydroxyalkanoates can be produced via genetically enhanced cyanobacteria. Genes for the production of these valuable compounds can, for example, be put under the control of an inducible promoter so that the cyanobacterial cells can grow in an uninduced state, accumulating biomass and after induction produce the compound of interest. One of these valuable compounds is ethanol. In this context, the PCT patent application WO 2009/098089 A2 discloses the use of ethanologenic genes, for example pyruvate decarboxylase and alcohol dehydrogenase for the production of ethanol. High ethanol production rates can be obtained by bringing these genes under the transcriptional control of the promoter from the petJ gene which is induced by copper deprivation and repressed by addition of at least 1.5 μM copper to the growth medium of the cyanobacteria. Therefore this promoter requires dilution of the medium in order to induce the culture, which is hard to achieve during the continuous process of culturing the cyanobacteria. Therefore, there is a need for improved inducible promoters for the transcriptional control of genes for the production of first chemical compounds.

This task is solved by providing a genetically enhanced cyanobacterium as described herein.

SUMMARY

In one aspect, a genetically enhanced cyanobacterium for the production of a first chemical compound is disclosed comprising wherein at least one first recombinant gene encoding a first biocatalyst for the production of the first chemical compound, wherein the gene is under the transcriptional control of a $Co^{2+}$ or $Zn^{2+}$-inducible promoter. In an embodiment, the first chemical compound is a biofuel or an organic compound. In another embodiment, the cyanobacterium biofuel or the organic compound is selected from a group consisting of: alkanols, alkanes, polyhydroxyalkanoates (e.g. PHB), fatty acids, fatty acid esters, carboxylic acids (such as amino acids), hydrogen, terpenes and terpenoids, peptides, polyketides, alkaloids, lactams, such as pyrrolidone, alkenes and ethers, such as THF or combinations thereof. In another embodiment, the first compound is an alkanol. In yet another embodiment, the first compound is ethanol. In an embodiment, the cyanobacterium contains at least one first recombinant gene that encodes a pyruvate decarboxylase as the first biocatalyst. In another embodiment, the cyanobacterium contains a first recombinant gene that encodes a first biocatalyst catalyzing a metabolic reaction not present in the wild-type cyanobacterium. In another embodiment, the cyanobacterium contains at least a second recombinant gene encoding a second biocatalyst for the production of a first chemical compound. In an embodiment, the cyanobacterium contains a first biocatalyst that produces an intermediate which is further converted by a second biocatalyst into a first chemical compound. In another embodiment, the cyanobacterium the second recombinant gene encodes an alcohol dehydrogenase. In yet another embodiment, the alcohol dehydrogenase is selected from the group consisting of: $Zn^{2+}$ dependent Alcohol dehydrogenase or $Fe^{2+}$-dependent Alcohol dehydrogenase, AdhI, *Synechocystis* Adh, AdhII and AdhE. In an embodiment, only the first, but not the second recombinant gene is under the transcriptional control of the $Co^{2+}$- or $Zn^{2+}$-inducible promoter. In an embodiment, the second gene is under the transcriptional control of a constitutive promoter. In an embodiment, the constitutive promoter is the rbcL promoter or an artificial derivate of the native rbcL promoter. In another embodiment, the both the first and second recombinant gene are under the control of the $Co^{2+}$- or $Zn^{2+}$-inducible promoter. In yet another embodiment, the $Co^{2+}$ or $Zn^{2+}$-inducible promoter is selected from a group consisting of: PziaA (*Synechocystis* 6803), PsmtA (*Synechococcus* 7942 and *Synechococcus* 7002), PcorT (*Synechocystis* 6803), PaztA (*Anabaena* 7120), PbmtA (*Oscillatoria brevis*), Pbxa1 (*Oscillatoria brevis*) PzntA (*Staphylococcus aureus*) PczrB (*Staphylococcus aureus* 912) and PnmtA (*Mycobacterium tuberculosis*). In another embodiment, the cyanobacterium contains a recombinant first control gene encoding a transcription factor binding to the $Co^{2+}$ or $Zn^{2+}$ inducible promoter. In another embodiment, the $Co^{2+}$ or $Zn^{2+}$-inducible promoter and the first control gene are endogenous to the wild type cyanobacterium. In another embodiment, the recombinant $Co^{2+}$ or $Zn^{2+}$-inducible promoter are heterologous to the cyanobacterium, which also has a recombinant first control gene encoding a transcription factor binding to the $Co^{2+}$ or $Zn^{2+}$-inducible promoter. In an embodiment, the first control gene is under the transcriptional control of a first control promoter, and the first control promoter harbors nucleotide changes in at least one of the following regions, the TATA box, and/or the ribosomal binding site. In an embodiment, the $Co^{2+}$ or $Zn^{2+}$-inducible promoter and the first control gene are selected from at least one of the following groups wherein the $Zn^{2+}$ inducible promoter is PziaA and the first control gene is ziaR, the $Zn^{2+}$ inducible promoter is PsmtA and the first control gene is smtB, the $Zn^{2+}$ inducible promoter is PaztA and the first control gene is aztR, the $Zn^{2+}$ inducible promoter is PbmtA and the first control gene is BxmR, the $Zn^{2+}$ inducible promoter is Pbxa1 and the first control gene is BxmR, the $Zn^{2+}$ inducible promoter is PzntA and the first control gene is zntR, and the $Co^{2+}$ inducible promoter is PcorT and the first control gene is corR. In yet another embodiment, the cyanobacterium has an endogenous gene coding for a $Co^{2+}$ or $Zn^{2+}$-transporting protein which is under the transcriptional control of an endogenous $Co^{2+}$ or $Zn^{2+}$-inducible promoter, and the endogenous $Co^{2+}$ or $Zn^{2+}$-inducible promoter contain an inactivation. In yet another embodiment, the endogenous $Co^{2+}$ or $Zn^{2+}$-inducible promoter is replaced by a recombinant constitutive promoter or a recombinant inducible promoter which is inducible under different conditions than said endogenous $Co^{2+}$ or $Zn^{2+}$-inducible promoter. In yet another embodiment, the endogenous gene which is transcriptionally controlled by the endogenous $Co^{2+}$ or $Zn^{2+}$ inducible promoter also contains an inactivation. In another embodiment, both of the endogenous $Co^{2+}$ or $Zn^{2+}$ inducible promoter and the endogenous gene are deleted. In an embodiment, the extrachromosomal plasmid harboring a recombinant gene coding for a $Co^{2+}$ or $Zn^{2+}$-transporting protein is present, the recombinant gene being transcriptionally controlled by either a constitutive promoter or a promoter which is inducible under different conditions than the endogenous $Co^{2+}$ or $Zn^{2+}$-inducible promoter. In another embodiment, the extrachromosomal plasmid also harbors the at least first and—if present—at least second recombinant genes. In another embodiment, the cyanobacterium is selected from a group consisting of: *Synechocystis, Synechococcus, Anabaena, Chroococcidiopsis, Chloreogloepsis, Cyanothece, Lyngbya, Phormidium, Nostoc, Spirulina, Arthrospira, Thermosynechococcus* BP1, *Trichodesmium, Leptolyngbya, Plectonema, Myxosarcina, Pleurocapsa, Oscillatoria, Pseudanabaena, Cyanobacterium, Geitlerinema, Calothrix, Euhalothece, Scytonema*. In an embodiment, the $Zn^{2+}$ or $Co^{2+}$-inducible promoter harbors nucleotide changes in comparison to the native promoter in at least one of the following regions, the TATA box, and/or, the ribosomal binding site, the operator and/or, the 5'-UTR (untranslated region). In another embodiment, the $Zn^{2+}$ inducible promoter has at least 70% sequence identity to the promoter ziaA, which has the nucleotide sequence of: $(N)_{11}$AATATCTGAGCATATCTTCAGGTGTT $(N)_{13}$TACGGT $(N)_{6}$A$(N)_{16}$ACGTTGGCCGCCATG (SEQ ID NO. 5), wherein each of the nucleotides N is independently selected from a group consisting of: A, T, C and G and wherein the 3'-ATG is the start codon of the first recombinant gene transcriptionally controlled by this promoter. In another embodiment, the $Zn^{2+}$-inducible promoter is selected from the group consisting of:

(SEQ ID NO. 6)
$N_{11}$AATATCTGAGCATATCTTCAGGTGTT$N_{13}$TATAAT$N_{6}$A$N_{17}$CGTTGGCCGCCATG, (SEQ ID NO. 7)
$N_{11}$AATATCTGAGCATATCTTCAGGTGTT$N_{13}$TACGGT$N_{6}$A$N_{17}$AGGAGGCCGCCATG, (SEQ ID NO. 8)
$N_{11}$AACATCTGAACATATCTTCAGATGTT$N_{13}$TACGGT$N_{6}$A$N_{17}$CGTTGGCCGCCATG, (SEQ ID NO. 9)
$N_{11}$AATATCTGAGCATATCTTCAGGTGTT$N_{13}$TATAAT$N_{6}$A$N_{17}$AGGAGGCCGCCATG, (SEQ ID NO. 10)
$N_{11}$AACATCTGAACATATCTTCAGATGTT$N_{13}$TATAAT$N_{6}$A$N_{17}$CGTTGGCCGCCATG, (SEQ ID NO. 11)
$N_{11}$AACATCTGAACATATCTTCAGATGTT$N_{13}$TACGGT$N_{6}$A$N_{17}$AGGAGGCCGCCATG, (SEQ ID NO. 12)
$N_{11}$AACATCTGAACATATCTTCAGATGTT$N_{13}$TATAAT$N_{6}$A$N_{17}$AGGAGGCCGCCATG, (SEQ ID NO. 13)
$N_{11}$AATATCTGAGCATATCTTCAGGTGTT$N_{13}$TATGGT$N_{6}$A$N_{17}$CGTTGGCCGCCATG, (SEQ ID NO. 14)
$N_{11}$AATATCTGAGCATATCTTCAGGTGTT$N_{13}$TACAGT$N_{6}$A$N_{17}$CGTTGGCCGCCATG, (SEQ ID NO. 15)
$N_{11}$AATATCTGAGCATATCTTCAGGTGTT$N_{13}$TACGAT$N_{6}$A$N_{17}$CGTTGGCCGCCATG, (SEQ ID NO. 16)
$N_{11}$AATATCTGAGCATATCTTCAGGTGTT$N_{13}$TATAGT$N_{6}$A$N_{17}$CGTTGGCCGCCATG, (SEQ ID NO. 17)
$N_{11}$AATATCTGAGCATATCTTCAGGTGTT$N_{13}$TACAAT$N_{6}$A$N_{17}$CGTTGGCCGCCATG, (SEQ ID NO. 18)
$N_{11}$AATATCTGAGCATATCTTCAGGTGTT$N_{13}$TATGAT$N_{6}$A$N_{17}$CGTTGGCCGCCATG, (SEQ ID NO. 19)
$N_{11}$AACATCTGAACATATCTTCAGATGTT$N_{13}$TATGGT$N_{6}$A$N_{17}$CGTTGGCCGCCATG, (SEQ ID NO. 20)
$N_{11}$AACATCTGAACATATCTTCAGATGTT$N_{13}$TACAGT$N_{6}$A$N_{17}$CGTTGGCCGCCATG, (SEQ ID NO. 21)
$N_{11}$AACATCTGAACATATCTTCAGATGTT$N_{13}$TACGAT$N_{6}$A$N_{17}$CGTTGGCCGCCATG, (SEQ ID NO. 22)
$N_{11}$AACATCTGAACATATCTTCAGATGTT$N_{13}$TATAGT$N_{6}$A$N_{17}$CGTTGGCCGCCATG,

-continued (SEQ ID NO. 23)
$N_{11}$AACATCTGAACATATCTTCAGATGTT$N_{13}$TACAAT$N_6$A$N_{17}$CGTTGGCCGCCATG, (SEQ ID NO. 24)
$N_{11}$AACATCTGAACATATCTTCAGATGTT$N_{13}$TATGAT$N_6$A$N_{17}$CGTTGGCCGCCATG, (SEQ ID NO. 25)
$N_{11}$AACATCTGAACATATCTTCAGATGTT$N_{13}$TATGGT$N_6$A$N_{17}$AGGAGGCCGCCATG, (SEQ ID NO. 26)
$N_{11}$AACATCTGAACATATCTTCAGATGTT$N_{13}$TACAGT$N_6$A$N_{17}$AGGAGGCCGCCATG, (SEQ ID NO. 27)
$N_{11}$AACATCTGAACATATCTTCAGATGTT$N_{13}$TACGAT$N_6$A$N_{17}$AGGAGGCCGCCATG, (SEQ ID NO. 28)
$N_{11}$AACATCTGAACATATCTTCAGATGTT$N_{13}$TATAGT$N_6$A$N_{17}$AGGAGGCCGCCATG, (SEQ ID NO. 29)
$N_{11}$AACATCTGAACATATCTTCAGATGTT$N_{13}$TACAAT$N_6$A$N_{17}$AGGAGGCCGCCATG, (SEQ ID NO. 30)
$N_{11}$AACATCTGAACATATCTTCAGATGTT$N_{13}$TATGAT$N_6$A$N_{17}$AGGAGGCCGCCATG, (SEQ ID NO. 90)
$N_{11}$AATATCTGAGCATATCTTCAGGTGTT$N_{13}$TACGGT$N_6$A$N_{16}$AAGGAGTTAACATTATGTCTCATATG, wherein the boldfaced and underlined nucleotides denote mutations in comparison to the wild type PziaA and wherein boldfaced framed nucleotides denote nucleotides coding for N-terminal extension of second or first recombinant gene. In an embodiment, the $Co^{2+}$-inducible promoter has at least 70% sequence identity to the promoter corT, which has the nucleotide sequence of: CAT $(N)_7$GTTTACTCAAAACCTTGACATTGACACTAATGTTAAGGTTTAGGCT $(N)_{15}$ CAAGTTAAAAAGCATG (SEQ ID NO. 31), wherein each of the nucleotides N is independently selected from a group consisting of: A, T, C and G and wherein the 5'-CAT is the start codon of corR (antisense orientation) the 3'-ATG is the start codon for the first recombinant gene transcriptionally controlled by this promoter. In another embodiment, the $Co^{2+}$-inducible promoter is selected from the group consisting of:

(SEQ ID NO. 32)
CAT$(N)_7$GTTTACTCAAAACCTTGACATTGACACTAATGTTAAGGTTTA
GAAT$(N)_{15}$CAAGTTAAAAAGCATG, (SEQ ID NO. 33)
CAT$(N)_7$GTTTACTCAAAACCTTGACATTGACACTAATGTTAAGGTTTA
GGAT$(N)_{15}$CAAGTTAAAAAGCATG, (SEQ ID NO. 34)
CAT$(N)_7$GTTTACTCAAAACCTTGACATTGACACTAATGTTAAGGTTTA
GACT$(N)_{15}$CAAGTTAAAAAGCATG, (SEQ ID NO. 35)
CAT$(N)_7$GTTTACTCAAAACCTTGACATTGACACTAATGTTAAGGTTTA
GGCT$(N)_{15}$GAGGATAAAAAGCATG, (SEQ ID NO. 36)
CAT$(N)_7$GTTTACTCAAAACCTTGACATTGACACTAATGTTAAGGTTTA
GGAT$(N)_{15}$GAGGATAAAAAGCATG, (SEQ ID NO. 37)
CAT$(N)_7$GTTTACTCAAAACCTTGACATTGACACTAATGTTAAGGTTTA
GACT$(N)_{15}$GAGGATAAAAAGCATG, (SEQ ID NO. 38)
CAT$(N)_7$GTTTACTCAAAACCTTGACATTGACACTAATGTCAAGGTTTA
GAAT$(N)_{15}$CAAGTTAAAAAGCATG,

-continued (SEQ ID NO. 39)
CAT$(N)_7$GTTTACTCAAAACCTTGACATTGACACTAATGTCAAGGTTTA
GGAT$(N)_{15}$CAAGTTAAAAAGCATG, (SEQ ID NO. 40)
CAT$(N)_7$GTTTACTCAAAACCTTGACATTGACACTAATGTCAAGGTTTA
GACT$(N)_{15}$CAAGTTAAAAAGCATG, (SEQ ID NO. 41)
CAT$(N)_7$GTTTACTCAAAACCTTGACATTGACACTAATGTCAAGGTTTA
GGCT$(N)_{15}$GAGGATAAAAAGCATG, (SEQ ID NO. 42)
CAT$(N)_7$GTTTACTCAAAACCTTGACATTGACACTAATGTCAAGGTTTA
GGAT$(N)_{15}$GAGGATAAAAAGCATG, (SEQ ID NO. 43)
CAT$(N)_7$GTTTACTCAAAACCTTGACATTGACACTAATGTCAAGGTTTA
GACT$(N)_{15}$GAGGATAAAAAGCATG.

wherein the boldfaced and underlined nucleotides denote mutations in comparison to the wildtype PcorT. In yet another embodiment, the $Zn^{2+}$-inducible promoter has at least 70% sequence identity to the more generalized nucleotide sequence of the aztA promoter, which is the sequence:

(SEQ ID NO. 44)
$(N)_{12}$TGTACAATTGAATAGTTGTTCAATTGTTGTATTAGAAT$(N)_5$C
$(N)_{17}$AATTCTAAAGCTGCTATG wherein each of the nucleotides N is independently selected from a group consisting of A, T, C and G and wherein the 3'-ATG is the start codon for the first recombinant gene transcriptionally controlled by this promoter.

In an aspect, a genetically enhanced cyanobacterium for the production of ethanol is disclosed comprising a first recombinant gene coding for a first biocatalyst for the production of ethanol, wherein the gene is under the transcriptional control of a $Ni^{2+}$-inducible promoter. In an embodiment, the $Ni^{2+}$ inducible promoter harbors nucleotide changes in comparison to the native promoter in at least one of the following regions, the TATA box, and/or, the ribosomal binding site, the operator and/or the 5'-UTR (untranslated region). In an embodiment, the $Ni^{2+}$ inducible promoter is selected from a group consisting of: nrsRS-PnrsB from *Synechocystis* PCC 6803 and nrsRS916-PnrsB916 from *Synechococcus* sp. In an embodiment, the $Ni^{2+}$-inducible promoter has at least 70% sequence identity to the more generalized nucleotide sequence of the nrsB promoter from *Synechocystis* PCC 6803, which is the sequence:

(SEQ ID NO. 91)
$(N)_{14}$GAGATTTTCACCTGAATTTCATACCCCCTTTGGCAGACTGGGAA
A$(N)_{17}$AATTTGAGGTGGTGTGATG, or the more generalized nucleotide sequence of the nrsB (916) promoter, which is the sequence:

(SEQ ID NO. 92)
$(N)_{14}$GCCTATTTCACTTAGATTTCATACCCCCTCTGGCAAACTGGAAA
AA$(N)_{24}$AATGTGAGGTGCTGTGATG, wherein each of the nucleotides N is independently selected from a group consisting of A, T, C and G and wherein the 3'-ATG is the start codon for the first recombinant gene transcriptionally controlled by this promoter. In another embodiment, the genetically enhanced cyanobacterium has at least a second recombinant gene encoding a second biocatalyst for the production of ethanol. In an embodiment, the first biocatalyst produces an intermediate, which is further converted by the second biocatalyst into the first chemical compound. In an embodiment, the cyanobacterium contains a first and second control gene coding for a two component signal transduction system essential for regulating the $Ni^{2+}$ inducible promoter. In another embodiment, the $Ni^{2+}$ inducible promoter is PnrsB and the first control gene is nrsR and the second control gene nrsS. In another embodiment, the cyanobacterium contains a first recombinant gene encodes a biocatalyst diverting the carbon flux away from the metabolism of the wild type cyanobacterium, and a second recombinant gene encodes a biocatalyst catalyzing a reaction already present in the wild type cyanobacterium, wherein the second recombinant gene is located downstream of the $Zn^{2+}$, $Co^{2+}$ or $Ni^{2+}$ inducible promoter and wherein the first recombinant gene is located downstream of the second recombinant gene, and wherein the $Zn^{2+}$, $Co^{2+}$ or $Ni^{2+}$ inducible promoter controls the transcription of both the first and second recombinant gene. In an embodiment, a cyanobacterium contains at least one recombinant gene that is integrated into an endogenous extrachromosomal plasmid of the cyanobacterium. In an embodiment, the cyanobacterium is *Synechococcus* PCC 7002 or a closely related *Synechococcus* species and the at least one recombinant gene is integrated into an endogenous plasmid selected from the group consisting of pAQ1, pAQ3, pAQ4, and pAQ5 or combinations thereof.

In an aspect, a method for producing a first chemical compound is disclosed which has the following method steps:

a. culturing the genetically enhanced cyanobacteria according to any of the methods described herein in a culture medium,
b. inducing the cyanobacteria by adding $Co^{2+}$, $Zn^{2+}$ or $Ni^{2+}$ to the culture medium, the cyanobacteria producing the first chemical compound.

In an embodiment, in the method step B) the cyanobacteria are induced by adding at least 2 μM $Zn^{2+}$, $Co^{2+}$ or $Ni^{2+}$. In an embodiment, the method step A) uses a culture medium already including $Co^{2+}$, $Zn^{2+}$ or $Ni^{2+}$ ions and is used for cultivation and wherein a chemical compound able to chelate bivalent metal ions is added. In another embodiment, the method uses compound selected from a group consisting of: EDTA (Ethylenediaminetetraacetic acid), EGTA (ethylene glycol tetraacetic acid), DTPA (diethylene triamine pentaacetic acid) or citrate or combinations thereof is added.

DESCRIPTION OF THE INVENTION

One aspect of the invention provides a genetically enhanced cyanobacterium for the production of a first chemical, compound, comprising:

at least one first recombinant gene encoding a first biocatalyst for the production of the first chemical compound, wherein the gene is under the transcriptional control of a $Co^{2+}$ or $Zn^{2+}$-inducible promoter.

The inventors of the present invention found out that in contrast to the inducible promoters of the state of the art, $Co^{2+}$ or $Zn^{2+}$-inducible promoters show certain advantages regarding the behavior of the cyanobacteria in the induced and uninduced state as well as the way the induction is carried out. In particular, $Co^{2+}$ or $Zn^{2+}$-inducible promoters were shown to be much more tightly controlled in the uninduced state than prior art promoters such as the petJ promoter. This tighter control enables a faster and thereby more efficient accumulation of biomass of the cyanobacteria during culturing in the uninduced state. A leaky promoter, even in the uninduced state, can lead to small amounts of production of the first chemical compound even during the upscaling of the cyanobacterial culture, thereby greatly increasing the risk of contamination with faster growing heterotrophic bacteria or fungi which do not produce the first chemical compound. In long-term cultures of at least 30 or 35 days of culturing time and especially during the upscaling process of precultures in industrial scale, leaky promoters can also greatly enhance the risk of accumulation of inactivating mutations in the genes and promoters for producing the first chemical compound, for example ethanol.

Furthermore, the inventors found out that the addition of $Co^{2+}$ or $Zn^{2+}$-salts to the growth medium of the cyanobacteria is much easier to accomplish than the dilution of the cultures when using inducible promoters which are induced via the deprivation of certain metals, such as $Cu^{2+}$ deprivation in the case of the petJ promoter. The induction by addition of metal ions occurs much faster than the induction by a deprivation protocol and in contrast to prior art promoters like PpetJ it is possible to reboost/refresh the production rate during the production process by further addition of $Co^{2+}$ or $Zn^{2+}$ especially in the later phase of production of the first chemical compound when the productivity is decreasing what is frequently seen due to a declining induction of the promoter over the time. In addition, after induction of the cobalt ($Co^{2+}$) or zinc ($Zn^{2+}$)-inducible promoters, in some cases even a higher production rate for the first chemical compound can be observed compared to prior art promoters. The use of $Co^{2+}$ or $Zn^{2+}$-inducible promoters also enables a better upscaling of small experimental cultures to large industrial scale cultures of up to about 4500 L per biorector, due to the reduction of the risk of early contamination events and due to the enhancement of the genetic stability until the induction of the production of the first chemical compound takes place. The inventors furthermore discovered that only small amounts of Zn2+ or Co2+ of about 3 to 20 μM are necessary for an induction, which enables a relatively cheap induction procedure in comparison to other conventional more expensive inductants such as IPTG (Isopropyl β-D-1-thiogalactopyranoside). Furthermore adding EDTA or other chelating agents, preferably in low concentrations (10 μM-30 μM) to the growth medium for defined reduction of induction in order to assure sufficient cell maintenance or recovery, respectively after a certain production phase can be a further option for adjusting metal-ion inducible promoters such as $Co^{2+}$ or $Zn^{2+}$-inducible promoters.

In addition using $Co^{2+}$ or $Zn^{2+}$-inducible promoters limitations that might be connected with an induction procedure based on (trace)nutrient deprivation promoters (e.g. petJ or nirA promoter) can avoid a negative impact on the production of the chemical compound due to the deprivation condition.

The introduction of the first as well as, if necessary, second recombinant gene or even further recombinant genes, directs the metabolic flux of the photoautotrophic cyanobacterium towards the production of the first chemical compound. During the course of the synthesis of the first chemical compound, $CO_2$ is consumed and oxygen and carbon based compounds, like sugars are produced. Owing to the first and/or second recombinant gene the carbon based compounds are further converted into the first chemical compound of interest.

In particular, the first chemical compound can be an organic compound or a biofuel which, for example, can be selected from the group of: alkanols, alkanes, polyhydroxyalkanoates, e.g. PHB, fatty acids, fatty acid esters, carboxylic acids, such as amino acids, hydrogen, terpenes and terpenoids, peptides, polyketides, alkaloids, lactams, such as pyrrolidone, alkenes and ethers, such as THF and combinations thereof.

Cyanobacteria according to certain embodiments of the invention can comprise a whole sequence of recombinant genes coding for biocatalysts for the production of the first chemical compound in the case that a cascade, for example of different enzymes, is necessary to produce the first chemical compound.

In particular, the first biocatalyst encoded by the first recombinant gene can produce a first intermediate which is further converted by the second biocatalyst into another second intermediate, which then in turn is further converted by a third biocatalyst encoded by a third recombinant gene into a third intermediate, so that a sequence of consecutive recombinant biocatalysts, which provide intermediates for the next recombinant enzyme for the production of the first chemical compound can be introduced into the cyanobacteria.

In a further variant of the genetically enhanced cyanobacteria of the invention, the first chemical compound is selected from various alkanols, such as ethanol, propanol or butanol, alkanes and alkenes, such as ethylene or propylene, biopolymers such as polyhdyroxyalkanoates like polyhydroxybutyrate, fatty acids, fatty acid esters, carboxylic acids such an amino acids, terpenes and terpenoids. Furthermore, the first valuable chemical compound can be selected from peptides, polyketides, alkaloids, lactams and ethers such as tetrahydrofuran or any combinations of the above-mentioned chemical compounds.

Depending on the first valuable chemical compound to be produced, the respective first recombinant genes encoding biocatalysts for the production of these first chemical compounds have to be introduced into the cyanobacteria. The biocatalyst can be so-called RNA-enzymes ribozymes or can be protein based enzymes. For example, if the first chemical compound is ethanol, the first recombinant genes encoding enzymes for ethanol production can be Pdc enzyme (pyruvate decarboxylase) catalyzing the reaction from pyruvate to acetaldehyde, Adh enzyme (alcohol dehydrogenase), catalyzing the reaction from acetaldehyde to ethanol, or a AdhE enzyme (alcohol dehydrogenase E) which directly converts acetyl-coenzyme A to ethanol. The Adh enzyme can, for example, be a $Zn^{2+}$-dependent alcohol dehydrogenase such as AdhI from *Zymomonas mobilis* (ZmAdhI) or the Adh enzyme from *Synechocystis* PCC6803 (SynAdh). Alternatively or in addition, the enzyme can also be an iron-dependent alcohol dehydrogenase (e.g. AdhII from *Zymomonas mobilis*—ZmAdhII). The $Zn^{2+}$-dependent alcohol dehydrogenase can, for example, be an alcohol dehydrogenase enzyme having at least 60%, 70%, preferably 80% and most preferred 90% or even more than 90% sequence identity to the amino acid sequence of $Zn^{2+}$ dependent *Synechocystis* Adh. Experiments have shown that in particular *Synechocystis* alcohol dehydrogenase SynAdh (slr1192) is able to ensure a high ethanol production in genetically enhanced cyanobacteria due to the fact that the forward reaction, the reduction of acetaldehyde to ethanol is much more preferred for *Synechocystis* alcohol dehydrogenase enzyme than the unwanted back reaction from ethanol to acetaldehyde. For these reasons the use of a SynAdh encoding recombinant gene for production of ethanol as a first chemical compound is preferred.

The AdhE is an iron-dependent, bifunctional enzyme containing a CoA-depending aldehyde dehydrogenase and an alcohol dehydrogenase activity. One characteristic of iron-dependent alcohol dehydrogenases (e.g. AdhE and AdhII) is the sensitivity to oxygen. In the case of the AdhE from *E. coli* a mutant was described that shows in contrast to the wild type also Adh activity under aerobic conditions. The site of the mutation was determined in the coding region at the codon position 568. The G to A nucleotide transition in this codon results in an amino acid exchange from glutamate to lysine (E568K). The E568K derivate of the *E. coli* AdhE is active both aerobically and anaerobically. [Holland-Staley et al., Aerobic activity of *Escherichia coli* alcohol dehydrogenase is determined by a single amino acid, J Bacteriol. 2000 November; 182(21):6049-54].

AdhE enzymes directly converting acetyl coenzyme A to ethanol can preferably be from a thermophilic source thereby conferring an enhanced degree of stability. The AdhE can be from *Thermosynechococcus elongatus* BP-1 or also can be a non-thermophilic AdhE enzyme from *E. coli.*

The pyruvate decarboxylase can for example be from *Zymomonas mobilis, Zymobacter palmae* or the yeast *Saccharomyces cerevisiae*. Regarding the nucleic acid sequences, protein sequences and properties of these above mentioned ethanologenic enzymes, reference is made to the PCT patent application WO 2009/098089 A2, which is incorporated for this purpose.

Two other alcohols which are relatively widespread are propanol and butanol. Similar to ethanol, they can be produced by fermentation processes. The following enzymes are involved in isopropanol fermentation and can be encoded by a first and/or second recombinant genes: acetyl-CoA acetyltransferase (EC:2.3.1.9), acetyl-CoA:acetoacetyl-CoA transferase (EC:2.8.3.8), acetoacetate decarboxylase (EC:4.1.1.4) and isopropanol dehydrogenase (EC:1.1.1.80).

The following enzymes are involved in isobutanol fermentation: acetolactate synthase (EC:2.2.1.6), acetolactate reductoisomerase (EC:1.1.1.86), 2,3-dihydroxy-3-methylbutanoate dehydratase (EC:4.2.1.9), α-ketoisovalerate decarboxylase (EC:4.1.1.74), and alcohol dehydrogenase (EC:1.1.1.1).

In the case that ethylene is to be produced as a first chemical compound, the at least one first recombinant gene encodes an enzyme for ethylene formation, in particular the ethylene-forming enzyme 1-aminocyclopropane-1-carboxylate oxidase (EC 1.14.17.4), which catalyzes the last step of ethylene formation, the oxidation of 1-aminocyclopropane-1-carboxylic acid to ethylene. The substrate for the ethylene-forming enzyme is synthesized by the enzyme 1-aminocyclopropane-1-carboxylic acid synthase (EC 4.4.1.14) from the amino acid methionine.

If the first chemical compound is an isoprenoid such as isoprene, the at least one first recombinant gene encodes an enzyme such as isoprene synthase. Isoprene synthase (EC 4.2.3.27) catalyzes the chemical reaction from dimethylallyl diphosphate to isoprene and diphosphate.

Terpenes are a large and very diverse class of organic compounds, produced primarily by a wide variety of plants, particularly conifers. Terpenes are derived biosynthetically from units of isoprene and are major biosynthetic building blocks in nearly every living organism. For example, steroids are derivatives of the triterpene squalene. When terpenes are modified chemically, such as by oxidation or rearrangement of the carbon skeleton, the resulting compounds are generally referred to as terpenoids. Terpenes and terpenoids are the primary constituents of the essential oils for many types of plants and flowers. Examples of biosynthetic enzymes are farnesyl pyrophosphate synthase (EC 2.5.1.1), which catalyzes the reaction of dimethylallylpyrophosphate and isopentenyl pryrophosphate yielding farnesyl pyrophosphate. Another example is geranylgeranyl pyrophosphate synthase (EC 2.5.1.29), which catalyzes the reaction between transfarnesyl diphosphate and isopentenyl diphosphate yielding diphosphate and geranylgeranyl diphosphate.

In the case that the first chemical compound is hydrogen, the first and/or second recombinant genes can for example code for hydrogenase an enzyme catalyzing the following reaction:

$$12H^{+}+12X_{reduced}\rightarrow 6\ H_2+12X_{oxidized},$$

wherein X is an electron carrier such as ferredoxin.

Further examples of first valuable chemical compounds are the so-called non-ribosomal peptides (NRP) and the polyketides (PK). These compounds are synthesized by plants, fungi and only a few bacteria such as actinomycetes, myxobacteria and cyanobacteria. They are a group of structurally diverse secondary metabolites and often possess bioactivities of high pharmacological relevance. Hybrids of non-ribosomal peptides and polyketides also exist, exhibiting both a peptide and a polyketide part. First recombinant genes for the production of non-ribosomal peptides as the first chemical compounds are for example gene clusters encoding for non-ribosomal peptide synthetases (NRPS). NRPS are characteristic modular multidomain enzyme complexes encoded by modular non-ribosomal peptide synthetase gene clusters. Examples for non-ribosomal peptide synthetases are actinomycin synthetase and gramicidin synthetase.

In general there are two distinct groups of polyketides (PK), the reduced polyketides of type I, the so-called macrolides and the aromatic polyketides of type II. Type I polyketides are synthesized by modular polyketide synthases (PKS), which are characteristic modular multidomain enzyme complexes encoded by modular PKS gene clusters. Examples for first recombinant genes for the production of type I polyketides are the rapamycin synthase gene cluster and the oleandomycin synthase gene cluster. One example for a first recombinant gene for type II polyketides is the actinorhodin polyketide synthase gene cluster.

Examples for first recombinant genes for the production of hybrids of polyketides and non-ribosomal peptides are the microcystin synthetase gene cluster, microginin synthetase gene cluster, and myxothiazole synthetase gene cluster.

Further examples of first valuable chemical compounds are the alkaloids. Alkaloids are a compound group which is synthesized by plants. Alkaloids have highly complex chemical structures and pronounced pharmacological activities. Examples for biosynthetic enzymes for alkaloids which can be encoded by first recombinant genes for the production of the chemical compound are strictosidine synthase, which catalyzes the stereoselective Pictet-Spengler reaction of tryptamine and secologanin to form 3a(S)-strictosidine. The primary importance of strictosidine is not only its precursor role for the biosynthetic pathway of ajmaline but also because it initiates all pathways leading to the entire monoterpene indol alkaloid family. Another example of an enzyme encoded by a first recombinant gene is strictosidine glucosidase from the ajmaline biosynthetic pathway. This enzyme is able to activate strictosidine by deglycosylation thus generating an aglycon. This aglycon of strictosidine is the precursor for more than 2,000 monoterpenoid indol alkaloids.

Further examples of enzymes encoded by first recombinant genes are:

(R,S)-3'-hydroxy-N-methylcoclaurine 4'-O-methyltransferase (4'OMT) central to the biosynthesis of most tetrahydrobenzyl-isoquinolin-derived alkaloids;

Berberine bridge enzyme (BBE) specific to the sanguinarine pathway;

(R,S)-reticuline 7-O-methyltransferase (7OMT) specific to laudanosine formation;

Salutaridinol 7-O-acetyltransferase (SalAT) and codeinone reductase that lead to morphine.

Vitamins, as further examples of first chemical compounds, are organic compounds that are essential nutrients for certain organisms and act mainly as cofactors in enzymatic reactions but can also have further importance, e.g. as anti-oxidants in case of vitamin C. Vitamin C can be synthesized via the L-Ascorbic acid (L-AA) biosynthetic pathway from D-glucose in plants. The following enzymes are involved in vitamin C synthesis and can be encoded by at least first and/or second recombinant genes:

Hexokinase, Glucose-6-phosphate isomerase, Mannose-6-phosphate isomerase, Phosphomannomutase, Mannose-1-phosphate guanylyltransferase, GDP-mannose-3,5-epimerase, GDP-L-galactose phosphorylase, L-Galactose 1-phosphate phosphatase, L-galactose dehydrogenase, L-galactono-1,4-lactone dehydrogenase.

Lactams are cyclic amides whereas the prefixes indicate how many carbon atoms (apart from the carbonyl moiety) are present in the ring: β-lactam (2 carbon atoms outside the carbonyl, 4 ring atoms in total), γ-lactam (3 and 5), δ-lactam (4 and 6). One example for a γ-lactam is Pyrrolidone, a colorless liquid which is used in industrial settings as a high-boiling, non-corrosive, polar solvent for a wide variety of applications. It is also an intermediate in the manufacture of polymers such as polyvinylpyrrolidone and polypyrrolidone.

Ethers are a class of organic compounds that contain an ether group—an oxygen atom connected to two alkyl or aryl groups—of general formula R—O—R. A well-known example is Tetrahydrofuran (THF), a colorless, water-miscible organic liquid. This heterocyclic compound is one of the most polar ethers with a wide liquid range. It is a useful solvent. Its main use, however, is as a precursor to polymers.

One example for the natural occurring ethers are the divinyl ether oxylipins. The main enzymes involved in their biosynthesis are the lipoxygenase and especially the divinyl ether synthase.

Alkanes (also known as saturated hydrocarbons) are chemical compounds that consist only of the elements carbon (C) and hydrogen (H) (i.e., hydrocarbons), wherein these atoms are linked together exclusively by single bonds (i.e., they are saturated compounds). Each carbon atom must have 4 bonds (either C—H or C—C bonds), and each hydrogen atom must be joined to a carbon atom (H—C bonds). The simplest possible alkane is methane, $CH_4$. There is no limit to the number of carbon atoms that can be linked together. Alkanes, observed throughout nature, are produced directly from fatty acid metabolites. A two-gene pathway widespread in cyanobacteria is responsible for alkane biosynthesis and can be included in the first recombinant genes. An acyl-ACP reductase (EC: 1.3.1.9) converts a fatty acyl-ACP into a fatty aldehyde that is subsequently converted into an alkane/alkene by an aldehyde decarbonylase (EC: 4.1.99.5.).

Biopolymers such as polyhydroxyalkanoates or PHAs are linear polyesters produced in nature by bacterial fermentation of sugar or lipids. They are produced by the bacteria to store carbon and energy. The simplest and most commonly occurring form of PHA is the fermentative production of poly-3-hydroxybutyrate (P3HB) but many other polymers of this class are produced by a variety of organisms: these include poly-4-hydroxybutyrate (P4HB), polyhydroxyvalerate (PHV), polyhydroxyhexanoate (PHH), polyhydroxyoctanoate (PHO) and their copolymers. The main enzymes involved in PHA synthesis are as follows: For P3HB synthesis two molecules of acetyl-CoA are condensed by a β-ketothiolase (EC:2.3.1.9) to synthesize acetoacetyl-CoA, which is converted to (R)-3-hydroxybutyryl-CoA (3HB-CoA) by NADPH-dependent acetoacetyl-CoA reductase (EC:1.1.1.36). The 3HBCoA is subsequently polymerized by poly(3-hydroxyalkanoate) synthase (EC:2.3.1.–) and converted to (P3HB).

About 100,000 metric tons of the natural fatty acids are consumed in the preparation of various fatty acid esters. The simple esters with lower chain alcohols (methyl-, ethyl-, n-propyl-, isopropyl- and butyl esters) are used as emollients in cosmetics and other personal care products and as lubricants. Esters of fatty acids with more complex alcohols, such as sorbitol, ethylene glycol, diethylene glycol and polyethylene glycol are consumed in foods, personal care, paper, water treatment, metal working fluids, rolling oils and synthetic lubricants. Fatty acids are typically present in the raw materials used for the production of biodiesel. A fatty acid ester (FAE) can be created by a transesterification reaction between fats or fatty acids and alcohols. The molecules in biodiesel are primarily fatty acid methyl esters FAMES, usually obtained from vegetable oils by transesterification with methanol. The esterification of the ethanol with the acyl moieties of coenzyme A thioesters of fatty acids can be realized enzymatically by an unspecific long-chain-alcohol 0-fatty-acyltransferase (EC 2.3.1.75) from *Acinetobacter baylyi* strain ADP1.

According to a further preferred embodiment of the invention, the first compound can be alkanols, particularly ethanol. The inventors could show that a particularly tight control of cobalt or zinc-inducible promoters in the uninduced state can result if these promoters control genes coding for ethanologenic enzymes. Upon induction of these ethanol producing cyanobacteria, a higher increase in ethanol production rate can be achieved compared to prior art inducible promoters such as the petJ promoter.

In the case of ethanol production as a first chemical compound, the at least one first recombinant gene preferably encodes a pyruvate decarboxylase as a first biocatalyst, which catalyzes the chemical reaction leading from pyruvate to acetaldehyde. According to a further embodiment of the invention, the cyanobacteria of the invention further comprise at least a second recombinant gene encoding a second biocatalyst for the production of the first chemical compound.

In the case that the first chemical compound of interest is ethanol, the second recombinant gene preferably encodes alcohol dehydrogenase, which is able to convert the acetaldehyde provided by the pyruvate decarboxylase, the first biocatalyst, into the final first chemical compound, ethanol.

The alcohol dehydrogenases can be $Zn^{2+}$ or iron dependent alcohol dehydrogenases, for example ADHI, ADHII from *Zymomonas mobilis*, SynADH from *Synechocystis* PCC6803 or even ADHE, which is able to directly convert acetyl coenzyme A into ethanol. Especially with regard to ADHE only one biocatalyst can be sufficient in order to produce the first chemical compound ethanol.

In addition the genes coding for the at least one first and/or second recombinant enzyme or biocatalyst can be degenerated in order to reduce the risk of homologous recombination between the endogenous gene and the introduced recombinant gene coding for the at least one first and/or second biocatalyst or between multiple copies of introduced genes, which might lead to inactivation of these genes. In particular the so-called wobble bases in the triplet codon for the amino acids of the proteins encoded by these genes might be replaced by other nucleotides so that the base triplets still code for the same amino acid in the first and/or second biocatalysts. In this context the term "$SynADH_{deg}$" denotes a degenerated DNA sequence having a sequence identity of 61% to the wild type *Synechocystis* ADH gene coding for the *Synechocystis* sp. PCC 6803 alcohol dehydrogenase enzyme.

Since smaller amounts of $Zn^{2+}$ are included in seawater, using seawater in order to prepare the growth medium for cyanobacteria, such as marine BG11 medium (mBG11) can lead to a higher leakiness of the $Zn^{2+}$ inducible promoter compared to other growth media which are prepared by using fresh water. If seawater or brackish water is used in order to prepare the growth medium for the cyanobacteria, it also might be possible to switch to $Co^{2+}$ or $Ni^{2+}$ inducible promoters because $Co^{2+}$ or $Ni^{2+}$ are not present in seawater or brackish water to the same extent as $Zn^{2+}$. Alternatively, one could add EDTA or another chelating agent of a certain amount (e.g. 10 μM-30 μM) depending from the natural $Zn^{2+}$ content of the used sea water to marine BG11 medium (mBG11) in order to tighten the $Zn^{2+}$ inducible promoter.

The recipe for the cyanobacterial growth medium BG11 is as follows:

a. $NaNO_3$: 1.5 g
b. $K_2HPO_4$: 0.04 g
c. $MgSO_4.7H_2O$: 0.075 g
d. $CaCl_2.2H_2O$: 0.036 g
e. Citric acid: 0.006 g
f. Ferric ammonium citrate: 0.006 g
g. EDTA (disodium salt): 0.001 g
h. $NaCO_3$: 0.02 g
i. Trace metal mix A5_1.0 ml
j. Agar (if needed): 10.0 g
k. Distilled water: 1.0 L l. The pH should be 7.1 after sterilization
m. Trace metal mix A5:
n. $H_3BO_3$: 2.86 g
o. $MnCl_2.4H_2O$: 1.81 g
p. *$ZnSO_4.7H_2O$: 0.222 g
q. $NaMoO_4.2H_2O$: 0.39 g
r. $CuSO_4.5H_2O$: 0.079 g
s. *Co $(NO_3)_2.6H_2O$: 49.4 mg Distilled water or seawater (35 practical salinity units=psu; see Unesco (1981a). The Practical Salinity Scale 1978 and the International Equation of State of Seawater 1980. *Tech. Pap. Mar. Sci.,* 36: 25 pp.)

The asterisk (*) denotes those metal supplements that can be either omitted or used in reduced amounts if these metals are also used as inductor for corresponding metal-inducible promoters in the metabolically enhanced cyanobacterial strain.

Genetically enhanced cyanobacteria according to some other embodiments of the present invention can also include another production pathway for a second chemical compound so that these cyanobacteria produce the first and the second chemical compound. The second chemical compound differs from the first chemical compound and can also be selected from the above mentioned chemicals.

If ethanol is produced as the first chemical compound, the first biocatalyst catalyzing metabolic reaction not present in the cyanobacterium can be pyruvate decarboxylase, which is not present in wild type cyanobacteria. In contrast to that, most wild type cyanobacteria are known to harbor alcohol dehydrogenases. Therefore, the introduction of additional recombinant copies of alcohol dehydrogenases into cyanobacteria is believed to influence the metabolism of the cyanobacterium to a lower extent in the absence of pyruvate decarboxylase enzyme compared to the expression of pyruvate decarboxylase.

In order to better control the metabolic flux of the genetically enhanced cyanobacterium only the first biocatalyst encoded by the first recombinant gene catalyzing a chemical reaction not present in the wild type cyanobacterium and further diverting the carbon flux away from the naturally occurring metabolism, is put under the control of the cobalt or zinc inducible promoters in a further embodiment of the invention. A chemical reaction diverts the carbon flux away from the wild type metabolism of a cyanobacterium, if it uses an intermediate of the natural occurring metabolism and converts this intermediate into a compound, which is not produced in the wild type cyanobacterium. For example, the Pdc enzyme catalyzes the conversion of pyruvate into acetaldehyde, an intermediate which is normally not produced by cyanobacteria because cyanobacteria lack the Pdc enzyme. In this case the metabolic reaction directing the metabolic flux away from the wild type cyanobacterial metabolism can be tightly controlled by these promoters.

In contrast to the biocatalysts diverting the carbon flux away from the wild type metabolism of a cyanobacterium, other biocatalysts can catalyze a reaction which is either already present in the wild type cyanobacterium and therefore only enhances a metabolic flux already present in the wild type cyanobacterium or may catalyze a reaction not present in the wild-type cyanobacterium, which does not use an intermediate of the naturally occurring metabolism of the wild type cyanobacterium and therefore does not affect the wild type metabolism to a great extent as long as the chemical reaction is not connected to the wild type metabolism of the cyanobacterium. These biocatalysts do not need to be as tightly controlled as the above mentioned biocatalysts diverting the carbon flux away from the wild type metabolism of a cyanobacterium and can therefore be put under the transcriptional control of either less tightly inducible promoters or even under the control of constitutive promoters.

Recombinant genes, which encode biocatalysts such as enzymes which catalyze metabolic reactions already present in the wild type cyanobacterium can be put under the control of promoters different from the cobalt or zinc inducible promoters, for example constitutive promoters such as Prbc promoter. This promoter controls the transcription of the rbcLXS operon encoding the ribulose biphosphate carboxylase/oxygenase (rbcL: slr0009 rbcX: slr0011 and rbcS: slr0012 from *Synechocystis* PCC6803), which is a constitutive and strong promoter under light conditions.

Alternatively, both the at least one first and at least one second recombinant gene are under the control of the cobalt or zinc-inducible promoter. In this case large parts or the complete recombinant metabolic pathway introduced into the genetically enhanced cyanobacterium for the production of the first chemical compound can be induced upon induction with cobalt or zinc and are silent in the absence of these metal ions.

According to a further embodiment of the invention, the genetically enhanced cyanobacteria can further comprise a recombinant first control gene encoding a transcription factor such as a repressor or a transcription initiator binding to the cobalt or zinc-inducible promoter.

In the case that the recombinant cobalt or zinc-inducible promoter controlling the transcription of the first and/or second recombinant gene are endogenous to the wild type cyanobacterium, the additional introduction of the transcription factor binding to the cobalt or zinc-inducible promoter can greatly enhance the tightness of the cobalt or zinc-inducible promoter in the uninduced state in comparison to genetically enhanced cyanobacteria which lack the first control gene.

In the case that the cobalt or zinc-inducible promoters are heterologous to the genetically enhanced cyanobacterium, it is necessary to introduce the first control gene into the cyanobacterium, in order to ensure that the heterologous cobalt or zinc-inducible promoter can be tightly controlled during the uninduced state.

If only the cobalt or zinc-inducible promoters are recombinantly introduced into a cyanobacterium as heterologous genes without the respective first control genes, these promoters are often constitutive promoters in these cyanobacteria in the case that the respective first control gene codes for a repressor protein binding to the promoter in the uninduced state. In the case that the first control gene is an activator protein, which binds to the respective promoter in the induced state and promotes binding of RNA polymerase to initiate transcription, these promoters would not be functional without the activator protein.

Different combinations of the zinc or cobalt inducible promoter and the first control gene coding for the transcription factor binding to the promoter are possible. For example if the zinc inducible promoter is PziaA then the first control gene is the gene ziaR (sll0792) coding for the repressor (NP_442635.1). The gene ziaA (slr0798) codes for a zinc transporting ATPase ZiaA (NP_442636.1) which can transport zinc ions out of the intracellular space of *Synechocystis* sp. PCC 6803. The gene coding for ZiaA is under the transcriptional control of the promoter PziaA which in turn is controlled by the repressor coded by the gene ziaR (sll0792), which in the uninduced state blocks or hinders transcription of ziaA. Upon induction with $Zn^{2+}$ the repressor is released from PziaA so that transcription will be greatly enhanced compared to the uninduced state. The nucleotide sequence of PziaA and ziaR are shown with SEQ ID No. 1 in the sequence listing. The gene encoding the regulator ziaR runs in anti-sense direction to PziaA wherein the ziaR stop codon is tta of nucleotides 11 to 13 and the ziaR start codon is cat of the nucleotides 407 to 409.

Another possibility is to use the promoter PsmtA which is endogenous to *Synechococcus* PCC 7942 and *Synechococcus* PCC 7002. The gene smtA (SYNPCC7002_2563) which is transcriptionally controlled by this promoter codes for a metallothionein (YP_001735795.1) involved in resistance to inter alia zinc. A repressor protein (YP_001735796.1) binds to the PsmtA in the uninduced state which is encoded by the gene smtB (SYNPCC7002_A2564). The nucleotide sequence of PsmtA and smtB are shown with SEQ ID No. 2 in the sequence listing. The gene encoding the regulator smtB runs in anti-sense direction to PsmtA wherein the smtB stop codon is tta of nucleotides 67 to 69 and the smtB start codon is cat of the nucleotides 391 to 393.

In *Anabaena* PCC 7120 the gene aztA (alr7622) codes for a $Zn^{2+}$, $Cd^{2+}$ and $Pb^{2+}$ transporting ATPase (NP_478269.1) which is transcriptionally controlled by the promoter PaztA. The promoter is blocked in the uninduced state by a repressor protein (NP_478268.1) coded by the gene aztR (all7621). The nucleotide sequence of PaztA and aztR are shown with SEQ ID No. 3 in the sequence listing. The gene encoding the regulator aztR runs in anti-sense direction to PaztA wherein the aztR stop codon is tca of nucleotides 98 to 100 and the aztR start codon is cat of the nucleotides 506 to 508.

In *Synechocystis* PCC 6803 the gene corT (slr0797) can be found coding for a cobalt transporting ATPase (NP_442633.1). This gene is transcriptionally controlled by the promoter PcorT, which is transcriptionally controlled by a regulator protein (NP_442632.1) coded by the gene corR (sll0794), which binds to the corT promoter. The nucleotide sequence of PcorT and corR are shown with SEQ ID No. 4 in the sequence listing. The gene encoding the regulator corR runs in anti-sense direction to PcorT wherein the corR stop codon is cta of nucleotides 55 to 57 and the corR start codon is cat of the nucleotides 1165 to 1167. The promoter PcorT is one example for a cobalt inducible promoter, whereas the other already mentioned promoters PziaA, PsmtA, and PaztA are examples for zinc inducible promoters.

A further zinc inducible promoter is for example Pbxa1 which controls the bxa1 gene encoding a heavy metal-translocating P-type ATPase (BAC10634.1) found in *Oscillatoria brevis* which is controlled by the repressor protein BxmR (BAD11074.1). This repressor also controls another zinc inducible promoter PbmtA which controls the bmtA gene coding for a metallothionein (BAC76027.1) that is also endogenous to *Oscillatoria brevis*. Another example is the zinc inducible promoter PzntA which controls the zntA gene encoding a cation-transporting ATPase (ZP_06379975.1) that can be found in *Staphylococcus aureus* which is controlled by a repressor protein (YP_041645.1) coded by the gene zntR.

The above described promoter/regulator combinations are non-limiting examples of zinc or cobalt inducible promoters which can be used in variants of the invention. Other zinc or cobalt inducible promoters, which can be endogenous to cyanobacteria or to other bacterial or non-bacterial species can also be used in the present invention.

Furthermore it has to be noted that the above-mentioned zinc or cobalt inducible promoters often can also be induced by a large variety of other metal ions such as $Cd^{2+}$, $Ag^{+}$, $Pb^{2+}$ or for example $Cu^{2+}$ ions.

According to a further variant of the invention, the cyanobacterium further comprises an endogenous gene coding for a cobalt or zinc-transporting protein or a zinc-binding metallothionein, which is under the transcriptional control of an endogenous cobalt or zinc-inducible promoter, wherein said endogenous cobalt or zinc-inducible promoter harbors an inactivation.

Cyanobacterial cells often harbor cobalt or zinc-transporting proteins which are under the control of endogenous cobalt or zinc-inducible promoters in order to confer a resistance to high cobalt or zinc concentrations within the cell. These cobalt or zinc-transporting proteins can, for example, be ATPases which actively transport cobalt or zinc ions out of the cell into the growth medium while consuming ATP, if the expression of these ATPases is induced by certain amounts or $Zn^{2+}$ or $Co^{2+}$. This transport mechanism, however, can greatly interfere with the cobalt or zinc induction of the first and/or second recombinant gene. In order to eliminate the impact of the endogenous cobalt and zinc-transporting protein on the intracellular concentration of these ions, an inactivation in the endogenous cobalt or zinc inducible promoter can ensure that the expression of the cobalt and zinc-transporting protein is not increased in the case of high levels of zinc or cobalt in the growth medium.

This inactivation can, for example, be a complete deletion of the cobalt or zinc-inducible promoter or can include mutations in the promoter region leading to an inactivation of this region. According to another possibility, the endogenous cobalt or zinc-inducible promoter can be replaced by another promoter, which can either be constitutive or inducible and which is not sensitive to cobalt or zinc so that it is inducible under different conditions than the recombinant cobalt or zinc-inducible promoter.

In addition the endogenous gene coding for the cobalt or zinc-transporting protein can also harbor an inactivation or can also be completely deleted, thereby ensuring that the transport of the cobalt and zinc ions out of the cyanobacterial cells does not take place via the endogenous ATPases to a great extent. Such a measure can lead to a cobalt or zinc-inducible promoter controlling exclusively the transcription of the first and/or second recombinant genes.

Furthermore in some cyanobacterial species like *Synechococcus* PCC 7002 and PCC 7942 the endogenous gene coding for the zinc-tolerance protein is a metallothionein e.g. SmtA instead of a zinc transporting ATPase. In this case the smtA gene can harbor an inactivation or can also be completely deleted, thereby ensuring that the detoxification by binding of zinc ions which enter the cyanobacterial cells does not take place via the endogenous metallothionein.

According to a further embodiment of the invention, the cyanobacterium harbors an extrachromosomal plasmid including recombinant genes coding for a cobalt or zinc-transporting protein or a zinc-binding metallothionein, wherein this recombinant gene is transcriptionally controlled by either a constitutive promoter or by a promoter which is inducible under different conditions than the recombinant cobalt or zinc-inducible promoter controlling the transcription of the first and/or second recombinant genes for production of the first chemical compound.

Such an extra-chromosomal plasmid can ensure a constant intracellular zinc concentration and can uncouple the function of the zinc or cobalt-transporting protein or the zinc-binding metallothionein from the zinc concentration within the cyanobacterial cell if the endogenous zinc or cobalt-transporting protein or the zinc-binding metallothionein was inactivated via either mutations or a complete deletion.

The zinc or cobalt-transporting protein encoded on the extrachromosomal plasmid can be the same protein, whose endogenous gene was inactivated by the gene inactivation or can be another homologous protein, which catalyzes the same reaction as the endogenous protein, which was inactivated. The zinc or cobalt-tolerance conferring protein encoded on the extrachromosomal plasmid can be also an analogous protein, for instance a metallothionein (encoded by smtA gene) that confers zinc tolerance to the host cell due its ability to sequester zinc ions.

According to another embodiment of the present invention, this extra-chromosomal plasmid can also harbor the at least first, and—if present—also second recombinant genes for production of the first chemical compound. In this case the genes for production of the first chemical compound are also included on this extrachromosomal plasmid along with the recombinant gene coding for the cobalt or zinc-transporting protein or the zinc-binding metallothionein. During the induced state of the genetically enhanced cyanobacteria, a high intracellular concentration of $Co^{2+}$ and $Zn^{2+}$ ions are present so that a certain level of zinc or cobalt tolerance conferred by the cobalt or zinc-transporting protein or the zinc-binding metallothionein encoded on this extra-chromosomal plasmid can ensure a constant concentration of these ions within the cyanobacteria on the one hand, and on the other hand also can increase the genetic stability of the extra-chromosomal plasmid. Since this plasmid also includes the first and second recombinant genes for the production of the first chemical compound, it is believed that this measure can also lead to a higher genetic stability of the genes or the genetic construct involved in the production of the first chemical compound. For example, owing to such an extra-chromosomal plasmid, it can be possible to run long-term cultures of more than 30 days or even longer without accumulating inactivating mutations in the first and/or second genes to a great extent.

According to another embodiment of the invention, the at least one first recombinant gene for the production of the first chemical compound can also be integrated into an endogenous plasmid of the genetically enhanced cyanobacterial cell. For example it is known that the cyanobacterium *Synechococcus* PCC 7002 contains six endogenous plasmids having different numbers of copy in the cyanobacterial cell (Xu et al.: "Expression of genes in cyanobacteria: Adaption of Endogenous Plasmids as platforms for High-Level gene Expression in *Synechococcus* PCC 7002", Photosynthesis Research Protocols, Methods in Molecular Biology, 684, pages 273 to 293 (2011)). The endogenous plasmid pAQ1 is present in a number of 50 copies per cell (high-copy), the plasmid pAQ3 with 27 copies, the plasmid pAQ4 with 15 copies and the plasmid pAQ5 with 10 copies per cell (low-copy) whereas the chromosome has 6 copies per cell. A great advantage of incorporating the at least one first recombinant gene for producing the first chemical compound into endogenous extrachromosomal plasmids of the cyanobacterium is that by the choice of the endogenous plasmid used for integration, the number of copies of these genes in the cyanobacterium can easily be controlled, depending on the copy number of the specific endogenous plasmid that is used for that purpose in the cyanobacterium. For example, a higher number of copies of the at least one first recombinant gene can be achieved via integration into the plasmid pAQ3 in comparison to integration into the plasmid pAQ4 with a lower number of copies in the cell. Additionally, there could be the positive effect of higher transcription efficiency if the at least one first recombinant gene is encoded on a plasmid in comparison to the chromosome (due to position effects or different condensation levels of the extrachromosomal DNA versus the chromosomal DNA). This could lead to higher expression levels if encoded on the plasmid in comparison to the chromosome even if the copy number and gene dosage, respectively is the same.

In the case that the first chemical compound is ethanol and the genetically enhanced cyanobacterial cell is *Synechococcus*, for example *Synechococcus* PCC7002, the first and second recombinant genes coding for Pdc enzyme and Adh enzyme can be integrated into an endogenous plasmid selected from a group consisting of pAQ1, pAQ3, pAQ4, and pAQ5 or combinations thereof.

According to one embodiment of the invention the inducible promoter is a zinc-inducible promoter, for example the promoter PziaA from *Synechocystis*, in particular *Synechocystis* PCC 6803. The zinc-inducible promoter according to a further variant of the invention can have at least 70% sequence identity to the more generalized nucleotide sequence of the ziaA promoter, which is the sequence (SEQ ID NO. 5):

$(N)_{11}$AATATCTGAGCATATCTTCAGGTGTT$(N)_{13}$TACGGT$(N)_6$A$(N)_{16}$ACGTTGGCCGCCATG, wherein each of the nucleotides N is independently selected from a group consisting of A, T, C and G and wherein the 3'-ATG is the start codon for the first recombinant gene transcriptionally controlled by this promoter.

The variable nucleotides N span different important, more or less conserved regions of the promoter, the operator with the sequence of AATATCTGAGCATATCTTCAGGTGTT (SEQ ID NO. 93) in the wild-type ziaA promoter, the TATA box (−10 region) having in the wild type PziaA the sequence TACGGT, and the ribosomal binding side (RBS) having in the wild type ziaA promoter the sequence CGTTGG.

Another object of the present invention is the improvement of the different cobalt or zinc-inducible promoters via the introduction of point mutations into the various functional promoter regions, in particular the operator, the TATA box, the 5'-UTR (untranslated region), and the ribosomal binding side.

The inventors found out that modifications in the TATA box lead to a greater activity of the promoter in the induced but also in the uninduced state. Modifications in the operator region lead to a greater tightness of the promoter in the uninduced state but also can reduce the expression of the controlled genes in the induced state to some extent. Modifications in the ribosomal binding site lead to a slightly higher protein expression in the induced and also uninduced state. The inventors tested the following variants of PziaA:

(SEQ ID NO. 6)
$N_{11}$AATATCTGAGCATATCTTCAGGTGTT$N_{13}$TATAAT$N_6$A$N_{17}$CGTTGGCCGCCATG i. (SEQ ID NO: 7)
$N_{11}$AATATCTGAGCATATCTTCAGGTGTT$N_{13}$TACGGT$N_6$A$N_{17}$AGGAGGCCGCCATG, ii. (SEQ ID NO. 8)
$N_{11}$AACATCTGAACATATCTTCAGATGTT$N_{13}$TACGGT$N_6$A$N_{17}$CGTTGGCCGCCATG iii. (SEQ ID NO. 9)
$N_{11}$AATATCTGAGCATATCTTCAGGTGTT$N_{13}$TATAAT$N_6$A$N_{17}$AGGAGGCCGCCATG iv. (SEQ ID NO. 10)
$N_{11}$AACATCTGAACATATCTTCAGATGTT$N_{13}$TATAAT$N_6$A$N_{17}$CGTTGGCCGCCATG v. (SEQ ID NO. 11)
$N_{11}$AACATCTGAACATATCTTCAGATGTT$N_{13}$TACGGT$N_6$A$N_{17}$AGGAGGCCGCCATG vi. (SEQ ID NO. 12)
$N_{11}$AACATCTGAACATATCTTCAGATGTT$N_{13}$TATAAT$N_6$A$N_{17}$AGGAGGCCGCCATG vii. (SEQ ID NO. 13)
$N_{11}$AATATCTGAGCATATCTTCAGGTGTT$N_{13}$TATGGT$N_6$A$N_{17}$CGTTGGCCGCCATG viii. (SEQ ID NO. 14)
$N_{11}$AATATCTGAGCATATCTTCAGGTGTT$N_{13}$TACAGT$N_6$A$N_{17}$CGTTGGCCGCCATG ix. (SEQ ID NO. 15)
$N_{11}$AATATCTGAGCATATCTTCAGGTGTT$N_{13}$TACGAT$N_6$N$A_{17}$CGTTGGCCGCCATG x. (SEQ ID NO. 16)
$N_{11}$AATATCTGAGCATATCTTCAGGTGTT$N_{13}$TATAGT$N_6$A$N_{17}$CGTTGGCCGCCATG xi. (SEQ ID NO. 17)
$N_{11}$AATATCTGAGCATATCTTCAGGTGTT$N_{13}$TACAAT$N_6$A$N_{17}$CGTTGGCCGCCATG xii. (SEQ ID NO. 18)
$N_{11}$AATATCTGAGCATATCTTCAGGTGTT$N_{13}$TATGAT$N_6$A$N_{17}$CGTTGGCCGCCATG xiii. (SEQ ID NO. 19)
$N_{11}$AACATCTGAACATATCTTCAGATGTT$N_{13}$TATGGT$N_6$A$N_{17}$CGTTGGCCGCCATG xiv. (SEQ ID NO. 20)
$N_{11}$AACATCTGAACATATCTTCAGATGTT$N_{13}$TACAGT$N_6$A$N_{17}$CGTTGGCCGCCATG xv. (SEQ ID NO. 21)
$N_{11}$AACATCTGAACATATCTTCAGATGTT$N_{13}$TACGAT$N_6$A$N_{17}$CGTTGGCCGCCATG -continued xvi. (SEQ ID NO. 22)
$N_{11}$AACATCTGAACATATCTTCAGATGTT$N_{13}$TATAGT$N_6$A$N_{17}$CGTTGGCCGCCATG xvii. (SEQ ID NO. 23)
$N_{11}$AACATCTGAACATATCTTCAGATGTT$N_{13}$TACAAT$N_6$A$N_{17}$CGTTGGCCGCCATG xviii. (SEQ ID NO. 24)
$N_{11}$AACATCTGAACATATCTTCAGATGTT$N_{13}$TATGAT$N_6$A$N_{17}$CGTTGGCCGCCATG xix. (SEQ ID NO. 25)
$N_{11}$AACATCTGAACATATCTTCAGATGTT$N_{13}$TATGGT$N_6$A$N_{17}$AGGAGGCCGCCATG xx. (SEQ ID NO. 26)
$N_{11}$AACATCTGAACATATCTTCAGATGTT$N_{13}$TACAGT$N_6$A$N_{17}$AGGAGGCCGCCATG xxi. (SEQ ID NO. 27)
$N_{11}$AACATCTGAACATATCTTCAGATGTT$N_{13}$TACGAT$N_6$A$N_{17}$AGGAGGCCGCCATG xxii. (SEQ ID NO. 28)
$N_{11}$AACATCTGAACATATCTTCAGATGTT$N_{13}$TATAGT$N_6$A$N_{17}$AGGAGGCCGCCATG xxiii. (SEQ ID NO. 29)
$N_{11}$AACATCTGAACATATCTTCAGATGTT$N_{13}$TACAAT$N_6$A$N_{17}$AGGAGGCCGCCATG xxiv. (SEQ ID NO. 30)
$N_{11}$AACATCTGAACATATCTTCAGATGTT$N_{13}$TATGAT$N_6$A$N_{17}$AGGAGGCCGCCATG wherein the boldfaced and underlined nucleotides denote mutations in comparison to the wild-type PziaA.

The above-mentioned promoter sequences are all variants of the native ziaA promoter. In these variants modifications were introduced either only in the operator sequence, only the TATA box or only the ribosomal binding sides or in different combinations of these important regions. In addition the numbers of generalized nucleotides N which are located between the different important regions can also vary. The later mentioned PziaA variants Pzia*4 and PziaA*6 show a higher induction rate compared to PziaA*. Furthermore the above-mentioned promoter variants were tested either in the presence or the absence of the repressor gene ziaR on the extrachromosomal plasmid along with the recombinant genes coding for Pdc and Adh.

According to one embodiment of the invention the inducible promoter is a cobalt-inducible promoter, for example the promoter PcorT from *Synechocystis*, in particular *Synechocystis* PCC 6803. The cobalt-inducible promoter according to a further variant of the invention can have at least 70% sequence identity to the more generalized nucleotide sequence of the corT promoter, which is the sequence (SEQ ID NO. 31):

CAT(N)$_7$GTTTACTCAAAACCTTGACATTGACACTAATGTTAA

GGTTTAGGCT(N)$_{15}$CAAGTTAAAAAGCATG wherein each of the nucleotides N is independently selected from a group consisting of A, T, C and G and wherein the 5'-CAT is the start codon (antisense) of the transcriptional regulator corR (in antisense orientation regarding the corT promoter) and wherein the 3'-ATG is the start codon for the first recombinant gene transcriptionally controlled by this promoter.

The variable nucleotides N span different important, more or less conserved regions of the promoter (see above SEQ ID NO. 31), the operator with the sequence of AACCTTGACATTGACACTAATGTTAAGGTT (SEQ ID NO. 94) in the wild-type corT promoter, the TATA box (−10 region) having in the wild type PcorT the sequence TAGGCT, and the ribosomal binding side (RBS) having in the wild type corT promoter the sequence CAAGTT.

Another object of the present invention is the improvement of the cobalt inducible promoter corT via the introduction of point mutations into the various functional promoter regions, in particular the operator, the TATA box and the ribosomal binding side. The inventors expect to obtain similar effects as already identified for the PziaA variants. The following variants of PcorT will be or have been tested:

(SEQ ID NO. 32)
CAT(N)$_{7}$GTTTACTCAAAACCTTGACATTGACACTAA
TGTTAAGGTTTAGAAT(N)$_{15}$CAAGTTAAAAAGCATG (SEQ ID NO. 33)
CAT(N)$_{7}$GTTTACTCAAAACCTTGACATTGACACTAA
TGTTAAGGTTTAGGAT(N)$_{15}$CAAGTTAAAAAGCATG (SEQ ID NO. 34)
CAT(N)$_{7}$GTTTACTCAAAACCTTGACATTGACACTAA
TGTTAAGGTTTAGACT(N)$_{15}$CAAGTTAAAAAGCATG (SEQ ID NO. 35)
CAT(N)$_{7}$GTTTACTCAAAACCTTGACATTGACACTAA
TGTTAAGGTTTAGGCT(N)$_{15}$GAGGATAAAAAGCATG (SEQ ID NO. 36)
CAT(N)$_{7}$GTTTACTCAAAACCTTGACATTGACACTAA
TGTTAAGGTTTAGGAT(N)$_{15}$GAGGATAAAAAGCATG (SEQ ID NO. 37)
CAT(N)$_{7}$GTTTACTCAAAACCTTGACATTGACACTAA
TGTTAAGGTTTAGACT(N)$_{15}$GAGGATAAAAAGCATG (SEQ ID NO. 38)
CAT(N)$_{7}$GTTTACTCAAAACCTTGACATTGACACTAA
TGTCAAGGTTTAGAAT(N)$_{15}$CAAGTTAAAAAGCATG (SEQ ID NO. 39)
CAT(N)$_{7}$GTTTACTCAAAACCTTGACATTGACACTAA
TGTCAAGGTTTAGGAT(N)$_{15}$CAAGTTAAAAAGCATG (SEQ ID NO. 40)
CAT(N)$_{7}$GTTTACTCAAAACCTTGACATTGACACTAA
TGTCAAGGTTTAGACT(N)$_{15}$CAAGTTAAAAAGCATG (SEQ ID NO. 41)
CAT(N)$_{7}$GTTTACTCAAAACCTTGACATTGACACTAA
TGTCAAGGTTTAGGCT(N)$_{15}$GAGGATAAAAAGCATG (SEQ ID NO. 42)
CAT(N)$_{7}$GTTTACTCAAAACCTTGACATTGACACTAA
TGTCAAGGTTTAGGAT(N)$_{15}$GAGGATAAAAAGCATG (SEQ ID NO. 43)
CAT(N)$_{7}$GTTTACTCAAAACCTTGACATTGACACTAA
TGTCAAGGTTTAGACT(N)$_{15}$GAGGATAAAAAGCATG

According to another embodiment of the invention the inducible promoter is a zinc-inducible promoter, for example the promoter PaztA from *Anabaena*, in particular *Anabaena* PCC 7120. The zinc-inducible promoter according to a further variant of the invention can have at least 70% sequence identity to the more generalized nucleotide sequence of the aztA promoter, which is the sequence (SEQ ID NO. 44):

(N)$_{12}$TGTACAATTGAATAGTTGTTCAATTGTTGTATTAGAAT(N)$_{5}$C (N)$_{17}$AATTCTAAAGCTGCTATG wherein each of the nucleotides N is independently selected from a group consisting of A, T, C and G and wherein the 3'-ATG is the start codon for the first recombinant gene transcriptionally controlled by this promoter.

The variable nucleotides N span different important, more or less conserved regions of the promoter, the operator with the sequence of ACAATTGAATAGTTGTTCAATTGT (SEQ ID NO. 95) in the wild-type aztA promoter, the TATA box (−10 region) having in the wild type PaztA the sequence TAGAAT, and the ribosomal binding side (RBS) having in the wild type aztA promoter the sequence ATTCTA (see above SEQ ID NO. 44).

Another object of the present invention is the improvement of the zinc inducible promoter from *Anabaena* PCC7120 PaztA via the introduction of point mutations into the various functional promoter regions, in particular the operator, the TATA box and the ribosomal binding side as it was already realized and tested for the zinc inducible promoter PziaA from *Synechocystis* PCC6803. The inventors expect to obtain similar effects as identified for the PziaA variants.

Alternatively or in addition to changing the nucleotide sequence of the $Zn^{2+}$ or $Co^{2+}$ inducible promoters, it is also possible to change the activity of the promoters by changing the expression level of the transcriptions factors controlling the $Zn^{2+}$ or $Co^{2+}$ inducible promoters. This can be done by changing the first control gene promoter sequences transcriptionally controlling the first and—if present—second control gene encoding the above mentioned transcription factors. In the case of PziaA, the promoter PziaR controlling the transcription of the gene encoding the repressor ziaR can be changed according to the same principles as laid out for the modifications in PziaA, i.e. nucleotide changes can be introduced into the TATA box and/or the RBS.

In the case that the first control gene encodes a repressor protein binding to the $Zn^{2+}$ or $Co^{2+}$ inducible promoter in their repressed states, such as ziaR, smtB and aztR, an increase in the expression of the repressors will lead to a greater tightness of the $Zn^{2+}$ or $Co^{2+}$ inducible promoters in the repressed state. If however the first control genes are activator proteins binding to the $Zn^{2+}$ or $Co^{2+}$ or $Ni^{2+}$ inducible promoters upon induction, a higher expression level of these activator proteins will lead to a higher expression of the recombinant genes controlled by these $Zn^{2+}$, $Co^{2+}$ or $Ni^{2+}$ inducible promoters in the induced state. One example would be the nrsB promoter which is positively controlled by the genes nrsR and nrsS encoding activator proteins binding the $Ni^{2+}$-inducible promoter.

A further aspect of the present invention is directed to a genetically enhanced cyanobacterium for the production of ethanol, comprising:

a first recombinant gene coding for a first biocatalyst for the production of ethanol, wherein the gene is under the transcriptional control of a $Ni^{2+}$ inducible promoter.

Similarly to the cobalt and zinc inducible promoters, also the nickel inducible promoter can be very tight in the uninduced state so that uninduced cyanobacterial cultures can easily accumulate biomass without producing ethanol. As mentioned above already, in the context of cobalt and zinc inducible promoters, the tightness of the $Ni^{2+}$ induced promoter in the uninduced state might also reduce the number of contaminants present in the culture which could overgrow the genetically enhanced cyanobacteria and can also reduce the genetic instability of the first recombinant gene thereby reducing the frequency and accumulation of inactivating mutations in this gene.

According to a further variant of this aspect of the invention, the $Ni^{2+}$ inducible promoter can be selected from PnrsB which is endogenous to *Synechocystis* PCC 6803. The gene nrsB (slr0793) which is transcriptionally controlled by this promoter encodes a protein which is part of a nickel resistance system including four proteins. The transcription of this gene as well as of the other genes nrsACD are controlled by a two component signal transduction system composed of a Ni(II)-sensor histidine kinase coded by the gene nrsS (sll0798) and a Ni(II)-responsive transcriptional activator protein coded by the gene nrsR (sll0797). Therefore as already mentioned above in the context of the cobalt and zinc inducible promoters the first control gene, which codes for a transcriptional regulator binding to the $Ni^{2+}$ inducible promoter can be nrsR and the second control gene, which codes for a Ni(II)-sensor histidine kinase that activates the transcriptional regulator can be nrsS (sll0798) in the case that the nickel inducible promoter is PnrsB. The nucleotide sequences of PnrsB, nrsS and nrsR are shown with SEQ ID No. 45 in the sequence listing. The gene encoding the regulator nrsS runs in anti-sense direction to PnrsB wherein the nrsS stop codon is tta of nucleotides 115 to 117 and the nrsS start codon is cat of the nucleotides 1477 to 1479. The gene encoding the regulator nrsR runs in anti-sense direction to PnrsB wherein the nrsR stop codon is tca of nucleotides 1476 to 1478 and the nrsR start codon is cat of the nucleotides 2178 to 2180.

Another object of the present invention is the improvement of the nickel-inducible promoter via the introduction of point mutations into the various functional promoter regions, in particular the operator, the TATA box, the 5'-UTR (untranslated region), and the ribosomal binding side.

According to one embodiment of the invention the inducible promoter is a nickel-inducible promoter, for example the promoter PnrsB from *Synechocystis*, in particular *Synechocystis* PCC 6803. The nickel-inducible promoter according to a further variant of the invention can have at least 70% sequence identity to the more generalized nucleotide sequence of the nrsB promoter, which is the sequence (SEQ ID NO. 46):

$(N)_{14}$GAGATTTTCACCTGAATTTCATACCCCCTTTGGCAGACTGGGAAA $(N)_{20}$TTGAGGTGGTGTGATG wherein each of the nucleotides N is independently selected from a group consisting of A, T, C and G and wherein the 3'ATG is the start codon for the first recombinant gene transcriptionally controlled by this promoter.

The variable nucleotides N span different important, more or less conserved regions of the promoter, the operator with the sequence of GATTTTCACCTGAATTTCA (SEQ ID NO. 96) in the wild-type nrsB promoter, the TATA box (−10 region) having in the wild type PnrsB the sequence CAGACT, and the ribosomal binding side (RBS) having in the wild type nrsB promoter the sequence TTGAGG (see above SEQ ID NO. 46).

The genetically enhanced cyanobacterium comprising the $Ni^{2+}$ inducible promoter can also further comprise at least a second recombinant gene encoding a second biocatalyst for the production of ethanol. As already mentioned above the first biocatalyst can produce an intermediate which is further converted by the second biocatalyst to ethanol. As already mentioned above the first recombinant gene can be pdc, whereas the second recombinant gene can be various alcohol dehydrogenase genes. In addition or alternatively, only one first recombinant gene might be necessary in order to produce ethanol in cyanobacteria, for example coding for the AdhE which directly converts acetyl coenzyme A to ethanol.

Another aspect of the present invention is directed to a method for producing a first chemical compound comprising the following method steps:

Culturing the genetically cyanobacteria which were already mentioned above in a culture medium, inducing the cyanobacteria by adding $Zn^{2+}$, $Co^{2+}$ or $Ni^{2+}$ salts to the culture medium, the cyanobacteria producing the first chemical compound.

Due to the tightness of the $Zn^{2+}$, $Co^{2+}$ or $Ni^{2+}$ inducible promoters, the cyanobacteria can grow very fast to a high density during method step A) in the uninduced state, so that after induction in method step B) a high production rate for the first chemical compound can be observed.

In method step B) the cyanobacteria can for example be induced by adding at least 2 μM $Zn^{2+}$, $Co^{2+}$ or $Ni^{2+}$ to the growth medium. The concentrations of these salts in the growth medium for induction of the promoters can be 5 μM, preferably at least 10 μM most preferred at least 15 μM or can be in the range of 3 μM to 20 μM depending on the cyanobacterial strain, the promoter and the metal ion used. For example in *Synechocystis* PCC 6803 the promoter/regulator pair ziaR-PziaA can be induced by addition of 10-20 μM $Zn^{2+}$, in *Synechocystis* the promoter/regulator pair corR-PcorT can be induced by addition of 5-15 μM $Co^{2+}$, and the promoter/regulator pair nrsR-PnrsB can be induced upon addition of 5-10 μM in *Synechocystis*. The promoter/regulator pair aztR-PaztA can be activated by adding 15-20 μM $Zn^{2+}$. In *Synechococcus* PCC 7002 smtB-PsmtA is induced by 3-10 μM $Zn^{2+}$ and corR-PcorT by adding 5-15 μM $Co^{2+}$. However the optimal induction is also depending on the cell density ($OD_{750\ nm}$), the growth phase and the net carbon assimilation, but can easily be determined by a person of ordinary skill in the art based on the technical teaching of the present invention.

Furthermore, in case that natural seawater or any other aqueous salty media such as brackish water, which already contain significant amounts of trace metals like $Zn^{2+}$, $Co^{2+}$ and $Ni^{2+}$ are used the addition of at least one chemical compound able to chelate bivalent metal ions, for example EDTA (Ethylenediaminetetraacetic acid), EGTA (ethylene glycol tetraacetic acid), DTPA (diethylene triamine pentaacetic acid) or citrate or combinations thereof, can further tighten the metal-ion inducible promoter and assures to prevent premature induction of the production of the first chemical compound such as ethanol during the scale-up. For example 30 μM EDTA can be added to the mBG11 medium.

DEFINITIONS AND GENERAL EXPLANATIONS

Database entry numbers given in the following are from the NCBI database (National Center for Biotechnology Information; available on the world wide web at ncbi.nlm.nih.gov) or from the CyanoBase, the genome database for cyanobacteria ((bacteria.kazusa.or.jp/cyanobase/index.html); Yazukazu et al. "CyanoBase, the genome database for *Synechocystis* sp. Strain PCC6803: status for the year 2000", Nucleic Acid Research, 2000, Vol. 18, page 72).

The EC numbers cited throughout this patent application are enzyme commission numbers which is a numerical classification scheme for enzymes based on the chemical reactions which are catalyzed by the enzymes.

As used herein, the term "genetically enhanced" refers to any change in the endogenous genome of a wild type cyanobacterial cell or to the addition of endogenous and non-endogenous, exogenous genetic code to a wild type cyanobacterial cell, for example the introduction of a heterologous gene. More specifically, such changes are made by the hand of man through the use of recombinant DNA technology or mutagenesis. The changes can involve protein coding sequences or non-protein coding sequences in the genome such regulatory sequences as non-coding RNA, antisense RNA, promoters or enhancers. Aspects of the invention utilize techniques and methods common to the fields of molecular biology, microbiology and cell culture. Useful laboratory references for these types of methodologies are readily available to those skilled in the art. See, for example, Molecular Cloning: A Laboratory Manual (Third Edition), Sambrook, J., et al. (2001) Cold Spring Harbor Laboratory Press; Current Protocols in Microbiology (2007) Edited by Coico, R., et al., John Wiley and Sons, Inc.; The Molecular Biology of Cyanobacteria (1994) Donald Bryant (Ed.), Springer Netherlands; Handbook Of Microalgal Culture: Biotechnology And Applied Phycology (2003) Richmond, A., (ed.), Blackwell Publishing; and "The cyanobacteria, molecular Biology, Genomics and Evolution", Edited by Antonia Herrero and Enrique Flores, Caister Academic Press, Norfolk, UK, 2008.

It is well known to a person of ordinary skill in the art that large plasmids can be produced using techniques such as the ones described in the U.S. Pat. No. 6,472,184 B1 titled "method for producing nucleic acid polymers" and U.S. Pat. No. 5,750,380 titled "DNA polymerase mediated synthesis of double stranded nucleic acid molecules", which are hereby incorporated in their entirety.

Denominations of genes are in the following presented in a three letter lower case name followed by a capitalized letter if more than one related gene exists, for example ziaA for the gene encoding a $Zn^{2+}$-transporting ATPase. The respective protein encoded by that gene is denominated by the same name with the first letter capitalized, such as ZiaA.

Denominations for promoter sequences, which control the transcription of a certain gene in their natural environment are given by a capitalized letter "P" followed by the gene name according to the above described nomenclature, for example "PziaA" for the promoter controlling the transcription of the ziaA gene.

Denominations for enzyme names can be given in a two or three letter code indicating the origin of the enzyme, followed by the above mentioned three letter code for the enzyme itself, such as SynAdh ($Zn^{2+}$ dependent Alcohol dehydrogenase from *Synechocystis* PCC6803), ZmPdc (pyruvate decarboxylase from *Zymomonas mobilis*).

The term "nucleic acid" is intended to include nucleic acid molecules, such as polynucleotides which include an open reading frame encoding a polypeptide, and can further include non-coding regulatory sequences of genes, such as promoters and enhancers as well as non-coding RNAs. In addition, the terms are intended to include one or more genes that are part of a functional operon. In addition the terms are intended to include a specific gene for a selected purpose. The gene can be endogenous to the host cell or can be recombinantly introduced into the host cell.

In a further aspect, the invention also provides nucleic acids, which are at least 60%, 70%, 80%, 90% or 95% identical to the promoter nucleic acids or to the nucleic acids encoding either the first and second biocatalysts for the production of the first chemical compound disclosed therein. With regard to the promoters, truncated versions of the promoters including only a small portion of the native promoters upstream of the transcription start point, such as the region ranging from −35 to the transcription start can often be used. The invention also provides amino acid sequences for enzymes for the production of first chemical compounds, which are at least 60%, 70%, 80%, 90% or 95% identical to the amino acid sequences disclosed therein.

The percentage of identity of two nucleic acid sequences or two amino acid sequences can be determined using the algorithm of Thompson et al. (Clustal W, 1994 Nucleic Acid Research 22: pages 4,673 to 4,680). A nucleotide sequence or an amino acid sequence can also be used as a so-called "query sequence" to perform a nucleic acid or amino acid sequence search against public nucleic acid or protein sequence databases in order to, for example identify further unknown homologous promoters, or homologous protein sequences and nucleic acid sequences which can also be used in embodiments of this invention. In addition, any nucleic acid sequences or protein sequences disclosed in this patent application can also be used as a "query sequence" in order to identify yet unknown sequences in public databases, which can encode for example new enzymes which could be useful in this invention. Such searches can be performed using the algorithm of Karlin and Altschul (1990 Proceedings of the National Academy of Sciences USA 87: pages 2264 to 2268), modified as in Karlin and Altschul (1993 Proceedings of the National Academy of Sciences USA, 90: pages 5873 to 5877). Such an algorithm is incorporated in the Nblast and Xblast programs of Altschul et al. (1999 Journal of Molecular Biology 215, pages 403 to 410) Suitable parameters for these database searches with these programs are, for example, a score of 100 and a word length of 12 for blast nucleotide searches as performed with the Nblast program. Blast (translated) protein searches are performed with the Xblast program with a score of 50 and a word length of 3. Where gaps exist between two sequences, gapped blast is utilized as described in Altschul et al. (1997 Nucleic Acid Research, 25: pages 3389 to 3402).

The term "genome" refers to the chromosomal genome as well as to extrachromosomal plasmids which are normally present in the wild type cyanobacterium without having performed recombinant DNA technology. For example, cyanobacteria such as *Synechococcus* PCC7002 can include at least up to 6 extrachromosomal plasmids in their wild type form.

The term "uninduced" state in the following refers to a state where only less than or equal to 15%, preferably less than or equal to 10%, most preferred less than or equal to 5% of the first chemical compound per $OD_{750}$ of the cyanobacteria are produced compared to the induced state.

The induction factor is defined as the quotient of the production rate of the first chemical compound per $OD_{750}$ in the induced state divided by the production rate of the first chemical compound per $OD_{750\ nm}$ in the uninduced state during the linear production phase.

In the following certain aspects of the invention will be explained in more detail with reference to experimental data and figures.

BRIEF DESCRIPTION OF THE FIGURES

Plasmid maps shown in the following include restriction sites for the respectively denoted restriction endonucleases. "Gm" denotes a gene conferring resistance to Gentamycin, and "aph (KanR2)" denotes a gene coding for aminoglycoside (3') phosphotransferase conferring resistance to Kanamycin. “Sp/Sm” designates a gene imparting resistance for spectinomycin/streptomycin and “Cm” depicts a gene conferring resistance to Chloramphenicol.

In general, plasmids were generated by inserting DNA constructs containing the promoters and the first and second recombinant genes into the plasmids pVZ322A and pVZ325A via a multiple cloning site using a SalI/SbfI restriction endonuclease digest.

FIGS. 2A and 2B show the sequences of the primers used to create constructs with the PziaA, ziaR-PziaA DNA sequences and the nucleotide sequence of ziaR-PziaA (see also SEQ ID No. 1). The nucleotide sequences of these primers are listed as SEQ ID NO. 49 to 51.

Figure 6A:
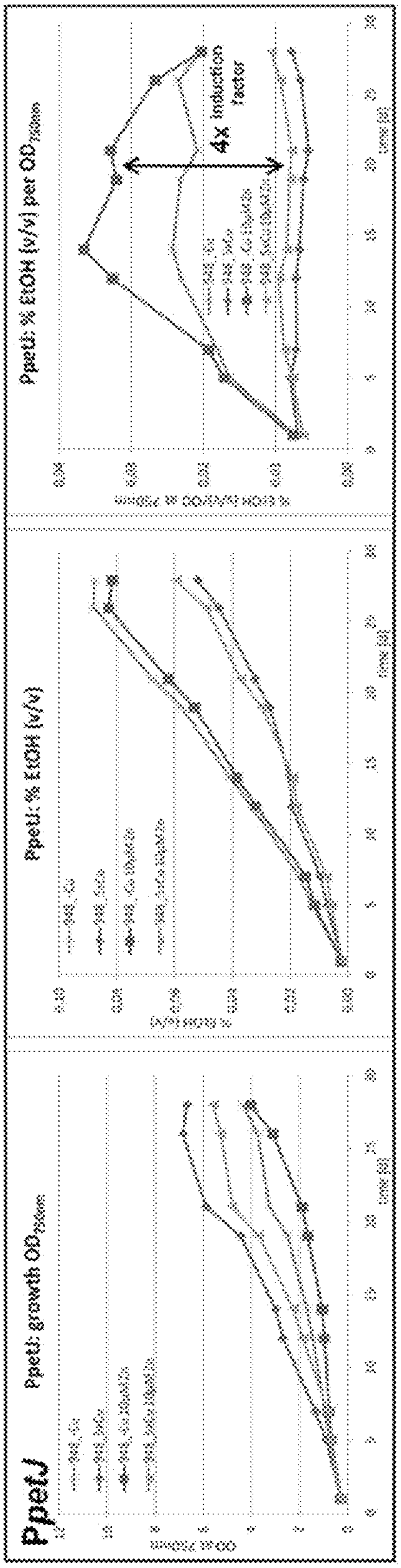
Figure 6B:
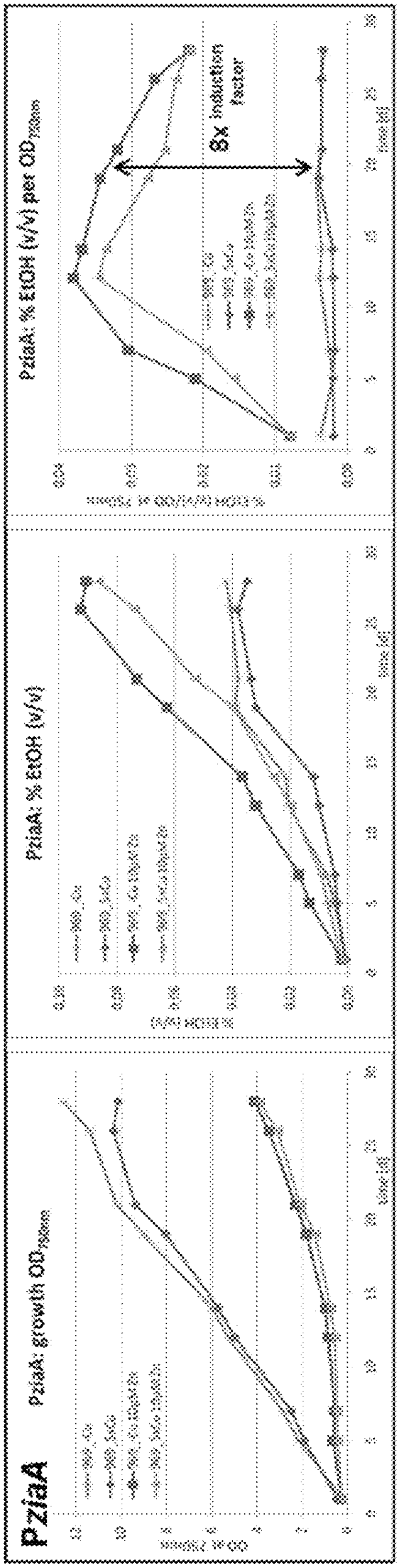

Optical densities at 750 nm, ethanol accumulation and ethanol production normalized to optical densities are shown in the FIGS. 6A and 6B for a prior art strain using the promoter petJ and another strain according to the invention employing PziaA.

Figure 7A:
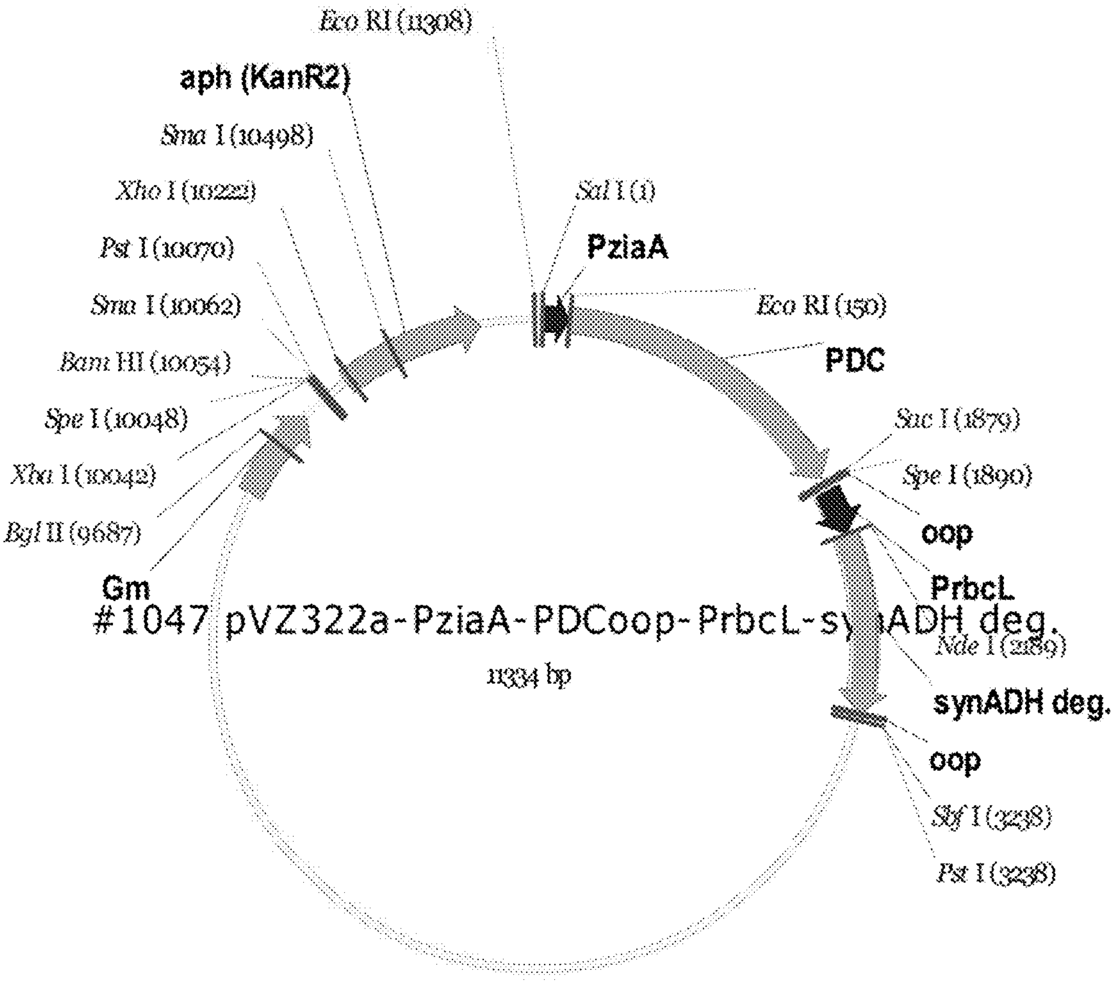
Figure 7B:
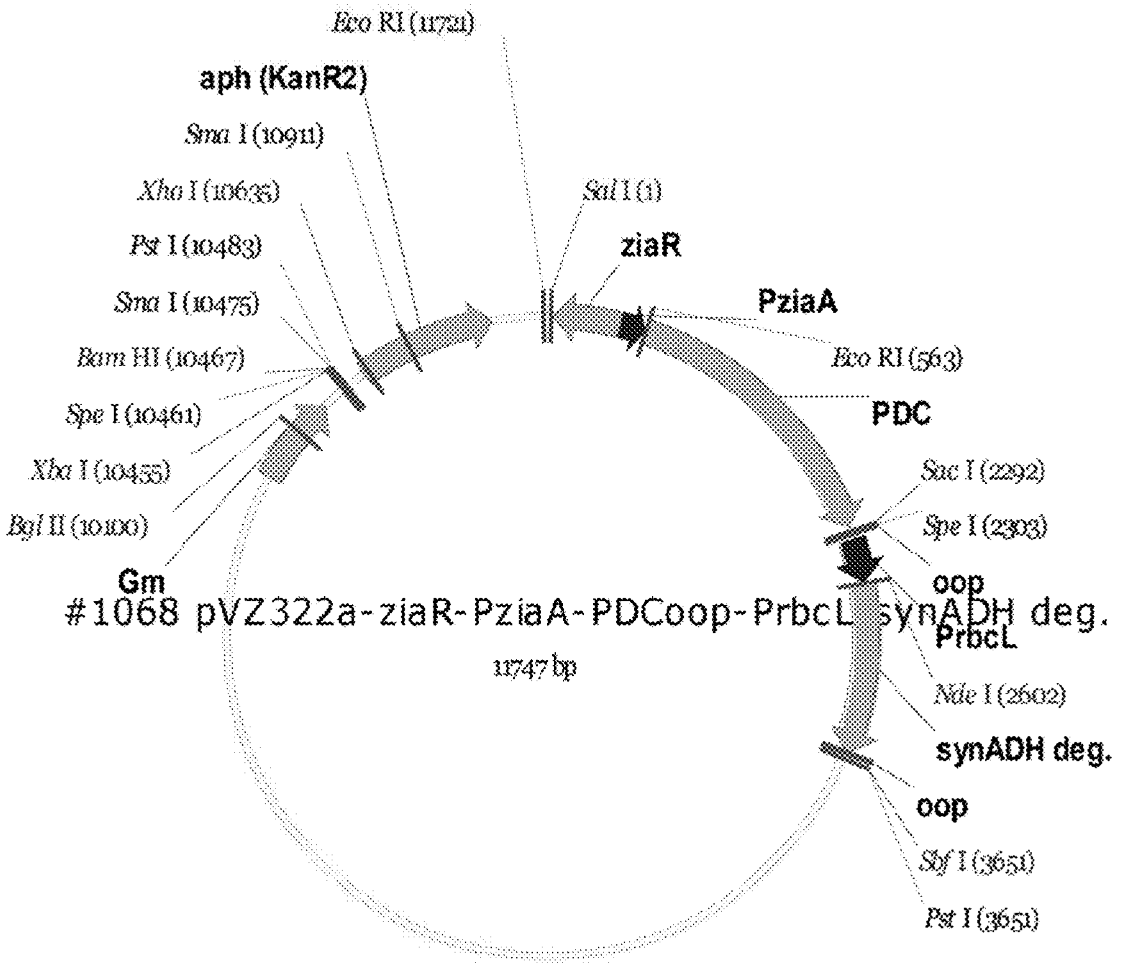

FIGS. 7A and 7B depict the plasmid maps of the plasmids #1047 and #1068.

Figure 8A:
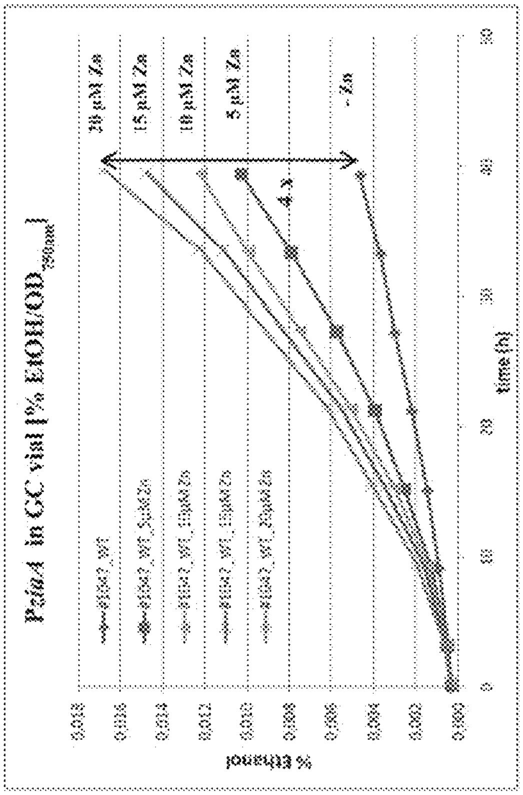
Figure 8A:
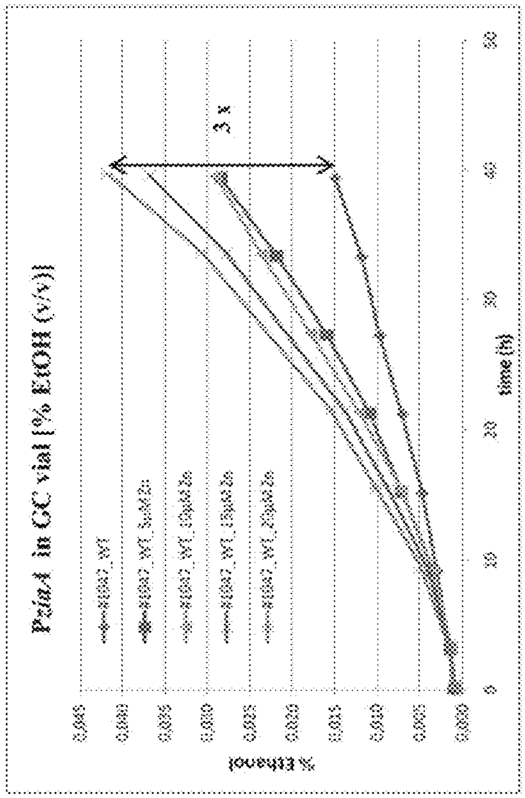
Figure 8B:
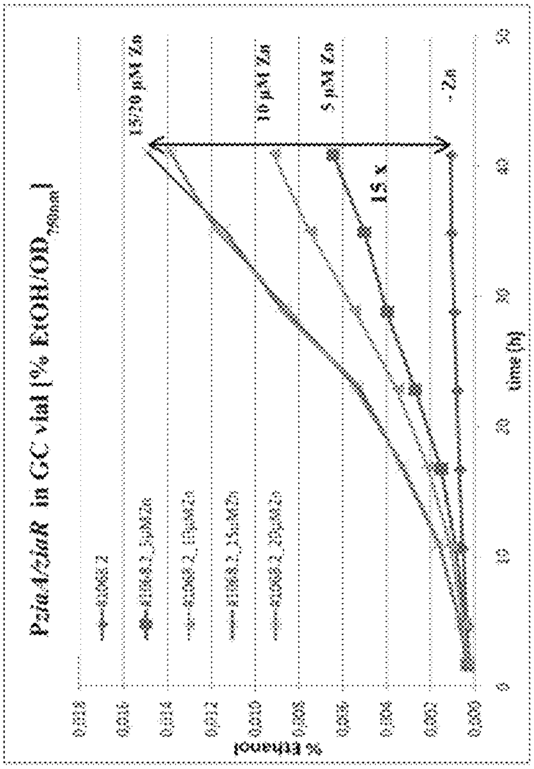
Figure 8B:
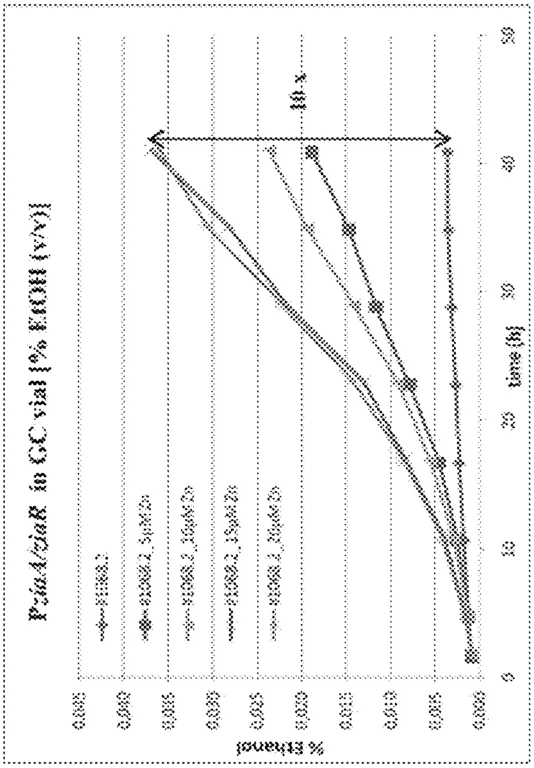

A comparison of the ethanol production rates for cyanobacterial strains including only PziaA and a combination of ziaR-PziaA is shown in the FIGS. 8A and 8B.

Figure 9A:
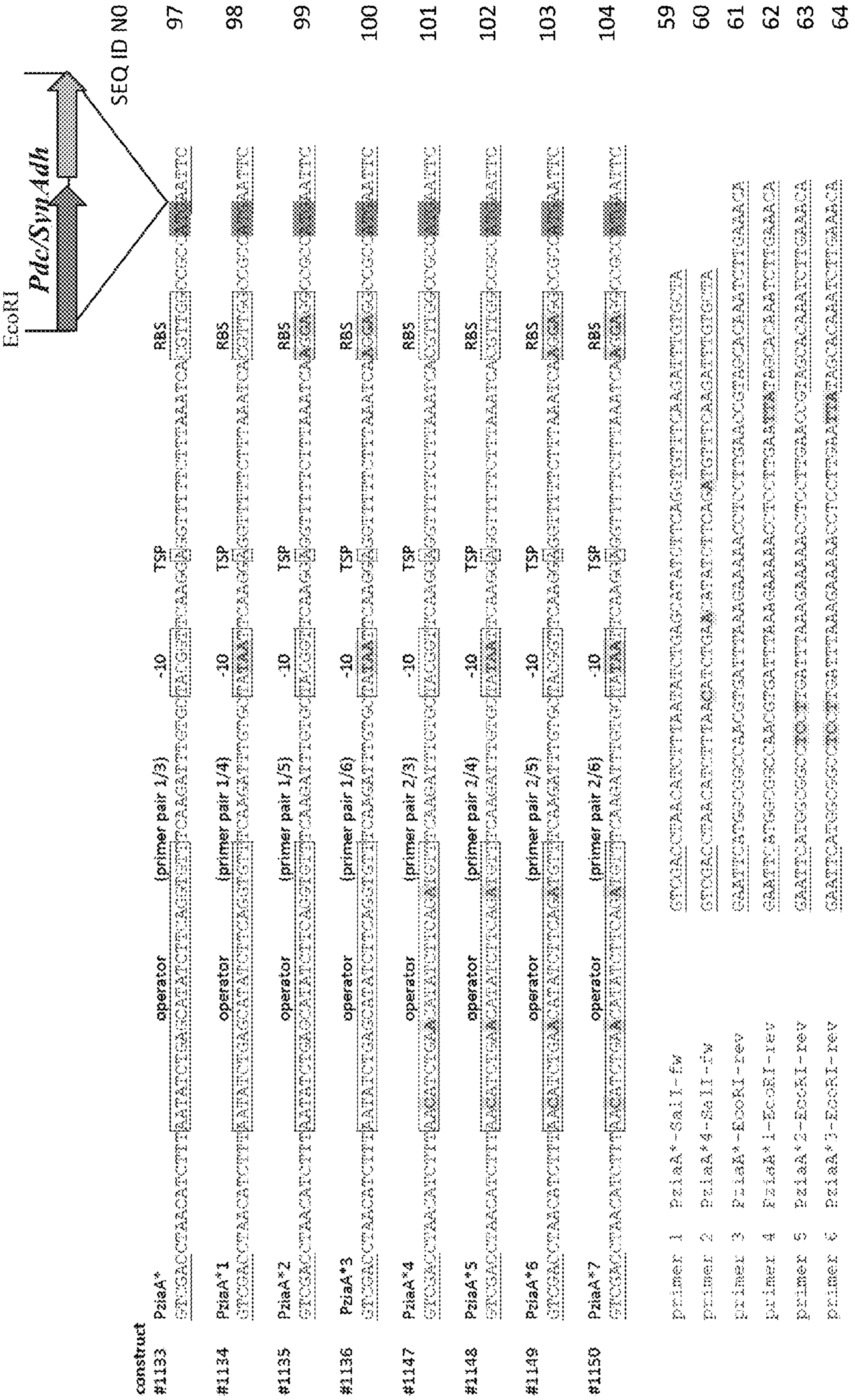

FIG. 9A depicts various variants of the ziaA promoter sequence along with primers for generating these variants. The sequences of the ziaA promoter variants are as follows: SEQ ID NO. 97 is the ziaA promoter variant—construct #1133, PziaA*. SEQ ID NO. 98 is the ziaA promoter variant—construct #1134, PziaA*1. SEQ ID NO. 99 is the ziaA promoter variant—construct #1135, PziaA*2. SEQ ID NO. 100 is the ziaA promoter variant—construct #1136, PziaA*3. SEQ ID NO. 101 is the ziaA promoter variant—construct #1147, PziaA*4. SEQ ID NO. 102 is the ziaA promoter variant—construct #1148, PziaA*5. SEQ ID NO. 103 is the ziaA promoter variant—construct #1149, PziaA*6. SEQ ID NO. 104 is the ziaA promoter variant—construct #1150, PziaA*7. The primer sequences are as follows: Primer 1: SEQ ID NO. 59; primer 2: SEQ ID NO. 60; Primer 3: SEQ ID NO. 61; Primer 4: SEQ ID NO. 62; Primer 5: SEQ ID NO. 63; Primer 6: SEQ ID NO. 64. Ethanol production rates, $OD_{750\ nm}$, OD normalized ethanol production rates and induction factors obtained by using these promoter variants are shown in FIGS. 9B to 9E. FIGS. 9F to 9K show the plasmid map and the nucleotide sequence of PziaA*2ext as well as the ethanol production rates and acetaldehyde to ethanol ratios for cyanobacteria harboring a plasmid with the promoter PziaA*2ext.

Figure 10:
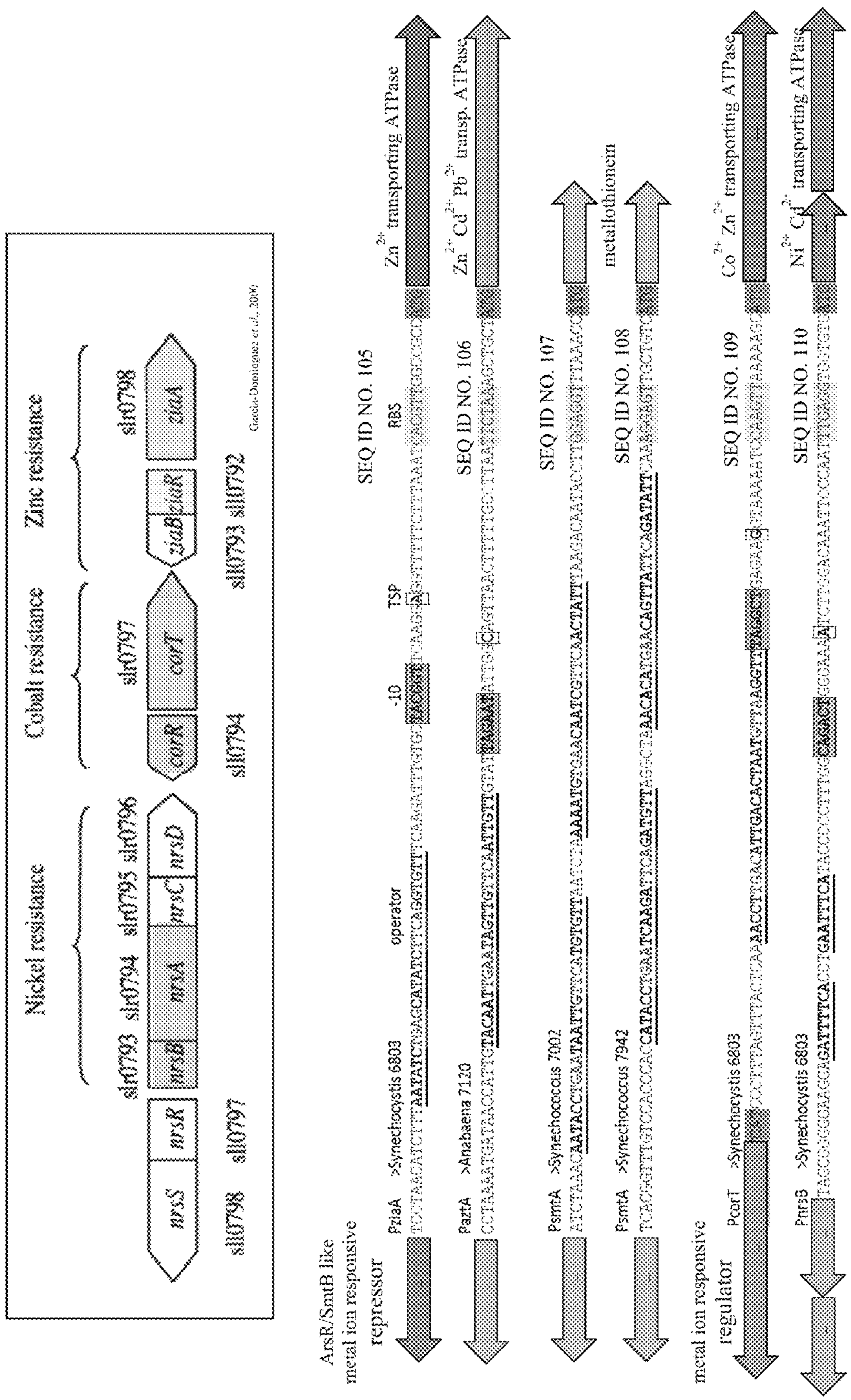

FIG. 10 shows a comparison of the DNA sequences of PziaA, PaztA, two different smtA promoters from *Synechococcus* PCC 7002 and *Synechococcus* PCC 7942 and the $Co^{2+}$ responsive promoter PcorT and the $Ni^{2+}$ inducible promoter PnrsB.

Figure 11A:
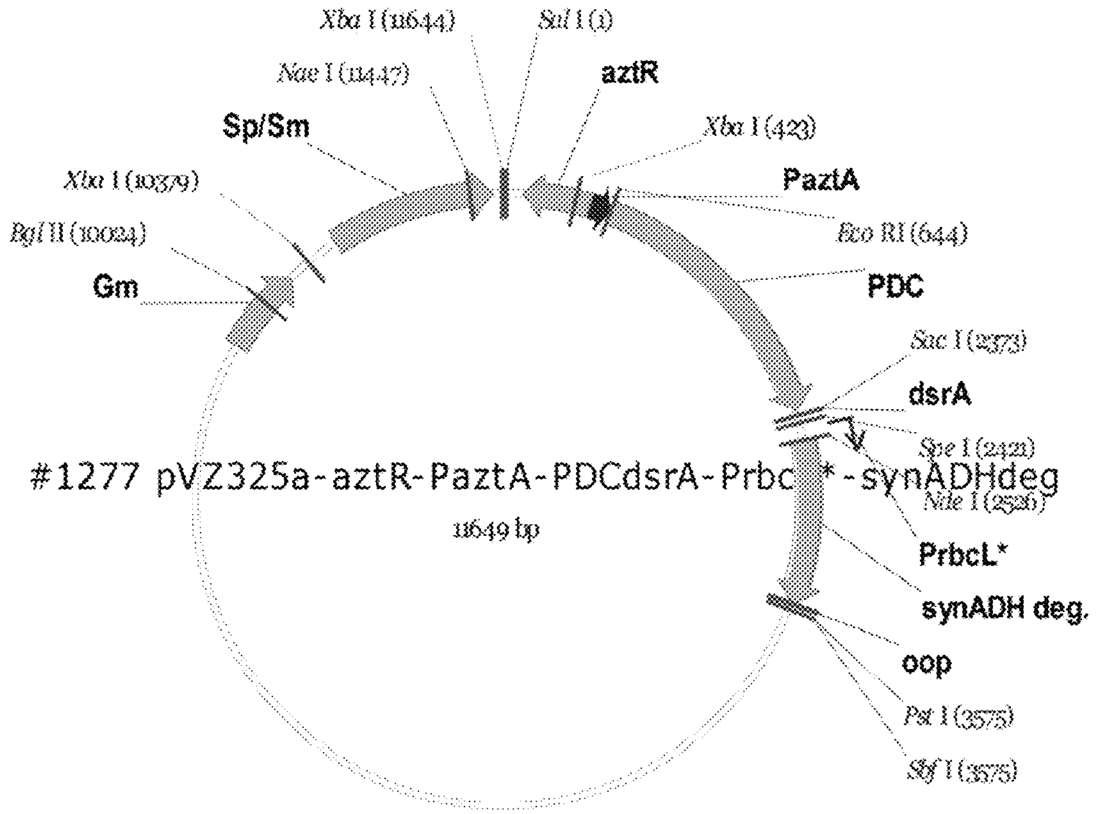
Figure 11B:
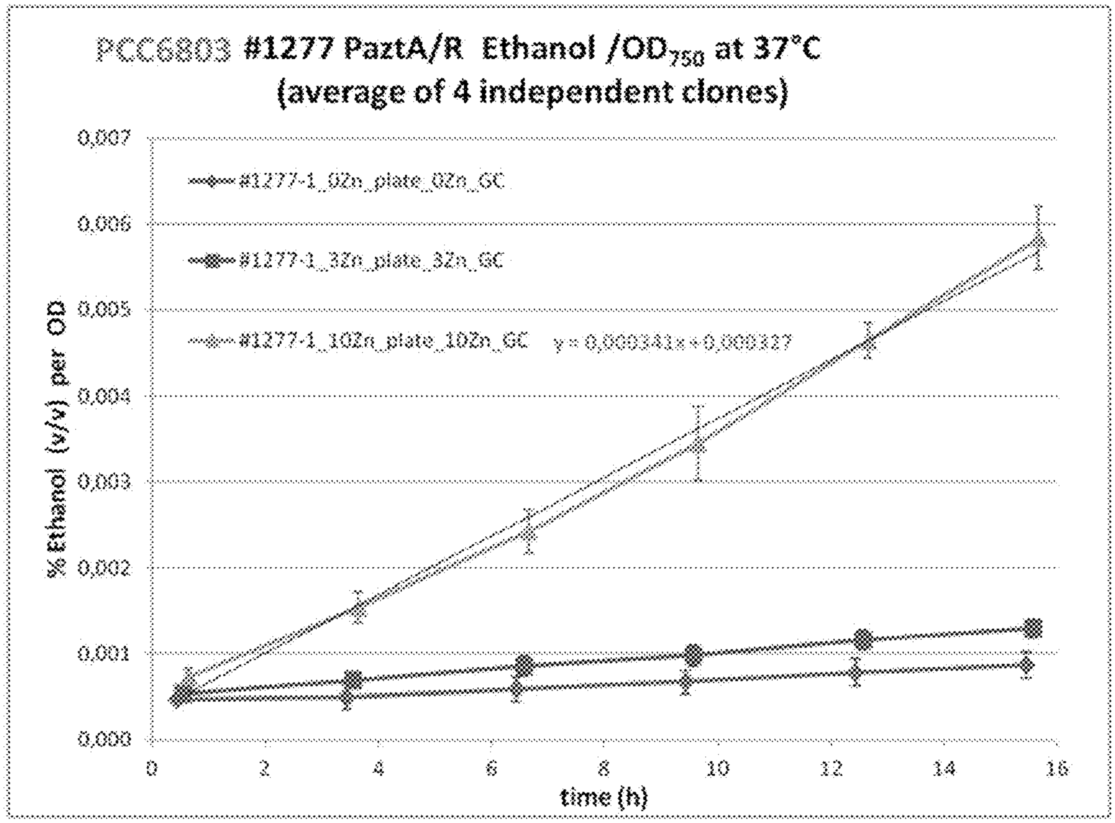

The plasmid organization of the plasmid #1277 including PaztA/aztR is shown in FIG. 11A. FIG. 11B shows a graphical representation of the ethanol production rates of *Synechocystis* PCC 6803 and FIG. 11C of *Synechococcus* PCC 7002 including the plasmid #1277 aztR-PaztA, respectively.

Figure 12A:
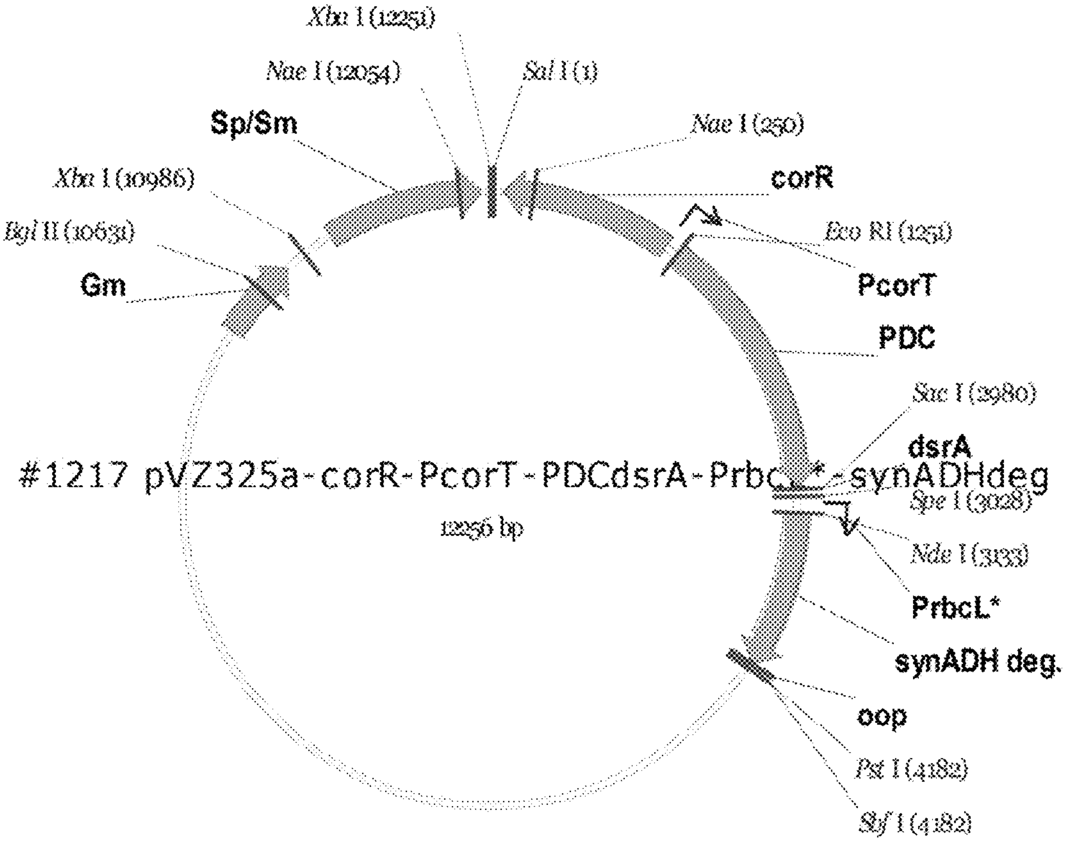

The plasmid organization of the plasmid #1217 including corR-PcorT is depicted in FIG. 12A. Ethanol formation rates using *Synechocystis* PCC 6803 harbouring the $Co^{2+}$ dependent corT promoter is given in FIG. 12B and for *Synechococcus* PCC 7002 harboring the $Co^{2+}$ dependent corT promoter in FIG. 12C.

Figure 13A:
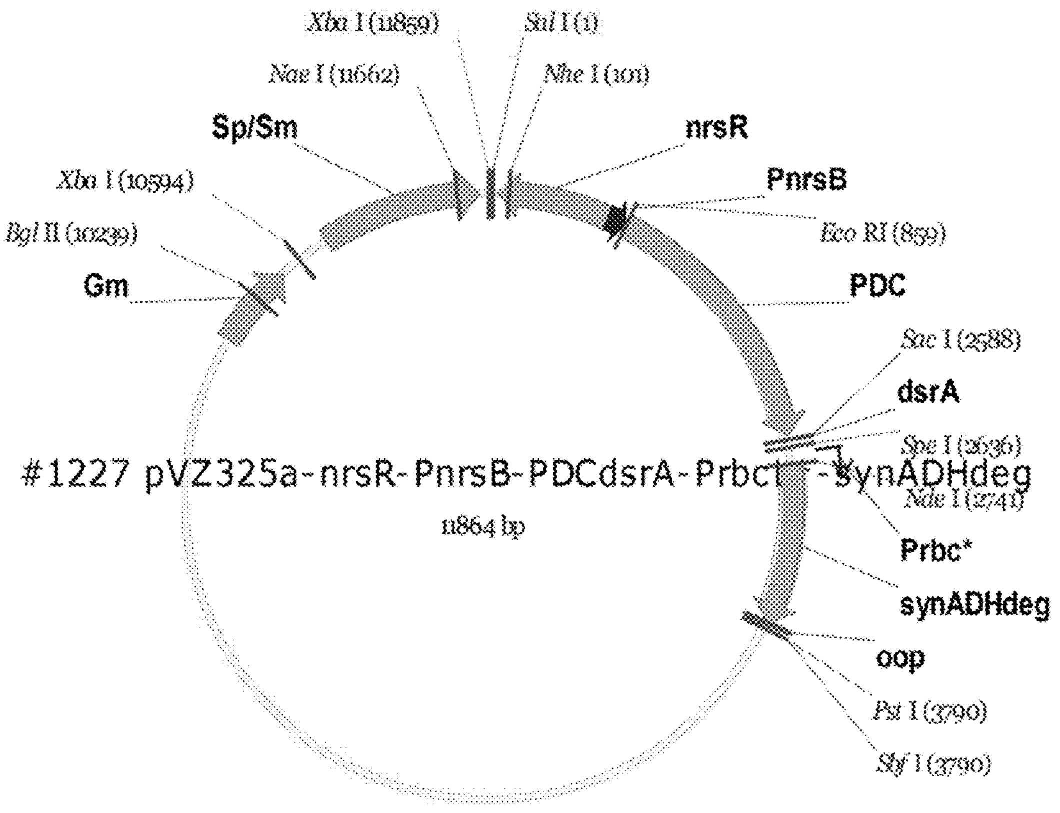
Figure 13B:
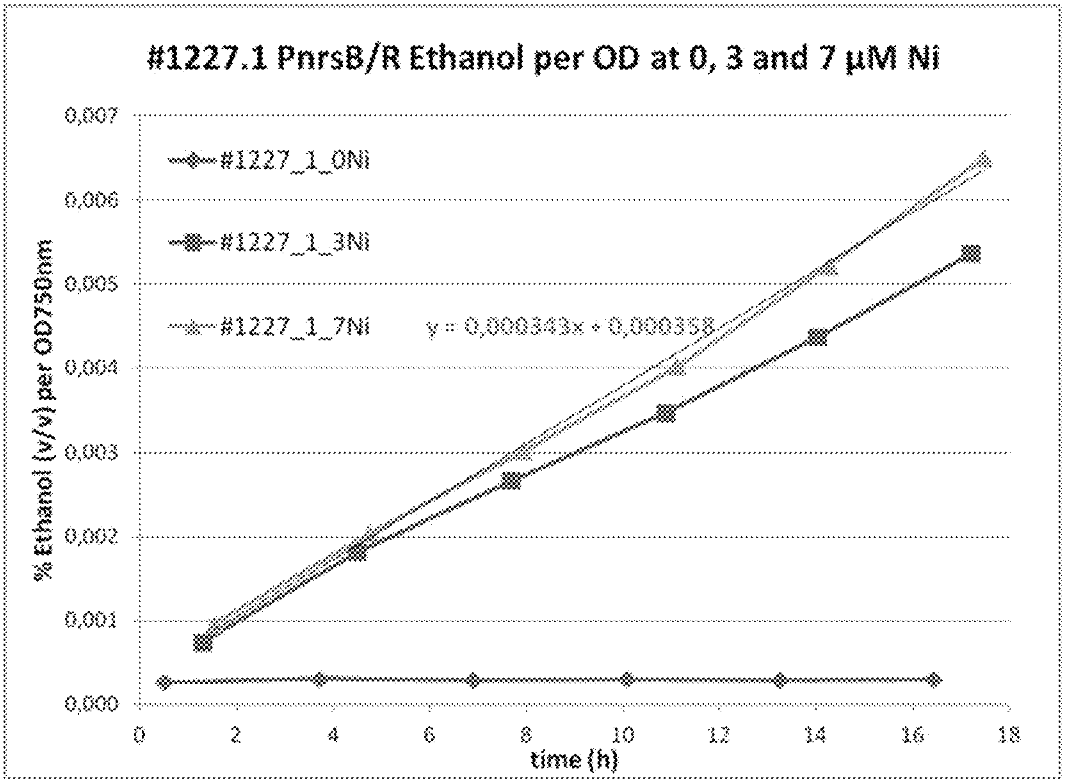
Figure 13C:
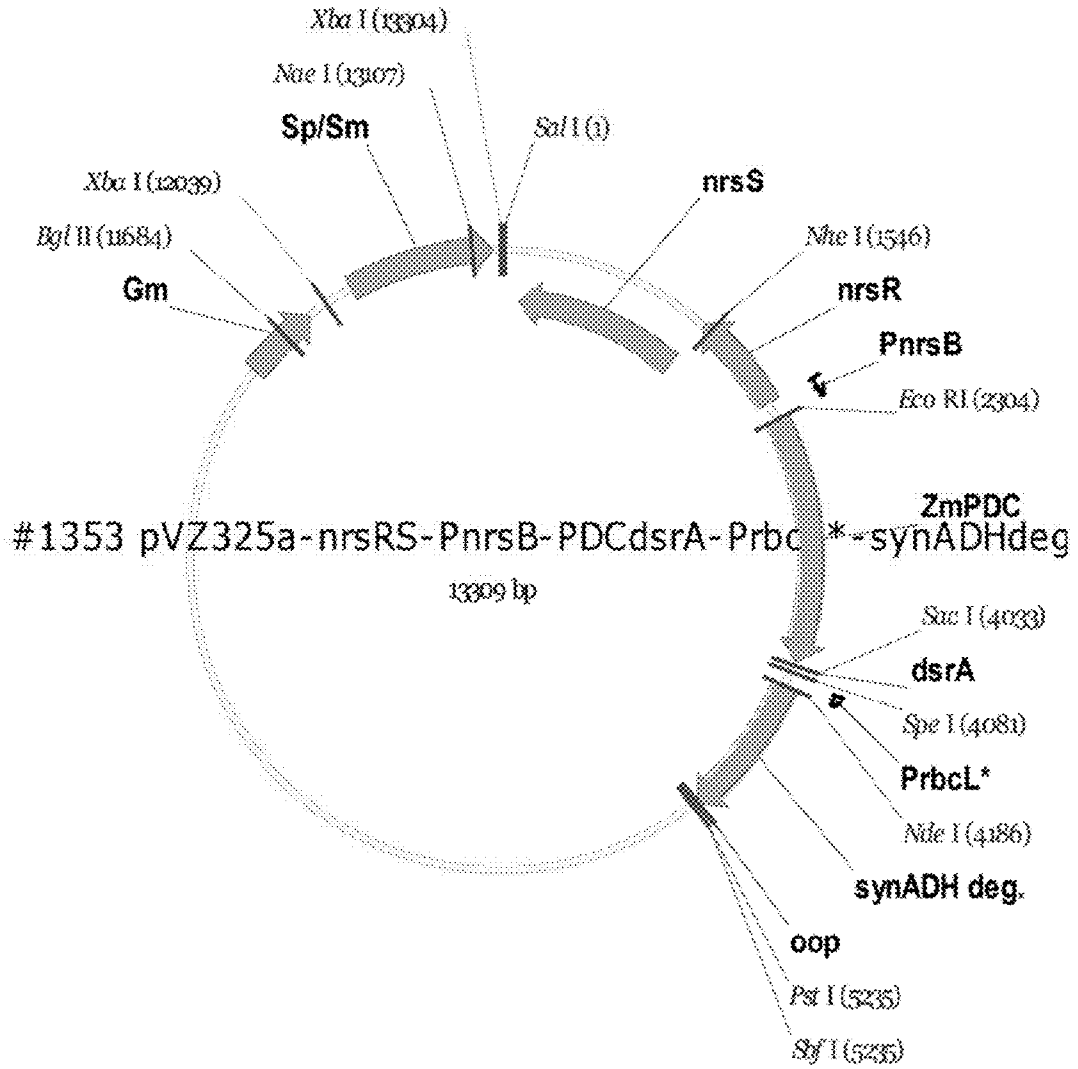
Figure 13D:
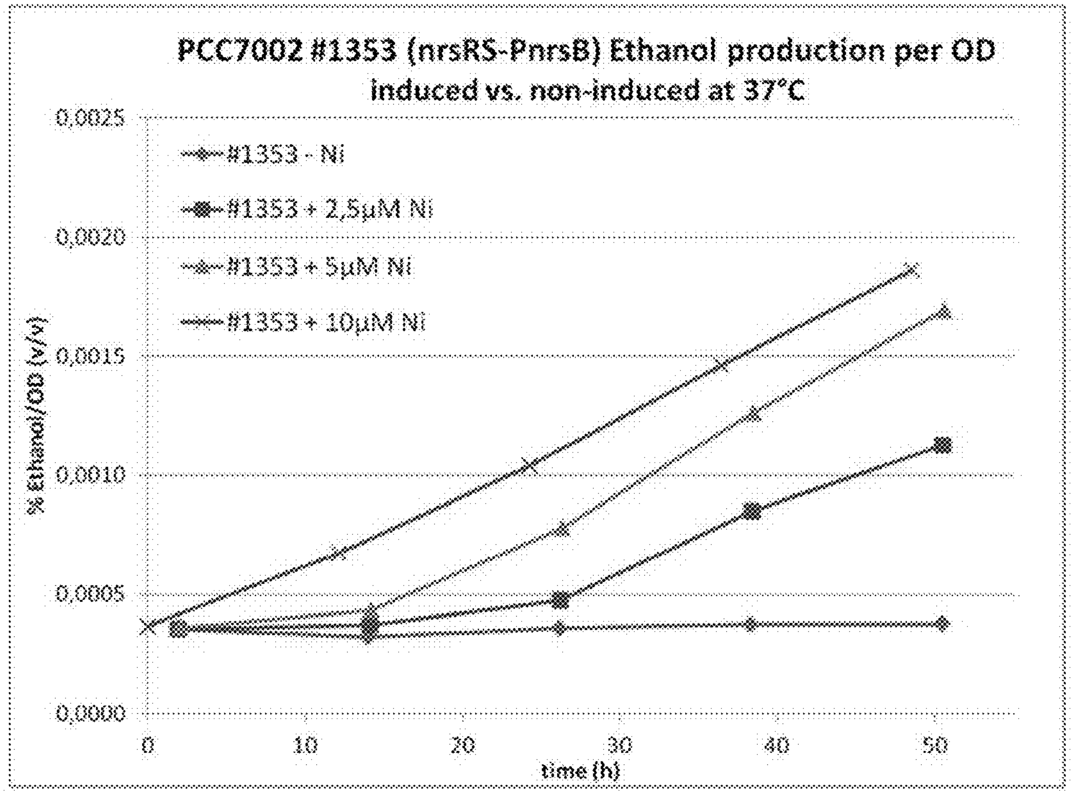

The plasmid organization of the plasmid #1227 including nrsR-PnrsB is shown in FIG. 13A. FIG. 13B shows the ethanol production rates of *Synechocystis* PCC6803 harboring the plasmid #1227 including Pdc and Adh encoding genes under the transcriptional control of nrsR-PnrsB. FIGS. 13C and 13D show the plasmid map for the plasmid #1353 containing SynAdh gene under the transcriptional control of the Prbc* promoter and Pdc gene under the control of PnrsB with the regulators nrsR and nrsS and the corresponding ethanol production rates of *Synechococcus* PCC 7002 transformed with this plasmid.

Figure 14A:
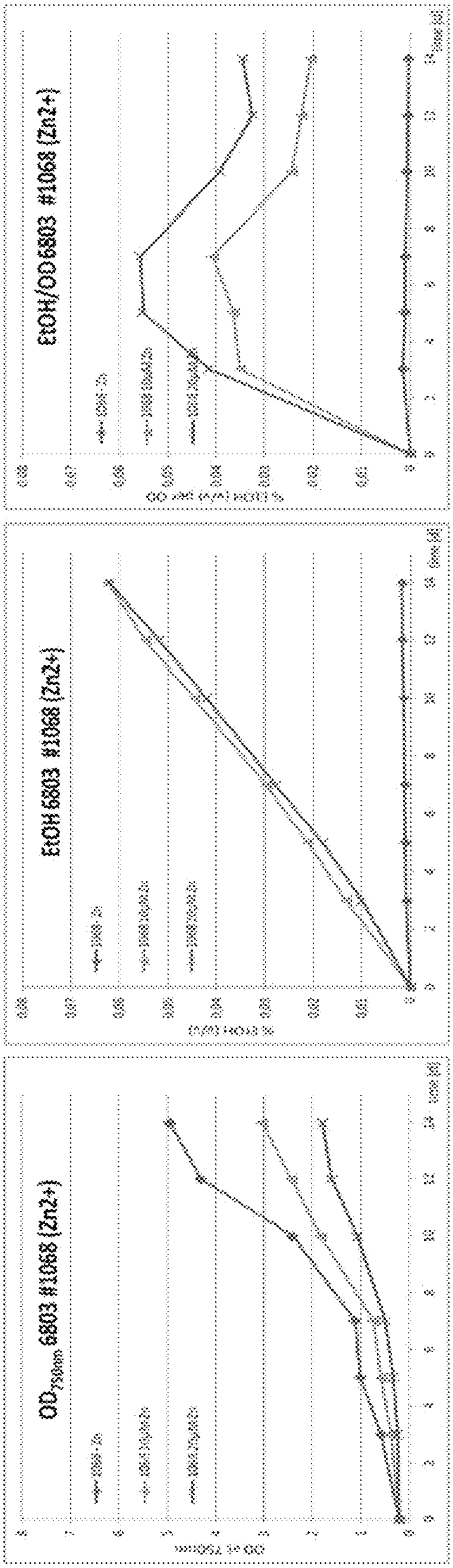
Figure 14B:
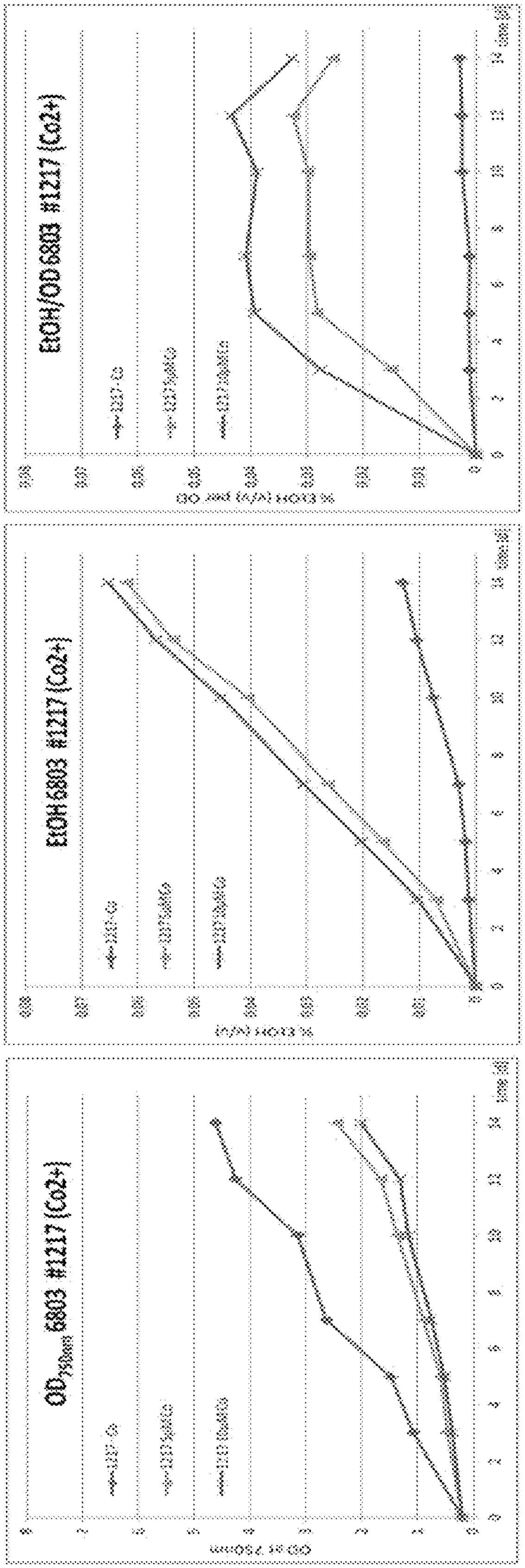
Figure 14C:
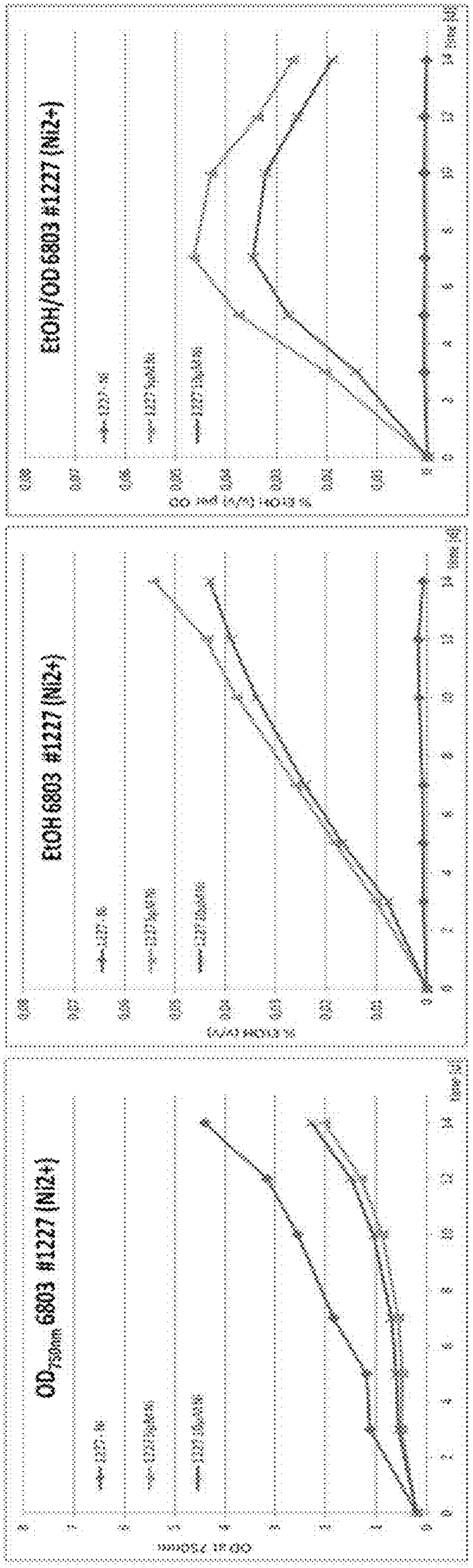

Optical densities at 750 nm, ethanol accumulation and ethanol production normalized to optical densities are shown in the FIG. 14A for *Synechocystis* PCC 6803 containing the plasmid #1068 including ziaR-PziaA, in the FIG. 14B for *Synechocystis* PCC 6803 containing the plasmid #1217 including corR-PcorT and in FIG. 14C for *Synechocystis* PCC 6803 containing the plasmid #1227 including nrsR-PnrsB.

Figure 15A:
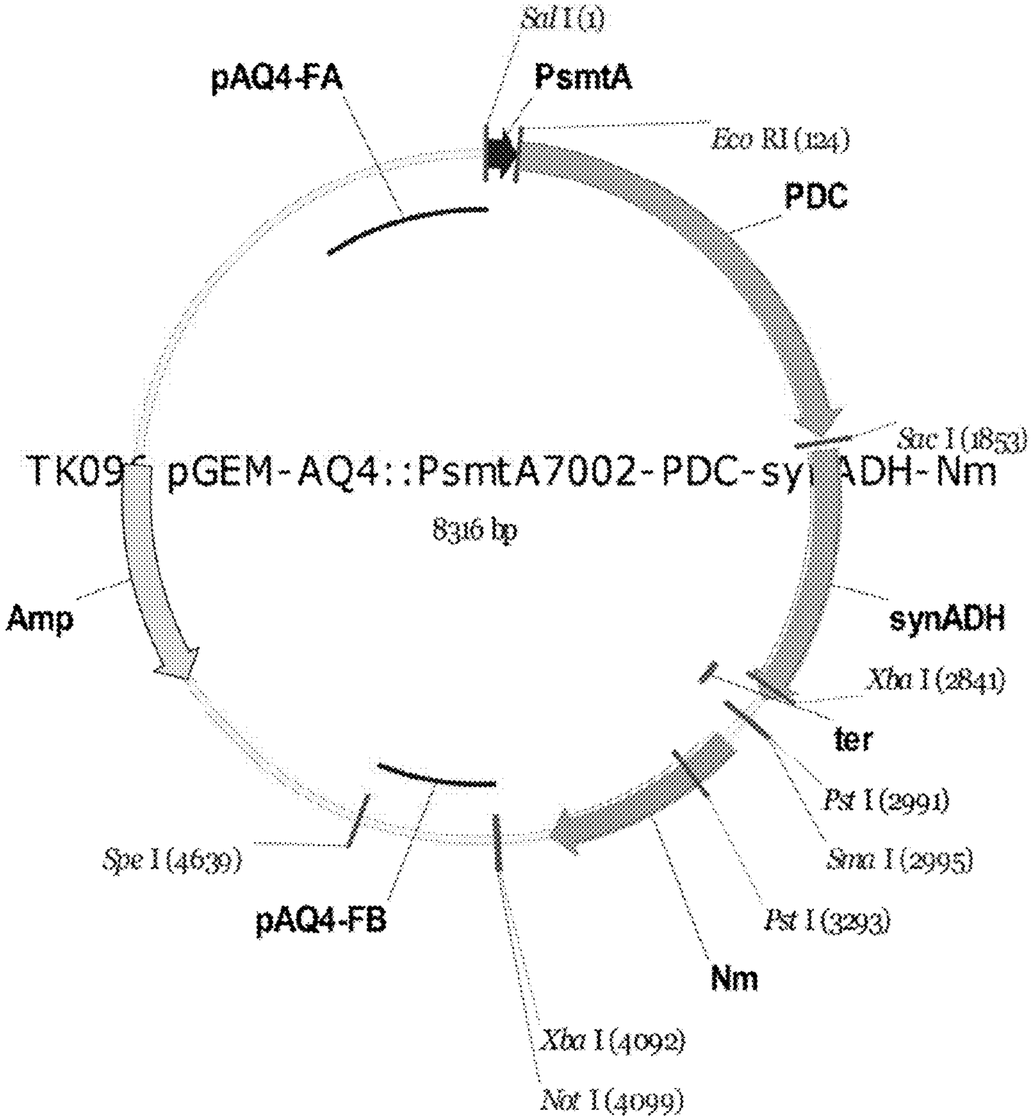
Figure 15B:
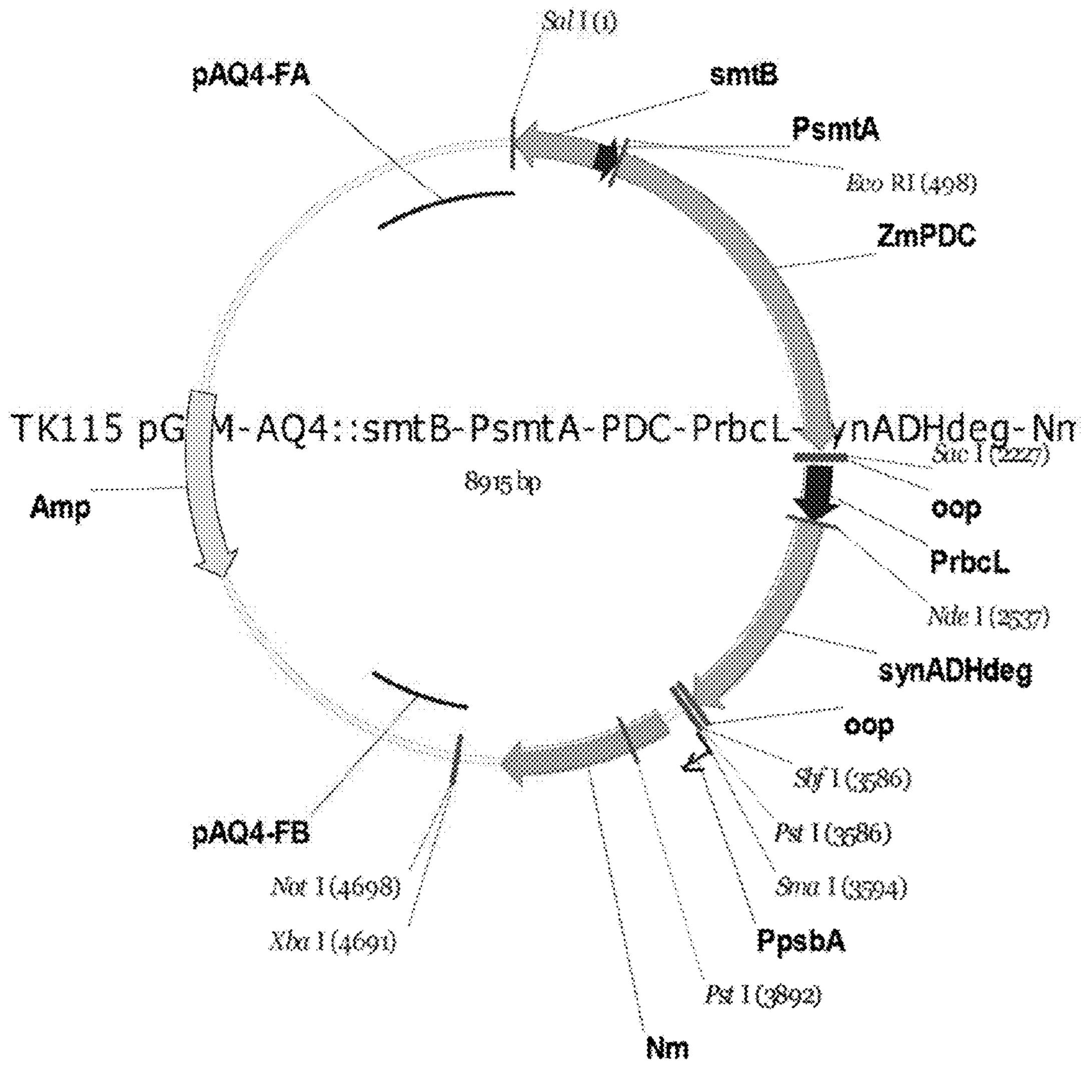
Figure 15C:
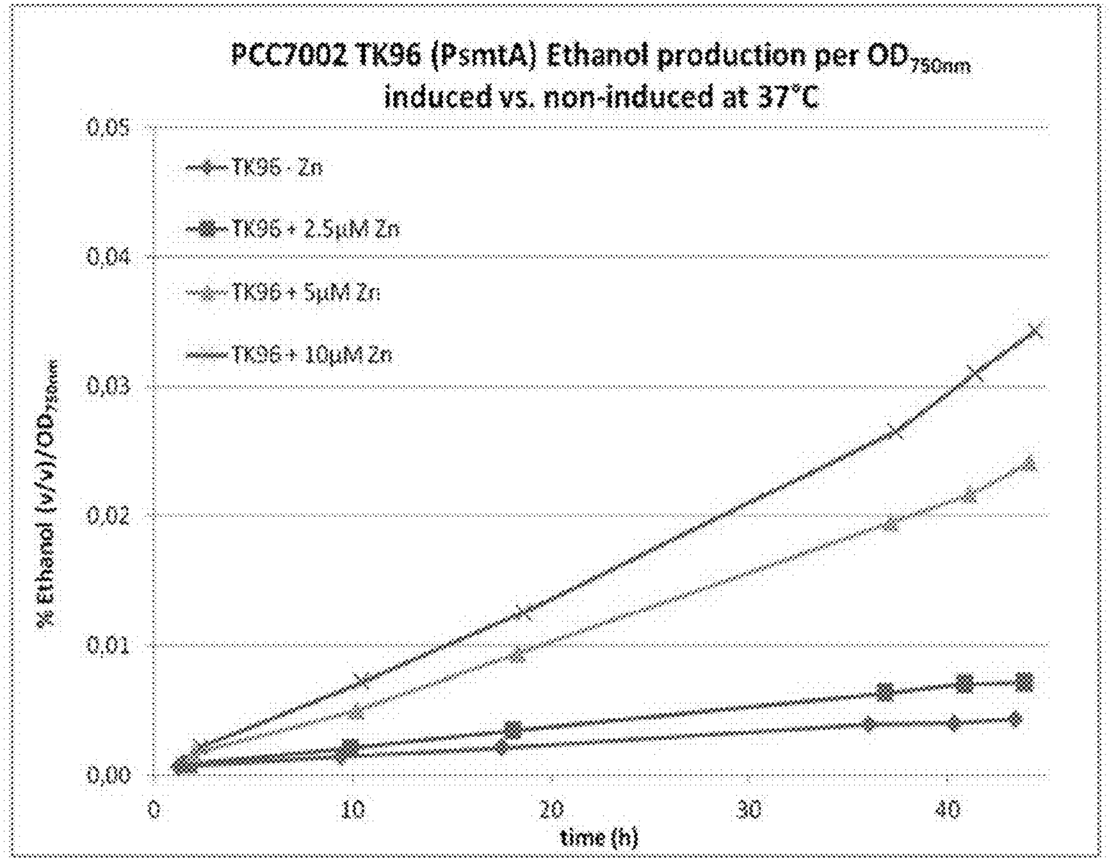
Figure 15D:
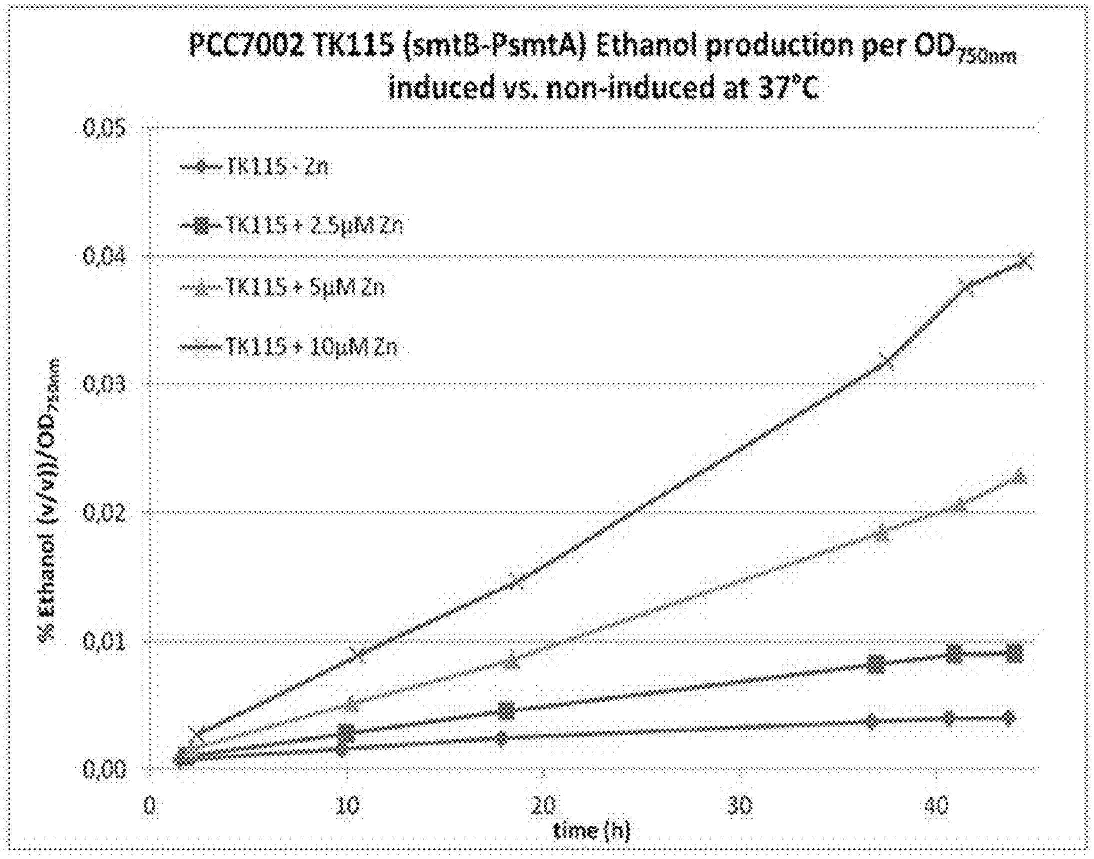
Figure 15E:
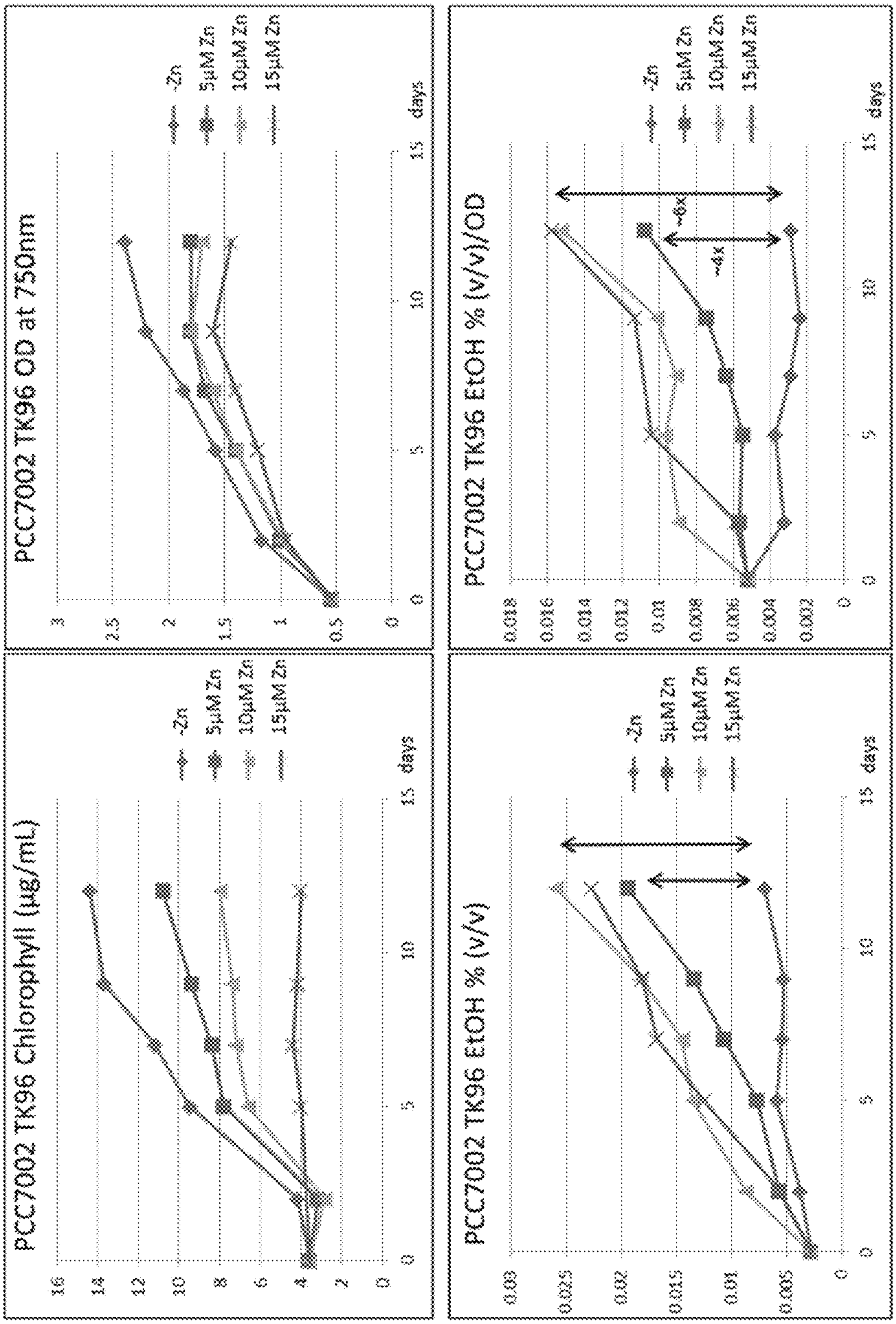

The plasmid organizations of the plasmids TK96 only including PsmtA and of the plasmid #TK115 including smtB-PsmtA are shown in the FIGS. 15A and 15B. Gas chromatography measurements over several time points (GC assay) for the ethanol production are shown in FIGS. 15C and 15D for both above mentioned strains transformed with the plasmids. The chlorophyll content, $OD_{750}$, ethanol production rate (v/v in %) and ethanol production rate (v/v in % per $OD_{750}$) are shown in FIG. 15E for *Synechococcus* sp. strain PCC 7002 transformed with the plasmid TK96 harboring ethanologenic genes under the transcriptional control of the smtA promoter.

Figure 16A:
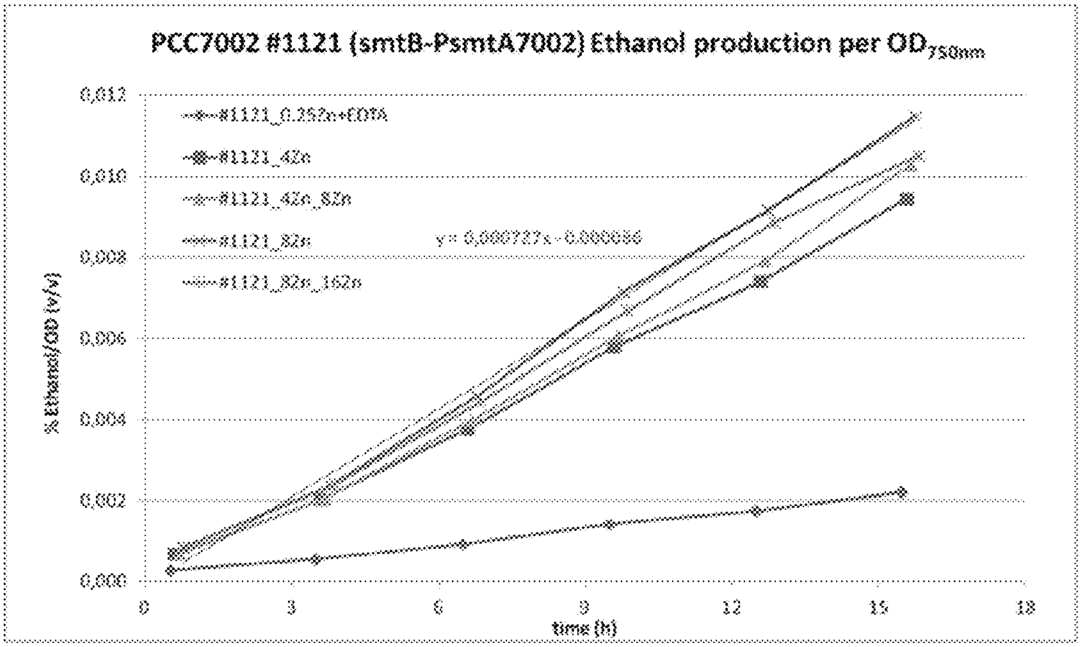
Figure 16B:
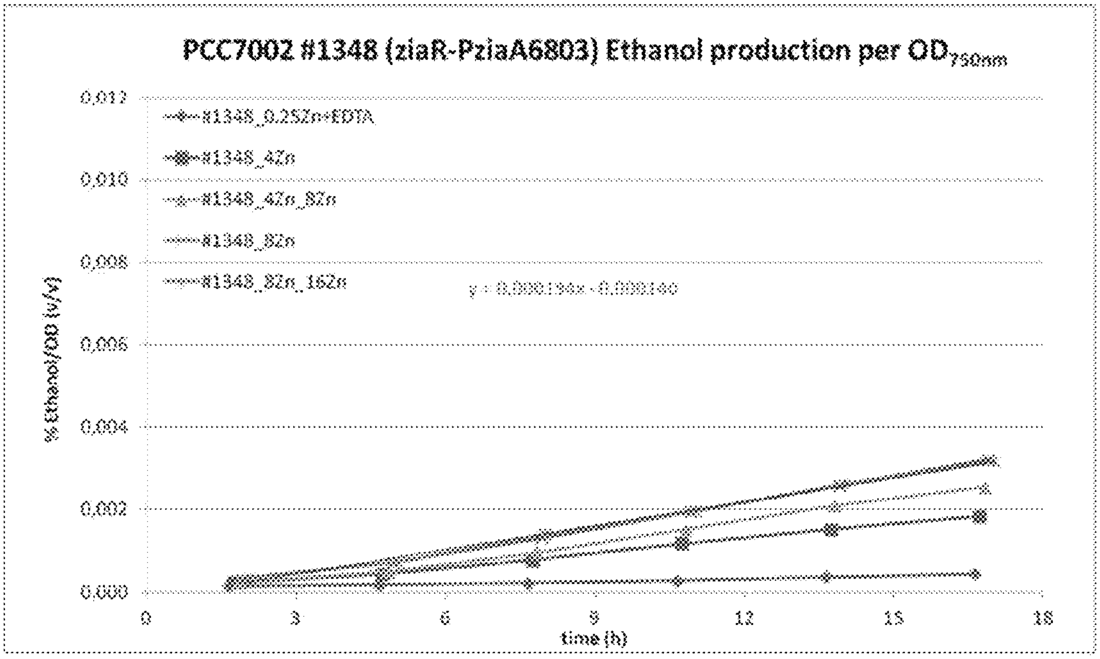

FIGS. 16A and 16 B shows the ethanol production over time of genetically enhanced *Synechococcus* PCC 7002 strains transformed with extrachromosomal plasmids #1121 with endogenous $Zn^{2+}$ inducible promoter in comparison to the same cyanobacterial strain harboring an extrachromosomal plasmid #1348 with heterologous $Zn^{2+}$ inducible promoter from PCC6803.

Figure 16C:
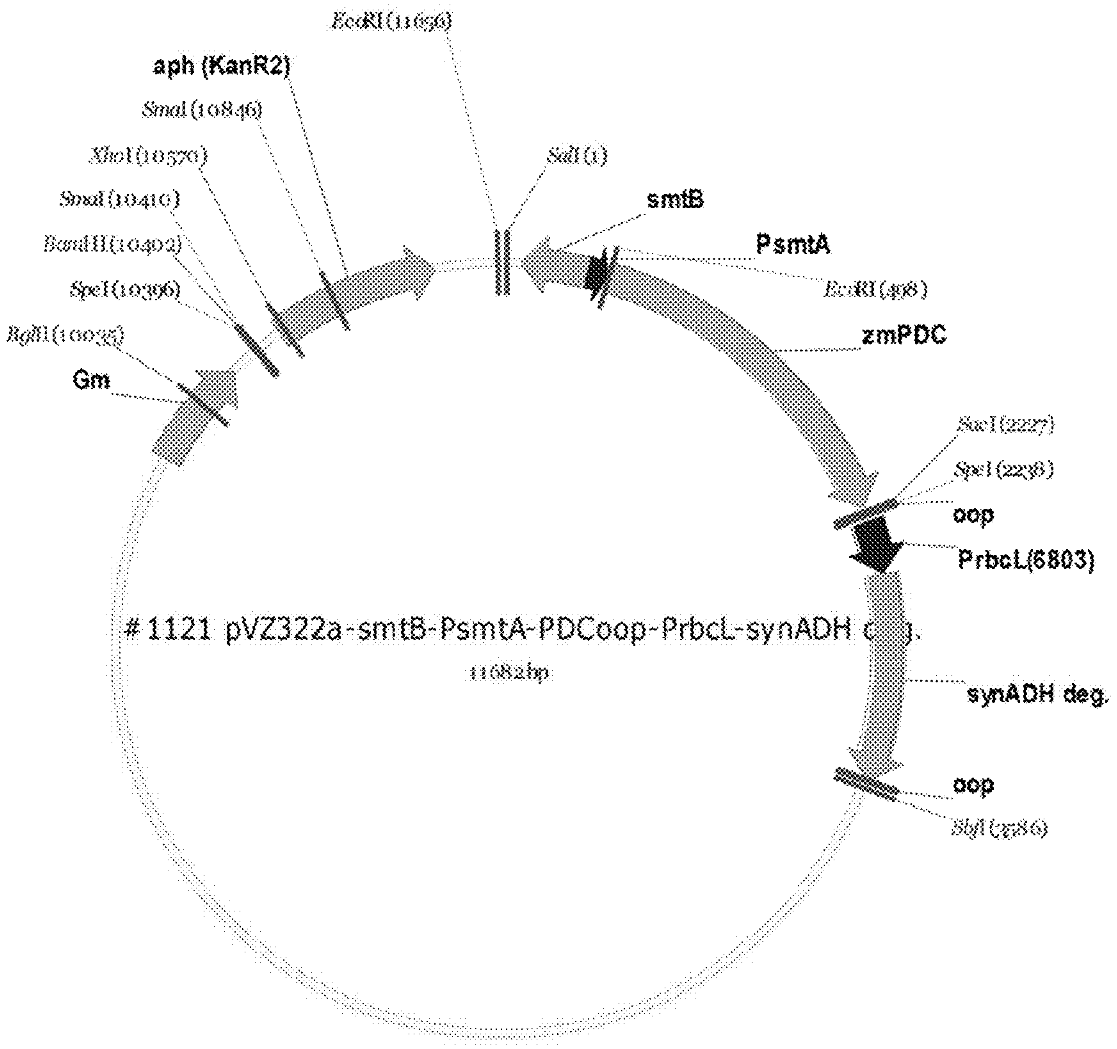
Figure 16D:
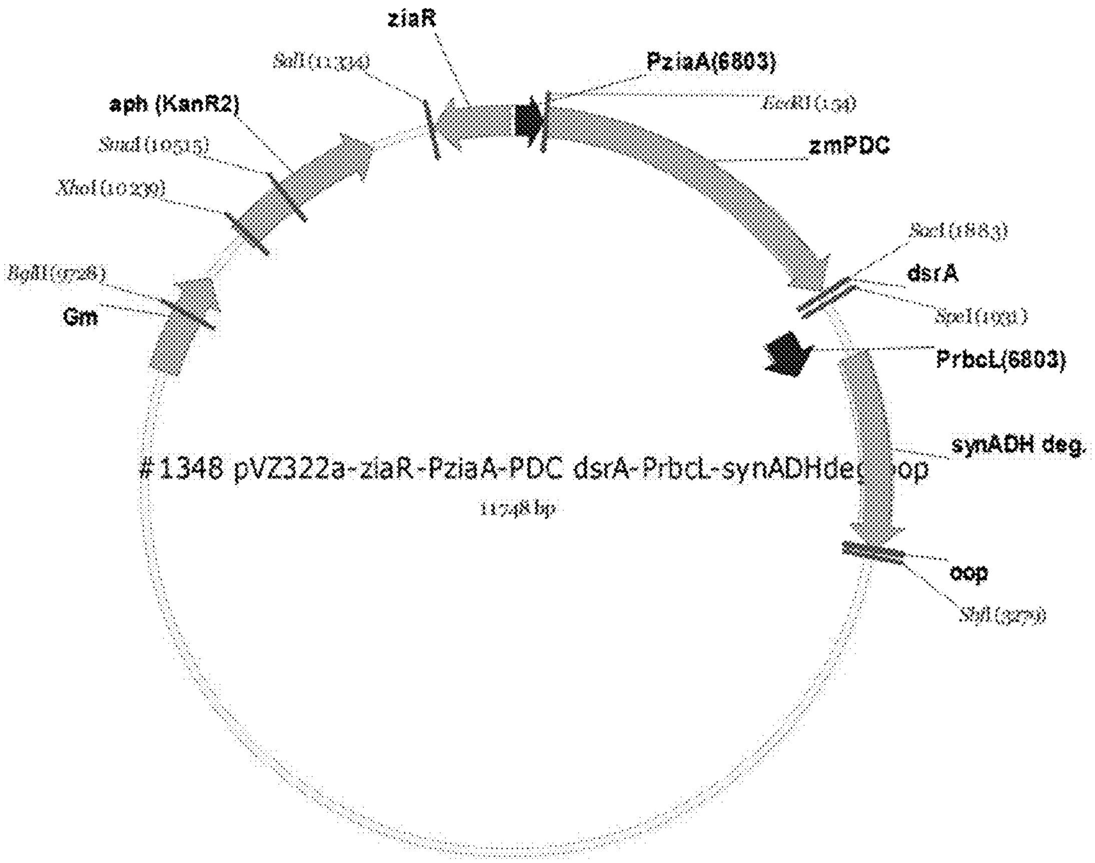

The FIGS. 16C and D show the plasmid maps of the plasmids #1121 and #1348, whose nucleotide sequences are included in the sequence listing with SEQ ID NO. 75 and SEQ ID NO. 76.

In plasmid #1121 the nucleotides 66 to 392 code for smtB, PsmtA runs from nucleotides 393 to 492, the gentamycin resistance cassette (Gm) runs from nucleotides 9721 to 10251, PrbcL (6803) runs from nucleotides 2276 to 2534, the terminator oop (derived from phage lambda oop RNA integrated downstream (3') of synAdh gene and ZmPdc) is located at nucleotides 2243 to 2275 and from nucleotides 3549 to 3579, and the gene $synADH_{deg}$ is present at nucleotides 2538 to 3548, the Kanamycin resistance cassette is located at nucleotides 10540 to 11354 and finally the gene coding for ZmPdc runs from 502 to 2202.

The plasmid #1348 contains the following genes and regulatory elements:

| Nucleotides | Gene/regulatory element |
|---|---|
| 10209 to 11023 | aph\(KanR2) |
| 9414 to 9944 | Gm |
| 1969 to 2221 | PrbcL(6803) |
| 2231 to 3241 | $synADH_{deg}$ |
| 3242 to 3272 | oop |
| 158 to 1858 | zmPDC |
| 1884 to 1929 | dsrA |
| 1 to 144 | PziaA(6803) |
| Antisense 11343 to 11741 | ziaR |

Figure 17A:
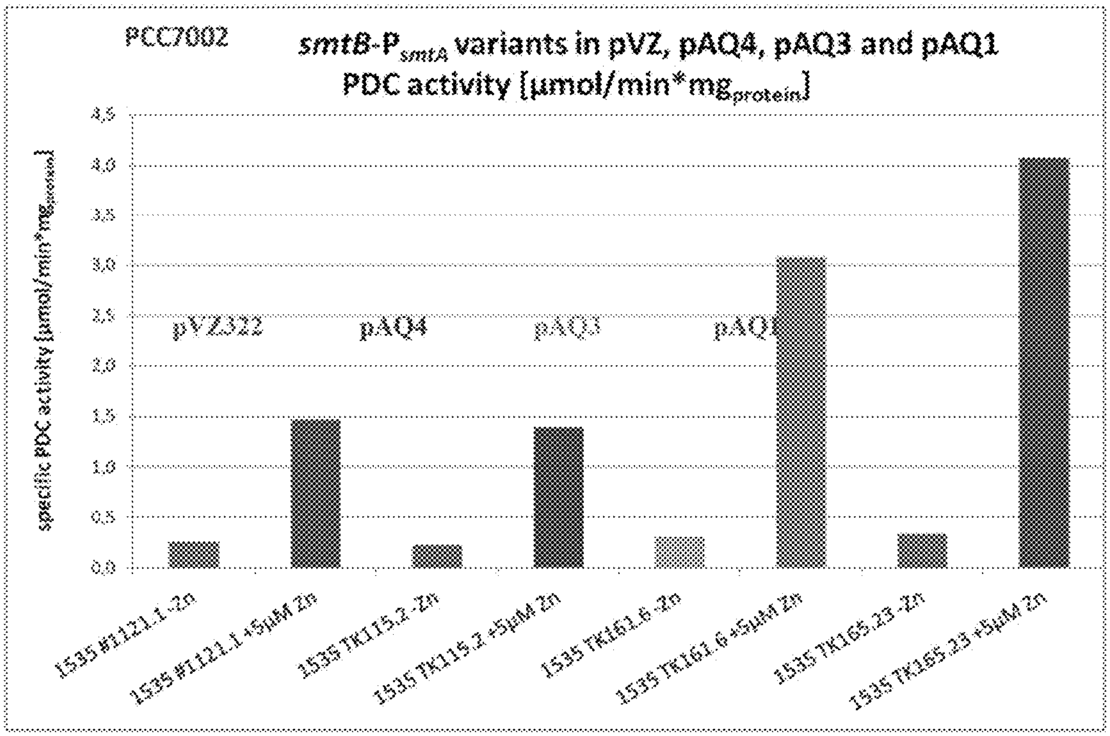
Figure 17B:
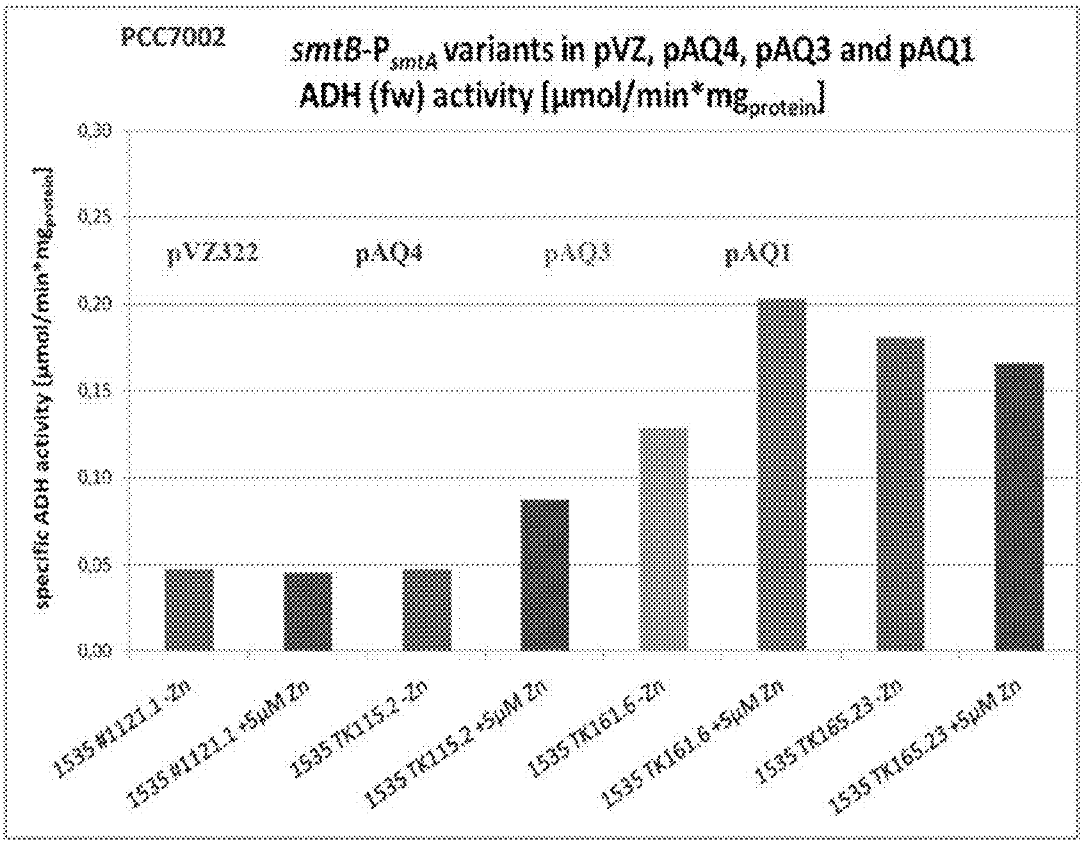

FIGS. 17A and 17B depict the activities of Pdc enzyme and Adh enzyme depending on the integration into the different endogenous plasmids in comparison to a pVZ322 based extrachromosomal plasmid #1535.

Figure 17C:
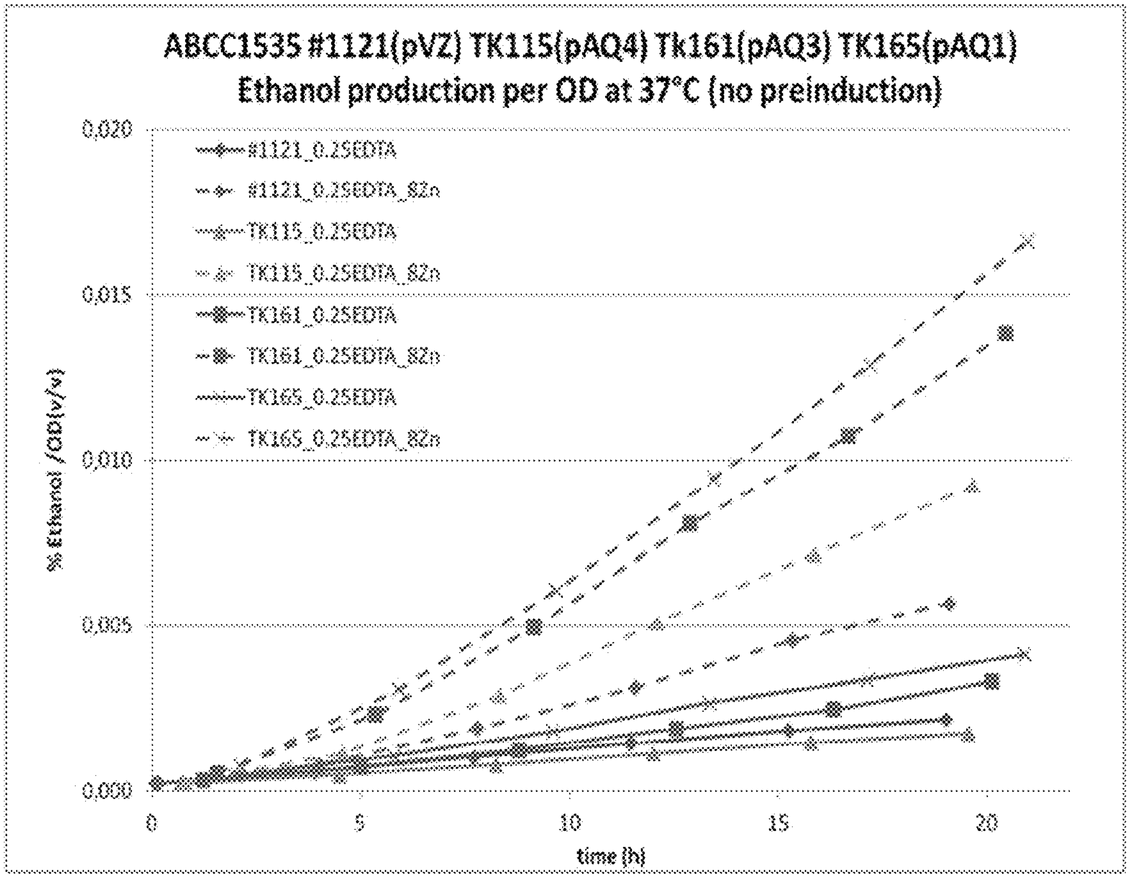
Figure 17D:
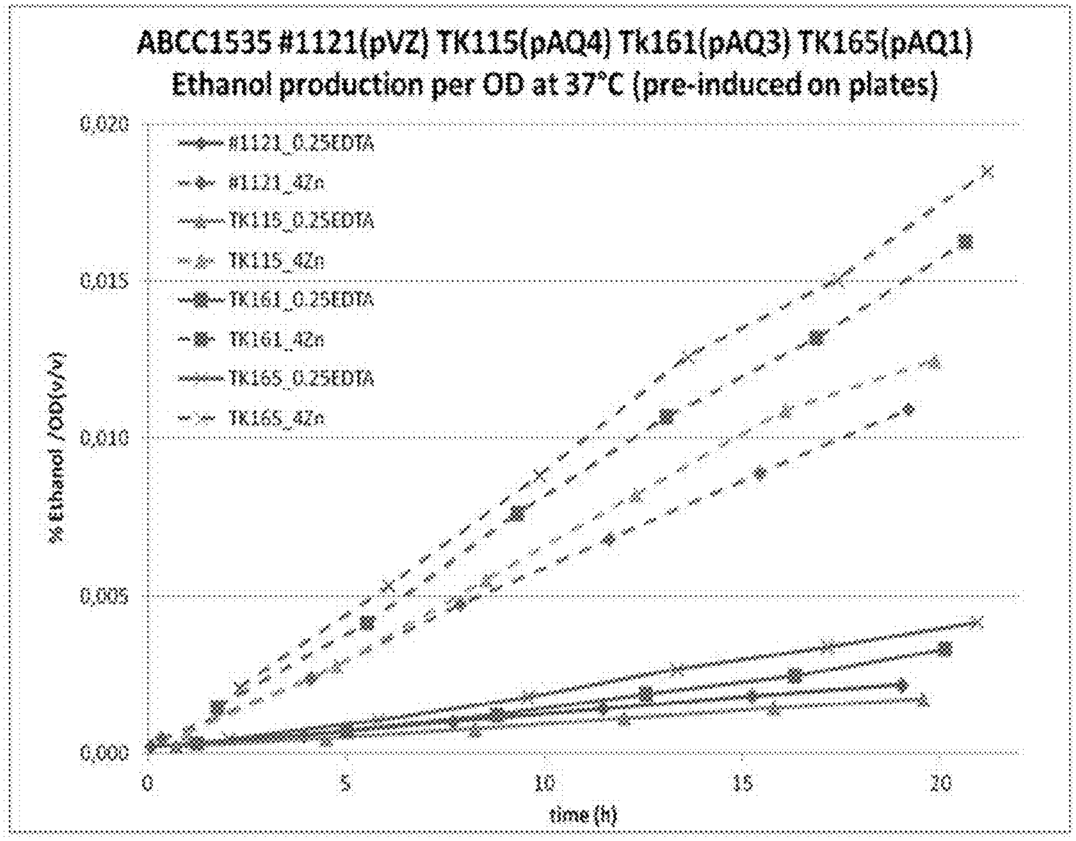

FIGS. 17C and 17D show the ethanol production over time of the strains already mentioned in FIGS. 17A and 17B. The plasmid maps of the plasmids TK 161, and TK 165, respectively are shown in the FIGS. 17E, and 17F and the nucleotide sequence of the plasmids TK 115, TK 161, and TK 165 is listed as SEQ ID NO. 77, 78 and 79, respectively.

The location of the genes and regulatory elements on these plasmids is as follows:

Plasmid TK 115

| nucleotides | Gene/regulatory element |
|---|---|
| 393 to 492 | PsmtA |
| Antisense 6 to 392 | smtB |
| 4698 to 5237 | pAQ4-FB |
| 3610 to 3670 | PpsbA (psbA promoter from *Amaranthus hybridus*) |
| 3710 to 4491 | Nm |
| Antisense 6105 to 6962 | Amp |
| 8179 to 8915 | pAQ4-FA |
| 2276 to 2534 | PrbcL(6803) |
| 2243 to 2275 | oop |
| 2538 to 3548 | $synADH_{deg}$ |
| 3549 to 3579 | oop |
| 502 to 2202 | ZmPDC |

Plasmid TK 161

| nucleotides | Gene/regulatory element |
|---|---|
| Antisense 8392 to 8778 | smtB |
| 8779 to 8878 | PsmtA |
| 5 to 1705 | zmPDC |
| 3052 to 3082 | oop |
| 2041 to 3051 | $synADH_{deg}$ |
| 1746 to 1778 | oop |
| 1779 to 2037 | PrbcL(6803) |
| 7818 to 8386 | pAQ3-FA |
| Antisense 5744 to 6601 | Amp |
| 4384 to 4876 | pAQ3-FB |
| 3239 to 4054 | KmR (kanamycin resistance cassette) |

Plasmid TK 165

| nucleotides | Gene/regulatory element |
|---|---|
| 502 to 2202 | zmPDC |
| 3549 to 3579 | oop |
| 2538 to 3548 | $synADH_{deg}$ |
| 2243 to 2275 | oop |
| 2276 to 2534 | PrbcL(6803) |
| 8330 to 9000 | pAQ1-FA2 |
| Antisense 6256 to 7113 | Amp |
| 4881 to 5388 | pAQ1-FB2 |
| Antisense 6 to 392 | smtB |
| 393 to 492 | PsmtA |
| 3736 to 4551 | KmR (kanamycin resistance cassette) |

Figure 18A:
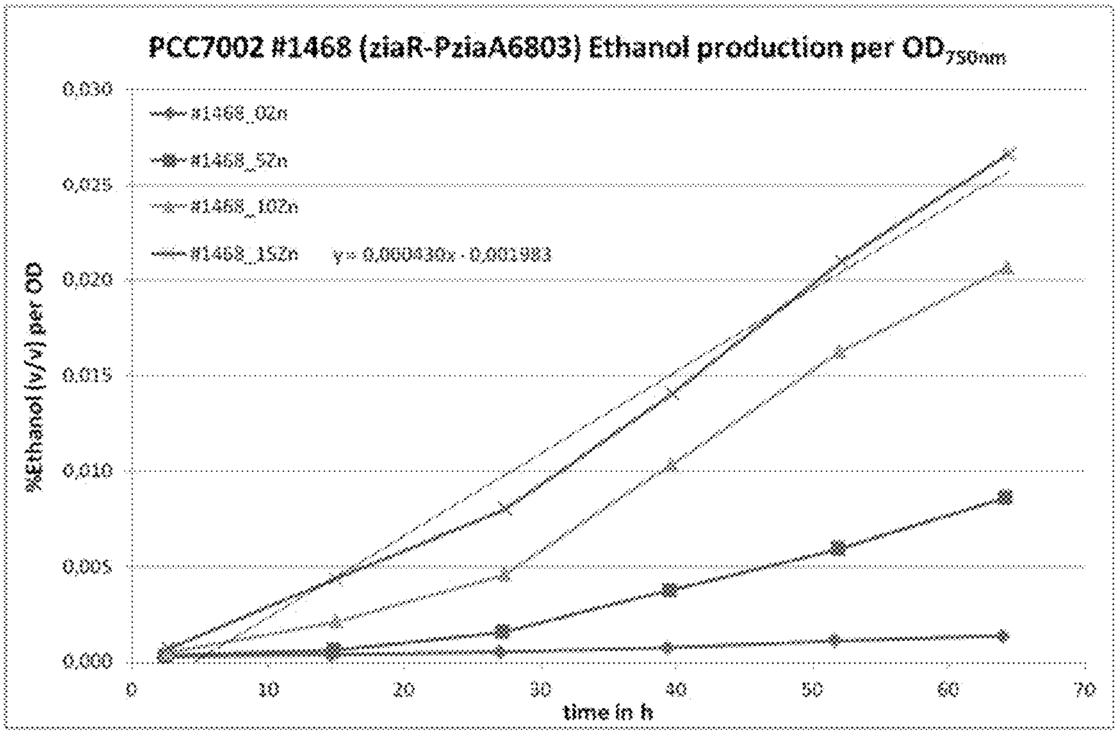
Figure 18B:
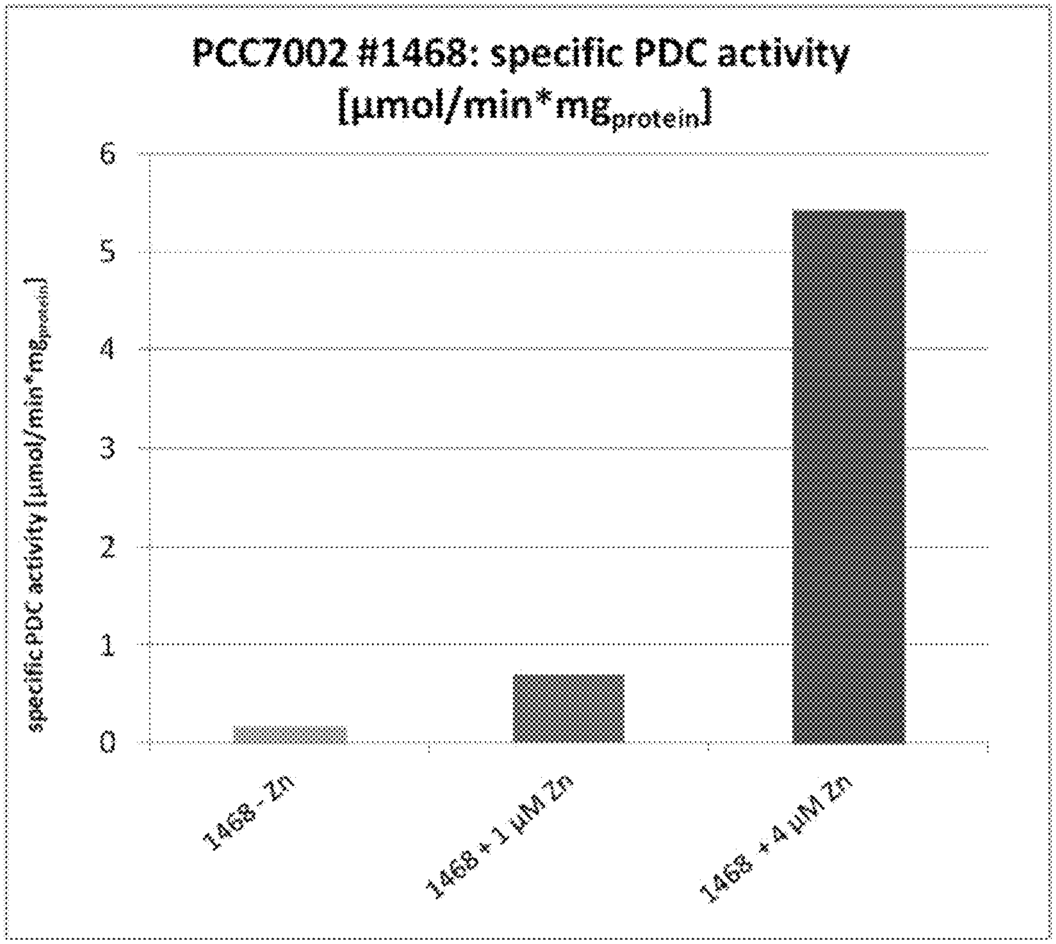
Figure 18C:
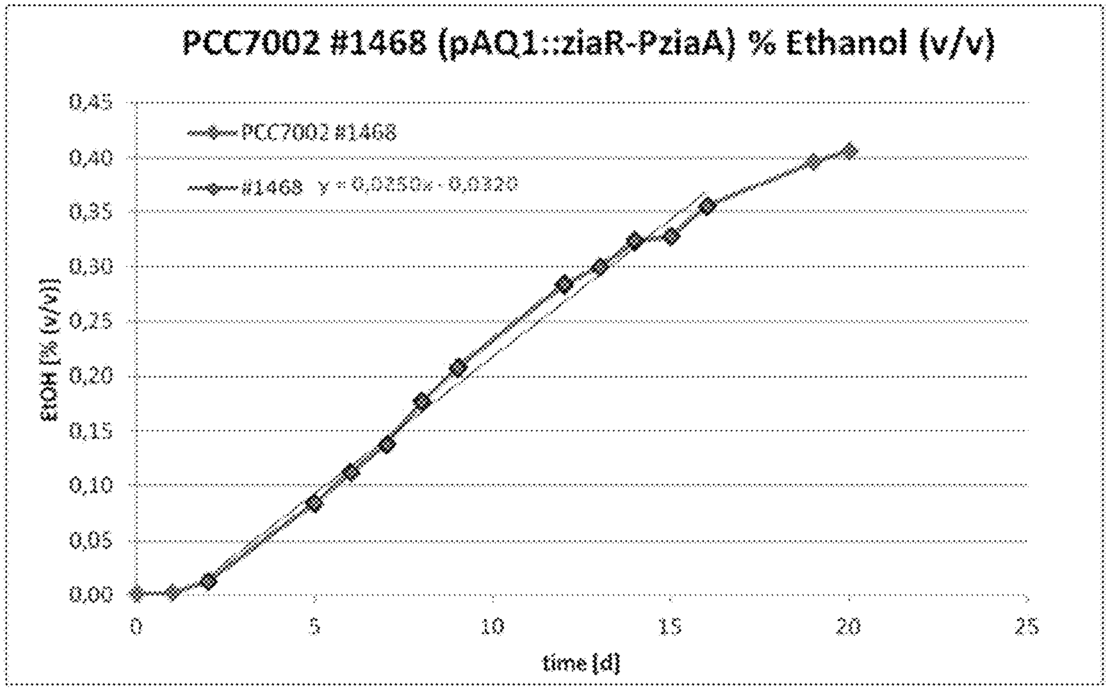
Figure 18D:
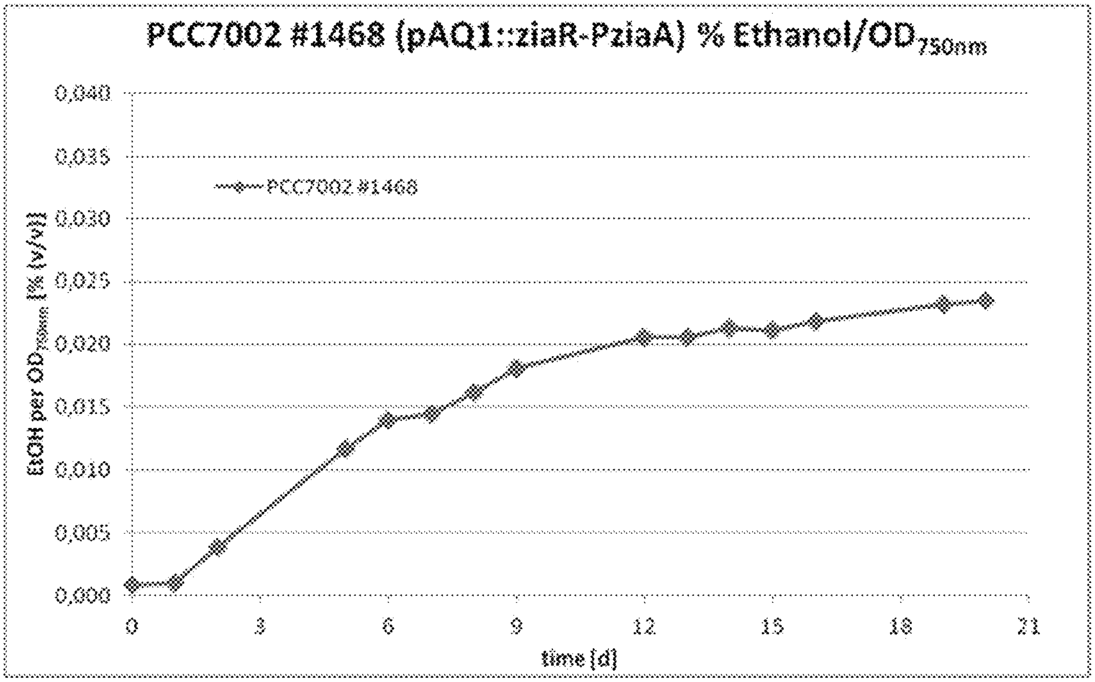
Figure 18E:
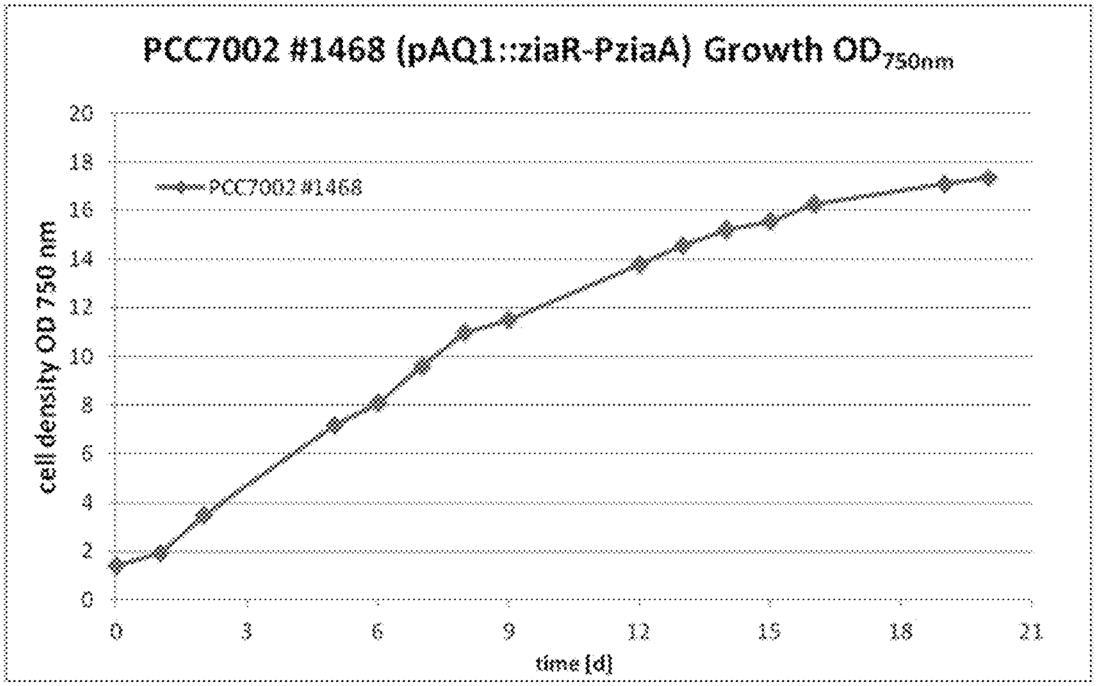
Figure 18F:
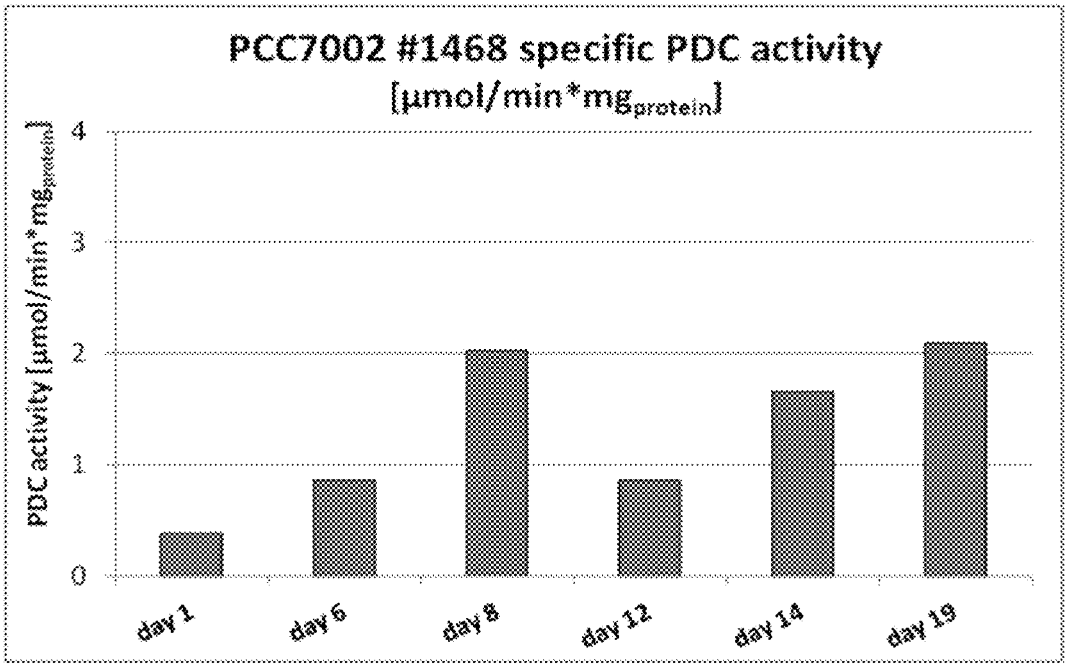

FIGS. 18A and 18B show the ethanol production over time and the specific activity of Pdc enzyme for *Synechococcus* PCC 7002 strains harboring plasmid pAQ1 into which an ethanologenic cassette including a heterologous $Zn^{2+}$-inducible promoter ziaR-PziaA from *Synechocystis* PCC 6803 was integrated via transformation with the plasmid #1468 including flanking regions as platforms for homologous recombination for integration of the ethanologenic cassette into pAQ1.

FIGS. 18C, 18D, 18E, 18F and 18 G show the ethanol production over time (v/v), the ethanol production over time (v/v) normalized to the $OD_{750}$ nm, the $OD_{750\ nm}$ and the specific Pdc activity for a 0.5 l cultivation of *Synechococcus* PCC 7002 over a time period for 19 days.

Figure 18H:
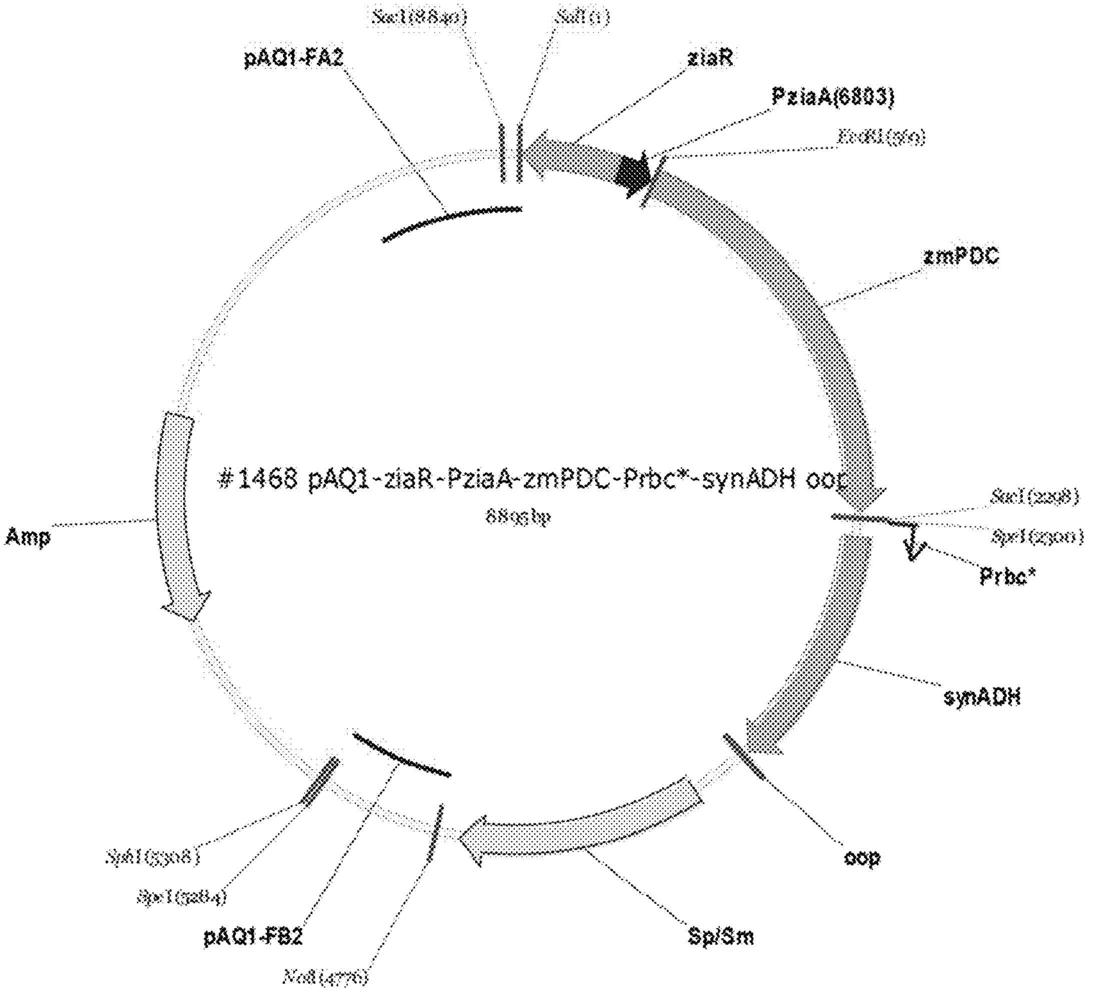

The Plasmid map of plasmid #1468 is depicted in FIG. 18H and the DNA sequence of this plasmid is included in the sequence listing as SEQ ID NO. 80.

The genes and regulatory elements included on this plasmid are as follows:

| Nucleotides | Gene/regulatory element |
|---|---|
| 573 to 2273 | zmPDC |
| 2312 to 2376 | Prbc* (optimized promoter version based on PrbcL from PCC6803) |
| 2378 to 3388 | synADH |
| 3418 to 3449 | oop |
| 4776 to 5283 | pAQ1-FB2 |
| Antisense 6151 to 7008 | Amp |
| 8225 to 8895 | pAQ1-FA2 |
| 3664 to 4672 | Sp/Sm |
| Antisense 10 to 408 | ziaR |
| 416 to 559 | PziaA(6803) |

Figure 19A:
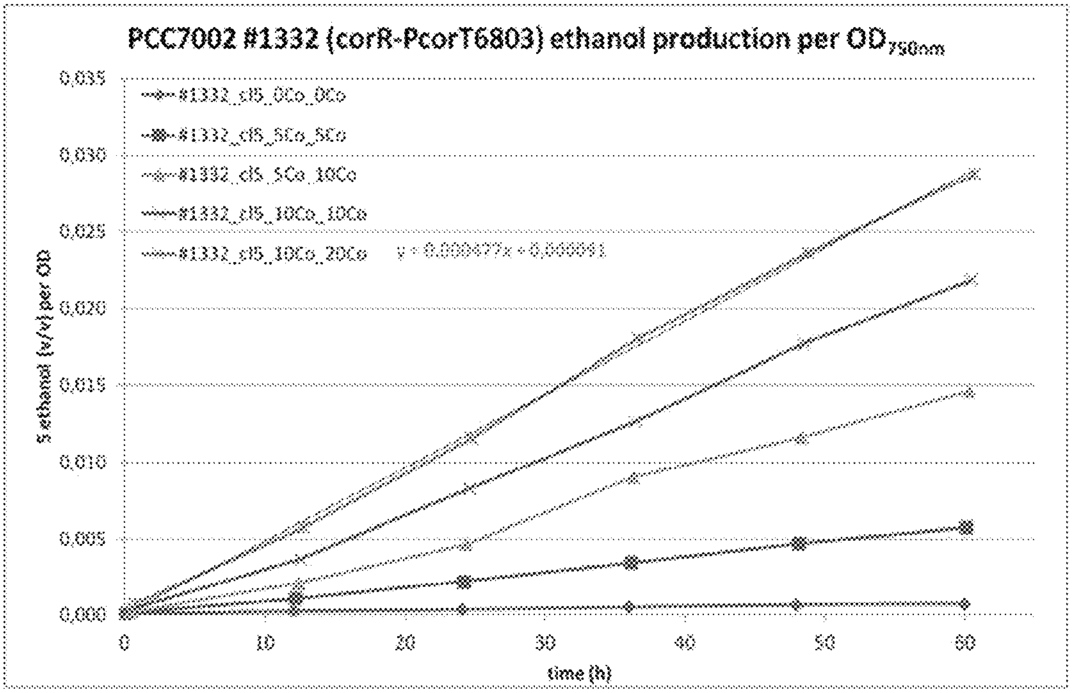

FIG. 19A depicts the ethanol production over time (v/v) at different induction conditions normalized to the $OD_{750\ nm}$ determined by the GC vial assay (multiple GC measurements over time sampled from an illuminated GC vial filled with culture) for *Synechococcus* PCC 7002 transformed with the plasmid #1332 for integration of the ethanologenic cassette with the $Co^{2+}$-inducible promoter corR-PcorT into the endogenous plasmid pAQ4.

Figure 19B:
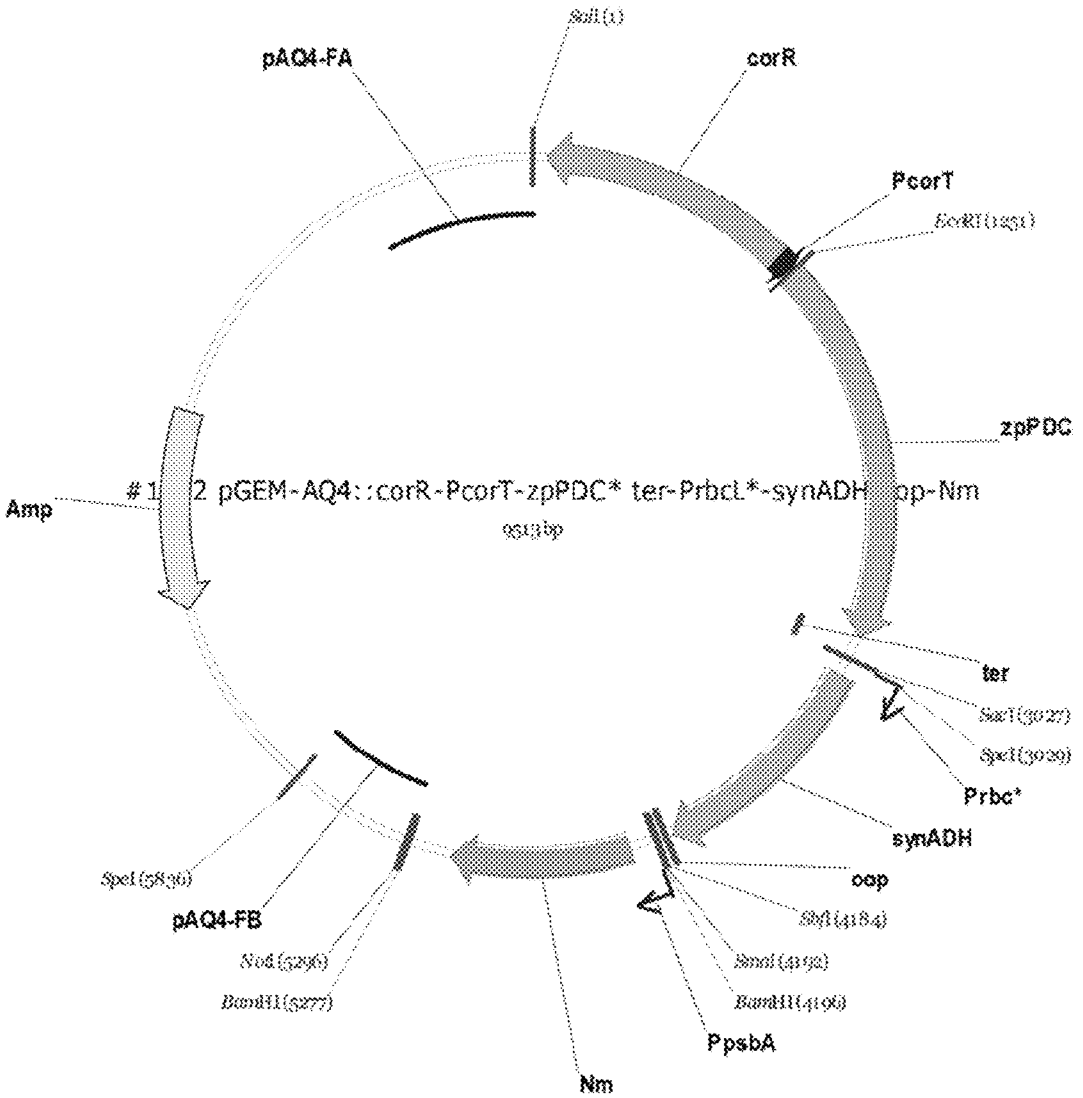

FIG. 19B depicts the plasmid map of plasmid #1332, whose nucleic acid sequence is given as SEQ ID NO. 81. The location of genes and regulatory elements on this plasmid is as follows:

| Nucleotides | Gene/regulatory element |
|---|---|
| 2925 . . . 3021 | native terminator of zpPDC |
| 1251 . . . 2924 | zpPDC |
| 1167 . . . 1249 | PcorT |
| complement(57 . . . 1166) | corR |
| 4147 . . . 4178 | oop |
| 3107 . . . 4117 | synADH |
| 3041 . . . 3105 | Prbc* |
| 8777 . . . 9513 | pAQ4-FA |
| complement(6703 . . . 7560) | Amp |
| 4308 . . . 5089 | Neomycin resistance cassette (Nm) |
| 4208 . . . 4268 | PpsbA (psbA promoter from *Amaranthus hybridus*) |
| 5296 . . . 5835 | pAQ4-FB |

Figure 20A:
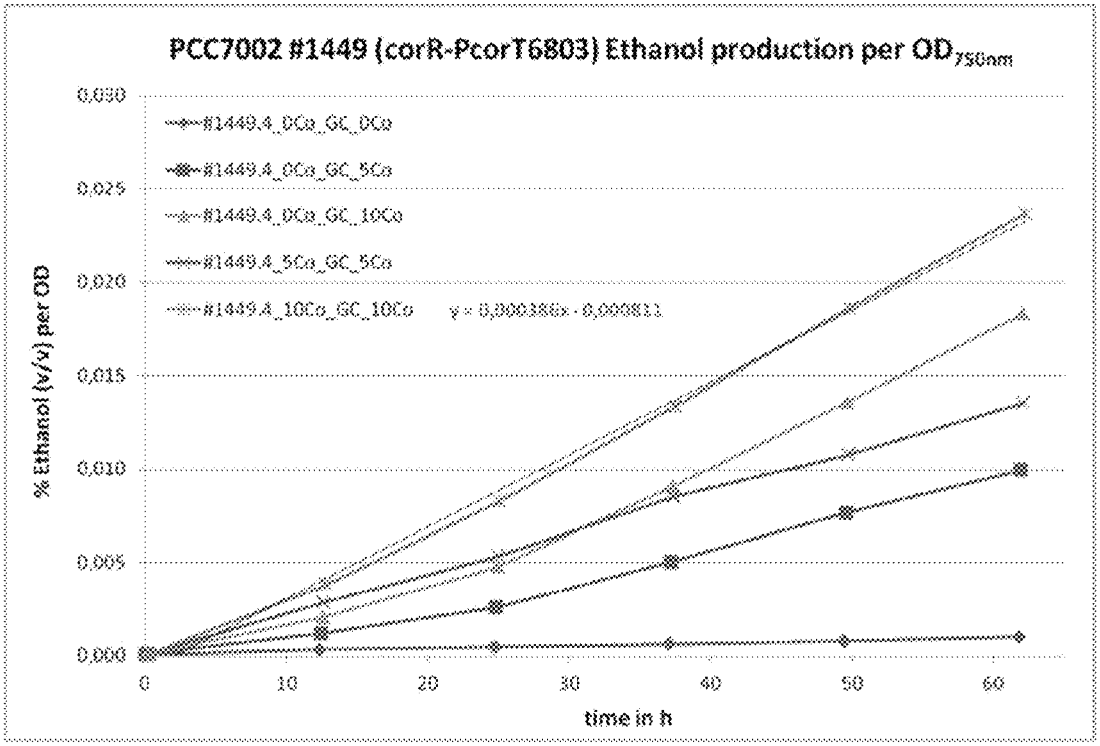
Figure 20B:
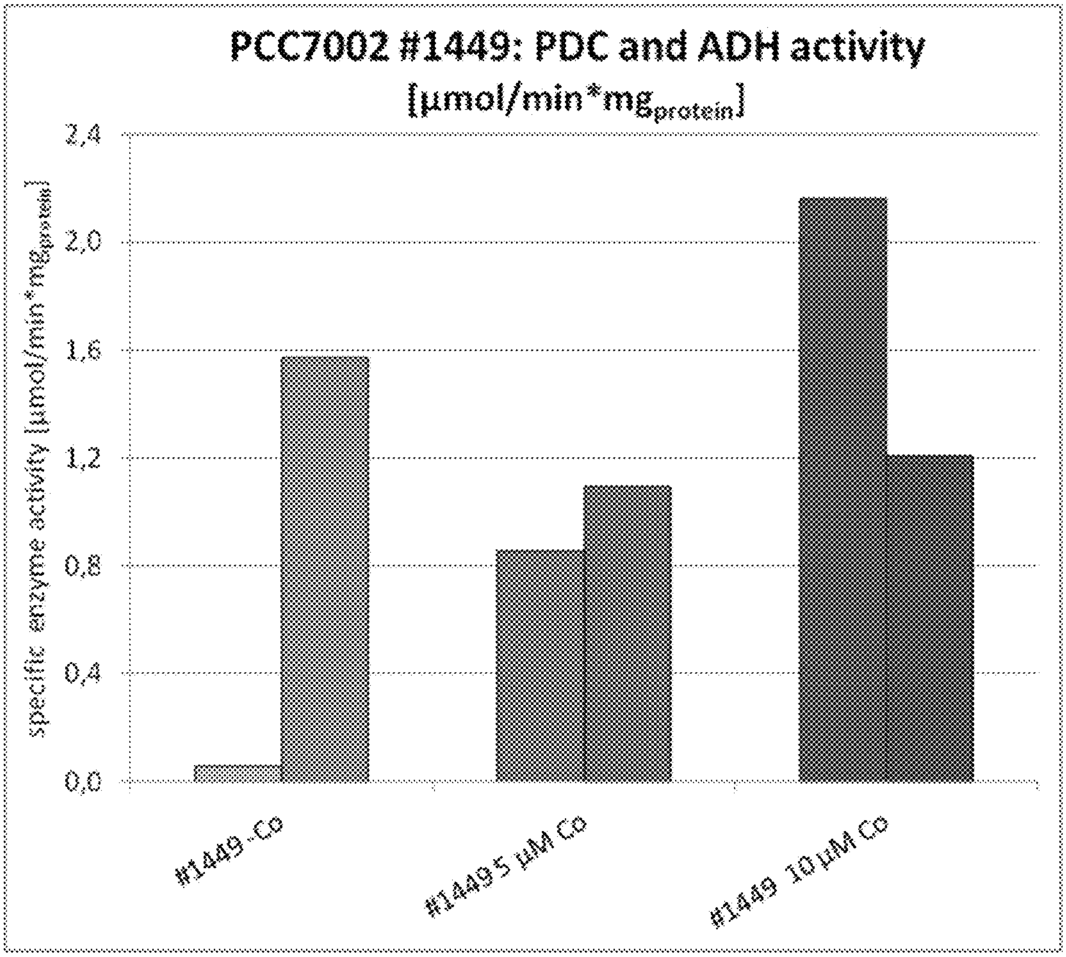
Figure 20C:
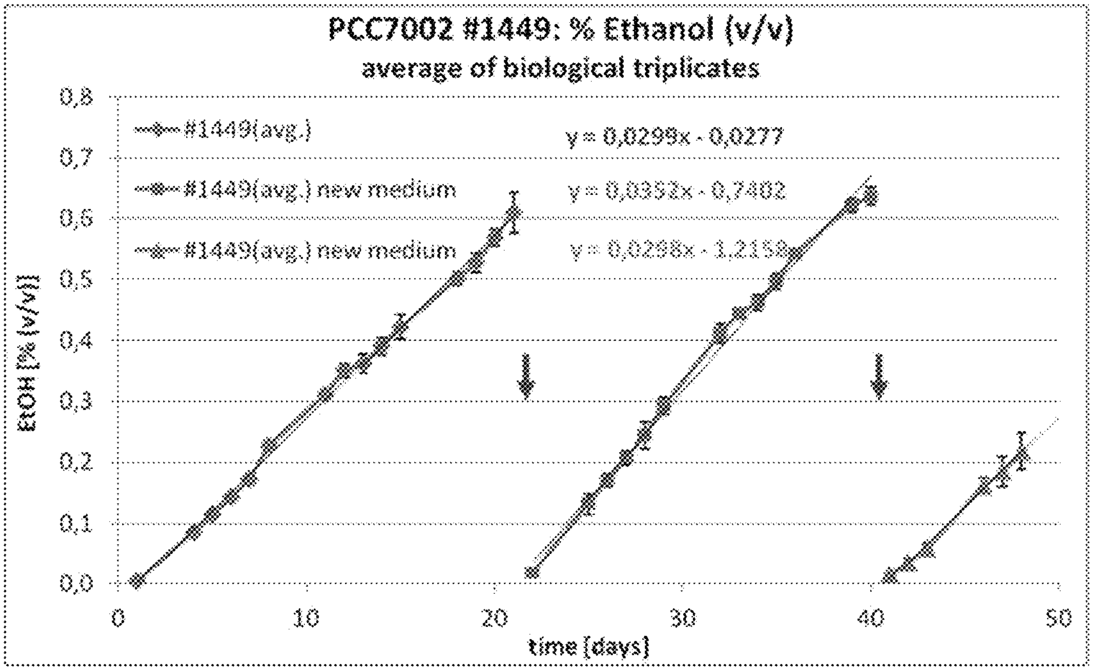
Figure 20D:
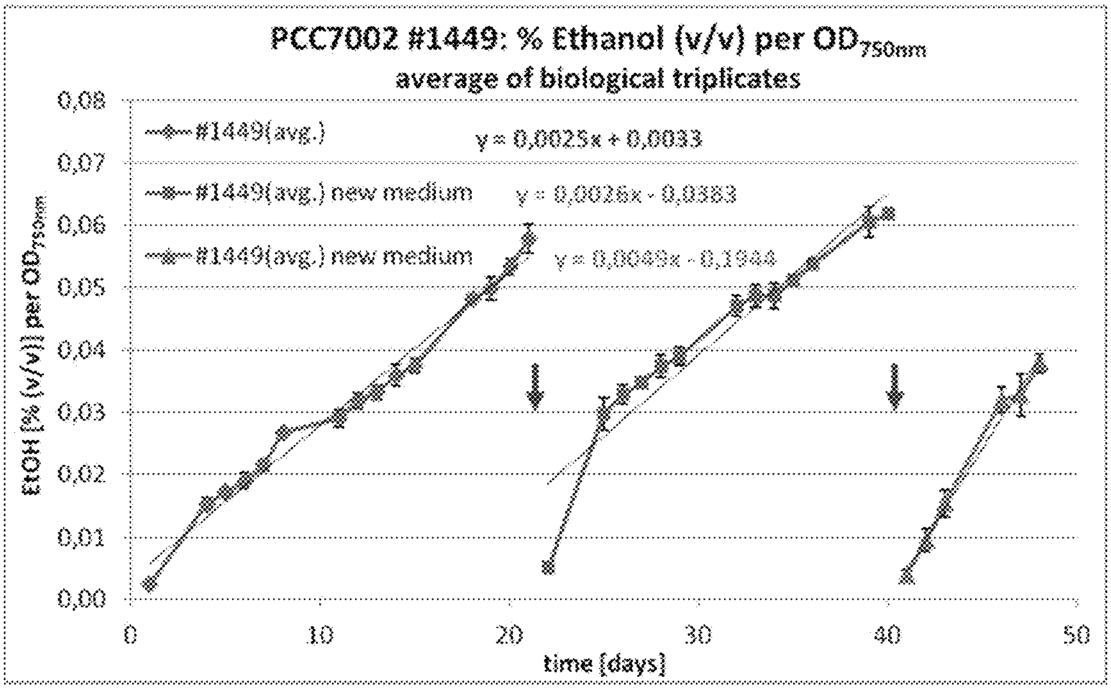
Figure 20E:
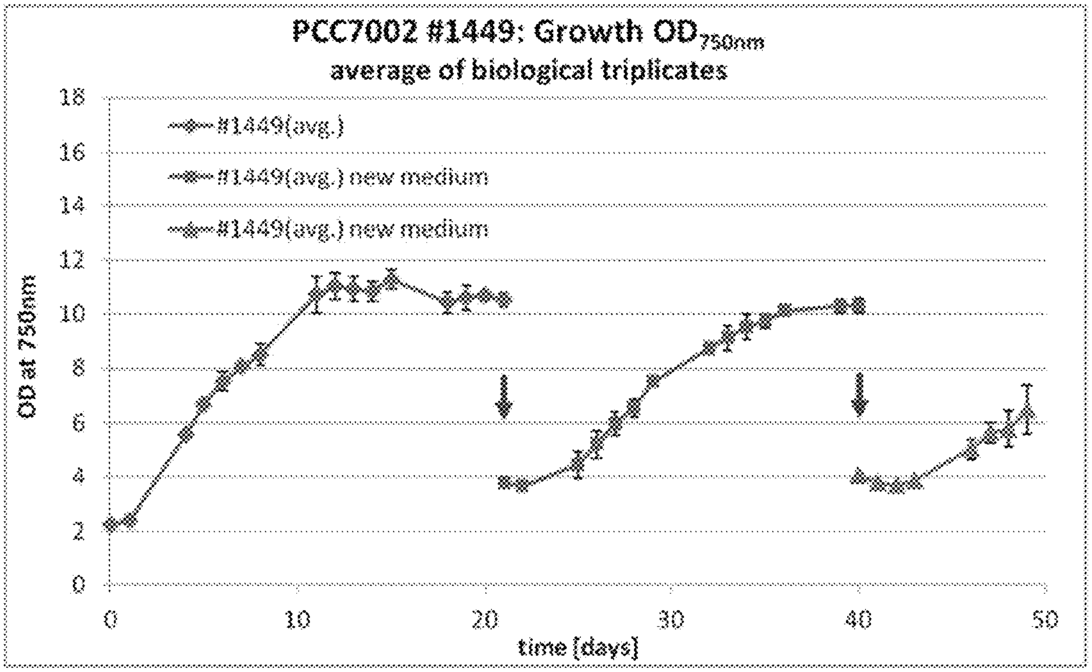
Figure 20F:
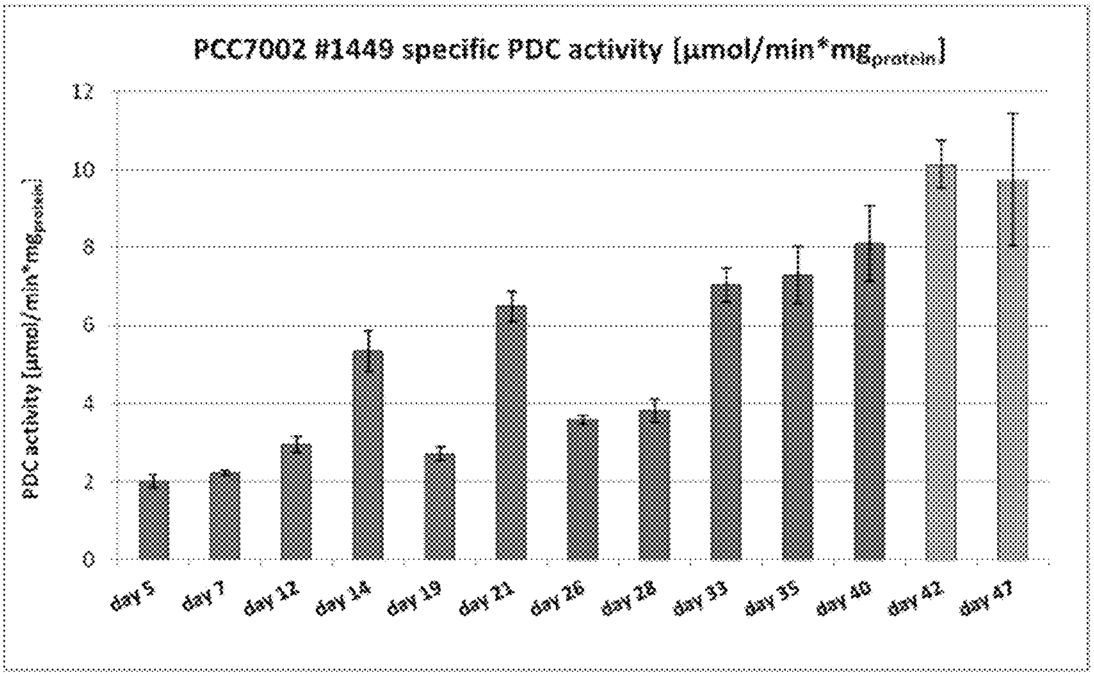

FIGS. 20A and 20B depict the ethanol production over time (v/v) at different induction conditions normalized to the $OD_{750\ nm}$ and the specific Adh and Pyruvate decarboxylase activities for cultivation over a time period of about 60 hours.

The FIGS. 20C, 20D, 20E, and 20F show the ethanol production over time (v/v), the ethanol production over time (v/v) normalized to the $OD_{750\ nm}$, the growth as $OD_{750\ nm}$, and the specific activity of Pdc enzyme for a cultivation of a *Synechococcus* strain in 0.5 l bioreactors over a time period of 50 days.

Figure 20G:
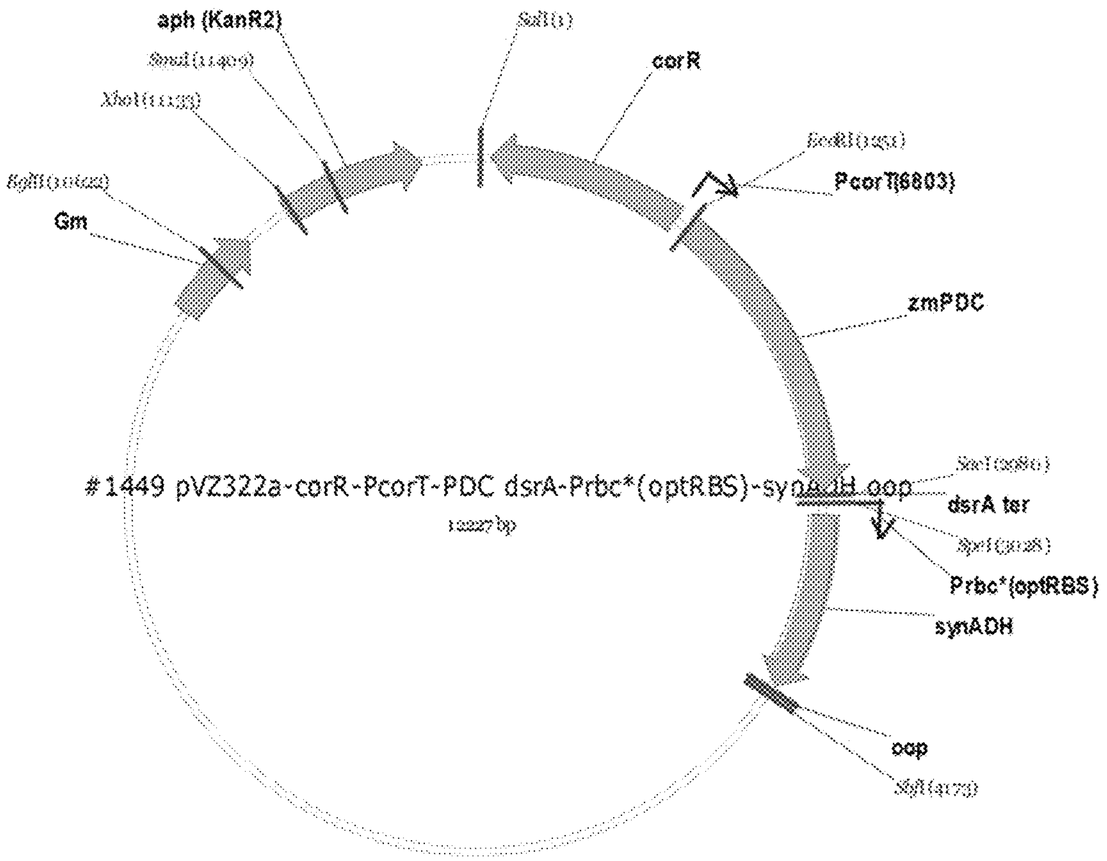

The plasmid map of plasmid #1449 is shown in FIG. 20G and its nucleic acid sequence is SEQ ID NO. 82. The location of genes on this plasmid is as follows:

| Nucleotides | Gene/regulatory element |
|---|---|
| 4136 to 4166 | oop |
| 3096 to 4106 | synADH |
| 10308 to 10838 | Gm |
| 1255 to 2955 | zmPDC |
| 2981 to 3026 | dsrA terminator |
| Antisense 57 to 1166 | corR |
| 1167 to 1249 | PcorT(6803) |
| 11103 to 11917 | aph\(KanR2) |
| 3027 to 3095 | Prbc*(optRBS) (improved version of rbcL(6803) promoter with optimized RBS) |

Figure 21A:
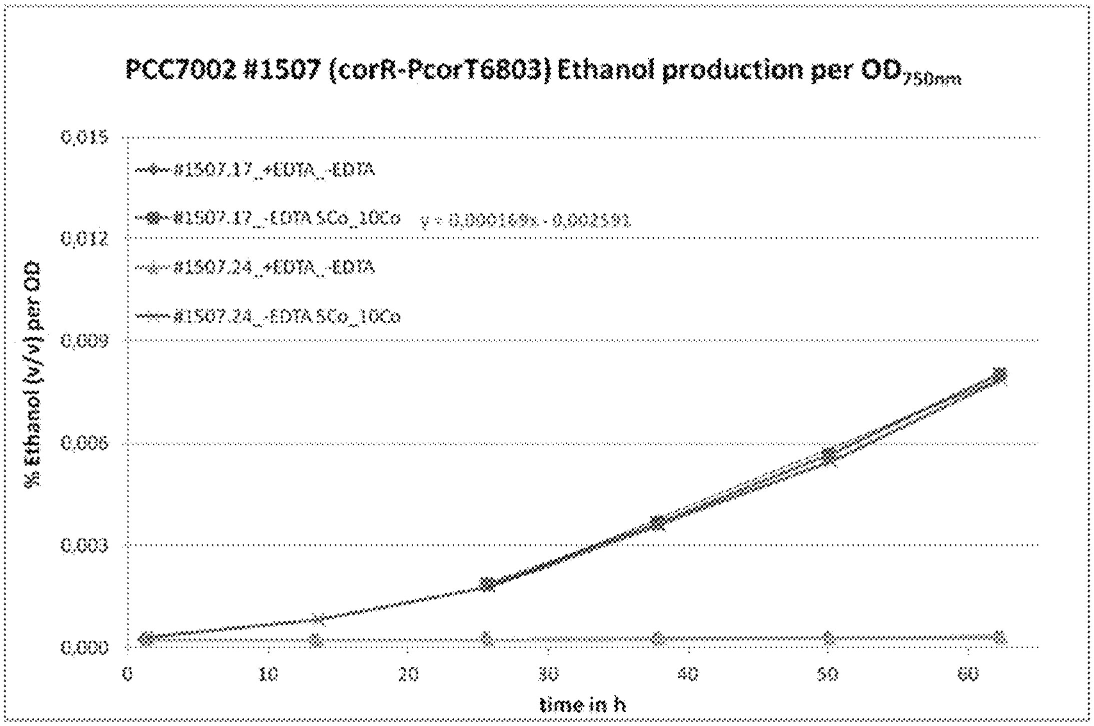
Figure 21B:
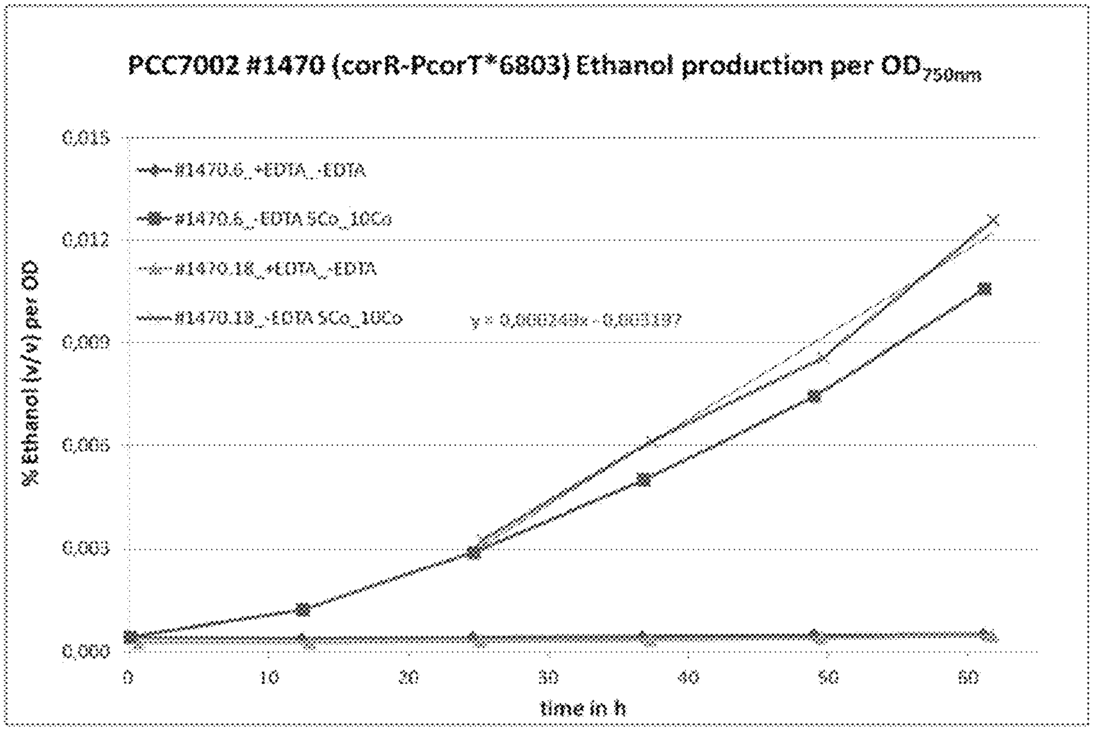

FIGS. 21A and 21B show the ethanol production (v/v) normalized to the $OD_{750\ nm}$ for a *Synechococcus* PCC 7002 strain transformed with two different plasmids #1507 and #1470.

Figure 21C:
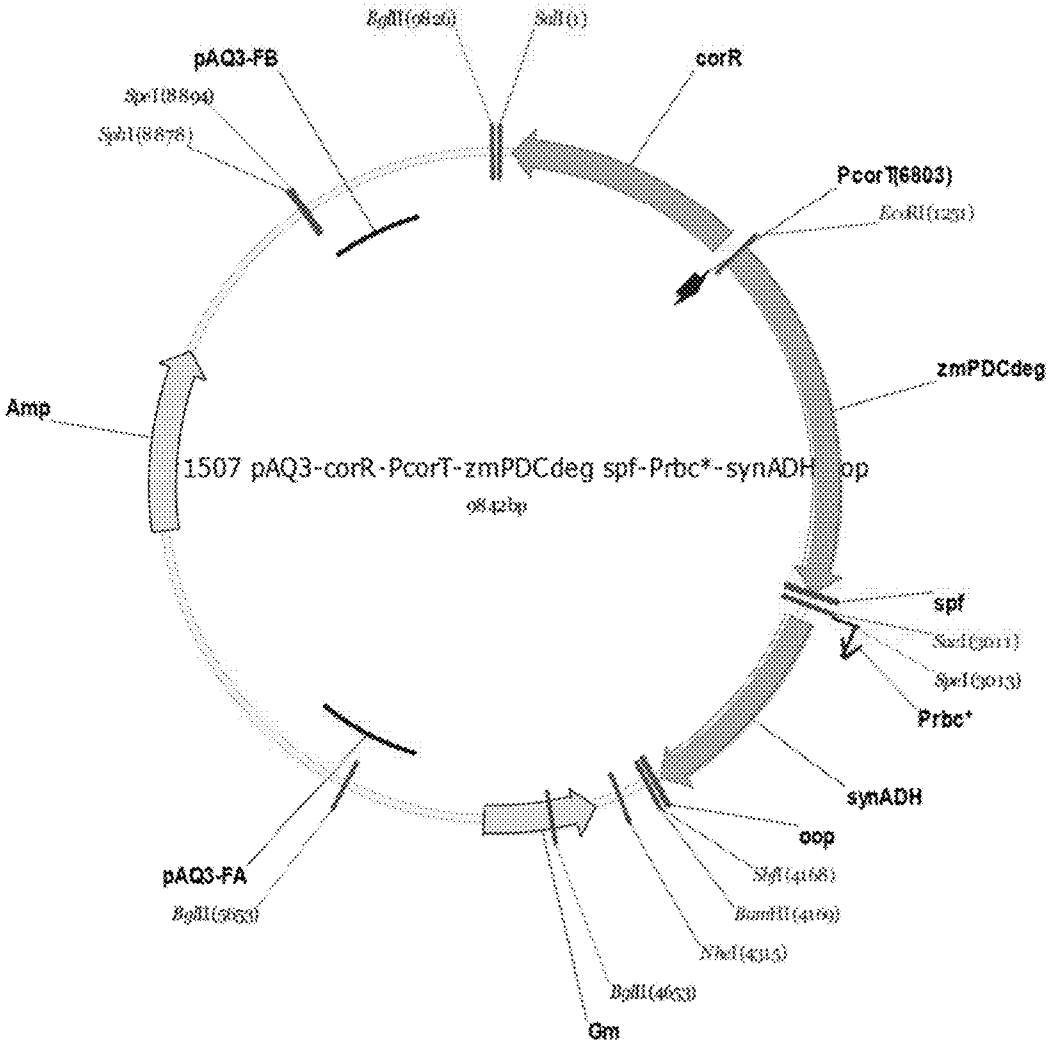
Figure 21D:
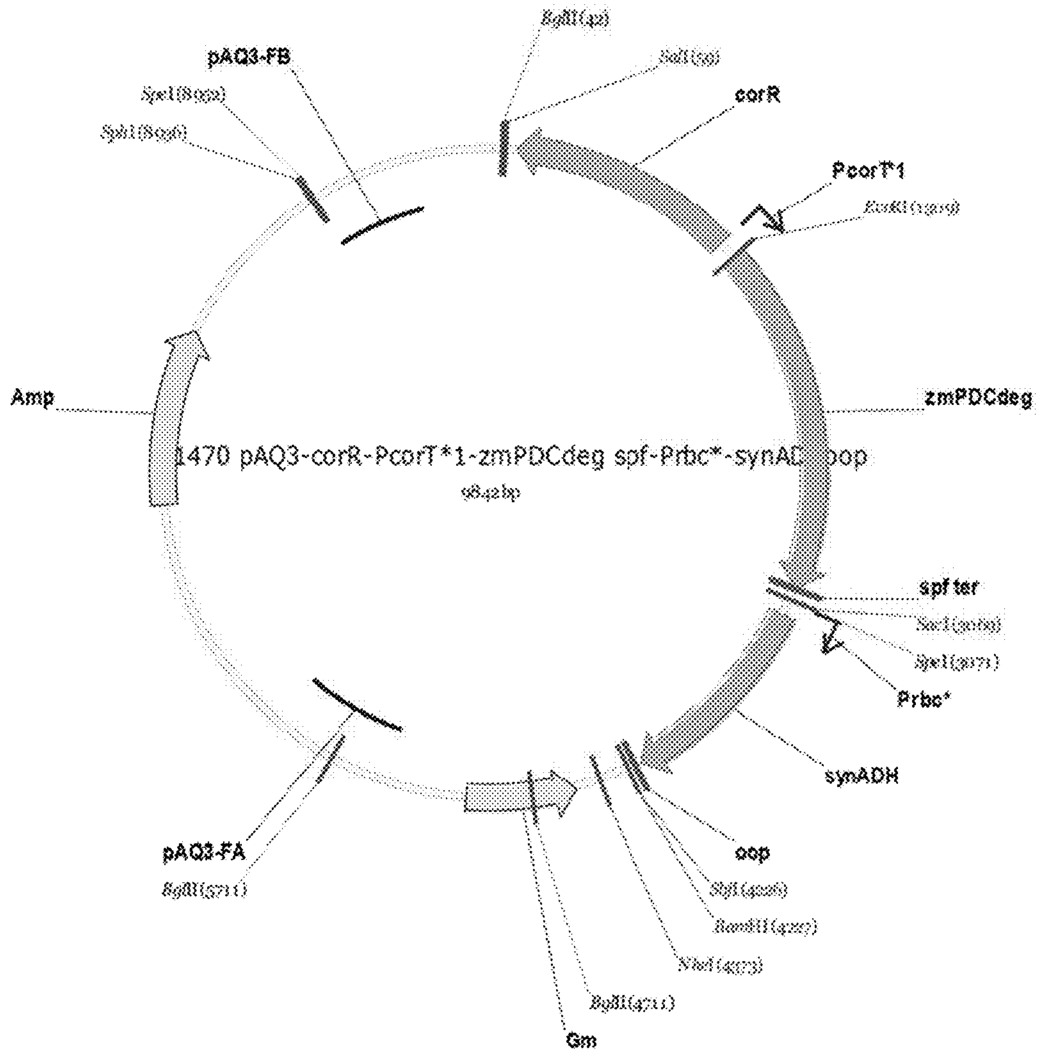
Figure 21E:
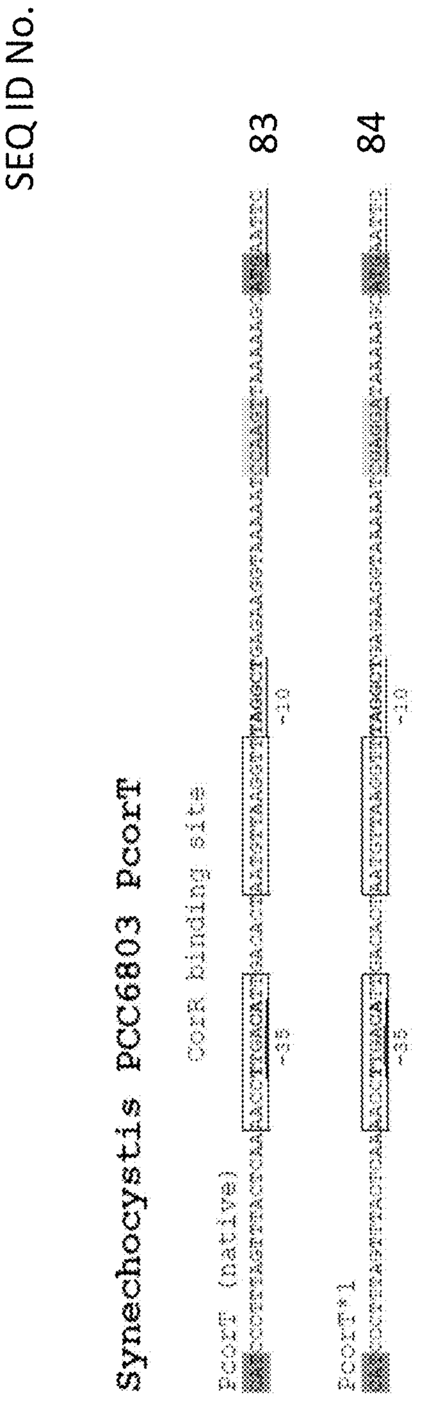

FIGS. 21C and 21D depict the plasmid maps of plasmids #1507 and 1470. FIG. 21E shows a comparison of the native corT and the modified corT*1 promoter including 5'- and 3'-neighboring nucleic acid sequences with restriction sites and start codons for genes transcriptionally controlled by the promoter. The nucleic acid sequence of plasmid #1507 is included in the sequence listing as SEQ ID NO. 83. SEQ ID NO. 84 shows the DNA sequence of the PcorT* promoter.

The location of genes and regulatory elements on the plasmid #1507 is as follows:

| Nucleotides | Gene/regulatory element |
|---|---|
| Antisense 4437 to 4970 | Gentamycin resistance cassette (Gm) |
| Antisense 5388 to 5956 | pAQ3-FA |
| 7173 to 8030 | Ampicillin resistance cassette (Amp) |
| Antisense 8898 to 9390 | pAQ3-FB |
| 4131 to 4162 | oop |
| 3091 to 4101 | synADH |
| 3025 to 3089 | Prbc*(improved version of rbcL promoter from PCC6803) |
| 2958 to 3005 | spf terminator (*E. coli*) |
| Antisense 57 to 1166 | corR |
| 1167 to 1249 | PcorT(6803) |
| 1248 to 2954 | zmPDCdeg |

Figure 22A:
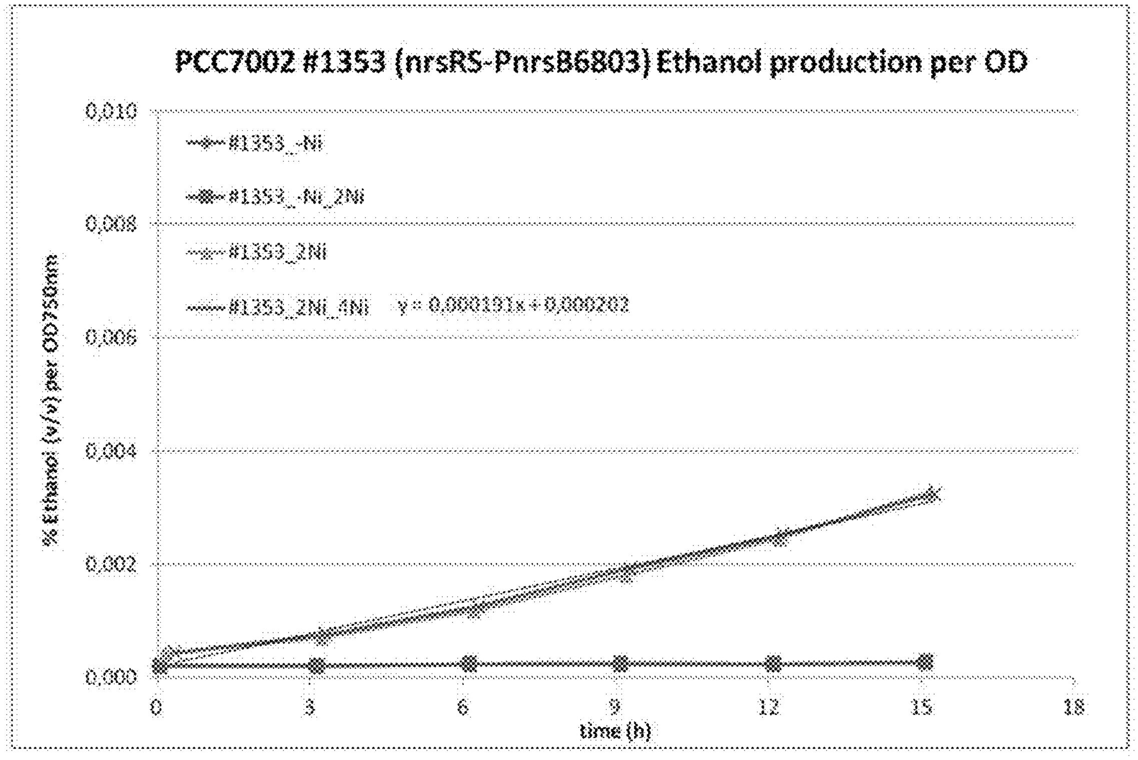
Figure 22B:
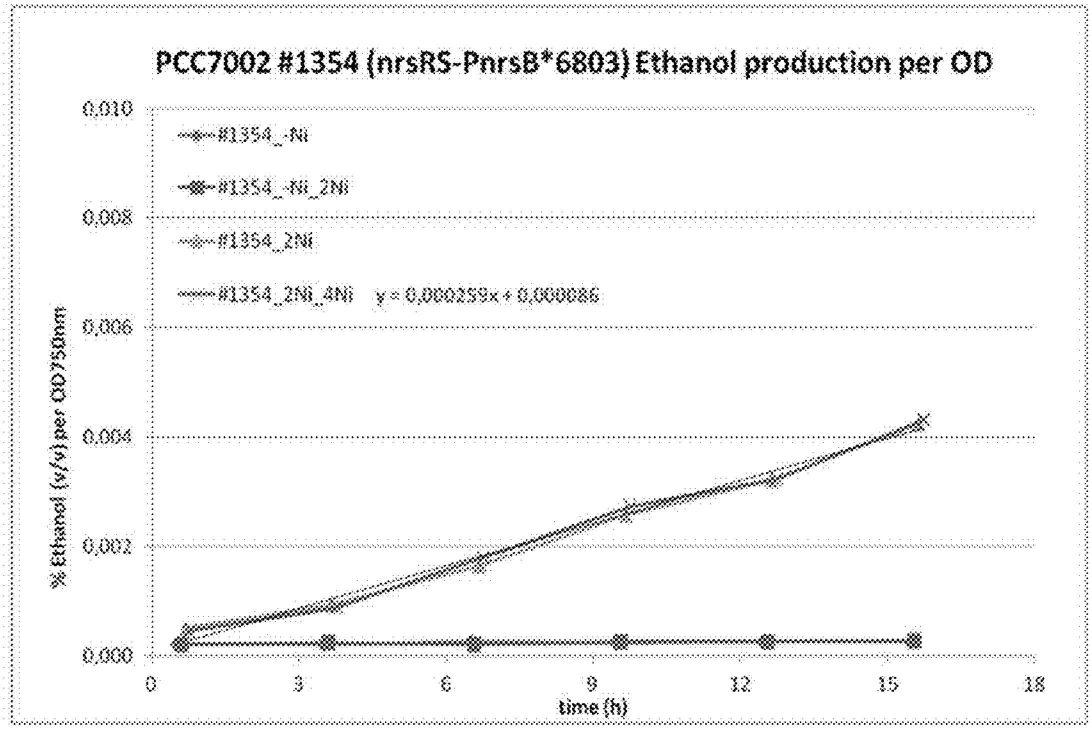

FIGS. 22A and 22B show the ethanol production (v/v) normalized to the $OD_{750\ nm}$ for *Synechococcus* PCC 7002 strains transformed with pVZ322 based extrachromosomal plasmids #1353 and #1354. The only difference between both plasmids are modifications in the ribosomal binding site of the heterologous $Ni^{2+}$-inducible promoter PnrsB from *Synechocystis* PCC 6803 in plasmid #1354 resulting in the promoter PnrsB* controlling the transcription of the pdc gene. By introducing these specific nucleotide substitutions into the ribosomal binding site of the nrsR promoter in construct #1354 (nrsRS-PnrsB*) the ethanol production rate was increased by 35% compared to the native nrsRS-PnrsB promoter from PCC6803 (strain transformed with #1353). However compared to *Synechococcus* PCC7002 strains with $Co^{2+}$ or $Zn^{2+}$ inducible promoter systems (e.g. #1449 and #1121), the ethanol production rate is still below 50%. The tight repression behavior of the nrsRS-PnrsB promoter in *Synechococcus* PCC7002 is not negatively influenced by the nucleotide substitutions introduced into PnrsB*.

Figure 22C:
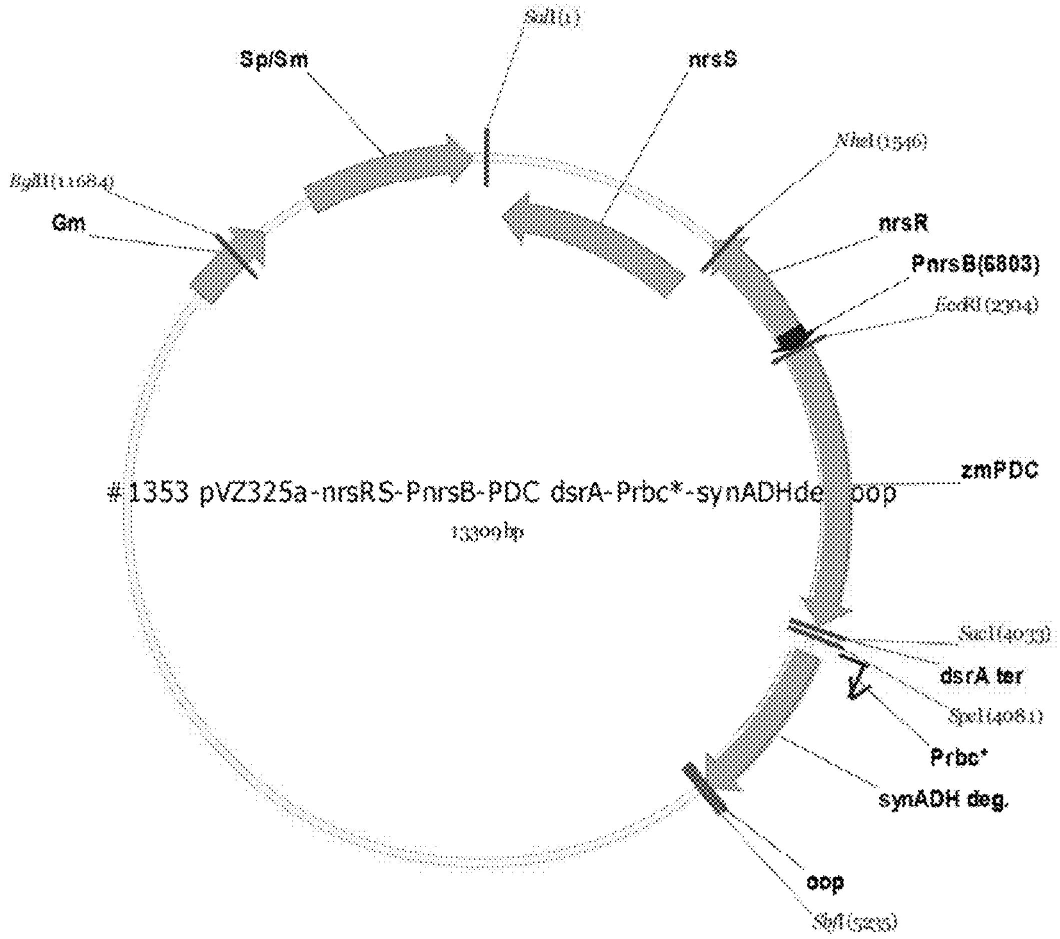
Figure 22D:
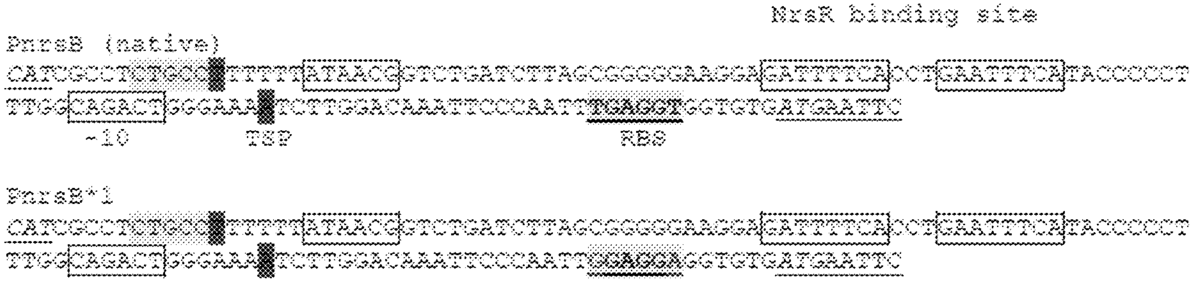

FIG. 22C depicts the plasmid map of plasmid #1353, whose nucleotide sequence is included in the sequence listing as SEQ ID NO. 85. FIG. 22D shows the differences in the nucleic acid sequence in the ribosomal binding site (RBS) between the native PnrsB and the modified PnrsB*1. The nucleic acid sequence of the modified promoter PnrsB* is included as SEQ ID NO. 86.

The location of the genes in plasmid #1353 is a follows:

| Nucleotides | Gene/regulatory element |
|---|---|
| Antisense 1476 to 2179 | nrsR |
| 2180 to 2300 | PnrsB(6803) |
| Antisense 117 to 1478 | nrsS |
| 4187 to 5197 | $synADH_{deg}$ |
| 5198 to 5228 | oop |
| 4034 to 4079 | dsrA ter |
| 2308 to 4008 | zmPDC |
| 12238 to 13248 | Sp/Sm |
| 11370 to 11900 | Gm |
| 4121 to 4185 | Prbc* (improved version of rbcL promoter from PCC6803) |

Figure 23A:
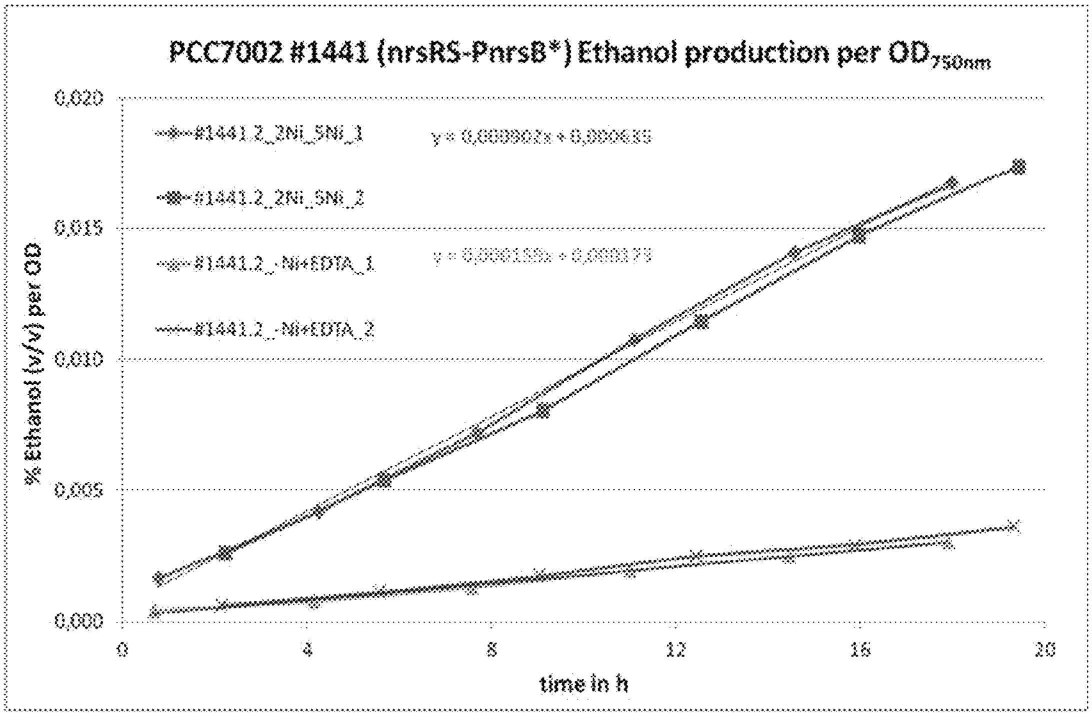
Figure 23B:
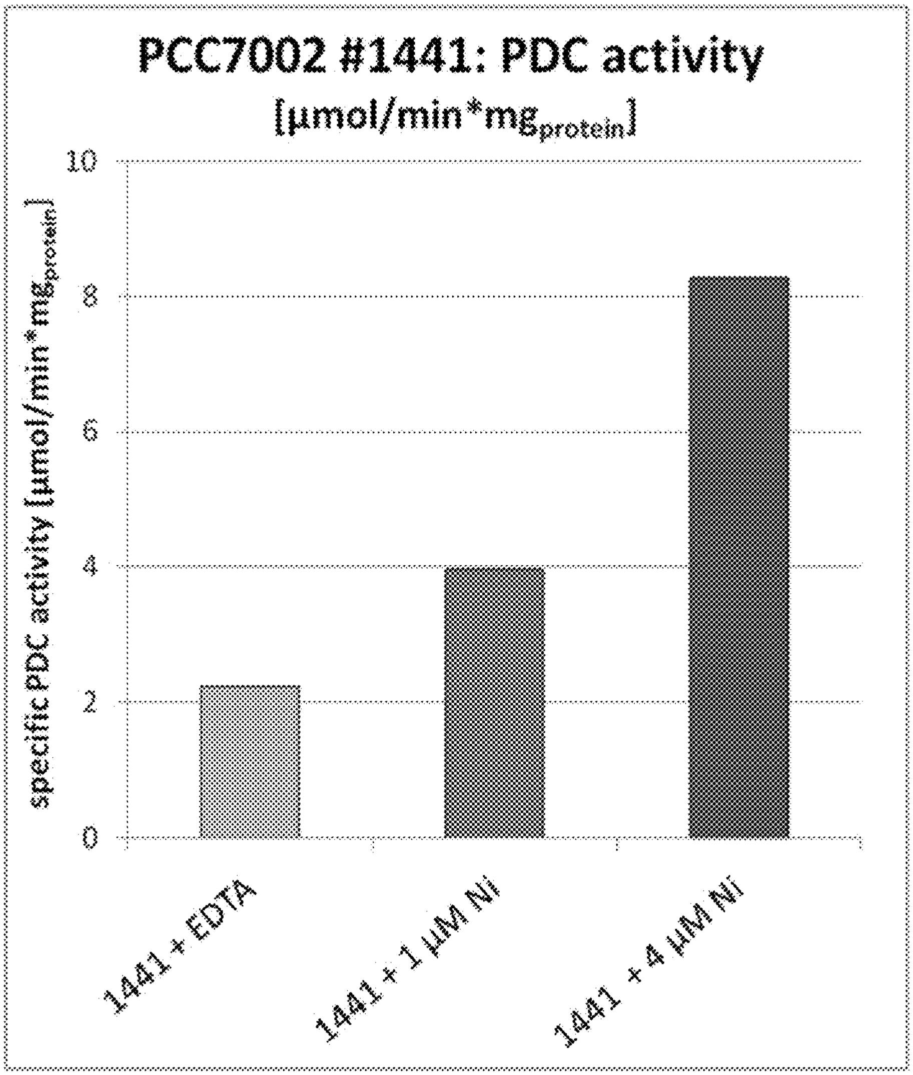

FIGS. 23A and 23B show the ethanol production (v/v) normalized to the $OD_{750\ nm}$ and the Pdc enzyme activity for *Synechococcus* PCC 7002 strains including an ethanologenic cassette integrated into the endogenous plasmid pAQ1 with a pdc gene transcriptionally controlled by a heterologous $Ni^{2+}$-inducible promoter from *Synechocystis* PCC 6803.

Figure 23C:
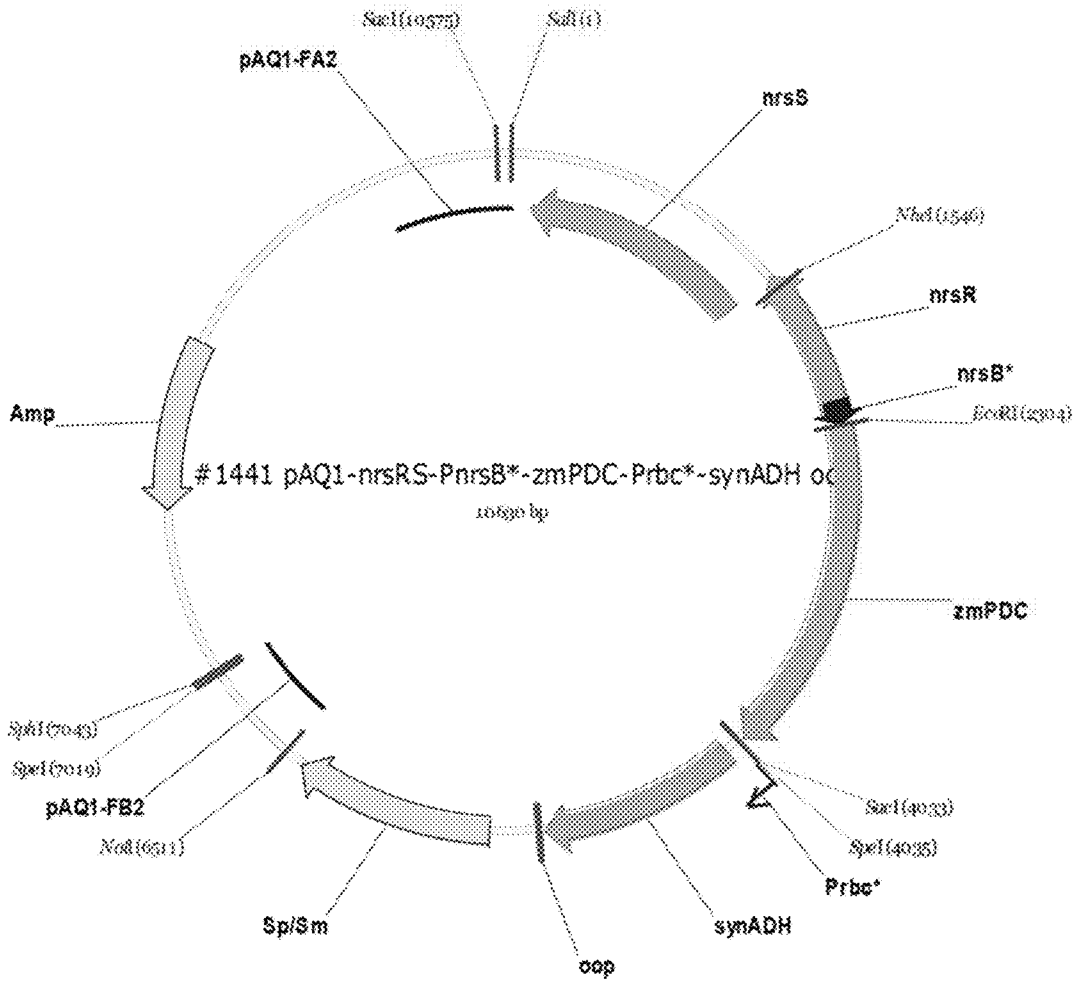

The plasmid map of the integrative plasmid #1441 is shown in FIG. 23C and its nucleic acid sequence is listed as SEQ ID NO. 87.

The location of genes and regulatory elements on the plasmid #1441 is as follows:

| Nucleotides | Gene/regulatory element |
|---|---|
| 5399 to 6407 | Sp/Sm |
| 2180 to 2300 | nrsB* |
| Antisense 1476 to 2179 | nrsR |
| Antisense 117 to 1478 | nrsS |
| 9960 to 10630 | pAQ1-FA2 |
| Antisense 7886 to 8743 | Amp |
| 6511 to 7018 | pAQ1-FB2 |
| 5153 to 5184 | oop |
| 4113 to 5123 | synADH |
| 4047 to 4111 | Prbc* |
| 2308 to 4008 | zmPDC |

Figure 24A:
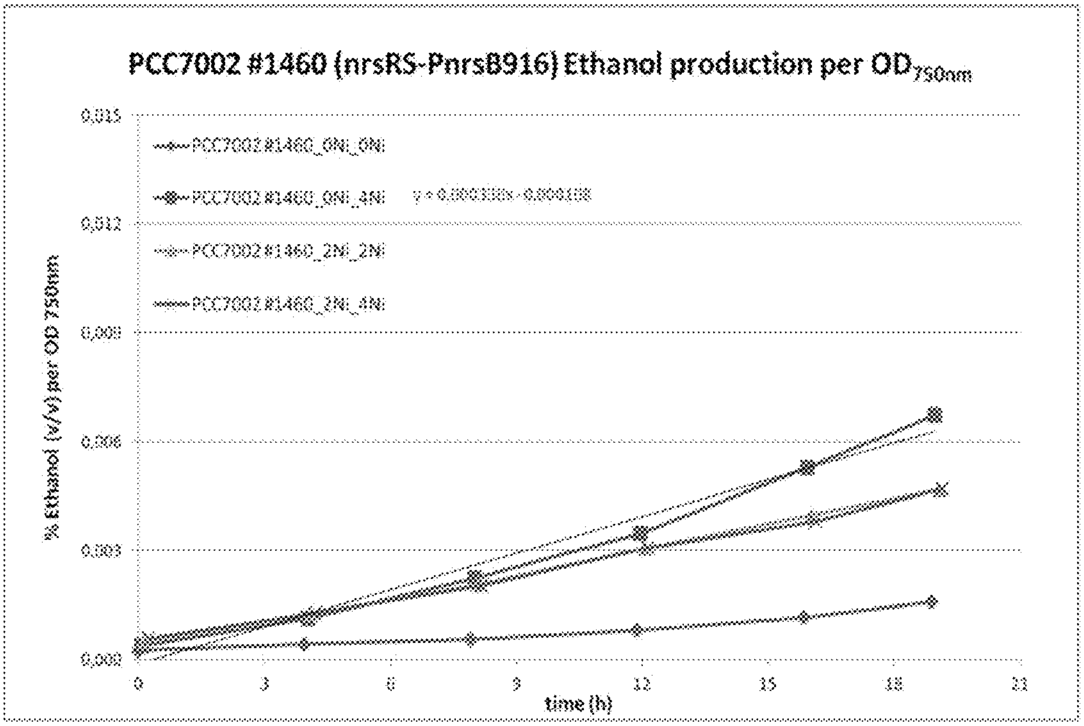
Figure 24B:
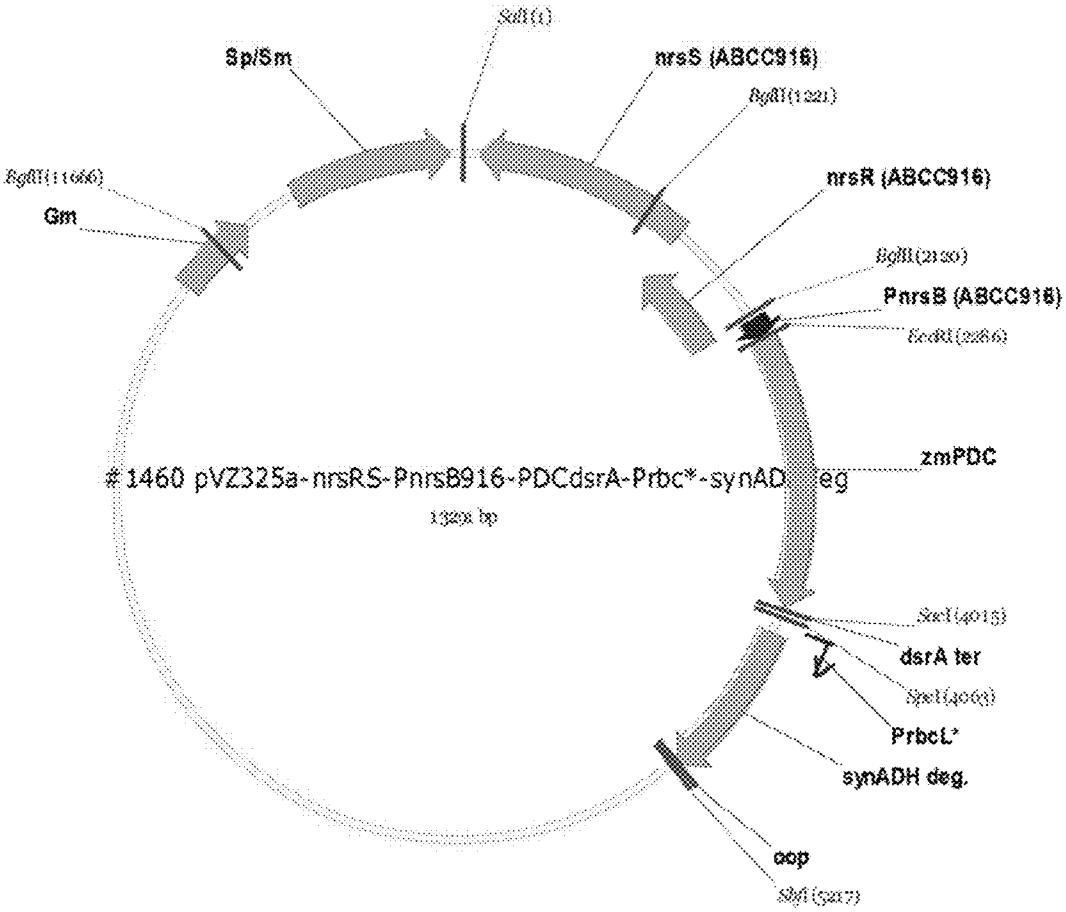

FIGS. 24A and 24B show the ethanol production normalized to the $OD_{750\ nm}$ of a *Synechococcus* strain transformed with the plasmid #1460 and the plasmid map of this extrachromosomal plasmid, respectively. In plasmid #1460 the pdc is transcriptionally controlled by a heterologous $Ni^{2+}$-inducible promoter from a *Synechococcus* species which is close related to *Synechococcus* PCC7003. The nucleic acid sequence of plasmid #1460 is presented as SEQ ID NO. 88.

The location of the genes and regulatory elements on the plasmid #1460 is as follows:

| Nucleotides | Gene/regulatory element |
|---|---|
| complement (100 . . . 1461) | nrsS |
| complement (1458 . . . 2153) | nrsR |
| 2154 . . . 2282 | PnrsB |
| 4169 . . . 5179 | $synADH_{deg}$. |
| 5180 . . . 5210 | oop |
| 4016 . . . 4061 | dsrA ter |
| 2290 . . . 3990 | zmPDC |
| 12220 . . . 13230 | Sp/Sm |
| 11352 . . . 11882 | Gm |
| 4103 . . . 4167 | PrbcL* |

Figure 25A:
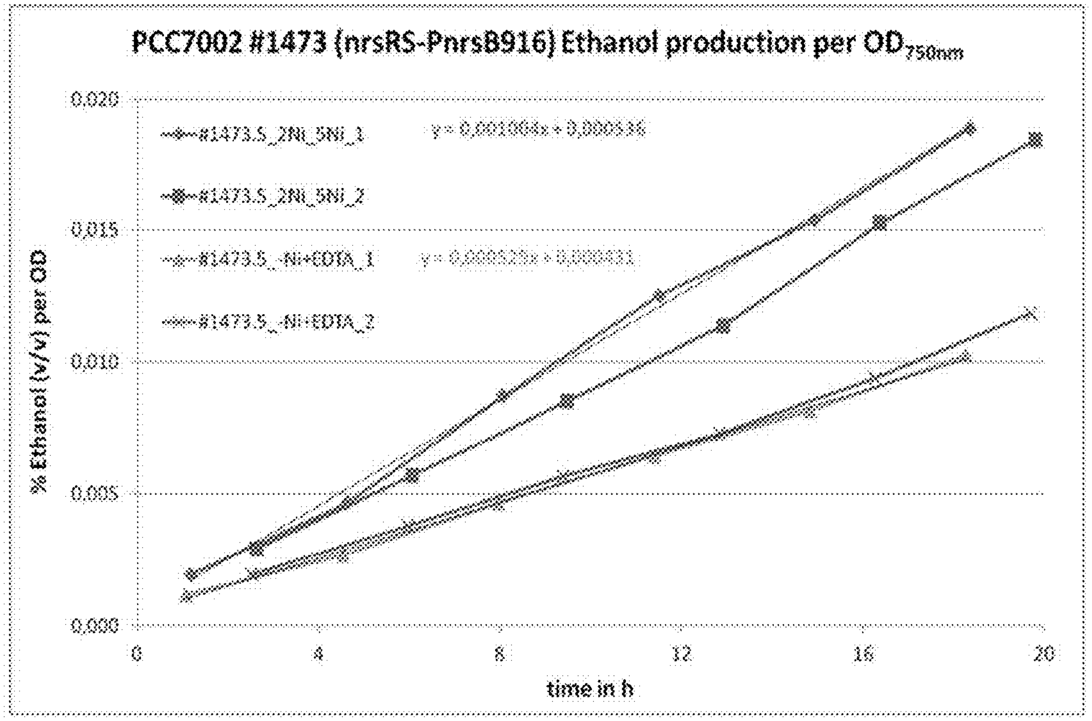
Figure 25B:
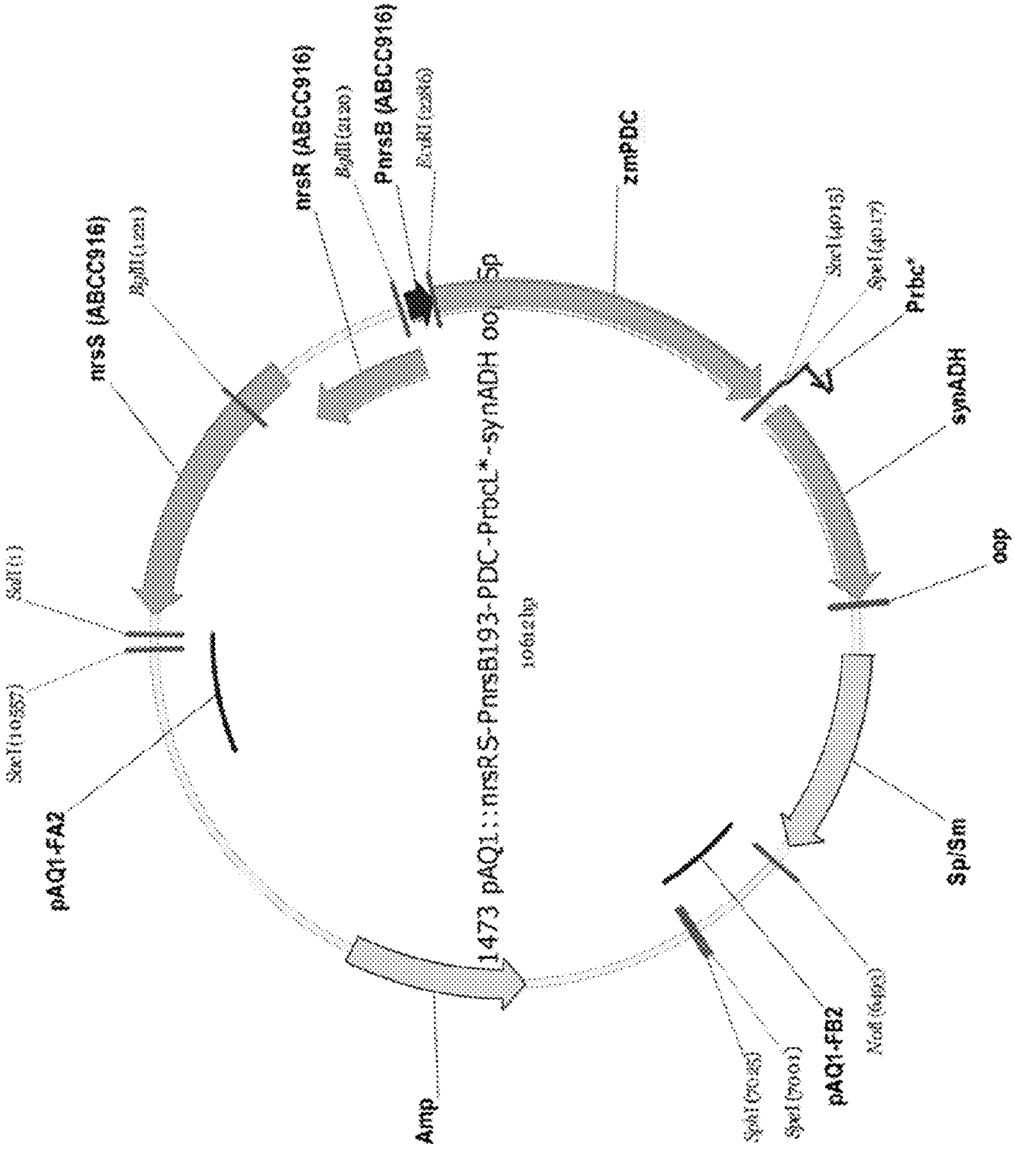

FIGS. 25A and 25B show the ethanol production normalized to the $OD_{750\ nm}$ of a *Synechococcus* strain transformed with the plasmid #1473 for integration into the endogenous plasmid pAQ1 and the plasmid map of this integrative plasmid, respectively. The nucleic acid sequence of plasmid #1473 is shown as SEQ ID NO. 89.

The location of the genes and regulatory elements on the plasmid #1473 is as follows:

| Nucleotides | Gene/regulatory element |
|---|---|
| Antisense 100 to 1461 | nrsS |
| antisense 1458 to 2153 | nrsR |
| 2154 to 2282 | PnrsB |
| 2290 to 3990 | zmPDC |
| 4029 to 4093 | Prbc* |
| 4095 to 5105 | synADH |
| 5135 to 5166 | oop |
| 6493 to 7000 | pAQ1-FB2 |
| 9942 to 10612 | pAQ1-FA2 |
| 5381 to 6389 | Sp/Sm |

DETAILED DESCRIPTION OF CERTAIN EMBODIMENTS OF THE INVENTION

In the following, certain embodiments of the invention pertaining to PziaA as one example for a $Zn^{2+}$-inducible promoter also in conjunction with ziaR as one example for a first control gene in comparison to prior art promoter systems will be discussed. Other embodiments are concerned with the transcriptional control of first and second recombinant genes coding for Pdc enzyme and Adh enzyme by $Co^{2+}$ oder $Ni^{2+}$ inducible promoters in various cyanobacteria. The concrete embodiments result in the generation of ethanol as one example of a first chemical compound.

Figure 2C:
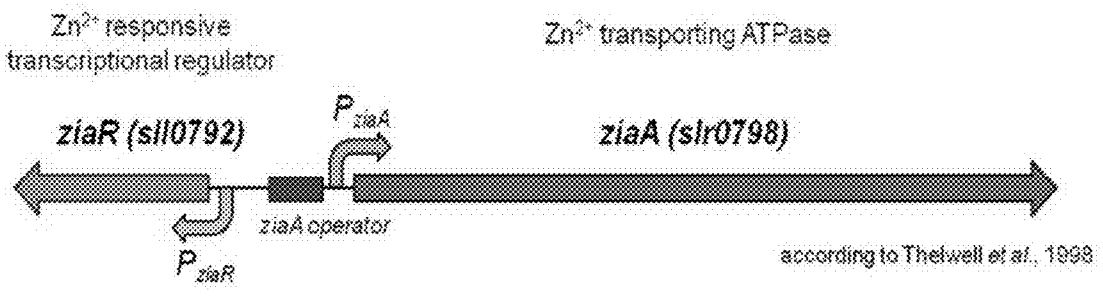
FIG. 2C depicts the promoter and gene orientation of ziaRA genes.

Generation of the Genetically Enhanced Cyanobacteria for the Production of Ethanol as a First Chemical Compound PziaA and ziaR-PziaA promoter fragments as examples of a $Zn^{2+}$ inducible promoter and its first control gene were amplified by PCR with a proof-reading DNA polymerase using the primer pairs 451/449 and 450/449 shown in FIG. 2A with the SEQ ID No. 49 to 51, respectively. The nucleotide sequences of the ziaR gene and the ziaA promoter are given in FIG. 2B, wherein the nucleotide sequence of the ziaR gene runs in antisense direction from 3' to 5' indicated by the shaded nucleotides. The nucleotide sequence for PziaA follows in 5'-direction downstream to the ziaR gene and underlined nucleotides denote the binding sites for the primers. A general representation of the gene organization and orientation is given in FIG. 2C.

Both promoter fragments for PziaA and ziaR-PziaA were subcloned into pJET.1.2/blunt for sequencing and subsequent cloning steps. The PziaA promoter fragment was cut out by SalI/EcoRI digestion and ligated into the SalI/EcoRI digested constructs #946 pVZ325a-$P_{petJ}$-PDC/SynADH and #948 pVZ325a-$P_{petJ}$-$PDC_{oop}$-$P_{rbc}$-$SynADH(deg)_{oop}$ leading to a swap of the initial present petJ promoter to the ziaA promoter. The plasmid map of the vector pVZ325a also indicating the SalI/EcoRI restriction site is given in FIG. 1B. Pdc and SynAdh encoding genes are ethanologenic genes whereas the Pdc gene encodes for Pyruvate decarboxylase and SynAdh gene for alcohol dehydrogenase for the production of ethanol as a first chemical compound. OOP denotes a terminator sequence taken from the phage Lambda OOP RNA. The OOP RNA is a major short (77 bases) transcript that is synthesized in the opposite direction to the mRNA for the Lambda cII gene.

This cloning step resulted in the constructs #968 pVZ325a-$P_{ziaA}$-PDC/SynADH and #969 pVZ325a-$P_{ziaA}$-$PDC_{oop}$-$P_{rbc}$-$SynADH(deg)_{oop}$. For assembly of corresponding pVZ322a derivates from the new created constructs #968 and #969 the ziaA promoter along with a 5'-part of the PDC coding sequence was cut by SalI/EagI digestion and ligated into the pre-existing constructs #990 pVZ322a-$P_{petJ}$-$PDC_{oop}$-$P_{rbc}$-$SynADH(deg)_{oop}$ and #996 pVZ322a-$P_{petJ}$-PDC/SynADH also SalI/EagI cut respectively. The plasmid map of the vector pVZ322a also indicating the SalI/EagI restriction site is given in FIG. 1A. Resulting constructs are #1047 and #1048.

The ziaR-PziaA promoter fragment was cut out by SalI/EcoRI digestion and ligated into the SalI/EcoRI digested construct #948 as described before. From the thereby created intermediate the ziaR-PziaA sequence along with a 5'-part of the Pdc coding sequence was cut by SalI/Kpn2I digestion and ligated into the already mentioned constructs #990 and #996 (SalI/Kpn2I cut) leading to the resulting pVZ322a constructs #1068 pVZ322a-$P_{petJ}$-$PDC_{oop}$-$P_{rbc}$-SynADH $(deg)_{oop}$ and #1069 pVZ322a-$P_{petJ}$-PDC/SynADH. $P_{rbc}$ denotes the native promoter of rbcLXS operon including the RBS and the ATG start codon of the rbcL gene (slr009) from *Synechocystis* PCC6803.

Characteristics of Genetically Enhanced *Synechocystis* Cyanobacteria Harboring PziaA and ziaR-PziaA as $Zn^{2+}$ Inducible Promoters for the Production of Ethanol as a First Chemical Compound For the first experiments six different ethanologenic *Synechocystis* sp. PCC6803 strains were used:

#948 pVZ325a-$P_{petJ}$-$PDC_{oop}$-$P_{rbc}$-$SynADH(deg)_{oop}$

#969 pVZ325a-$P_{ziaA}$-$PDC_{oop}$-$P_{rbc}$-$SynADH(deg)_{oop}$

Figure 1A:
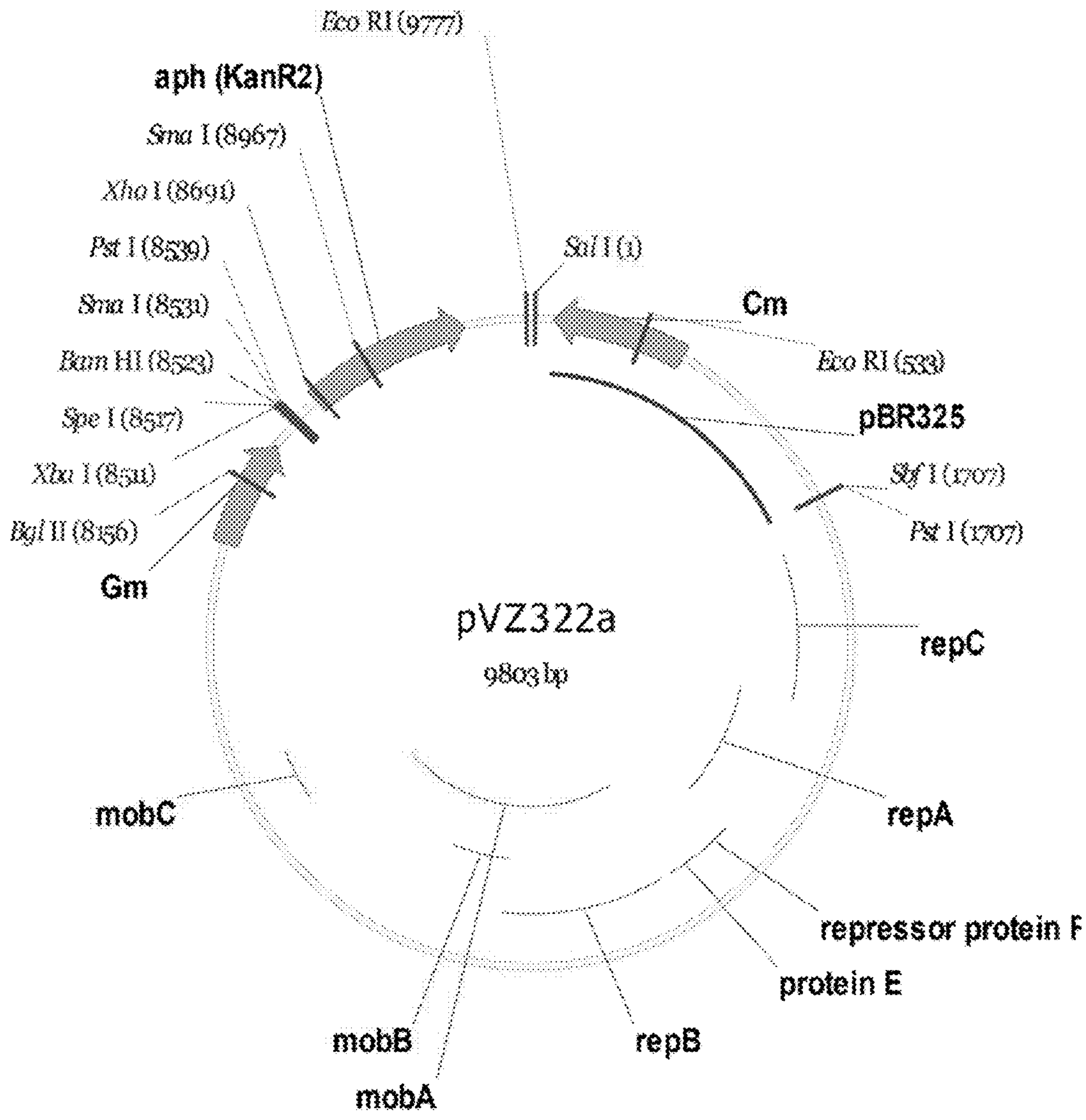
FIGS. 1A and 1B show the plasmid maps of the vectors pVZ322A and pVZ325A. The nucleotide sequences of these plasmids are shown in the sequence listing with SEQ ID NO 47 and 48.
Figure 1B:
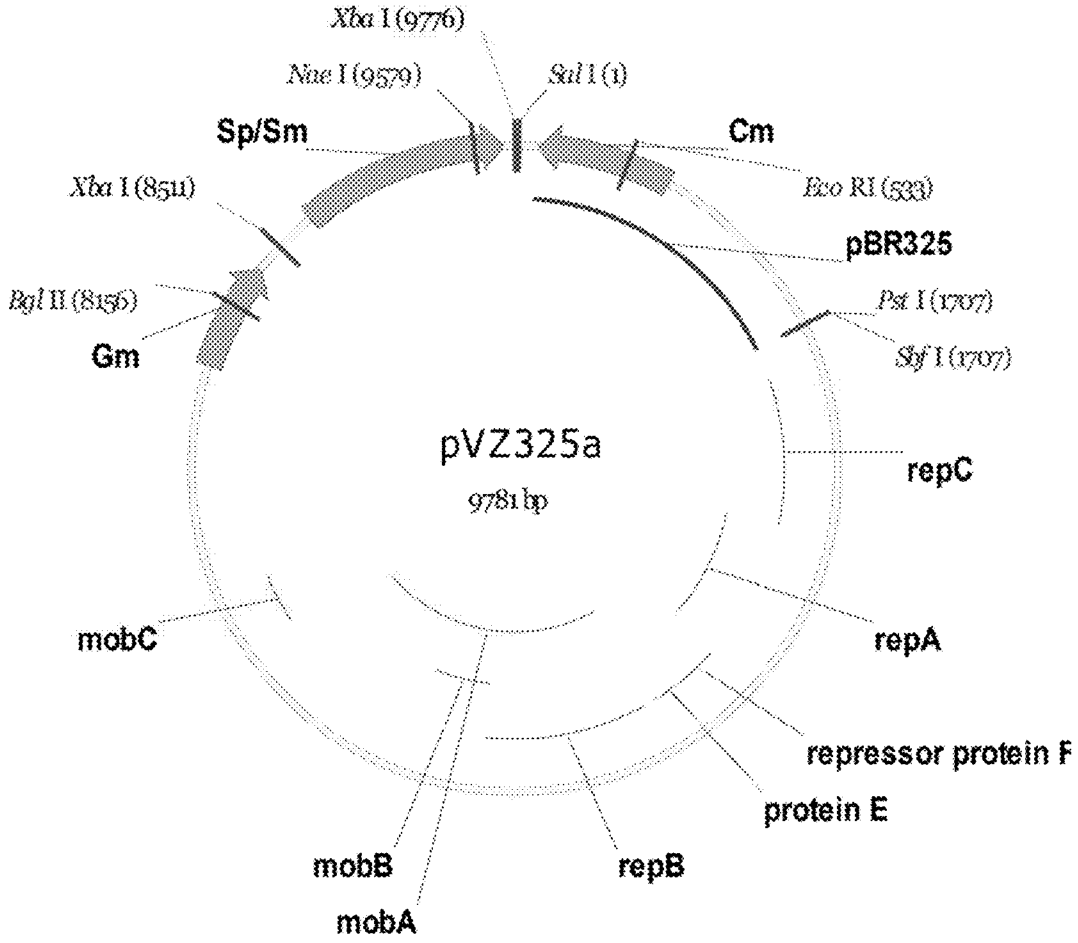

#996 pVZ322a-$P_{petJ}$-PDC/SynADH
#1047 pVZ322a-$P_{ziaA}$-$PDC_{oop}$-$P_{rbc}$-SynADH$(deg)_{oop}$
#1048 pVZ322a-$P_{ziaA}$-PDC/SynADH
#1068 pVZ322a-ziaR-$P_{ziaA}$-$PDC_{oop}$-$P_{rbc}$-SynADH$(deg)_{oop}$ The pVZ325a backbone comprises a Gentamycin/Streptomycin (Gm/St) resistance and the pVZ322a backbone comprises a Gentamycin/Kanamycin (Gm/Km) resistance after insertion of the ethanologenic gene cassette via SalI/SbfI (FIGS. 1A and 1B).

GC Vial Measurements

For GC vial measurements using a gas chromatograph (GC assay) the ethanol production of the culture has to be induced 1-3 days before the experiment that is realized by triggering the overexpression of Pdc and SynAdh. Induction of the petJ promoter occurs under copper depletion whereas the induction of the ziaA promoter occurs under zinc addition. Induced hybrid cells are either scratched from BG11 agar plates or harvested from liquid cultures by centrifugation and are resuspended in appropriate fresh medium ensuring induction conditions (for petJ promoter copper-free BG11 or marine BG11 (mBG11) prepared with seawater or a seawater supplement, for ziaA promoter mBG11 with 10 μM zinc sulfate), supplemented with 50 mM TES, pH 7.3 and 20 mM $NaHCO_3$.

The sample will be adjusted to an $OD_{750}$ of about 1 and 2 ml are filled in each 20 ml GC vial supplemented with 3 ml pure $CO_2$. The tightly closed GC vials were placed onto temperature controlled and illuminated (150 μE $m^{-2}$ $s^{-1}$) headspace auto sampler where the cultivation takes place. Samples from the cultures were analyzed on the same day on a Shimadzu GC-2010 gas chromatograph equipped with medium-bore capillary column (FS-CS-624, length 30 m; I.D. 0.32 mm; film 1.8 μm) and flame ionisation detector. After completion of the GC measurements the final $OD_{750}$ of cultures is determined for the calculation of the ethanol production rate per $OD_{750}$. The average $OD_{750}$ is calculated by addition of $OD_{750}$ at $t_{start}$ and $OD_{750}$ at $t_{end}$ divided by two.

GC Measurements of Strains Harboring Constructs with PziaA and ziaR-PziaA

In order to test the capacity of the new created hybrid strain #1048 for ethanol production gas chromatography (GC) measurements were performed in comparison to a reference strain carrying an isogenic pVZ325a plasmid however under control of the petJ promoter (#996). Cells of two independent clones were grown for at least 3 days on BG11 plates under repressed and induced conditions respectively before the GC vial assay was started. For the reference strain #996 agar plates containing 5× copper (1.5 μM) and no copper (—Cu) were used, whereas for the ziaA promoter strain #1048 agar plates with no additional (0.77 μM $ZnSO_4$) and 10 μM $ZnSO_4$ were used. The GC vial assay were done by measuring the ethanol production rates by gas chromatography over at least 18 hours of cultivation in an illuminated GC vial (150 $μE*m^{-2}*s^{-1}$) as described above.

Figure 3A:
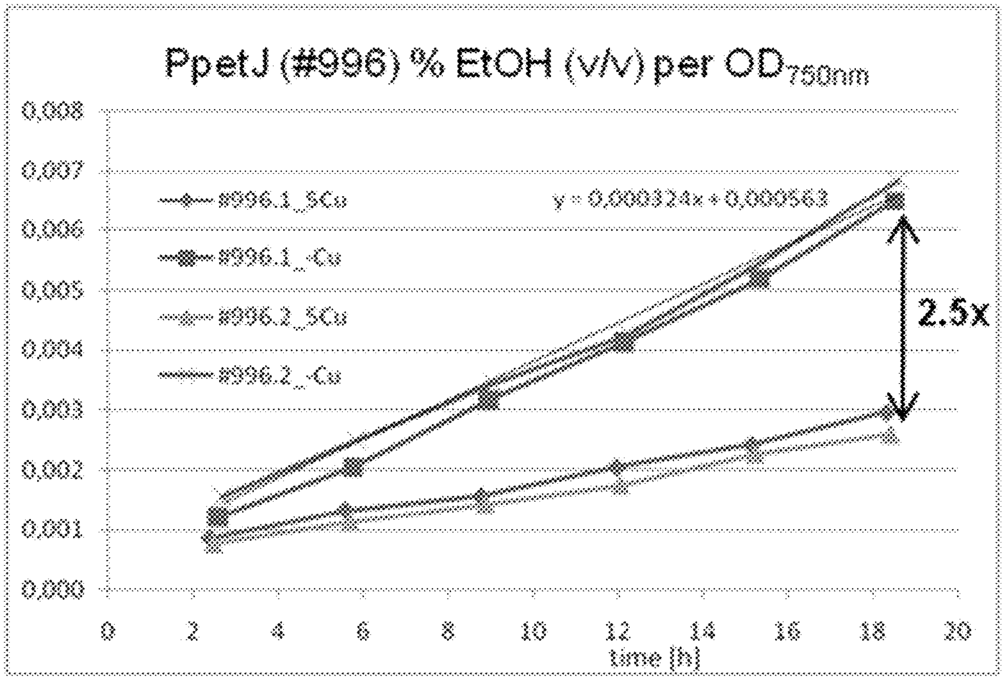
FIGS. 3A and 3B shows the ethanol production rates % EtOH (v/v) per optical density of the culture at 750 nm ($OD_{750\ nm}$) of another cyanobacterial strain using the promoter petJ compared to a cyanobacterial strain including PziaA.
Figure 3B:
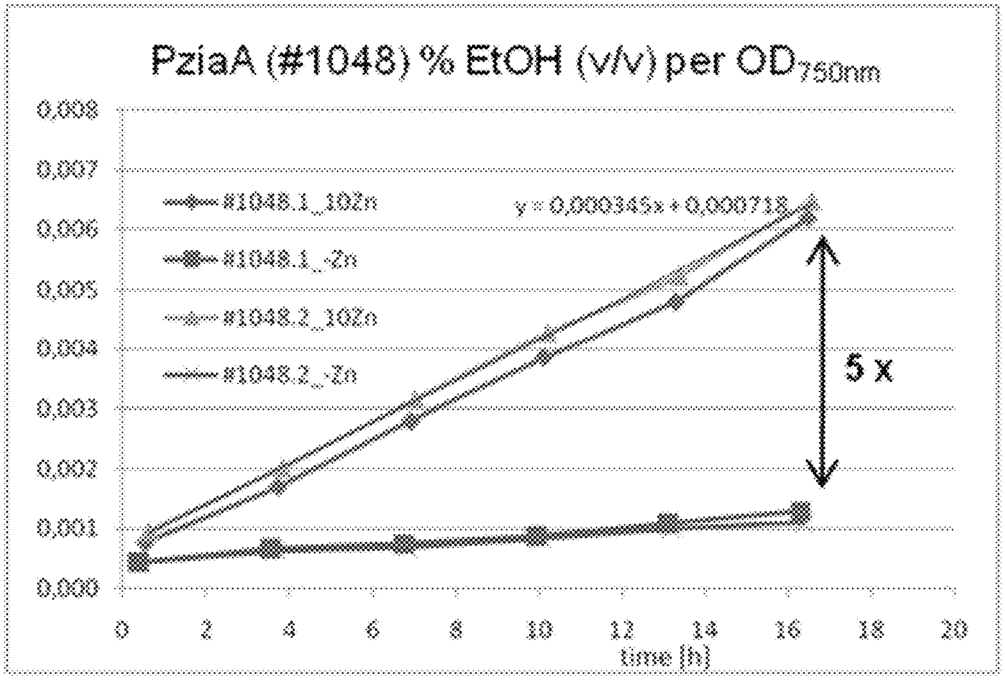
Figure 4A:
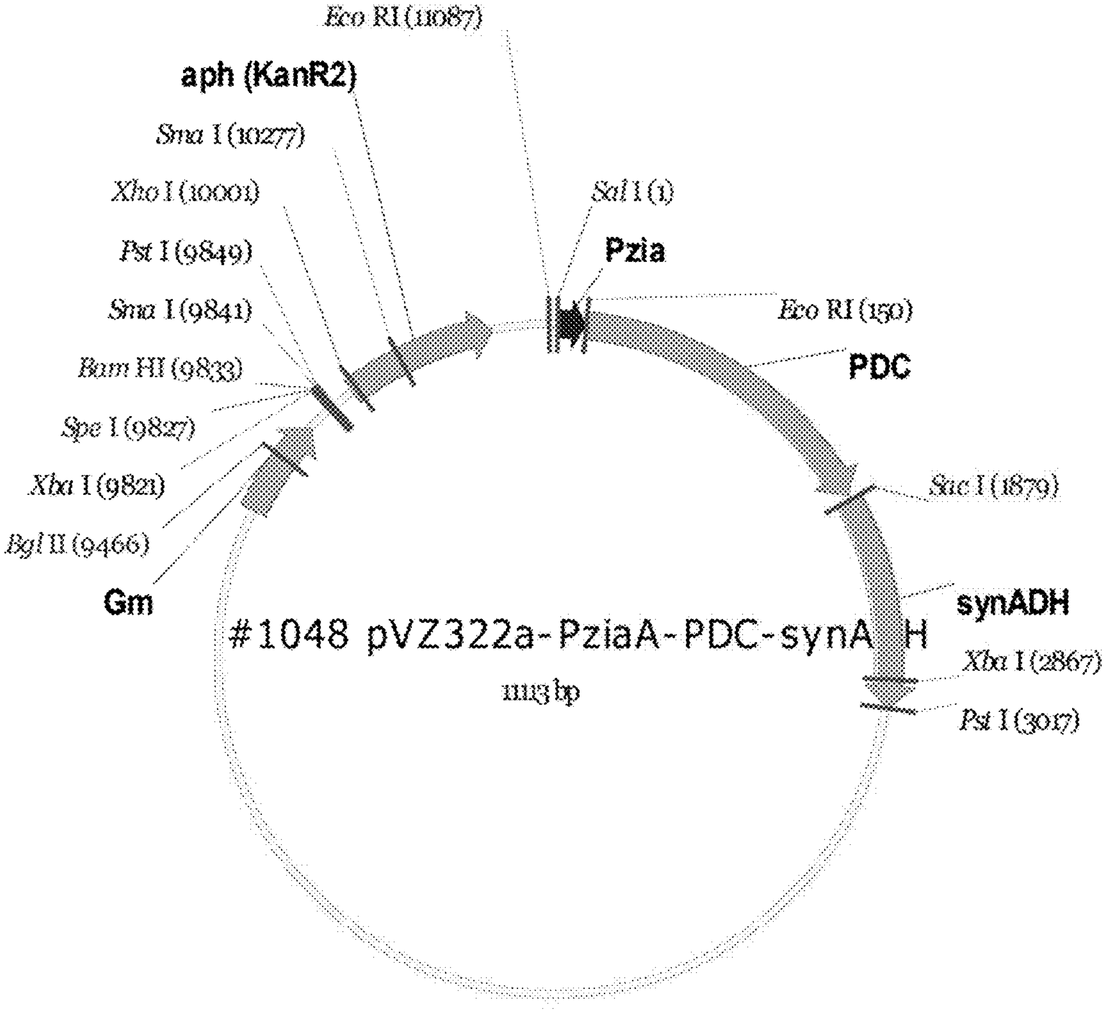
FIGS. 4A and 4B depict the plasmid maps of the strains #1048 and #996.
Figure 4B:
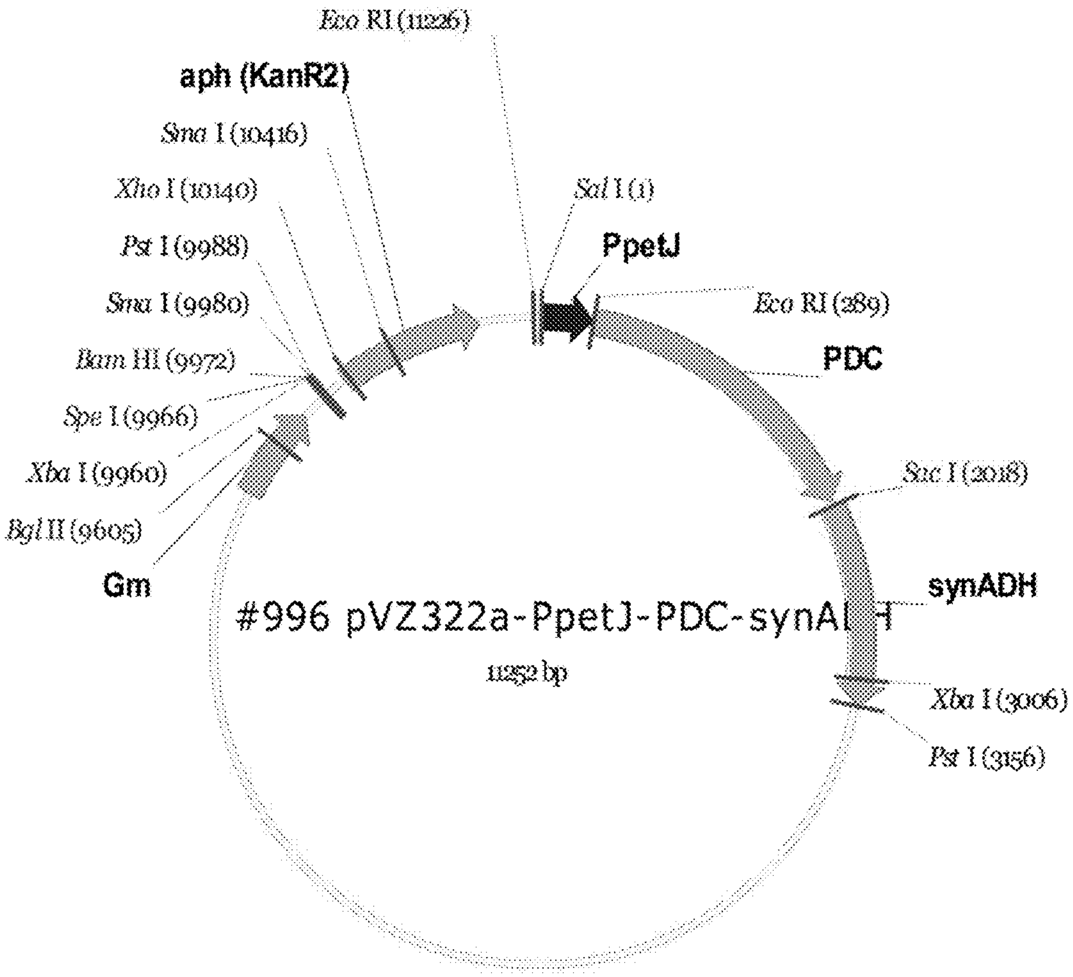

FIGS. 3A and 3B show the ethanol production rates of the ethanologenic strains harboring the plasmids #996 and #1048 (the plasmid maps are shown in FIGS. 4A and 4B and the sequence of the inserts containing the ethanologenic genes and the promoters are shown in the sequence listing with the SEQ ID Numbers. 52 and 53. It can be clearly seen that both *Synechocystis* strains exhibit a similar ethanol production rate under induced conditions. In the repressed, uninduced state the strain harboring the ethanologenic genes under the control of PpetJ at a concentration of 1.5 μm $Cu^{2+}$, denoted with #996.2_5Cu and #996.1_5Cu produces higher amounts of ethanol compared to the strain with the ethanologenic enzymes under the control of PziaA in the repressed state at a concentration of 0.77 μM $Zn^{2+}$ (denoted with #1048.1_-Zn and #1048.2_-Zn). Consequently, the induction factor is much higher for the PziaA strain (induction factor of 5 at a concentration of 10 μM $Zn^{2+}$) compared to the PpetJ strain (induction factor of 2.5 in the absence of $Cu^{2+}$). This means that under repressed conditions the ziaA promoter is less leaky than the petJ promoter and allows thereby a tighter control of ethanol production.

Figure 5A:
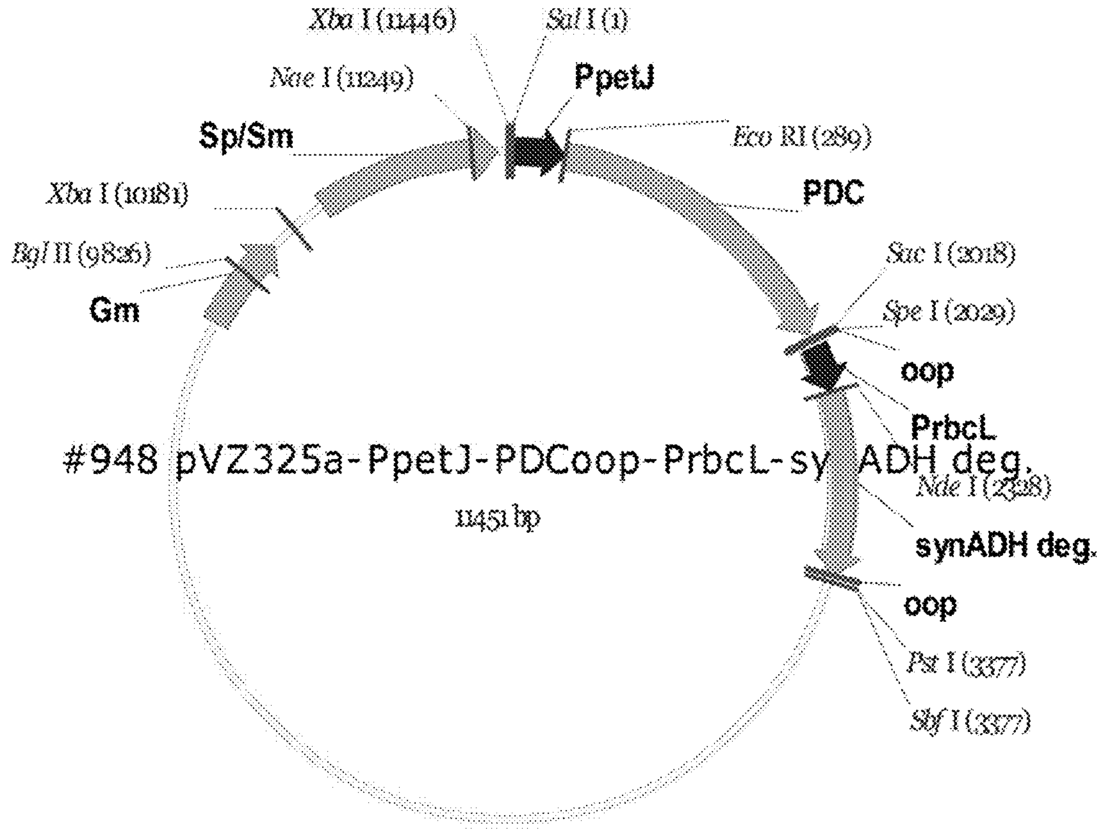
FIGS. 5A and 5B depict the plasmid maps of the strains #948 and #969.
Figure 5B:
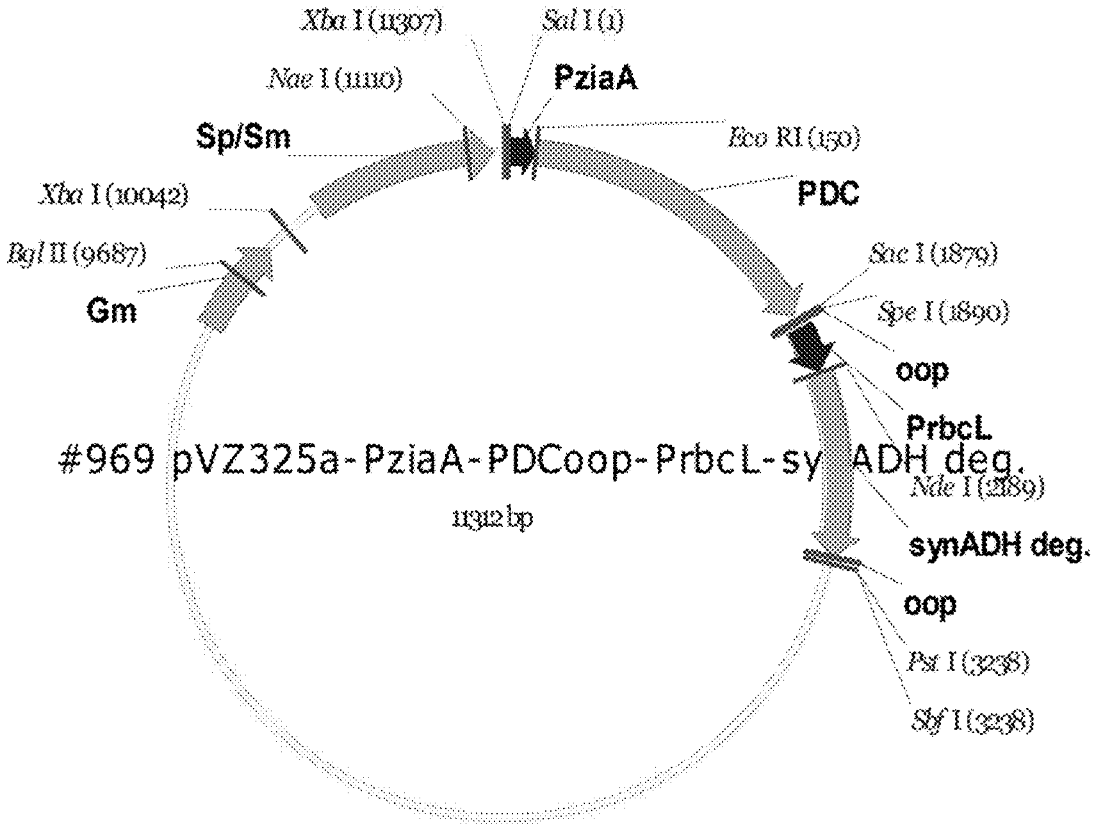

In a further experiment the ethanol production and growth behavior of *Synechocystis* strains under control of the ziaA promoter in relation to the petJ promoter were analyzed in shaken 50 ml Erlenmeyer flasks. The strains used for this purpose were #948 with the petJ promoter and #969 with the ziaA promoter controlling the expression of the improved ethanologenic gene cassette $P_{xxx}$-$PDC_{oop}$-$P_{rbc}$-SynADH $(deg)_{oop}$ respectively comprising a separate, constitutive promoter (native rbc promoter of *Synechocystis* PCC6803) to drive the SynADH expression. Pxxx denotes either PpetJ or PziaA. Plasmid maps of these plasmids are shown in FIG. 5A and FIG. 5B, respectively and the nucleotide sequences of the inserts containing the ethanologenic genes and the promoters are shown in the sequence listing with the SEQ ID NOs. 54 and 55. Both strains were grown in 50 ml pre-cultures under repressed conditions (BG11 5× Cu for #948 and usual BG11 for #969) to an $OD_{750\ nm}$ of about 2. The cells of the pre-cultures were harvested by centrifugation and afterwards divided into four new 50 ml BG11 subcultures containing either 5× copper, no copper, 5× copper plus 10 μM $ZnSO_4$ or no copper plus 10 μM $ZnSO_4$. Thus all together eight different Erlenmeyer flaks were cultivated in parallel in order to test the response of both ethanol producing hybrids to the availability of $Zn^{2+}$ and $Cu^{2+}$ in the growth medium.

In FIGS. 6A and 6B the data for culture growth, ethanol accumulation as well as the ethanol accumulation normalized on the optical density (growth) collected over a time frame of about 30 days are summarized for PpetJ and PziaA, respectively. As shown in FIGS. 6A and 6B (left hand side) there are substantial differences in growth. While both strains show a similarly reduced growth under induced conditions (—$Cu^{2+}$ for PpetJ and 10 μM $Zn^{2+}$ for PziaA), the growth rate at repressed state is almost doubled for hybrid strain #969 with PziaA when compared to the PpetJ reference #948. This is a direct effect from the almost completely deactivated ethanol synthesis due to the tighter repressed ziaA promoter. If no ethanol is produced all carbon fixed by photosynthesis is used for cell growth and biomass formation whereas carbon that goes into ethanol is lost for biomass formation. Since the petJ promoter is rather a leaky promoter there is still carbon lost for growth even if 5× copper is added. So the lower ethanol accumulation and therefore reduced "carbon loss" of strain #969 at repressed state allows to grow faster compared to the #948 reference that exhibits a significant growth retardation even if the petJ promoter is repressed by addition of 5× copper.

Furthermore in FIGS. 6A and 6B (in the middle) the ethanol accumulation is shown. As already detected in the GC online experiment described before, both strains exhibit a very similar ethanol accumulation under induced cultivation conditions. Also the ethanol accumulation at repressed state appears to be similar but one have to consider that the optical density of the PziaA strain is almost twice as high as for the PpetJ control strain at repressed conditions. Thus when for this experiment the OD normalized ethanol production is calculated (FIGS. 6A and 6B—right hand side)

again a two times higher induction factor is obtained for the ziaA promoter (induction factor of about 8×) in comparison to the reference strain (#948) with the petJ promoter (induction factor of about 4×).

So far the ziaA promoter sequence was taken without the coding region of the repressor gene ziaR that is needed for the zinc dependent transcriptional regulation by binding of the repressor protein to the operator sequence of the ziaA promoter. Because the repressor is present in the genome of *Synechocystis* it is actually not necessary to consider the repressor gene in respective ethanologenic pVZ plasmids. However if other species than *Synechocystis* were used it is necessary to employ the ziaA promoter along with its transcriptional repressor in order to ensure that PziaA can be used as a $Zn^{2+}$-inducible promoter. On the other hand due to introduction of additional copies of the ziaA operator encoded on the pVZ-PziaA-Pdc/Adh plasmid the availability of binding sites for the ZiaR repressor is substantially elevated. This might lead to a repressor/operator imbalance and a less tight repression of Pdc (controlled by the ziaA promoter) as well as the ziaA gene (zinc transporting ATPase involved in zinc homeostasis). In order to address this question a new construct (#1068) was created that additionally to the previous constructs (e.g. #969 and #1047) contains the sequence of the ziaR repressor (see FIGS. 7A and 7B for the plasmid maps; the nucleotide sequence of the inserts containing the ethanologenic genes and the promoters for the plasmids #1068 and #1047 are included in the sequence listing with the SEQ ID NOs. 56 and 57). Respective *Synechocystis* cells with ziaR-PziaA promoter were analyzed in comparison to strains without ziaR repressor.

In FIGS. 8A and 8B the results of respective GC online measurements comparing #1047 with #1068 are summarized for PziaA alone and PziaA in combination with ziaR, respectively. Both hybrid lines were tested without or in the presence of 5 μM, 10 μM, 15 μM and 20 μM $ZnSO_4$. Cells were grown on BG11 agar plates (without additional zinc). For harvesting, the cells were scratched from the plates and suspended in mBG11 medium containing respective amounts of zinc. The GC vials were analyzed for a duration of 40 hours in continuous light (150 $\mu E/m^2*s$) at 35° C.

As visible from FIGS. 8A and 8B for both strains there is a correlation of the ethanol produced to the amount of zinc added. The more zinc is present the more ethanol is produced by the cells, so that the ethanol production rate can be gradually adjusted by the addition of zinc. Highest ethanol production is achieved at 15 μM and 20 μM $ZnSO_4$ with a low increase (#1047) or in case of #1068 without a further increase from 15 μM to 20 μM indicating that these zinc concentrations mark the upper threshold suited for induction of both ziaA promoter variants for ethanol production in *Synechocystis* PCC6803.

Furthermore from FIGS. 8A and 8B it is evident that the hybrid strain #1068 exhibits especially at 5 μM and 10 μM zinc a slightly lower production rate when compared to respective production rates found for #1047 in the same experiment. However, at 15 μM zinc comparable production rates were achieved for both promoter variants. The strongest effect as a consequence of addition of the ziaR repressor is found at the repressed state (without added zinc) where #1068 in contrast to #1047 shows almost no ethanol production. This indicates that the addition of the repressor improves the tightness of the ziaA promoter but only marginal influences the maximal production rate at fully induced state (15-20 μM zinc). Due to the much lower production rate at a repressed state but at the same time similar productivity as #1047 at fully induced state the induction factor for the ziaA promoter along with the ziaR repressor is about 15× in #1068 whereas for #1047 in this experiment the factor is about 4×.

This result is of importance because the already tight regulation of the ziaA promoter previously shown in direct comparison to the prior art petJ promoter was further improved by the addition of the repressor to the promoter sequence. The better induction factor of #1068 in comparison to #1047 should lead to a superior performance of this hybrid especially under repressed state with regard to the growth rate and the genetic stability.

Improvement of the ziaA Promoter from *Synechocystis* PCC6803 as Examples for Variants of a Native $Zn^{2+}$ Inducible Promoter with Respect to the Production of Ethanol as a First Chemical Compound Furthermore the ziaA promoter from *Synechocystis* PCC6803 was optimized for better performance and/or control of ethanol production by introducing nucleotide changes in the TATA box, the operator sequence and/or the ribosomal binding site (RBS). ZiaA* denotes the native, however partly truncated ziaA promoter from *Synechocystis* PCC6803 containing all promoter elements necessary for a zinc-dependent regulation (operator, −35 and −10 region and RBS).

FIG. 9A illustrates eight different recombinant ziaA* promoter variants which were tested in comparison to the native ziaA promoter present in plasmid #1116 (sequence of the insert containing the ethanologenic genes and the promoters is shown in the sequence listing with SEQ ID NO. 58) with respect to an improved performance for ethanol production. TATA box, the transcription start point (TSP), the operator sequence and the ribosomal binding site (RBS) are marked by boxes and changed nucleotides are indicated by shaded characters in bold face type. Underlined sequence at the 5'- and 3'-end indicate the introduced restriction sites SalI and EcoRI used for cloning into the ethanologenic pVZ constructs #1116 comprising Pdc and Adh encoding genes. ZiaA* promoter variants were created by PCR using of different combinations of partially overlapping synthetic oligonucleotides (primers 1-6) shown in FIG. 9A. The sequences are also included in the sequence listing with the SEQ ID NOs 59 to 64. The overlapping part of the respective forward (fw) and reverse (rev) primers at the 3'-end as well as the introduced restriction sites at the 5'-end are underlined.

*Synechocystis* hybrid lines carrying ethanologenic pVZ constructs with the above described ziaA* promoter variants were grown on BG11 agar plates in the presence or absence of 15 μM zinc) for 4 days in continuous light. For harvesting, the cells were scratched from the plates and suspended in mBG11 medium containing either no or 15 μM of zinc. The GC vials were analyzed by GC measurements for a duration of about 20 hours in continuous light (150 $\mu E/m^2*s$) at 35° C.

Figure 9B:
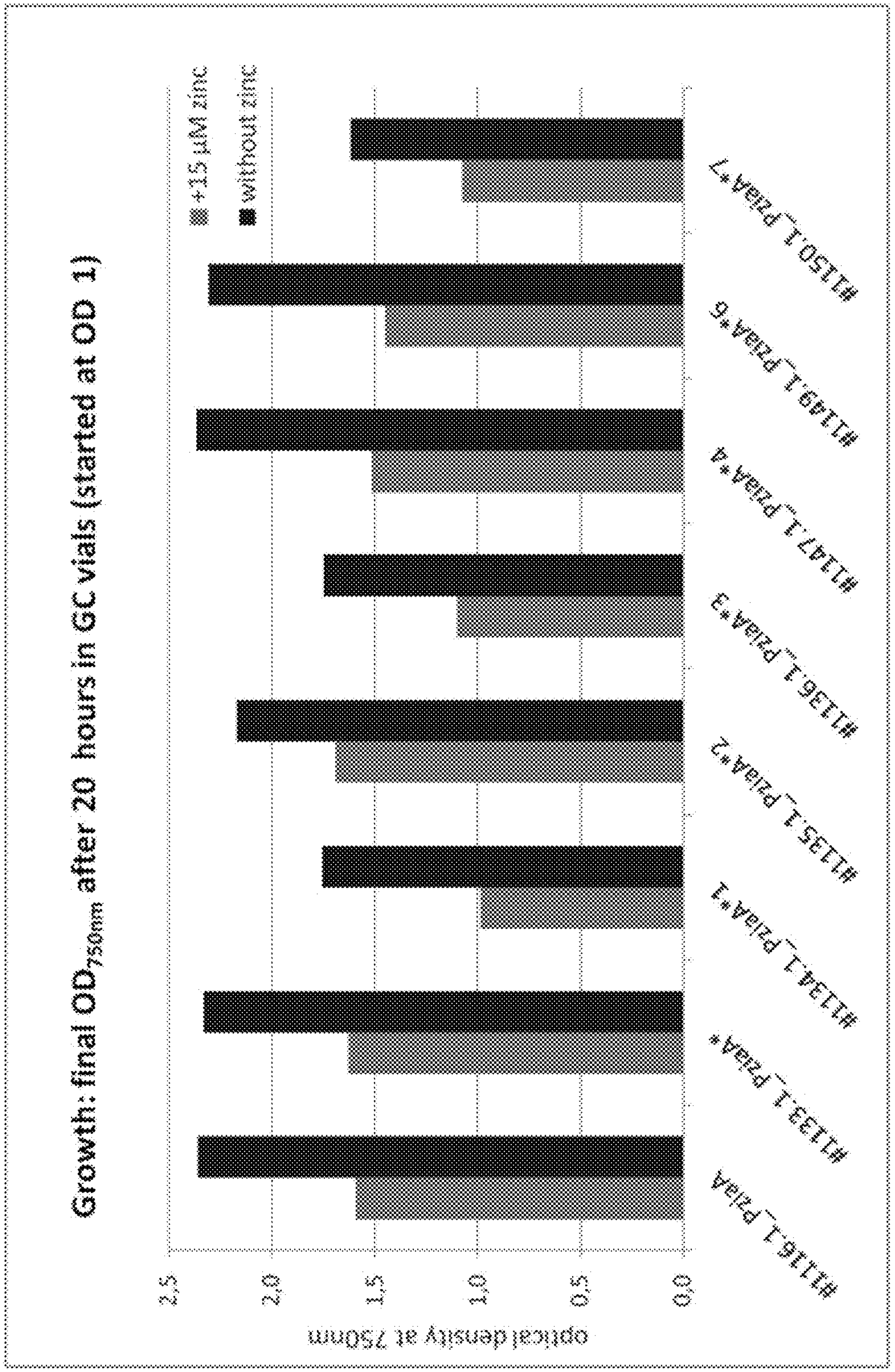

FIG. 9B illustrates the final optical densities at 750 nm ($OD_{750\ nm}$) for different promoter variants PziaA* to PziaA*7 in gas chromatography (GC) online experiments in the presence or absence of 15 μM zinc in comparison to the wild-type ziaA promoter after 20 hours in the light (150 $\mu E/m^2*s$ and each culture started with an OD750 nm of 1.0). All variants show a higher final $OD_{750}$ in the absence of zinc compared to the $OD_{750}$ in the presence of 15 μM zinc indicating a better growth at the repressed condition of the promoter. Interestingly all variants comprising the TATA box modification show a substantial reduced growth (lower final $OD_{750}$) at the repressed but also at the induced condition. In the presence of 15 μM zinc for the variants of the TATA box consensus sequence (PziaA*1, PziaA*3 and PziaA*7) almost no increase in $OD_{750}$ and therefore no growth is detectable. All other variants show comparable $OD_{750}$ values to the wild-type PziaA promoter after 20 hours growth in the repressed and induced state.

Figure 9C:
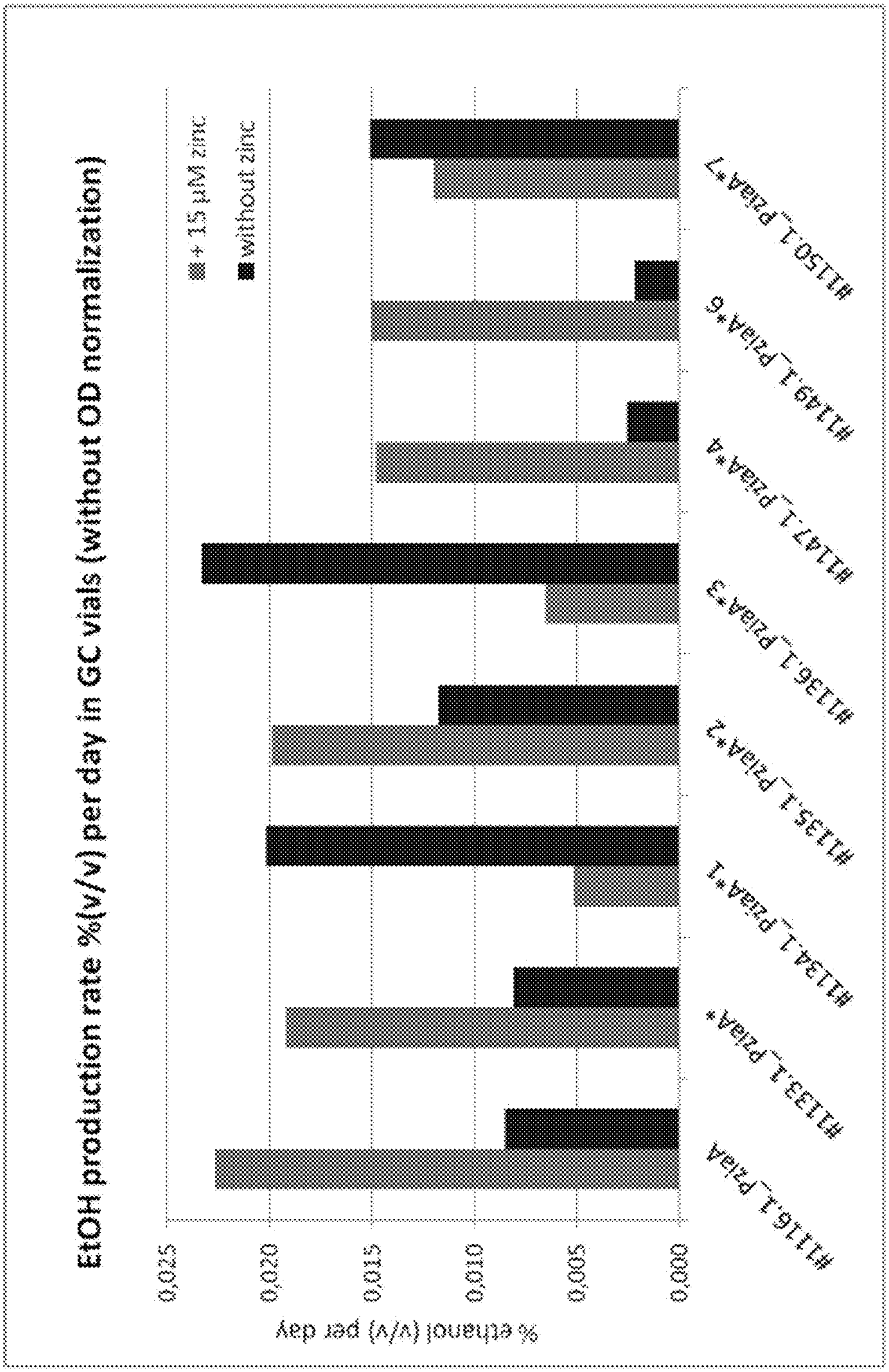
Figure 9D:
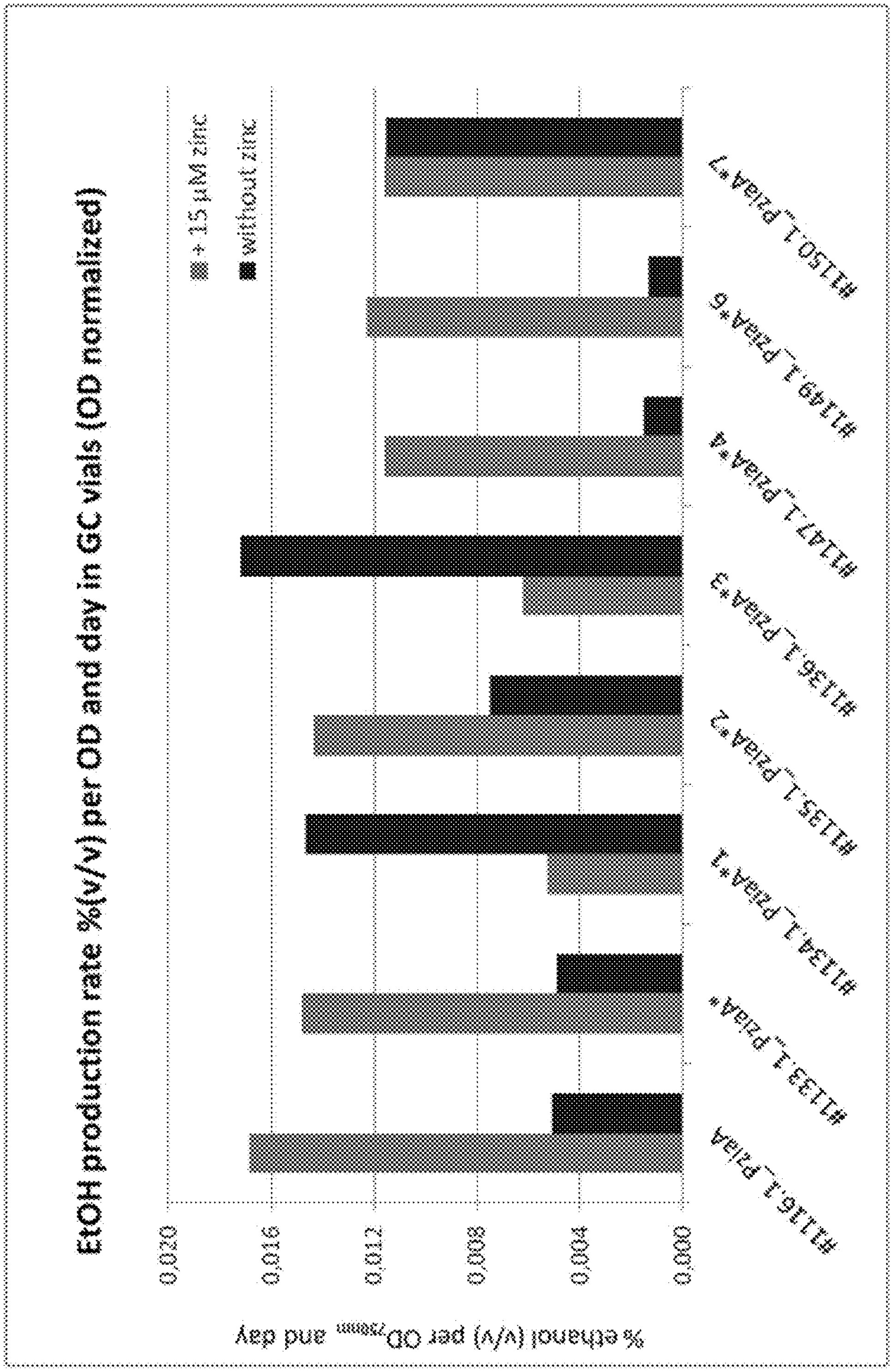
Figure 9E:
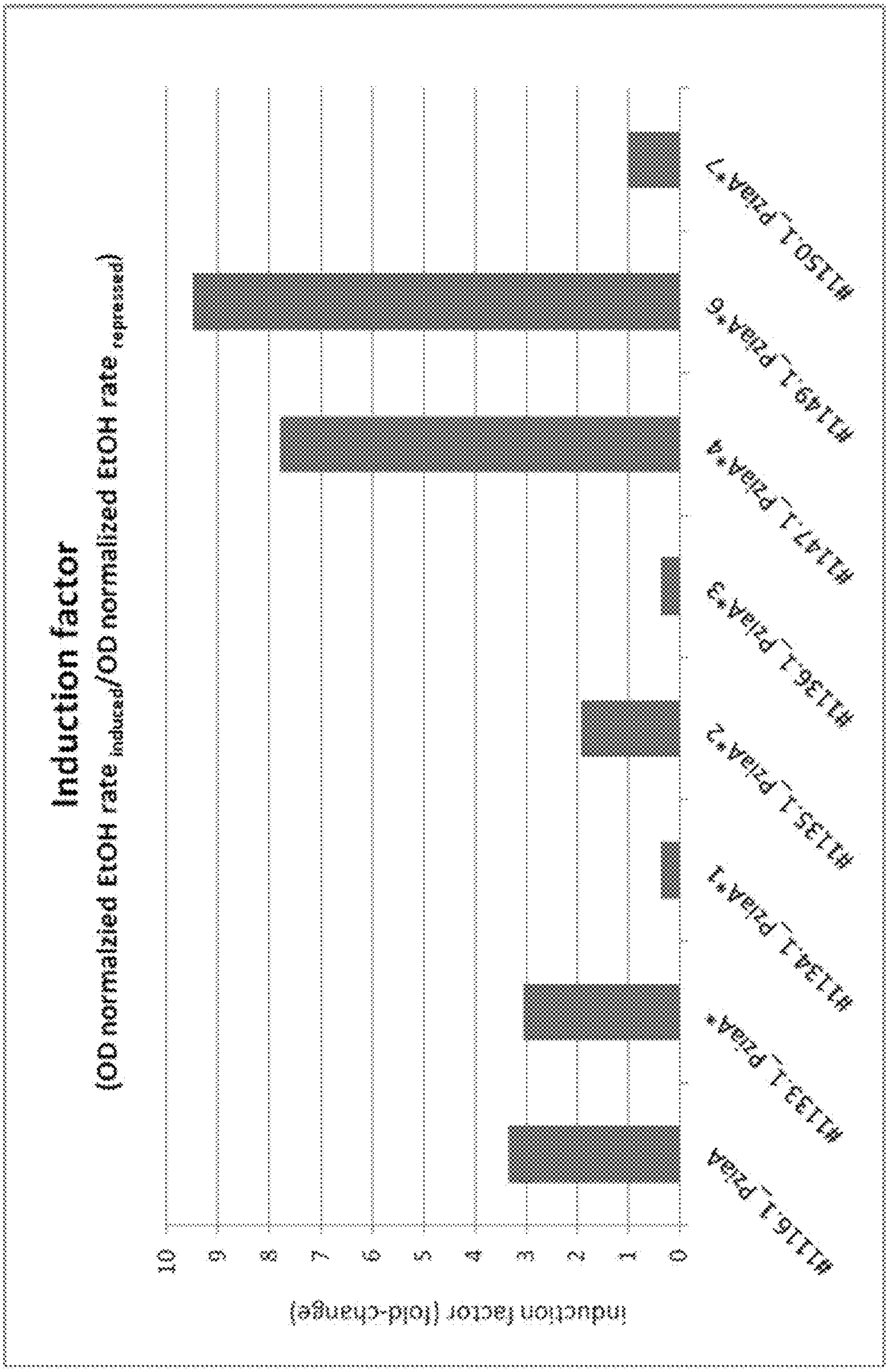

FIG. 9C shows the ethanol production rates per day and FIG. 9D the $OD_{750}$ normalized ethanol production rates for the different PziaA* variants in the GC online experiments in comparison to the wild-type PziaA. Some of the variants (PziaA*, PziaA*2, PziaA*4 and PziaA*6) show a comparable ethanol production rate to PziaA wild type in the induced state, but different rates in the repressed state. For example PziaA*4 and PziaA*6 accumulate only 30% of the ethanol produced by the wild-type PziaA at the repressed state which indicates a tighter control of those promoter variants. On the other hand the promoter variants comprising the TATA box consensus (PziaA*1, PziaA*3 and PziaA*7) show a higher ethanol production rate at the repressed state than under induced conditions. This result is somehow puzzling and might indicate that those promoter variants exhibit a substantial enhancement of the promoter activity in the repressed as well as the induced state. Further analyses revealed that at the induced state of the promoter variants PziaA*1 and PziaA*3 the PDC activity raises above a critical threshold for the cell where further ethanol production collapses. This finding is supported by Western Blot detection of the Pdc protein amount as well as by the fact that both promoter variants are not able to grow at induced conditions (addition of 15 μM zinc). This effect is obviously not advantageous for an inducible ethanol production in *Synechocystis* using that kind of ethanologenic plasmid, however it might be useful for genomic integration or plasmids with lower copy number leading to a lower gene dosage and gene expression. Furthermore the PziaA* variants might be useful for cyanobacteria other than *Synechocystis* as well as for other products of interest where higher expression rates of respective heterologous pathway enzymes are needed for sufficient formation of the first chemical compound. Another possibility of using these strong PziaA*1 and PziaA*3 promoters for the production of a first chemical compound is inserting directly downstream of these promoters a second recombinant gene coding for a second biocatalyst for the production of the first chemical compound (upstream of the first recombinant gene coding for the first biocatalyst), which is either already present in the wild type cyanobacterium or which does not divert the naturally occurring carbon flux away from the wild type metabolism or which does not produce an intermediate harmful for the cyanobacterium. An example for such an enzyme is Adh enzyme for the production of ethanol. The first recombinant gene encoding a first biocatalyst for the production of the first chemical compound, which does interfere with the wild type metabolism to a greater extent, because it diverts the carbon flux away from the natural occurring metabolism of the cyanobacterium can then be located downstream to the second recombinant gene. In this case, the transcriptional activation by the strong $Zn^{2+}$, $Co^{2+}$ or $Ni^{2+}$ inducible promoter will be stronger for the second than for the first recombinant gene so that the harmful consequences of the expression of the first biocatalyst for the cyanobacterial cell are reduced. One example of such a first biocatalyst is Pdc enzyme. FIG. 9E depicts the induction factors for the different ziaA* promoter variants (ethanol production per $OD_{750}$ in the induced state divided by the ethanol production per $OD_{750}$ in the uninduced state). In particular the variants PziaA*4 and PziaA*6 exhibit a 3-fold increased induction factor in comparison to PziaA due to the tighter control at repressed state and at the same time limited decrease in the production rate at the induced state (~75% of wild-type PziaA). However the slight decrease in the production rate at the induced state observed for PziaA*4 and PziaA*6 could be compensated by a higher gene dose (e.g. by a higher plasmid copy number) if necessary. This would allow for taking advantage of the higher induction level too. For the promoter variants of the consensus TATA box (PziaA*1, PziaA*3 and PziaA*7) the observed effects are too strong. It could be useful to employ variants of the consensus TATA box with only one or maximal two nucleotide changes, which could give the intended effect of a higher production rate at induced condition but at the same time also a tight control in the repressed state. The described ziaA promoter variants have demonstrated the big potential of an artificial optimization of ziaA-like promotors (e.g. PsmtA or PaztA) in order to improve cyanobacteria for the synthesis of first chemical compounds. Taken all the possibilities to manipulate such metal-ion inducible promoter systems into account, there is a high potential to end up with a perfect, absolutely fine-tuned inducible promoter system for ethanol production in cyanobacteria. This is certainly not restricted in terms of the species *Synechocystis* and the product ethanol, it is applicable for any first chemical compound that can be produced by a specific cyanobacterium at a certain environmental condition (temperature and salinity) and culture condition (e.g. culture density and growth phase), resp. However for each specific application the promoter has to be optimized individually for the cyanobacterial host strain and the intended first chemical compound.

Figure 9F:
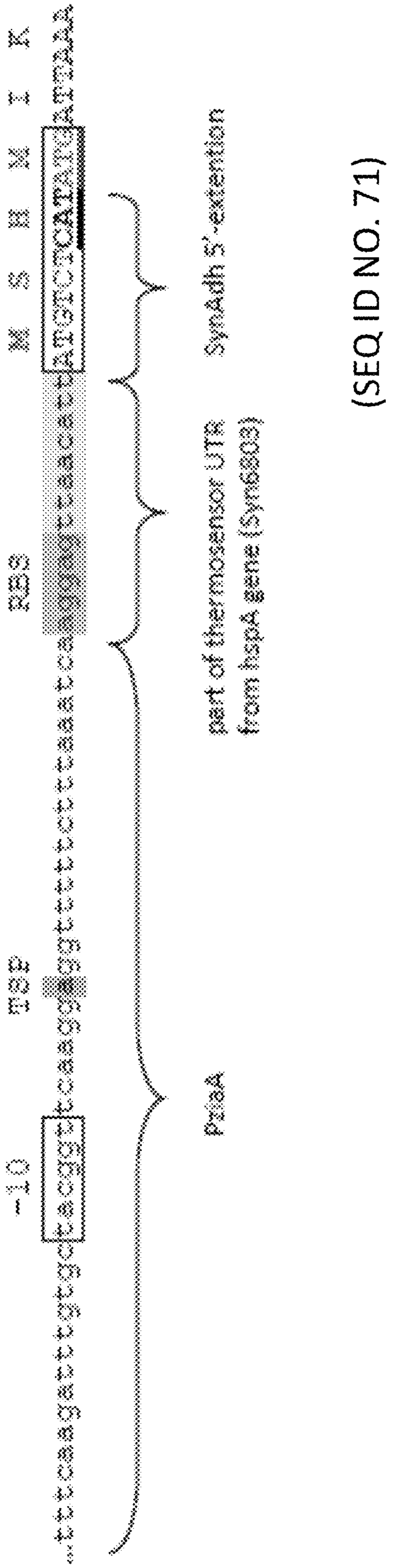

Another example for a PziaA variant is PziaA*2ext shown in FIG. 9F (listed in the sequence listing as SEQ ID No. 71). The two primers ziaR-PziaA-SalI-fw and PziaA*2ext-NdeI-rev used for the amplification of this promoter are listed in the sequence listing as SEQ ID NO. 72 and 73. This artificial PziaA variant contains the sequence of PziaA, a part of a RNA-based thermosensor untranslated region (UTR) derived from the hspA gene (sll1514) of *Synechocystis* PCC6803 (see publication Kortmann et al.: "Translation on demand by a simple RNA-based thermosensor", Nucleic Acids Res. 2011 April; 39(7): 2855-2868) in which the ribosomal binding site is embedded and a 5'-extension of the first recombinant gene by three amino acids. The inventors surprisingly found out that this promoter is much stronger than the native PziaA* promoter, but is still Zn2+ inducible. This promoter only contains a part of the thermosensor of the hspA gene reported in the above publication, which is used for the temperature controlled expression of hspA and therefore does not appear to show a strong temperature dependent protein expression. Without being bound by any theory, the PziaA*2ext promoter seems to enhance the stability of the mRNA transcript and/or the efficiency of translation. A more generalized form of the PziaA*2ext promoter is:

(SEQ ID NO. 90)

$N_{11}$AATATCTGAGCATATCTTCAGGTGTT$N_{13}$TACGGT$N_{6}$A$N_{16}$AAGGAGTTAACATTATGTCTCATATG, wherein the boldfaced and underlined nucleotides denote mutations in comparison to the wild type PziaA and wherein boldfaced framed nucleotides denote nucleotides coding for N-terminal extension of the second or first recombinant gene.

Due to the potency of this promoter, a first recombinant gene encoding a biocatalyst for the production of the first chemical compound, which does interfere with the wild type metabolism to a greater extent, because it diverts the carbon flux away from the natural occurring metabolism of the cyanobacterium can be located further downstream of the PziaA*2ext promoter than it is usually the case for weaker promoters. In particular, the first recombinant gene can encode Pdc enzyme. The second recombinant gene coding for a second biocatalyst such as Adh enzyme, which catalyzes a chemical reaction already present in the wild type cyanobacterium not diverting the carbon flux away from the natural occurring metabolism can be located immediately downstream of the PziaA*2ext promoter. If ethanol is the first chemical compound, an alcohol dehydrogenase encoding gene can be located immediately downstream of the promoter followed by a Pdc enzyme encoding gene so that the transcriptional activation is higher for the adh gene than for the pdc gene which is co-transcribed.

Figure 9G:
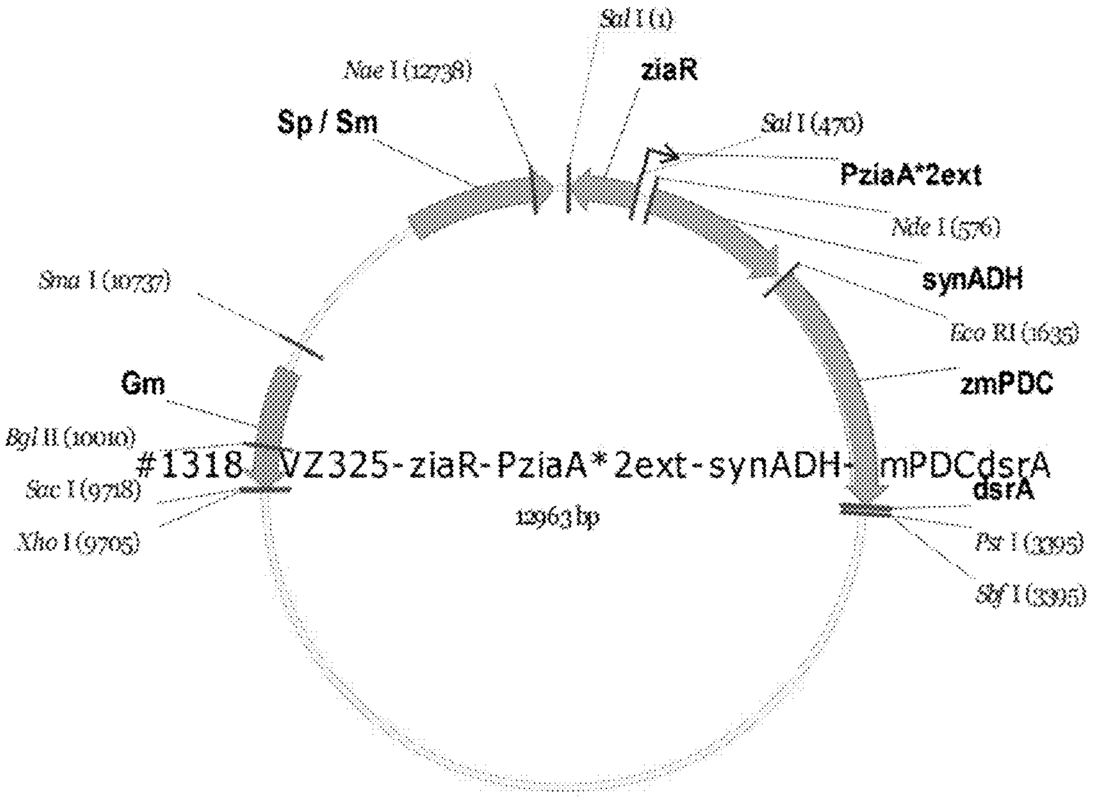

FIG. 9G depicts the plasmid map of the plasmid #1318, which includes an insert with an ethanologenic cassette wherein PziaA*2ext controls the transcription of both a SynAdh gene and a ZmPdc gene located downstream of the SynAdh gene so that the transcriptional activation for the SynAdh gene is higher than for the ZmPdc gene. The SEQ ID NO. 74 shows the nucleotide sequence of this insert pVZ325-ziaR-PziaA*2ext-synADH-zmPDCdsrA.

Figure 9H:
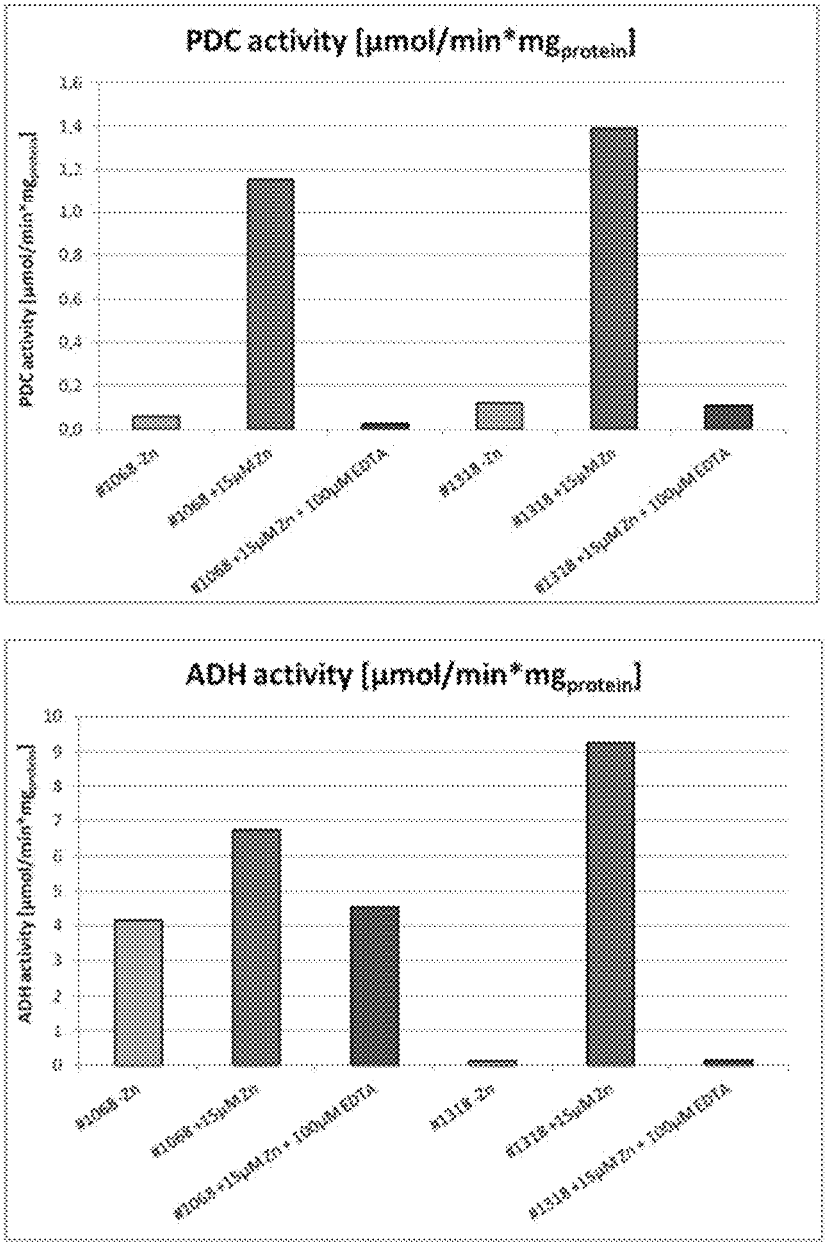

The FIG. 9H shows the activities of the Pdc enzyme and the Adh enzyme of *Synechocystis* PCC6803 cells transformed with this plasmid #1318 in comparison to cells transformed with the above described plasmid #1068 harboring Adh enzyme under the transcriptional control of the constitutive $P_{rbcL}$ promoter and Pdc under the control of the native ziaA promoter. For the Pdc enzyme as well as for the Adh enzyme the activities in the induced state are both higher for plasmid #1318 than for plasmid #1068. The addition of 100 μM EDTA sufficiently suppresses the actual induction due to addition of 15 μM $Zn^{2+}$ for cells transformed with this plasmid #1318 and #1068 by chelating the metal-ions and preventing thereby the release of ZiaR protein from the operator of the ziaA promoter. Titration of metal-ions by addition of EDTA (<100 μM) is an efficient way to further tighten and/or modify the induction behavior metal ion responsive promoters and respective production genes transcriptionally controlled thereby.

Figure 9I:
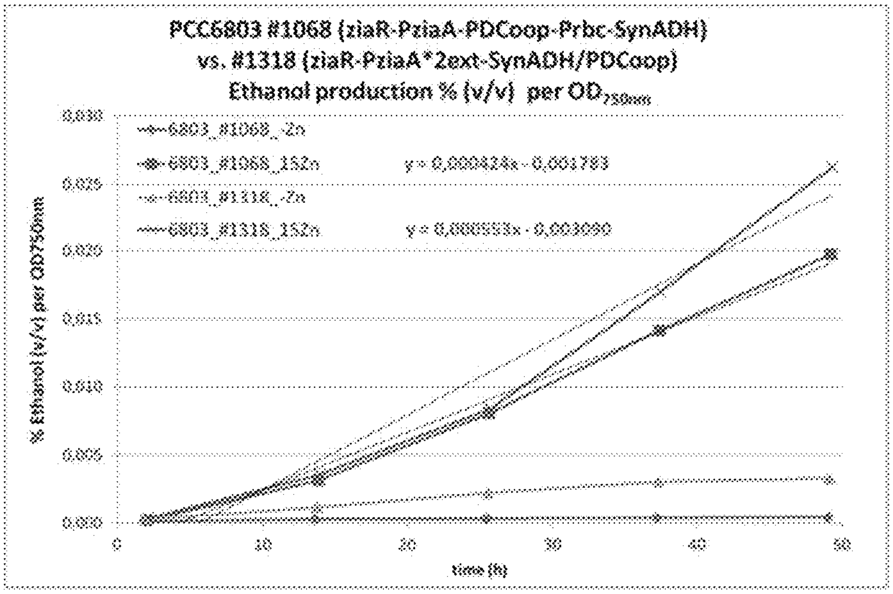
Figure 9I:
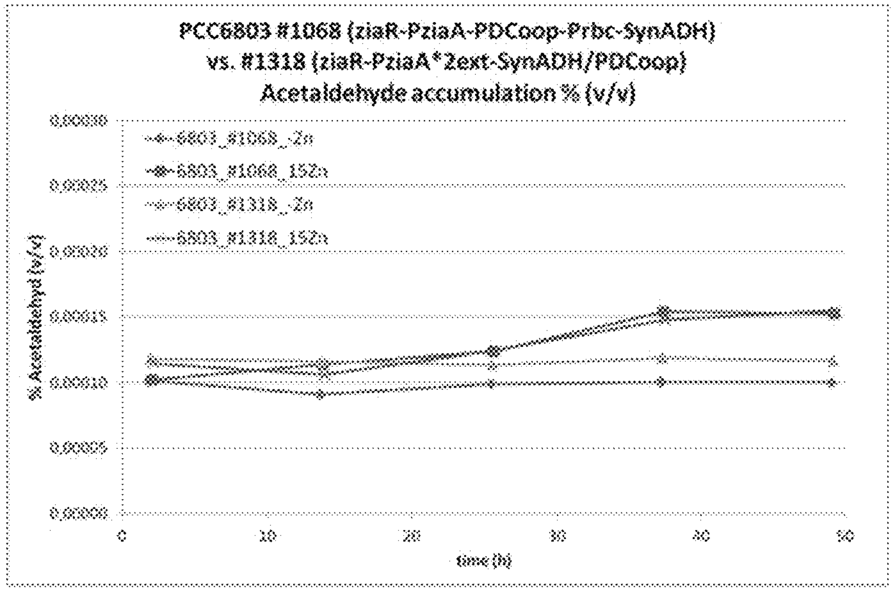
Figure 9J:
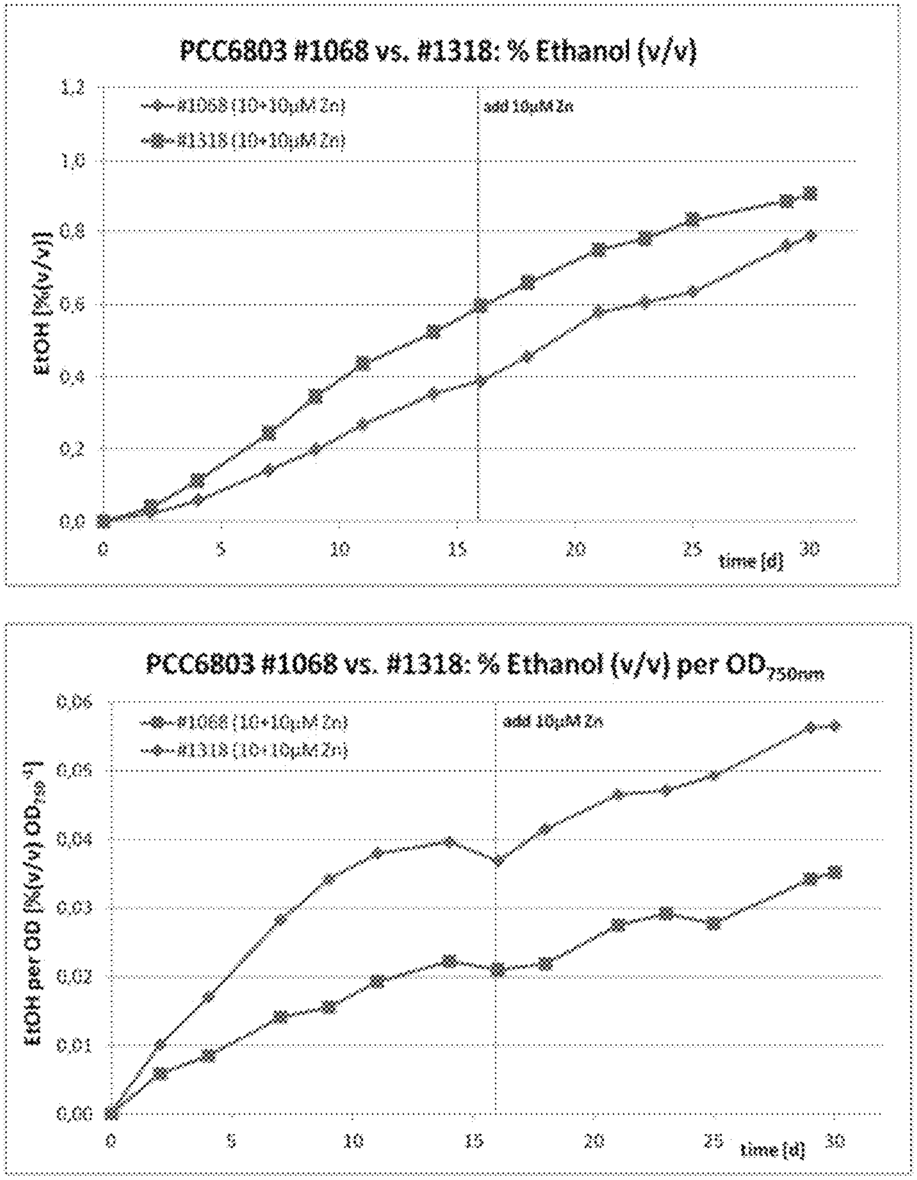

FIG. 9I shows that the ethanol production over time (v/v) are also slightly higher for #1318 than for #1068, whereas the acetaldehyde accumulation in % (v/v) is lower for the *Synechocystis* strain with the PziaA*2ext promoter indicating that acetaldehyde is converted to ethanol to a higher extent than for #1068 so that intermediate accumulation of toxically acetaldehyde is decreased.

FIG. 9 J shows a direct comparison of the ethanol production (v/v) and of the ethanol production (v/v) normalized to the $OD_{750\ nm}$ for the cyanobacterial strains transformed with the plasmids #1068 and #1318 over a cultivation period of 30 days. It can clearly be seen that the ethanol production rate is much higher for #1318.

Figure 9K:
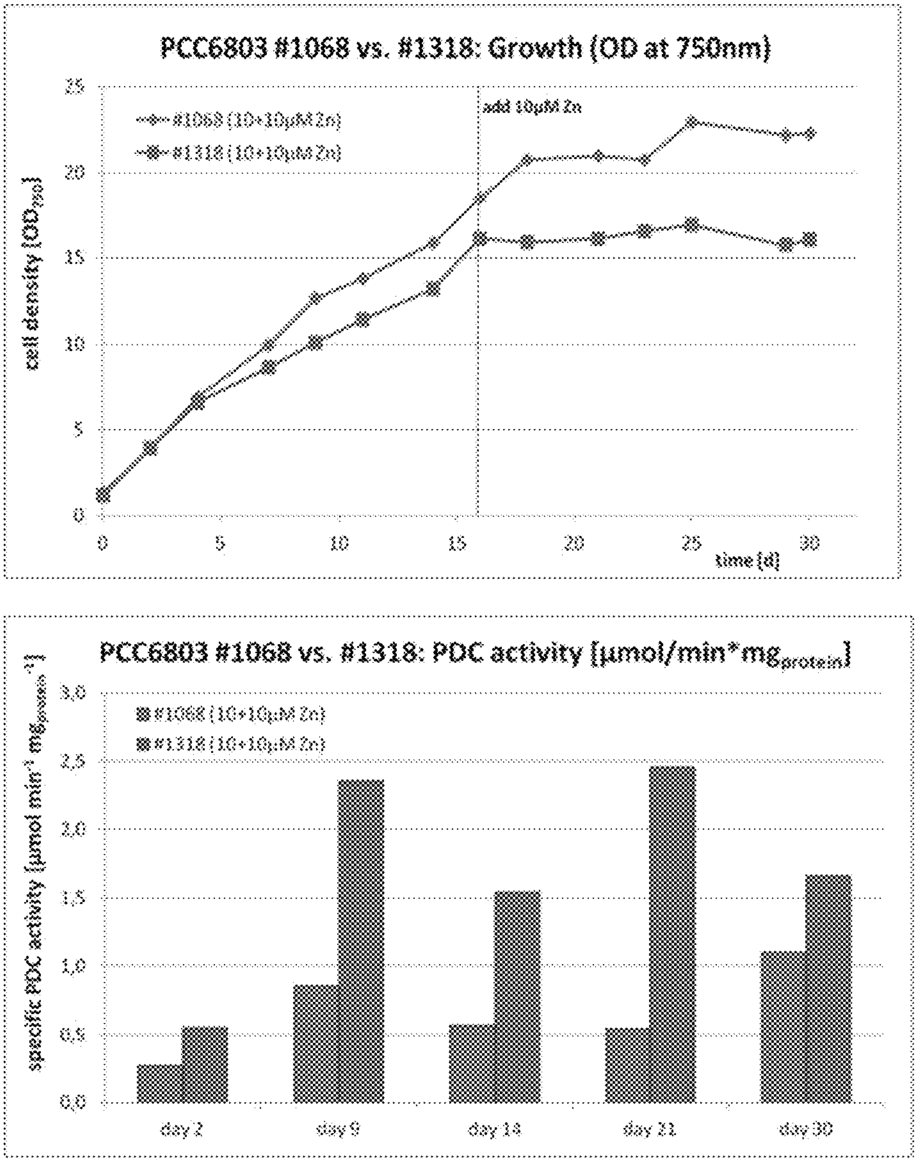

FIG. 9K shows a direct comparison of the growth rate ($OD_{750\ nm}$) and of the specific Pdc enzyme activity (μmol/min*$mg_{protein}$) for the cyanobacterial strains transformed with the plasmids #1068 and #1318 over a cultivation period of 30 days. It is evident that on one hand the Pdc activity of strain #1318 is higher than the Pdc activity of strain #1068, but one the other hand the growth is lower for strain #1318.

Sequence Comparison of PziaA with Other $Zn^{2+}$, $Co^{2+}$ and $Ni^{2+}$ Inducible Promoters FIG. 10 shows a comparison of the nucleotide sequences of the Zn2+ inducible PziaA, PaztA, PsmtA from *Synechococcus* PCC 7002 and PsmtA from *Synechococcus* PCC 7942. The nucleotide sequences of the $Co^{2+}$ and $Ni^{2+}$ inducible promoters PcorT and PnrsB are also shown. These promoters are already included in the sequence listing with the SEQ ID NOs. 1, 2, 3, 4 and 45.

FIG. 10 also indicates the anti-sense orientation of the genes coding for the various regulator proteins ziaR, aztR, smtB, corR and nrsR and the sense orientation of the $Zn^{2+}$, $Co^{2+}$ or $Ni^{2+}$ transporting proteins, whose transcription is controlled by the above promoters. The positions of the various operator sequences, TATA boxes and ribosomal binding sites are also indicated.

The boxed upper part of FIG. 10 shows the identified gene cluster composed of eleven open reading frames involved in $Ni^{2+}$, $Co^{2+}$, and $Zn^{2+}$ sensing and tolerance from *Synechocystis* PCC 6803 (García-Domínguez M, Lopez-Maury L, Florencio F J, Reyes J C. J Bacteriol. 2000 March; 182(6): 1507-14).

Characteristics of Genetically Enhanced Cyanobacteria Harboring aztR-PaztA as a Further Example of a $Zn^{2+}$ Inducible Promoter from *Anabaena* PCC7120 for the Production of Ethanol as a First Chemical Compound FIG. 11A shows a map of the plasmid #1277 (sequence of the insert including the ethanologenic genes and the promoters is part of the sequence listing with SEQ ID NO. 65) used for conjugation of *Synechocystis* PCC 6803 including the ethanologenic genes coding for pyruvate decarboxylase enzyme under the transcriptional control of PaztA from *Anabaena* PCC 7120 and alcohol dehydrogenase enzyme under the transcriptional control of the constitutive PrbcL* (truncated rbc core promoter from *Synechocystis* PCC6803). The plasmid also harbors the gene aztR coding for a repressor binding to PaztA. Apart from the oop terminator a further terminator sequence derived from the small non-coding RNA DsrA from *E. coli* was introduced. Four independent *Synechocystis* clones carrying the ethanologenic pVZ construct #1277 were grown on BG11 agar plates containing different amounts of zinc (no, 3 μM and 10 μM zinc) for 3 days in continuous light. For harvesting, the cells were scratched from the plates and suspended in mBG11 medium containing either no, 3 μM and 10 μM zinc. The EtOH production in the GC vials was analyzed by GC measurements for a duration of about 16 hours in continuous light (150ρE/$m^2$*s) at 37° C.

Figure 11C:
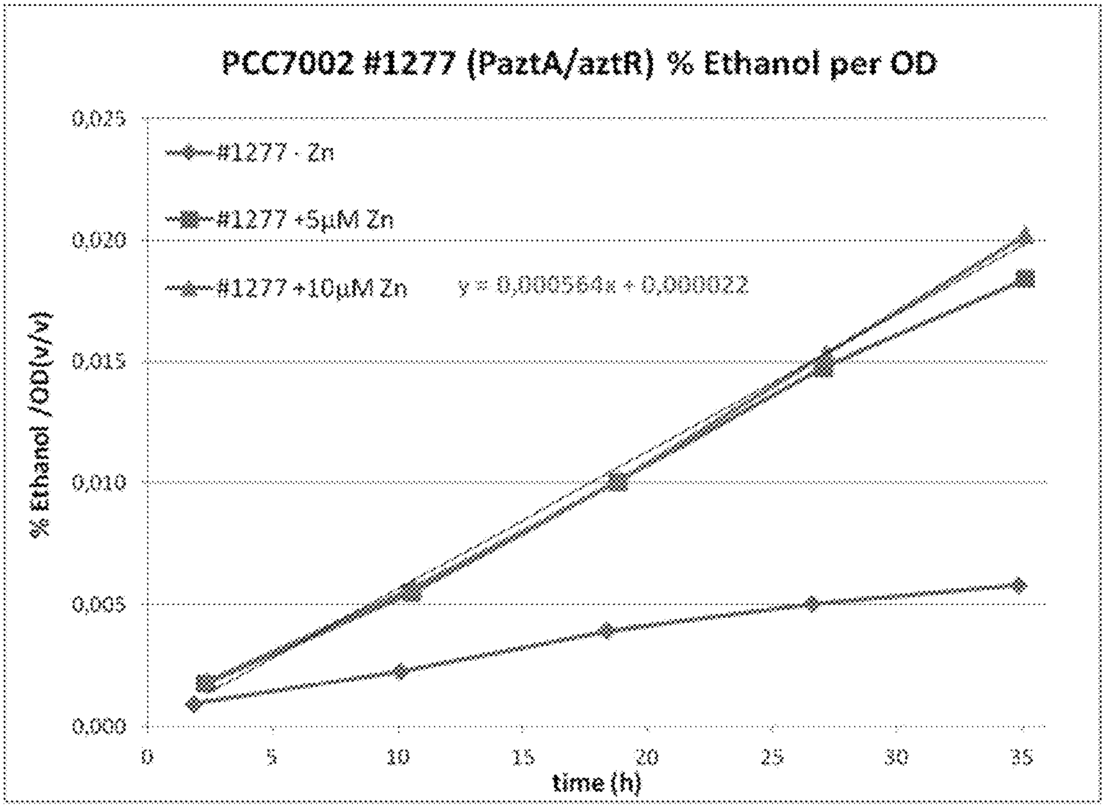

FIG. 11B shows that in mBG11 medium the aztR-PaztA promoter seems to be repressed to a comparable extent like ziaR-PziaA in the absence of $Zn^{2+}$. However, upon addition of 3 μM $Zn^{2+}$ the ethanol production appears to be still repressed. This might indicate an advantage of the aztR-PaztA promoter in comparison to ziaR-PziaA with regard to potential zinc contaminations in seawater or instant ocean extracts used for preparation of the mBG11 culture medium which might have an impact on the tightness of the zinc-inducible promoter. If an amount of 10 μM $Zn^{2+}$ is added, the ethanol production is substantially increased to a production rate of around 0.008% (v/v)/$OD_{750}$*d that is slightly lower than for the corresponding ziaR-PziaA strain (#1068). FIG. 11C depicts a similar GC online experiment as described before for *Synechococcus* PCC7002 carrying the plasmid #1277 (see FIG. 11A). FIG. 11C indicates a zinc dependent regulation of the ethanol production using the aztR-PaztA promoter from *Anabaena* PCC7120. In the absence of zinc, only a marginal ethanol accumulation is detectable whereas upon addition of 5 μM and 10 μM zinc the ethanol production can be switched on to a production rate of about 0.014% (v/v)/$OD_{750}$*d. As shown in FIGS. 11A and 11B the aztA promoter with the repressor gene aztR (smtB-like) seems to be functional and well suited for inducible production of ethanol and probably many other first chemical compounds in *Synechocystis* PCC6803 and *Synechococcus* PCC7002. It is very likely that the results obtained here with plasmid #1277 are transferable also to other cyanobacterial genera beside *Synechocystis* and *Synechococcus.*

Figure 12B:
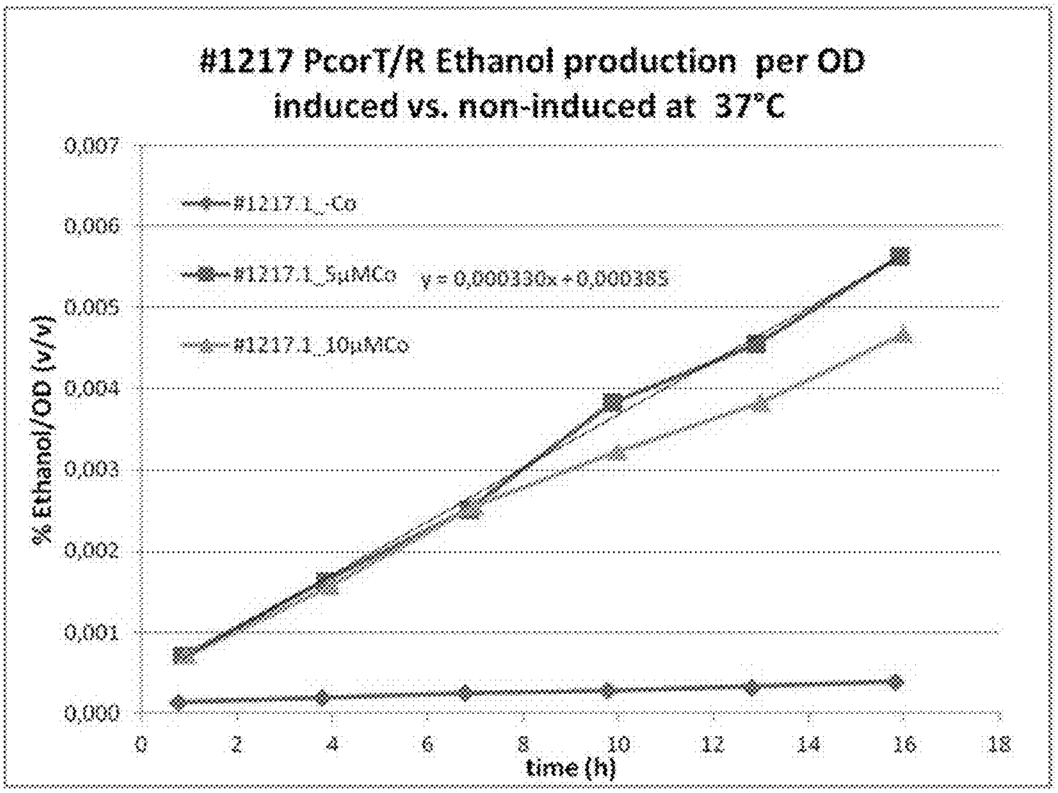
Figure 12C:
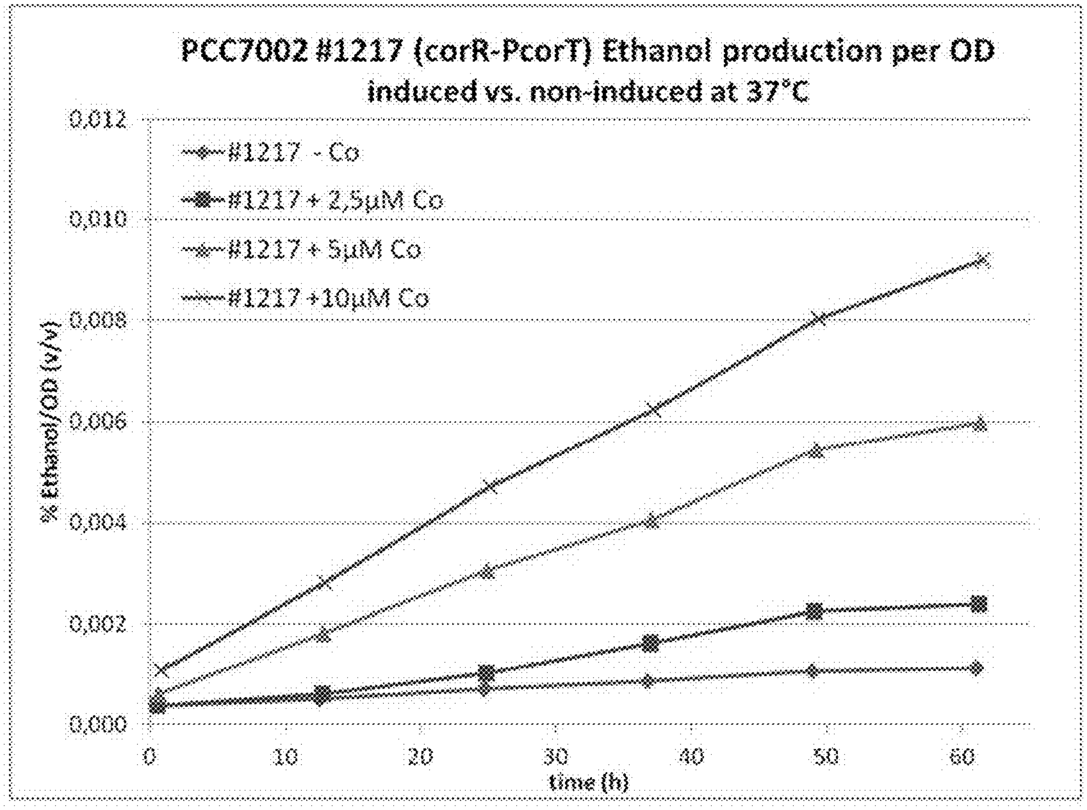

Characteristics of Genetically Enhanced Cyanobacteria Harboring corR-PcorT as an Example for a $Co^{2+}$ Inducible Promoter from *Synechocystis* PCC6803 for the Production of Ethanol as a First Chemical Compound FIG. 12A shows a map of the plasmid #1217 (sequence of the insert including the ethanologenic genes and the promoters is shown in the sequence listing with SEQ ID NO. 66) used for conjugation of *Synechocystis* PCC 6803 that includes the ethanologenic genes coding for Pdc under the transcriptional control of the endogenous corT promoter and the SynAdh under the transcriptional control of the constitutive PrbcL*. The plasmid also harbors the gene corR coding for a transcriptional regulator that binds to the corT promoter. A *Synechocystis* hybrid carrying the ethanologenic pVZ construct #1217 was cultivated by growing on BG11 agar plates containing different amounts of cobalt (no, 5 μM and 10 μM cobalt) for 3 days in continuous light. For harvesting, the cells were scratched from the plates and suspended in mBG11 medium containing the same concentrations of cobalt (no, 5 μM and 10 μM cobalt) and transferred to GC vials. The ethanol production in GC vials was analyzed by GC measurements for a duration of about 16 hours in continuous light (150 μE/$m^2$*s) at 37° C. FIG. 12B depicts the ethanol production of *Synechocystis* harboring the plasmid #1217 including the $Co^{2+}$-inducible promoter corT along with the corR gene. In the absence of cobalt the corT promoter seems to be very tight repressed in mBG11 similar to ziaR-PziaA (without zinc). In the presence of 5 μM cobalt the ethanol production substantial increased to a production rate of around 0.008% (v/v)/$OD_{750}$*d that is slightly lower than measured for the corresponding ziaR-PziaA strain (#1068). Interestingly addition of 10 μM cobalt does not show significantly higher ethanol production rates than observed for a Co2+ concentrations of 5 μM. FIG. 12C depicts a similar GC assay experiment for *Synechococcus* PCC7002 carrying the plasmid #1217 (see FIG. 12A). Cells were cultivated by growing on BG11 agar plates containing different amounts of cobalt (no, 2.5 μM, 5 μM and 10 μM cobalt) for 3 days in continuous light. For harvesting, the cells were scratched from the plates and suspended in mBG11 medium containing the same concentrations of cobalt (no, 2.5 μM, 5 μM and 10 μM cobalt) and transferred to GC vials. The ethanol production of cultures in the GC vials were analyzed by GC measurements for a duration of about 60 hours in continuous light (150 μE/$m^2$*s) at 37° C. FIG. 12C depicts the ethanol accumulation per $OD_{750\ nm}$ and shows that a cobalt dependent regulation of the ethanol production using the corR-PcorT promoter from *Synechocystis* PCC6803 can be achieved. In the absence of cobalt the ethanol accumulation is very low whereas upon addition of 5 μM and 10 μM cobalt the ethanol production can be boosted to a production rate of about 0.004% (v/v)/$OD_{750}$*d. As shown in FIGS. 12B and 12C the corT promoter with the regulator gene corR is functional in *Synechocystis* PCC6803 and *Synechococcus* PCC7002 and is well suited for inducible production of ethanol and potentially also of other first chemical compounds in cyanobacteria.

Characteristics of Genetically Enhanced Cyanobacteria Harboring nrsR-PnrsB as an Example of a $Ni^{2+}$ Inducible Promoter from *Synechocystis* PCC6803 for the Production of Ethanol as a First Chemical Compound FIG. 13A shows a map of the plasmid #1227 (sequence of the insert with the ethanologenic genes and the promoters is included in the sequence listing with SEQ ID NO: 67) used for conjugation of *Synechocystis* PCC6803 that includes the ethanologenic genes coding for Pdc under the transcriptional control of the endogenous nrsB promoter and the SynAdh under the transcriptional control of the constitutive PrbcL*. The plasmid also harbors the gene nrsR coding for a transcriptional activator that binds to the nrsB promoter. A *Synechocystis* hybrid carrying the ethanologenic pVZ construct #1227 was cultivated by growing on BG11 agar plates containing different amounts of nickel (no, 3 μM and 7 μM nickel) for 3 days in continuous light. For harvesting, the cells were scratched from the plates and suspended in mBG11 medium containing the same concentrations of nickel as the BG11 agar plates before. The ethanol production in GC vials was analyzed by GC measurements for a duration of about 17 hours in continuous light (150 μE/$m^2$*s) at 37° C. FIG. 13B depicts the recorded ethanol accumulation normalized to $OD_{750\ nm}$ of *Synechocystis* harboring the plasmid #1227. As visible from FIG. 13B the ethanol production of *Synechocystis* harboring the plasmid #1227 is induced upon induction with nickel. In the absence of $Ni^{2+}$ there is almost no ethanol formed indicating a very tight promoter control whereas in the presence of 3 μM and 7 μM $Ni^{2+}$ the ethanol production is strongly increased to a production rate of around 0.008% (v/v)/$OD_{750}$*d that is similar to the construct #1217 (corR-PcorT) and slightly lower than measured for the corresponding ziaR-PziaA strain (#1068) in *Synechocystis* PCC6803. The nrsB promoter seems to allow a very tight control of the ethanol production in *Synechocystis.*

FIG. 13C shows the plasmid map for the plasmid #1353 containing SynAdh encoding gene under the transcriptional control of the Prbc* promoter and Pdc encoding gene under the control of PnrsB with the regulators nrsR and nrsS. The insert containing the ethanologenic genes and the promoters is included in the sequence listing with SEQ ID NO. 70.

FIG. 13D depicts the corresponding ethanol production rates of *Synechococcus* PCC 7002 per $OD_{750}$ transformed with the plasmid #1353. It can be clearly seen that with increasing nickel concentrations ranging from 2.5 μM to 10 μM the ethanol production rate increases.

Figure 14D:
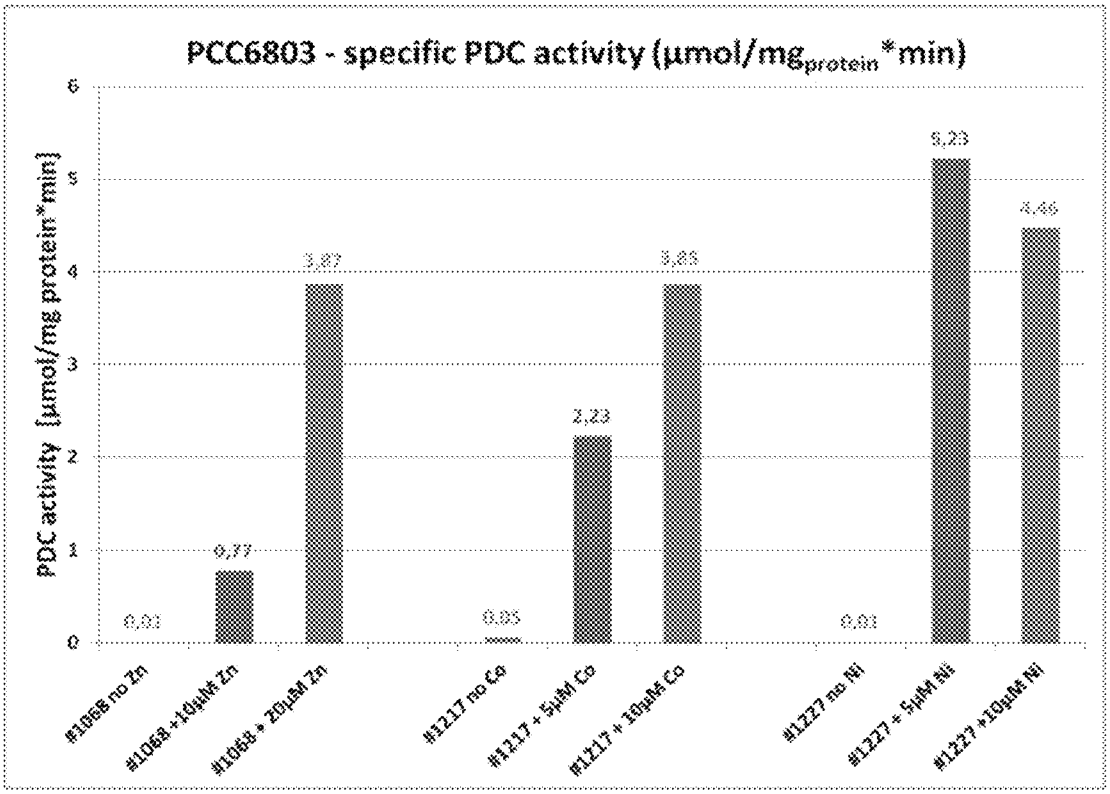

Comparison of Genetically Enhanced *Synechocystis* Strains Harboring ziaR-PziaA, corR-PcorT and nrsR-PnrsB In FIGS. 14A-14C the data for culture growth, ethanol accumulation as well as the ethanol accumulation normalized to the optical density collected in a cultivation experiment over a period of 14 days in Erlenmeyer flasks using mBG11 are summarized for the hybrid strains ziaR-PziaA (#1068), corR-PcorT (#1217) and nrsR-PnrsB (#1227), respectively. As shown in FIGS. 14A-C (left hand side) there are substantial differences in growth depending on the amount of the corresponding metal, which is added for induction of the ethanologenic genes. All three strains show a similarly reduced growth behavior at the highest concentration of respective metal-ion in the culture, so that for ziaR-PziaA (#1068) at 20 μM zinc, for corR-PcorT (#1217) at 10 μM cobalt and for nrsR-PnrsB (#1227) at 10 μM nickel the final $OD_{750\ nm}$ reached after 14 days of cultivation is only about 2. In contrast to that, the $OD_{750\ nm}$ at repressed conditions (without added zinc, cobalt or nickel) is about 2.5× as high as found for the respective induced culture condition. This large difference between the induced and repressed state is obviously a direct effect of the almost completely deactivated ethanol synthesis due to the tight repression realized by the mode of action of these metal-ion inducible promoters. Furthermore in FIGS. 14A-14C (in the middle) the ethanol accumulation is shown. As already detected in the GC assay experiment described before, all three strains show a similar ethanol accumulation under induced cultivation conditions. The ethanol accumulation at the repressed state is very low for all three ethanologenic strains although the optical density and therefore the amount of cells per ml is about 2.5× as high as for the culture at fully induced state. Thus when for this experiment the OD normalized ethanol accumulation is calculated (FIGS. 14A-14C right hand side) the corresponding induction factors for each of the hybrid strains are very high reaching values of about 40-60× that exceed by far the results obtained in a similar cultivation experiment using plasmid #969 containing the ziaA promoter without ziaR repressor encoded on the plasmid (see FIG. 6B—induction factor of ~8× for #969). Furthermore in FIG. 14D the measured Pdc activities from the cultivation experiment shown in FIG. 14A-14C for the ziaR-PziaA (#1068), for corR-PcorT (#1217) and for nrsR-PnrsB (#1227) cultures at the different metal ion concentrations are shown (activities of Pyruvate decarboxylase determined according to Hoppner, T. C. and Doelle, H. W. (1983). *Purification and kinetic characteristics of pyruvate decarboxylase and ethanol dehydrogenase from Zymomonas mobilis in relation to ethanol production*. Eur. J. Appl. Microbiol. Biotechnol). It is evident that as long as no metal ion is present in the growth medium all three promoters are almost completely switched off leading to a remaining Pdc base activity below a value of 0.05 μmol/$mg_{protein}$*min. In contrast to that if the respective metal ions are added the measured PDC activities reach values of 4-5 μmol/$mg_{protein}$*min that is about 100 times higher than found for the respective repressed state. This additionally demonstrates the excellent characteristics of the three tested metal-ion inducible promoters from *Synechocystis* PCC6803. The results shown in FIGS. 14A-14D demonstrate the superior functioning of the ziaA promoter in combination with the ziaR gene encoded on the same plasmid and also show the superior performance of corR-PcorT and nrsR-PnrsB in direct comparison to PziaA.

Characteristics of Genetically Enhanced *Synechococcus* PCC 7002 Cyanobacteria Harboring smtB-PsmtA as an Example of a $Zn^{2+}$ Inducible Promoter for the Production of Ethanol as a First Chemical Compound FIG. 15A shows a map of the plasmid TK96 (plasmid sequence of TK96 including the ethanologenic genes is part of the sequence listing with SEQ ID NO. 68) used for transformation of *Synechococcus* PCC 7002 via integration into the endogenous pAQ4 plasmid that includes the ethanologenic genes coding for Pdc and SynAdh under the transcriptional control of the endogenous smtA promoter. FIG. 15B shows a map of the plasmid #TK115 (sequence of the complete plasmid TK 115 available in the sequence listing under SEQ ID NO. 69) used for conjugation of *Synechococcus* PCC 7002 via integration into the endogenous pAQ4 plasmid that comprises the ethanologenic genes coding for Pdc under the transcriptional control of the endogenous smtA promoter and the $SynAdh_{deg}$ under the transcriptional control of the constitutive PrbcL* from *Synechocystis*. Plasmid #TK115 also harbors the gene smtB coding for a transcriptional repressor that binds to the smtA promoter. FIGS. 15C and 15D depict the ethanol production of *Synechococcus* PCC 7002 TK96 vs. #TK115 in dependence from the zinc availability in the growth medium measured by GC online experiment over more than 40 hours. It can clearly be seen that upon addition of 2.5, 5 and 10 μM $Zn^{2+}$ high ethanol production rates with induction factors of 8 and 10, respectively were achieved.

FIG. 15E shows the chlorophyll content, the $OD_{750}$ and the ethanol production rates (absolute and normalized on OD) of *Synechococcus* PCC 7002 containing the ethanologenic gene cassette present in plasmid TK96 (see FIG. 15A) integrated into the endogenous pAQ4 plasmid from *Synechococcus* PCC 7002 via homologous recombination. Cultures were cultivated in 0.5 L flasks aerated with $CO_2$ enriched air. Upon induction with 5, 10 or 15 μM $Zn^{2+}$ a high ethanol production rate can be observed, whereas the $OD_{750}$ goes down, because more carbon is shuffled into ethanol synthesis and not into the growth of the culture. If no zinc is added to the culture medium, the ethanol accumulation remains low, so that the induction factor which is indicated by the double arrows shown in the diagram with the ethanol production per OD (bottom right in FIG. 15E) is about 6× when calculated for the cultures with 10 μM and 15 μM zinc whereas for 5 μM zinc the factor is about 4×.

Comparison of the Ethanol Production Rate of *Synechococcus* PCC 7002 Strains Harboring Plasmids for Ethanol Production with an Endogenous $Zn^{2+}$ Inducible Promoter and Plasmids with a Heterologous $Zn^{2+}$ Inducible Promoter FIGS. 16A and 16 B shows the ethanol production of genetically enhanced *Synechochoccus* PCC 7002 strains transformed with extrachromosomal plasmids #1121 including an endogenous PsmtA/smtB promoter/regulator pair in comparison to the same cyanobacterial strain harboring an extrachromosomal plasmid #1348 including a heterologous promoter/regulator pair PziaA/ziaR from *Synechocystis* PCC 6803. The ethanol production rates were measured via the GC vial assay as mentioned above. The *Synechococcus* strain with plasmid #1121 shows much higher ethanol production rates compared to the same cyanobacterial strain plasmid #1348 comprising the heterologous promoter system. However the endogenous smtB-PsmtA promoter system is less tightly repressed in the absence of $Zn^{2+}$ in the growth medium whereas the ziaR-PziaA construct #1348 appears very tight without $Zn^{2+}$ addition. With increasing $Zn^{2+}$ concentrations the ethanol production of the cells including construct #1348 gradually increases while for cyanobacterial cells including plasmid #1121 (smtB-PsmtA) addition of 4 μM $Zn^{2+}$ already leads to full promoter activation, and further $Zn^{2+}$ addition does not increase ethanol production significantly.

The FIGS. 16C and D show the plasmid maps of the plasmids #1121 and #1348, whose nucleotide sequences are included in the sequence listing with SEQ ID NO. 75 and SEQ ID NO. 76.

Characterization of *Synechococcus* PCC 7002 Strains with Inserted Ethanol Cassettes into the Endogenous Extrachromosomal Plasmids pAQ4, pAQ3 and pAQ1

*Synechococcus* PCC 7002 strains were transformed with the plasmids TK 115, TK 161, and TK 165, respectively, which all contain a gene coding for ZmPDC enzyme transcriptionally controlled by the promoter/regulator pair PsmtA/smtB and which also include a $SynAdh_{deg}$ gene, which is constitutively transcribed under control of PrbcL (6803). The main difference between these plasmids is that they all contain different integrative platforms, homologous sequences named FA2 and FB2 respectively, which are used for homologous recombination of the ethanologenic cassettes of these plasmids into the endogenous plasmids pAQ4, pAQ3 and pAQ1 of *Synechococcus* PCC 7002, respectively.

FIGS. 17A and 17B depict the activities of the Pdc enzyme and the Adh enzyme depending on the integration of the different endogenous plasmids in comparison to a pVZ322 based extrachromosomal plasmid #1121 in *Synechococcus* PCC7002. It is evident from these graphs that both the activities of Pdc enzyme and Adh enzyme are correlating with increasing copy number of respective plasmids, i.e. the higher the number of copies of used endogenous plasmid for integration, the higher the activities are. In particular, the determined Pdc and Adh activities for pAQ4 integration (15 copies per cell) and the above mentioned broad-host range plasmid #1121 are very similar under induced conditions ($Zn^{2+}$ addition) and repressed conditions indicating a similar copy number/gene dosage for both plasmids. In contrast, cyanobacterial strains with higher copy number plasmids generated by integration into pAQ3 (27 copies per cell) and pAQ1 (50 copies per cell) exhibit substantially elevated Pdc and Adh activities respectively, compared to the broad-host range shuttle plasmid #1121.

FIGS. 17C and 17D show the ethanol production over time of the strains already mentioned above and discussed in FIGS. 17A and 17B measured by the GC vial assay. According to the determined Pdc and Adh activity for the different pAQ integrations, the observed ethanol production rates are increasing gradually with increasing copy number/gene dosage of corresponding pAQ plasmid used for integration of the ethanologenic gene cassette. At the same time with increasing copy number (pAQ4<pAQ3<pAQ1) the applied smtB-PsmtA promoter system gets more leaky due to the higher gene dosage of the ethanologenic gene cassette.

Figure 17E:
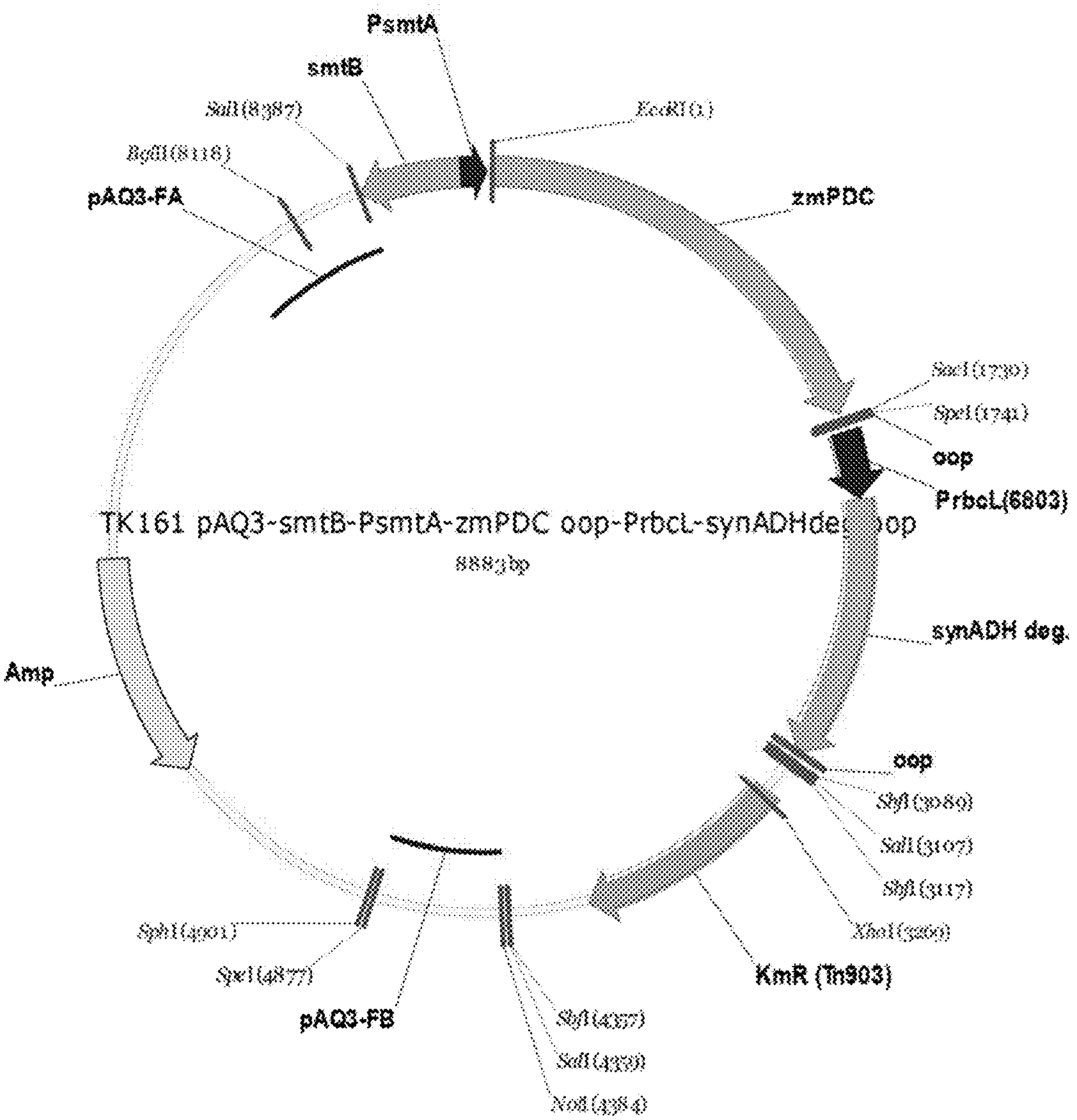
Figure 17F:
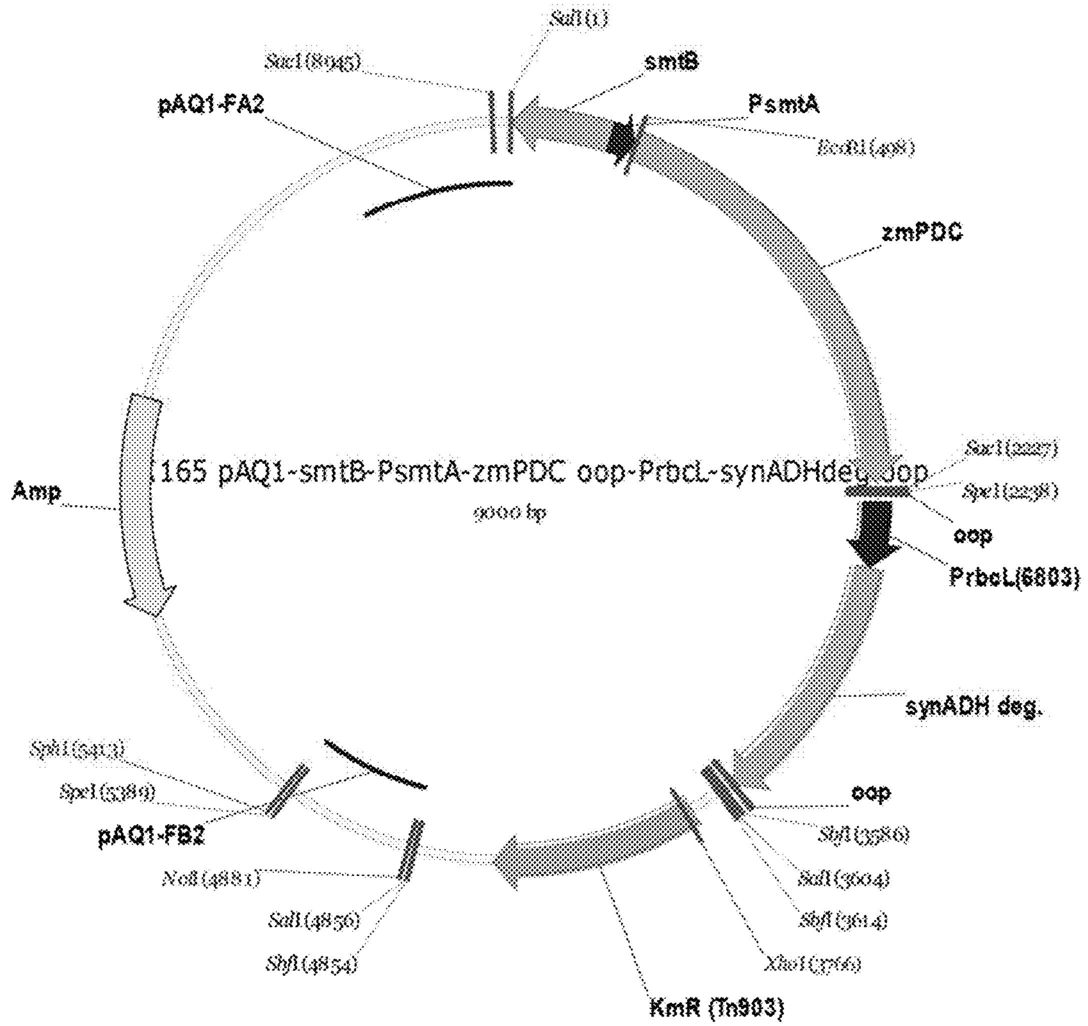

The plasmid maps of these plasmids TK 161, and TK 165, respectively are shown in the FIGS. 17E, and 17F, and the nucleotide sequence of the plasmids TK 115, TK 161 and TK 165 is listed as SEQ ID NO. 77, 78 and 79, respectively, in the sequence listing.

Characteristics of *Synechococcus* PCC 7002 Strains Including an Ethanologenic Cassette with a Heterologous $Zn^{2+}$-Inducible Promoter FIGS. 18A and 18B show the ethanol production and the specific activity of the Pdc enzyme depending on the induction condition (0, 5, 10 and 15 μM zinc) for *Synechococcus* PCC 7002 strains for a time period of about 60 hours. An ethanologenic cassette including a heterologous $Zn^{2+}$-inducible promoter ziaR-PziaA from *Synechocystis* PCC 6803 was integrated into this strain via transformation with the plasmid #1468 including homologous platforms for integration of the ethanologenic cassette into the endogenous pAQ1. The ethanol production rates were determined via the GC vial assay as described above. The low efficiency/activity of the ziaR-PziaA promoter system in *Synechococcus* strains as detected for plasmid #1348 (FIG. 16B) can be successfully compensated by integration of the ethanologenic gene cassette into the high copy number plasmid pAQ1 present in PCC7002, instead of using a broad-host range shuttle plasmid like #1348. The higher gene dosage when integrated into pAQ1 elevates substantially the gene expression from the ziaR-PziaA promoter which is less active than the endogenous smtB-PsmtA promoter upon $Zn^{2+}$ induction (FIG. 16A). By combining ziaR-PziaA with a pAQ1 integration strategy this heterologous promoter provides a transcriptional activity comparable to endogenous promoters despite its rather weak activity in *Synechococcus* PCC7002. In comparison to pAQ1 with the endogenous Zn2+ inducible promoter system (FIGS. 17C and 17D) the *Synechococcus* including plasmid #1468 appears to be more tightly repressed and needs at the same time higher $Zn^{2+}$ concentrations (up to 15 μM $Zn^{2+}$) for its complete activation. Thereby the induction of ethanol production can be realized more gradually. The determined Pdc activity confirms the tighter controllable gene expression for *Synechococcus* including plasmid #1468 compared to TK165 (FIGS. 17C and 17D).

FIGS. 18C, 18D, 18E, 18F and 18G show the ethanol production (v/v), the ethanol production (v/v) normalized to the $OD_{750\ nm}$, the $OD_{750\ nm}$ and the specific Pdc activity for a 0.5 l cultivation of *Synechococcus* PCC 7002 over a time period of 19 days. This strain was transformed with the plasmid #1468 for integration of the ethanologenic cassette into the high copy number plasmid pAQ1. The low efficiency/activity observed for the ziaR-PziaA from *Synechocystis* PCC6803 in *Synechococcus* strains was compensated by integration of the ethanologenic gene cassette into the high copy number plasmid pAQ1. The accomplished ethanol production rate of about 0.025%/day (12 h/12 h day night cycle) over 2 weeks is substantial higher than detected for a conventional pVZ322 based ethanologenic plasmid comprising a ziaR-PziaA controlled ethanologenic gene cassette. Measured Pdc activities indicate a sufficient high expression level enabling high ethanol production rates.

The plasmid map of plasmid #1468 is depicted in FIG. 18H and the DNA sequence of this plasmid is included in the sequence listing as SEQ ID NO. 80.

Characterization of *Synechococcus* PCC 7002 Comprising an Ethanologenic Cassette with a Heterologous $Co^{2+}$-Inducible Promoter Integrated into the Extrachromosomal Plasmid pAQ4

FIG. 19A depicts the ethanol production over time (v/v) depending on the induction condition (0, 5, 10 and 20 μM cobalt) normalized to the $OD_{750\ nm}$ determined by the GC vial assay for *Synechococcus* PCC 7002 transformed with the plasmid #1332 for integration of the ethanologenic cassette with the $Co^{2+}$-inducible promoter corR-PcorT into the endogenous plasmid pAQ4. In comparison to pAQ4-based genetically enhanced *Synechococcus* strains with the endogenous $Zn^{2+}$-inducible smtB-PsmtA promoter system (FIGS. 17C and 17D) the genetically enhanced strain transformed with plasmid #1332 appears to be very tightly repressed and is gradually inducible by increasing $Co^{2+}$ concentrations. The more Co2+ is added, the stronger the ethanol production is.

FIG. 19B depicts the plasmid map of plasmid #1332, whose nucleic acid sequence is given as SEQ ID NO. 81.

Characterization of *Synechococcus* PCC 7002 Transformed with the Extrachromosomal Plasmid #1449 Including an Ethanologenic Cassette with a $Co^{2+}$-Inducible Promoter System FIGS. 20A and 20B depict the ethanol production (v/v) depending on the induction condition (0, 5 and 10 μM cobalt) normalized to the $OD_{750\ nm}$ and the specific Adh and Pdc activities for cultivation over a time period of about 60 hours in GC vials of *Synechococcus* #1449 comprising an ethanologenic gene cassette with a heterologous $Co^{2+}$ inducible promoter system, corR-PcorT from *Synechocystis* PCC6803 integrated into the extrachromosomal pVZ322 based shuttle plasmid. The ethanol production rate as well as the response to $Co^{2+}$ addition is very similar to the pAQ4 based genetically enhanced strain transformed with the plasmid #1332 with corR-PcorT promoter system (see FIG. 19A). Pdc activity measurements reveal that this heterologous promoter system is very tightly repressed and is gradually inducible by an increasing $Co^{2+}$ addition. In contrast, the Adh activity from the separately transcribed adh gene controlled by a modified version of the *Synechocystis* rbcL core promoter reveals a constantly high ADH expression level independent from the addition of $Co^{2+}$.

The FIGS. 20C, 20D, 20E, and 20F show the ethanol production (v/v), the ethanol production (v/v) normalized to the $OD_{750\ nm}$, the growth as $OD_{750\ nm}$, and the specific activity of Pdc enzyme for a cultivation of a *Synechococcus* strain in 0.5 l bioreactors over a time period of 50 days. The *Synechococcus* PCC 7002 strain was transformed with the pVZ322-based broad host range shuttle plasmid #1449, which comprises an ethanologenic gene cassette with a heterologous $Co^{2+}$ inducible promoter system (corR-PcorT from *Synechocystis* PCC6803). The accomplished ethanol production rates between 0.030%/day and 0.035%/day (12 h/12 h day night cycle) over almost 50 days appears to be very good and meet the needs for commercial ethanol production and appears to be remarkably stable. Measured Pdc activities indicate a sufficient high and stable expression level enabling a very high ethanol production rate with long duration (arrows indicate cell dilution steps with complete medium removal).

The plasmid map of plasmid #1449 is shown in FIG. 20G and its nucleic acid sequence is SEQ ID NO. 82.

Characterization of a *Synechococcus* Strain Including Two Variants of a Heterologous $Co^{2+}$-Inducible Promoter System FIGS. 21A and 21B show the ethanol production (v/v) normalized to the OD750 nm for two *Synechococcus* PCC 7002 hybrid strains one was transformed with the plasmids #1507 and the other with plasmid #1470. The only difference between both plasmids is that in plasmid #1507 the native version of the heterologous promoter/regulator pair PcorT/corR from *Synechocystis* PCC6803 is included, whereas in plasmid #1470 a modified variant PcorT* of the promoter PcorT is used, harboring specific nucleotide modifications in the ribosomal binding site (RBS) of the promoter. Both plasmids are integrative plasmids able to integrate into the endogenous plasmid pAQ3, respectively. The ethanol production rates were measured by the GC vial assay. By introducing specific nucleotide substitutions into the ribosomal binding site of the corT promoter as realized in construct #1470 (corR-PcorT*1) the ethanol production rate was increased by about 50% compared to the native corR-PcorT promoter from PCC6803 (#1507). The tight repression behavior of the corR-PcorT promoter is thereby not negatively impacted. The Pdc encoding gene variant $Zmpdc_{deg}$ (codon degenerated version of Zzmpdc) that was used normally leads to a lower Pdc enzyme expression level in general. Due to this fact one would not expect higher ethanol production from these constructs compared to constructs described before as #1332 (FIG. 19A) and #1449 (FIGS. 20A and 20B) with the same $Co^{2+}$ inducible promoter system but the native pdc gene from *Zymomonas mobilis*. However, the promoter efficiency can be compared between #1470 and #1507.

FIGS. 21C and 21D depict the plasmid maps of plasmids #1507 and 1470. FIG. 21E shows a comparison of the native corT and the modified corT*1 promoter including 5'- and 3'-neighboring nucleic acid sequences with restriction sites and start codons for genes transcriptionally controlled by the promoter. The nucleic acid sequence of plasmid #1507 is included in the sequence listing as SEQ ID NO. 83. SEQ ID NO. 84 shows the DNA sequence of the PcorT* promoter.

Comparison of *Synechococcus* PCC 7002 Strains Transformed with Extrachromosomal Plasmids Containing an Ethanologenic Cassette with a Pdc Gene Under the Control of a Heterologous $Ni^{2+}$- and a Modified $Ni^{2+}$-Inducible Promoter FIGS. 22A and 22B show the ethanol production (v/v) normalized to the $OD_{750\ nm}$ for two *Synechococcus* PCC 7002 strains transformed with pVZ322 based extrachromosomal plasmids #1353 and #1354. The only difference between both plasmids are modifications in the ribosomal binding site of the heterologous $Ni^{2+}$-inducible promoter PnrsB from *Synechocystis* PCC 6803 in plasmid #1354 resulting in the promoter PnrsB* controlling the transcription of the pdc gene. By introducing these specific nucleotide substitutions into the ribosomal binding site of the nrsR promoter in construct #1354 (nrsRS-PnrsB*) the ethanol production rate was increased by 35% compared to the native nrsRS-PnrsB promoter from PCC6803 (strain transformed with #1353). However compared to *Synechococcus* PCC7002 strains with $Co^{2+}$ or $Zn^{2+}$ inducible promoter systems (e.g. #1449 and #1121), the ethanol production rate is still below 50%. The tight repression behavior of the nrsRS-PnrsB promoter in *Synechococcus* PCC7002 is not negatively influenced by the nucleotide substitutions introduced into PnrsB*.

FIG. 22C depicts the plasmid map of plasmid #1353, whose nucleotide sequence is included in the sequence listing as SEQ ID NO. 85. The nucleic acid sequence of the modified promoter PnrsB* is included as SEQ ID NO. 86.

Characterization of *Synechococcus* PCC 7002 Including an Ethanologenic Cassette with a Pdc Gene Under the Control of a Heterologous $Ni^{2+}$-Inducible Promoter FIGS. 23A and 23B show the ethanol production (v/v) normalized to the $OD_{750\ nm}$ and the Pdc enzyme activity for *Synechococcus* PCC 7002 strains including an ethanologenic cassette integrated into the endogenous plasmid pAQ1 with a pdc gene transcriptionally controlled by a heterologous $Ni^{2+}$-inducible promoter from *Synechocystis* PCC 6803. The relatively low efficiency/activity of the nrsRS-PnrsB promoter system from *Synechocystis* PCC6803 in *Synechococcus* PCC 7002 as detected for the strains transformed with plasmid #1353 (FIG. 22A) was successfully compensated by integration of a respective ethanologenic gene cassette into the high copy number plasmid pAQ1 present in PCC7002 by transformation with the integrative plasmid #1441. The higher gene dosage when integrated into pAQ1 elevates substantially the gene expression from the nrsRS-PnrsB promoter upon $Ni^{2+}$ induction. By combining the improved nrsRS-PnrsB* variant of the native PCC6803 promoter (FIG. 22B #1354) with the pAQ1 integration strategy this heterologous promoter becomes applicable despite its rather moderate activity in PCC7002. Pdc enzyme activity measurements reveal that PDC activity of PCC7002 #1441 hybrid is gradually inducible by increasing $Ni^{2+}$ concentrations.

The plasmid map of the integrative plasmid #1441 is shown in FIG. 23C and its nucleic acid sequence is listed as SEQ ID NO. 87.

Characterization of Another *Synechococcus* PCC 7002 Strain Transformed with an Extrachromosomal Plasmid Harboring a Pdc Gene Under the Control of a Further Heterologous $Ni^{2+}$-Inducible Promoter FIGS. 24A and 24B show the ethanol production normalized to the $OD_{750\ nm}$ of a *Synechococcus* strain transformed with the plasmid #1460 and the plasmid map of this extrachromosomal plasmid, respectively. This plasmid contains a pdc gene transcriptionally controlled by another heterologous $Ni^{2+}$-inducible promoter from another *Synechococcus* strain with the internal denomination 916 that is closely related to *Synechococcus* PCC 7002. Compared to the native nrsRS-PnrsB promoter from PCC6803 this *Synechococcus* promoter appears less tight in the repressed state, but enables at the same time a higher ethanol production than observed for *Synechococcus* PCC7002 carrying plasmid #1353 (FIG. 22A). The nucleic acid sequence of plasmid #1460 is presented as SEQ ID NO. 88.

Characterization of Another *Synechococcus* PCC 7002 Strain Transformed with an Integrative Plasmid Harboring a Pdc Gene Under the Control of a Heterologous $Ni^{2+}$-Inducible Promoter from a Closely Related *Synechococcus* Species FIGS. 25A and 25B show the ethanol production normalized to the $OD_{750\ nm}$ of a *Synechococcus* PCC 7002 strain transformed with the plasmid #1473 for integration into the endogenous plasmid pAQ1 and the plasmid map of this integrative plasmid, respectively. It can clearly be seen that the ethanol production in comparison to the last embodiment (see FIG. 24A) can strongly be increased by integration of the respective ethanologenic gene cassette into the endogenous high-copy number plasmid pAQ1 instead using a and broad-host range extrachromosomal plasmid like #1460. This integration into pAQ1 elevates substantially the gene expression from the heterologous nrsRS-PnrsB promoter. The ethanol production rate is thereby increased 3-fold compared to the pVZ322 based shuttle plasmid #1460 (FIG. 24A). However the promoter system appears to be leakier. The nucleic acid sequence of plasmid #1473 is shown as SEQ ID NO. 89.

The scope of the protection of the invention is not limited to the example given herein above. The invention is embodied in each novel characteristic and each combination of characteristics, which particularly includes every combination of any features which are stated in the claims, even if this feature or this combination of features is not explicitly stated in the claims or in the examples.

SEQUENCE LISTING

```
<160> NUMBER OF SEQ ID NOS: 110

<210> SEQ ID NO 1
<211> LENGTH: 568
<212> TYPE: DNA
<213> ORGANISM: Artificial
<220> FEATURE:
<223> OTHER INFORMATION: nucleotide sequence of PziaA and ziaR. The gene
      encoding the regulator ziaR runs in anti-sense direction to PziaA
      wherein the ziaR stop codon is tta of nucleotides 11 to 13 and the
      ziaR start codon is cat of the nucleotides 407 to 409.

<400> SEQUENCE: 1

gtcgacctcc ttaatccgat tcctgcaaat ggtctgcaac ttcccgatac aaattcatca      60

catgattatc cgccaagctg tagtaaacat tacggccgac ccggcgatac tttaccaggc     120

gctgcgatcg taaaattcgt aattgatggg aaactgccga ttcactcact ttcatcgccg     180

ctgctaaatc acagacacag agttcttggc gggccaatgc cgacattaaa cgcaaccgac     240

tcggatcagc tagtgcactg aaaaactccg ccatttgctg ggcctggtcc aatgacatca     300

cctctggttg aacctgtcgt acctgctcaa gatgaacaag aggttgatca caaaggggca     360

tctcttcgtt ctggcaggat tgtgactttg acaacgagga cttactcata gaggttggcg     420

ttaggagcta gggaaaaatt taaactggat ttagaaaatg attttcatcc taacatcttt     480

aatatctgag catatcttca ggtgtttcaa gatttgtgct acggttcaag gaggtttttc     540

tttaaatcac gttggccgcc atgaattc                                        568


<210> SEQ ID NO 2
<211> LENGTH: 503
<212> TYPE: DNA
<213> ORGANISM: Artificial
<220> FEATURE:
<223> OTHER INFORMATION: nucleotide sequence of PsmtA and smtB. The gene
      encoding the regulator smtB runs in anti-sense direction to PsmtA
      wherein the smtB stop codon is tta of nucleotides 67 to 69 and the
      smtB start codon is cat of the nucleotides 391 to 393.

<400> SEQUENCE: 2

gtcgacgggc aaactttatg aagcagatca agcctatatc cgccaagcaa ccggcagccg      60

cgttgattag tgggtgtgtc catcctctgg ttcgtctagg tgctccgaag cgtcacgata     120

gagattaaga atgtggtgat ccttgaggcg ataaatcaca ttccgccctt ccttgcgata     180

gctcactaaa cgtgctgtgc gcagggttct tagttggtga gagacagccg attcactcat     240
```

```
ttcaacggcg gcggcgagtt cccccacccg catctctcca gtggccaggg ccgaaagaat    300

acgccagcgg ttggcatccc ccaagacacc aaaaaattcg gccatccgtt gggccttggc    360

ttggttcaag attttgccac tgtggtctgt cattgttcgc tgatctaaac aatacctgaa    420

taattgttca tgtgttaatc taaaaatgtg aacaatcgtt caactattta agacaatacc    480

ttggaggttt aaaccatgaa ttc                                            503


<210> SEQ ID NO 3
<211> LENGTH: 649
<212> TYPE: DNA
<213> ORGANISM: Artificial
<220> FEATURE:
<223> OTHER INFORMATION: The nucleotide sequence of PaztA and aztR. The
      gene encoding the regulator aztR runs in anti-sense direction to
      PaztA wherein the aztR stop codon is tca of nucleotides 98 to 100
      and the aztR start codon is cat of the nucleotides 506 to 508.

<400> SEQUENCE: 3

gtcgactaaa tcgtaatacc taaatcagcc aacaaaattt agcacaattg cacaggggag     60

aagttcagat taatacattt atactattaa tttgcgatca ccctgtgcca gttgcgtaag    120

tattgttttc cactaaagag cgatataagt taatgacgtg actgtcagcc aaactataat    180

aaacattccg accttctcga cgatagctga ctaaacgcat agctttcaat aaccgcagct    240

gatgacaaac agctgattca ctcattttgg ttaatgcagc tagatcgcaa acacacaact    300

cactagaagc caaagctgat aggaggcgta tacggtttgt atctgctaac accccaaaaa    360

tttctgccat ttgttgtgct ttatctgtcg gtaagatttg agcctgagat gagcgtacat    420

tatctagatg caccagatga gtatcacagg taggggtatc agaactttga attaagtcta    480

agtcctgctt tttcttgtgc ttattcatag caagttttac ttagcaatag ttatcaatct    540

caataatacc taaaatgata accattgtac aattgaatag ttgttcaatt gttgtattag    600

aatattggca gttaactttt tgccttaatt ctaaagctgc tatgaattc                649


<210> SEQ ID NO 4
<211> LENGTH: 1256
<212> TYPE: DNA
<213> ORGANISM: Artificial
<220> FEATURE:
<223> OTHER INFORMATION: nucleotide sequence of PcorT and corR. The gene
      encoding the regulator corR runs in anti-sense direction to PcorT
      wherein the corR stop codon is cta of nucleotides 55 to 57 and the
      corR start codon is cat of the nucleotides 1165 to 1167.

<400> SEQUENCE: 4

gtcgaccatg cgtccaaaac tttcaccatc ctttccctat caacctttac tgcactaaag     60

acaagtgaga tagcagtggc aatctggctt tgcaatcaat gtttccacta aagcgtttag    120

cgttactgcg gctagaagtc ctccaccgag gctcccctga atggtgatat ggggaatggg    180

actggtcatc agtcgtcgtt ttgcccccgg agcatgacta aaaccgatcg gcattccgat    240

cacaagagcc ggctgaatat gttgttgctc tatcagctta caggcagtga gtaaaacaga    300

aggggcatag ccgatcgcca gcacacatcc ttggggaatc tgttgtaacc gctgttgcca    360

atggtcatgg tgccaaaaag cttgctcggc ttccctaagc cctgtgatgt gagggtcgtc    420

aatcagcgtt ttaaccgtac atcctaaatg agctaaccga gtttgatcaa gagccgcagc    480

cacaaccgga acatcggtga cgactggaca ccctgctttc agtgcatctc gtgccgaggc    540

gatcgctccc tgactcaatc gaacggcgtt taccaagcta acatcaccac aggccagcac    600

taattgatgt agtaagtgaa tggtaatttc agagtaagcc gataaatccg gtagcaggtg    660
```

tttgagggat tcctgaaagg cttctggatg agttgttgtc tccgcatcta ggttcgtcca 720
caactgatcg agttttccta acccctcctg gacatccaca tcaagctgtt tcagttgggc 780
cagagcttcc gcttgggtaa tctggcaact ctggtcgcgt cccagtaatc cttctaaagc 840
agatgcggtt tggcggagtc gagtaatctg ctgaatcaca gcctgatatt gctgttgcaa 900
ctgcaccatt agggtgggat caaggctctc ttcagaatgg ctatccagca gttgccgaat 960
atgagacaac tgaaagccct gctgtttgag ggcaatgact cgttggagcc gttgtacgtc 1020
ctgctgagta taaaggcggt agttgccctc tgagcgttga acggggggaa gcaatcccag 1080
ggtgtggtaa tggcgcacca tgcgaggcgt aacgccacct cccactgcat ctgtgagttc 1140
tttaatcgtt aagtgattag tcttcatccc tttagtttac tcaaaacctt gacattgaca 1200
ctaatgttaa ggtttaggct gagaaggtaa aaatccaagt taaaaagcat gaattc 1256

<210> SEQ ID NO 5
<211> LENGTH: 94
<212> TYPE: DNA
<213> ORGANISM: Artificial
<220> FEATURE:
<223> OTHER INFORMATION: generalized nucleotide sequence of PziaA
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(79)
<223> OTHER INFORMATION: n is a, c, g, or t

<400> SEQUENCE: 5
nnnnnnnnnn naatatctga gcatatcttc aggtgttnnn nnnnnnnnnn tacggtnnnn 60
nnannnnnnn nnnnnnnnna cgttggccgc catg 94

<210> SEQ ID NO 6
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 6
nnnnnnnnnn naatatctga gcatatcttc aggtgttnnn nnnnnnnnnn tataatnnnn 60
nnannnnnnn nnnnnnnnnn cgttggccgc catg 94

<210> SEQ ID NO 7
<211> LENGTH: 94
<212> TYPE: DNA
<213> ORGANISM: Artificial
<220> FEATURE:
<223> OTHER INFORMATION: generalized variant of PziaA
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 7
nnnnnnnnnn naatatctga gcatatcttc aggtgttnnn nnnnnnnnnn tacggtnnnn 60
nnannnnnnn nnnnnnnnnn aggaggccgc catg 94

<210> SEQ ID NO 8
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 8
nnnnnnnnnn naacatctga acatatcttc agatgttnnn nnnnnnnnnn tacggtnnnn 60
nnannnnnnn nnnnnnnnnn cgttggccgc catg 94

<210> SEQ ID NO 9
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 9
nnnnnnnnnn naatatctga gcatatcttc aggtgttnnn nnnnnnnnnn tataatnnnn 60
nnannnnnnn nnnnnnnnnn aggaggccgc catg 94

<210> SEQ ID NO 10
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 10
nnnnnnnnnn naacatctga acatatcttc agatgttnnn nnnnnnnnnn tataatnnnn 60
nnannnnnnn nnnnnnnnnn cgttggccgc catg 94

<210> SEQ ID NO 11
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 11
nnnnnnnnnn naacatctga acatatcttc agatgttnnn nnnnnnnnnn tacggtnnnn 60
nnannnnnnn nnnnnnnnnn aggaggccgc catg 94

<210> SEQ ID NO 12
<211> LENGTH: 94
<212> TYPE: DNA
<213> ORGANISM: Artificial
<220> FEATURE:

<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 12
nnnnnnnnnn naacatctga acatatcttc agatgttnnn nnnnnnnnnn tataatnnnn 60
nnannnnnnn nnnnnnnnnn aggaggccgc catg 94

<210> SEQ ID NO 13
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 13
nnnnnnnnnn naatatctga gcatatcttc aggtgttnnn nnnnnnnnnn tatggtnnnn 60
nnannnnnnn nnnnnnnnnn cgttggccgc catg 94

<210> SEQ ID NO 14
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 14

```
nnnnnnnnnn naatatctga gcatatcttc aggtgttnnn nnnnnnnnnn tacagtnnnn     60

nnannnnnnn nnnnnnnnnn cgttggccgc catg                                 94


<210> SEQ ID NO 15
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 15

nnnnnnnnnn naatatctga gcatatcttc aggtgttnnn nnnnnnnnnn tacgatnnnn     60

nnannnnnnn nnnnnnnnnn cgttggccgc catg                                 94


<210> SEQ ID NO 16
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 16

nnnnnnnnnn naatatctga gcatatcttc aggtgttnnn nnnnnnnnnn tatagtnnnn     60

nnannnnnnn nnnnnnnnnn cgttggccgc catg                                 94


<210> SEQ ID NO 17
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
```

-continued

<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 17
nnnnnnnnnn naatatctga gcatatcttc aggtgttnnn nnnnnnnnnn tacaatnnnn 60
nnannnnnnn nnnnnnnnnn cgttggccgc catg 94

<210> SEQ ID NO 18
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 18
nnnnnnnnnn naatatctga gcatatcttc aggtgttnnn nnnnnnnnnn tatgatnnnn 60
nnannnnnnn nnnnnnnnnn cgttggccgc catg 94

<210> SEQ ID NO 19
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 19
nnnnnnnnnn naacatctga acatatcttc agatgttnnn nnnnnnnnnn tatggtnnnn 60
nnannnnnnn nnnnnnnnnn cgttggccgc catg 94

<210> SEQ ID NO 20
<211> LENGTH: 94

<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 20
nnnnnnnnnn naacatctga acatatcttc agatgttnnn nnnnnnnnnn tacagtnnnn 60
nnannnnnnn nnnnnnnnnn cgttggccgc catg 94

<210> SEQ ID NO 21
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 21
nnnnnnnnnn naacatctga acatatcttc agatgttnnn nnnnnnnnnn tacgatnnnn 60
nnannnnnnn nnnnnnnnnn cgttggccgc catg 94

<210> SEQ ID NO 22
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)

<223> OTHER INFORMATION: n is a, c, g, or t

<400> SEQUENCE: 22
nnnnnnnnnn naacatctga acatatcttc agatgttnnn nnnnnnnnnn tatagtnnnn 60
nnannnnnnn nnnnnnnnnn cgttggccgc catg 94

<210> SEQ ID NO 23
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 23
nnnnnnnnnn naacatctga acatatcttc agatgttnnn nnnnnnnnnn tacaatnnnn 60
nnannnnnnn nnnnnnnnnn cgttggccgc catg 94

<210> SEQ ID NO 24
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 24
nnnnnnnnnn naacatctga acatatcttc agatgttnnn nnnnnnnnnn tatgatnnnn 60
nnannnnnnn nnnnnnnnnn cgttggccgc catg 94

<210> SEQ ID NO 25
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t -continued
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 25
nnnnnnnnnn naacatctga acatatcttc agatgttnnn nnnnnnnnnn tatggtnnnn 60
nnannnnnnn nnnnnnnnnn aggaggccgc catg 94

<210> SEQ ID NO 26
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 26
nnnnnnnnnn naacatctga acatatcttc agatgttnnn nnnnnnnnnn tacagtnnnn 60
nnannnnnnn nnnnnnnnnn aggaggccgc catg 94

<210> SEQ ID NO 27
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 27
nnnnnnnnnn naacatctga acatatcttc agatgttnnn nnnnnnnnnn tacgatnnnn 60
nnannnnnnn nnnnnnnnnn aggaggccgc catg 94

```
<210> SEQ ID NO 28
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 28

nnnnnnnnnn naacatctga acatatcttc agatgttnnn nnnnnnnnnn tacaatnnnn     60

nnannnnnnn nnnnnnnnnn aggaggccgc catg                                 94


<210> SEQ ID NO 29
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(80)
<223> OTHER INFORMATION: n is a, c, g, or t

<400> SEQUENCE: 29

nnnnnnnnnn naacatctga acatatcttc agatgttnnn nnnnnnnnnn tacaatnnnn     60

nnannnnnnn nnnnnnnnnn aggaggccgc catg                                 94


<210> SEQ ID NO 30
<211> LENGTH: 94
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
```

<220> FEATURE:
<221> NAME/KEY: misc_feature
<222> LOCATION: (64)..(80)
<223> OTHER INFORMATION: n is a, c, g, or t

<400> SEQUENCE: 30
nnnnnnnnnn naacatctga acatatcttc agatgttnnn nnnnnnnnnn tatgatnnnn 60
nnannnnnnn nnnnnnnnnn aggaggccgc catg 94

<210> SEQ ID NO 31
<211> LENGTH: 87
<212> TYPE: DNA
<213> ORGANISM: Artificial
<220> FEATURE:
<223> OTHER INFORMATION: generalized nucleotide sequence of the corT
promoter
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 31
catnnnnnnn gtttactcaa aaccttgaca ttgacactaa tgttaaggtt taggctnnnn 60
nnnnnnnnnn ncaagttaaa aagcatg 87

<210> SEQ ID NO 32
<211> LENGTH: 87
<212> TYPE: DNA
<213> ORGANISM: Artificial
<220> FEATURE:
<223> OTHER INFORMATION: generalized variant of PcorT
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 32
catnnnnnnn gtttactcaa aaccttgaca ttgacactaa tgttaaggtt tagaatnnnn 60
nnnnnnnnnn ncaagttaaa aagcatg 87

<210> SEQ ID NO 33
<211> LENGTH: 87
<212> TYPE: DNA
<213> ORGANISM: Artificial
<220> FEATURE:
<223> OTHER INFORMATION: generalized PcortT Variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 33
catnnnnnnn gtttactcaa aaccttgaca ttgacactaa tgttaaggtt taggatnnnn 60
nnnnnnnnnn ncaagttaaa aagcatg 87

<210> SEQ ID NO 34
<211> LENGTH: 87
<212> TYPE: DNA
<213> ORGANISM: Artificial
<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 34
catnnnnnnn gtttactcaa aaccttgaca ttgacactaa tgttaaggtt tagactnnnn 60
nnnnnnnnnn ncaagttaaa aagcatg 87

<210> SEQ ID NO 35
<211> LENGTH: 87
<212> TYPE: DNA
<213> ORGANISM: Artificial
<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 35
catnnnnnnn gtttactcaa aaccttgaca ttgacactaa tgttaaggtt taggctnnnn 60
nnnnnnnnnn ngaggataaa aagcatg 87

<210> SEQ ID NO 36
<211> LENGTH: 87
<212> TYPE: DNA
<213> ORGANISM: Artificial
<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 36
catnnnnnnn gtttactcaa aaccttgaca ttgacactaa tgttaaggtt taggatnnnn 60
nnnnnnnnnn ngaggataaa aagcatg 87

<210> SEQ ID NO 37
<211> LENGTH: 87
<212> TYPE: DNA
<213> ORGANISM: Artificial
<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)

<223> OTHER INFORMATION: n is a, c, g, or t

<400> SEQUENCE: 37
catnnnnnnn gtttactcaa aaccttgaca ttgacactaa tgttaaggtt tagactnnnn 60
nnnnnnnnnn ngaggataaa aagcatg 87

<210> SEQ ID NO 38
<211> LENGTH: 87
<212> TYPE: DNA
<213> ORGANISM: Artificial
<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 38
catnnnnnnn gtttactcaa aaccttgaca ttgacactaa tgtcaaggtt tagaatnnnn 60
nnnnnnnnnn ncaagttaaa aagcatg 87

<210> SEQ ID NO 39
<211> LENGTH: 87
<212> TYPE: DNA
<213> ORGANISM: Artificial
<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 39
catnnnnnnn gtttactcaa aaccttgaca ttgacactaa tgtcaaggtt taggatnnnn 60
nnnnnnnnnn ncaagttaaa aagcatg 87

<210> SEQ ID NO 40
<211> LENGTH: 87
<212> TYPE: DNA
<213> ORGANISM: Artificial
<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 40
catnnnnnnn gtttactcaa aaccttgaca ttgacactaa tgtcaaggtt tagactnnnn 60
nnnnnnnnnn ncaagttaaa aagcatg 87

<210> SEQ ID NO 41
<211> LENGTH: 87
<212> TYPE: DNA
<213> ORGANISM: Artificial

<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 41
catnnnnnnn gtttactcaa aaccttgaca ttgacactaa tgtcaaggtt taggctnnnn 60
nnnnnnnnnn ngaggataaa aagcatg 87

<210> SEQ ID NO 42
<211> LENGTH: 87
<212> TYPE: DNA
<213> ORGANISM: Artificial
<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 42
catnnnnnnn gtttactcaa aaccttgaca ttgacactaa tgtcaaggtt taggatnnnn 60
nnnnnnnnnn ngaggataaa aagcatg 87

<210> SEQ ID NO 43
<211> LENGTH: 87
<212> TYPE: DNA
<213> ORGANISM: Artificial
<220> FEATURE:
<223> OTHER INFORMATION: generalized PcorT variant
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 43
catnnnnnnn gtttactcaa aaccttgaca ttgacactaa tgtcaaggtt tagactnnnn 60
nnnnnnnnnn ngaggataaa aagcatg 87

<210> SEQ ID NO 44
<211> LENGTH: 91
<212> TYPE: DNA
<213> ORGANISM: Artificial
<220> FEATURE:
<223> OTHER INFORMATION: generalized nucleotide sequence of the aztA promoter
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (51)..(55)
<223> OTHER INFORMATION: n is a, c, g, or t
<220> FEATURE:
<221> NAME/KEY: misc_feature
<222> LOCATION: (57)..(73)
<223> OTHER INFORMATION: n is a, c, g, or t

<400> SEQUENCE: 44
nnnnnnnnnn nntgtacaat tgaatagttg ttcaattgtt gtattagaat nnnnncnnnn 60
nnnnnnnnnn nnnaattcta aagctgctat g 91

<210> SEQ ID NO 45
<211> LENGTH: 2309
<212> TYPE: DNA
<213> ORGANISM: Artificial
<220> FEATURE:
<223> OTHER INFORMATION: nucleotide sequences of PnrsB, nrsS and nrsR. The gene encoding the regulator nrsS runs in anti-sense direction to PnrsB wherein the nrsS stop codon is tta of nucleotides 115 to 117 and the nrsS start codon is cat of the nucleotides 1477 to 1479.

<400> SEQUENCE: 45
gtcgacccta tatcgggctt ttctcaataa aatctttatt ttttgaggtg ctttttagcc 60
ataaataatc actttagtat aaaattttga cggcgtaaag ttgataaaat agaattaaga 120
atggactatc ggtacagaaa aaatgggtaa ctggatggtg aataaacttc ccttacccaa 180
tgcactctcc accgttaaag accccctatg cttaacggtg atcacctggg caatggcgag 240
tcccaaccct gtcccccccg ttttgcgcga acgatctcga ttaactcggt aaaaacgctc 300
aaaaatgtgt tcctgttggt cgggggcaat gccgatgccg gtatcttgca cggtgatgat 360
agccatctgt tcatgggatg tcagggtaat atcaacacgt cccccagcag ttgtgtattg 420
aatggcgttg gcaattaggt ttgagaccag tcgatagagt tgggattcat taccccaggc 480
gtaaacttcc cctgaactca gatcactgct gagatcaatg tgggcggcga tcgctaattc 540
taaaaactct tcggtgaggt cactgactaa atcatttaaa caacaaagcc gccaatcttc 600
ggcggtggtt tcctgctcta agcgacttag tagcaataaa tccgtaatca attggcttaa 660
tcgccttccc tgtcgttcaa cggtatgtag catggtgtta atttctgggg aatggcttga 720
gtcgatgcgt aataccgctt ccaccgtggc caacagacta gccaatggcg atcgtaattc 780
atgggctgca ttcgcggtga attgttgttg ttgttggtag gactggtaaa tgggacgcat 840
ggctaacccc gctaagcccc aactggagaa ggcgaccaaa cccagggcaa tgggaaaact 900
aagccctaaa atccaaagaa tacgtttatt ttcggcatca aaggctgcca ggctccggcc 960
aatttgtaga tagccccagg aagatttgtc tgtattaccg gcgctatgca aaatggtggt 1020
gaattgtcga taccgatcgc cggttggggg gtgaatagtc tgccaagttt cctggttaaa 1080
aatggaggat agggaagccg gttgattagg cgaaaaagcc agcaggttgc cttgataatc 1140
aaataaacga atgtaatata aactgcgatc actaatgccc aacgtgtgac gttcaatcag 1200
ggtggggttg acctggcagg gttggttgac caaacacaga tcgggcaaca ttttttgtaa 1260
tactccggtg ggactagcat tactcggcaa catcggctct aaactgtcat gcaacgtccc 1320
ggcgatcgac tccacttctc gctccaacgc catccagttg gcctgcacaa tggcacgata 1380
aacccccaac cccaacaggg taagaatacc ccccattact agggcatacc agaaagccaa 1440
ttgcagacga ctacgggcaa agaggcgacg ggtattcatg gcgatagggt gaaccgatag 1500
ccttgaccgg gaactgtttt aattgggcaa ggacaatttt gttgagctag cttgcgtcgt 1560
atcaaacgca tttgggccgc caccacatta ctcatgggct cctcatcaag atcccacagt 1620
tgttgccgga tcttgctacc ggaaatgatc cgctctgggt tttgcatcag atattgaaaa 1680

-continued atttgaaatt ctcttacggt taaagcaatt tcctgtcttt ctaggtttag tggctccgag 1740
atagttaccg ataacagatt attactggga tcaaggctga agttgcccaa agttaaaatt 1800
tgcggttgga attgtggcga tcgccgttgt agtgcccgca gtcttgctaa tagctctgcc 1860
atcacaaacg gttttgttag atagtcatct gccccggcat ctagtccttc gacacggttt 1920
tccggttctc ctaacgctgt taacatcaac accggcaagg aattaccctg ggttctcagt 1980
ttttgacaga gttccaaacc cgataatccc ggcagtaacc aatccacaat ggcaagggtg 2040
tattccgtcc attgattttc caaataatcc caagcttggg agccatccgt cacccaatcc 2100
accacatact tttcactaac tagcactttc ttaatagcca ttcccaaatc cgtctcatct 2160
tccaccagca aaattcgcat cgcctctgcc ttttttataa cggtctgatc ttagcggggg 2220
aaggagattt tcacctgaat ttcatacccc ctttggcaga ctgggaaaat cttggacaaa 2280
ttcccaattt gaggtggtgt gatgaattc 2309

<210> SEQ ID NO 46
<211> LENGTH: 96
<212> TYPE: DNA
<213> ORGANISM: Artificial
<220> FEATURE:
<223> OTHER INFORMATION: generalized nucleotide sequence of the nrsB promoter
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (61)..(80)
<223> OTHER INFORMATION: n is a, c, g, or t

<400> SEQUENCE: 46
nnnnnnnnnn nnnnngagat tttcacctga atttcatacc ccctttggca gactgggaaa 60
nnnnnnnnnn nnnnnnnnnn ttgaggtggt gtgatg 96

<210> SEQ ID NO 47
<211> LENGTH: 9803
<212> TYPE: DNA
<213> ORGANISM: Artificial
<220> FEATURE:
<223> OTHER INFORMATION: pVZ322a plasmid (self-replicating broad host range vector)

<400> SEQUENCE: 47
tcgacgaatt tctgccattc atccgcttat tatcacttat tcaggcgtag caccaggcgt 60
ttaagggcac caataactgc cttaaaaaaa ttacgccccg ccctgccact catcgcagta 120
ctgttgtaat tcattaagca ttctgccgac atggaagcca tcacagacgg catgatgaac 180
ctgaatcgcc agcggcatca gcaccttgtc gccttgcgta taatatttgc ccatggtgaa 240
aacgggggcg aagaagttgt ccatattggc cacgtttaaa tcaaaactgg tgaaactcac 300
ccagggattg gctgagacga aaaacatatt ctcaataaac cctttaggga aataggccag 360
gttttcaccg taacacgcca catcttgcga atatatgtgt agaaactgcc ggaaatcgtc 420
gtggtattca ctccagagcg atgaaaacgt ttcagtttgc tcatggaaaa cggtgtaaca 480
agggtgaaca ctatcccata tcaccagctc accgtctttc attgccatac ggaattccgg 540
atgagcattc atcaggcggg caagaatgtg aataaaggcc ggataaaact tgtgcttatt 600
tttctttacg gtctttaaaa aggccgtaat atccagctga acggtctggt tataggtaca 660
ttgagcaact gactgaaatg cctcaaaatg ttctttacga tgccattggg atatatcaac 720

-continued ggtggtatat ccagtgattt ttttctccat tttagcttcc ttagctcctg aaaatctcga 780
taactcaaaa aatacgcccg gtagtgatct tatttcatta tggtgaaagt tggaacctct 840
tacgtgccga tcaacgtctc attttcgcca aaagttggcc cagggcttcc cggtatcaac 900
agggacacca ggatttattt attctgcgaa gtgatcttcc gtcacaggta tttattcgaa 960
gacgaaaggg cctcgtgata cgcctatttt tataggttaa tgtcatgata ataatggttt 1020
cttagacgtc aggtggcact tttcggggaa atgtgcgcgg aacccctatt tgtttatttt 1080
tctaaataca ttcaaatatg tatccgctca tgagacaata accctgataa atgcttcaat 1140
aatattgaaa aaggaagagt atgagtattc aacatttccg tgtcgccctt attccctttt 1200
ttgcggcatt ttgccttcct gtttttgctc acccagaaac gctggtgaaa gtaaaagatg 1260
ctgaagatca gttgggtgca cgagtgggtt acatcgaact ggatctcaac agcggtaaga 1320
tccttgagag ttttcgcccc gaagaacgtt ttccaatgat gagcactttt aaagttctgc 1380
tatgtggcgc ggtattatcc cgtgttgacg ccgggcaaga gcaactcggt cgccgcatac 1440
actattctca gaatgacttg gttgagtact caccagtcac agaaaagcat cttacggatg 1500
gcatgacagt aagagaatta tgcagtgctg ccataaccat gagtgataac actgcggcca 1560
acttacttct gacaacgatc ggaggaccga aggagctaac cgcttttttg cacaacatgg 1620
gggatcatgt aactcgcctt gatcgttggg aaccggagct gaatgaagcc ataccaaacg 1680
acgagcgtga caccacgatg cctgcaggag cagaagagca tacatctgga agcaaagcca 1740
ggaaagcggc ctatggagct gtgcggcagc gctcagtagg caatttttca aaatattgtt 1800
aagccttttc tgagcatggt atttttcatg gtattaccaa ttagcaggaa aataagccat 1860
tgaatataaa agataaaaat gtcttgttta caatagagtg gggggggtca gcctgccgcc 1920
ttgggccggg tgatgtcgta cttgcccgcc gcgaactcgg ttaccgtcca gcccagcgcg 1980
accagctccg gcaacgcctc gcgcacccgc tggcggcgct tgcgcatggt cgaaccactg 2040
gcctctgacg gccagacata gccgcacaag gtatctatgg aagccttgcc ggttttgccg 2100
gggtcgatcc agccacacag ccgctggtgc agcaggcggg cggtttcgct gtccagcgcc 2160
cgcacctcgt ccatgctgat gcgcacatgc tggccgccac ccatgacggc ctgcgcgatc 2220
aaggggttca gggccacgta caggcgcccg tccgcctcgt cgctggcgta ctccgacagc 2280
agccgaaacc cctgccgctt gcggccattc tgggcgatga tggatacctt ccaaaggcgc 2340
tcgatgcagt cctgtatgtg cttgagcgcc ccaccactat cgacctctgc cccgatttcc 2400
tttgccagcg cccgatagct acctttgacc acatggcatt cagcggtgac ggcctcccac 2460
ttgggttcca ggaacagccg gagctgccgt ccgccttcgg tcttgggttc cgggccaagc 2520
actaggccat taggcccagc catggccacc agcccttgca ggatgcgcag atcatcagcg 2580
cccagcggct ccgggccgct gaactcgatc cgcttgccgt cgccgtagtc atacgtcacg 2640
tccagcttgc tgcgcttgcg ctcgccccgc ttgagggcac ggaacaggcc gggggccaga 2700
cagtgcgccg ggtcgtgccg gacgtggctg aggctgtgct tgttcttagg cttcaccacg 2760
gggcaccccc ttgctcttgc gctgcctctc cagcacggcg ggcttgagca ccccgccgtc 2820
atgccgcctg aaccaccgat cagcgaacgg tgcgccatag ttggccttgc tcacaccgaa 2880
gcggacgaag aaccggcgct ggtcgtcgtc cacaccccat tcctcggcct cggcgctggt 2940
catgctcgac aggtaggact gccagcggat gttatcgacc agtaccgagc tgccccggct 3000
ggcctgctgc tggtcgcctg cgcccatcat ggccgcgccc ttgctggcat ggtgcaggaa 3060

-continued

```
cacgatagag cacccggtat cggcggcgat ggcctccatg cgaccgatga cctgggccat   3120
ggggccgctg gcgttttctt cctcgatgtg gaaccggcgc agcgtgtcca gcaccatcag   3180
gcggcggccc tcggcggcgc gcttgaggcc gtcgaaccac tccggggcca tgatgttggg   3240
caggctgccg atcagcggct ggatcagcag gccgtcagcc acggcttgcc gttcctcggc   3300
gctgaggtgc gccccaaggg cgtgcaggcg gtgatgaatg gcggtgggcg ggtcttcggc   3360
gggcaggtag atcaccgggc cggtgggcag ttcgcccacc tccagcagat ccggcccgcc   3420
tgcaatctgt gcggccagtt gcagggccag catggattta ccggcaccac cgggcgacac   3480
cagcgccccg accgtaccgg ccaccatgtt gggcaaaacg tagtccagcg gtggcggcgc   3540
tgctgcgaac gcctccagaa tattgatagg cttatgggta gccattgatt gcctcctttg   3600
caggcagttg gtggttaggc gctggcgggg tcactacccc cgccctgcgc cgctctgagt   3660
tcttccaggc actcgcgcag cgcctcgtat tcgtcgtcgg tcagccagaa cttgcgctga   3720
cgcatccctt tggccttcat gcgctcggca tatcgcgctt ggcgtacagc gtcagggctg   3780
gccagcaggt cgccggtctg cttgtccttt tggtctttca tatcagtcac cgagaaactt   3840
gccggggccg aaaggcttgt cttcgcggaa caaggacaag gtgcagccgt caaggttaag   3900
gctggccata tcagcgactg aaaagcggcc agcctcggcc ttgtttgacg tataaccaaa   3960
gccaccgggc aaccaatagc ccttgtcact tttgatcagg tagaccgacc ctgaagcgct   4020
tttttcgtat tccataaaac ccccttctgt gcgtgagtac tcatagtata acaggcgtga   4080
gtaccaacgc aagcactaca tgctgaaatc tggcccgccc ctgtccatgc ctcgctggcg   4140
gggtgccggt gcccgtgcca gctcggcccg cgcaagctgg acgctgggca gacccatgac   4200
cttgctgacg gtgcgctcga tgtaatccgc ttcgtggccg ggcttgcgct ctgccagcgc   4260
tgggctggcc tcggccatgg ccttgccgat ttcctcggca ctgcggcccc ggctggccag   4320
cttctgcgcg gcgataaagt cgcacttgct gaggtcatca ccgaagcgct tgaccagccc   4380
ggccatctcg ctgcggtact cgtccagcgc cgtgcgccgg tggcggctaa gctgccgctc   4440
gggcagttcg aggctggcca gcctgcgggc cttctcctgc tgccgctggg cctgctcgat   4500
ctgctggcca gcctgctgca ccagcgccgg gccagcggtg gcggtcttgc ccttggattc   4560
acgcagcagc acccacggct gataaccggc gcgggtggtg tgcttgtcct tgcggttggt   4620
gaagcccgcc aagcggccat agtggcggct gtcggcgctg gccgggtcgg cgtcgtactc   4680
gctggccagc gtccgggcaa tctgccccccg aagttcaccg cctgcggcgt cggccacctt   4740
gacccatgcc tgatagttct tcgggctggt ttccactacc agggcaggct cccggccctc   4800
ggctttcatg tcatccaggt caaactcgct gaggtcgtcc accagcacca gaccatgccg   4860
ctcctgctcg gcgggcctga tatacacgtc attgccctgg gcattcatcc gcttgagcca   4920
tggcgtgttc tggagcactt cggcggctga ccattcccgg ttcatcatct ggccggtggt   4980
ggcgtccctg acgccgatat cgaagcgctc acagcccatg gccttgagct gtcggcctat   5040
ggcctgcaaa gtcctgtcgt tcttcatcgg gccaccaagc gcagccagat cgagccgtcc   5100
tcggttgtca gtggcgtcag gtcgagcaag agcaacgatg cgatcagcag caccaccgta   5160
ggcatcatgg aagccagcat cacggttagc catagcttcc agtgccaccc ccgcgacgcg   5220
ctccgggcgc tctgcgcggc gctgctcacc tcggcggcta cctcccgcaa ctctttggcc   5280
agctccaccc atgccgcccc tgtctggcgc tgggctttca gccactccgc cgcctgcgcc   5340
tcgctggcct gctgggtctg gctcatgacc tgccgggctt cgtcggccag tgtcgccatg   5400
ctctgggcca gcggttcgat ctgctccgct aactcgttga tgcctctgga tttcttcact   5460
```

ctgtcgattg cgttcatggt ctattgcctc ccggtattcc tgtaagtcga tgatctgggc 5520
gttggcggtg tcgatgttca gggccacgtc tgcccggtcg gtgcggatgc cccggccttc 5580
catctccacc acgttcggcc ccaggtgaac accgggcagg cgctcgatgc cctgcgcctc 5640
aagtgttctg tggtcaatgc gggcgtcgtg gccagcccgc tctaatgccc ggttggcatg 5700
gtcggcccat gcctcgcggg tctgctcaag ccatgccttg ggcttgagcg cttcggtctt 5760
ctgtgccccg cccttctccg gggtcttgcc gttgtaccgc ttgaaccact gagcggcggg 5820
ccgctcgatg ccgtcattga tccgctcgga gatcatcagg tggcagtgcg ggttctcgcc 5880
gccaccggca tggatggcca gcgtatacgg caggcgctcg gcaccggtca ggtgctgggc 5940
gaactcggac gccagcgcct tctgctggtc gagggtcagc tcgaccggca gggcaaattc 6000
gacctccttg aacagccgcc cattggcgcg ttcatacagg tcggcagcat cccagtagtc 6060
ggcgggccgc tcgacgaact ccggcatgtg cccggattcg gcgtgcaaga cttcatccat 6120
gtcgcgggca tacttgcctt cgcgctggat gtagtcggcc ttggccctgg ccgattggcc 6180
gcccgacctg ctgccggttt tcgccgtaag gtgataaatc gccatgctgc ctcgctgttg 6240
cttttgcttt tcggctccat gcaatggccc tcggagagcg caccgcccga agggtggccg 6300
ttaggccagt ttctcgaaga gaaaccggta agtgcgccct cccctacaaa gtagggtcgg 6360
gattgccgcc gctgtgcctc catgatagcc tacgagacag cacattaaca atggggtgtc 6420
aagatggtta aggggagcaa caaggcggcg gatcggctgg ccaagctcga agaacaacga 6480
gcgcgaatca atgccgaaat tcagcgggtg cgggcaaggg aacagcagca agagcgcaag 6540
aacgaaacaa ggcgcaaggt gctggtgggg gccatgattt tggccaaggt gaacagcagc 6600
gagtggccgg aggatcggct catggcggca atggatgcgt accttgaacg cgaccacgac 6660
cgcgccttgt tcggtctgcc gccacgccag aaggatgagc cgggctgaat gatcgaccga 6720
gacaggccct gcggggctgc acacgcgccc ccacccttcg ggtaggggga aaggccgcta 6780
aagcggctaa aagcgctcca gcgtatttct gcggggtttg gtgtggggtt tagcgggctt 6840
tgcccgcctt tccccctgcc gcgcagcggt ggggcggtgt gtagcctagc gcagcgaata 6900
gaccagctat ccggcctctg gccgggcata ttgggcaagg gcagcagcgc cccacaaggg 6960
cgctgataac cgcgcctagt ggattattct tagataatca tggatggatt tttccaacac 7020
cccgccagcc cccgcccctg ctgggtttgc aggtttgggg gcgtgacagt tattgcaggg 7080
gttcgtgaca gttattgcag gggggcgtga cagttattgc aggggttcgt gacagttagt 7140
acgggagtga cgggcactgg ctggcaatgt ctagcaacgg caggcatttc ggctgagggt 7200
aaaagaactt tccgctaagc gatagactgt atgtaaacac agtattgcaa ggacgcggaa 7260
catgcctcat gtggcggcca ggacggccag ccgggatcgg gatactggtc gttaccagag 7320
ccaccgaccc gagcaaaccc ttctctatca gatcgttgac gagtattacc cggcattcgc 7380
tgcgcttatg gcagagcagg gaaaggaatt gccgggctat gtgcaacggg aatttgaaga 7440
atttctccaa tgcgggcggc tggagcatgg ctttctacgg gttcgctgcg agtcttgcca 7500
cgccgagcac ctggtcgctt tcagctgtaa tccgggcagc gcaacggaac attcatcagt 7560
gtaaaaatgg aatcaataaa gccctgcgca gcgcgcaggg tcagcctgaa tacgcgtgct 7620
cgaattgaca taagcctgtt cggttcgtaa actgtaatgc aagtagcgta tgcgctcacg 7680
caactggtcc agaaccttga ccgaacgcag cggtggtaac ggcgcagtgg cggttttcat 7740
ggcttgttat gactgttttt ttgtacagtc tatgcctcgg gcatccaagc agcaagcgcg 7800
ttacgccgtg ggtcgatgtt tgatgttatg gagcagcaac gatgttacgc agcagcaacg 7860
atgttacgca gcagggcagt cgccctaaaa caaagttagg tggctcaagt atgggcatca 7920
ttcgcacatg taggctcggc cctgaccaag tcaaatccat gcgggctgct cttgatcttt 7980
tcggtcgtga gttcggagac gtagccacct actcccaaca tcagccggac tccgattacc 8040
tcgggaactt gctccgtagt aagacattca tcgcgcttgc tgccttcgac caagaagcgg 8100
ttgttggcgc tctcgcggct tacgttctgc ccaggtttga gcagccgcgt agtgagatct 8160
atatctatga tctcgcagtc tccggcgagc accggaggca gggcattgcc accgcgctca 8220
tcaatctcct caagcatgag gccaacgcgc ttggtgctta tgtgatctac gtgcaagcag 8280
attacggtga cgatcccgca gtggctctct atacaaagtt gggcatacgg gaagaagtga 8340
tgcactttga tatcgaccca agtaccgcca cctaacaatt cgttcaagcc gagatcggct 8400
tcccggccct agacgcgtat tcaggctgac cctgcgcgct gcgcagggct ttattgattc 8460
catttttaca ctgatgaatg ttccgttgcg ctgcccggat tacagatcct ctagaactag 8520
tggatccccc gggctgcagg gggggggggg aaagccacgt tgtgtctcaa aatctctgat 8580
gttacattgc acaagataaa aatatatcat catgaacaat aaaactgtct gcttacataa 8640
acagtaatac aaggggtgtt atgagccata ttcaacggga aacgtcttgc tcgaggccgc 8700
gattaaattc caacatggat gctgatttat atgggtataa atgggctcgc gataatgtcg 8760
ggcaatcagg tgcgacaatc tatcgattgt atgggaagcc cgatgcgcca gagttgtttc 8820
tgaaacatgg caaaggtagc gttgccaatg atgttacaga tgagatggtc agactaaact 8880
ggctgacgga atttatgcct cttccgacca tcaagcattt tatccgtact cctgatgatg 8940
catggttact caccactgcg atccccggga aaacagcatt ccaggtatta gaagaatatc 9000
ctgattcagg tgaaaatatt gttgatgcgc tggcagtgtt cctgcgccgg ttgcattcga 9060
ttcctgtttg taattgtcct tttaacagcg atcgcgtatt tcgtctcgct caggcgcaat 9120
cacgaatgaa taacggtttg gttgatgcga gtgattttga tgacgagcgt aatggctggc 9180
ctgttgaaca agtctggaaa gaaatgcata agcttttgcc attctcaccg gattcagtcg 9240
tcactcatgg tgatttctca cttgataacc ttatttttga cgaggggaaa ttaataggtt 9300
gtattgatgt tggacgagtc ggaatcgcag accgatacca ggatcttgcc atcctatgga 9360
actgcctcgg tgagttttct ccttcattac agaaacggct ttttcaaaaa tatggtattg 9420
ataatcctga tatgaataaa ttgcagtttc atttgatgct cgatgagttt ttctaatcag 9480
aattggttaa ttggttgtaa cactggcaga gcattacgct gacttgacgg gacggcggct 9540
ttgttgaata aatcgaactt ttgctgagtt gaaggatcag atcacgcatc ttcccgacaa 9600
cgcagaccgt tccgtggcaa agcaaaagtt caaaatcacc aactggtcca cctacaacaa 9660
agctctcatc aaccgtggct ccctcacttt ctggctggat gatggggcga ttcaggcctg 9720
gtatgagtca gcaacacctt cttcacgagg cagacctcag cgcccccccc ccccggaatt 9780
cgatatcaag cttatcgata ccg 9803

<210> SEQ ID NO 48
<211> LENGTH: 9781
<212> TYPE: DNA
<213> ORGANISM: Artificial
<220> FEATURE:
<223> OTHER INFORMATION: pVZ325a plasmid (self-replicating broad host range vector)

<400> SEQUENCE: 48

-continued

```
tcgacgaatt tctgccattc atccgcttat tatcacttat tcaggcgtag caccaggcgt     60
ttaagggcac caataactgc cttaaaaaaa ttacgccccg ccctgccact catcgcagta    120
ctgttgtaat tcattaagca ttctgccgac atggaagcca tcacagacgg catgatgaac    180
ctgaatcgcc agcggcatca gcaccttgtc gccttgcgta taatatttgc ccatggtgaa    240
aacgggggcg aagaagttgt ccatattggc cacgtttaaa tcaaaactgg tgaaactcac    300
ccagggattg gctgagacga aaaacatatt ctcaataaac cctttaggga aataggccag    360
gttttcaccg taacacgcca catcttgcga atatatgtgt agaaactgcc ggaaatcgtc    420
gtggtattca ctccagagcg atgaaaacgt ttcagtttgc tcatggaaaa cggtgtaaca    480
agggtgaaca ctatcccata tcaccagctc accgtctttc attgccatac ggaattccgg    540
atgagcattc atcaggcggg caagaatgtg aataaaggcc ggataaaact tgtgcttatt    600
tttctttacg gtctttaaaa aggccgtaat atccagctga acggtctggt tataggtaca    660
ttgagcaact gactgaaatg cctcaaaatg ttctttacga tgccattggg atatatcaac    720
ggtggtatat ccagtgattt ttttctccat tttagcttcc ttagctcctg aaaatctcga    780
taactcaaaa aatacgcccg gtagtgatct tatttcatta tggtgaaagt tggaacctct    840
tacgtgccga tcaacgtctc attttcgcca aaagttggcc cagggcttcc cggtatcaac    900
agggacacca ggatttattt attctgcgaa gtgatcttcc gtcacaggta tttattcgaa    960
gacgaaaggg cctcgtgata cgcctatttt tataggttaa tgtcatgata ataatggttt   1020
cttagacgtc aggtggcact tttcggggaa atgtgcgcgg aacccctatt tgtttatttt   1080
tctaaataca ttcaaatatg tatccgctca tgagacaata accctgataa atgcttcaat   1140
aatattgaaa aaggaagagt atgagtattc aacatttccg tgtcgccctt attccctttt   1200
ttgcggcatt ttgccttcct gtttttgctc acccagaaac gctggtgaaa gtaaaagatg   1260
ctgaagatca gttgggtgca cgagtgggtt acatcgaact ggatctcaac agcggtaaga   1320
tccttgagag ttttcgcccc gaagaacgtt ttccaatgat gagcactttt aaagttctgc   1380
tatgtggcgc ggtattatcc cgtgttgacg ccgggcaaga gcaactcggt cgccgcatac   1440
actattctca gaatgacttg gttgagtact caccagtcac agaaaagcat cttacggatg   1500
gcatgacagt aagagaatta tgcagtgctg ccataaccat gagtgataac actgcggcca   1560
acttacttct gacaacgatc ggaggaccga aggagctaac cgcttttttg cacaacatgg   1620
gggatcatgt aactcgcctt gatcgttggg aaccggagct gaatgaagcc ataccaaacg   1680
acgagcgtga caccacgatg cctgcaggag cagaagagca tacatctgga agcaaagcca   1740
ggaaagcggc ctatggagct gtgcggcagc gctcagtagg caatttttca aaatattgtt   1800
aagccttttc tgagcatggt atttttcatg gtattaccaa ttagcaggaa aataagccat   1860
tgaatataaa agataaaaat gtcttgttta caatagagtg gggggggtca gcctgccgcc   1920
ttgggccggg tgatgtcgta cttgcccgcc gcgaactcgg ttaccgtcca gcccagcgcg   1980
accagctccg gcaacgcctc gcgcacccgc tggcggcgct tgcgcatggt cgaaccactg   2040
gcctctgacg gccagacata gccgcacaag gtatctatgg aagccttgcc ggttttgccg   2100
gggtcgatcc agccacacag ccgctggtgc agcaggcggg cggtttcgct gtccagcgcc   2160
cgcacctcgt ccatgctgat gcgcacatgc tggccgccac ccatgacggc ctgcgcgatc   2220
aaggggttca gggccacgta caggcgcccg tccgcctcgt cgctggcgta ctccgacagc   2280
agccgaaacc cctgccgctt gcggccattc tgggcgatga tggatacctt ccaaaggcgc   2340
tcgatgcagt cctgtatgtg cttgagcgcc ccaccactat cgacctctgc cccgatttcc   2400
```

-continued

```
tttgccagcg cccgatagct acctttgacc acatggcatt cagcggtgac ggcctcccac   2460
ttgggttcca ggaacagccg gagctgccgt ccgccttcgg tcttgggttc cgggccaagc   2520
actaggccat taggcccagc catggccacc agcccttgca ggatgcgcag atcatcagcg   2580
cccagcggct ccgggccgct gaactcgatc cgcttgccgt cgccgtagtc atacgtcacg   2640
tccagcttgc tgcgcttgcg ctcgccccgc ttgagggcac ggaacaggcc gggggccaga   2700
cagtgcgccg ggtcgtgccg gacgtggctg aggctgtgct tgttcttagg cttcaccacg   2760
gggcaccccc ttgctcttgc gctgcctctc cagcacggcg ggcttgagca ccccgccgtc   2820
atgccgcctg aaccaccgat cagcgaacgg tgcgccatag ttggccttgc tcacaccgaa   2880
gcggacgaag aaccggcgct ggtcgtcgtc cacaccccat tcctcggcct cggcgctggt   2940
catgctcgac aggtaggact gccagcggat gttatcgacc agtaccgagc tgccccggct   3000
ggcctgctgc tggtcgcctg cgcccatcat ggccgcgccc ttgctggcat ggtgcaggaa   3060
cacgatagag cacccggtat cggcggcgat ggcctccatg cgaccgatga cctgggccat   3120
ggggccgctg gcgttttctt cctcgatgtg gaaccggcgc agcgtgtcca gcaccatcag   3180
gcggcggccc tcggcggcgc gcttgaggcc gtcgaaccac tccggggcca tgatgttggg   3240
caggctgccg atcagcggct ggatcagcag gccgtcagcc acggcttgcc gttcctcggc   3300
gctgaggtgc gccccaaggg cgtgcaggcg gtgatgaatg gcggtgggcg ggtcttcggc   3360
gggcaggtag atcaccgggc cggtgggcag ttcgcccacc tccagcagat ccggcccgcc   3420
tgcaatctgt gcggccagtt gcagggccag catggattta ccggcaccac cgggcgacac   3480
cagcgccccg accgtaccgg ccaccatgtt gggcaaaacg tagtccagcg gtggcggcgc   3540
tgctgcgaac gcctccagaa tattgatagg cttatgggta gccattgatt gcctcctttg   3600
caggcagttg gtggttaggc gctggcgggg tcactacccc cgccctgcgc cgctctgagt   3660
tcttccaggc actcgcgcag cgcctcgtat tcgtcgtcgg tcagccagaa cttgcgctga   3720
cgcatccctt tggccttcat gcgctcggca tatcgcgctt ggcgtacagc gtcagggctg   3780
gccagcaggt cgccggtctg cttgtccttt tggtctttca tatcagtcac cgagaaactt   3840
gccggggccg aaaggcttgt cttcgcggaa caaggacaag gtgcagccgt caaggttaag   3900
gctggccata tcagcgactg aaaagcggcc agcctcggcc ttgtttgacg tataaccaaa   3960
gccaccgggc aaccaatagc ccttgtcact tttgatcagg tagaccgacc ctgaagcgct   4020
tttttcgtat tccataaaac cccctctgt gcgtgagtac tcatagtata acaggcgtga   4080
gtaccaacgc aagcactaca tgctgaaatc tggcccgccc ctgtccatgc ctcgctggcg   4140
gggtgccggt gcccgtgcca gctcggcccg cgcaagctgg acgctgggca gacccatgac   4200
cttgctgacg gtgcgctcga tgtaatccgc ttcgtggccg ggcttgcgct ctgccagcgc   4260
tgggctggcc tcggccatgg ccttgccgat ttcctcggca ctgcggcccc ggctggccag   4320
cttctgcgcg gcgataaagt cgcacttgct gaggtcatca ccgaagcgct tgaccagccc   4380
ggccatctcg ctgcggtact cgtccagcgc cgtgcgccgg tggcggctaa gctgccgctc   4440
gggcagttcg aggctggcca gcctgcgggc cttctcctgc tgccgctggg cctgctcgat   4500
ctgctggcca gcctgctgca ccagcgccgg gccagcggtg gcggtcttgc ccttggattc   4560
acgcagcagc acccacggct gataaccggc gcgggtggtg tgcttgtcct tgcggttggt   4620
gaagcccgcc aagcggccat agtggcggct gtcggcgctg gccgggtcgg cgtcgtactc   4680
gctggccagc gtccgggcaa tctgccccg aagttcaccg cctgcggcgt cggccacctt   4740
```

-continued

```
gacccatgcc tgatagttct tcgggctggt ttccactacc agggcaggct cccggccctc   4800

ggctttcatg tcatccaggt caaactcgct gaggtcgtcc accagcacca gaccatgccg   4860

ctcctgctcg gcgggcctga tatacacgtc attgccctgg gcattcatcc gcttgagcca   4920

tggcgtgttc tggagcactt cggcggctga ccattcccgg ttcatcatct ggccggtggt   4980

ggcgtccctg acgccgatat cgaagcgctc acagcccatg gccttgagct gtcggcctat   5040

ggcctgcaaa gtcctgtcgt tcttcatcgg gccaccaagc gcagccagat cgagccgtcc   5100

tcggttgtca gtggcgtcag gtcgagcaag agcaacgatg cgatcagcag caccaccgta   5160

ggcatcatgg aagccagcat cacggttagc catagcttcc agtgccaccc ccgcgacgcg   5220

ctccgggcgc tctgcgcggc gctgctcacc tcggcggcta cctcccgcaa ctctttggcc   5280

agctccaccc atgccgcccc tgtctggcgc tgggctttca gccactccgc cgcctgcgcc   5340

tcgctggcct gctgggtctg gctcatgacc tgccgggctt cgtcggccag tgtcgccatg   5400

ctctgggcca gcggttcgat ctgctccgct aactcgttga tgcctctgga tttcttcact   5460

ctgtcgattg cgttcatggt ctattgcctc ccggtattcc tgtaagtcga tgatctgggc   5520

gttggcggtg tcgatgttca gggccacgtc tgcccggtcg gtgcggatgc cccggccttc   5580

catctccacc acgttcggcc ccaggtgaac accgggcagg cgctcgatgc cctgcgcctc   5640

aagtgttctg tggtcaatgc gggcgtcgtg gccagcccgc tctaatgccc ggttggcatg   5700

gtcggcccat gcctcgcggg tctgctcaag ccatgccttg ggcttgagcg cttcggtctt   5760

ctgtgccccg cccttctccg ggtcttgcc gttgtaccgc ttgaaccact gagcggcggg   5820

ccgctcgatg ccgtcattga tccgctcgga gatcatcagg tggcagtgcg ggttctcgcc   5880

gccaccggca tggatggcca gcgtatacgg caggcgctcg gcaccggtca ggtgctgggc   5940

gaactcggac gccagcgcct tctgctggtc gagggtcagc tcgaccggca gggcaaattc   6000

gacctccttg aacagccgcc cattggcgcg ttcatacagg tcggcagcat cccagtagtc   6060

ggcgggccgc tcgacgaact ccggcatgtg cccggattcg gcgtgcaaga cttcatccat   6120

gtcgcgggca tacttgcctt cgcgctggat gtagtcggcc ttggccctgg ccgattggcc   6180

gcccgacctg ctgccggttt tcgccgtaag gtgataaatc gccatgctgc ctcgctgttg   6240

cttttgcttt tcggctccat gcaatggccc tcggagagcg caccgcccga agggtggccg   6300

ttaggccagt ttctcgaaga gaaaccggta agtgcgccct cccctacaaa gtagggtcgg   6360

gattgccgcc gctgtgcctc catgatagcc tacgagacag cacattaaca atggggtgtc   6420

aagatggtta aggggagcaa caaggcggcg gatcggctgg ccaagctcga agaacaacga   6480

gcgcgaatca atgccgaaat tcagcgggtg cgggcaaggg aacagcagca agagcgcaag   6540

aacgaaacaa ggcgcaaggt gctggtgggg gccatgattt tggccaaggt gaacagcagc   6600

gagtggccgg aggatcggct catggcggca atggatgcgt accttgaacg cgaccacgac   6660

cgcgccttgt tcggtctgcc gccacgccag aaggatgagc cgggctgaat gatcgaccga   6720

gacaggccct gcggggctgc acacgcgccc ccacccttcg ggtaggggga aaggccgcta   6780

aagcggctaa aagcgctcca gcgtatttct gcggggtttg gtgtggggtt tagcgggctt   6840

tgcccgcctt tccccctgcc gcgcagcggt ggggcggtgt gtagcctagc gcagcgaata   6900

gaccagctat ccggcctctg gccgggcata ttgggcaagg gcagcagcgc cccacaaggg   6960

cgctgataac cgcgcctagt ggattattct tagataatca tggatggatt tttccaacac   7020

cccgccagcc cccgcccctg ctgggtttgc aggtttgggg gcgtgacagt tattgcaggg   7080

gttcgtgaca gttattgcag gggggcgtga cagttattgc aggggttcgt gacagttagt   7140
```

-continued

```
acgggagtga cgggcactgg ctggcaatgt ctagcaacgg caggcatttc ggctgagggt   7200
aaaagaactt tccgctaagc gatagactgt atgtaaacac agtattgcaa ggacgcggaa   7260
catgcctcat gtggcggcca ggacggccag ccgggatcgg gatactggtc gttaccagag   7320
ccaccgaccc gagcaaaccc ttctctatca gatcgttgac gagtattacc cggcattcgc   7380
tgcgcttatg gcagagcagg gaaaggaatt gccgggctat gtgcaacggg aatttgaaga   7440
atttctccaa tgcgggcggc tggagcatgg ctttctacgg gttcgctgcg agtcttgcca   7500
cgccgagcac ctggtcgctt tcagctgtaa tccgggcagc gcaacggaac attcatcagt   7560
gtaaaaatgg aatcaataaa gccctgcgca gcgcgcaggg tcagcctgaa tacgcgtgct   7620
cgaattgaca taagcctgtt cggttcgtaa actgtaatgc aagtagcgta tgcgctcacg   7680
caactggtcc agaaccttga ccgaacgcag cggtggtaac ggcgcagtgg cggttttcat   7740
ggcttgttat gactgttttt ttgtacagtc tatgcctcgg gcatccaagc agcaagcgcg   7800
ttacgccgtg ggtcgatgtt tgatgttatg gagcagcaac gatgttacgc agcagcaacg   7860
atgttacgca gcagggcagt cgccctaaaa caaagttagg tggctcaagt atgggcatca   7920
ttcgcacatg taggctcggc cctgaccaag tcaaatccat gcgggctgct cttgatcttt   7980
tcggtcgtga gttcggagac gtagccacct actcccaaca tcagccggac tccgattacc   8040
tcgggaactt gctccgtagt aagacattca tcgcgcttgc tgccttcgac caagaagcgg   8100
ttgttggcgc tctcgcggct tacgttctgc ccaggtttga gcagccgcgt agtgagatct   8160
atatctatga tctcgcagtc tccggcgagc accggaggca gggcattgcc accgcgctca   8220
tcaatctcct caagcatgag gccaacgcgc ttggtgctta tgtgatctac gtgcaagcag   8280
attacggtga cgatcccgca gtggctctct atacaaagtt gggcatacgg gaagaagtga   8340
tgcactttga tatcgaccca agtaccgcca cctaacaatt cgttcaagcc gagatcggct   8400
tcccggccct agacgcgtat tcaggctgac cctgcgcgct gcgcagggct ttattgattc   8460
catttttaca ctgatgaatg ttccgttgcg ctgcccggat tacagatcct ctagaagaac   8520
agcaaggccg ccaatgcctg acgatgcgtg gagaccgaaa ccttgcgctc gttcgccagc   8580
caggacagaa atgcctcgac ttcgctgctg cccaaggttg ccgggtgacg cacaccgtgg   8640
aaacggatga aggcacgaac ccagtggaca taagcctgtt cggttcgtaa gctgtaatgc   8700
aagtagcgta tgcgctcacg caactggtcc agaaccttga ccgaacgcag cggtggtaac   8760
ggcgcagtgg cggttttcat ggcttgttat gactgttttt ttggggtaca gtctatgcct   8820
cgggcatcca agcagcaagc gcgttacgcc gtgggtcgat gtttgatgtt atggagcagc   8880
aacgatgtta cgcagcaggg cagtcgccct aaaacaaagt taaacatcat gagggaagcg   8940
gtgatcgccg aagtatcgac tcaactatca gaggtagttg gcgtcatcga gcgccatctc   9000
gaaccgacgt tgctggccgt acatttgtac ggctccgcag tggatggcgg cctgaagcca   9060
cacagtgata ttgatttgct ggttacggtg accgtaaggc ttgatgaaac aacgcggcga   9120
gctttgatca acgacctttt ggaaacttcg gcttcccctg gagagagcga gattctccgc   9180
gctgtagaag tcaccattgt tgtgcacgac gacatcattc cgtggcgtta tccagctaag   9240
cgcgaactgc aatttggaga atggcagcgc aatgacattc ttgcaggtat cttcgagcca   9300
gccacgatcg acattgatct ggctatcttg ctgacaaaag caagagaaca tagcgttgcc   9360
ttggtaggtc cagcggcgga ggaactcttt gatccggttc ctgaacagga tctatttgag   9420
gcgctaaatg aaaccttaac gctatggaac tcgccgcccg actgggctgg cgatgagcga   9480
```

aatgtagtgc ttacgttgtc ccgcatttgg tacagcgcag taaccggcaa aatcgcgccg 9540
aaggatgtcg ctgccgactg ggcaatggag cgcctgccgg cccagtatca gcccgtcata 9600
cttgaagcta gacaggctta tcttggacaa gaagaagatc gcttggcctc gcgcgcagat 9660
cagttggaag aatttgtcca ctacgtgaaa ggcgagatca ccaaggtagt cggcaaataa 9720
tgtctaacaa ttcgttcaag ccgacgccgc ttcgcggcgc ggcttaactc aagctctaga 9780
g 9781

<210> SEQ ID NO 49
<211> LENGTH: 21
<212> TYPE: DNA
<213> ORGANISM: Artificial
<220> FEATURE:
<223> OTHER INFORMATION: PziaA-SalI-fw

<400> SEQUENCE: 49
aggtcgacgt taggagctag g 21

<210> SEQ ID NO 50
<211> LENGTH: 21
<212> TYPE: DNA
<213> ORGANISM: Artificial
<220> FEATURE:
<223> OTHER INFORMATION: PziaA/ziaR-SalI-fw

<400> SEQUENCE: 50
atcgtcgacc tccttaatcc g 21

<210> SEQ ID NO 51

<400> SEQUENCE: 51

000

<210> SEQ ID NO 52
<211> LENGTH: 3158
<212> TYPE: DNA
<213> ORGANISM: Artificial
<220> FEATURE:
<223> OTHER INFORMATION: insert from plasmid #996 pVZ322a-PpetJ-PDC-synADH

<400> SEQUENCE: 52
gtcgacggga attgctctgg caactgatta atccactgag caacagccca agacacgcaa 60
acaaaaacca acgtcttggc gatcgccatc ggcaccatga aaccatcgta aaagctgggg 120
aaagaataaa aaacagtggt tcaggaattg cattgccatg gccacttcac aaacctagcc 180
aattttagct tgaccgcagc tttgacagat tgtcttttga ctttgcctgg accgcctccc 240
ataatacctt cgcgtcttga agactttatc cttgaaagga gaactaatga attcttatac 300
tgtcggtacc tatttagcgg agcggcttgt ccagattggt ctcaagcatc acttcgcagt 360
cgcgggcgac tacaacctcg tccttcttga caacctgctt ttgaacaaaa acatggagca 420
ggtttattgc tgtaacgaac tgaactgcgg tttcagtgca gaaggttatg ctcgtgccaa 480
aggcgcagca gcagccgtcg ttacctacag cgtcggtgcg ctttccgcat ttgatgctat 540
cggtggcgcc tatgcagaaa accttccggt tatcctgatc tccggtgctc cgaacaacaa 600
tgatcacgct gctggtcacg tgttgcatca cgctcttggc aaaaccgact atcactatca 660
gttggaaatg gccaagaaca tcacggccgc agctgaagcg atttacaccc cagaagaagc 720
tccggctaaa atcgatcacg tgattaaaac tgctcttcgt gagaagaagc cggtttatct 780

-continued cgaaatcgct tgcaacattg cttccatgcc ctgcgccgct cctggaccgg caagcgcatt 840
gttcaatgac gaagccagcg acgaagcttc tttgaatgca gcggttgaag aaaccctgaa 900
attcatcgcc aaccgcgaca aagttgccgt cctcgtcggc agcaagctgc gcgcagctgg 960
tgctgaagaa gctgctgtca aatttgctga tgctctcggt ggcgcagttg ctaccatggc 1020
tgctgcaaaa agcttcttcc cagaagaaaa cccgcattac atcggtacct catggggtga 1080
agtcagctat ccgggcgttg aaaagacgat gaaagaagcc gatgcggtta tcgctctggc 1140
tcctgtcttc aacgactact ccaccactgg ttggacggat attcctgatc ctaagaaact 1200
ggttctcgct gaaccgcgtt ctgtcgtcgt taacggcgtt cgcttcccca gcgttcatct 1260
gaaagactat ctgacccgtt tggctcagaa agtttccaag aaaaccggtg ctttggactt 1320
cttcaaatcc ctcaatgcag gtgaactgaa gaaagccgct ccggctgatc cgagtgctcc 1380
gttggtcaac gcagaaatcg cccgtcaggt cgaagctctt ctgaccccga acacgacggt 1440
tattgctgaa accggtgact cttggttcaa tgctcagcgc atgaagctcc cgaacggtgc 1500
tcgcgttgaa tatgaaatgc agtggggtca catcggttgg tccgttcctg ccgccttcgg 1560
ttatgccgtc ggtgctccgg aacgtcgcaa catcctcatg gttggtgatg gttccttcca 1620
gctgacggct caggaagtcg ctcagatggt tcgcctgaaa ctgccggtta tcatcttctt 1680
gatcaataac tatggttaca ccatcgaagt tatgatccat gatggtccgt acaacaacat 1740
caagaactgg gattatgccg gtctgatgga agtgttcaac ggtaacggtg gttatgacag 1800
cggtgctggt aaaggcctga aggctaaaac cggtggcgaa ctggcagaag ctatcaaggt 1860
tgctctggca aacaccgacg gcccaaccct gatcgaatgc ttcatcggtc gtgaagactg 1920
cactgaagaa ttggtcaaat ggggtaagcg cgttgctgcc gccaacagcc gtaagcctgt 1980
taacaagctc ctctagtttt tggggatcaa ttcgagctct ctggataaaa ctaataaact 2040
ctattaccca tgattaaagc ctacgctgcc ctggaagcca acggaaaact ccaacccttt 2100
gaatacgacc ccggtgccct gggtgctaat gaggtggaga ttgaggtgca gtattgtggg 2160
gtgtgccaca gtgatttgtc catgattaat aacgaatggg gcatttccaa ttacccccta 2220
gtgccgggtc atgaggtggt gggtactgtg gccgccatgg gcgaaggggt gaaccatgtt 2280
gaggtggggg atttagtggg gctgggttgg cattcgggct actgcatgac ctgccatagt 2340
tgtttatctg gctaccacaa cctttgtgcc acggcggaat cgaccattgt gggccactac 2400
ggtggctttg gcgatcgggt tcgggccaag ggagtcagcg tggtgaaatt acctaaaggc 2460
attgacctag ccagtgccgg gcccctttc tgtggaggaa ttaccgtttt cagtcctatg 2520
gtggaactga gtttaaagcc cactgcaaaa gtggcagtga tcggcattgg gggcttgggc 2580
catttagcgg tgcaatttct ccgggcctgg ggctgtgaag tgactgcctt tacctccagt 2640
gccaggaagc aaacggaagt gttggaattg ggcgctcacc acatactaga ttccaccaat 2700
ccagaggcga tcgccagtgc ggaaggcaaa tttgactata ttatctccac tgtgaacctg 2760
aagcttgact ggaacttata catcagcacc ctggcgcccc agggacattt ccactttgtt 2820
ggggtggtgt tggagccttt ggatctaaat cttttcccc ttttgatggg acaacgctcc 2880
gtttctgcct ccccagtggg tagtcccgcc accattgcca ccatgttgga ctttgctgtg 2940
cgccatgaca ttaaacccgt ggtggaacaa tttagctttg atcagatcaa cgaggcgatc 3000
gcccatctag aaagcggcaa agcccattat cgggtagtgc tcagccatag taaaaattag 3060
ctctgcaaag gttgcttctg ggtccgtgga atggtcaaac ggagtcgatc tcagttttga 3120
tacgctctat ctggaaagct tgacattcga cctgcagg 3158

<210> SEQ ID NO 53
<211> LENGTH: 3019
<212> TYPE: DNA
<213> ORGANISM: Artificial
<220> FEATURE:
<223> OTHER INFORMATION: insert from plasmid #1048 pVZ322a-PziaA-PDC-
synADH

<400> SEQUENCE: 53
gtcgacgtta ggagctaggg aaaaatttaa actggattta gaaaatgatt ttcatcctaa 60
catctttaat atctgagcat atcttcaggt gtttcaagat ttgtgctacg gttcaaggag 120
gtttttcttt aaatcacgtt ggccgccatg aattcttata ctgtcggtac ctatttagcg 180
gagcggcttg tccagattgg tctcaagcat cacttcgcag tcgcgggcga ctacaacctc 240
gtccttcttg acaacctgct tttgaacaaa aacatggagc aggtttattg ctgtaacgaa 300
ctgaactgcg gtttcagtgc agaaggttat gctcgtgcca aaggcgcagc agcagccgtc 360
gttacctaca gcgtcggtgc gctttccgca tttgatgcta tcggtggcgc ctatgcagaa 420
aaccttccgg ttatcctgat ctccggtgct ccgaacaaca atgatcacgc tgctggtcac 480
gtgttgcatc acgctcttgg caaaaccgac tatcactatc agttggaaat ggccaagaac 540
atcacggccg cagctgaagc gatttacacc ccagaagaag ctccggctaa aatcgatcac 600
gtgattaaaa ctgctcttcg tgagaagaag ccggtttatc tcgaaatcgc ttgcaacatt 660
gcttccatgc cctgcgccgc tcctggaccg gcaagcgcat tgttcaatga cgaagccagc 720
gacgaagctt ctttgaatgc agcggttgaa gaaaccctga aattcatcgc caaccgcgac 780
aaagttgccg tcctcgtcgg cagcaagctg cgcgcagctg gtgctgaaga agctgctgtc 840
aaatttgctg atgctctcgg tggcgcagtt gctaccatgg ctgctgcaaa aagcttcttc 900
ccagaagaaa acccgcatta catcggtacc tcatggggtg aagtcagcta tccgggcgtt 960
gaaaagacga tgaaagaagc cgatgcggtt atcgctctgg ctcctgtctt caacgactac 1020
tccaccactg gttggacgga tattcctgat cctaagaaac tggttctcgc tgaaccgcgt 1080
tctgtcgtcg ttaacggcgt tcgcttcccc agcgttcatc tgaaagacta tctgacccgt 1140
ttggctcaga aagtttccaa gaaaaccggt gctttggact tcttcaaatc cctcaatgca 1200
ggtgaactga agaaagccgc tccggctgat ccgagtgctc cgttggtcaa cgcagaaatc 1260
gcccgtcagg tcgaagctct tctgaccccg aacacgacgg ttattgctga aaccggtgac 1320
tcttggttca atgctcagcg catgaagctc ccgaacggtg ctcgcgttga atatgaaatg 1380
cagtggggtc acatcggttg gtccgttcct gccgccttcg gttatgccgt cggtgctccg 1440
gaacgtcgca acatcctcat ggttggtgat ggttccttcc agctgacggc tcaggaagtc 1500
gctcagatgg ttcgcctgaa actgccggtt atcatcttct tgatcaataa ctatggttac 1560
accatcgaag ttatgatcca tgatggtccg tacaacaaca tcaagaactg ggattatgcc 1620
ggtctgatgg aagtgttcaa cggtaacggt ggttatgaca gcggtgctgg taaaggcctg 1680
aaggctaaaa ccggtggcga actggcagaa gctatcaagg ttgctctggc aaacaccgac 1740
ggcccaaccc tgatcgaatg cttcatcggt cgtgaagact gcactgaaga attggtcaaa 1800
tggggtaagc gcgttgctgc cgccaacagc cgtaagcctg ttaacaagct cctctagttt 1860
ttggggatca attcgagctc tctggataaa actaataaac tctattaccc atgattaaag 1920
cctacgctgc cctggaagcc aacggaaaac tccaaccctt tgaatacgac cccggtgccc 1980

-continued

```
tgggtgctaa tgaggtggag attgaggtgc agtattgtgg ggtgtgccac agtgatttgt   2040
ccatgattaa taacgaatgg ggcatttcca attacccccct agtgccgggt catgaggtgg   2100
tgggtactgt ggccgccatg ggcgaagggg tgaaccatgt tgaggtgggg gatttagtgg   2160
ggctgggttg gcattcgggc tactgcatga cctgccatag ttgtttatct ggctaccaca   2220
acctttgtgc cacggcggaa tcgaccattg tgggccacta cggtggcttt ggcgatcggg   2280
ttcgggccaa gggagtcagc gtggtgaaat tacctaaagg cattgaccta gccagtgccg   2340
ggcccctttt ctgtggagga attaccgttt tcagtcctat ggtggaactg agtttaaagc   2400
ccactgcaaa agtggcagtg atcggcattg gggggcttggg ccatttagcg gtgcaatttc   2460
tccgggcctg ggctgtgaa gtgactgcct ttacctccag tgccaggaag caaacggaag   2520
tgttggaatt gggcgctcac cacatactag attccaccaa tccagaggcg atcgccagtg   2580
cggaaggcaa atttgactat attatctcca ctgtgaacct gaagcttgac tggaacttat   2640
acatcagcac cctggcgccc cagggacatt tccactttgt tggggtggtg ttggagcctt   2700
tggatctaaa tctttttccc cttttgatgg gacaacgctc cgtttctgcc tccccagtgg   2760
gtagtcccgc caccattgcc accatgttgg actttgctgt gcgccatgac attaaacccg   2820
tggtggaaca atttagcttt gatcagatca acgaggcgat cgcccatcta gaaagcggca   2880
aagcccatta tcgggtagtg ctcagccata gtaaaaatta gctctgcaaa ggttgcttct   2940
gggtccgtgg aatggtcaaa cggagtcgat ctcagttttg atacgctcta tctggaaagc   3000
ttgacattcg atccgcagg                                                3019
```

<210> SEQ ID NO 54
<211> LENGTH: 3379
<212> TYPE: DNA
<213> ORGANISM: Artificial
<220> FEATURE:
<223> OTHER INFORMATION: insert from plasmid #948 pVZ325a-PpetJ-PDCoop-PrbcL-synADH(deg)

<400> SEQUENCE: 54

```
gtcgacggga attgctctgg caactgatta atccactgag caacagccca agacacgcaa     60
acaaaaacca acgtcttggc gatcgccatc ggcaccatga aaccatcgta aaagctgggg    120
aaagaataaa aaacagtggt tcaggaattg cattgccatg gccacttcac aaacctagcc    180
aattttagct tgaccgcagc tttgacagat tgtcttttga ctttgcctgg accgcctccc    240
ataatacctt cgcgtcttga agactttatc cttgaaagga gaactaatga attcttatac    300
tgtcggtacc tatttagcgg agcggcttgt ccagattggt ctcaagcatc acttcgcagt    360
cgcgggcgac tacaacctcg tccttcttga caacctgctt ttgaacaaaa acatggagca    420
ggtttattgc tgtaacgaac tgaactgcgg tttcagtgca gaaggttatg ctcgtgccaa    480
aggcgcagca gcagccgtcg ttacctacag cgtcggtgcg ctttccgcat ttgatgctat    540
cggtggcgcc tatgcagaaa accttccggt tatcctgatc tccggtgctc cgaacaacaa    600
tgatcacgct gctggtcacg tgttgcatca cgctcttggc aaaaccgact atcactatca    660
gttggaaatg gccaagaaca tcacggccgc agctgaagcg atttacaccc cagaagaagc    720
tccggctaaa atcgatcacg tgattaaaac tgctcttcgt gagaagaagc cggtttatct    780
cgaaatcgct tgcaacattg cttccatgcc ctgcgccgct cctggaccgg caagcgcatt    840
gttcaatgac gaagccagcg acgaagcttc tttgaatgca gcggttgaag aaaccctgaa    900
attcatcgcc aaccgcgaca aagttgccgt cctcgtcggc agcaagctgc gcgcagctgg    960
```

-continued

```
tgctgaagaa gctgctgtca aatttgctga tgctctcggt ggcgcagttg ctaccatggc   1020
tgctgcaaaa agcttcttcc cagaagaaaa cccgcattac atcggtacct catggggtga   1080
agtcagctat ccgggcgttg aaaagacgat gaaagaagcc gatgcggtta tcgctctggc   1140
tcctgtcttc aacgactact ccaccactgg ttggacggat attcctgatc ctaagaaact   1200
ggttctcgct gaaccgcgtt ctgtcgtcgt taacggcgtt cgcttcccca gcgttcatct   1260
gaaagactat ctgacccgtt tggctcagaa agtttccaag aaaaccggtg ctttggactt   1320
cttcaaatcc ctcaatgcag gtgaactgaa gaaagccgct ccggctgatc cgagtgctcc   1380
gttggtcaac gcagaaatcg cccgtcaggt cgaagctctt ctgaccccga acacgacggt   1440
tattgctgaa accggtgact cttggttcaa tgctcagcgc atgaagctcc cgaacggtgc   1500
tcgcgttgaa tatgaaatgc agtggggtca catcggttgg tccgttcctg ccgccttcgg   1560
ttatgccgtc ggtgctccgg aacgtcgcaa catcctcatg gttggtgatg gttccttcca   1620
gctgacggct caggaagtcg ctcagatggt tcgcctgaaa ctgccggtta tcatcttctt   1680
gatcaataac tatggttaca ccatcgaagt tatgatccat gatggtccgt acaacaacat   1740
caagaactgg gattatgccg gtctgatgga agtgttcaac ggtaacggtg gttatgacag   1800
cggtgctggt aaaggcctga aggctaaaac cggtggcgaa ctggcagaag ctatcaaggt   1860
tgctctggca aacaccgacg gcccaaccct gatcgaatgc ttcatcggtc gtgaagactg   1920
cactgaagaa ttggtcaaat ggggtaagcg cgttgctgcc gccaacagcc gtaagcctgt   1980
taacaagctc ctctagtttt tggggatcaa ttcgagctcg gtacccaaac tagtaacgct   2040
cggttgccgc cgggcgtttt ttattccgac atcaggaatt gtaattagaa agtccaaaaa   2100
ttgtaattta aaaaacagtc aatggagagc attgccataa gtaaaggcat cccctgcgtg   2160
ataagattac cttcagaaaa cagatagttg ctgggttatc gcagattttt ctcgcaacca   2220
aataactgta aataataact gtctctgggg cgacggtagg ctttatattg ccaaatttcg   2280
cccgtgggag aaagctaggc tattcaatgt ttatggagga ctgacccata tgatcaaggc   2340
ttatgccgct ttagaggcta atggcaagtt gcagccgttc gagtatgatc cgggcgcttt   2400
aggcgccaac gaagttgaaa tcgaagttca atactgcggt gtttgtcatt ccgacctcag   2460
tatgatcaac aatgagtggg gtatcagtaa ctatccgttg gttcccggcc acgaagttgt   2520
tggcaccgtt gctgctatgg gtgagggtgt taatcacgtg gaagttggtg acctggttgg   2580
tttaggctgg cacagtggtt attgtatgac ttgtcactcc tgcctgagcg gttatcataa   2640
tttgtgcgct accgccgaga gtactatcgt tggtcattat ggcggtttcg gtgaccgtgt   2700
gcgtgctaaa ggtgtgtccg ttgttaagct gcccaagggt atcgatttgg cttccgctgg   2760
tccgttgttt tgcggtggta tcactgtgtt ttcccccatg gttgagttat ccctgaaacc   2820
gaccgccaag gttgccgtta ttggtatcgg tggtctcggt cacctggccg ttcagttctt   2880
gcgtgcttgg ggttgcgagg ttaccgcttt cactagctcc gctcgtaaac agaccgaggt   2940
tctggagctg ggtgcccatc atattttgga cagtactaac cccgaagcca ttgcttccgc   3000
cgagggtaag ttcgattaca tcattagtac cgttaattta aaattggatt ggaatctgta   3060
tatttccact ttagccccgc aaggtcactt tcatttcgtg ggtgttgttc tcgaacccct   3120
cgacttgaac ttgttcccgt tgctcatggg tcagcggagt gtgtccgcta gtccggttgg   3180
ctccccggct actatcgcta ctatgctcga tttcgccgtt cggcacgata tcaagccggt   3240
tgttgagcag ttctccttcg accaaattaa tgaagccatt gctcacttgg agtccggtaa   3300
ggctcactac cgtgtggttt tgagtcactc caagaactga aacgctcggt tgccgccggg   3360
```

cgtttttat tcctgcagg 3379

<210> SEQ ID NO 55
<211> LENGTH: 3240
<212> TYPE: DNA
<213> ORGANISM: Artificial
<220> FEATURE:
<223> OTHER INFORMATION: insert from plasmid #969 pVZ325a-PziaA-PDCoop-
PrbcL-synADH(deg)

<400> SEQUENCE: 55
gtcgacgtta ggagctaggg aaaaatttaa actggattta gaaaatgatt ttcatcctaa 60
catctttaat atctgagcat atcttcaggt gtttcaagat ttgtgctacg gttcaaggag 120
gtttttcttt aaatcacgtt ggccgccatg aattcttata ctgtcggtac ctatttagcg 180
gagcggcttg tccagattgg tctcaagcat cacttcgcag tcgcgggcga ctacaacctc 240
gtccttcttg acaacctgct tttgaacaaa aacatggagc aggtttattg ctgtaacgaa 300
ctgaactgcg gtttcagtgc agaaggttat gctcgtgcca aaggcgcagc agcagccgtc 360
gttacctaca gcgtcggtgc gctttccgca tttgatgcta tcggtggcgc ctatgcagaa 420
aaccttccgg ttatcctgat ctccggtgct ccgaacaaca atgatcacgc tgctggtcac 480
gtgttgcatc acgctcttgg caaaaccgac tatcactatc agttggaaat ggccaagaac 540
atcacggccg cagctgaagc gatttacacc ccagaagaag ctccggctaa aatcgatcac 600
gtgattaaaa ctgctcttcg tgagaagaag ccggtttatc tcgaaatcgc ttgcaacatt 660
gcttccatgc cctgcgccgc tcctggaccg gcaagcgcat tgttcaatga cgaagccagc 720
gacgaagctt ctttgaatgc agcggttgaa gaaaccctga aattcatcgc caaccgcgac 780
aaagttgccg tcctcgtcgg cagcaagctg cgcgcagctg gtgctgaaga agctgctgtc 840
aaatttgctg atgctctcgg tggcgcagtt gctaccatgg ctgctgcaaa aagcttcttc 900
ccagaagaaa acccgcatta catcggtacc tcatggggtg aagtcagcta tccgggcgtt 960
gaaaagacga tgaaagaagc cgatgcggtt atcgctctgg ctcctgtctt caacgactac 1020
tccaccactg gttggacgga tattcctgat cctaagaaac tggttctcgc tgaaccgcgt 1080
tctgtcgtcg ttaacggcgt tcgcttcccc agcgttcatc tgaaagacta tctgacccgt 1140
ttggctcaga aagtttccaa gaaaaccggt gctttggact tcttcaaatc cctcaatgca 1200
ggtgaactga agaaagccgc tccggctgat ccgagtgctc cgttggtcaa cgcagaaatc 1260
gcccgtcagg tcgaagctct tctgaccccg aacacgacgg ttattgctga aaccggtgac 1320
tcttggttca atgctcagcg catgaagctc ccgaacggtg ctcgcgttga atatgaaatg 1380
cagtggggtc acatcggttg gtccgttcct gccgccttcg gttatgccgt cggtgctccg 1440
gaacgtcgca acatcctcat ggttggtgat ggttccttcc agctgacggc tcaggaagtc 1500
gctcagatgg ttcgcctgaa actgccggtt atcatcttct tgatcaataa ctatggttac 1560
accatcgaag ttatgatcca tgatggtccg tacaacaaca tcaagaactg ggattatgcc 1620
ggtctgatgg aagtgttcaa cggtaacggt ggttatgaca gcggtgctgg taaaggcctg 1680
aaggctaaaa ccggtggcga actggcagaa gctatcaagg ttgctctggc aaacaccgac 1740
ggcccaaccc tgatcgaatg cttcatcggt cgtgaagact gcactgaaga attggtcaaa 1800
tggggtaagc gcgttgctgc cgccaacagc cgtaagcctg ttaacaagct cctctagttt 1860
ttggggatca attcgagctc ggtacccaaa ctagtaacgc tcggttgccg ccgggcgttt 1920
tttattccga catcaggaat tgtaattaga aagtccaaaa attgtaattt aaaaaacagt 1980

```
caatggagag cattgccata agtaaaggca tcccctgcgt gataagatta ccttcagaaa   2040

acagatagtt gctgggttat cgcagatttt tctcgcaacc aaataactgt aaataataac   2100

tgtctctggg gcgacggtag gctttatatt gccaaatttc gcccgtggga gaaagctagg   2160

ctattcaatg tttatggagg actgacccat atgatcaagg cttatgccgc tttagaggct   2220

aatggcaagt tgcagccgtt cgagtatgat ccgggcgctt taggcgccaa cgaagttgaa   2280

atcgaagttc aatactgcgg tgtttgtcat tccgacctca gtatgatcaa caatgagtgg   2340

ggtatcagta actatccgtt ggttcccggc cacgaagttg ttggcaccgt tgctgctatg   2400

ggtgagggtg ttaatcacgt ggaagttggt gacctggttg gtttaggctg gcacagtggt   2460

tattgtatga cttgtcactc ctgcctgagc ggttatcata atttgtgcgc taccgccgag   2520

agtactatcg ttggtcatta tggcggtttc ggtgaccgtg tgcgtgctaa aggtgtgtcc   2580

gttgttaagc tgcccaaggg tatcgatttg gcttccgctg gtccgttgtt ttgcggtggt   2640

atcactgtgt tttcccccat ggttgagtta tccctgaaac cgaccgccaa ggttgccgtt   2700

attggtatcg gtggtctcgg tcacctggcc gttcagttct tgcgtgcttg ggttgcgag    2760

gttaccgctt tcactagctc cgctcgtaaa cagaccgagg ttctggagct gggtgcccat   2820

catattttgg acagtactaa ccccgaagcc attgcttccg ccgagggtaa gttcgattac   2880

atcattagta ccgttaattt aaaattggat tggaatctgt atatttccac tttagccccg   2940

caaggtcact ttcatttcgt gggtgttgtt ctcgaacccc tcgacttgaa cttgttcccg   3000

ttgctcatgg gtcagcggag tgtgtccgct agtccggttg gctccccggc tactatcgct   3060

actatgctcg atttcgccgt tcggcacgat atcaagccgg ttgttgagca gttctccttc   3120

gaccaaatta atgaagccat tgctcacttg gagtccggta aggctcacta ccgtgtggtt   3180

ttgagtcact ccaagaactg aaacgctcgg ttgccgccgg gcgtttttta ttcctgcagg   3240
```

```
<210> SEQ ID NO 56
<211> LENGTH: 3653
<212> TYPE: DNA
<213> ORGANISM: Artificial
<220> FEATURE:
<223> OTHER INFORMATION: insert from plasmid #1068
      pVZ322a-ziaR-PziaA-PDCoop-PrbcL-synADH(deg)

<400> SEQUENCE: 56
```

```
gtcgacctcc ttaatccgat tcctgcaaat ggtctgcaac ttcccgatac aaattcatca     60

catgattatc cgccaagctg tagtaaacat tacggccgac ccggcgatac tttaccaggc    120

gctgcgatcg taaaattcgt aattgatggg aaactgccga ttcactcact ttcatcgccg    180

ctgctaaatc acagacacag agttcttggc gggccaatgc cgacattaaa cgcaaccgac    240

tcggatcagc tagtgcactg aaaaactccg ccatttgctg ggcctggtcc aatgacatca    300

cctctggttg aacctgtcgt acctgctcaa gatgaacaag aggttgatca caaaggggca    360

tctcttcgtt ctggcaggat tgtgactttg acaacgagga cttactcata gaggttggcg    420

ttaggagcta gggaaaaatt taaactggat ttagaaaatg attttcatcc taacatcttt    480

aatatctgag catatcttca ggtgtttcaa gatttgtgct acggttcaag gaggtttttc    540

tttaaatcac gttggccgcc atgaattctt atactgtcgg tacctattta gcggagcggc    600

ttgtccagat tggtctcaag catcacttcg cagtcgcggg cgactacaac ctcgtccttc    660

ttgacaacct gcttttgaac aaaaacatgg agcaggttta ttgctgtaac gaactgaact    720

gcggtttcag tgcagaaggt tatgctcgtg ccaaaggcgc agcagcagcc gtcgttacct    780
```

-continued acagcgtcgg tgcgctttcc gcatttgatg ctatcggtgg cgcctatgca gaaaaccttc 840
cggttatcct gatctccggt gctccgaaca acaatgatca cgctgctggt cacgtgttgc 900
atcacgctct tggcaaaacc gactatcact atcagttgga aatggccaag aacatcacgg 960
ccgcagctga agcgatttac accccagaag aagctccggc taaaatcgat cacgtgatta 1020
aaactgctct tcgtgagaag aagccggttt atctcgaaat cgcttgcaac attgcttcca 1080
tgccctgcgc cgctcctgga ccggcaagcg cattgttcaa tgacgaagcc agcgacgaag 1140
cttctttgaa tgcagcggtt gaagaaaccc tgaaattcat cgccaaccgc gacaaagttg 1200
ccgtcctcgt cggcagcaag ctgcgcgcag ctggtgctga agaagctgct gtcaaatttg 1260
ctgatgctct cggtggcgca gttgctacca tggctgctgc aaaaagcttc ttcccagaag 1320
aaaacccgca ttacatcggt acctcatggg gtgaagtcag ctatccgggc gttgaaaaga 1380
cgatgaaaga agccgatgcg gttatcgctc tggctcctgt cttcaacgac tactccacca 1440
ctggttggac ggatattcct gatcctaaga aactggttct cgctgaaccg cgttctgtcg 1500
tcgttaacgg cgttcgcttc cccagcgttc atctgaaaga ctatctgacc cgtttggctc 1560
agaaagtttc caagaaaacc ggtgctttgg acttcttcaa atccctcaat gcaggtgaac 1620
tgaagaaagc cgctccggct gatccgagtg ctccgttggt caacgcagaa atcgcccgtc 1680
aggtcgaagc tcttctgacc ccgaacacga cggttattgc tgaaaccggt gactcttggt 1740
tcaatgctca gcgcatgaag ctcccgaacg gtgctcgcgt tgaatatgaa atgcagtggg 1800
gtcacatcgg ttggtccgtt cctgccgcct tcggttatgc cgtcggtgct ccggaacgtc 1860
gcaacatcct catggttggt gatggttcct tccagctgac ggctcaggaa gtcgctcaga 1920
tggttcgcct gaaactgccg gttatcatct tcttgatcaa taactatggt tacaccatcg 1980
aagttatgat ccatgatggt ccgtacaaca acatcaagaa ctgggattat gccggtctga 2040
tggaagtgtt caacggtaac ggtggttatg acagcggtgc tggtaaaggc ctgaaggcta 2100
aaaccggtgg cgaactggca gaagctatca aggttgctct ggcaaacacc gacggcccaa 2160
ccctgatcga atgcttcatc ggtcgtgaag actgcactga agaattggtc aaatggggta 2220
agcgcgttgc tgccgccaac agccgtaagc ctgttaacaa gctcctctag tttttgggga 2280
tcaattcgag ctcggtaccc aaactagtaa cgctcggttg ccgccgggcg tttttttattc 2340 cgacatcagg aattgtaatt agaaagtcca aaaattgtaa tttaaaaaac agtcaatgga 2400
gagcattgcc ataagtaaag gcatcccctg cgtgataaga ttaccttcag aaaacagata 2460
gttgctgggt tatcgcagat ttttctcgca accaaataac tgtaaataat aactgtctct 2520
ggggcgacgg taggctttat attgccaaat ttcgcccgtg ggagaaagct aggctattca 2580
atgtttatgg aggactgacc catatgatca aggcttatgc cgctttagag gctaatggca 2640
agttgcagcc gttcgagtat gatccgggcg ctttaggcgc caacgaagtt gaaatcgaag 2700
ttcaatactg cggtgtttgt cattccgacc tcagtatgat caacaatgag tggggtatca 2760
gtaactatcc gttggttccc ggccacgaag ttgttggcac cgttgctgct atgggtgagg 2820
gtgttaatca cgtggaagtt ggtgacctgg ttggtttagg ctggcacagt ggttattgta 2880
tgacttgtca ctcctgcctg agcggttatc ataatttgtg cgctaccgcc gagagtacta 2940
tcgttggtca ttatggcggt ttcggtgacc gtgtgcgtgc taaaggtgtg tccgttgtta 3000
agctgcccaa gggtatcgat ttggcttccg ctggtccgtt gttttgcggt ggtatcactg 3060
tgttttcccc catggttgag ttatccctga aaccgaccgc caaggttgcc gttattggta 3120

```
tcggtggtct cggtcacctg gccgttcagt tcttgcgtgc ttggggttgc gaggttaccg   3180

ctttcactag ctccgctcgt aaacagaccg aggttctgga gctgggtgcc catcatattt   3240

tggacagtac taaccccgaa gccattgctt ccgccgaggg taagttcgat tacatcatta   3300

gtaccgttaa tttaaaattg gattggaatc tgtatatttc cactttagcc ccgcaaggtc   3360

actttcattt cgtgggtgtt gttctcgaac ccctcgactt gaacttgttc ccgttgctca   3420

tgggtcagcg gagtgtgtcc gctagtccgg ttggctcccc ggctactatc gctactatgc   3480

tcgatttcgc cgttcggcac gatatcaagc cggttgttga gcagttctcc ttcgaccaaa   3540

ttaatgaagc cattgctcac ttggagtccg gtaaggctca ctaccgtgtg gttttgagtc   3600

actccaagaa ctgaaacgct cggttgccgc cgggcgtttt ttattcctgc agg          3653
```

<210> SEQ ID NO 57
<211> LENGTH: 3240
<212> TYPE: DNA
<213> ORGANISM: Artificial
<220> FEATURE:
<223> OTHER INFORMATION: insert from plasmid #1047 pVZ322a-PziaA-PDCoop-PrbcL-synADH(deg)

<400> SEQUENCE: 57

```
gtcgacgtta ggagctaggg aaaaatttaa actggattta gaaaatgatt ttcatcctaa     60

catctttaat atctgagcat atcttcaggt gtttcaagat ttgtgctacg gttcaaggag    120

gtttttcttt aaatcacgtt ggccgccatg aattcttata ctgtcggtac ctatttagcg    180

gagcggcttg tccagattgg tctcaagcat cacttcgcag tcgcgggcga ctacaacctc    240

gtccttcttg acaacctgct tttgaacaaa aacatggagc aggtttattg ctgtaacgaa    300

ctgaactgcg gtttcagtgc agaaggttat gctcgtgcca aaggcgcagc agcagccgtc    360

gttacctaca gcgtcggtgc gctttccgca tttgatgcta tcggtggcgc ctatgcagaa    420

aaccttccgg ttatcctgat ctccggtgct ccgaacaaca atgatcacgc tgctggtcac    480

gtgttgcatc acgctcttgg caaaaccgac tatcactatc agttggaaat ggccaagaac    540

atcacggccg cagctgaagc gatttacacc ccagaagaag ctccggctaa aatcgatcac    600

gtgattaaaa ctgctcttcg tgagaagaag ccggtttatc tcgaaatcgc ttgcaacatt    660

gcttccatgc cctgcgccgc tcctggaccg gcaagcgcat tgttcaatga cgaagccagc    720

gacgaagctt ctttgaatgc agcggttgaa gaaaccctga aattcatcgc caaccgcgac    780

aaagttgccg tcctcgtcgg cagcaagctg cgcgcagctg gtgctgaaga agctgctgtc    840

aaatttgctg atgctctcgg tggcgcagtt gctaccatgg ctgctgcaaa aagcttcttc    900

ccagaagaaa acccgcatta catcggtacc tcatggggtg aagtcagcta tccgggcgtt    960

gaaaagacga tgaaagaagc cgatgcggtt atcgctctgg ctcctgtctt caacgactac   1020

tccaccactg gttggacgga tattcctgat cctaagaaac tggttctcgc tgaaccgcgt   1080

tctgtcgtcg ttaacggcgt tcgcttcccc agcgttcatc tgaaagacta tctgacccgt   1140

ttggctcaga aagtttccaa gaaaaccggt gctttggact tcttcaaatc cctcaatgca   1200

ggtgaactga agaaagccgc tccggctgat ccgagtgctc cgttggtcaa cgcagaaatc   1260

gcccgtcagg tcgaagctct tctgaccccg aacacgacgg ttattgctga aaccggtgac   1320

tcttggttca atgctcagcg catgaagctc ccgaacggtg ctcgcgttga atatgaaatg   1380

cagtggggtc acatcggttg gtccgttcct gccgccttcg gttatgccgt cggtgctccg   1440

gaacgtcgca acatcctcat ggttggtgat ggttccttcc agctgacggc tcaggaagtc   1500
```

```
gctcagatgg ttcgcctgaa actgccggtt atcatcttct tgatcaataa ctatggttac   1560

accatcgaag ttatgatcca tgatggtccg tacaacaaca tcaagaactg ggattatgcc   1620

ggtctgatgg aagtgttcaa cggtaacggt ggttatgaca gcggtgctgg taaaggcctg   1680

aaggctaaaa ccggtggcga actggcagaa gctatcaagg ttgctctggc aaacaccgac   1740

ggcccaaccc tgatcgaatg cttcatcggt cgtgaagact gcactgaaga attggtcaaa   1800

tggggtaagc gcgttgctgc cgccaacagc cgtaagcctg ttaacaagct cctctagttt   1860

ttggggatca attcgagctc ggtacccaaa ctagtaacgc tcggttgccg ccgggcgttt   1920

tttattccga catcaggaat tgtaattaga aagtccaaaa attgtaattt aaaaaacagt   1980

caatggagag cattgccata agtaaaggca tcccctgcgt gataagatta ccttcagaaa   2040

acagatagtt gctgggttat cgcagatttt tctcgcaacc aaataactgt aaataataac   2100

tgtctctggg gcgacggtag gctttatatt gccaaatttc gcccgtggga gaaagctagg   2160

ctattcaatg tttatggagg actgacccat atgatcaagg cttatgccgc tttagaggct   2220

aatggcaagt tgcagccgtt cgagtatgat ccgggcgctt taggcgccaa cgaagttgaa   2280

atcgaagttc aatactgcgg tgtttgtcat tccgacctca gtatgatcaa caatgagtgg   2340

ggtatcagta actatccgtt ggttcccggc cacgaagttg ttggcaccgt tgctgctatg   2400

ggtgagggtg ttaatcacgt ggaagttggt gacctggttg gtttaggctg gcacagtggt   2460

tattgtatga cttgtcactc ctgcctgagc ggttatcata atttgtgcgc taccgccgag   2520

agtactatcg ttggtcatta tggcggtttc ggtgaccgtg tgcgtgctaa aggtgtgtcc   2580

gttgttaagc tgcccaaggg tatcgatttg gcttccgctg gtccgttgtt ttgcggtggt   2640

atcactgtgt tttcccccat ggttgagtta tccctgaaac cgaccgccaa ggttgccgtt   2700

attggtatcg gtggtctcgg tcacctggcc gttcagttct tgcgtgcttg ggggttgcgag   2760

gttaccgctt tcactagctc cgctcgtaaa cagaccgagg ttctggagct gggtgcccat   2820

catattttgg acagtactaa ccccgaagcc attgcttccg ccgagggtaa gttcgattac   2880

atcattagta ccgttaattt aaaattggat tggaatctgt atatttccac tttagccccg   2940

caaggtcact ttcatttcgt gggtgttgtt ctcgaacccc tcgacttgaa cttgttcccg   3000

ttgctcatgg gtcagcggag tgtgtccgct agtccggttg gctccccggc tactatcgct   3060

actatgctcg atttcgccgt tcggcacgat atcaagccgg ttgttgagca gttctccttc   3120

gaccaaatta atgaagccat tgctcacttg gagtccggta aggctcacta ccgtgtggtt   3180

ttgagtcact ccaagaactg aaacgctcgg ttgccgccgg gcgtttttta ttcctgcagg   3240
```

```
<210> SEQ ID NO 58
<211> LENGTH: 3083
<212> TYPE: DNA
<213> ORGANISM: Artificial
<220> FEATURE:
<223> OTHER INFORMATION: insert from plasmid #1116
      pVZ325a-PziaA-PDCdsrA/oop-PrbcL*-synADH(deg)

<400> SEQUENCE: 58

gtcgacgtta ggagctaggg aaaaatttaa actggattta gaaaatgatt ttcatcctaa     60

catctttaat atctgagcat atcttcaggt gtttcaagat ttgtgctacg gttcaaggag    120

gtttttcttt aaatcacgtt ggccgccatg aattcttata ctgtcggtac ctatttagcg    180

gagcggcttg tccagattgg tctcaagcat cacttcgcag tcgcgggcga ctacaacctc    240

gtccttcttg acaacctgct tttgaacaaa aacatggagc aggtttattg ctgtaacgaa    300
```

-continued

```
ctgaactgcg gtttcagtgc agaaggttat gctcgtgcca aaggcgcagc agcagccgtc    360
gttacctaca gcgtcggtgc gctttccgca tttgatgcta tcggtggcgc ctatgcagaa    420
aaccttccgg ttatcctgat ctccggtgct ccgaacaaca atgatcacgc tgctggtcac    480
gtgttgcatc acgctcttgg caaaaccgac tatcactatc agttggaaat ggccaagaac    540
atcacggccg cagctgaagc gatttacacc ccagaagaag ctccggctaa aatcgatcac    600
gtgattaaaa ctgctcttcg tgagaagaag ccggtttatc tcgaaatcgc ttgcaacatt    660
gcttccatgc cctgcgccgc tcctggaccg gcaagcgcat tgttcaatga cgaagccagc    720
gacgaagctt ctttgaatgc agcggttgaa gaaaccctga aattcatcgc caaccgcgac    780
aaagttgccg tcctcgtcgg cagcaagctg cgcgcagctg gtgctgaaga agctgctgtc    840
aaatttgctg atgctctcgg tggcgcagtt gctaccatgg ctgctgcaaa aagcttcttc    900
ccagaagaaa acccgcatta catcggtacc tcatggggtg aagtcagcta tccgggcgtt    960
gaaaagacga tgaaagaagc cgatgcggtt atcgctctgg ctcctgtctt caacgactac   1020
tccaccactg gttggacgga tattcctgat cctaagaaac tggttctcgc tgaaccgcgt   1080
tctgtcgtcg ttaacggcgt tcgcttcccc agcgttcatc tgaaagacta tctgacccgt   1140
ttggctcaga aagtttccaa gaaaaccggt gctttggact tcttcaaatc cctcaatgca   1200
ggtgaactga agaaagccgc tccggctgat ccgagtgctc cgttggtcaa cgcagaaatc   1260
gcccgtcagg tcgaagctct tctgaccccg aacacgacgg ttattgctga aaccggtgac   1320
tcttggttca atgctcagcg catgaagctc ccgaacggtg ctcgcgttga atatgaaatg   1380
cagtggggtc acatcggttg gtccgttcct gccgccttcg gttatgccgt cggtgctccg   1440
gaacgtcgca acatcctcat ggttggtgat ggttccttcc agctgacggc tcaggaagtc   1500
gctcagatgg ttcgcctgaa actgccggtt atcatcttct tgatcaataa ctatggttac   1560
accatcgaag ttatgatcca tgatggtccg tacaacaaca tcaagaactg ggattatgcc   1620
ggtctgatgg aagtgttcaa cggtaacggt ggttatgaca gcggtgctgg taaaggcctg   1680
aaggctaaaa ccggtggcga actggcagaa gctatcaagg ttgctctggc aaacaccgac   1740
ggcccaaccc tgatcgaatg cttcatcggt cgtgaagact gcactgaaga attggtcaaa   1800
tggggtaagc gcgttgctgc cgccaacagc cgtaagcctg ttaacaagct cctctagttt   1860
ttggggatca attcgagctc agcaagtttc atcccgaccc cctcagggtc gggatttttt   1920
tattgtacta gtaacgcccg gttgccaccg ggcgtttttt attccgacat tgccataagt   1980
aaaggcatcc cctgcgtgat aagattacct tcagtttatg gaggactgac catatgatca   2040
aggcttatgc cgctttagag gctaatggca agttgcagcc gttcgagtat gatccgggcg   2100
ctttaggcgc caacgaagtt gaaatcgaag ttcaatactg cggtgtttgt cattccgacc   2160
tcagtatgat caacaatgag tggggtatca gtaactatcc gttggttccc ggccacgaag   2220
ttgttggcac cgttgctgct atgggtgagg gtgttaatca cgtggaagtt ggtgacctgg   2280
ttggtttagg ctggcacagt ggttattgta tgacttgtca ctcctgcctg agcggttatc   2340
ataatttgtg cgctaccgcc gagagtacta tcgttggtca ttatggcggt ttcggtgacc   2400
gtgtgcgtgc taaaggtgtg tccgttgtta agctgcccaa gggtatcgat ttggcttccg   2460
ctggtccgtt gttttgcggt ggtatcactg tgttttcccc catggttgag ttatccctga   2520
aaccgaccgc caaggttgcc gttattggta tcggtggtct cggtcacctg gccgttcagt   2580
tcttgcgtgc ttggggttgc gaggttaccg ctttcactag ctccgctcgt aaacagaccg   2640
aggttctgga gctgggtgcc catcatattt tggacagtac taaccccgaa gccattgctt   2700
```

ccgccgaggg taagttcgat tacatcatta gtaccgttaa tttaaaattg gattggaatc 2760
tgtatatttc cactttagcc ccgcaaggtc actttcattt cgtgggtgtt gttctcgaac 2820
ccctcgactt gaacttgttc ccgttgctca tgggtcagcg gagtgtgtcc gctagtccgg 2880
ttggctcccc ggctactatc gctactatgc tcgatttcgc cgttcggcac gatatcaagc 2940
cggttgttga gcagttctcc ttcgaccaaa ttaatgaagc cattgctcac ttggagtccg 3000
gtaaggctca ctaccgtgtg gttttgagtc actccaagaa ctgaaacgct cggttgccgc 3060
cgggcgtttt ttattcctgc agg 3083

<210> SEQ ID NO 59
<211> LENGTH: 58
<212> TYPE: DNA
<213> ORGANISM: Artificial
<220> FEATURE:
<223> OTHER INFORMATION: PziaA*-SalI-fw

<400> SEQUENCE: 59
gtcgacctaa catctttaat atctgagcat atcttcaggt gtttcaagat ttgtgcta 58

<210> SEQ ID NO 60
<211> LENGTH: 58
<212> TYPE: DNA
<213> ORGANISM: Artificial
<220> FEATURE:
<223> OTHER INFORMATION: PziaA*4-SalI-fw

<400> SEQUENCE: 60
gtcgacctaa catctttaac atctgaacat atcttcagat gtttcaagat ttgtgcta 58

<210> SEQ ID NO 61
<211> LENGTH: 66
<212> TYPE: DNA
<213> ORGANISM: Artificial
<220> FEATURE:
<223> OTHER INFORMATION: PziaA*-EcoRI-rev

<400> SEQUENCE: 61
gaattcatgg cggccaacgt gatttaaaga aaaacctcct tgaaccgtag cacaaatctt 60
gaaaca 66

<210> SEQ ID NO 62
<211> LENGTH: 66
<212> TYPE: DNA
<213> ORGANISM: Artificial
<220> FEATURE:
<223> OTHER INFORMATION: PziaA*1-EcoRI-rev

<400> SEQUENCE: 62
gaattcatgg cggccaacgt gatttaaaga aaaacctcct tgaattatag cacaaatctt 60
gaaaca 66

<210> SEQ ID NO 63
<211> LENGTH: 66
<212> TYPE: DNA
<213> ORGANISM: Artificial
<220> FEATURE:
<223> OTHER INFORMATION: PziaA*2-EcoRI-rev

<400> SEQUENCE: 63
gaattcatgg cggcctcctt gatttaaaga aaaacctcct tgaaccgtag cacaaatctt 60
gaaaca 66

<210> SEQ ID NO 64
<211> LENGTH: 66
<212> TYPE: DNA
<213> ORGANISM: Artificial
<220> FEATURE:
<223> OTHER INFORMATION: PziaA*3-EcoRI-rev

<400> SEQUENCE: 64
gaattcatgg cggcctcctt gatttaaaga aaaacctcct tgaattatag cacaaatctt 60
gaaaca 66

<210> SEQ ID NO 65
<211> LENGTH: 3577
<212> TYPE: DNA
<213> ORGANISM: Artificial
<220> FEATURE:
<223> OTHER INFORMATION: insert from plasmid #1277
pVZ325a-aztR-PaztA-PDCdsrA/oop-PrbcL*-synADH(deg)

<400> SEQUENCE: 65
gtcgactaaa tcgtaatacc taaatcagcc aacaaaattt agcacaattg cacaggggag 60
aagttcagat taatacattt atactattaa tttgcgatca ccctgtgcca gttgcgtaag 120
tattgttttc cactaaagag cgatataagt taatgacgtg actgtcagcc aaactataat 180
aaacattccg accttctcga cgatagctga ctaaacgcat agctttcaat aaccgcagct 240
gatgacaaac agctgattca ctcattttgg ttaatgcagc tagatcgcaa acacacaact 300
cactagaagc caaagctgat aggaggcgta tacggtttgt atctgctaac accccaaaaa 360
tttctgccat ttgttgtgct ttatctgtcg gtaagatttg agcctgagat gagcgtacat 420
tatctagatg caccagatga gtatcacagg taggggtatc agaactttga attaagtcta 480
agtcctgctt tttcttgtgc ttattcatag caagttttac ttagcaatag ttatcaatct 540
caataatacc taaaatgata accattgtac aattgaatag ttgttcaatt gttgtattag 600
aatattggca gttaactttt tgccttaatt ctaaagctgc tatgaattct tatactgtcg 660
gtacctattt agcggagcgg cttgtccaga ttggtctcaa gcatcacttc gcagtcgcgg 720
gcgactacaa cctcgtcctt cttgacaacc tgcttttgaa caaaaacatg gagcaggttt 780
attgctgtaa cgaactgaac tgcggtttca gtgcagaagg ttatgctcgt gccaaaggcg 840
cagcagcagc cgtcgttacc tacagcgtcg gtgcgctttc cgcatttgat gctatcggtg 900
gcgcctatgc agaaaacctt ccggttatcc tgatctccgg tgctccgaac aacaatgatc 960
acgctgctgg tcacgtgttg catcacgctc ttggcaaaac cgactatcac tatcagttgg 1020
aaatggccaa gaacatcacg gccgcagctg aagcgattta caccccagaa gaagctccgg 1080
ctaaaatcga tcacgtgatt aaaactgctc ttcgtgagaa gaagccggtt tatctcgaaa 1140
tcgcttgcaa cattgcttcc atgccctgcg ccgctcctgg accggcaagc gcattgttca 1200
atgacgaagc cagcgacgaa gcttctttga atgcagcggt tgaagaaacc ctgaaattca 1260
tcgccaaccg cgacaaagtt gccgtcctcg tcggcagcaa gctgcgcgca gctggtgctg 1320
aagaagctgc tgtcaaattt gctgatgctc tcggtggcgc agttgctacc atggctgctg 1380
caaaaagctt cttcccagaa gaaaacccgc attacatcgg tacctcatgg ggtgaagtca 1440
gctatccggg cgttgaaaag acgatgaaag aagccgatgc ggttatcgct ctggctcctg 1500
tcttcaacga ctactccacc actggttgga cggatattcc tgatcctaag aaactggttc 1560

-continued

```
tcgctgaacc gcgttctgtc gtcgttaacg gcgttcgctt ccccagcgtt catctgaaag   1620
actatctgac ccgtttggct cagaaagttt ccaagaaaac cggtgctttg gacttcttca   1680
aatccctcaa tgcaggtgaa ctgaagaaag ccgctccggc tgatccgagt gctccgttgg   1740
tcaacgcaga aatcgcccgt caggtcgaag ctcttctgac ccgaacacg acggttattg    1800
ctgaaaccgg tgactcttgg ttcaatgctc agcgcatgaa gctcccgaac ggtgctcgcg   1860
ttgaatatga aatgcagtgg ggtcacatcg gttggtccgt tcctgccgcc ttcggttatg   1920
ccgtcggtgc tccggaacgt cgcaacatcc tcatggttgg tgatggttcc ttccagctga   1980
cggctcagga agtcgctcag atggttcgcc tgaaactgcc ggttatcatc ttcttgatca   2040
ataactatgg ttacaccatc gaagttatga tccatgatgg tccgtacaac aacatcaaga   2100
actgggatta tgccggtctg atggaagtgt tcaacggtaa cggtggttat gacagcggtg   2160
ctggtaaagg cctgaaggct aaaaccggtg gcgaactggc agaagctatc aaggttgctc   2220
tggcaaacac cgacggccca accctgatcg aatgcttcat cggtcgtgaa gactgcactg   2280
aagaattggt caaatggggt aagcgcgttg ctgccgccaa cagccgtaag cctgttaaca   2340
agctcctcta gtttttgggg atcaattcga gctcagcaag tttcatcccg accccctcag   2400
ggtcgggatt tttttattgt actagtaacg cccggttgcc accgggcgtt ttttattccg   2460
acattgccat aagtaaaggc atcccctgcg tgataagatt accttcagtt tatggaggac   2520
tgaccatatg atcaaggctt atgccgcttt agaggctaat ggcaagttgc agccgttcga   2580
gtatgatccg ggcgctttag gcgccaacga agttgaaatc gaagttcaat actgcggtgt   2640
ttgtcattcc gacctcagta tgatcaacaa tgagtggggt atcagtaact atccgttggt   2700
tcccggccac gaagttgttg gcaccgttgc tgctatgggt gagggtgtta atcacgtgga   2760
agttggtgac ctggttggtt taggctggca cagtggttat tgtatgactt gtcactcctg   2820
cctgagcggt tatcataatt tgtgcgctac cgccgagagt actatcgttg gtcattatgg   2880
cggtttcggt gaccgtgtgc gtgctaaagg tgtgtccgtt gttaagctgc ccaagggtat   2940
cgatttggct tccgctggtc cgttgttttg cggtggtatc actgtgtttt cccccatggt   3000
tgagttatcc ctgaaaccga ccgccaaggt tgccgttatt ggtatcggtg gtctcggtca   3060
cctggccgtt cagttcttgc gtgcttgggg ttgcgaggtt accgctttca ctagctccgc   3120
tcgtaaacag accgaggttc tggagctggg tgcccatcat attttggaca gtactaaccc   3180
cgaagccatt gcttccgccg agggtaagtt cgattacatc attagtaccg ttaatttaaa   3240
attggattgg aatctgtata tttccacttt agccccgcaa ggtcactttc atttcgtggg   3300
tgttgttctc gaacccctcg acttgaactt gttcccgttg ctcatgggtc agcggagtgt   3360
gtccgctagt ccggttggct ccccggctac tatcgctact atgctcgatt tcgccgttcg   3420
gcacgatatc aagccggttg ttgagcagtt ctccttcgac caaattaatg aagccattgc   3480
tcacttggag tccggtaagg ctcactaccg tgtggttttg agtcactcca agaactgaaa   3540
cgctcggttg ccgccgggcg tttttattc ctgcagg                             3577
```

<210> SEQ ID NO 66
<211> LENGTH: 4184
<212> TYPE: DNA
<213> ORGANISM: Artificial
<220> FEATURE:
<223> OTHER INFORMATION: insert from plasmid #1217
pVZ325a-corR-PcorT-PDCdsrA/oop-PrbcL*-synADH(deg)

<400> SEQUENCE: 66

-continued

```
gtcgaccatg cgtccaaaac tttcaccatc ctttccctat caacctttac tgcactaaag     60
acaagtgaga tagcagtggc aatctggctt tgcaatcaat gtttccacta aagcgtttag    120
cgttactgcg gctagaagtc ctccaccgag gctcccctga atggtgatat ggggaatggg    180
actggtcatc agtcgtcgtt ttgcccccgg agcatgacta aaaccgatcg gcattccgat    240
cacaagagcc ggctgaatat gttgttgctc tatcagctta caggcagtga gtaaaacaga    300
aggggcatag ccgatcgcca gcacacatcc ttggggaatc tgttgtaacc gctgttgcca    360
atggtcatgg tgccaaaaag cttgctcggc ttccctaagc cctgtgatgt gagggtcgtc    420
aatcagcgtt ttaaccgtac atcctaaatg agctaaccga gtttgatcaa gagccgcagc    480
cacaaccgga acatcggtga cgactggaca ccctgctttc agtgcatctc gtgccgaggc    540
gatcgctccc tgactcaatc gaacggcgtt taccaagcta acatcaccac aggccagcac    600
taattgatgt agtaagtgaa tggtaatttc agagtaagcc gataaatccg gtagcaggtg    660
tttgagggat tcctgaaagg cttctggatg agttgttgtc tccgcatcta ggttcgtcca    720
caactgatcg agttttccta acccctcctg gacatccaca tcaagctgtt tcagttgggc    780
cagagcttcc gcttgggtaa tctggcaact ctggtcgcgt cccagtaatc cttctaaagc    840
agatgcggtt tggcggagtc gagtaatctg ctgaatcaca gcctgatatt gctgttgcaa    900
ctgcaccatt agggtgggat caaggctctc ttcagaatgg ctatccagca gttgccgaat    960
atgagacaac tgaaagccct gctgtttgag ggcaatgact cgttggagcc gttgtacgtc   1020
ctgctgagta taaaggcggt agttgccctc tgagcgttga acggggggaa gcaatcccag   1080
ggtgtggtaa tggcgcacca tgcgaggcgt aacgccacct cccactgcat ctgtgagttc   1140
tttaatcgtt aagtgattag tcttcatccc tttagtttac tcaaaacctt gacattgaca   1200
ctaatgttaa ggtttaggct gagaaggtaa aaatccaagt taaaaagcat gaattcttat   1260
actgtcggta cctatttagc ggagcggctt gtccagattg gtctcaagca tcacttcgca   1320
gtcgcgggcg actacaacct cgtccttctt gacaacctgc ttttgaacaa aaacatggag   1380
caggtttatt gctgtaacga actgaactgc ggtttcagtg cagaaggtta tgctcgtgcc   1440
aaaggcgcag cagcagccgt cgttacctac agcgtcggtg cgctttccgc atttgatgct   1500
atcggtggcg cctatgcaga aaaccttccg gttatcctga tctccggtgc tccgaacaac   1560
aatgatcacg ctgctggtca cgtgttgcat cacgctcttg gcaaaaccga ctatcactat   1620
cagttggaaa tggccaagaa catcacggcc gcagctgaag cgatttacac cccagaagaa   1680
gctccggcta aaatcgatca cgtgattaaa actgctcttc gtgagaagaa gccggtttat   1740
ctcgaaatcg cttgcaacat tgcttccatg ccctgcgccg ctcctggacc ggcaagcgca   1800
ttgttcaatg acgaagccag cgacgaagct tctttgaatg cagcggttga agaaaccctg   1860
aaattcatcg ccaaccgcga caaagttgcc gtcctcgtcg gcagcaagct gcgcgcagct   1920
ggtgctgaag aagctgctgt caaatttgct gatgctctcg gtggcgcagt tgctaccatg   1980
gctgctgcaa aaagcttctt cccagaagaa aacccgcatt acatcggtac ctcatggggt   2040
gaagtcagct atccgggcgt tgaaaagacg atgaaagaag ccgatgcggt tatcgctctg   2100
gctcctgtct tcaacgacta ctccaccact ggttggacgg atattcctga tcctaagaaa   2160
ctggttctcg ctgaaccgcg ttctgtcgtc gttaacggcg ttcgcttccc cagcgttcat   2220
ctgaaagact atctgacccg tttggctcag aaagtttcca agaaaaccgg tgctttggac   2280
ttcttcaaat ccctcaatgc aggtgaactg aagaaagccg ctccggctga tccgagtgct   2340
ccgttggtca acgcagaaat cgcccgtcag gtcgaagctc ttctgacccc gaacacgacg   2400
```

```
gttattgctg aaaccggtga ctcttggttc aatgctcagc gcatgaagct cccgaacggt   2460

gctcgcgttg aatatgaaat gcagtggggt cacatcggtt ggtccgttcc tgccgccttc   2520

ggttatgccg tcggtgctcc ggaacgtcgc aacatcctca tggttggtga tggttccttc   2580

cagctgacgg ctcaggaagt cgctcagatg gttcgcctga aactgccggt tatcatcttc   2640

ttgatcaata actatggtta caccatcgaa gttatgatcc atgatggtcc gtacaacaac   2700

atcaagaact gggattatgc cggtctgatg gaagtgttca acggtaacgg tggttatgac   2760

agcggtgctg gtaaaggcct gaaggctaaa accggtggcg aactggcaga agctatcaag   2820

gttgctctgg caaacaccga cggcccaacc ctgatcgaat gcttcatcgg tcgtgaagac   2880

tgcactgaag aattggtcaa atggggtaag cgcgttgctg ccgccaacag ccgtaagcct   2940

gttaacaagc tcctctagtt tttggggatc aattcgagct cagcaagttt catcccgacc   3000

ccctcagggt cgggattttt ttattgtact agtaacgccc ggttgccacc gggcgttttt   3060

tattccgaca ttgccataag taaaggcatc ccctgcgtga taagattacc ttcagtttat   3120

ggaggactga ccatatgatc aaggcttatg ccgctttaga ggctaatggc aagttgcagc   3180

cgttcgagta tgatccgggc gctttaggcg ccaacgaagt tgaaatcgaa gttcaatact   3240

gcggtgtttg tcattccgac ctcagtatga tcaacaatga gtggggtatc agtaactatc   3300

cgttggttcc cggccacgaa gttgttggca ccgttgctgc tatgggtgag ggtgttaatc   3360

acgtggaagt tggtgacctg gttggtttag gctggcacag tggttattgt atgacttgtc   3420

actcctgcct gagcggttat cataatttgt gcgctaccgc cgagagtact atcgttggtc   3480

attatggcgg tttcggtgac cgtgtgcgtg ctaaaggtgt gtccgttgtt aagctgccca   3540

agggtatcga tttggcttcc gctggtccgt tgttttgcgg tggtatcact gtgttttccc   3600

ccatggttga gttatccctg aaaccgaccg ccaaggttgc cgttattggt atcggtggtc   3660

tcggtcacct ggccgttcag ttcttgcgtg cttggggttg cgaggttacc gctttcacta   3720

gctccgctcg taaacagacc gaggttctgg agctgggtgc ccatcatatt ttggacagta   3780

ctaaccccga agccattgct tccgccgagg gtaagttcga ttacatcatt agtaccgtta   3840

atttaaaatt ggattggaat ctgtatattt ccactttagc cccgcaaggt cactttcatt   3900

tcgtgggtgt tgttctcgaa cccctcgact tgaacttgtt cccgttgctc atgggtcagc   3960

ggagtgtgtc cgctagtccg gttggctccc cggctactat cgctactatg ctcgatttcg   4020

ccgttcggca cgatatcaag ccggttgttg agcagttctc cttcgaccaa attaatgaag   4080

ccattgctca cttggagtcc ggtaaggctc actaccgtgt ggttttgagt cactccaaga   4140

actgaaacgc tcggttgccg ccgggcgttt tttattcctg cagg                    4184
```

<210> SEQ ID NO 67
<211> LENGTH: 3792
<212> TYPE: DNA
<213> ORGANISM: Artificial
<220> FEATURE:
<223> OTHER INFORMATION: insert from plasmid #1227
pVZ325a-nrsR-PnrsB-PDCdsrA/oop-PrbcL*-synADH(deg)

<400> SEQUENCE: 67

```
gtcgacggga gtttgcaaac tccctcatat tcatggcgat agggtgaacc gatagccttg     60

accgggaact gttttaattg ggcaaggaca attttgttga gctagcttgc gtcgtatcaa    120

acgcatttgg gccgccacca cattactcat gggctcctca tcaagatccc acagttgttg    180

ccggatcttg ctaccggaaa tgatccgctc tgggttttgc atcagatatt gaaaaatttg    240
```

```
aaattctctt acggttaaag caatttcctg tctttctagg tttagtggct ccgagatagt    300
taccgataac agattattac tgggatcaag gctgaagttg cccaaagtta aaatttgcgg    360
ttggaattgt ggcgatcgcc gttgtagtgc ccgcagtctt gctaatagct ctgccatcac    420
aaacggtttt gttagatagt catctgcccc ggcatctagt ccttcgacac ggttttccgg    480
ttctcctaac gctgttaaca tcaacaccgg caaggaatta ccctgggttc tcagtttttg    540
acagagttcc aaacccgata atcccggcag taaccaatcc acaatggcaa gggtgtattc    600
cgtccattga ttttccaaat aatcccaagc ttgggagcca tccgtcaccc aatccaccac    660
atacttttca ctaactagca ctttcttaat agccattccc aaatccgtct catcttccac    720
cagcaaaatt cgcatcgcct ctgccttttt tataacggtc tgatcttagc gggggaagga    780
gattttcacc tgaatttcat acccccttg gcagactggg aaaatcttgg acaaattccc    840
aatttgaggt ggtgtgatga attcttatac tgtcggtacc tatttagcgg agcggcttgt    900
ccagattggt ctcaagcatc acttcgcagt cgcgggcgac tacaacctcg tccttcttga    960
caacctgctt ttgaacaaaa acatggagca ggtttattgc tgtaacgaac tgaactgcgg   1020
tttcagtgca gaaggttatg ctcgtgccaa aggcgcagca gcagccgtcg ttacctacag   1080
cgtcggtgcg ctttccgcat ttgatgctat cggtggcgcc tatgcagaaa accttccggt   1140
tatcctgatc tccggtgctc cgaacaacaa tgatcacgct gctggtcacg tgttgcatca   1200
cgctcttggc aaaaccgact atcactatca gttggaaatg gccaagaaca tcacggccgc   1260
agctgaagcg atttacaccc cagaagaagc tccggctaaa atcgatcacg tgattaaaac   1320
tgctcttcgt gagaagaagc cggtttatct cgaaatcgct tgcaacattg cttccatgcc   1380
ctgcgccgct cctggaccgg caagcgcatt gttcaatgac gaagccagcg acgaagcttc   1440
tttgaatgca gcggttgaag aaaccctgaa attcatcgcc aaccgcgaca aagttgccgt   1500
cctcgtcggc agcaagctgc gcgcagctgg tgctgaagaa gctgctgtca aatttgctga   1560
tgctctcggt ggcgcagttg ctaccatggc tgctgcaaaa agcttcttcc cagaagaaaa   1620
cccgcattac atcggtacct catggggtga agtcagctat ccgggcgttg aaaagacgat   1680
gaaagaagcc gatgcggtta tcgctctggc tcctgtcttc aacgactact ccaccactgg   1740
ttggacggat attcctgatc ctaagaaact ggttctcgct gaaccgcgtt ctgtcgtcgt   1800
taacggcgtt cgcttcccca gcgttcatct gaaagactat ctgacccgtt tggctcagaa   1860
agtttccaag aaaaccggtg ctttggactt cttcaaatcc ctcaatgcag gtgaactgaa   1920
gaaagccgct ccggctgatc cgagtgctcc gttggtcaac gcagaaatcg cccgtcaggt   1980
cgaagctctt ctgaccccga acacgacggt tattgctgaa accggtgact cttggttcaa   2040
tgctcagcgc atgaagctcc cgaacggtgc tcgcgttgaa tatgaaatgc agtggggtca   2100
catcggttgg tccgttcctg ccgccttcgg ttatgccgtc ggtgctccgg aacgtcgcaa   2160
catcctcatg gttggtgatg gttccttcca gctgacggct caggaagtcg ctcagatggt   2220
tcgcctgaaa ctgccggtta tcatcttctt gatcaataac tatggttaca ccatcgaagt   2280
tatgatccat gatggtccgt acaacaacat caagaactgg gattatgccg gtctgatgga   2340
agtgttcaac ggtaacggtg gttatgacag cggtgctggt aaaggcctga aggctaaaac   2400
cggtggcgaa ctggcagaag ctatcaaggt tgctctggca aacaccgacg gcccaaccct   2460
gatcgaatgc ttcatcggtc gtgaagactg cactgaagaa ttggtcaaat ggggtaagcg   2520
cgttgctgcc gccaacagcc gtaagcctgt taacaagctc ctctagtttt tggggatcaa   2580
```

-continued

```
ttcgagctca gcaagtttca tcccgacccc ctcagggtcg ggattttttt attgtactag   2640

taacgcccgg ttgccaccgg gcgtttttta ttccgacatt gccataagta aaggcatccc   2700

ctgcgtgata agattacctt cagtttatgg aggactgacc atatgatcaa ggcttatgcc   2760

gctttagagg ctaatggcaa gttgcagccg ttcgagtatg atccgggcgc tttaggcgcc   2820

aacgaagttg aaatcgaagt tcaatactgc ggtgtttgtc attccgacct cagtatgatc   2880

aacaatgagt ggggtatcag taactatccg ttggttcccg gccacgaagt tgttggcacc   2940

gttgctgcta tgggtgaggg tgttaatcac gtggaagttg gtgacctggt tggtttaggc   3000

tggcacagtg gttattgtat gacttgtcac tcctgcctga gcggttatca taatttgtgc   3060

gctaccgccg agagtactat cgttggtcat tatggcggtt tcggtgaccg tgtgcgtgct   3120

aaaggtgtgt ccgttgttaa gctgcccaag ggtatcgatt tggcttccgc tggtccgttg   3180

ttttgcggtg gtatcactgt gttttccccc atggttgagt tatccctgaa accgaccgcc   3240

aaggttgccg ttattggtat cggtggtctc ggtcacctgg ccgttcagtt cttgcgtgct   3300

tggggttgcg aggttaccgc tttcactagc tccgctcgta aacagaccga ggttctggag   3360

ctgggtgccc atcatatttt ggacagtact aaccccgaag ccattgcttc cgccgagggt   3420

aagttcgatt acatcattag taccgttaat ttaaaattgg attggaatct gtatatttcc   3480

actttagccc cgcaaggtca ctttcatttc gtgggtgttg ttctcgaacc cctcgacttg   3540

aacttgttcc cgttgctcat gggtcagcgg agtgtgtccg ctagtccggt tggctccccg   3600

gctactatcg ctactatgct cgatttcgcc gttcggcacg atatcaagcc ggttgttgag   3660

cagttctcct tcgaccaaat taatgaagcc attgctcact tggagtccgg taaggctcac   3720

taccgtgtgg ttttgagtca ctccaagaac tgaaacgctc ggttgccgcc gggcgttttt   3780

tattcctgca gg                                                        3792
```

<210> SEQ ID NO 68
<211> LENGTH: 8316
<212> TYPE: DNA
<213> ORGANISM: Artificial
<220> FEATURE:
<223> OTHER INFORMATION: plasmid TK96 pGEM-AQ4::PsmtA7002-PDC-synADH-Nm

<400> SEQUENCE: 68

```
tcgactgtgg tctgtctttg ttcgctgatc taaacaatac ctgaataatt gttcatgtgt     60

taatctaaaa atgtgaacaa tcgttcaact atttaagaca ataccttgga ggtttaaacc    120

atgaattctt atactgtcgg tacctattta gcggagcggc ttgtccagat tggtctcaag    180

catcacttcg cagtcgcggg cgactacaac ctcgtccttc ttgacaacct gcttttgaac    240

aaaaacatgg agcaggttta ttgctgtaac gaactgaact gcggtttcag tgcagaaggt    300

tatgctcgtg ccaaaggcgc agcagcagcc gtcgttacct acagcgtcgg tgcgctttcc    360

gcatttgatg ctatcggtgg cgcctatgca gaaaaccttc cggttatcct gatctccggt    420

gctccgaaca acaatgatca cgctgctggt cacgtgttgc atcacgctct tggcaaaacc    480

gactatcact atcagttgga aatggccaag aacatcacgg ccgcagctga agcgatttac    540

accccagaag aagctccggc taaaatcgat cacgtgatta aaactgctct tcgtgagaag    600

aagccggttt atctcgaaat cgcttgcaac attgcttcca tgccctgcgc cgctcctgga    660

ccggcaagcg cattgttcaa tgacgaagcc agcgacgaag cttctttgaa tgcagcggtt    720

gaagaaaccc tgaaattcat cgccaaccgc gacaaagttg ccgtcctcgt cggcagcaag    780

ctgcgcgcag ctggtgctga agaagctgct gtcaaatttg ctgatgctct cggtggcgca    840
```

-continued

```
gttgctacca tggctgctgc aaaaagcttc ttcccagaag aaaacccgca ttacatcggt    900
acctcatggg gtgaagtcag ctatccgggc gttgaaaaga cgatgaaaga agccgatgcg    960
gttatcgctc tggctcctgt cttcaacgac tactccacca ctggttggac ggatattcct   1020
gatcctaaga aactggttct cgctgaaccg cgttctgtcg tcgttaacgg cgttcgcttc   1080
cccagcgttc atctgaaaga ctatctgacc cgtttggctc agaaagtttc caagaaaacc   1140
ggtgctttgg acttcttcaa atccctcaat gcaggtgaac tgaagaaagc cgctccggct   1200
gatccgagtg ctccgttggt caacgcagaa atcgcccgtc aggtcgaagc tcttctgacc   1260
ccgaacacga cggttattgc tgaaaccggt gactcttggt tcaatgctca gcgcatgaag   1320
ctcccgaacg gtgctcgcgt tgaatatgaa atgcagtggg gtcacatcgg ttggtccgtt   1380
cctgccgcct tcggttatgc cgtcggtgct ccggaacgtc gcaacatcct catggttggt   1440
gatggttcct tccagctgac ggctcaggaa gtcgctcaga tggttcgcct gaaactgccg   1500
gttatcatct tcttgatcaa taactatggt tacaccatcg aagttatgat ccatgatggt   1560
ccgtacaaca acatcaagaa ctgggattat gccggtctga tggaagtgtt caacggtaac   1620
ggtggttatg acagcggtgc tggtaaaggc ctgaaggcta aaaccggtgg cgaactggca   1680
gaagctatca aggttgctct ggcaaacacc gacggcccaa ccctgatcga atgcttcatc   1740
ggtcgtgaag actgcactga agaattggtc aaatggggta agcgcgttgc tgccgccaac   1800
agccgtaagc ctgttaacaa gctcctctag tttttgggga tcaattcgag ctctctggat   1860
aaaactaata aactctatta cccatgatta aagcctacgc tgccctggaa gccaacggaa   1920
aactccaacc ctttgaatac gaccccggtg ccctgggtgc taatgaggtg gagattgagg   1980
tgcagtattg tggggtgtgc cacagtgatt tgtccatgat taataacgaa tggggcattt   2040
ccaattaccc cctagtgccg ggtcatgagg tggtgggtac tgtggccgcc atgggcgaag   2100
gggtgaacca tgttgaggtg ggggatttag tggggctggg ttggcattcg ggctactgca   2160
tgacctgcca tagttgttta tctggctacc acaacctttg tgccacggcg gaatcgacca   2220
ttgtgggcca ctacggtggc tttggcgatc gggttcgggc caagggagtc agcgtggtga   2280
aattacctaa aggcattgac ctagccagtg ccgggcccct tttctgtgga ggaattaccg   2340
ttttcagtcc tatggtggaa ctgagtttaa agcccactgc aaaagtggca gtgatcggca   2400
ttgggggctt gggccattta gcggtgcaat ttctccgggc ctggggctgt gaagtgactg   2460
cctttacctc cagtgccagg aagcaaacgg aagtgttgga attgggcgct caccacatac   2520
tagattccac caatccagag gcgatcgcca gtgcggaagg caaatttgac tatattatct   2580
ccactgtgaa cctgaagctt gactggaact tatacatcag caccctggcg ccccagggac   2640
atttccactt tgttggggtg gtgttggagc ctttggatct aaatcttttt ccccttttga   2700
tgggacaacg ctccgtttct gcctccccag tgggtagtcc cgccaccatt gccaccatgt   2760
tggactttgc tgtgcgccat gacattaaac ccgtggtgga acaatttagc tttgatcaga   2820
tcaacgaggc gatcgcccat ctagaaagcg gcaaagccca ttatcgggta gtgctcagcc   2880
atagtaaaaa ttagctctgc aaaggttgct tctgggtccg tggaatggtc aaacggagtc   2940
gatctcagtt ttgatacgct ctatctggaa agcttgacat tcgatctgca gcccggggga   3000
tccactagag gatctcaatg aatattggtt gacacgggcg tataagacat gttatactgt   3060
tgaataacaa ggacggatct gatcaagaga caggatgagg atcgtttcgc atgattgaac   3120
aagatggatt gcacgcaggt tctccggccg cttgggtgga gaggctattc ggctatgact   3180
```

-continued

```
gggcacaaca gacaatcggc tgctctgatg ccgccgtgtt ccggctgtca gcgcaggggc   3240
gcccggttct ttttgtcaag accgacctgt ccggtgccct gaatgaactg caggacgagg   3300
cagcgcggct atcgtggctg gccacgacgg gcgttccttg cgcagctgtg ctcgacgttg   3360
tcactgaagc gggaagggac tggctgctat tgggcgaagt gccggggcag gatctcctgt   3420
catctcacct tgctcctgcc gagaaagtat ccatcatggc tgatgcaatg cggcggctgc   3480
atacgcttga tccggctacc tgcccattcg accaccaagc gaaacatcgc atcgagcgag   3540
cacgtactcg gatggaagcc ggtcttgtcg atcaggatga tctggacgaa gagcatcagg   3600
ggctcgcgcc agccgaactg ttcgccaggc tcaaggcgcg catgcccgac ggcgaggatc   3660
tcgtcgtgac ccatggcgat gcctgcttgc cgaatatcat ggtggaaaat ggccgctttt   3720
ctggattcat cgactgtggc cggctgggtg tggcggaccg ctatcaggac atagcgttgg   3780
ctacccgtga tattgctgaa gagcttggcg gcgaatgggc tgaccgcttc ctcgtgcttt   3840
acggtatcgc cgctcccgat tcgcagcgca tcgccttcta tcgccttctt gacgagttct   3900
tctgagcggg actctggggt tcgaaatgac cgaccaagcg acgcccaacc tgccatcacg   3960
agatttcgat tccaccgccg ccttctatga aaggttgggc ttcggaatcg ttttccggga   4020
cgccggctgg atgatcctcc agcgcgggga tctcatgctg gagttcttcg cccaccgggg   4080
atcctctagt tctagagcgg ccgcatcatc aatccccgtg atgtttcagt cccgtagtcg   4140
ggatttagtg gttggaaagc ggaacgtcgc gccgaaacca tcgccaggac gggtttcagt   4200
cccgtagtcg ggatttagtg gttggaaagt gattatgttc aagaaatcac aacgcaaaag   4260
aaaaagtttc agtcccgtag tcgggattta gtggttggaa agtcaagcga gatacccacc   4320
agaaagcctt tgacctggtt tcagtcccga gtcgggattt agtggttgga aaggcggcgg   4380
ctgatgtcgc caatgcggtt atcgatggcc agtttcagtc ccgtagtcgg gatttagtgg   4440
ttggaaagtc ccaaggggga cagggcggtg atcctcgatg ttgcgtgttt cagtcccgta   4500
gtcgggattt agtggttgga aagactcgtc tatatataca gagattacta cagagatgtt   4560
tcagtcccgt agtcgggatt tagtggttgg aaagcgggaa agtagcctgt tttgtggaga   4620
attgcaggcg tttcagtact agtgatggcg gccgggagca tgcgacgtcg ggcccaattc   4680
gccctatagt gagtcgtatt acaattcact ggccgtcgtt ttacaacgtc gtgactggga   4740
aaaccctggc gttacccaac ttaatcgcct tgcagcacat ccccctttcg ccagctggcg   4800
taatagcgaa gaggcccgca ccgatcgccc ttcccaacag ttgcgcagcc tgaatggcga   4860
atggacgcgc cctgtagcgg cgcattaagc gcggcgggtg tggtggttac gcgcagcgtg   4920
accgctacac ttgccagcgc cctagcgccc gctcctttcg ctttcttccc ttcctttctc   4980
gccacgttcg ccggctttcc ccgtcaagct ctaaatcggg ggctcccttt agggttccga   5040
tttagagctt tacggcacct cgaccgcaaa aaacttgatt tgggtgatgg ttcacgtagt   5100
gggccatcgc cctgatagac ggtttttcgc cctttgacgt tggagtccac gttctttaat   5160
agtggactct tgttccaaac tggaacaaca ctcaacccta tctcggtcta ttcttttgat   5220
ttataaggga ttttgccgat ttcggcctat tggttaaaaa atgagctgat ttaacaaata   5280
tttaacgcga attttaacaa aatattaacg tttacaattt cgcctgatgc ggtattttct   5340
ccttacgcat ctgtgcggta tttcacaccg catacaggtg gcacttttcg gggaaatgtg   5400
cgcggaaccc ctatttgttt atttttctaa atacattcaa atatgtatcc gctcatgaga   5460
caataaccct gataaatgct tcaataatat tgaaaaagga agagtatgag tattcaacat   5520
ttccgtgtcg cccttattcc ctttttgcg gcattttgcc ttcctgtttt tgctcaccca   5580
```

-continued gaaacgctgg tgaaagtaaa agatgctgaa gatcagttgg gtgcacgagt gggttacatc 5640
gaactggatc tcaacagcgg taagatcctt gagagttttc gccccgaaga acgttttcca 5700
atgatgagca cttttaaagt tctgctatgt ggcgcggtat tatcccgtat tgacgccggg 5760
caagagcaac tcggtcgccg catacactat tctcagaatg acttggttga gtactcacca 5820
gtcacagaaa agcatcttac ggatggcatg acagtaagag aattatgcag tgctgccata 5880
accatgagtg ataacactgc ggccaactta cttctgacaa cgatcggagg accgaaggag 5940
ctaaccgctt ttttgcacaa catgggggat catgtaactc gccttgatcg ttgggaaccg 6000
gagctgaatg aagccatacc aaacgacgag cgtgacacca cgatgcctgt agcaatgcca 6060
acaacgttgc gcaaactatt aactggcgaa ctacttactc tagcttcccg gcaacaatta 6120
atagactgga tggaggcgga taaagttgca ggaccacttc tgcgctcggc ccttccggct 6180
ggctggttta ttgctgataa atctggagcc ggtgagcgtg ggtctcgcgg tatcattgca 6240
gcactggggc cagatggtaa gccctcccgt atcgtagtta tctacacgac ggggagtcag 6300
gcaactatgg atgaacgaaa tagacagatc gctgagatag gtgcctcact gattaagcat 6360
tggtaactgt cagaccaagt ttactcatat atactttaga ttgatttaaa acttcatttt 6420
taatttaaaa ggatctaggt gaagatcctt tttgataatc tcatgaccaa aatcccttaa 6480
cgtgagtttt cgttccactg agcgtcagac cccgtagaaa agatcaaagg atcttcttga 6540
gatccttttt ttctgcgcgt aatctgctgc ttgcaaacaa aaaaaccacc gctaccagcg 6600
gtggtttgtt tgccggatca agagctacca actctttttc cgaaggtaac tggcttcagc 6660
agagcgcaga taccaaatac tgtccttcta gtgtagccgt agttaggcca ccacttcaag 6720
aactctgtag caccgcctac atacctcgct ctgctaatcc tgttaccagt ggctgctgcc 6780
agtggcgata agtcgtgtct taccgggttg gactcaagac gatagttacc ggataaggcg 6840
cagcggtcgg gctgaacggg gggttcgtgc acacagccca gcttggagcg aacgacctac 6900
accgaactga gatacctaca gcgtgagcta tgagaaagcg ccacgcttcc cgaagggaga 6960
aaggcggaca ggtatccggt aagcggcagg gtcggaacag gagagcgcac gagggagctt 7020
ccagggggaa acgcctggta tctttatagt cctgtcgggt ttcgccacct ctgacttgag 7080
cgtcgatttt tgtgatgctc gtcagggggg cggagcctat ggaaaaacgc cagcaacgcg 7140
gcctttttac ggttcctggc cttttgctgg ccttttgctc acatgttctt tcctgcgtta 7200
tcccctgatt ctgtggataa ccgtattacc gcctttgagt gagctgatac cgctcgccgc 7260
agccgaacga ccgagcgcag cgagtcagtg agcgaggaag cggaagagcg cccaatacgc 7320
aaaccgcctc tccccgcgcg ttggccgatt cattaatgca gctggcacga caggtttccc 7380
gactggaaag cgggcagtga gcgcaacgca attaatgtga gttagctcac tcattaggca 7440
ccccaggctt tacactttat gcttccggct cgtatgttgt gtggaattgt gagcggataa 7500
caatttcaca caggaaacag ctatgaccat gattacgcca agctatttag gtgacactat 7560
agaatactca agctatgcat gagggtgcaa tttgagtggt ttcagtcccg taatcgggat 7620
ttagtggttg gaaagaacga caaggcttac aagggggtaa ttcgtgattt gtttcagtcc 7680
cgtaatcggg atttagtggt tggaaagtag gcaggggagt gaaatggttt catgttgggc 7740
tcatgtttca gtcccgtaat cgggatttag tggttggaaa gcagtaagat gaaggaggtg 7800
gtgcatatca cttgcgtttc agtcccgtaa tcgggattta gtggttggaa agctagattt 7860
gcttatagag ttgactgtta tcgggacttg tttcagtccc gtaatcggga tttagtggtt 7920

-continued

```
ggaaagatga tggcgttgcc agcgttctcg gattggagaa tttaacgttt cagtcccgta   7980

atcgggattt agtggttgga aagccctgag aagtttggct gttttgctga ctgcgatctg   8040

gtttcagtcc cgtaatcggg atttagtggt tggaaagcat cgaggcagta gagcaaatcg   8100

caggccacct catagtttca gtcccgtaat cgggatttag tggttggaaa gtcattgggg   8160

tctgcattgg ggccatcgct atcgtcctgt ttcagtcccg taatcgggat ttagtggttg   8220

gaaagtggga cgctccgtaa ggtttggaga atagggtcta gtgtttcagt cccgtaatcg   8280

ggatttagtg gttggaaagc acttcgtcgc tgattg                             8316


<210> SEQ ID NO 69
<211> LENGTH: 8915
<212> TYPE: DNA
<213> ORGANISM: Artificial
<220> FEATURE:
<223> OTHER INFORMATION: plasmid TK115 pGEM-AQ4::smtB-PsmtA-ZmPDC-PrbcL-
      synADH(deg)-Nm

<400> SEQUENCE: 69

tcgacgggca aactttatga agcagatcaa gcctatatcc gccaagcaac cggcagccgc     60

gttgattagt gggtgtgtcc atcctctggt tcgtctaggt gctccgaagc gtcacgatag    120

agattaagaa tgtggtgatc cttgaggcga taaatcacat tccgcccttc cttgcgatag    180

ctcactaaac gtgctgtgcg cagggttctt agttggtgag agacagccga ttcactcatt    240

tcaacggcgg cggcgagttc ccccacccgc atctctccag tggccagggc cgaaagaata    300

cgccagcggt tggcatcccc caagacacca aaaaattcgg ccatccgttg ggccttggct    360

tggttcaaga ttttgccact gtggtctgtc attgttcgct gatctaaaca atacctgaat    420

aattgttcat gtgttaatct aaaaatgtga acaatcgttc aactatttaa gacaatacct    480

tggaggttta aaccatgaat tcttatactg tcggtaccta tttagcggag cggcttgtcc    540

agattggtct caagcatcac ttcgcagtcg cgggcgacta caacctcgtc cttcttgaca    600

acctgctttt gaacaaaaac atggagcagg tttattgctg taacgaactg aactgcggtt    660

tcagtgcaga aggttatgct cgtgccaaag gcgcagcagc agccgtcgtt acctacagcg    720

tcggtgcgct ttccgcattt gatgctatcg gtggcgccta tgcagaaaac cttccggtta    780

tcctgatctc cggtgctccg aacaacaatg atcacgctgc tggtcacgtg ttgcatcacg    840

ctcttggcaa aaccgactat cactatcagt tggaaatggc caagaacatc acggccgcag    900

ctgaagcgat ttacacccca gaagaagctc cggctaaaat cgatcacgtg attaaaactg    960

ctcttcgtga gaagaagccg gtttatctcg aaatcgcttg caacattgct tccatgccct   1020

gcgccgctcc tggaccggca agcgcattgt tcaatgacga agccagcgac gaagcttctt   1080

tgaatgcagc ggttgaagaa accctgaaat tcatcgccaa ccgcgacaaa gttgccgtcc   1140

tcgtcggcag caagctgcgc gcagctggtg ctgaagaagc tgctgtcaaa tttgctgatg   1200

ctctcggtgg cgcagttgct accatggctg ctgcaaaaag cttcttccca gaagaaaacc   1260

cgcattacat cggtacctca tggggtgaag tcagctatcc gggcgttgaa aagacgatga   1320

aagaagccga tgcggttatc gctctggctc ctgtcttcaa cgactactcc accactggtt   1380

ggacggatat tcctgatcct aagaaactgg ttctcgctga accgcgttct gtcgtcgtta   1440

acggcgttcg cttccccagc gttcatctga aagactatct gacccgtttg gctcagaaag   1500

tttccaagaa aaccggtgct ttggacttct tcaaatccct caatgcaggt gaactgaaga   1560

aagccgctcc ggctgatccg agtgctccgt tggtcaacgc agaaatcgcc cgtcaggtcg   1620
```

-continued

```
aagctcttct gaccccgaac acgacggtta ttgctgaaac cggtgactct tggttcaatg   1680
ctcagcgcat gaagctcccg aacggtgctc gcgttgaata tgaaatgcag tggggtcaca   1740
tcggttggtc cgttcctgcc gccttcggtt atgccgtcgg tgctccggaa cgtcgcaaca   1800
tcctcatggt tggtgatggt tccttccagc tgacggctca ggaagtcgct cagatggttc   1860
gcctgaaact gccggttatc atcttcttga tcaataacta tggttacacc atcgaagtta   1920
tgatccatga tggtccgtac aacaacatca agaactggga ttatgccggt ctgatggaag   1980
tgttcaacgg taacggtggt tatgacagcg gtgctggtaa aggcctgaag gctaaaaccg   2040
gtggcgaact ggcagaagct atcaaggttg ctctggcaaa caccgacggc ccaaccctga   2100
tcgaatgctt catcggtcgt gaagactgca ctgaagaatt ggtcaaatgg ggtaagcgcg   2160
ttgctgccgc caacagccgt aagcctgtta acaagctcct ctagtttttg ggatcaatt   2220
cgagctcggt acccaaacta gtaacgctcg gttgccgccg ggcgtttttt attccgacat   2280
caggaattgt aattagaaag tccaaaaatt gtaatttaaa aaacagtcaa tggagagcat   2340
tgccataagt aaaggcatcc cctgcgtgat aagattacct tcagaaaaca gatagttgct   2400
gggttatcgc agatttttct cgcaaccaaa taactgtaaa taataactgt ctctggggcg   2460
acggtaggct ttatattgcc aaatttcgcc cgtgggagaa agctaggcta ttcaatgttt   2520
atggaggact gacccatatg atcaaggctt atgccgcttt agaggctaat ggcaagttgc   2580
agccgttcga gtatgatccg ggcgctttag gcgccaacga agttgaaatc gaagttcaat   2640
actgcggtgt ttgtcattcc gacctcagta tgatcaacaa tgagtggggt atcagtaact   2700
atccgttggt tcccggccac gaagttgttg gcaccgttgc tgctatgggt gagggtgtta   2760
atcacgtgga agttggtgac ctggttggtt taggctggca cagtggttat tgtatgactt   2820
gtcactcctg cctgagcggt tatcataatt tgtgcgctac cgccgagagt actatcgttg   2880
gtcattatgg cggtttcggt gaccgtgtgc gtgctaaagg tgtgtccgtt gttaagctgc   2940
ccaagggtat cgatttggct tccgctggtc cgttgttttg cggtggtatc actgtgtttt   3000
cccccatggt tgagttatcc ctgaaaccga ccgccaaggt tgccgttatt ggtatcggtg   3060
gtctcggtca cctggccgtt cagttcttgc gtgcttgggg ttgcgaggtt accgctttca   3120
ctagctccgc tcgtaaacag accgaggttc tggagctggg tgcccatcat attttggaca   3180
gtactaaccc cgaagccatt gcttccgccg agggtaagtt cgattacatc attagtaccg   3240
ttaatttaaa attggattgg aatctgtata tttccacttt agccccgcaa ggtcactttc   3300
atttcgtggg tgttgttctc gaacccctcg acttgaactt gttcccgttg ctcatgggtc   3360
agcggagtgt gtccgctagt ccggttggct ccccggctac tatcgctact atgctcgatt   3420
tcgccgttcg gcacgatatc aagccggttg ttgagcagtt ctccttcgac caaattaatg   3480
aagccattgc tcacttggag tccggtaagg ctcactaccg tgtggttttg agtcactcca   3540
agaactgaaa cgctcggttg ccgccgggcg ttttttattc ctgcaggccc cccgggggat   3600
ccactagagg atctcaatga atattggttg acacgggcgt ataagacatg ttatactgtt   3660
gaataacaag gacggatctg atcaagagac aggatgagga tcgtttcgca tgattgaaca   3720
agatggattg cacgcaggtt ctccggccgc ttgggtggag aggctattcg gctatgactg   3780
ggcacaacag acaatcggct gctctgatgc cgccgtgttc cggctgtcag cgcaggggcg   3840
cccggttctt tttgtcaaga ccgacctgtc cggtgccctg aatgaactgc aggacgaggc   3900
agcgcggcta tcgtggctgg ccacgacggg cgttccttgc gcagctgtgc tcgacgttgt   3960
cactgaagcg ggaagggact ggctgctatt gggcgaagtg ccggggcagg atctcctgtc   4020
```

-continued atctcacctt gctcctgccg agaaagtatc catcatggct gatgcaatgc ggcggctgca 4080
tacgcttgat ccggctacct gcccattcga ccaccaagcg aaacatcgca tcgagcgagc 4140
acgtactcgg atggaagccg gtcttgtcga tcaggatgat ctggacgaag agcatcaggg 4200
gctcgcgcca gccgaactgt tcgccaggct caaggcgcgc atgcccgacg gcgaggatct 4260
cgtcgtgacc catggcgatg cctgcttgcc gaatatcatg gtggaaaatg gccgcttttc 4320
tggattcatc gactgtggcc ggctgggtgt ggcggaccgc tatcaggaca tagcgttggc 4380
tacccgtgat attgctgaag agcttggcgg cgaatgggct gaccgcttcc tcgtgcttta 4440
cggtatcgcc gctcccgatt cgcagcgcat cgccttctat cgccttcttg acgagttctt 4500
ctgagcggga ctctggggtt cgaaatgacc gaccaagcga cgcccaacct gccatcacga 4560
gatttcgatt ccaccgccgc cttctatgaa aggttgggct tcggaatcgt tttccgggac 4620
gccggctgga tgatcctcca gcgcggggat ctcatgctgg agttcttcgc ccaccgggga 4680
tcctctagtt ctagagcggc cgcatcatca atccccgtga tgtttcagtc ccgtagtcgg 4740
gatttagtgg ttggaaagcg gaacgtcgcg ccgaaaccat cgccaggacg ggtttcagtc 4800
ccgtagtcgg gatttagtgg ttggaaagtg attatgttca agaaatcaca acgcaaaaga 4860
aaaagtttca gtcccgtagt cgggatttag tggttggaaa gtcaagcgag atacccacca 4920
gaaagccttt gacctggttt cagtcccgag tcgggattta gtggttggaa aggcggcggc 4980
tgatgtcgcc aatgcggtta tcgatggcca gtttcagtcc cgtagtcggg atttagtggt 5040
tggaaagtcc caagggggac agggcggtga tcctcgatgt tgcgtgtttc agtcccgtag 5100
tcgggattta gtggttggaa agactcgtct atatatacag agattactac agagatgttt 5160
cagtcccgta gtcgggattt agtggttgga aagcgggaaa gtagcctgtt ttgtggagaa 5220
ttgcaggcgt ttcagtacta gtgatggcgg ccgggagcat gcgacgtcgg gcccaattcg 5280
ccctatagtg agtcgtatta caattcactg gccgtcgttt tacaacgtcg tgactgggaa 5340
aaccctggcg ttacccaact taatcgcctt gcagcacatc ccccttcgc cagctggcgt 5400
aatagcgaag aggcccgcac cgatcgccct tcccaacagt tgcgcagcct gaatggcgaa 5460
tggacgcgcc ctgtagcggc gcattaagcg cggcgggtgt ggtggttacg cgcagcgtga 5520
ccgctacact tgccagcgcc ctagcgcccg ctcctttcgc tttcttccct tcctttctcg 5580
ccacgttcgc cggctttccc cgtcaagctc taaatcgggg gctcccttta gggttccgat 5640
ttagagcttt acggcacctc gaccgcaaaa aacttgattt gggtgatggt tcacgtagtg 5700
ggccatcgcc ctgatagacg gtttttcgcc ctttgacgtt ggagtccacg ttctttaata 5760
gtggactctt gttccaaact ggaacaacac tcaaccctat ctcggtctat tcttttgatt 5820
tataagggat tttgccgatt tcggcctatt ggttaaaaaa tgagctgatt taacaaatat 5880
ttaacgcgaa ttttaacaaa atattaacgt ttacaatttc gcctgatgcg gtattttctc 5940
cttacgcatc tgtgcggtat ttcacaccgc atacaggtgg cacttttcgg ggaaatgtgc 6000
gcggaacccc tatttgttta tttttctaaa tacattcaaa tatgtatccg ctcatgagac 6060
aataaccctg ataaatgctt caataatatt gaaaaaggaa gagtatgagt attcaacatt 6120
tccgtgtcgc ccttattccc ttttttgcgg cattttgcct tcctgttttt gctcacccag 6180
aaacgctggt gaaagtaaaa gatgctgaag atcagttggg tgcacgagtg ggttacatcg 6240
aactggatct caacagcggt aagatccttg agagttttcg ccccgaagaa cgttttccaa 6300
tgatgagcac ttttaaagtt ctgctatgtg gcgcggtatt atcccgtatt gacgccgggc 6360

-continued

```
aagagcaact cggtcgccgc atacactatt ctcagaatga cttggttgag tactcaccag   6420
tcacagaaaa gcatcttacg gatggcatga cagtaagaga attatgcagt gctgccataa   6480
ccatgagtga taacactgcg gccaacttac ttctgacaac gatcggagga ccgaaggagc   6540
taaccgcttt tttgcacaac atgggggatc atgtaactcg ccttgatcgt tgggaaccgg   6600
agctgaatga agccatacca aacgacgagc gtgacaccac gatgcctgta gcaatgccaa   6660
caacgttgcg caaactatta actggcgaac tacttactct agcttcccgg caacaattaa   6720
tagactggat ggaggcggat aaagttgcag gaccacttct gcgctcggcc cttccggctg   6780
gctggtttat tgctgataaa tctggagccg gtgagcgtgg gtctcgcggt atcattgcag   6840
cactggggcc agatggtaag ccctcccgta tcgtagttat ctacacgacg gggagtcagg   6900
caactatgga tgaacgaaat agacagatcg ctgagatagg tgcctcactg attaagcatt   6960
ggtaactgtc agaccaagtt tactcatata tactttagat tgatttaaaa cttcattttt   7020
aatttaaaag gatctaggtg aagatccttt ttgataatct catgaccaaa atcccttaac   7080
gtgagttttc gttccactga gcgtcagacc ccgtagaaaa gatcaaagga tcttcttgag   7140
atcctttttt tctgcgcgta atctgctgct tgcaaacaaa aaaaccaccg ctaccagcgg   7200
tggtttgttt gccggatcaa gagctaccaa ctctttttcc gaaggtaact ggcttcagca   7260
gagcgcagat accaaatact gtccttctag tgtagccgta gttaggccac cacttcaaga   7320
actctgtagc accgcctaca tacctcgctc tgctaatcct gttaccagtg gctgctgcca   7380
gtggcgataa gtcgtgtctt accgggttgg actcaagacg atagttaccg gataaggcgc   7440
agcggtcggg ctgaacgggg ggttcgtgca cacagcccag cttggagcga acgacctaca   7500
ccgaactgag atacctacag cgtgagctat gagaaagcgc cacgcttccc gaagggagaa   7560
aggcggacag gtatccggta agcggcaggg tcggaacagg agagcgcacg agggagcttc   7620
caggggggaaa cgcctggtat ctttatagtc ctgtcgggtt tcgccacctc tgacttgagc   7680
gtcgattttt gtgatgctcg tcaggggggc ggagcctatg gaaaaacgcc agcaacgcgg   7740
cctttttacg gttcctggcc ttttgctggc cttttgctca catgttcttt cctgcgttat   7800
cccctgattc tgtggataac cgtattaccg cctttgagtg agctgatacc gctcgccgca   7860
gccgaacgac cgagcgcagc gagtcagtga gcgaggaagc ggaagagcgc ccaatacgca   7920
aaccgcctct ccccgcgcgt tggccgattc attaatgcag ctggcacgac aggtttcccg   7980
actggaaagc gggcagtgag cgcaacgcaa ttaatgtgag ttagctcact cattaggcac   8040
cccaggcttt acactttatg cttccggctc gtatgttgtg tggaattgtg agcggataac   8100
aatttcacac aggaaacagc tatgaccatg attacgccaa gctatttagg tgacactata   8160
gaatactcaa gctatgcatg agggtgcaat ttgagtggtt tcagtcccgt aatcgggatt   8220
tagtggttgg aaagaacgac aaggcttaca agggggtaat tcgtgatttg tttcagtccc   8280
gtaatcggga tttagtggtt ggaaagtagg caggggagtg aaatggtttc atgttgggct   8340
catgtttcag tcccgtaatc gggatttagt ggttggaaag cagtaagatg aaggaggtgg   8400
tgcatatcac ttgcgtttca gtcccgtaat cgggatttag tggttggaaa gctagatttg   8460
cttatagagt tgactgttat cgggacttgt ttcagtcccg taatcgggat ttagtggttg   8520
gaaagatgat ggcgttgcca gcgttctcgg attggagaat ttaacgtttc agtcccgtaa   8580
tcgggattta gtggttggaa agccctgaga agtttggctg ttttgctgac tgcgatctgg   8640
tttcagtccc gtaatcggga tttagtggtt ggaaagcatc gaggcagtag agcaaatcgc   8700
aggccacctc atagtttcag tcccgtaatc gggatttagt ggttggaaag tcattggggt   8760
```

ctgcattggg gccatcgcta tcgtcctgtt tcagtcccgt aatcgggatt tagtggttgg 8820
aaagtgggac gctccgtaag gtttggagaa tagggtctag tgtttcagtc ccgtaatcgg 8880
gatttagtgg ttggaaagca cttcgtcgct gattg 8915

<210> SEQ ID NO 70
<211> LENGTH: 5237
<212> TYPE: DNA
<213> ORGANISM: Artificial
<220> FEATURE:
<223> OTHER INFORMATION: insert from plasmid #1353
pVZ325a-nrsRS-PnrsB-PDCdsrA/oop-PrbcL*-synADH(deg)

<400> SEQUENCE: 70
gtcgacccta tatcgggctt ttctcaataa aatctttatt ttttgaggtg ctttttagcc 60
ataaataatc actttagtat aaaattttga cggcgtaaag ttgataaaat agaattaaga 120
atggactatc ggtacagaaa aaatgggtaa ctggatggtg aataaacttc ccttacccaa 180
tgcactctcc accgttaaag accccctatg cttaacggtg atcacctggg caatggcgag 240
tcccaaccct gtcccccccg ttttgcgcga acgatctcga ttaactcggt aaaaacgctc 300
aaaaatgtgt tcctgttggt cgggggcaat gccgatgccg gtatcttgca cggtgatgat 360
agccatctgt tcatgggatg tcagggtaat atcaacacgt cccccagcag ttgtgtattg 420
aatggcgttg gcaattaggt ttgagaccag tcgatagagt tgggattcat taccccaggc 480
gtaaacttcc cctgaactca gatcactgct gagatcaatg tgggcggcga tcgctaattc 540
taaaaactct tcggtgaggt cactgactaa atcatttaaa caacaaagcc gccaatcttc 600
ggcggtggtt tcctgctcta agcgacttag tagcaataaa tccgtaatca attggcttaa 660
tcgccttccc tgtcgttcaa cggtatgtag catggtgtta atttctgggg aatggcttga 720
gtcgatgcgt aataccgctt ccaccgtggc caacagacta gccaatggcg atcgtaattc 780
atgggctgca ttcgcggtga attgttgttg ttgttggtag gactggtaaa tgggacgcat 840
ggctaacccc gctaagcccc aactggagaa ggcgaccaaa cccagggcaa tgggaaaact 900
aagccctaaa atccaaagaa tacgtttatt ttcggcatca aaggctgcca ggctccggcc 960
aatttgtaga tagccccagg aagatttgtc tgtattaccg gcgctatgca aaatggtggt 1020
gaattgtcga taccgatcgc cggttggggg gtgaatagtc tgccaagttt cctggttaaa 1080
aatggaggat agggaagccg gttgattagg cgaaaaagcc agcaggttgc cttgataatc 1140
aaataaacga atgtaatata aactgcgatc actaatgccc aacgtgtgac gttcaatcag 1200
ggtggggttg acctggcagg gttggttgac caaacacaga tcgggcaaca ttttttgtaa 1260
tactccggtg ggactagcat tactcggcaa catcggctct aaactgtcat gcaacgtccc 1320
ggcgatcgac tccacttctc gctccaacgc catccagttg gcctgcacaa tggcacgata 1380
aacccccaac cccaacaggg taagaatacc ccccattact agggcatacc agaaagccaa 1440
ttgcagacga ctacgggcaa agaggcgacg ggtattcatg gcgatagggt gaaccgatag 1500
ccttgaccgg gaactgtttt aattgggcaa ggacaatttt gttgagctag cttgcgtcgt 1560
atcaaacgca tttgggccgc caccacatta ctcatgggct cctcatcaag atcccacagt 1620
tgttgccgga tcttgctacc ggaaatgatc cgctctgggt tttgcatcag atattgaaaa 1680
atttgaaatt ctcttacggt taaagcaatt tcctgtcttt ctaggtttag tggctccgag 1740
atagttaccg ataacagatt attactggga tcaaggctga agttgcccaa agttaaaatt 1800
tgcggttgga attgtggcga tcgccgttgt agtgcccgca gtcttgctaa tagctctgcc 1860

-continued

```
atcacaaacg gttttgttag atagtcatct gccccggcat ctagtccttc gacacggttt   1920
tccggttctc ctaacgctgt taacatcaac accggcaagg aattaccctg ggttctcagt   1980
ttttgacaga gttccaaacc cgataatccc ggcagtaacc aatccacaat ggcaagggtg   2040
tattccgtcc attgattttc caaataatcc caagcttggg agccatccgt cacccaatcc   2100
accacatact tttcactaac tagcactttc ttaatagcca ttcccaaatc cgtctcatct   2160
tccaccagca aaattcgcat cgcctctgcc ttttttataa cggtctgatc ttagcggggg   2220
aaggagattt tcacctgaat ttcatacccc ctttggcaga ctgggaaaat cttggacaaa   2280
ttcccaattt gaggtggtgt gatgaattct tatactgtcg gtacctattt agcggagcgg   2340
cttgtccaga ttggtctcaa gcatcacttc gcagtcgcgg gcgactacaa cctcgtcctt   2400
cttgacaacc tgcttttgaa caaaaacatg gagcaggttt attgctgtaa cgaactgaac   2460
tgcggtttca gtgcagaagg ttatgctcgt gccaaaggcg cagcagcagc cgtcgttacc   2520
tacagcgtcg gtgcgctttc cgcatttgat gctatcggtg gcgcctatgc agaaaacctt   2580
ccggttatcc tgatctccgg tgctccgaac aacaatgatc acgctgctgg tcacgtgttg   2640
catcacgctc ttggcaaaac cgactatcac tatcagttgg aaatggccaa gaacatcacg   2700
gccgcagctg aagcgattta caccccagaa gaagctccgg ctaaaatcga tcacgtgatt   2760
aaaactgctc ttcgtgagaa gaagccggtt tatctcgaaa tcgcttgcaa cattgcttcc   2820
atgccctgcg ccgctcctgg accggcaagc gcattgttca atgacgaagc cagcgacgaa   2880
gcttctttga atgcagcggt tgaagaaacc ctgaaattca tcgccaaccg cgacaaagtt   2940
gccgtcctcg tcggcagcaa gctgcgcgca gctggtgctg aagaagctgc tgtcaaattt   3000
gctgatgctc tcggtggcgc agttgctacc atggctgctg caaaaagctt cttcccagaa   3060
gaaaacccgc attacatcgg tacctcatgg ggtgaagtca gctatccggg cgttgaaaag   3120
acgatgaaag aagccgatgc ggttatcgct ctggctcctg tcttcaacga ctactccacc   3180
actggttgga cggatattcc tgatcctaag aaactggttc tcgctgaacc gcgttctgtc   3240
gtcgttaacg gcgttcgctt ccccagcgtt catctgaaag actatctgac ccgtttggct   3300
cagaaagttt ccaagaaaac cggtgctttg gacttcttca aatccctcaa tgcaggtgaa   3360
ctgaagaaag ccgctccggc tgatccgagt gctccgttgg tcaacgcaga aatcgcccgt   3420
caggtcgaag ctcttctgac cccgaacacg acggttattg ctgaaaccgg tgactcttgg   3480
ttcaatgctc agcgcatgaa gctcccgaac ggtgctcgcg ttgaatatga aatgcagtgg   3540
ggtcacatcg gttggtccgt tcctgccgcc ttcggttatg ccgtcggtgc tccggaacgt   3600
cgcaacatcc tcatggttgg tgatggttcc ttccagctga cggctcagga agtcgctcag   3660
atggttcgcc tgaaactgcc ggttatcatc ttcttgatca ataactatgg ttacaccatc   3720
gaagttatga tccatgatgg tccgtacaac aacatcaaga actgggatta tgccggtctg   3780
atggaagtgt tcaacggtaa cggtggttat gacagcggtg ctggtaaagg cctgaaggct   3840
aaaaccggtg gcgaactggc agaagctatc aaggttgctc tggcaaacac cgacggccca   3900
accctgatcg aatgcttcat cggtcgtgaa gactgcactg aagaattggt caaatggggt   3960
aagcgcgttg ctgccgccaa cagccgtaag cctgttaaca agctcctcta gtttttgggg   4020
atcaattcga gctcagcaag tttcatcccg accccctcag ggtcgggatt tttttattgt   4080
actagtaacg cccggttgcc accgggcgtt ttttattccg acattgccat aagtaaaggc   4140
atcccctgcg tgataagatt accttcagtt tatggaggac tgaccatatg atcaaggctt   4200
```

-continued

```
atgccgcttt agaggctaat ggcaagttgc agccgttcga gtatgatccg ggcgctttag   4260

gcgccaacga agttgaaatc gaagttcaat actgcggtgt ttgtcattcc gacctcagta   4320

tgatcaacaa tgagtggggt atcagtaact atccgttggt tcccggccac gaagttgttg   4380

gcaccgttgc tgctatgggt gagggtgtta atcacgtgga agttggtgac ctggttggtt   4440

taggctggca cagtggttat tgtatgactt gtcactcctg cctgagcggt tatcataatt   4500

tgtgcgctac cgccgagagt actatcgttg gtcattatgg cggtttcggt gaccgtgtgc   4560

gtgctaaagg tgtgtccgtt gttaagctgc ccaagggtat cgatttggct tccgctggtc   4620

cgttgttttg cggtggtatc actgtgtttt cccccatggt tgagttatcc ctgaaaccga   4680

ccgccaaggt tgccgttatt ggtatcggtg gtctcggtca cctggccgtt cagttcttgc   4740

gtgcttgggg ttgcgaggtt accgctttca ctagctccgc tcgtaaacag accgaggttc   4800

tggagctggg tgcccatcat attttggaca gtactaaccc cgaagccatt gcttccgccg   4860

agggtaagtt cgattacatc attagtaccg ttaatttaaa attggattgg aatctgtata   4920

tttccacttt agccccgcaa ggtcactttc atttcgtggg tgttgttctc gaaccccctcg   4980

acttgaactt gttcccgttg ctcatgggtc agcggagtgt gtccgctagt ccggttggct   5040

ccccggctac tatcgctact atgctcgatt tcgccgttcg gcacgatatc aagccggttg   5100

ttgagcagtt ctccttcgac caaattaatg aagccattgc tcacttggag tccggtaagg   5160

ctcactaccg tgtggttttg agtcactcca agaactgaaa cgctcggttg ccgccgggcg   5220

tttttattc ctgcagg                                                  5237
```

<210> SEQ ID NO 71
<211> LENGTH: 76
<212> TYPE: DNA
<213> ORGANISM: Artificial
<220> FEATURE:
<223> OTHER INFORMATION: ziaR-PziaA*2ext promoter present in construct #1318

<400> SEQUENCE: 71

```
tttcaagatt tgtgctacgg ttcaaggagg tttttcttta aatcaaggag ttaacattat     60

gtctcatatg attaaa                                                     76
```

<210> SEQ ID NO 72
<211> LENGTH: 21
<212> TYPE: DNA
<213> ORGANISM: Artificial
<220> FEATURE:
<223> OTHER INFORMATION: ziaR-PziaA-SalI-fw

<400> SEQUENCE: 72

```
atcgtcgacc tccttaatcc g                                               21
```

<210> SEQ ID NO 73
<211> LENGTH: 42
<212> TYPE: DNA
<213> ORGANISM: Artificial
<220> FEATURE:
<223> OTHER INFORMATION: PziaA*2ext-NdeI-rev

<400> SEQUENCE: 73

```
catatgagac ataatgttaa ctccttgatt taaagaaaaa cc                        42
```

<210> SEQ ID NO 74
<211> LENGTH: 3397
<212> TYPE: DNA

<213> ORGANISM: Artificial
<220> FEATURE:
<223> OTHER INFORMATION: insert from plasmid #1318 pVZ325-ziaR-
PziaA*2ext-synADH-zmPDCdsrA

<400> SEQUENCE: 74

```
gtcgacctcc ttaatccgat tcctgcaaat ggtctgcaac ttcccgatac aaattcatca     60
catgattatc cgccaagctg tagtaaacat tacggccgac ccggcgatac tttaccaggc    120
gctgcgatcg taaaattcgt aattgatggg aaactgccga ttcactcact ttcatcgccg    180
ctgctaaatc acagacacag agttcttggc gggccaatgc cgacattaaa cgcaaccgac    240
tcggatcagc tagtgcactg aaaaactccg ccatttgctg ggcctggtcc aatgacatca    300
cctctggttg aacctgtcgt acctgctcaa gatgaacaag aggttgatca caaaggggca    360
tctcttcgtt ctggcaggat tgtgactttg acaacgagga cttactcata gaggttggcg    420
ttaggagcta gggaaaaatt taaactggat ttagaaaatg attttcatcg tcgacctaac    480
atctttaata tctgagcata tcttcaggtg tttcaagatt tgtgctacgg ttcaaggagg    540
tttttcttta aatcaaggag ttaacattat gtctcatatg attaaagcct acgctgccct    600
ggaagccaac ggaaaactcc aaccctttga atacgacccc ggtgccctgg gtgctaatga    660
ggtggagatt gaggtgcagt attgtggggt gtgccacagt gatttgtcca tgattaataa    720
cgaatggggc atttccaatt acccccctagt gccgggtcat gaggtggtgg gtactgtggc    780
cgccatgggc gaaggggtga accatgttga ggtgggggat ttagtggggc tgggttggca    840
ttcgggctac tgcatgacct gccatagttg tttatctggc taccacaacc tttgtgccac    900
ggcggaatcg accattgtgg gccactacgg tggctttggc gatcgggttc gggccaaggg    960
agtcagcgtg gtgaaattac ctaaaggcat tgacctagcc agtgccgggc cccttttctg   1020
tggaggaatt accgttttca gtcctatggt ggaactgagt ttaaagccca ctgcaaaagt   1080
ggcagtgatc ggcattgggg gcttgggcca tttagcggtg caatttctcc gggcctgggg   1140
ctgtgaagtg actgccttta cctccagtgc caggaagcaa acggaagtgt tggaattggg   1200
cgctcaccac atactagatt ccaccaatcc agaggcgatc gccagtgcgg aaggcaaatt   1260
tgactatatt atctccactg tgaacctgaa gcttgactgg aacttataca tcagcaccct   1320
ggcgccccag ggacatttcc actttgttgg ggtggtgttg gagcctttgg atctaaatct   1380
ttttcccctt ttgatgggac aacgctccgt ttctgcctcc ccagtgggta gtcccgccac   1440
cattgccacc atgttggact ttgctgtgcg ccatgacatt aaacccgtgg tggaacaatt   1500
tagctttgat cagatcaacg aggcgatcgc ccatctagaa agcggcaaag cccattatcg   1560
ggtagtgctc agccatagta aaaattagct ctgcaaaggt tgcttctggc tagtaccttg   1620
gaggtttaaa ccatgaattc ttatactgtc ggtacctatt tagcggagcg gcttgtccag   1680
attggtctca agcatcactt cgcagtcgcg ggcgactaca acctcgtcct tcttgacaac   1740
ctgcttttga acaaaaacat ggagcaggtt tattgctgta acgaactgaa ctgcggtttc   1800
agtgcagaag gttatgctcg tgccaaaggc gcagcagcag ccgtcgttac ctacagcgtc   1860
ggtgcgcttt ccgcatttga tgctatcggt ggcgcctatg cagaaaacct tccggttatc   1920
ctgatctccg gtgctccgaa caacaatgat cacgctgctg gtcacgtgtt gcatcacgct   1980
cttggcaaaa ccgactatca ctatcagttg gaaatggcca agaacatcac ggccgcagct   2040
gaagcgattt acaccccaga agaagctccg gctaaaatcg atcacgtgat taaaactgct   2100
cttcgtgaga agaagccggt ttatctcgaa atcgcttgca acattgcttc catgccctgc   2160
```

-continued gccgctcctg gaccggcaag cgcattgttc aatgacgaag ccagcgacga agcttctttg 2220
aatgcagcgg ttgaagaaac cctgaaattc atcgccaacc gcgacaaagt tgccgtcctc 2280
gtcggcagca agctgcgcgc agctggtgct gaagaagctg ctgtcaaatt tgctgatgct 2340
ctcggtggcg cagttgctac catggctgct gcaaaaagct tcttcccaga agaaaacccg 2400
cattacatcg gtacctcatg gggtgaagtc agctatccgg gcgttgaaaa gacgatgaaa 2460
gaagccgatg cggttatcgc tctggctcct gtcttcaacg actactccac cactggttgg 2520
acggatattc ctgatcctaa gaaactggtt ctcgctgaac cgcgttctgt cgtcgttaac 2580
ggcgttcgct tccccagcgt tcatctgaaa gactatctga cccgtttggc tcagaaagtt 2640
tccaagaaaa ccggtgcttt ggacttcttc aaatccctca atgcaggtga actgaagaaa 2700
gccgctccgg ctgatccgag tgctccgttg gtcaacgcag aaatcgcccg tcaggtcgaa 2760
gctcttctga ccccgaacac gacggttatt gctgaaaccg gtgactcttg gttcaatgct 2820
cagcgcatga agctcccgaa cggtgctcgc gttgaatatg aaatgcagtg gggtcacatc 2880
ggttggtccg ttcctgccgc cttcggttat gccgtcggtg ctccggaacg tcgcaacatc 2940
ctcatggttg gtgatggttc cttccagctg acggctcagg aagtcgctca gatggttcgc 3000
ctgaaactgc cggttatcat cttcttgatc aataactatg gttacaccat cgaagttatg 3060
atccatgatg gtccgtacaa caacatcaag aactgggatt atgccggtct gatggaagtg 3120
ttcaacggta acggtggtta tgacagcggt gctggtaaag gcctgaaggc taaaaccggt 3180
ggcgaactgg cagaagctat caaggttgct ctggcaaaca ccgacggccc aaccctgatc 3240
gaatgcttca tcggtcgtga agactgcact gaagaattgg tcaaatgggg taagcgcgtt 3300
gctgccgcca acagccgtaa gcctgttaac aagctcctct agtttcaagt ttcatcccga 3360 ccccccctcag ggtcgggatt tttttagatc ctgcagg 3397

<210> SEQ ID NO 75
<211> LENGTH: 11682
<212> TYPE: DNA
<213> ORGANISM: Artificial
<220> FEATURE:
<223> OTHER INFORMATION: #1121¶VZ322a-smtB-PsmtA-PDCoop-PrbcL-
synADH+eg.

<400> SEQUENCE: 75
tcgacgggca aactttatga agcagatcaa gcctatatcc gccaagcaac cggcagccgc 60
gttgattagt gggtgtgtcc atcctctggt tcgtctaggt gctccgaagc gtcacgatag 120
agattaagaa tgtggtgatc cttgaggcga taaatcacat tccgcccttc cttgcgatag 180
ctcactaaac gtgctgtgcg cagggttctt agttggtgag agacagccga ttcactcatt 240
tcaacggcgg cggcgagttc ccccacccgc atctctccag tggccagggc cgaaagaata 300
cgccagcggt tggcatcccc caagacacca aaaaattcgg ccatccgttg ggccttggct 360
tggttcaaga ttttgccact gtggtctgtc attgttcgct gatctaaaca atacctgaat 420
aattgttcat gtgttaatct aaaaatgtga acaatcgttc aactatttaa gacaatacct 480
tggaggttta aaccatgaat tcttatactg tcggtaccta tttagcggag cggcttgtcc 540
agattggtct caagcatcac ttcgcagtcg cgggcgacta caacctcgtc cttcttgaca 600
acctgctttt gaacaaaaac atggagcagg tttattgctg taacgaactg aactgcggtt 660
tcagtgcaga aggttatgct cgtgccaaag gcgcagcagc agccgtcgtt acctacagcg 720
tcggtgcgct ttccgcattt gatgctatcg gtggcgccta tgcagaaaac cttccggtta 780

-continued

```
tcctgatctc cggtgctccg aacaacaatg atcacgctgc tggtcacgtg ttgcatcacg    840
ctcttggcaa aaccgactat cactatcagt tggaaatggc caagaacatc acggccgcag    900
ctgaagcgat ttacacccca gaagaagctc cggctaaaat cgatcacgtg attaaaactg    960
ctcttcgtga gaagaagccg gtttatctcg aaatcgcttg caacattgct tccatgccct   1020
gcgccgctcc tggaccggca agcgcattgt tcaatgacga agccagcgac gaagcttctt   1080
tgaatgcagc ggttgaagaa accctgaaat tcatcgccaa ccgcgacaaa gttgccgtcc   1140
tcgtcggcag caagctgcgc gcagctggtg ctgaagaagc tgctgtcaaa tttgctgatg   1200
ctctcggtgg cgcagttgct accatggctg ctgcaaaaag cttcttccca gaagaaaacc   1260
cgcattacat cggtacctca tggggtgaag tcagctatcc gggcgttgaa aagacgatga   1320
aagaagccga tgcggttatc gctctggctc ctgtcttcaa cgactactcc accactggtt   1380
ggacggatat tcctgatcct aagaaactgg ttctcgctga accgcgttct gtcgtcgtta   1440
acggcgttcg cttccccagc gttcatctga aagactatct gacccgtttg gctcagaaag   1500
tttccaagaa aaccggtgct ttggacttct tcaaatccct caatgcaggt gaactgaaga   1560
aagccgctcc ggctgatccg agtgctccgt tggtcaacgc agaaatcgcc cgtcaggtcg   1620
aagctcttct gaccccgaac acgacggtta ttgctgaaac cggtgactct tggttcaatg   1680
ctcagcgcat gaagctcccg aacggtgctc gcgttgaata tgaaatgcag tggggtcaca   1740
tcggttggtc cgttcctgcc gccttcggtt atgccgtcgg tgctccggaa cgtcgcaaca   1800
tcctcatggt tggtgatggt tccttccagc tgacggctca ggaagtcgct cagatggttc   1860
gcctgaaact gccggttatc atcttcttga tcaataacta tggttacacc atcgaagtta   1920
tgatccatga tggtccgtac aacaacatca agaactggga ttatgccggt ctgatggaag   1980
tgttcaacgg taacggtggt tatgacagcg gtgctggtaa aggcctgaag gctaaaaccg   2040
gtggcgaact ggcagaagct atcaaggttg ctctggcaaa caccgacggc ccaaccctga   2100
tcgaatgctt catcggtcgt gaagactgca ctgaagaatt ggtcaaatgg ggtaagcgcg   2160
ttgctgccgc caacagccgt aagcctgtta acaagctcct ctagtttttg gggatcaatt   2220
cgagctcggt acccaaacta gtaacgctcg gttgccgccg ggcgtttttt attccgacat   2280
caggaattgt aattagaaag tccaaaaatt gtaatttaaa aaacagtcaa tggagagcat   2340
tgccataagt aaaggcatcc cctgcgtgat aagattacct tcagaaaaca gatagttgct   2400
gggttatcgc agatttttct cgcaaccaaa taactgtaaa taataactgt ctctggggcg   2460
acggtaggct ttatattgcc aaatttcgcc cgtgggagaa agctaggcta ttcaatgttt   2520
atggaggact gacccatatg atcaaggctt atgccgcttt agaggctaat ggcaagttgc   2580
agccgttcga gtatgatccg ggcgctttag gcgccaacga agttgaaatc gaagttcaat   2640
actgcggtgt ttgtcattcc gacctcagta tgatcaacaa tgagtggggt atcagtaact   2700
atccgttggt tcccggccac gaagttgttg gcaccgttgc tgctatgggt gagggtgtta   2760
atcacgtgga agttggtgac ctggttggtt taggctggca cagtggttat tgtatgactt   2820
gtcactcctg cctgagcggt tatcataatt tgtgcgctac cgccgagagt actatcgttg   2880
gtcattatgg cggtttcggt gaccgtgtgc gtgctaaagg tgtgtccgtt gttaagctgc   2940
ccaagggtat cgatttggct tccgctggtc cgttgttttg cggtggtatc actgtgtttt   3000
cccccatggt tgagttatcc ctgaaaccga ccgccaaggt tgccgttatt ggtatcggtg   3060
gtctcggtca cctggccgtt cagttcttgc gtgcttgggg ttgcgaggtt accgctttca   3120
ctagctccgc tcgtaaacag accgaggttc tggagctggg tgcccatcat attttggaca   3180
```

-continued

```
gtactaaccc cgaagccatt gcttccgccg agggtaagtt cgattacatc attagtaccg   3240
ttaatttaaa attggattgg aatctgtata tttccacttt agccccgcaa ggtcactttc   3300
atttcgtggg tgttgttctc gaacccctcg acttgaactt gttcccgttg ctcatgggtc   3360
agcggagtgt gtccgctagt ccggttggct ccccggctac tatcgctact atgctcgatt   3420
tcgccgttcg gcacgatatc aagccggttg ttgagcagtt ctccttcgac caaattaatg   3480
aagccattgc tcacttggag tccggtaagg ctcactaccg tgtggttttg agtcactcca   3540
agaactgaaa cgctcggttg ccgccgggcg ttttttattc ctgcaggagc agaagagcat   3600
acatctggaa gcaaagccag gaaagcggcc tatggagctg tgcggcagcg ctcagtaggc   3660
aatttttcaa aatattgtta agccttttct gagcatggta tttttcatgg tattaccaat   3720
tagcaggaaa ataagccatt gaatataaaa gataaaaatg tcttgtttac aatagagtgg   3780
ggggggtcag cctgccgcct tgggccgggt gatgtcgtac ttgcccgccg cgaactcggt   3840
taccgtccag cccagcgcga ccagctccgg caacgcctcg cgcacccgct ggcggcgctt   3900
gcgcatggtc gaaccactgg cctctgacgg ccagacatag ccgcacaagg tatctatgga   3960
agccttgccg gttttgccgg ggtcgatcca gccacacagc cgctggtgca gcaggcgggc   4020
ggtttcgctg tccagcgccc gcacctcgtc catgctgatg cgcacatgct ggccgccacc   4080
catgacggcc tgcgcgatca aggggttcag ggccacgtac aggcgcccgt ccgcctcgtc   4140
gctggcgtac tccgacagca gccgaaaccc ctgccgcttg cggccattct gggcgatgat   4200
ggataccttc caaaggcgct cgatgcagtc ctgtatgtgc ttgagcgccc caccactatc   4260
gacctctgcc ccgatttcct ttgccagcgc ccgatagcta cctttgacca catggcattc   4320
agcggtgacg gcctcccact tgggttccag gaacagccgg agctgccgtc cgccttcggt   4380
cttgggttcc gggccaagca ctaggccatt aggcccagcc atggccacca gcccttgcag   4440
gatgcgcaga tcatcagcgc ccagcggctc cgggccgctg aactcgatcc gcttgccgtc   4500
gccgtagtca tacgtcacgt ccagcttgct gcgcttgcgc tcgccccgct tgagggcacg   4560
gaacaggccg gggccagac agtgcgccgg gtcgtgccgg acgtggctga ggctgtgctt   4620
gttcttaggc ttcaccacgg ggcacccct tgctcttgcg ctgcctctcc agcacggcgg   4680
gcttgagcac cccgccgtca tgccgcctga accaccgatc agcgaacggt gcgccatagt   4740
tggccttgct cacaccgaag cggacgaaga accggcgctg gtcgtcgtcc acaccccatt   4800
cctcggcctc ggcgctggtc atgctcgaca ggtaggactg ccagcggatg ttatcgacca   4860
gtaccgagct gccccggctg gcctgctgct ggtcgcctgc gcccatcatg gccgcgccct   4920
tgctggcatg gtgcaggaac acgatagagc acccggtatc ggcggcgatg gcctccatgc   4980
gaccgatgac ctgggccatg gggccgctgg cgttttcttc ctcgatgtgg aaccggcgca   5040
gcgtgtccag caccatcagg cggcggccct cggcggcgcg cttgaggccg tcgaaccact   5100
ccggggccat gatgttgggc aggctgccga tcagcggctg gatcagcagg ccgtcagcca   5160
cggcttgccg ttcctcggcg ctgaggtgcg ccccaagggc gtgcaggcgg tgatgaatgg   5220
cggtgggcgg gtcttcggcg ggcaggtaga tcaccgggcc ggtgggcagt tcgcccacct   5280
ccagcagatc cggcccgcct gcaatctgtg cggccagttg cagggccagc atggatttac   5340
cggcaccacc gggcgacacc agcgccccga ccgtaccggc caccatgttg ggcaaaacgt   5400
agtccagcgg tggcggcgct gctgcgaacg cctccagaat attgataggc ttatgggtag   5460
ccattgattg cctcctttgc aggcagttgg tggttaggcg ctggcggggt cactaccccc   5520
```

-continued

```
gccctgcgcc gctctgagtt cttccaggca ctcgcgcagc gcctcgtatt cgtcgtcggt   5580
cagccagaac ttgcgctgac gcatcccttt ggccttcatg cgctcggcat atcgcgcttg   5640
gcgtacagcg tcagggctgg ccagcaggtc gccggtctgc ttgtcctttt ggtctttcat   5700
atcagtcacc gagaaacttg ccggggccga aaggcttgtc ttcgcggaac aaggacaagg   5760
tgcagccgtc aaggttaagg ctggccatat cagcgactga aaagcggcca gcctcggcct   5820
tgtttgacgt ataaccaaag ccaccgggca accaatagcc cttgtcactt ttgatcaggt   5880
agaccgaccc tgaagcgctt ttttcgtatt ccataaaacc cccttctgtg cgtgagtact   5940
catagtataa caggcgtgag taccaacgca agcactacat gctgaaatct ggcccgcccc   6000
tgtccatgcc tcgctggcgg ggtgccggtg cccgtgccag ctcggcccgc gcaagctgga   6060
cgctgggcag acccatgacc ttgctgacgg tgcgctcgat gtaatccgct tcgtggccgg   6120
gcttgcgctc tgccagcgct gggctggcct cggccatggc cttgccgatt tcctcggcac   6180
tgcggccccg gctggccagc ttctgcgcgg cgataaagtc gcacttgctg aggtcatcac   6240
cgaagcgctt gaccagcccg gccatctcgc tgcggtactc gtccagcgcc gtgcgccggt   6300
ggcggctaag ctgccgctcg ggcagttcga ggctggccag cctgcgggcc ttctcctgct   6360
gccgctgggc ctgctcgatc tgctggccag cctgctgcac cagcgccggg ccagcggtgg   6420
cggtcttgcc cttggattca cgcagcagca cccacggctg ataaccggcg cgggtggtgt   6480
gcttgtcctt gcggttggtg aagcccgcca agcggccata gtggcggctg tcggcgctgg   6540
ccgggtcggc gtcgtactcg ctggccagcg tccgggcaat ctgcccccga agttcaccgc   6600
ctgcggcgtc ggccaccttg acccatgcct gatagttctt cgggctggtt tccactacca   6660
gggcaggctc ccggccctcg gctttcatgt catccaggtc aaactcgctg aggtcgtcca   6720
ccagcaccag accatgccgc tcctgctcgg cgggcctgat atacacgtca ttgccctggg   6780
cattcatccg cttgagccat ggcgtgttct ggagcacttc ggcggctgac cattcccggt   6840
tcatcatctg gccggtggtg gcgtccctga cgccgatatc gaagcgctca cagcccatgg   6900
ccttgagctg tcggcctatg gcctgcaaag tcctgtcgtt cttcatcggg ccaccaagcg   6960
cagccagatc gagccgtcct cggttgtcag tggcgtcagg tcgagcaaga gcaacgatgc   7020
gatcagcagc accaccgtag gcatcatgga agccagcatc acggttagcc atagcttcca   7080
gtgccacccc cgcgacgcgc tccgggcgct ctgcgcggcg ctgctcacct cggcggctac   7140
ctcccgcaac tctttggcca gctccaccca tgccgcccct gtctggcgct gggctttcag   7200
ccactccgcc gcctgcgcct cgctggcctg ctgggtctgg ctcatgacct gccgggcttc   7260
gtcggccagt gtcgccatgc tctgggccag cggttcgatc tgctccgcta actcgttgat   7320
gcctctggat ttcttcactc tgtcgattgc gttcatggtc tattgcctcc cggtattcct   7380
gtaagtcgat gatctgggcg ttggcggtgt cgatgttcag ggccacgtct gcccggtcgg   7440
tgcggatgcc ccggccttcc atctccacca cgttcggccc caggtgaaca ccgggcaggc   7500
gctcgatgcc ctgcgcctca agtgttctgt ggtcaatgcg ggcgtcgtgg ccagcccgct   7560
ctaatgcccg gttggcatgg tcggcccatg cctcgcgggt ctgctcaagc catgccttgg   7620
gcttgagcgc ttcggtcttc tgtgccccgc ccttctccgg ggtcttgccg ttgtaccgct   7680
tgaaccactg agcggcgggc cgctcgatgc cgtcattgat ccgctcggag atcatcaggt   7740
ggcagtgcgg gttctcgccg ccaccggcat ggatggccag cgtatacggc aggcgctcgg   7800
caccggtcag gtgctgggcg aactcggacg ccagcgcctt ctgctggtcg agggtcagct   7860
cgaccggcag ggcaaattcg acctccttga acagccgccc attggcgcgt tcatacaggt   7920
```

```
cggcagcatc ccagtagtcg gcgggccgct cgacgaactc cggcatgtgc ccggattcgg   7980
cgtgcaagac ttcatccatg tcgcgggcat acttgccttc gcgctggatg tagtcggcct   8040
tggccctggc cgattggccg cccgacctgc tgccggtttt cgccgtaagg tgataaatcg   8100
ccatgctgcc tcgctgttgc ttttgctttt cggctccatg caatggccct cggagagcgc   8160
accgcccgaa gggtggccgt taggccagtt tctcgaagag aaaccggtaa gtgcgccctc   8220
ccctacaaag tagggtcggg attgccgccg ctgtgcctcc atgatagcct acgagacagc   8280
acattaacaa tggggtgtca agatggttaa ggggagcaac aaggcggcgg atcggctggc   8340
caagctcgaa gaacaacgag cgcgaatcaa tgccgaaatt cagcgggtgc gggcaaggga   8400
acagcagcaa gagcgcaaga acgaaacaag gcgcaaggtg ctggtggggg ccatgatttt   8460
ggccaaggtg aacagcagcg agtggccgga ggatcggctc atggcggcaa tggatgcgta   8520
ccttgaacgc gaccacgacc gcgccttgtt cggtctgccg ccacgccaga aggatgagcc   8580
gggctgaatg atcgaccgag acaggccctg cggggctgca cacgcgcccc cacccttcgg   8640
gtagggggaa aggccgctaa agcggctaaa agcgctccag cgtatttctg cggggtttgg   8700
tgtggggttt agcgggcttt gcccgccttt ccccctgccg cgcagcggtg gggcggtgtg   8760
tagcctagcg cagcgaatag accagctatc cggcctctgg ccgggcatat tgggcaaggg   8820
cagcagcgcc ccacaagggc gctgataacc gcgcctagtg gattattctt agataatcat   8880
ggatggattt ttccaacacc ccgccagccc ccgcccctgc tgggtttgca ggtttggggg   8940
cgtgacagtt attgcagggg ttcgtgacag ttattgcagg ggggcgtgac agttattgca   9000
ggggttcgtg acagttagta cgggagtgac gggcactggc tggcaatgtc tagcaacggc   9060
aggcatttcg gctgagggta aaagaacttt ccgctaagcg atagactgta tgtaaacaca   9120
gtattgcaag gacgcggaac atgcctcatg tggcggccag gacggccagc cgggatcggg   9180
atactggtcg ttaccagagc caccgacccg agcaaaccct tctctatcag atcgttgacg   9240
agtattaccc ggcattcgct gcgcttatgg cagagcaggg aaaggaattg ccgggctatg   9300
tgcaacggga atttgaagaa tttctccaat gcgggcggct ggagcatggc tttctacggg   9360
ttcgctgcga gtcttgccac gccgagcacc tggtcgcttt cagctgtaat ccgggcagcg   9420
caacggaaca ttcatcagtg taaaaatgga atcaataaag ccctgcgcag cgcgcagggt   9480
cagcctgaat acgcgtgctc gaattgacat aagcctgttc ggttcgtaaa ctgtaatgca   9540
agtagcgtat gcgctcacgc aactggtcca gaaccttgac cgaacgcagc ggtggtaacg   9600
gcgcagtggc ggttttcatg gcttgttatg actgtttttt tgtacagtct atgcctcggg   9660
catccaagca gcaagcgcgt tacgccgtgg gtcgatgttt gatgttatgg agcagcaacg   9720
atgttacgca gcagcaacga tgttacgcag cagggcagtc gccctaaaac aaagttaggt   9780
ggctcaagta tgggcatcat tcgcacatgt aggctcggcc ctgaccaagt caaatccatg   9840
cgggctgctc ttgatctttt cggtcgtgag ttcggagacg tagccaccta ctcccaacat   9900
cagccggact ccgattacct cgggaacttg ctccgtagta agacattcat cgcgcttgct   9960
gccttcgacc aagaagcggt tgttggcgct ctcgcggctt acgttctgcc caggtttgag  10020
cagccgcgta gtgagatcta tatctatgat ctcgcagtct ccggcgagca ccggaggcag  10080
ggcattgcca ccgcgctcat caatctcctc aagcatgagg ccaacgcgct tggtgcttat  10140
gtgatctacg tgcaagcaga ttacggtgac gatcccgcag tggctctcta tacaaagttg  10200
ggcatacggg aagaagtgat gcactttgat atcgacccaa gtaccgccac ctaacaattc  10260
```

```
gttcaagccg agatcggctt cccggcccta gacgcgtatt caggctgacc ctgcgcgctg  10320

cgcagggctt tattgattcc atttttacac tgatgaatgt tccgttgcgc tgcccggatt  10380

acagatcctc tagaactagt ggatcccccg ggctgcaggg gggggggga aagccacgtt  10440

gtgtctcaaa atctctgatg ttacattgca caagataaaa atatatcatc atgaacaata  10500

aaactgtctg cttacataaa cagtaataca aggggtgtta tgagccatat tcaacgggaa  10560

acgtcttgct cgaggccgcg attaaattcc aacatggatg ctgatttata tgggtataaa  10620

tgggctcgcg ataatgtcgg gcaatcaggt gcgacaatct atcgattgta tgggaagccc  10680

gatgcgccag agttgtttct gaaacatggc aaaggtagcg ttgccaatga tgttacagat  10740

gagatggtca gactaaactg gctgacggaa tttatgcctc ttccgaccat caagcatttt  10800

atccgtactc ctgatgatgc atggttactc accactgcga tccccgggaa aacagcattc  10860

caggtattag aagaatatcc tgattcaggt gaaaatattg ttgatgcgct ggcagtgttc  10920

ctgcgccggt tgcattcgat tcctgtttgt aattgtcctt ttaacagcga tcgcgtattt  10980

cgtctcgctc aggcgcaatc acgaatgaat aacggtttgg ttgatgcgag tgattttgat  11040

gacgagcgta atggctggcc tgttgaacaa gtctggaaag aaatgcataa gcttttgcca  11100

ttctcaccgg attcagtcgt cactcatggt gatttctcac ttgataacct tatttttgac  11160

gaggggaaat taataggttg tattgatgtt ggacgagtcg gaatcgcaga ccgataccag  11220

gatcttgcca tcctatggaa ctgcctcggt gagttttctc cttcattaca gaaacggctt  11280

tttcaaaaat atggtattga taatcctgat atgaataaat tgcagtttca tttgatgctc  11340

gatgagtttt tctaatcaga attggttaat tggttgtaac actggcagag cattacgctg  11400

acttgacggg acggcggctt tgttgaataa atcgaacttt tgctgagttg aaggatcaga  11460

tcacgcatct tcccgacaac gcagaccgtt ccgtggcaaa gcaaaagttc aaaatcacca  11520

actggtccac ctacaacaaa gctctcatca accgtggctc cctcactttc tggctggatg  11580

atggggcgat tcaggcctgg tatgagtcag caacaccttc ttcacgaggc agacctcagc  11640

gcccccccc cccggaattc gatatcaagc ttatcgatac cg                     11682
```

<210> SEQ ID NO 76
<211> LENGTH: 11748
<212> TYPE: DNA
<213> ORGANISM: Artificial
<220> FEATURE:
<223> OTHER INFORMATION: #1348¶VZ322a-ziaR-PziaA-PDC_dsrA-PrbcL-synADHdeg_oop

<400> SEQUENCE: 76

```
ggcgttagga gctagggaaa aatttaaact ggatttagaa aatgattttc atcctaacat     60

ctttaatatc tgagcatatc ttcaggtgtt tcaagatttg tgctacggtt caaggaggtt    120

tttctttaaa tcacgttggc cgccatgtct atgaattctt atactgtcgg tacctattta    180

gcggagcggc ttgtccagat tggtctcaag catcacttcg cagtcgcggg cgactacaac    240

ctcgtccttc ttgacaacct gcttttgaac aaaaacatgg agcaggttta ttgctgtaac    300

gaactgaact gcggtttcag tgcagaaggt tatgctcgtg ccaaaggcgc agcagcagcc    360

gtcgttacct acagcgtcgg tgcgctttcc gcatttgatg ctatcggtgg cgcctatgca    420

gaaaaccttc cggttatcct gatctccggt gctccgaaca acaatgatca cgctgctggt    480

cacgtgttgc atcacgctct tggcaaaacc gactatcact atcagttgga aatggccaag    540

aacatcacgg ccgcagctga agcgatttac accccagaag aagctccggc taaaatcgat    600
```

```
cacgtgatta aaactgctct tcgtgagaag aagccggttt atctcgaaat cgcttgcaac    660
attgcttcca tgccctgcgc cgctcctgga ccggcaagcg cattgttcaa tgacgaagcc    720
agcgacgaag cttctttgaa tgcagcggtt gaagaaaccc tgaaattcat cgccaaccgc    780
gacaaagttg ccgtcctcgt cggcagcaag ctgcgcgcag ctggtgctga agaagctgct    840
gtcaaatttg ctgatgctct cggtggcgca gttgctacca tggctgctgc aaaaagcttc    900
ttcccagaag aaaacccgca ttacatcggt acctcatggg gtgaagtcag ctatccgggc    960
gttgaaaaga cgatgaaaga agccgatgcg gttatcgctc tggctcctgt cttcaacgac   1020
tactccacca ctggttggac ggatattcct gatcctaaga aactggttct cgctgaaccg   1080
cgttctgtcg tcgttaacgg cgttcgcttc cccagcgttc atctgaaaga ctatctgacc   1140
cgtttggctc agaaagtttc caagaaaacc ggtgctttgg acttcttcaa atccctcaat   1200
gcaggtgaac tgaagaaagc cgctccggct gatccgagtg ctccgttggt caacgcagaa   1260
atcgcccgtc aggtcgaagc tcttctgacc ccgaacacga cggttattgc tgaaaccggt   1320
gactcttggt tcaatgctca gcgcatgaag ctcccgaacg gtgctcgcgt tgaatatgaa   1380
atgcagtggg gtcacatcgg ttggtccgtt cctgccgcct tcggttatgc cgtcggtgct   1440
ccggaacgtc gcaacatcct catggttggt gatggttcct tccagctgac ggctcaggaa   1500
gtcgctcaga tggttcgcct gaaactgccg gttatcatct tcttgatcaa taactatggt   1560
tacaccatcg aagttatgat ccatgatggt ccgtacaaca acatcaagaa ctgggattat   1620
gccggtctga tggaagtgtt caacggtaac ggtggttatg acagcggtgc tggtaaaggc   1680
ctgaaggcta aaaccggtgg cgaactggca gaagctatca aggttgctct ggcaaacacc   1740
gacggcccaa ccctgatcga atgcttcatc ggtcgtgaag actgcactga agaattggtc   1800
aaatggggta agcgcgttgc tgccgccaac agccgtaagc ctgttaacaa gctcctctag   1860
tttttgggga tcaattcgag ctcagcaagt ttcatcccga ccccctcagg gtcgggattt   1920
ttttattgta ctagtaacgc tcggttgccg ccgggcgttt tttattccga catcaggaat   1980
tgtaattaga aagtccaaaa attgtaattt aaaaaacagt caatggagag cattgccata   2040
agtaaaggca tcccctgcgt gataagatta ccttcagaaa acagatagtt gctgggttat   2100
cgcagatttt tctcgcaacc aaataactgt aaataataac tgtctctggg gcgacggtag   2160
gctttatatt gccaaatttc gcccgtggga gaaagctagg ctattcaatg tttatggagg   2220
actgacccat atgatcaagg cttatgccgc tttagaggct aatggcaagt tgcagccgtt   2280
cgagtatgat ccgggcgctt taggcgccaa cgaagttgaa atcgaagttc aatactgcgg   2340
tgtttgtcat tccgacctca gtatgatcaa caatgagtgg ggtatcagta actatccgtt   2400
ggttcccggc cacgaagttg ttggcaccgt tgctgctatg ggtgagggtg ttaatcacgt   2460
ggaagttggt gacctggttg gtttaggctg gcacagtggt tattgtatga cttgtcactc   2520
ctgcctgagc ggttatcata atttgtgcgc taccgccgag agtactatcg ttggtcatta   2580
tggcggtttc ggtgaccgtg tgcgtgctaa aggtgtgtcc gttgttaagc tgcccaaggg   2640
tatcgatttg gcttccgctg gtccgttgtt ttgcggtggt atcactgtgt tttcccccat   2700
ggttgagtta tccctgaaac cgaccgccaa ggttgccgtt attggtatcg gtggtctcgg   2760
tcacctggcc gttcagttct tgcgtgcttg ggggttgcgag gttaccgctt tcactagctc   2820
cgctcgtaaa cagaccgagg ttctggagct gggtgcccat catattttgg acagtactaa   2880
ccccgaagcc attgcttccg ccgagggtaa gttcgattac atcattagta ccgttaattt   2940
aaaattggat tggaatctgt atatttccac tttagccccg caaggtcact ttcatttcgt   3000
```

gggtgttgtt ctcgaacccc tcgacttgaa cttgttcccg ttgctcatgg gtcagcggag 3060
tgtgtccgct agtccggttg gctccccggc tactatcgct actatgctcg atttcgccgt 3120
tcggcacgat atcaagccgg ttgttgagca gttctccttc gaccaaatta atgaagccat 3180
tgctcacttg gagtccggta aggctcacta ccgtgtggtt ttgagtcact ccaagaactg 3240
aaacgctcgg ttgccgccgg gcgtttttta ttcctgcagg agcagaagag catacatctg 3300
gaagcaaagc caggaaagcg gcctatggag ctgtgcggca gcgctcagta ggcaattttt 3360
caaaatattg ttaagccttt tctgagcatg gtatttttca tggtattacc aattagcagg 3420
aaaataagcc attgaatata aaagataaaa atgtcttgtt tacaatagag tgggggggt 3480
cagcctgccg ccttgggccg ggtgatgtcg tacttgcccg ccgcgaactc ggttaccgtc 3540
cagcccagcg cgaccagctc cggcaacgcc tcgcgcaccc gctggcggcg cttgcgcatg 3600
gtcgaaccac tggcctctga cggccagaca tagccgcaca aggtatctat ggaagccttg 3660
ccggttttgc cggggtcgat ccagccacac agccgctggt gcagcaggcg ggcggtttcg 3720
ctgtccagcg cccgcacctc gtccatgctg atgcgcacat gctggccgcc acccatgacg 3780
gcctgcgcga tcaaggggtt cagggccacg tacaggcgcc cgtccgcctc gtcgctggcg 3840
tactccgaca gcagccgaaa cccctgccgc ttgcggccat tctgggcgat gatggatacc 3900
ttccaaaggc gctcgatgca gtcctgtatg tgcttgagcg ccccaccact atcgacctct 3960
gccccgattt cctttgccag cgcccgatag ctacctttga ccacatggca ttcagcggtg 4020
acggcctccc acttgggttc caggaacagc cggagctgcc gtccgccttc ggtcttgggt 4080
tccgggccaa gcactaggcc attaggccca gccatggcca ccagcccttg caggatgcgc 4140
agatcatcag cgcccagcgg ctccgggccg ctgaactcga tccgcttgcc gtcgccgtag 4200
tcatacgtca cgtccagctt gctgcgcttg cgctcgcccc gcttgagggc acggaacagg 4260
ccgggggcca gacagtgcgc cgggtcgtgc cggacgtggc tgaggctgtg cttgttctta 4320
ggcttcacca cggggcaccc ccttgctctt gcgctgcctc tccagcacgg cgggcttgag 4380
caccccgccg tcatgccgcc tgaaccaccg atcagcgaac ggtgcgccat agttggcctt 4440
gctcacaccg aagcggacga agaaccggcg ctggtcgtcg tccacacccc attcctcggc 4500
ctcggcgctg gtcatgctcg acaggtagga ctgccagcgg atgttatcga ccagtaccga 4560
gctgccccgg ctggcctgct gctggtcgcc tgcgcccatc atggccgcgc ccttgctggc 4620
atggtgcagg aacacgatag agcacccggt atcggcggcg atggcctcca tgcgaccgat 4680
gacctgggcc atggggccgc tggcgttttc ttcctcgatg tggaaccggc gcagcgtgtc 4740
cagcaccatc aggcggcggc cctcggcggc gcgcttgagg ccgtcgaacc actccggggc 4800
catgatgttg ggcaggctgc cgatcagcgg ctggatcagc aggccgtcag ccacggcttg 4860
ccgttcctcg gcgctgaggt gcgccccaag ggcgtgcagg cggtgatgaa tggcggtggg 4920
cgggtcttcg gcgggcaggt agatcaccgg gccggtgggc agttcgccca cctccagcag 4980
atccggcccg cctgcaatct gtgcggccag ttgcagggcc agcatggatt taccggcacc 5040
accgggcgac accagcgccc cgaccgtacc ggccaccatg ttgggcaaaa cgtagtccag 5100
cggtggcggc gctgctgcga acgcctccag aatattgata ggcttatggg tagccattga 5160
ttgcctcctt tgcaggcagt tggtggttag gcgctggcgg ggtcactacc cccgccctgc 5220
gccgctctga gttcttccag gcactcgcgc agcgcctcgt attcgtcgtc ggtcagccag 5280
aacttgcgct gacgcatccc tttggccttc atgcgctcgg catatcgcgc ttggcgtaca 5340

-continued

```
gcgtcagggc tggccagcag gtcgccggtc tgcttgtcct tttggtcttt catatcagtc   5400
accgagaaac ttgccggggc cgaaaggctt gtcttcgcgg aacaaggaca aggtgcagcc   5460
gtcaaggtta aggctggcca tatcagcgac tgaaaagcgg ccagcctcgg ccttgtttga   5520
cgtataacca aagccaccgg gcaaccaata gcccttgtca cttttgatca ggtagaccga   5580
ccctgaagcg ctttttcgt attccataaa accccttct gtgcgtgagt actcatagta   5640
taacaggcgt gagtaccaac gcaagcacta catgctgaaa tctggcccgc ccctgtccat   5700
gcctcgctgg cggggtgccg gtgcccgtgc cagctcggcc cgcgcaagct ggacgctggg   5760
cagacccatg accttgctga cggtgcgctc gatgtaatcc gcttcgtggc cgggcttgcg   5820
ctctgccagc gctgggctgg cctcggccat ggccttgccg atttcctcgg cactgcggcc   5880
ccggctggcc agcttctgcg cggcgataaa gtcgcacttg ctgaggtcat caccgaagcg   5940
cttgaccagc ccggccatct cgctgcggta ctcgtccagc gccgtgcgcc ggtggcggct   6000
aagctgccgc tcgggcagtt cgaggctggc cagcctgcgg gccttctcct gctgccgctg   6060
ggcctgctcg atctgctggc cagcctgctg caccagcgcc gggccagcgg tggcggtctt   6120
gcccttggat tcacgcagca gcacccacgg ctgataaccg gcgcgggtgg tgtgcttgtc   6180
cttgcggttg gtgaagcccg ccaagcggcc atagtggcgg ctgtcggcgc tggccgggtc   6240
ggcgtcgtac tcgctggcca gcgtccgggc aatctgcccc cgaagttcac cgcctgcggc   6300
gtcggccacc ttgacccatg cctgatagtt cttcgggctg gtttccacta ccagggcagg   6360
ctcccggccc tcggctttca tgtcatccag gtcaaactcg ctgaggtcgt ccaccagcac   6420
cagaccatgc cgctcctgct cggcgggcct gatatacacg tcattgccct gggcattcat   6480
ccgcttgagc catggcgtgt tctggagcac ttcggcggct gaccattccc ggttcatcat   6540
ctggccggtg gtggcgtccc tgacgccgat atcgaagcgc tcacagccca tggccttgag   6600
ctgtcggcct atggcctgca aagtcctgtc gttcttcatc gggccaccaa gcgcagccag   6660
atcgagccgt cctcggttgt cagtggcgtc aggtcgagca agagcaacga tgcgatcagc   6720
agcaccaccg taggcatcat ggaagccagc atcacggtta gccatagctt ccagtgccac   6780
ccccgcgacg cgctccgggc gctctgcgcg gcgctgctca cctcggcggc tacctcccgc   6840
aactctttgg ccagctccac ccatgccgcc cctgtctggc gctgggcttt cagccactcc   6900
gccgcctgcg cctcgctggc ctgctgggtc tggctcatga cctgccgggc ttcgtcggcc   6960
agtgtcgcca tgctctgggc cagcggttcg atctgctccg ctaactcgtt gatgcctctg   7020
gatttcttca ctctgtcgat tgcgttcatg gtctattgcc tcccggtatt cctgtaagtc   7080
gatgatctgg gcgttggcgg tgtcgatgtt cagggccacg tctgcccggt cggtgcggat   7140
gccccggcct tccatctcca ccacgttcgg ccccaggtga acaccgggca ggcgctcgat   7200
gccctgcgcc tcaagtgttc tgtggtcaat gcgggcgtcg tggccagccc gctctaatgc   7260
ccggttggca tggtcggccc atgcctcgcg ggtctgctca agccatgcct tgggcttgag   7320
cgcttcggtc ttctgtgccc cgcccttctc cggggtcttg ccgttgtacc gcttgaacca   7380
ctgagcggcg ggccgctcga tgccgtcatt gatccgctcg gagatcatca ggtggcagtg   7440
cgggttctcg ccgccaccgg catggatggc cagcgtatac ggcaggcgct cggcaccggt   7500
caggtgctgg gcgaactcgg acgccagcgc cttctgctgg tcgagggtca gctcgaccgg   7560
cagggcaaat tcgacctcct tgaacagccg cccattggcg cgttcataca ggtcggcagc   7620
atcccagtag tcggcgggcc gctcgacgaa ctccggcatg tgcccggatt cggcgtgcaa   7680
gacttcatcc atgtcgcggg catacttgcc ttcgcgctgg atgtagtcgg ccttggccct   7740
```

```
ggccgattgg ccgcccgacc tgctgccggt tttcgccgta aggtgataaa tcgccatgct   7800
gcctcgctgt tgcttttgct tttcggctcc atgcaatggc cctcggagag cgcaccgccc   7860
gaagggtggc cgttaggcca gtttctcgaa gagaaaccgg taagtgcgcc ctcccctaca   7920
aagtagggtc gggattgccg ccgctgtgcc tccatgatag cctacgagac agcacattaa   7980
caatggggtg tcaagatggt taaggggagc aacaaggcgg cggatcggct ggccaagctc   8040
gaagaacaac gagcgcgaat caatgccgaa attcagcggg tgcgggcaag ggaacagcag   8100
caagagcgca agaacgaaac aaggcgcaag gtgctggtgg gggccatgat tttggccaag   8160
gtgaacagca gcgagtggcc ggaggatcgg ctcatggcgg caatggatgc gtaccttgaa   8220
cgcgaccacg accgcgcctt gttcggtctg ccgccacgcc agaaggatga gccgggctga   8280
atgatcgacc gagacaggcc ctgcggggct gcacacgcgc cccccaccctt cgggtagggg   8340
gaaaggccgc taaagcggct aaaagcgctc cagcgtattt ctgcggggtt tggtgtgggg   8400
tttagcgggc tttgcccgcc tttcccccctg ccgcgcagcg gtggggcggt gtgtagccta   8460
gcgcagcgaa tagaccagct atccggcctc tggccgggca tattgggcaa gggcagcagc   8520
gccccacaag ggcgctgata accgcgccta gtggattatt cttagataat catggatgga   8580
tttttccaac accccgccag cccccgcccc tgctgggttt gcaggtttgg gggcgtgaca   8640
gttattgcag gggttcgtga cagttattgc aggggggcgt gacagttatt gcaggggttc   8700
gtgacagtta gtacgggagt gacgggcact ggctggcaat gtctagcaac ggcaggcatt   8760
tcggctgagg gtaaaagaac tttccgctaa gcgatagact gtatgtaaac acagtattgc   8820
aaggacgcgg aacatgcctc atgtggcggc caggacggcc agccgggatc gggatactgg   8880
tcgttaccag agccaccgac ccgagcaaac ccttctctat cagatcgttg acgagtatta   8940
cccggcattc gctgcgctta tggcagagca gggaaaggaa ttgccgggct atgtgcaacg   9000
ggaatttgaa gaatttctcc aatgcgggcg gctggagcat ggctttctac gggttcgctg   9060
cgagtcttgc cacgccgagc acctggtcgc tttcagctgt aatccgggca gcgcaacgga   9120
acattcatca gtgtaaaaat ggaatcaata aagccctgcg cagcgcgcag ggtcagcctg   9180
aatacgcgtg ctcgaattga cataagcctg ttcggttcgt aaactgtaat gcaagtagcg   9240
tatgcgctca cgcaactggt ccagaacctt gaccgaacgc agcggtggta acggcgcagt   9300
ggcggttttc atggcttgtt atgactgttt ttttgtacag tctatgcctc gggcatccaa   9360
gcagcaagcg cgttacgccg tgggtcgatg tttgatgtta tggagcagca acgatgttac   9420
gcagcagcaa cgatgttacg cagcagggca gtcgccctaa aacaaagtta ggtggctcaa   9480
gtatgggcat cattcgcaca tgtaggctcg gccctgacca agtcaaatcc atgcgggctg   9540
ctcttgatct tttcggtcgt gagttcggag acgtagccac ctactcccaa catcagccgg   9600
actccgatta cctcgggaac ttgctccgta gtaagacatt catcgcgctt gctgccttcg   9660
accaagaagc ggttgttggc gctctcgcgg cttacgttct gcccaggttt gagcagccgc   9720
gtagtgagat ctatatctat gatctcgcag tctccggcga gcaccggagg cagggcattg   9780
ccaccgcgct catcaatctc ctcaagcatg aggccaacgc gcttggtgct tatgtgatct   9840
acgtgcaagc agattacggt gacgatcccg cagtggctct ctatacaaag ttgggcatac   9900
gggaagaagt gatgcacttt gatatcgacc caagtaccgc cacctaacaa ttcgttcaag   9960
ccgagatcgg cttcccggcc ctagacgcgt attcaggctg accctgcgcg ctgcgcaggg  10020
ctttattgat tccattttta cactgatgaa tgttccgttg cgctgcccgg attacagatc  10080
```

```
ctctagaggg ggggggggaa agccacgttg tgtctcaaaa tctctgatgt tacattgcac  10140

aagataaaaa tatatcatca tgaacaataa aactgtctgc ttacataaac agtaatacaa  10200

ggggtgttat gagccatatt caacgggaaa cgtcttgctc gaggccgcga ttaaattcca  10260

acatggatgc tgatttatat gggtataaat gggctcgcga taatgtcggg caatcaggtg  10320

cgacaatcta tcgattgtat gggaagcccg atgcgccaga gttgtttctg aaacatggca  10380

aaggtagcgt tgccaatgat gttacagatg agatggtcag actaaactgg ctgacggaat  10440

ttatgcctct tccgaccatc aagcatttta tccgtactcc tgatgatgca tggttactca  10500

ccactgcgat ccccgggaaa acagcattcc aggtattaga agaatatcct gattcaggtg  10560

aaaatattgt tgatgcgctg gcagtgttcc tgcgccggtt gcattcgatt cctgtttgta  10620

attgtccttt taacagcgat cgcgtatttc gtctcgctca ggcgcaatca cgaatgaata  10680

acggtttggt tgatgcgagt gattttgatg acgagcgtaa tggctggcct gttgaacaag  10740

tctggaaaga aatgcataag cttttgccat tctcaccgga ttcagtcgtc actcatggtg  10800

atttctcact tgataacctt atttttgacg aggggaaatt aataggttgt attgatgttg  10860

gacgagtcgg aatcgcagac cgataccagg atcttgccat cctatggaac tgcctcggtg  10920

agttttctcc ttcattacag aaacggcttt ttcaaaaata tggtattgat aatcctgata  10980

tgaataaatt gcagtttcat ttgatgctcg atgagttttt ctaatcagaa ttggttaatt  11040

ggttgtaaca ctggcagagc attacgctga cttgacggga cggcggcttt gttgaataaa  11100

tcgaactttt gctgagttga aggatcagat cacgcatctt cccgacaacg cagaccgttc  11160

cgtggcaaag caaaagttca aaatcaccaa ctggtccacc tacaacaaag ctctcatcaa  11220

ccgtggctcc ctcactttct ggctggatga tggggcgatt caggcctggt atgagtcagc  11280

aacaccttct tcacgaggca gacctcagcg cccccccccc ccggaatcta gagtcgacct  11340

ccttaatccg attcctgcaa atggtctgca acttcccgat acaaattcat cacatgatta  11400

tccgccaagc tgtagtaaac attacggccg acccggcgat actttaccag gcgctgcgat  11460

cgtaaaattc gtaattgatg ggaaactgcc gattcactca ctttcatcgc cgctgctaaa  11520

tcacagacac agagttcttg gcgggccaat gccgacatta aacgcaaccg actcggatca  11580

gctagtgcac tgaaaaactc cgccatttgc tgggcctggt ccaatgacat cacctctggt  11640

tgaacctgtc gtacctgctc aagatgaaca agaggttgat cacaaagggg catctcttcg  11700

ttctggcagg attgtgactt tgacaacgag gacttactca tagaggtt              11748
```

<210> SEQ ID NO 77
<211> LENGTH: 8915
<212> TYPE: DNA
<213> ORGANISM: Artificial
<220> FEATURE:
<223> OTHER INFORMATION: TK115¶GEM-AQ4::smtB-PsmtA-PDC-PrbcL-
synADHdeg-Nm

<400> SEQUENCE: 77

```
tcgacgggca aactttatga agcagatcaa gcctatatcc gccaagcaac cggcagccgc     60

gttgattagt gggtgtgtcc atcctctggt tcgtctaggt gctccgaagc gtcacgatag    120

agattaagaa tgtggtgatc cttgaggcga taaatcacat tccgcccttc cttgcgatag    180

ctcactaaac gtgctgtgcg cagggttctt agttggtgag agacagccga ttcactcatt    240

tcaacggcgg cggcgagttc ccccacccgc atctctccag tggccagggc cgaaagaata    300

cgccagcggt tggcatcccc caagacacca aaaaattcgg ccatccgttg ggccttggct    360
```

-continued

```
tggttcaaga ttttgccact gtggtctgtc attgttcgct gatctaaaca atacctgaat    420
aattgttcat gtgttaatct aaaaatgtga acaatcgttc aactatttaa gacaatacct    480
tggaggttta aaccatgaat tcttatactg tcggtaccta tttagcggag cggcttgtcc    540
agattggtct caagcatcac ttcgcagtcg cgggcgacta caacctcgtc cttcttgaca    600
acctgctttt gaacaaaaac atggagcagg tttattgctg taacgaactg aactgcggtt    660
tcagtgcaga aggttatgct cgtgccaaag gcgcagcagc agccgtcgtt acctacagcg    720
tcggtgcgct ttccgcattt gatgctatcg gtggcgccta tgcagaaaac cttccggtta    780
tcctgatctc cggtgctccg aacaacaatg atcacgctgc tggtcacgtg ttgcatcacg    840
ctcttggcaa aaccgactat cactatcagt tggaaatggc caagaacatc acggccgcag    900
ctgaagcgat ttacacccca gaagaagctc cggctaaaat cgatcacgtg attaaaactg    960
ctcttcgtga gaagaagccg gtttatctcg aaatcgcttg caacattgct tccatgccct   1020
gcgccgctcc tggaccggca agcgcattgt tcaatgacga agccagcgac gaagcttctt   1080
tgaatgcagc ggttgaagaa accctgaaat tcatcgccaa ccgcgacaaa gttgccgtcc   1140
tcgtcggcag caagctgcgc gcagctggtg ctgaagaagc tgctgtcaaa tttgctgatg   1200
ctctcggtgg cgcagttgct accatggctg ctgcaaaaag cttcttccca gaagaaaacc   1260
cgcattacat cggtacctca tggggtgaag tcagctatcc gggcgttgaa aagacgatga   1320
aagaagccga tgcggttatc gctctggctc ctgtcttcaa cgactactcc accactggtt   1380
ggacggatat tcctgatcct aagaaactgg ttctcgctga accgcgttct gtcgtcgtta   1440
acggcgttcg cttccccagc gttcatctga aagactatct gacccgtttg gctcagaaag   1500
tttccaagaa aaccggtgct ttggacttct tcaaatccct caatgcaggt gaactgaaga   1560
aagccgctcc ggctgatccg agtgctccgt tggtcaacgc agaaatcgcc cgtcaggtcg   1620
aagctcttct gaccccgaac acgacggtta ttgctgaaac cggtgactct tggttcaatg   1680
ctcagcgcat gaagctcccg aacggtgctc gcgttgaata tgaaatgcag tggggtcaca   1740
tcggttggtc cgttcctgcc gccttcggtt atgccgtcgg tgctccggaa cgtcgcaaca   1800
tcctcatggt tggtgatggt tccttccagc tgacggctca ggaagtcgct cagatggttc   1860
gcctgaaact gccggttatc atcttcttga tcaataacta tggttacacc atcgaagtta   1920
tgatccatga tggtccgtac aacaacatca agaactggga ttatgccggt ctgatggaag   1980
tgttcaacgg taacggtggt tatgacagcg gtgctggtaa aggcctgaag gctaaaaccg   2040
gtggcgaact ggcagaagct atcaaggttg ctctggcaaa caccgacggc ccaaccctga   2100
tcgaatgctt catcggtcgt gaagactgca ctgaagaatt ggtcaaatgg ggtaagcgcg   2160
ttgctgccgc caacagccgt aagcctgtta acaagctcct ctagtttttg gggatcaatt   2220
cgagctcggt acccaaacta gtaacgctcg gttgccgccg ggcgtttttt attccgacat   2280
caggaattgt aattagaaag tccaaaaatt gtaatttaaa aaacagtcaa tggagagcat   2340
tgccataagt aaaggcatcc cctgcgtgat aagattacct tcagaaaaca gatagttgct   2400
gggttatcgc agatttttct cgcaaccaaa taactgtaaa taataactgt ctctggggcg   2460
acggtaggct ttatattgcc aaatttcgcc cgtgggagaa agctaggcta ttcaatgttt   2520
atggaggact gacccatatg atcaaggctt atgccgcttt agaggctaat ggcaagttgc   2580
agccgttcga gtatgatccg ggcgctttag gcgccaacga agttgaaatc gaagttcaat   2640
actgcggtgt ttgtcattcc gacctcagta tgatcaacaa tgagtggggt atcagtaact   2700
atccgttggt tcccggccac gaagttgttg gcaccgttgc tgctatgggt gagggtgtta   2760
```

atcacgtgga agttggtgac ctggttggtt taggctggca cagtggttat tgtatgactt 2820
gtcactcctg cctgagcggt tatcataatt tgtgcgctac cgccgagagt actatcgttg 2880
gtcattatgg cggtttcggt gaccgtgtgc gtgctaaagg tgtgtccgtt gttaagctgc 2940
ccaagggtat cgatttggct tccgctggtc cgttgttttg cggtggtatc actgtgtttt 3000
cccccatggt tgagttatcc ctgaaaccga ccgccaaggt tgccgttatt ggtatcggtg 3060
gtctcggtca cctggccgtt cagttcttgc gtgcttgggg ttgcgaggtt accgctttca 3120
ctagctccgc tcgtaaacag accgaggttc tggagctggg tgcccatcat attttggaca 3180
gtactaaccc cgaagccatt gcttccgccg agggtaagtt cgattacatc attagtaccg 3240
ttaatttaaa attggattgg aatctgtata tttccacttt agccccgcaa ggtcactttc 3300
atttcgtggg tgttgttctc gaacccctcg acttgaactt gttcccgttg ctcatgggtc 3360
agcggagtgt gtccgctagt ccggttggct ccccggctac tatcgctact atgctcgatt 3420
tcgccgttcg gcacgatatc aagccggttg ttgagcagtt ctccttcgac caaattaatg 3480
aagccattgc tcacttggag tccggtaagg ctcactaccg tgtggttttg agtcactcca 3540
agaactgaaa cgctcggttg ccgccgggcg ttttttattc ctgcaggccc cccgggggat 3600
ccactagagg atctcaatga atattggttg acacgggcgt ataagacatg ttatactgtt 3660
gaataacaag gacggatctg atcaagagac aggatgagga tcgtttcgca tgattgaaca 3720
agatggattg cacgcaggtt ctccggccgc ttgggtggag aggctattcg gctatgactg 3780
ggcacaacag acaatcggct gctctgatgc cgccgtgttc cggctgtcag cgcaggggcg 3840
cccggttctt tttgtcaaga ccgacctgtc cggtgccctg aatgaactgc aggacgaggc 3900
agcgcggcta tcgtggctgg ccacgacggg cgttccttgc gcagctgtgc tcgacgttgt 3960
cactgaagcg ggaagggact ggctgctatt gggcgaagtg ccggggcagg atctcctgtc 4020
atctcacctt gctcctgccg agaaagtatc catcatggct gatgcaatgc ggcggctgca 4080
tacgcttgat ccggctacct gcccattcga ccaccaagcg aaacatcgca tcgagcgagc 4140
acgtactcgg atggaagccg gtcttgtcga tcaggatgat ctggacgaag agcatcaggg 4200
gctcgcgcca gccgaactgt tcgccaggct caaggcgcgc atgcccgacg gcgaggatct 4260
cgtcgtgacc catggcgatg cctgcttgcc gaatatcatg gtggaaaatg gccgcttttc 4320
tggattcatc gactgtggcc ggctgggtgt ggcggaccgc tatcaggaca tagcgttggc 4380
tacccgtgat attgctgaag agcttggcgg cgaatgggct gaccgcttcc tcgtgcttta 4440
cggtatcgcc gctcccgatt cgcagcgcat cgccttctat cgccttcttg acgagttctt 4500
ctgagcggga ctctggggtt cgaaatgacc gaccaagcga cgcccaacct gccatcacga 4560
gatttcgatt ccaccgccgc cttctatgaa aggttgggct tcggaatcgt tttccgggac 4620
gccggctgga tgatcctcca gcgcggggat ctcatgctgg agttcttcgc ccaccgggga 4680
tcctctagtt ctagagcggc cgcatcatca atccccgtga tgtttcagtc ccgtagtcgg 4740
gatttagtgg ttggaaagcg gaacgtcgcg ccgaaaccat cgccaggacg ggtttcagtc 4800
ccgtagtcgg gatttagtgg ttggaaagtg attatgttca agaaatcaca acgcaaaaga 4860
aaaagtttca gtcccgtagt cgggatttag tggttggaaa gtcaagcgag atacccacca 4920
gaaagccttt gacctggttt cagtcccgag tcgggattta gtggttggaa aggcggcggc 4980
tgatgtcgcc aatgcggtta tcgatggcca gtttcagtcc cgtagtcggg atttagtggt 5040
tggaaagtcc caagggggac agggcggtga tcctcgatgt tgcgtgtttc agtcccgtag 5100

-continued

```
tcgggattta gtggttggaa agactcgtct atatatacag agattactac agagatgttt   5160
cagtcccgta gtcgggattt agtggttgga aagcgggaaa gtagcctgtt ttgtggagaa   5220
ttgcaggcgt ttcagtacta gtgatggcgg ccgggagcat gcgacgtcgg gcccaattcg   5280
ccctatagtg agtcgtatta caattcactg gccgtcgttt tacaacgtcg tgactgggaa   5340
aaccctggcg ttacccaact taatcgcctt gcagcacatc ccccctttcgc cagctggcgt  5400
aatagcgaag aggcccgcac cgatcgccct tcccaacagt tgcgcagcct gaatggcgaa   5460
tggacgcgcc ctgtagcggc gcattaagcg cggcgggtgt ggtggttacg cgcagcgtga   5520
ccgctacact tgccagcgcc ctagcgcccg ctcctttcgc tttcttccct tcctttctcg   5580
ccacgttcgc cggctttccc cgtcaagctc taaatcgggg gctcccttta gggttccgat   5640
ttagagcttt acggcacctc gaccgcaaaa aacttgattt gggtgatggt tcacgtagtg   5700
ggccatcgcc ctgatagacg gtttttcgcc ctttgacgtt ggagtccacg ttctttaata   5760
gtggactctt gttccaaact ggaacaacac tcaaccctat ctcggtctat tcttttgatt   5820
tataagggat tttgccgatt tcggcctatt ggttaaaaaa tgagctgatt taacaaatat   5880
ttaacgcgaa ttttaacaaa atattaacgt ttacaatttc gcctgatgcg gtattttctc   5940
cttacgcatc tgtgcggtat ttcacaccgc atacaggtgg cacttttcgg ggaaatgtgc   6000
gcggaacccc tatttgttta tttttctaaa tacattcaaa tatgtatccg ctcatgagac   6060
aataaccctg ataaatgctt caataatatt gaaaaaggaa gagtatgagt attcaacatt   6120
tccgtgtcgc ccttattccc ttttttgcgg cattttgcct tcctgttttt gctcacccag   6180
aaacgctggt gaaagtaaaa gatgctgaag atcagttggg tgcacgagtg ggttacatcg   6240
aactggatct caacagcggt aagatccttg agagttttcg ccccgaagaa cgttttccaa   6300
tgatgagcac ttttaaagtt ctgctatgtg gcgcggtatt atcccgtatt gacgccgggc   6360
aagagcaact cggtcgccgc atacactatt ctcagaatga cttggttgag tactcaccag   6420
tcacagaaaa gcatcttacg gatggcatga cagtaagaga attatgcagt gctgccataa   6480
ccatgagtga taacactgcg gccaacttac ttctgacaac gatcggagga ccgaaggagc   6540
taaccgcttt tttgcacaac atgggggatc atgtaactcg ccttgatcgt tgggaaccgg   6600
agctgaatga agccatacca aacgacgagc gtgacaccac gatgcctgta gcaatgccaa   6660
caacgttgcg caaactatta actggcgaac tacttactct agcttcccgg caacaattaa   6720
tagactggat ggaggcggat aaagttgcag gaccacttct gcgctcggcc cttccggctg   6780
gctggtttat tgctgataaa tctggagccg gtgagcgtgg gtctcgcggt atcattgcag   6840
cactggggcc agatggtaag ccctcccgta tcgtagttat ctacacgacg gggagtcagg   6900
caactatgga tgaacgaaat agacagatcg ctgagatagg tgcctcactg attaagcatt   6960
ggtaactgtc agaccaagtt tactcatata tactttagat tgatttaaaa cttcattttt   7020
aatttaaaag gatctaggtg aagatccttt ttgataatct catgaccaaa atcccttaac   7080
gtgagttttc gttccactga gcgtcagacc ccgtagaaaa gatcaaagga tcttcttgag   7140
atcctttttt tctgcgcgta atctgctgct tgcaaacaaa aaaaccaccg ctaccagcgg   7200
tggtttgttt gccggatcaa gagctaccaa ctcttttttcc gaaggtaact ggcttcagca  7260
gagcgcagat accaaatact gtccttctag tgtagccgta gttaggccac cacttcaaga   7320
actctgtagc accgcctaca tacctcgctc tgctaatcct gttaccagtg gctgctgcca   7380
gtggcgataa gtcgtgtctt accgggttgg actcaagacg atagttaccg gataaggcgc   7440
agcggtcggg ctgaacgggg ggttcgtgca cacagcccag cttggagcga acgacctaca   7500
```

-continued

```
ccgaactgag atacctacag cgtgagctat gagaaagcgc cacgcttccc gaagggagaa   7560

aggcggacag gtatccggta agcggcaggg tcggaacagg agagcgcacg agggagcttc   7620

caggggggaaa cgcctggtat ctttatagtc ctgtcgggtt tcgccacctc tgacttgagc   7680

gtcgattttt gtgatgctcg tcaggggggc ggagcctatg gaaaaacgcc agcaacgcgg   7740

cctttttacg gttcctggcc ttttgctggc cttttgctca catgttcttt cctgcgttat   7800

cccctgattc tgtggataac cgtattaccg cctttgagtg agctgatacc gctcgccgca   7860

gccgaacgac cgagcgcagc gagtcagtga gcgaggaagc ggaagagcgc ccaatacgca   7920

aaccgcctct ccccgcgcgt tggccgattc attaatgcag ctggcacgac aggtttcccg   7980

actggaaagc gggcagtgag cgcaacgcaa ttaatgtgag ttagctcact cattaggcac   8040

cccaggcttt acactttatg cttccggctc gtatgttgtg tggaattgtg agcggataac   8100

aatttcacac aggaaacagc tatgaccatg attacgccaa gctatttagg tgacactata   8160

gaatactcaa gctatgcatg agggtgcaat ttgagtggtt tcagtcccgt aatcgggatt   8220

tagtggttgg aaagaacgac aaggcttaca agggggtaat tcgtgatttg tttcagtccc   8280

gtaatcggga tttagtggtt ggaaagtagg caggggagtg aaatggtttc atgttgggct   8340

catgtttcag tcccgtaatc gggatttagt ggttggaaag cagtaagatg aaggaggtgg   8400

tgcatatcac ttgcgtttca gtcccgtaat cgggatttag tggttggaaa gctagatttg   8460

cttatagagt tgactgttat cgggacttgt ttcagtcccg taatcgggat ttagtggttg   8520

gaaagatgat ggcgttgcca gcgttctcgg attggagaat ttaacgtttc agtcccgtaa   8580

tcgggattta gtggttggaa agccctgaga agtttggctg ttttgctgac tgcgatctgg   8640

tttcagtccc gtaatcggga tttagtggtt ggaaagcatc gaggcagtag agcaaatcgc   8700

aggccacctc atagtttcag tcccgtaatc gggatttagt ggttggaaag tcattggggt   8760

ctgcattggg gccatcgcta tcgtcctgtt tcagtcccgt aatcgggatt tagtggttgg   8820

aaagtgggac gctccgtaag gtttggagaa tagggtctag tgtttcagtc ccgtaatcgg   8880

gatttagtgg ttggaaagca cttcgtcgct gattg                              8915
```

<210> SEQ ID NO 78
<211> LENGTH: 8883
<212> TYPE: DNA
<213> ORGANISM: Artificial
<220> FEATURE:
<223> OTHER INFORMATION: TK161¶AQ3-smtB-PsmtA-zmPDC_oop-PrbcL-
synADHdeg_oop

<400> SEQUENCE: 78

```
aattcttata ctgtcggtac ctatttagcg gagcggcttg tccagattgg tctcaagcat     60

cacttcgcag tcgcgggcga ctacaacctc gtccttcttg acaacctgct tttgaacaaa    120

aacatggagc aggtttattg ctgtaacgaa ctgaactgcg gtttcagtgc agaaggttat    180

gctcgtgcca aaggcgcagc agcagccgtc gttacctaca gcgtcggtgc gctttccgca    240

tttgatgcta tcggtggcgc ctatgcagaa aaccttccgg ttatcctgat ctccggtgct    300

ccgaacaaca atgatcacgc tgctggtcac gtgttgcatc acgctcttgg caaaaccgac    360

tatcactatc agttggaaat ggccaagaac atcacggccg cagctgaagc gatttacacc    420

ccagaagaag ctccggctaa aatcgatcac gtgattaaaa ctgctcttcg tgagaagaag    480

ccggtttatc tcgaaatcgc ttgcaacatt gcttccatgc cctgcgccgc tcctggaccg    540

gcaagcgcat tgttcaatga cgaagccagc gacgaagctt ctttgaatgc agcggttgaa    600
```

```
gaaaccctga aattcatcgc caaccgcgac aaagttgccg tcctcgtcgg cagcaagctg    660
cgcgcagctg gtgctgaaga agctgctgtc aaatttgctg atgctctcgg tggcgcagtt    720
gctaccatgg ctgctgcaaa aagcttcttc ccagaagaaa acccgcatta catcggtacc    780
tcatggggtg aagtcagcta tccgggcgtt gaaaagacga tgaaagaagc cgatgcggtt    840
atcgctctgg ctcctgtctt caacgactac tccaccactg gttggacgga tattcctgat    900
cctaagaaac tggttctcgc tgaaccgcgt tctgtcgtcg ttaacggcgt tcgcttcccc    960
agcgttcatc tgaaagacta tctgacccgt ttggctcaga aagtttccaa gaaaaccggt   1020
gctttggact tcttcaaatc cctcaatgca ggtgaactga agaaagccgc tccggctgat   1080
ccgagtgctc cgttggtcaa cgcagaaatc gcccgtcagg tcgaagctct tctgaccccg   1140
aacacgacgg ttattgctga aaccggtgac tcttggttca atgctcagcg catgaagctc   1200
ccgaacggtg ctcgcgttga atatgaaatg cagtggggtc acatcggttg gtccgttcct   1260
gccgccttcg gttatgccgt cggtgctccg gaacgtcgca acatcctcat ggttggtgat   1320
ggttccttcc agctgacggc tcaggaagtc gctcagatgg ttcgcctgaa actgccggtt   1380
atcatcttct tgatcaataa ctatggttac accatcgaag ttatgatcca tgatggtccg   1440
tacaacaaca tcaagaactg ggattatgcc ggtctgatgg aagtgttcaa cggtaacggt   1500
ggttatgaca gcggtgctgg taaaggcctg aaggctaaaa ccggtggcga actggcagaa   1560
gctatcaagg ttgctctggc aaacaccgac ggcccaaccc tgatcgaatg cttcatcggt   1620
cgtgaagact gcactgaaga attggtcaaa tggggtaagc gcgttgctgc cgccaacagc   1680
cgtaagcctg ttaacaagct cctctagttt ttggggatca attcgagctc ggtacccaaa   1740
ctagtaacgc tcggttgccg ccgggcgttt tttattccga catcaggaat tgtaattaga   1800
aagtccaaaa attgtaattt aaaaaacagt caatggagag cattgccata agtaaaggca   1860
tcccctgcgt gataagatta ccttcagaaa acagatagtt gctgggttat cgcagatttt   1920
tctcgcaacc aaataactgt aaataataac tgtctctggg gcgacggtag gctttatatt   1980
gccaaatttc gcccgtggga gaaagctagg ctattcaatg tttatggagg actgacccat   2040
atgatcaagg cttatgccgc tttagaggct aatggcaagt tgcagccgtt cgagtatgat   2100
ccgggcgctt taggcgccaa cgaagttgaa atcgaagttc aatactgcgg tgtttgtcat   2160
tccgacctca gtatgatcaa caatgagtgg ggtatcagta actatccgtt ggttcccggc   2220
cacgaagttg ttggcaccgt tgctgctatg ggtgagggtg ttaatcacgt ggaagttggt   2280
gacctggttg gtttaggctg gcacagtggt tattgtatga cttgtcactc ctgcctgagc   2340
ggttatcata atttgtgcgc taccgccgag agtactatcg ttggtcatta tggcggtttc   2400
ggtgaccgtg tgcgtgctaa aggtgtgtcc gttgttaagc tgcccaaggg tatcgatttg   2460
gcttccgctg gtccgttgtt ttgcggtggt atcactgtgt tttcccccat ggttgagtta   2520
tccctgaaac cgaccgccaa ggttgccgtt attggtatcg gtggtctcgg tcacctggcc   2580
gttcagttct tgcgtgcttg ggttgcgag gttaccgctt tcactagctc cgctcgtaaa    2640
cagaccgagg ttctggagct gggtgcccat catattttgg acagtactaa ccccgaagcc   2700
attgcttccg ccgagggtaa gttcgattac atcattagta ccgttaattt aaaattggat   2760
tggaatctgt atatttccac tttagccccg caaggtcact ttcatttcgt gggtgttgtt   2820
ctcgaacccc tcgacttgaa cttgttcccg ttgctcatgg gtcagcggag tgtgtccgct   2880
agtccggttg gctccccggc tactatcgct actatgctcg atttcgccgt tcggcacgat   2940
```

atcaagccgg ttgttgagca gttctccttc gaccaaatta atgaagccat tgctcacttg 3000
gagtccggta aggctcacta ccgtgtggtt ttgagtcact ccaagaactg aaacgctcgg 3060
ttgccgccgg gcgtttttta ttcctgcagg ccccccgggg gatccgtcga cctgcagggg 3120
ggggggggaa agccacgttg tgtctcaaaa tctctgatgt tacattgcac aagataaaaa 3180
tatatcatca tgaacaataa aactgtctgc ttacataaac agtaatacaa ggggtgttat 3240
gagccatatt caacgggaaa cgtcttgctc gaggccgcga ttaaattcca acatggatgc 3300
tgatttatat gggtataaat gggctcgcga taatgtcggg caatcaggtg cgacaatcta 3360
tcgattgtat gggaagcccg atgcgccaga gttgtttctg aaacatggca aaggtagcgt 3420
tgccaatgat gttacagatg agatggtcag actaaactgg ctgacggaat ttatgcctct 3480
tccgaccatc aagcatttta tccgtactcc tgatgatgca tggttactca ccactgcgat 3540
ccccgggaaa acagcattcc aggtattaga agaatatcct gattcaggtg aaaatattgt 3600
tgatgcgctg gcagtgttcc tgcgccggtt gcattcgatt cctgtttgta attgtccttt 3660
taacagcgat cgcgtatttc gtctcgctca ggcgcaatca cgaatgaata acggtttggt 3720
tgatgcgagt gattttgatg acgagcgtaa tggctggcct gttgaacaag tctggaaaga 3780
aatgcataag cttttgccat tctcaccgga ttcagtcgtc actcatggtg atttctcact 3840
tgataacctt atttttgacg aggggaaatt aataggttgt attgatgttg gacgagtcgg 3900
aatcgcagac cgataccagg atcttgccat cctatggaac tgcctcggtg agttttctcc 3960
ttcattacag aaacggcttt ttcaaaaata tggtattgat aatcctgata tgaataaatt 4020
gcagtttcat ttgatgctcg atgagttttt ctaatcagaa ttggttaatt ggttgtaaca 4080
ctggcagagc attacgctga cttgacggga cggcggcttt gttgaataaa tcgaactttt 4140
gctgagttga aggatcagat cacgcatctt cccgacaacg cagaccgttc cgtggcaaag 4200
caaaagttca aaatcaccaa ctggtccacc tacaacaaag ctctcatcaa ccgtggctcc 4260
ctcactttct ggctggatga tggggcgatt caggcctggt atgagtcagc aacaccttct 4320
tcacgaggca gacctcagcg cccccccccc cctgcaggtc gacggatcct ctagttctag 4380
agcggccgcc ctgccttgaa cgagaaagag ttatgacaaa ttaaaattct gactcttaga 4440
ttatttccag agaggctgat ttcccaatc tttgggaaag cctaagtttt tagattctat 4500
ttctggatac atctcaaaag ttctttttaa atgctgtgca aaattatgct ctggtttaat 4560
tctgtctaag agatactgaa tacaacataa gccagtgaaa attttacggc tgtttctttg 4620
attaatatcc tccaatactt ctctagagag ccattttcct tttaacctat caggcaattt 4680
aggtgattct cctagctgta tattccagag ccttgaatga tgagcgcaaa tatttctaat 4740
atgcgacaaa gaccgtaacc aagatataaa aaacttgtta ggtaattgga aatgagtatg 4800
tattttttgt cgtgtcttag atggtaataa atttgtgtac attctagata actgcccaaa 4860
ggcgattatc tccaaactag tgatggcggc cgggagcatg cgacgtcggg cccaattcgc 4920
cctatagtga gtcgtattac aattcactgg ccgtcgtttt acaacgtcgt gactgggaaa 4980
accctggcgt tacccaactt aatcgccttg cagcacatcc ccctttcgcc agctggcgta 5040
atagcgaaga ggcccgcacc gatcgccctt cccaacagtt gcgcagcctg aatggcgaat 5100
ggacgcgccc tgtagcggcg cattaagcgc ggcgggtgtg gtggttacgc gcagcgtgac 5160
cgctacactt gccagcgccc tagcgcccgc tcctttcgct ttcttccctt cctttctcgc 5220
cacgttcgcc ggctttcccc gtcaagctct aaatcggggg ctccctttag ggttccgatt 5280
tagagcttta cggcacctcg accgcaaaaa acttgatttg ggtgatggtt cacgtagtgg 5340

```
gccatcgccc tgatagacgg tttttcgccc tttgacgttg gagtccacgt tctttaatag   5400
tggactcttg ttccaaactg gaacaacact caaccctatc tcggtctatt cttttgattt   5460
ataagggatt ttgccgattt cggcctattg gttaaaaaat gagctgattt aacaaatatt   5520
taacgcgaat tttaacaaaa tattaacgtt tacaatttcg cctgatgcgg tattttctcc   5580
ttacgcatct gtgcggtatt tcacaccgca tacaggtggc acttttcggg gaaatgtgcg   5640
cggaacccct atttgtttat ttttctaaat acattcaaat atgtatccgc tcatgagaca   5700
ataaccctga taaatgcttc aataatattg aaaaaggaag agtatgagta ttcaacattt   5760
ccgtgtcgcc cttattccct tttttgcggc attttgcctt cctgtttttg ctcacccaga   5820
aacgctggtg aaagtaaaag atgctgaaga tcagttgggt gcacgagtgg gttacatcga   5880
actggatctc aacagcggta agatccttga gagttttcgc cccgaagaac gttttccaat   5940
gatgagcact tttaaagttc tgctatgtgg cgcggtatta tcccgtattg acgccgggca   6000
agagcaactc ggtcgccgca tacactattc tcagaatgac ttggttgagt actcaccagt   6060
cacagaaaag catcttacgg atggcatgac agtaagagaa ttatgcagtg ctgccataac   6120
catgagtgat aacactgcgg ccaacttact tctgacaacg atcggaggac cgaaggagct   6180
aaccgctttt ttgcacaaca tgggggatca tgtaactcgc cttgatcgtt gggaaccgga   6240
gctgaatgaa gccataccaa acgacgagcg tgacaccacg atgcctgtag caatgccaac   6300
aacgttgcgc aaactattaa ctggcgaact acttactcta gcttcccggc aacaattaat   6360
agactggatg gaggcggata aagttgcagg accacttctg cgctcggccc ttccggctgg   6420
ctggtttatt gctgataaat ctggagccgg tgagcgtggg tctcgcggta tcattgcagc   6480
actggggcca gatggtaagc cctcccgtat cgtagttatc tacacgacgg ggagtcaggc   6540
aactatggat gaacgaaata gacagatcgc tgagataggt gcctcactga ttaagcattg   6600
gtaactgtca gaccaagttt actcatatat actttagatt gatttaaaac ttcattttta   6660
atttaaaagg atctaggtga agatcctttt tgataatctc atgaccaaaa tcccttaacg   6720
tgagttttcg ttccactgag cgtcagaccc cgtagaaaag atcaaaggat cttcttgaga   6780
tccttttttt ctgcgcgtaa tctgctgctt gcaaacaaaa aaaccaccgc taccagcggt   6840
ggtttgtttg ccggatcaag agctaccaac tctttttccg aaggtaactg gcttcagcag   6900
agcgcagata ccaaatactg tccttctagt gtagccgtag ttaggccacc acttcaagaa   6960
ctctgtagca ccgcctacat acctcgctct gctaatcctg ttaccagtgg ctgctgccag   7020
tggcgataag tcgtgtctta ccgggttgga ctcaagacga tagttaccgg ataaggcgca   7080
gcggtcgggc tgaacggggg gttcgtgcac acagcccagc ttggagcgaa cgacctacac   7140
cgaactgaga tacctacagc gtgagctatg agaaagcgcc acgcttcccg aagggagaaa   7200
ggcggacagg tatccggtaa gcggcagggt cggaacagga gagcgcacga gggagcttcc   7260
agggggaaac gcctggtatc tttatagtcc tgtcgggttt cgccacctct gacttgagcg   7320
tcgatttttg tgatgctcgt caggggggcg gagcctatgg aaaaacgcca gcaacgcggc   7380
ctttttacgg ttcctggcct tttgctggcc ttttgctcac atgttctttc ctgcgttatc   7440
ccctgattct gtggataacc gtattaccgc ctttgagtga gctgataccg ctcgccgcag   7500
ccgaacgacc gagcgcagcg agtcagtgag cgaggaagcg gaagagcgcc caatacgcaa   7560
accgcctctc cccgcgcgtt ggccgattca ttaatgcagc tggcacgaca ggtttcccga   7620
ctggaaagcg ggcagtgagc gcaacgcaat taatgtgagt tagctcactc attaggcacc   7680
```

```
ccaggcttta cactttatgc ttccggctcg tatgttgtgt ggaattgtga gcggataaca   7740
atttcacaca ggaaacagct atgaccatga ttacgccaag ctatttaggt gacactatag   7800
aatactcaag ctatgcatcc acaacttttt gggatgctga tggtaaaccc atttccgccc   7860
aagaatttat cgaaaagcta tttggcgacc tgcccgacct cttcaaggat gaagccgaac   7920
tacgcaccat ctgggggaaa cccgataccc gtaaatcgtt cctgaccgga ctcgcggaaa   7980
aaggctacgg tgacacccaa ctgaaggcga tcgcacgcat tgccgaagcg gaaaaaagtg   8040
atgtctatga tgtcctgact tgggttgcct acaacaccaa acccattagc agagaagagc   8100
gagtaattaa gcatcgagat ctgattttct cgaagtacac cggaaagcag caagaatttt   8160
tagattttgt cctagaccaa tacattcgag aaggagtgga ggaacttgat cgggggaaac   8220
tgcctaccct catcgaaatc aaataccaaa ccgttaatga aggtttagtg atcttgggtc   8280
aggatatcgg tcaagtattc gcagattttc aggcggattt atataccgaa gatgtggcat   8340
aaaaaaggac ggcgatcgcc gggggcgttg cctgccttga acgaggtcga cgggcaaact   8400
ttatgaagca gatcaagcct atatccgcca agcaaccggc agccgcgttg attagtgggt   8460
gtgtccatcc tctggttcgt ctaggtgctc cgaagcgtca cgatagagat taagaatgtg   8520
gtgatccttg aggcgataaa tcacattccg cccttccttg cgatagctca ctaaacgtgc   8580
tgtgcgcagg gttcttagtt ggtgagagac agccgattca ctcatttcaa cggcggcggc   8640
gagttccccc acccgcatct ctccagtggc cagggccgaa agaatacgcc agcggttggc   8700
atcccccaag acaccaaaaa attcggccat ccgttgggcc ttggcttggt tcaagatttt   8760
gccactgtgg tctgtcattg ttcgctgatc taaacaatac ctgaataatt gttcatgtgt   8820
taatctaaaa atgtgaacaa tcgttcaact atttaagaca ataccttgga ggtttaaacc   8880
atg                                                                 8883
```

<210> SEQ ID NO 79
<211> LENGTH: 9000
<212> TYPE: DNA
<213> ORGANISM: Artificial
<220> FEATURE:
<223> OTHER INFORMATION: TK165¶AQ1-smtB-PsmtA-zmPDC_oop-PrbcL-synADHdeg_oop

<400> SEQUENCE: 79

```
tcgacgggca aactttatga agcagatcaa gcctatatcc gccaagcaac cggcagccgc     60
gttgattagt gggtgtgtcc atcctctggt tcgtctaggt gctccgaagc gtcacgatag    120
agattaagaa tgtggtgatc cttgaggcga taaatcacat tccgcccttc cttgcgatag    180
ctcactaaac gtgctgtgcg cagggttctt agttggtgag agacagccga ttcactcatt    240
tcaacggcgg cggcgagttc ccccacccgc atctctccag tggccagggc cgaaagaata    300
cgccagcggt tggcatcccc caagacacca aaaaattcgg ccatccgttg ggccttggct    360
tggttcaaga ttttgccact gtggtctgtc attgttcgct gatctaaaca atacctgaat    420
aattgttcat gtgttaatct aaaaatgtga acaatcgttc aactatttaa gacaatacct    480
tggaggttta aaccatgaat tcttatactg tcggtaccta tttagcggag cggcttgtcc    540
agattggtct caagcatcac ttcgcagtcg cgggcgacta caacctcgtc cttcttgaca    600
acctgctttt gaacaaaaac atggagcagg tttattgctg taacgaactg aactgcggtt    660
tcagtgcaga aggttatgct cgtgccaaag gcgcagcagc agccgtcgtt acctacagcg    720
tcggtgcgct ttccgcattt gatgctatcg gtggcgccta tgcagaaaac cttccggtta    780
```

-continued

```
tcctgatctc cggtgctccg aacaacaatg atcacgctgc tggtcacgtg ttgcatcacg    840
ctcttggcaa aaccgactat cactatcagt tggaaatggc caagaacatc acggccgcag    900
ctgaagcgat ttacacccca gaagaagctc cggctaaaat cgatcacgtg attaaaactg    960
ctcttcgtga gaagaagccg gtttatctcg aaatcgcttg caacattgct tccatgccct   1020
gcgccgctcc tggaccggca agcgcattgt tcaatgacga agccagcgac gaagcttctt   1080
tgaatgcagc ggttgaagaa accctgaaat tcatcgccaa ccgcgacaaa gttgccgtcc   1140
tcgtcggcag caagctgcgc gcagctggtg ctgaagaagc tgctgtcaaa tttgctgatg   1200
ctctcggtgg cgcagttgct accatggctg ctgcaaaaag cttcttccca gaagaaaacc   1260
cgcattacat cggtacctca tggggtgaag tcagctatcc gggcgttgaa aagacgatga   1320
aagaagccga tgcggttatc gctctggctc ctgtcttcaa cgactactcc accactggtt   1380
ggacggatat tcctgatcct aagaaactgg ttctcgctga accgcgttct gtcgtcgtta   1440
acggcgttcg cttccccagc gttcatctga aagactatct gacccgtttg gctcagaaag   1500
tttccaagaa aaccggtgct ttggacttct tcaaatccct caatgcaggt gaactgaaga   1560
aagccgctcc ggctgatccg agtgctccgt tggtcaacgc agaaatcgcc cgtcaggtcg   1620
aagctcttct gaccccgaac acgacggtta ttgctgaaac cggtgactct tggttcaatg   1680
ctcagcgcat gaagctcccg aacggtgctc gcgttgaata tgaaatgcag tggggtcaca   1740
tcggttggtc cgttcctgcc gccttcggtt atgccgtcgg tgctccggaa cgtcgcaaca   1800
tcctcatggt tggtgatggt tccttccagc tgacggctca ggaagtcgct cagatggttc   1860
gcctgaaact gccggttatc atcttcttga tcaataacta tggttacacc atcgaagtta   1920
tgatccatga tggtccgtac aacaacatca agaactggga ttatgccggt ctgatggaag   1980
tgttcaacgg taacggtggt tatgacagcg gtgctggtaa aggcctgaag gctaaaaccg   2040
gtggcgaact ggcagaagct atcaaggttg ctctggcaaa caccgacggc ccaaccctga   2100
tcgaatgctt catcggtcgt gaagactgca ctgaagaatt ggtcaaatgg ggtaagcgcg   2160
ttgctgccgc caacagccgt aagcctgtta acaagctcct ctagtttttg ggatcaatt    2220
cgagctcggt acccaaacta gtaacgctcg gttgccgccg ggcgtttttt attccgacat   2280
caggaattgt aattagaaag tccaaaaatt gtaatttaaa aaacagtcaa tggagagcat   2340
tgccataagt aaaggcatcc cctgcgtgat aagattacct tcagaaaaca gatagttgct   2400
gggttatcgc agatttttct cgcaaccaaa taactgtaaa taataactgt ctctggggcg   2460
acggtaggct ttatattgcc aaatttcgcc cgtgggagaa agctaggcta ttcaatgttt   2520
atggaggact gacccatatg atcaaggctt atgccgcttt agaggctaat ggcaagttgc   2580
agccgttcga gtatgatccg ggcgctttag gcgccaacga agttgaaatc gaagttcaat   2640
actgcggtgt ttgtcattcc gacctcagta tgatcaacaa tgagtggggt atcagtaact   2700
atccgttggt tcccggccac gaagttgttg gcaccgttgc tgctatgggt gagggtgtta   2760
atcacgtgga agttggtgac ctggttggtt taggctggca cagtggttat tgtatgactt   2820
gtcactcctg cctgagcggt tatcataatt tgtgcgctac cgccgagagt actatcgttg   2880
gtcattatgg cggtttcggt gaccgtgtgc gtgctaaagg tgtgtccgtt gttaagctgc   2940
ccaagggtat cgatttggct tccgctggtc cgttgttttg cggtggtatc actgtgtttt   3000
cccccatggt tgagttatcc ctgaaaccga ccgccaaggt tgccgttatt ggtatcggtg   3060
gtctcggtca cctggccgtt cagttcttgc gtgcttgggg ttgcgaggtt accgctttca   3120
ctagctccgc tcgtaaacag accgaggttc tggagctggg tgcccatcat attttggaca   3180
```

gtactaaccc cgaagccatt gcttccgccg agggtaagtt cgattacatc attagtaccg 3240
ttaatttaaa attggattgg aatctgtata tttccacttt agccccgcaa ggtcactttc 3300
atttcgtggg tgttgttctc gaacccctcg acttgaactt gttcccgttg ctcatgggtc 3360
agcggagtgt gtccgctagt ccggttggct ccccggctac tatcgctact atgctcgatt 3420
tcgccgttcg gcacgatatc aagccggttg ttgagcagtt ctccttcgac caaattaatg 3480
aagccattgc tcacttggag tccggtaagg ctcactaccg tgtggttttg agtcactcca 3540
agaactgaaa cgctcggttg ccgccgggcg ttttttattc ctgcaggccc cccgggggat 3600
ccgtcgacct gcaggggggg gggggaaagc cacgttgtgt ctcaaaatct ctgatgttac 3660
attgcacaag ataaaaatat atcatcatga acaataaaac tgtctgctta cataaacagt 3720
aatacaaggg gtgttatgag ccatattcaa cgggaaacgt cttgctcgag gccgcgatta 3780
aattccaaca tggatgctga tttatatggg tataaatggg ctcgcgataa tgtcgggcaa 3840
tcaggtgcga caatctatcg attgtatggg aagcccgatg cgccagagtt gtttctgaaa 3900
catggcaaag gtagcgttgc caatgatgtt acagatgaga tggtcagact aaactggctg 3960
acggaattta tgcctcttcc gaccatcaag cattttatcc gtactcctga tgatgcatgg 4020
ttactcacca ctgcgatccc cgggaaaaca gcattccagg tattagaaga atatcctgat 4080
tcaggtgaaa atattgttga tgcgctggca gtgttcctgc gccggttgca ttcgattcct 4140
gtttgtaatt gtccttttaa cagcgatcgc gtatttcgtc tcgctcaggc gcaatcacga 4200
atgaataacg gtttggttga tgcgagtgat tttgatgacg agcgtaatgg ctggcctgtt 4260
gaacaagtct ggaaagaaat gcataagctt ttgccattct caccggattc agtcgtcact 4320
catggtgatt tctcacttga taaccttatt tttgacgagg ggaaattaat aggttgtatt 4380
gatgttggac gagtcggaat cgcagaccga taccaggatc ttgccatcct atggaactgc 4440
ctcggtgagt tttctccttc attacagaaa cggctttttc aaaaatatgg tattgataat 4500
cctgatatga ataaattgca gtttcatttg atgctcgatg agtttttcta atcagaattg 4560
gttaattggt tgtaacactg gcagagcatt acgctgactt gacgggacgg cggctttgtt 4620
gaataaatcg aacttttgct gagttgaagg atcagatcac gcatcttccc gacaacgcag 4680
accgttccgt ggcaaagcaa aagttcaaaa tcaccaactg gtccacctac aacaaagctc 4740
tcatcaaccg tggctccctc actttctggc tggatgatgg ggcgattcag gcctggtatg 4800
agtcagcaac accttcttca cgaggcagac ctcagcgccc ccccccccct gcaggtcgac 4860
ggatcctcta gttctagagc ggccgctgga atttcccgat tctctgatgg gagatccaaa 4920
aattctcgca gtccctcaat cacgatatcg gtcttggatc gccctgtagc ttccgacaac 4980
tgctcaattt tttcgagcat ctctaccggg catcggaatg aaattaacgg tgttttagcc 5040
atgtgttata cagtgtttac aacttgacta acaaatacct gctagtgtat acatattgta 5100
ttgcaatgta tacgctattt tcactgctgt ctttaatggg gattatcgca agcaagtaaa 5160
aaagcctgaa aaccccaata ggtaagggat tccgagctta ctcgataatt atcacctttg 5220
agcgccccta ggaggaggcg aaaagctatg tctgacaagg ggtttgaccc ctgaagtcgt 5280
tgcgcgagca ttaaggtctg cggatagccc ataacatact tttgttgaac ttgtgcgctt 5340
ttatcaaccc cttaagggct tgggagcgtt ttatacgagt gcggggaact agtgatggcg 5400
gccgggagca tgcgacgtcg ggcccaattc gccctatagt gagtcgtatt acaattcact 5460
ggccgtcgtt ttacaacgtc gtgactggga aaaccctggc gttacccaac ttaatcgcct 5520

-continued tgcagcacat ccccctttcg ccagctggcg taatagcgaa gaggcccgca ccgatcgccc 5580
ttcccaacag ttgcgcagcc tgaatggcga atggacgcgc cctgtagcgg cgcattaagc 5640
gcggcgggtg tggtggttac gcgcagcgtg accgctacac ttgccagcgc cctagcgccc 5700
gctcctttcg ctttcttccc ttcctttctc gccacgttcg ccggctttcc ccgtcaagct 5760
ctaaatcggg ggctcccttt agggttccga tttagagctt tacggcacct cgaccgcaaa 5820
aaacttgatt tgggtgatgg ttcacgtagt gggccatcgc cctgatagac ggtttttcgc 5880
cctttgacgt tggagtccac gttctttaat agtggactct tgttccaaac tggaacaaca 5940
ctcaacccta tctcggtcta ttcttttgat ttataaggga ttttgccgat ttcggcctat 6000
tggttaaaaa atgagctgat ttaacaaata tttaacgcga attttaacaa aatattaacg 6060
tttacaattt cgcctgatgc ggtattttct ccttacgcat ctgtgcggta tttcacaccg 6120
catacaggtg gcacttttcg gggaaatgtg cgcggaaccc ctatttgttt atttttctaa 6180
atacattcaa atatgtatcc gctcatgaga caataaccct gataaatgct tcaataatat 6240
tgaaaaagga agagtatgag tattcaacat ttccgtgtcg cccttattcc cttttttgcg 6300
gcattttgcc ttcctgtttt tgctcaccca gaaacgctgg tgaaagtaaa agatgctgaa 6360
gatcagttgg gtgcacgagt gggttacatc gaactggatc tcaacagcgg taagatcctt 6420
gagagttttc gccccgaaga acgttttcca atgatgagca cttttaaagt tctgctatgt 6480
ggcgcggtat tatcccgtat tgacgccggg caagagcaac tcggtcgccg catacactat 6540
tctcagaatg acttggttga gtactcacca gtcacagaaa agcatcttac ggatggcatg 6600
acagtaagag aattatgcag tgctgccata accatgagtg ataacactgc ggccaactta 6660
cttctgacaa cgatcggagg accgaaggag ctaaccgctt ttttgcacaa catgggggat 6720
catgtaactc gccttgatcg ttgggaaccg gagctgaatg aagccatacc aaacgacgag 6780
cgtgacacca cgatgcctgt agcaatggca acaacgttgc gcaaactatt aactggcgaa 6840
ctacttactc tagcttcccg gcaacaatta atagactgga tggaggcgga taaagttgca 6900
ggaccacttc tgcgctcggc ccttccggct ggctggttta ttgctgataa atctggagcc 6960
ggtgagcgtg ggtctcgcgg tatcattgca gcactggggc cagatggtaa gccctcccgt 7020
atcgtagtta tctacacgac ggggagtcag gcaactatgg atgaacgaaa tagacagatc 7080
gctgagatag gtgcctcact gattaagcat tggtaactgt cagaccaagt ttactcatat 7140
atactttaga ttgatttaaa acttcatttt taatttaaaa ggatctaggt gaagatcctt 7200
tttgataatc tcatgaccaa aatcccttaa cgtgagtttt cgttccactg agcgtcagac 7260
cccgtagaaa agatcaaagg atcttcttga gatccttttt ttctgcgcgt aatctgctgc 7320
ttgcaaacaa aaaaaccacc gctaccagcg gtggtttgtt tgccggatca agagctacca 7380
actctttttc cgaaggtaac tggcttcagc agagcgcaga taccaaatac tgtccttcta 7440
gtgtagccgt agttaggcca ccacttcaag aactctgtag caccgcctac atacctcgct 7500
ctgctaatcc tgttaccagt ggctgctgcc agtggcgata agtcgtgtct taccgggttg 7560
gactcaagac gatagttacc ggataaggcg cagcggtcgg gctgaacggg gggttcgtgc 7620
acacagccca gcttggagcg aacgacctac accgaactga gatacctaca gcgtgagcta 7680
tgagaaagcg ccacgcttcc cgaagggaga aaggcggaca ggtatccggt aagcggcagg 7740
gtcggaacag gagagcgcac gagggagctt ccagggggaa acgcctggta tctttatagt 7800
cctgtcgggt ttcgccacct ctgacttgag cgtcgatttt tgtgatgctc gtcagggggg 7860
cggagcctat ggaaaaacgc cagcaacgcg gcctttttac ggttcctggc cttttgctgg 7920

```
ccttttgctc acatgttctt tcctgcgtta tcccctgatt ctgtggataa ccgtattacc   7980
gcctttgagt gagctgatac cgctcgccgc agccgaacga ccgagcgcag cgagtcagtg   8040
agcgaggaag cggaagagcg cccaatacgc aaaccgcctc tccccgcgcg ttggccgatt   8100
cattaatgca gctggcacga caggtttccc gactggaaag cgggcagtga gcgcaacgca   8160
attaatgtga gttagctcac tcattaggca ccccaggctt tacactttat gcttccggct   8220
cgtatgttgt gtggaattgt gagcggataa caatttcaca caggaaacag ctatgaccat   8280
gattacgcca agctatttag gtgacactat agaatactca agctatgcat ctccaacatg   8340
agggctttgt atttaagccg gatatcaaca ggcgatcgct ctcaccaaag attcacctgt   8400
tagagctact caacatccat cagttcttaa aaccaggggt gacattcacc ggggcgagcc   8460
ttgaagggtt caaggaaaat tgtttgcggt atgccaagcc gatcaagtgg attcttggca   8520
gaacgatcac cgacaaaatg agcccgctcg aaattgctca ggcgctccta ggcaagcttg   8580
accggaaatt ggaatacaag gggcgctttg gatcgcggga taaccgtcag cgggtctatg   8640
aggcgatcgc ccctaacgat cagcgcgaaa aggtctttgc tcattggtta cagcgtgacc   8700
aagcaaaatt aggggccgtg tccaacccct gtataaatag atttattcag gaggcttaga   8760
cccgtgatcg aaatactcgt tgtgcagctc tcccttggca atcccaaaca atctcaagat   8820
ttgctctgcg gtatcgggac gttttatgcc cttgcggaaa gcgcctttgc tcttctggta   8880
gcccctagac tgtgccagat cataagcctc actgagggtg agggcactac cgggggcatg   8940
agctcgccca agagattcag cgaccggggc gatcgccctt ggtaattctc tcaggcgctg   9000
```

```
<210> SEQ ID NO 80
<211> LENGTH: 8895
<212> TYPE: DNA
<213> ORGANISM: Artificial
<220> FEATURE:
<223> OTHER INFORMATION: #1468¶AQ1-ziaR-PziaA-zmPDC-Prbc*-synADH_oop
      standard

<400> SEQUENCE: 80
```

```
tcgacctcct taatccgatt cctgcaaatg gtctgcaact tcccgataca aattcatcac     60
atgattatcc gccaagctgt agtaaacatt acggccgacc cggcgatact ttaccaggcg    120
ctgcgatcgt aaaattcgta attgatggga aactgccgat tcactcactt tcatcgccgc    180
tgctaaatca cagacacaga gttcttggcg ggccaatgcc gacattaaac gcaaccgact    240
cggatcagct agtgcactga aaaactccgc catttgctgg gcctggtcca atgacatcac    300
ctctggttga acctgtcgta cctgctcaag atgaacaaga ggttgatcac aaaggggcat    360
ctcttcgttc tggcaggatt gtgactttga caacgaggac ttactcatag aggttggcgt    420
taggagctag ggaaaaattt aaactggatt tagaaaatga ttttcatcct aacatcttta    480
atatctgagc atatcttcag gtgtttcaag atttgtgcta cggttcaagg aggtttttct    540
ttaaatcacg ttggccgcca tgtctatgaa ttcttatact gtcggtacct atttagcgga    600
gcggcttgtc cagattggtc tcaagcatca cttcgcagtc gcgggcgact acaacctcgt    660
ccttcttgac aacctgcttt tgaacaaaaa catggagcag gtttattgct gtaacgaact    720
gaactgcggt ttcagtgcag aaggttatgc tcgtgccaaa ggcgcagcag cagccgtcgt    780
tacctacagc gtcggtgcgc tttccgcatt tgatgctatc ggtggcgcct atgcagaaaa    840
ccttccggtt atcctgatct ccggtgctcc gaacaacaat gatcacgctg ctggtcacgt    900
gttgcatcac gctcttggca aaaccgacta tcactatcag ttggaaatgg ccaagaacat    960
```

-continued

```
cacggccgca gctgaagcga tttacacccc agaagaagct ccggctaaaa tcgatcacgt   1020
gattaaaact gctcttcgtg agaagaagcc ggtttatctc gaaatcgctt gcaacattgc   1080
ttccatgccc tgcgccgctc ctggaccggc aagcgcattg ttcaatgacg aagccagcga   1140
cgaagcttct ttgaatgcag cggttgaaga aaccctgaaa ttcatcgcca accgcgacaa   1200
agttgccgtc ctcgtcggca gcaagctgcg cgcagctggt gctgaagaag ctgctgtcaa   1260
atttgctgat gctctcggtg gcgcagttgc taccatggct gctgcaaaaa gcttcttccc   1320
agaagaaaac ccgcattaca tcggtacctc atggggtgaa gtcagctatc cgggcgttga   1380
aaagacgatg aaagaagccg atgcggttat cgctctggct cctgtcttca acgactactc   1440
caccactggt tggacggata ttcctgatcc taagaaactg gttctcgctg aaccgcgttc   1500
tgtcgtcgtt aacggcgttc gcttccccag cgttcatctg aaagactatc tgacccgttt   1560
ggctcagaaa gtttccaaga aaaccggtgc tttggacttc ttcaaatccc tcaatgcagg   1620
tgaactgaag aaagccgctc cggctgatcc gagtgctccg ttggtcaacg cagaaatcgc   1680
ccgtcaggtc gaagctcttc tgaccccgaa cacgacggtt attgctgaaa ccggtgactc   1740
ttggttcaat gctcagcgca tgaagctccc gaacggtgct cgcgttgaat atgaaatgca   1800
gtggggtcac atcggttggt ccgttcctgc cgccttcggt tatgccgtcg gtgctccgga   1860
acgtcgcaac atcctcatgg ttggtgatgg ttccttccag ctgacggctc aggaagtcgc   1920
tcagatggtt cgcctgaaac tgccggttat catcttcttg atcaataact atggttacac   1980
catcgaagtt atgatccatg atggtccgta caacaacatc aagaactggg attatgccgg   2040
tctgatggaa gtgttcaacg gtaacggtgg ttatgacagc ggtgctggta aaggcctgaa   2100
ggctaaaacc ggtggcgaac tggcagaagc tatcaaggtt gctctggcaa acaccgacgg   2160
cccaaccctg atcgaatgct tcatcggtcg tgaagactgc actgaagaat tggtcaaatg   2220
ggtaagcgc gttgctgccg ccaacagccg taagcctgtt aacaagctcc tctagttttt    2280
ggggatcaat tcgagctcac tagtcgatcg acattgccat aagtaaaggc atcccctgcg   2340
tgataagatt accttcagtt tatggaggac tgaccatatg attaaagcct acgctgccct   2400
ggaagccaac ggaaaactcc aaccctttga atacgacccc ggtgccctgg gtgctaatga   2460
ggtggagatt gaggtgcagt attgtggggt gtgccacagt gatttgtcca tgattaataa   2520
cgaatggggc atttccaatt acccccctagt gccgggtcat gaggtggtgg gtactgtggc   2580
cgccatgggc gaaggggtga accatgttga ggtgggggat ttagtggggc tgggttggca   2640
ttcgggctac tgcatgacct gccatagttg tttatctggc taccacaacc tttgtgccac   2700
ggcggaatcg accattgtgg gccactacgg tggctttggc gatcgggttc gggccaaggg   2760
agtcagcgtg gtgaaattac ctaaaggcat tgacctagcc agtgccgggc ccctttttctg   2820
tggaggaatt accgttttca gtcctatggt ggaactgagt ttaaagccca ctgcaaaagt   2880
ggcagtgatc ggcattgggg gcttgggcca tttagcggtg caatttctcc gggcctgggg   2940
ctgtgaagtg actgccttta cctccagtgc caggaagcaa acggaagtgt tggaattggg   3000
cgctcaccac atactagatt ccaccaatcc agaggcgatc gccagtgcgg aaggcaaatt   3060
tgactatatt atctccactg tgaacctgaa gcttgactgg aacttataca tcagcaccct   3120
ggcgccccag ggacatttcc actttgttgg ggtggtgttg gagcctttgg atctaaatct   3180
ttttcccctt ttgatgggac aacgctccgt ttctgcctcc ccagtgggta gtcccgccac   3240
cattgccacc atgttggact ttgctgtgcg ccatgacatt aaacccgtgg tggaacaatt   3300
```

-continued

```
tagctttgat cagatcaacg aggcgatcgc ccatctagaa agcggcaaag cccattatcg   3360
ggtagtgctc agccatagta aaaattagct ctgcaaaggt tgcttctggg tccgtggaac   3420
gctcggttgc cgccgggcgt tttttattcc tgcagccttg ctctagaaga acagcaaggc   3480
cgccaatgcc tgacgatgcg tggagaccga aaccttgcgc tcgttcgcca gccaggacag   3540
aaatgcctcg acttcgctgc tgcccaaggt tgccgggtga cgcacaccgt ggaaacggat   3600
gaaggcacga acccagtgga cataagcctg ttcggttcgt aagctgtaat gcaagtagcg   3660
tatgcgctca cgcaactggt ccagaacctt gaccgaacgc agcggtggta acggcgcagt   3720
ggcggttttc atggcttgtt atgactgttt ttttggggta cagtctatgc ctcgggcatc   3780
caagcagcaa gcgcgttacg ccgtgggtcg atgtttgatg ttatggagca gcaacgatgt   3840
tacgcagcag ggcagtcgcc ctaaaacaaa gttaaacatc atgagggaag cggtgatcgc   3900
cgaagtatcg actcaactat cagaggtagt tggcgtcatc gagcgccatc tcgaaccgac   3960
gttgctggcc gtacatttgt acggctccgc agtggatggc ggcctgaagc cacacagtga   4020
tattgatttg ctggttacgg tgaccgtaag gcttgatgaa acaacgcggc gagctttgat   4080
caacgacctt ttggaaactt cggcttcccc tggagagagc gagattctcc gcgctgtaga   4140
agtcaccatt gttgtgcacg acgacatcat tccgtggcgt tatccagcta agcgcgaact   4200
gcaatttgga gaatggcagc gcaatgacat tcttgcaggt atcttcgagc cagccacgat   4260
cgacattgat ctggctatct tgctgacaaa agcaagagaa catagcgttg ccttggtagg   4320
tccagcggcg gaggaactct ttgatccggt tcctgaacag gatctatttg aggcgctaaa   4380
tgaaacctta acgctatgga actcgccgcc cgactgggct ggcgatgagc gaaatgtagt   4440
gcttacgttg tcccgcattt ggtacagcgc agtaaccggc aaaatcgcgc cgaaggatgt   4500
cgctgccgac tgggcaatgg agcgcctgcc ggcccagtat cagcccgtca tacttgaagc   4560
tagacaggct tatcttggac aagaagaaga tcgcttggcc tcgcgcgcag atcagttgga   4620
agaatttgtc cactacgtga aaggcgagat caccaaggta gtcggcaaat aatgtctaac   4680
aattcgttca agccgacgcc gcttcgcggc gcggcttaac tcaagcgtta gatgcactac   4740
cggtatcttt ctagaagatc ctctagttct agagcggccg ctggaatttc ccgattctct   4800
gatgggagat ccaaaaattc tcgcagtccc tcaatcacga tatcggtctt ggatcgccct   4860
gtagcttccg acaactgctc aatttttttcg agcatctcta ccgggcatcg gaatgaaatt   4920
aacggtgttt tagccatgtg ttatacagtg tttacaactt gactaacaaa tacctgctag   4980
tgtatacata ttgtattgca atgtatacgc tattttcact gctgtcttta atggggatta   5040
tcgcaagcaa gtaaaaaagc ctgaaaaccc caataggtaa gggattccga gcttactcga   5100
taattatcac ctttgagcgc ccctaggagg aggcgaaaag ctatgtctga caaggggttt   5160
gacccctgaa gtcgttgcgc gagcattaag gtctgcggat agcccataac atacttttgt   5220
tgaacttgtg cgcttttatc aaccccttaa gggcttggga gcgttttata cgagtgcggg   5280
gaactagtga tggcggccgg gagcatgcga cgtcgggccc aattcgccct atagtgagtc   5340
gtattacaat tcactggccg tcgttttaca acgtcgtgac tgggaaaacc ctggcgttac   5400
ccaacttaat cgccttgcag cacatccccc tttcgccagc tggcgtaata gcgaagaggc   5460
ccgcaccgat cgcccttccc aacagttgcg cagcctgaat ggcgaatgga cgcgccctgt   5520
agcggcgcat taagcgcggc gggtgtggtg gttacgcgca gcgtgaccgc tacacttgcc   5580
agcgccctag cgcccgctcc tttcgctttc ttcccttcct ttctcgccac gttcgccggc   5640
tttccccgtc aagctctaaa tcgggggctc cctttagggt tccgatttag agctttacgg   5700
```

```
cacctcgacc gcaaaaaact tgatttgggt gatggttcac gtagtgggcc atcgccctga   5760
tagacggttt ttcgcccttt gacgttggag tccacgttct ttaatagtgg actcttgttc   5820
caaactggaa caacactcaa ccctatctcg gtctattctt ttgatttata agggattttg   5880
ccgatttcgg cctattggtt aaaaaatgag ctgatttaac aaatatttaa cgcgaatttt   5940
aacaaaatat taacgtttac aatttcgcct gatgcggtat tttctcctta cgcatctgtg   6000
cggtatttca caccgcatac aggtggcact tttcggggaa atgtgcgcgg aacccctatt   6060
tgtttatttt tctaaataca ttcaaatatg tatccgctca tgagacaata accctgataa   6120
atgcttcaat aatattgaaa aaggaagagt atgagtattc aacatttccg tgtcgccctt   6180
attccctttt ttgcggcatt ttgccttcct gtttttgctc acccagaaac gctggtgaaa   6240
gtaaaagatg ctgaagatca gttgggtgca cgagtgggtt acatcgaact ggatctcaac   6300
agcggtaaga tccttgagag ttttcgcccc gaagaacgtt ttccaatgat gagcactttt   6360
aaagttctgc tatgtggcgc ggtattatcc cgtattgacg ccgggcaaga gcaactcggt   6420
cgccgcatac actattctca gaatgacttg gttgagtact caccagtcac agaaaagcat   6480
cttacggatg gcatgacagt aagagaatta tgcagtgctg ccataaccat gagtgataac   6540
actgcggcca acttacttct gacaacgatc ggaggaccga aggagctaac cgcttttttg   6600
cacaacatgg gggatcatgt aactcgcctt gatcgttggg aaccggagct gaatgaagcc   6660
ataccaaacg acgagcgtga caccacgatg cctgtagcaa tgccaacaac gttgcgcaaa   6720
ctattaactg gcgaactact tactctagct tcccggcaac aattaataga ctggatggag   6780
gcggataaag ttgcaggacc acttctgcgc tcggcccttc cggctggctg gtttattgct   6840
gataaatctg gagccggtga gcgtgggtct cgcggtatca ttgcagcact ggggccagat   6900
ggtaagccct cccgtatcgt agttatctac acgacgggga gtcaggcaac tatggatgaa   6960
cgaaatagac agatcgctga gataggtgcc tcactgatta agcattggta actgtcagac   7020
caagtttact catatatact ttagattgat ttaaaacttc atttttaatt taaaaggatc   7080
taggtgaaga tcctttttga taatctcatg accaaaatcc cttaacgtga gttttcgttc   7140
cactgagcgt cagaccccgt agaaaagatc aaaggatctt cttgagatcc tttttttctg   7200
cgcgtaatct gctgcttgca aacaaaaaaa ccaccgctac cagcggtggt ttgtttgccg   7260
gatcaagagc taccaactct ttttccgaag gtaactggct tcagcagagc gcagatacca   7320
aatactgtcc ttctagtgta gccgtagtta ggccaccact tcaagaactc tgtagcaccg   7380
cctacatacc tcgctctgct aatcctgtta ccagtggctg ctgccagtgg cgataagtcg   7440
tgtcttaccg ggttggactc aagacgatag ttaccggata aggcgcagcg gtcgggctga   7500
acggggggtt cgtgcacaca gcccagcttg gagcgaacga cctacaccga actgagatac   7560
ctacagcgtg agctatgaga aagcgccacg cttcccgaag ggagaaaggc ggacaggtat   7620
ccggtaagcg gcagggtcgg aacaggagag cgcacgaggg agcttccagg gggaaacgcc   7680
tggtatcttt atagtcctgt cgggtttcgc cacctctgac ttgagcgtcg atttttgtga   7740
tgctcgtcag gggggcggag cctatggaaa aacgccagca acgcggcctt tttacggttc   7800
ctggcctttt gctggccttt tgctcacatg ttctttcctg cgttatcccc tgattctgtg   7860
gataaccgta ttaccgcctt tgagtgagct gataccgctc gccgcagccg aacgaccgag   7920
cgcagcgagt cagtgagcga ggaagcggaa gagcgcccaa tacgcaaacc gcctctcccc   7980
gcgcgttggc cgattcatta atgcagctgg cacgacaggt ttcccgactg gaaagcgggc   8040
```

```
agtgagcgca acgcaattaa tgtgagttag ctcactcatt aggcacccca ggctttacac   8100

tttatgcttc cggctcgtat gttgtgtgga attgtgagcg gataacaatt tcacacagga   8160

aacagctatg accatgatta cgccaagcta tttaggtgac actatagaat actcaagcta   8220

tgcatctcca acatgagggc tttgtattta agccggatat caacaggcga tcgctctcac   8280

caaagattca cctgttagag ctactcaaca tccatcagtt cttaaaacca ggggtgacat   8340

tcaccggggc gagccttgaa gggttcaagg aaaattgttt gcggtatgcc aagccgatca   8400

agtggattct tggcagaacg atcaccgaca aaatgagccc gctcgaaatt gctcaggcgc   8460

tcctaggcaa gcttgaccgg aaattggaat acaaggggcg ctttggatcg cgggataacc   8520

gtcagcgggt ctatgaggcg atcgccccta acgatcagcg cgaaaaggtc tttgctcatt   8580

ggttacagcg tgaccaagca aaattagggg ccgtgtccaa cccctgtata aatagattta   8640

ttcaggaggc ttagacccgt gatcgaaata ctcgttgtgc agctctccct tggcaatccc   8700

aaacaatctc aagatttgct ctgcggtatc gggacgtttt atgcccttgc ggaaagcgcc   8760

tttgctcttc tggtagcccc tagactgtgc cagatcataa gcctcactga gggtgagggc   8820

actaccgggg gcatgagctc gcccaagaga ttcagcgacc ggggcgatcg cccttggtaa   8880

ttctctcagg cgctg                                                    8895
```

<210> SEQ ID NO 81
<211> LENGTH: 9513
<212> TYPE: DNA
<213> ORGANISM: Artificial
<220> FEATURE:
<223> OTHER INFORMATION: #1332¶GEM-AQ4::corR-PcorT-zpPDC*_ter-PrbcL*-synADH_oop-Nm standard

<400> SEQUENCE: 81

```
tcgaccatgc gtccaaaact ttcaccatcc tttccctatc aacctttact gcactaaaga     60

caagtgagat agcagtggca atctggcttt gcaatcaatg tttccactaa agcgtttagc    120

gttactgcgg ctagaagtcc tccaccgagg ctcccctgaa tggtgatatg gggaatggga    180

ctggtcatca gtcgtcgttt tgcccccgga gcatgactaa aaccgatcgg cattccgatc    240

acaagagccg gctgaatatg ttgttgctct atcagcttac aggcagtgag taaaacagaa    300

ggggcatagc cgatcgccag cacacatcct tggggaatct gttgtaaccg ctgttgccaa    360

tggtcatggt gccaaaaagc ttgctcggct tccctaagcc ctgtgatgtg agggtcgtca    420

atcagcgttt taaccgtaca tcctaaatga gctaaccgag tttgatcaag agccgcagcc    480

acaaccggaa catcggtgac gactggacac cctgctttca gtgcatctcg tgccgaggcg    540

atcgctccct gactcaatcg aacggcgttt accaagctaa catcaccaca ggccagcact    600

aattgatgta gtaagtgaat ggtaatttca gagtaagccg ataaatccgg tagcaggtgt    660

ttgagggatt cctgaaaggc ttctggatga gttgttgtct ccgcatctag gttcgtccac    720

aactgatcga gttttcctaa cccctcctgg acatccacat caagctgttt cagttgggcc    780

agagcttccg cttgggtaat ctggcaactc tggtcgcgtc ccagtaatcc ttctaaagca    840

gatgcggttt ggcggagtcg agtaatctgc tgaatcacag cctgatattg ctgttgcaac    900

tgcaccatta gggtgggatc aaggctctct tcagaatggc tatccagcag ttgccgaata    960

tgagacaact gaaagccctg ctgtttgagg gcaatgactc gttggagccg ttgtacgtcc   1020

tgctgagtat aaaggcggta gttgccctct gagcgttgaa cggggggaag caatcccagg   1080

gtgtggtaat ggcgcaccat gcgaggcgta acgccacctc ccactgcatc tgtgagttct   1140
```

-continued

```
ttaatcgtta agtgattagt cttcatccct ttagtttact caaaaccttg acattgacac   1200
taatgttaag gtttaggctg agaaggtaaa aatccaagtt aaaaagcatg aattcctata   1260
ccgttggtat gtacttggca gaacgcctag cccagatcgg cctgaaacac cactttgccg   1320
tggccggtga ctacaacctg gtgttgcttg atcagctcct gctgaacaaa gacatggagc   1380
aggtctactg ctgtaacgaa cttaactgcg gctttagcgc cgaaggttac gctcgtgcac   1440
gtggtgccgc cgctgccatc gtcacgttca gcgtaggtgc tatctctgca atgaacgcca   1500
tcggtggcgc ctatgcagaa aacctgccgg tcatcctgat ctctggctca ccgaacacca   1560
atgactacgg cacaggccac atcctgcacc acaccattgg tactactgac tataactatc   1620
agctggaaat ggtaaaacac gttacctgcg cagctgaaag catcgtttct gccgaagaag   1680
caccggcaaa aatcgaccac gtcatccgta cggctctacg tgaacgcaaa ccggcttatc   1740
tggaaatcgc atgcaacgtc gctggcgctg aatgtgttcg tccgggcccg atcaatagcc   1800
tgctgcgtga actcgaagtt gaccagacca gtgtcactgc cgctgtagat gccgccgtag   1860
aatggctgca ggaccgccag aacgtcgtca tgctggtcgg tagcaaactg cgtgccgctg   1920
ccgctgaaaa acaggctgtt gccctagcgg accgcctggg ctgcgctgtc acgatcatgg   1980
ctgccgcaaa aggcttcttc ccggaagatc atccgaactt ccgcggcctg tactggggtg   2040
aagtcagctc cgaaggtgca caggaactgg ttgaaaacgc cgatgccatc ctgtgtctgg   2100
caccggtatt caacgactat gctaccgttg gctggaactc ctggccgaaa ggcgacaatg   2160
tcatggtcat ggacaccgac cgcgtcactt tcgcaggaca gtccttcgaa ggtctgtcat   2220
tgagcacctt cgccgcagca ctggctgaga aagcaccttc tcgcccggca acgactcaag   2280
gcactcaagc accggtactg ggtattgagg ccgcagagcc caatgcaccg ctgaccaatg   2340
acgaaatgac gcgtcagatc cagtcgctga tcacttccga cactactctg acagcagaaa   2400
caggtgactc ttggttcaac gcttctcgca tgccgattcc tggcggtgct cgtgtcgaac   2460
tggaaatgca atggggtcat atcggttggt ccgtaccttc tgcattcggt aacgccgttg   2520
gttctccgga gcgtcgccac atcatgatgg tcggtgatgg ctctttccag ctgactgctc   2580
aagaagttgc tcagatgatc cgctatgaaa tcccggtcat catcttcctg atcaacaacc   2640
gcggttacgt catcgaaatc gctatccatg acggccctta caactacatc aaaaactgga   2700
actacgctgg cctgatcgac gtcttcaatg acgaagatgg tcatggcctg ggtctgaaag   2760
cttctactgg tgcagaacta gaaggcgcta tcaagaaagc actcgacaat cgtcgcggtc   2820
cgacgctgat cgaatgtaac atcgctcagg acgactgcac tgaaaccctg attgcttggg   2880
gtaaacgtgt agcagctacc aactctcgca aaccacaagc gtaagttgat gtagtgaatt   2940
aggcggggcc tattagggcc ccaccacata gcccctctta cggcgcaata cccgtaagag   3000
gggctgtttt atataattaa agagctcact agtcgatcga cattgccata agtaaaggca   3060
tcccctgcgt gataagatta ccttcagttt atggaggact gaccatatga ttaaagccta   3120
cgctgccctg gaagccaacg gaaaactcca accctttgaa tacgaccccg gtgccctggg   3180
tgctaatgag gtggagattg aggtgcagta ttgtggggtg tgccacagtg atttgtccat   3240
gattaataac gaatggggca tttccaatta ccccctagtg ccgggtcatg aggtggtggg   3300
tactgtggcc gccatgggcg aaggggtgaa ccatgttgag gtgggggatt tagtggggct   3360
gggttggcat tcgggctact gcatgacctg ccatagttgt ttatctggct accacaacct   3420
ttgtgccacg gcggaatcga ccattgtggg ccactacggt ggctttggcg atcgggttcg   3480
ggccaaggga gtcagcgtgg tgaaattacc taaaggcatt gacctagcca gtgccgggcc   3540
```

```
cctttttctgt ggaggaatta ccgttttcag tcctatggtg gaactgagtt taaagcccac   3600
tgcaaaagtg gcagtgatcg gcattggggg cttgggccat ttagcggtgc aatttctccg   3660
ggcctggggc tgtgaagtga ctgcctttac ctccagtgcc aggaagcaaa cggaagtgtt   3720
ggaattgggc gctcaccaca tactagattc caccaatcca gaggcgatcg ccagtgcgga   3780
aggcaaattt gactatatta tctccactgt gaacctgaag cttgactgga acttatacat   3840
cagcaccctg gcgccccagg gacatttcca ctttgttggg gtggtgttgg agcctttgga   3900
tctaaatctt tttccccttt tgatgggaca acgctccgtt tctgcctccc cagtgggtag   3960
tcccgccacc attgccacca tgttggactt tgctgtgcgc catgacatta aacccgtggt   4020
ggaacaattt agctttgatc agatcaacga ggcgatcgcc catctagaaa gcggcaaagc   4080
ccattatcgg gtagtgctca gccatagtaa aaattagctc tgcaaaggtt gcttctgggt   4140
ccgtggaacg ctcggttgcc gccgggcgtt ttttattcct gcaggccccc cgggggatcc   4200
actagaggat ctcaatgaat attggttgac acgggcgtat aagacatgtt atactgttga   4260
ataacaagga cggatctgat caagagacag gatgaggatc gtttcgcatg attgaacaag   4320
atggattgca cgcaggttct ccggccgctt gggtggagag gctattcggc tatgactggg   4380
cacaacagac aatcggctgc tctgatgccg ccgtgttccg gctgtcagcg caggggcgcc   4440
cggttctttt tgtcaagacc gacctgtccg gtgccctgaa tgaactgcag gacgaggcag   4500
cgcggctatc gtggctggcc acgacgggcg ttccttgcgc agctgtgctc gacgttgtca   4560
ctgaagcggg aagggactgg ctgctattgg gcgaagtgcc ggggcaggat ctcctgtcat   4620
ctcaccttgc tcctgccgag aaagtatcca tcatggctga tgcaatgcgg cggctgcata   4680
cgcttgatcc ggctacctgc ccattcgacc accaagcgaa acatcgcatc gagcgagcac   4740
gtactcggat ggaagccggt cttgtcgatc aggatgatct ggacgaagag catcaggggc   4800
tcgcgccagc cgaactgttc gccaggctca aggcgcgcat gcccgacggc gaggatctcg   4860
tcgtgaccca tggcgatgcc tgcttgccga atatcatggt ggaaaatggc cgcttttctg   4920
gattcatcga ctgtggccgg ctgggtgtgg cggaccgcta tcaggacata gcgttggcta   4980
cccgtgatat tgctgaagag cttggcggcg aatgggctga ccgcttcctc gtgctttacg   5040
gtatcgccgc tcccgattcg cagcgcatcg ccttctatcg ccttcttgac gagttcttct   5100
gagcgggact ctggggttcg aaatgaccga ccaagcgacg cccaacctgc catcacgaga   5160
tttcgattcc accgccgcct tctatgaaag gttgggcttc ggaatcgttt tccgggacgc   5220
cggctggatg atcctccagc gcggggatct catgctggag ttcttcgccc accggggatc   5280
ctctagttct agagcggccg catcatcaat ccccgtgatg tttcagtccc gtagtcggga   5340
tttagtggtt ggaaagcgga acgtcgcgcc gaaaccatcg ccaggacggg tttcagtccc   5400
gtagtcggga tttagtggtt ggaaagtgat tatgttcaag aaatcacaac gcaaaagaaa   5460
aagtttcagt cccgtagtcg ggatttagtg gttggaaagt caagcgagat acccaccaga   5520
aagcctttga cctggtttca gtcccgagtc gggatttagt ggttggaaag gcggcggctg   5580
atgtcgccaa tgcggttatc gatggccagt ttcagtcccg tagtcgggat ttagtggttg   5640
gaaagtccca agggggacag ggcggtgatc ctcgatgttg cgtgtttcag tcccgtagtc   5700
gggatttagt ggttggaaag actcgtctat atatacagag attactacag agatgtttca   5760
gtcccgtagt cgggatttag tggttggaaa gcgggaaagt agcctgtttt gtggagaatt   5820
gcaggcgttt cagtactagt gatggcggcc gggagcatgc gacgtcgggc ccaattcgcc   5880
```

-continued

```
ctatagtgag tcgtattaca attcactggc cgtcgtttta caacgtcgtg actgggaaaa   5940
ccctggcgtt acccaactta atcgccttgc agcacatccc cctttcgcca gctggcgtaa   6000
tagcgaagag gcccgcaccg atcgcccttc ccaacagttg cgcagcctga atggcgaatg   6060
gacgcgccct gtagcggcgc attaagcgcg gcgggtgtgg tggttacgcg cagcgtgacc   6120
gctacacttg ccagcgccct agcgcccgct cctttcgctt tcttcccttc ctttctcgcc   6180
acgttcgccg gctttccccg tcaagctcta aatcgggggc tccctttagg gttccgattt   6240
agagctttac ggcacctcga ccgcaaaaaa cttgatttgg gtgatggttc acgtagtggg   6300
ccatcgccct gatagacggt ttttcgccct ttgacgttgg agtccacgtt ctttaatagt   6360
ggactcttgt tccaaactgg aacaacactc aaccctatct cggtctattc ttttgattta   6420
taagggattt tgccgatttc ggcctattgg ttaaaaaatg agctgattta acaaatattt   6480
aacgcgaatt ttaacaaaat attaacgttt acaatttcgc ctgatgcggt attttctcct   6540
tacgcatctg tgcggtattt cacaccgcat acaggtggca cttttcgggg aaatgtgcgc   6600
ggaaccccta tttgtttatt tttctaaata cattcaaata tgtatccgct catgagacaa   6660
taaccctgat aaatgcttca ataatattga aaaaggaaga gtatgagtat tcaacatttc   6720
cgtgtcgccc ttattccctt ttttgcggca ttttgccttc ctgtttttgc tcacccagaa   6780
acgctggtga aagtaaaaga tgctgaagat cagttgggtg cacgagtggg ttacatcgaa   6840
ctggatctca acagcggtaa gatccttgag agttttcgcc ccgaagaacg ttttccaatg   6900
atgagcactt ttaaagttct gctatgtggc gcggtattat cccgtattga cgccgggcaa   6960
gagcaactcg gtcgccgcat acactattct cagaatgact tggttgagta ctcaccagtc   7020
acagaaaagc atcttacgga tggcatgaca gtaagagaat tatgcagtgc tgccataacc   7080
atgagtgata acactgcggc caacttactt ctgacaacga tcggaggacc gaaggagcta   7140
accgcttttt tgcacaacat gggggatcat gtaactcgcc ttgatcgttg ggaaccggag   7200
ctgaatgaag ccataccaaa cgacgagcgt gacaccacga tgcctgtagc aatgccaaca   7260
acgttgcgca aactattaac tggcgaacta cttactctag cttcccggca acaattaata   7320
gactggatgg aggcggataa agttgcagga ccacttctgc gctcggccct tccggctggc   7380
tggtttattg ctgataaatc tggagccggt gagcgtgggt ctcgcggtat cattgcagca   7440
ctggggccag atggtaagcc ctcccgtatc gtagttatct acacgacggg gagtcaggca   7500
actatggatg aacgaaatag acagatcgct gagataggtg cctcactgat taagcattgg   7560
taactgtcag accaagttta ctcatatata ctttagattg atttaaaact tcatttttaa   7620
tttaaaagga tctaggtgaa gatccttttt gataatctca tgaccaaaat cccttaacgt   7680
gagttttcgt tccactgagc gtcagacccc gtagaaaaga tcaaaggatc ttcttgagat   7740
cctttttttc tgcgcgtaat ctgctgcttg caaacaaaaa aaccaccgct accagcggtg   7800
gtttgtttgc cggatcaaga gctaccaact ctttttccga aggtaactgg cttcagcaga   7860
gcgcagatac caaatactgt ccttctagtg tagccgtagt taggccacca cttcaagaac   7920
tctgtagcac cgcctacata cctcgctctg ctaatcctgt taccagtggc tgctgccagt   7980
ggcgataagt cgtgtcttac cgggttggac tcaagacgat agttaccgga taaggcgcag   8040
cggtcgggct gaacgggggg ttcgtgcaca cagcccagct tggagcgaac gacctacacc   8100
gaactgagat acctacagcg tgagctatga gaaagcgcca cgcttcccga agggagaaag   8160
gcggacaggt atccggtaag cggcagggtc ggaacaggag agcgcacgag ggagcttcca   8220
gggggaaacg cctggtatct ttatagtcct gtcgggtttc gccacctctg acttgagcgt   8280
```

cgatttttgt gatgctcgtc aggggggcgg agcctatgga aaaacgccag caacgcggcc 8340
tttttacggt tcctggcctt ttgctggcct tttgctcaca tgttctttcc tgcgttatcc 8400
cctgattctg tggataaccg tattaccgcc tttgagtgag ctgataccgc tcgccgcagc 8460
cgaacgaccg agcgcagcga gtcagtgagc gaggaagcgg aagagcgccc aatacgcaaa 8520
ccgcctctcc ccgcgcgttg gccgattcat taatgcagct ggcacgacag gtttcccgac 8580
tggaaagcgg gcagtgagcg caacgcaatt aatgtgagtt agctcactca ttaggcaccc 8640
caggctttac actttatgct tccggctcgt atgttgtgtg gaattgtgag cggataacaa 8700
tttcacacag gaaacagcta tgaccatgat tacgccaagc tatttaggtg acactataga 8760
atactcaagc tatgcatgag ggtgcaattt gagtggtttc agtcccgtaa tcgggattta 8820
gtggttggaa agaacgacaa ggcttacaag gggtaattc gtgatttgtt tcagtcccgt 8880
aatcgggatt tagtggttgg aaagtaggca ggggagtgaa atggtttcat gttgggctca 8940
tgtttcagtc ccgtaatcgg gatttagtgg ttggaaagca gtaagatgaa ggaggtggtg 9000
catatcactt gcgtttcagt cccgtaatcg ggatttagtg gttggaaagc tagatttgct 9060
tatagagttg actgttatcg ggacttgttt cagtcccgta atcgggattt agtggttgga 9120
aagatgatgg cgttgccagc gttctcggat tggagaattt aacgtttcag tcccgtaatc 9180
gggatttagt ggttggaaag ccctgagaag tttggctgtt ttgctgactg cgatctggtt 9240
tcagtcccgt aatcgggatt tagtggttgg aaagcatcga ggcagtagag caaatcgcag 9300
gccacctcat agtttcagtc ccgtaatcgg gatttagtgg ttggaaagtc attggggtct 9360
gcattggggc catcgctatc gtcctgtttc agtcccgtaa tcgggattta gtggttggaa 9420
agtgggacgc tccgtaaggt ttggagaata gggtctagtg tttcagtccc gtaatcggga 9480
tttagtggtt ggaaagcact tcgtcgctga ttg 9513

<210> SEQ ID NO 82
<211> LENGTH: 12227
<212> TYPE: DNA
<213> ORGANISM: Artificial
<220> FEATURE:
<223> OTHER INFORMATION: #1449¶VZ322a-corR-PcorT-PDC_dsrA-
Prbc*(optRBS)-synADH_oop standard

<400> SEQUENCE: 82
tcgaccatgc gtccaaaact ttcaccatcc tttccctatc aacctttact gcactaaaga 60
caagtgagat agcagtggca atctggcttt gcaatcaatg tttccactaa agcgtttagc 120
gttactgcgg ctagaagtcc tccaccgagg ctcccctgaa tggtgatatg gggaatggga 180
ctggtcatca gtcgtcgttt tgcccccgga gcatgactaa aaccgatcgg cattccgatc 240
acaagagccg gctgaatatg ttgttgctct atcagcttac aggcagtgag taaaacagaa 300
ggggcatagc cgatcgccag cacacatcct tggggaatct gttgtaaccg ctgttgccaa 360
tggtcatggt gccaaaaagc ttgctcggct tccctaagcc ctgtgatgtg agggtcgtca 420
atcagcgttt taaccgtaca tcctaaatga gctaaccgag tttgatcaag agccgcagcc 480
acaaccggaa catcggtgac gactggacac cctgctttca gtgcatctcg tgccgaggcg 540
atcgctccct gactcaatcg aacggcgttt accaagctaa catcaccaca ggccagcact 600
aattgatgta gtaagtgaat ggtaatttca gagtaagccg ataaatccgg tagcaggtgt 660
ttgagggatt cctgaaaggc ttctggatga gttgttgtct ccgcatctag gttcgtccac 720
aactgatcga gttttcctaa cccctcctgg acatccacat caagctgttt cagttgggcc 780

-continued

```
agagcttccg cttgggtaat ctggcaactc tggtcgcgtc ccagtaatcc ttctaaagca    840
gatgcggttt ggcggagtcg agtaatctgc tgaatcacag cctgatattg ctgttgcaac    900
tgcaccatta gggtgggatc aaggctctct tcagaatggc tatccagcag ttgccgaata    960
tgagacaact gaaagccctg ctgtttgagg gcaatgactc gttggagccg ttgtacgtcc   1020
tgctgagtat aaaggcggta gttgccctct gagcgttgaa cggggggaag caatcccagg   1080
gtgtggtaat ggcgcaccat gcgaggcgta acgccacctc ccactgcatc tgtgagttct   1140
ttaatcgtta agtgattagt cttcatccct ttagtttact caaaaccttg acattgacac   1200
taatgttaag gtttaggctg agaaggtaaa aatccaagtt aaaaagcatg aattcttata   1260
ctgtcggtac ctatttagcg gagcggcttg tccagattgg tctcaagcat cacttcgcag   1320
tcgcgggcga ctacaacctc gtccttcttg acaacctgct tttgaacaaa aacatggagc   1380
aggtttattg ctgtaacgaa ctgaactgcg gtttcagtgc agaaggttat gctcgtgcca   1440
aaggcgcagc agcagccgtc gttacctaca gcgtcggtgc gctttccgca tttgatgcta   1500
tcggtggcgc ctatgcagaa aaccttccgg ttatcctgat ctccggtgct ccgaacaaca   1560
atgatcacgc tgctggtcac gtgttgcatc acgctcttgg caaaaccgac tatcactatc   1620
agttggaaat ggccaagaac atcacggccg cagctgaagc gatttacacc ccagaagaag   1680
ctccggctaa aatcgatcac gtgattaaaa ctgctcttcg tgagaagaag ccggtttatc   1740
tcgaaatcgc ttgcaacatt gcttccatgc cctgcgccgc tcctggaccg gcaagcgcat   1800
tgttcaatga cgaagccagc gacgaagctt ctttgaatgc agcggttgaa gaaaccctga   1860
aattcatcgc caaccgcgac aaagttgccg tcctcgtcgg cagcaagctg cgcgcagctg   1920
gtgctgaaga agctgctgtc aaatttgctg atgctctcgg tggcgcagtt gctaccatgg   1980
ctgctgcaaa aagcttcttc ccagaagaaa acccgcatta catcggtacc tcatggggtg   2040
aagtcagcta tccgggcgtt gaaaagacga tgaaagaagc cgatgcggtt atcgctctgg   2100
ctcctgtctt caacgactac tccaccactg gttggacgga tattcctgat cctaagaaac   2160
tggttctcgc tgaaccgcgt tctgtcgtcg ttaacggcgt tcgcttcccc agcgttcatc   2220
tgaaagacta tctgacccgt ttggctcaga aagtttccaa gaaaaccggt gctttggact   2280
tcttcaaatc cctcaatgca ggtgaactga agaaagccgc tccggctgat ccgagtgctc   2340
cgttggtcaa cgcagaaatc gcccgtcagg tcgaagctct tctgaccccg aacacgacgg   2400
ttattgctga aaccggtgac tcttggttca atgctcagcg catgaagctc ccgaacggtg   2460
ctcgcgttga atatgaaatg cagtggggtc acatcggttg gtccgttcct gccgccttcg   2520
gttatgccgt cggtgctccg gaacgtcgca acatcctcat ggttggtgat ggttccttcc   2580
agctgacggc tcaggaagtc gctcagatgg ttcgcctgaa actgccggtt atcatcttct   2640
tgatcaataa ctatggttac accatcgaag ttatgatcca tgatggtccg tacaacaaca   2700
tcaagaactg ggattatgcc ggtctgatgg aagtgttcaa cggtaacggt ggttatgaca   2760
gcggtgctgg taaaggcctg aaggctaaaa ccggtggcga actggcagaa gctatcaagg   2820
ttgctctggc aaacaccgac ggcccaaccc tgatcgaatg cttcatcggt cgtgaagact   2880
gcactgaaga attggtcaaa tggggtaagc gcgttgctgc cgccaacagc cgtaagcctg   2940
ttaacaagct cctctagttt ttggggatca attcgagctc agcaagtttc atcccgaccc   3000
cctcagggtc gggatttttt tattgtacta gttgacataa gtaaaggcat cccctgcgtg   3060
atataattac cttcagttta aggaggtata cacatatgat taaagcctac gctgccctgg   3120
```

-continued

```
aagccaacgg aaaactccaa ccctttgaat acgaccccgg tgccctgggt gctaatgagg   3180
tggagattga ggtgcagtat tgtggggtgt gccacagtga tttgtccatg attaataacg   3240
aatggggcat ttccaattac cccctagtgc cgggtcatga ggtggtgggt actgtggccg   3300
ccatgggcga aggggtgaac catgttgagg tgggggattt agtggggctg ggttggcatt   3360
cgggctactg catgacctgc catagttgtt tatctggcta ccacaacctt tgtgccacgg   3420
cggaatcgac cattgtgggc cactacggtg gctttggcga tcgggttcgg gccaagggag   3480
tcagcgtggt gaaattacct aaaggcattg acctagccag tgccgggccc cttttctgtg   3540
gaggaattac cgttttcagt cctatggtgg aactgagttt aaagcccact gcaaaagtgg   3600
cagtgatcgg cattgggggc ttgggccatt tagcggtgca atttctccgg gcctggggct   3660
gtgaagtgac tgcctttacc tccagtgcca ggaagcaaac ggaagtgttg gaattgggcg   3720
ctcaccacat actagattcc accaatccag aggcgatcgc cagtgcggaa ggcaaatttg   3780
actatattat ctccactgtg aacctgaagc ttgactggaa cttatacatc agcaccctgg   3840
cgccccaggg acatttccac tttgttgggg tggtgttgga gcctttggat ctaaatcttt   3900
ttcccctttt gatgggacaa cgctccgttt ctgcctcccc agtgggtagt cccgccacca   3960
ttgccaccat gttggacttt gctgtgcgcc atgacattaa acccgtggtg gaacaattta   4020
gctttgatca gatcaacgag gcgatcgccc atctagaaag cggcaaagcc cattatcggg   4080
tagtgctcag ccatagtaaa aattagctct gcaaaggttg cttctgggtc cgtggaacgc   4140
tcggttgccg ccgggcgttt tttattcctg caggagcaga agagcataca tctggaagca   4200
aagccaggaa agcggcctat ggagctgtgc ggcagcgctc agtaggcaat tttcaaaat    4260
attgttaagc cttttctgag catggtattt ttcatggtat taccaattag caggaaaata   4320
agccattgaa tataaaagat aaaaatgtct tgtttacaat agagtggggg gggtcagcct   4380
gccgccttgg gccgggtgat gtcgtacttg cccgccgcga actcggttac cgtccagccc   4440
agcgcgacca gctccggcaa cgcctcgcgc acccgctggc ggcgcttgcg catggtcgaa   4500
ccactggcct ctgacggcca gacatagccg cacaaggtat ctatggaagc cttgccggtt   4560
ttgccggggt cgatccagcc acacagccgc tggtgcagca ggcgggcggt ttcgctgtcc   4620
agcgcccgca cctcgtccat gctgatgcgc acatgctggc cgccacccat gacggcctgc   4680
gcgatcaagg ggttcagggc cacgtacagg cgcccgtccg cctcgtcgct ggcgtactcc   4740
gacagcagcc gaaacccctg ccgcttgcgg ccattctggg cgatgatgga taccttccaa   4800
aggcgctcga tgcagtcctg tatgtgcttg agcgccccac cactatcgac ctctgccccg   4860
atttcctttg ccagcgcccg atagctacct ttgaccacat ggcattcagc ggtgacggcc   4920
tcccacttgg gttccaggaa cagccggagc tgccgtccgc cttcggtctt gggttccggg   4980
ccaagcacta ggccattagg cccagccatg gccaccagcc cttgcaggat gcgcagatca   5040
tcagcgccca gcggctccgg gccgctgaac tcgatccgct tgccgtcgcc gtagtcatac   5100
gtcacgtcca gcttgctgcg cttgcgctcg ccccgcttga gggcacggaa caggccgggg   5160
gccagacagt gcgccgggtc gtgccggacg tggctgaggc tgtgcttgtt cttaggcttc   5220
accacggggc accccccttgc tcttgcgctg cctctccagc acggcgggct tgagcacccc  5280
gccgtcatgc cgcctgaacc accgatcagc gaacggtgcg ccatagttgg ccttgctcac   5340
accgaagcgg acgaagaacc ggcgctggtc gtcgtccaca ccccattcct cggcctcggc   5400
gctggtcatg ctcgacaggt aggactgcca gcggatgtta tcgaccagta ccgagctgcc   5460
ccggctggcc tgctgctggt cgcctgcgcc catcatggcc gcgcccttgc tggcatggtg   5520
```

```
caggaacacg atagagcacc cggtatcggc ggcgatggcc tccatgcgac cgatgacctg   5580
ggccatgggg ccgctggcgt tttcttcctc gatgtggaac cggcgcagcg tgtccagcac   5640
catcaggcgg cggccctcgg cggcgcgctt gaggccgtcg aaccactccg gggccatgat   5700
gttgggcagg ctgccgatca gcggctggat cagcaggccg tcagccacgg cttgccgttc   5760
ctcggcgctg aggtgcgccc caagggcgtg caggcggtga tgaatggcgg tgggcgggtc   5820
ttcggcgggc aggtagatca ccgggccggt gggcagttcg cccacctcca gcagatccgg   5880
cccgcctgca atctgtgcgg ccagttgcag ggccagcatg gatttaccgg caccaccggg   5940
cgacaccagc gccccgaccg taccggccac catgttgggc aaaacgtagt ccagcggtgg   6000
cggcgctgct gcgaacgcct ccagaatatt gataggctta tgggtagcca ttgattgcct   6060
cctttgcagg cagttggtgg ttaggcgctg gcggggtcac tacccccgcc ctgcgccgct   6120
ctgagttctt ccaggcactc gcgcagcgcc tcgtattcgt cgtcggtcag ccagaacttg   6180
cgctgacgca tccctttggc cttcatgcgc tcggcatatc gcgcttggcg tacagcgtca   6240
gggctggcca gcaggtcgcc ggtctgcttg tccttttggt ctttcatatc agtcaccgag   6300
aaacttgccg gggccgaaag gcttgtcttc gcggaacaag gacaaggtgc agccgtcaag   6360
gttaaggctg gccatatcag cgactgaaaa gcggccagcc tcggccttgt ttgacgtata   6420
accaaagcca ccgggcaacc aatagccctt gtcacttttg atcaggtaga ccgaccctga   6480
agcgcttttt tcgtattcca taaaaccccc ttctgtgcgt gagtactcat agtataacag   6540
gcgtgagtac caacgcaagc actacatgct gaaatctggc ccgcccctgt ccatgcctcg   6600
ctggcggggt gccggtgccc gtgccagctc ggcccgcgca agctggacgc tgggcagacc   6660
catgaccttg ctgacggtgc gctcgatgta atccgcttcg tggccgggct tgcgctctgc   6720
cagcgctggg ctggcctcgg ccatggcctt gccgatttcc tcggcactgc ggccccggct   6780
ggccagcttc tgcgcggcga taaagtcgca cttgctgagg tcatcaccga agcgcttgac   6840
cagcccggcc atctcgctgc ggtactcgtc cagcgccgtg cgccggtggc ggctaagctg   6900
ccgctcgggc agttcgaggc tggccagcct gcgggccttc tcctgctgcc gctgggcctg   6960
ctcgatctgc tggccagcct gctgcaccag cgccgggcca gcggtggcgg tcttgccctt   7020
ggattcacgc agcagcaccc acggctgata accggcgcgg gtggtgtgct tgtccttgcg   7080
gttggtgaag cccgccaagc ggccatagtg gcggctgtcg gcgctggccg ggtcggcgtc   7140
gtactcgctg gccagcgtcc gggcaatctg cccccgaagt tcaccgcctg cggcgtcggc   7200
caccttgacc catgcctgat agttcttcgg gctggtttcc actaccaggg caggctcccg   7260
gccctcggct ttcatgtcat ccaggtcaaa ctcgctgagg tcgtccacca gcaccagacc   7320
atgccgctcc tgctcggcgg gcctgatata cacgtcattg ccctgggcat tcatccgctt   7380
gagccatggc gtgttctgga gcacttcggc ggctgaccat tcccggttca tcatctggcc   7440
ggtggtggcg tccctgacgc cgatatcgaa gcgctcacag cccatggcct tgagctgtcg   7500
gcctatggcc tgcaaagtcc tgtcgttctt catcgggcca ccaagcgcag ccagatcgag   7560
ccgtcctcgg ttgtcagtgg cgtcaggtcg agcaagagca acgatgcgat cagcagcacc   7620
accgtaggca tcatggaagc cagcatcacg gttagccata gcttccagtg ccacccccgc   7680
gacgcgctcc gggcgctctg cgcggcgctg ctcacctcgg cggctacctc ccgcaactct   7740
ttggccagct ccacccatgc cgcccctgtc tggcgctggg ctttcagcca ctccgccgcc   7800
tgcgcctcgc tggcctgctg ggtctggctc atgacctgcc gggcttcgtc ggccagtgtc   7860
```

-continued

```
gccatgctct gggccagcgg ttcgatctgc tccgctaact cgttgatgcc tctggatttc   7920
ttcactctgt cgattgcgtt catggtctat tgcctcccgg tattcctgta agtcgatgat   7980
ctgggcgttg gcggtgtcga tgttcagggc cacgtctgcc cggtcggtgc ggatgccccg   8040
gccttccatc tccaccacgt tcggccccag gtgaacaccg ggcaggcgct cgatgccctg   8100
cgcctcaagt gttctgtggt caatgcgggc gtcgtggcca gcccgctcta atgcccggtt   8160
ggcatggtcg gcccatgcct cgcgggtctg ctcaagccat gccttgggct tgagcgcttc   8220
ggtcttctgt gccccgccct tctccggggt cttgccgttg taccgcttga accactgagc   8280
ggcgggccgc tcgatgccgt cattgatccg ctcggagatc atcaggtggc agtgcgggtt   8340
ctcgccgcca ccggcatgga tggccagcgt atacggcagg cgctcggcac cggtcaggtg   8400
ctgggcgaac tcggacgcca gcgccttctg ctggtcgagg gtcagctcga ccggcagggc   8460
aaattcgacc tccttgaaca gccgcccatt ggcgcgttca tacaggtcgg cagcatccca   8520
gtagtcggcg ggccgctcga cgaactccgg catgtgcccg gattcggcgt gcaagacttc   8580
atccatgtcg cgggcatact tgccttcgcg ctggatgtag tcggccttgg ccctggccga   8640
ttggccgccc gacctgctgc cggttttcgc cgtaaggtga taaatcgcca tgctgcctcg   8700
ctgttgcttt tgcttttcgg ctccatgcaa tggccctcgg agagcgcacc gcccgaaggg   8760
tggccgttag gccagtttct cgaagagaaa ccggtaagtg cgccctcccc tacaaagtag   8820
ggtcgggatt gccgccgctg tgcctccatg atagcctacg agacagcaca ttaacaatgg   8880
ggtgtcaaga tggttaaggg gagcaacaag gcggcggatc ggctggccaa gctcgaagaa   8940
caacgagcgc gaatcaatgc cgaaattcag cgggtgcggg caagggaaca gcagcaagag   9000
cgcaagaacg aaacaaggcg caaggtgctg gtgggggcca tgattttggc caaggtgaac   9060
agcagcgagt ggccggagga tcggctcatg gcggcaatgg atgcgtacct tgaacgcgac   9120
cacgaccgcg ccttgttcgg tctgccgcca cgccagaagg atgagccggg ctgaatgatc   9180
gaccgagaca ggccctgcgg ggctgcacac gcgcccccac ccttcgggta gggggaaagg   9240
ccgctaaagc ggctaaaagc gctccagcgt atttctgcgg ggtttggtgt ggggtttagc   9300
gggctttgcc cgcctttccc cctgccgcgc agcggtgggg cggtgtgtag cctagcgcag   9360
cgaatagacc agctatccgg cctctggccg ggcatattgg gcaagggcag cagcgcccca   9420
caagggcgct gataaccgcg cctagtggat tattcttaga taatcatgga tggatttttc   9480
caacaccccg ccagcccccg cccctgctgg gtttgcaggt ttgggggcgt gacagttatt   9540
gcaggggttc gtgacagtta ttgcaggggg gcgtgacagt tattgcaggg gttcgtgaca   9600
gttagtacgg gagtgacggg cactggctgg caatgtctag caacggcagg catttcggct   9660
gagggtaaaa gaactttccg ctaagcgata gactgtatgt aaacacagta ttgcaaggac   9720
gcggaacatg cctcatgtgg cggccaggac ggccagccgg gatcgggata ctggtcgtta   9780
ccagagccac cgacccgagc aaacccttct ctatcagatc gttgacgagt attacccggc   9840
attcgctgcg cttatggcag agcagggaaa ggaattgccg ggctatgtgc aacgggaatt   9900
tgaagaattt ctccaatgcg ggcggctgga gcatggcttt ctacgggttc gctgcgagtc   9960
ttgccacgcc gagcacctgg tcgctttcag ctgtaatccg ggcagcgcaa cggaacattc  10020
atcagtgtaa aaatggaatc aataaagccc tgcgcagcgc gcagggtcag cctgaatacg  10080
cgtgctcgaa ttgacataag cctgttcggt tcgtaaactg taatgcaagt agcgtatgcg  10140
ctcacgcaac tggtccagaa ccttgaccga acgcagcggt ggtaacggcg cagtggcggt  10200
tttcatggct tgttatgact gtttttttgt acagtctatg cctcgggcat ccaagcagca  10260
```

agcgcgttac gccgtgggtc gatgtttgat gttatggagc agcaacgatg ttacgcagca 10320
gcaacgatgt tacgcagcag ggcagtcgcc ctaaaacaaa gttaggtggc tcaagtatgg 10380
gcatcattcg cacatgtagg ctcggccctg accaagtcaa atccatgcgg gctgctcttg 10440
atcttttcgg tcgtgagttc ggagacgtag ccacctactc ccaacatcag ccggactccg 10500
attacctcgg gaacttgctc cgtagtaaga cattcatcgc gcttgctgcc ttcgaccaag 10560
aagcggttgt tggcgctctc gcggcttacg ttctgcccag gtttgagcag ccgcgtagtg 10620
agatctatat ctatgatctc gcagtctccg gcgagcaccg gaggcagggc attgccaccg 10680
cgctcatcaa tctcctcaag catgaggcca acgcgcttgg tgcttatgtg atctacgtgc 10740
aagcagatta cggtgacgat cccgcagtgg ctctctatac aaagttgggc atacgggaag 10800
aagtgatgca ctttgatatc gacccaagta ccgccaccta acaattcgtt caagccgaga 10860
tcggcttccc ggccctagac gcgtattcag gctgaccctg cgcgctgcgc agggctttat 10920
tgattccatt tttacactga tgaatgttcc gttgcgctgc ccggattaca gatcctctag 10980
aggggggggg ggaaagccac gttgtgtctc aaaatctctg atgttacatt gcacaagata 11040
aaaatatatc atcatgaaca ataaaactgt ctgcttacat aaacagtaat acaaggggtg 11100
ttatgagcca tattcaacgg gaaacgtctt gctcgaggcc gcgattaaat tccaacatgg 11160
atgctgattt atatgggtat aaatgggctc gcgataatgt cgggcaatca ggtgcgacaa 11220
tctatcgatt gtatgggaag cccgatgcgc cagagttgtt tctgaaacat ggcaaaggta 11280
gcgttgccaa tgatgttaca gatgagatgg tcagactaaa ctggctgacg gaatttatgc 11340
ctcttccgac catcaagcat tttatccgta ctcctgatga tgcatggtta ctcaccactg 11400
cgatccccgg gaaaacagca ttccaggtat tagaagaata tcctgattca ggtgaaaata 11460
ttgttgatgc gctggcagtg ttcctgcgcc ggttgcattc gattcctgtt tgtaattgtc 11520
cttttaacag cgatcgcgta tttcgtctcg ctcaggcgca atcacgaatg aataacggtt 11580
tggttgatgc gagtgatttt gatgacgagc gtaatggctg gcctgttgaa caagtctgga 11640
aagaaatgca taagcttttg ccattctcac cggattcagt cgtcactcat ggtgatttct 11700
cacttgataa ccttattttt gacgagggga aattaatagg ttgtattgat gttggacgag 11760
tcggaatcgc agaccgatac caggatcttg ccatcctatg gaactgcctc ggtgagtttt 11820
ctccttcatt acagaaacgg ctttttcaaa aatatggtat tgataatcct gatatgaata 11880
aattgcagtt tcatttgatg ctcgatgagt ttttctaatc agaattggtt aattggttgt 11940
aacactggca gagcattacg ctgacttgac gggacggcgg ctttgttgaa taaatcgaac 12000
ttttgctgag ttgaaggatc agatcacgca tcttcccgac aacgcagacc gttccgtggc 12060
aaagcaaaag ttcaaaatca ccaactggtc cacctacaac aaagctctca tcaaccgtgg 12120
ctccctcact ttctggctgg atgatggggc gattcaggcc tggtatgagt cagcaacacc 12180
ttcttcacga ggcagacctc agcgcccccc cccccggaa tctagag 12227

<210> SEQ ID NO 83
<211> LENGTH: 9842
<212> TYPE: DNA
<213> ORGANISM: Artificial
<220> FEATURE:
<223> OTHER INFORMATION: #1507¶AQ3-corR-PcorT-zmPDCdeg_spf-Prbc*-
synADH_oop standard

<400> SEQUENCE: 83
tcgaccatgc gtccaaaact ttcaccatcc tttccctatc aacctttact gcactaaaga 60

-continued

```
caagtgagat agcagtggca atctggcttt gcaatcaatg tttccactaa agcgtttagc    120
gttactgcgg ctagaagtcc tccaccgagg ctcccctgaa tggtgatatg gggaatggga    180
ctggtcatca gtcgtcgttt tgcccccgga gcatgactaa aaccgatcgg cattccgatc    240
acaagagccg gctgaatatg ttgttgctct atcagcttac aggcagtgag taaaacagaa    300
ggggcatagc cgatcgccag cacacatcct tggggaatct gttgtaaccg ctgttgccaa    360
tggtcatggt gccaaaaagc ttgctcggct tccctaagcc ctgtgatgtg agggtcgtca    420
atcagcgttt taaccgtaca tcctaaatga gctaaccgag tttgatcaag agccgcagcc    480
acaaccggaa catcggtgac gactggacac cctgctttca gtgcatctcg tgccgaggcg    540
atcgctccct gactcaatcg aacggcgttt accaagctaa catcaccaca ggccagcact    600
aattgatgta gtaagtgaat ggtaatttca gagtaagccg ataaatccgg tagcaggtgt    660
ttgagggatt cctgaaaggc ttctggatga gttgttgtct ccgcatctag gttcgtccac    720
aactgatcga gttttcctaa cccctcctgg acatccacat caagctgttt cagttgggcc    780
agagcttccg cttgggtaat ctggcaactc tggtcgcgtc ccagtaatcc ttctaaagca    840
gatgcggttt ggcggagtcg agtaatctgc tgaatcacag cctgatattg ctgttgcaac    900
tgcaccatta gggtgggatc aaggctctct tcagaatggc tatccagcag ttgccgaata    960
tgagacaact gaaagccctg ctgtttgagg gcaatgactc gttggagccg ttgtacgtcc   1020
tgctgagtat aaaggcggta gttgccctct gagcgttgaa cggggggaag caatcccagg   1080
gtgtggtaat ggcgcaccat gcgaggcgta acgccacctc ccactgcatc tgtgagttct   1140
ttaatcgtta agtgattagt cttcatccct ttagtttact caaaaccttg acattgacac   1200
taatgttaag gtttaggctg agaaggtaaa aatccaagtt aaaaagcatg aattcctaca   1260
ccgttggcac ttacctggct gaacgcttgg ttcagatcgg cttaaaacac cattttgctg   1320
ttgctggtga ttataatttg gttttgttag ataatttatt gctcaataag aatatggaac   1380
aggtgtactg ttgcaatgag ttaaattgtg gcttttccgc tgagggctac gcccgtgcta   1440
agggtgctgc tgctgctgtt gtgacttatt ctgttggcgc tttgagtgct tttgacgcca   1500
ttggcggtgc ttacgctgag aatttgccag tgattttaat tagtggcgcc ccaaataata   1560
acgaccatgc cgccggccat gtcctccacc atgccttggg taagactgat taccattacc   1620
aactggagat ggctaaaaat attaccgctg ctgccgaagc tatctatact cctgaggaag   1680
ccccagccaa gattgaccat gtcatcaaga ccgccttgcg ggaaaaaaaa ccagtgtact   1740
tagagattgc ctgtaatatc gccagtatgc cttgtgctgc ccccggtcca gcttctgctc   1800
tctttaacga tgaagcttct gatgaggcca gtctcaacgc tgctgtggag gaaactttaa   1860
agtttattgc taatcgtgat aaggtggctg ttttagttgg ttctaaatta cgtgctgccg   1920
gcgccgagga agccgccgtt aagtttgccg acgccttagg cggtgctgtg gccactatgg   1980
ccgccgctaa gtcttttttt cctgaagaga atccacacta tattggcact agctggggcg   2040
aggtttctta cccaggtgtg gagaaaacca tgaaggaggc tgacgctgtg attgccttag   2100
ccccggtttt taatgattat agtactaccg gctggaccga catcccggac ccgaaaaagt   2160
tagtgttagc cgaaccacgg agtgttgttg tgaatggtgt gcgttttcct tctgtgcact   2220
taaaggatta cttaactcgg ctcgcccaga aggtgagtaa aaagactggc gccctcgatt   2280
tttttaagag tttaaacgct ggcgagttaa aaaaggctgc cccagccgac ccatccgccc   2340
cactcgttaa tgctgaaatt gctcggcagg ttgaggcctt gttaactcca aataccaccg   2400
```

tgatcgccga aactggcgat agttggttta acgcccaacg tatgaaatta ccaaatggcg 2460
cccgtgtgga gtacgagatg caatggggcc atattggctg gagtgtgccg gctgcttttg 2520
gctacgctgt tggcgcccca gagcggcgta atattttaat ggtgggcgac ggcagttttc 2580
agttaaccgc ccaagaggtt gcccaaatgg tgcgtttaaa gttaccagtg attatttttc 2640
tcattaacaa ttacggctat actattgagg tgatgattca cgacggccca tataataata 2700
ttaaaaattg ggactacgct ggcttaatgg aggtctttaa tggcaatggc ggctacgatt 2760
ctggcgccgg caagggttta aaagccaaga ctggcggtga gttagctgaa gccattaaag 2820
tggccttagc taatactgat ggtcctactt taattgagtg ttttattggc cgggaagatt 2880
gtaccgagga actcgttaag tggggcaaac gtgtggccgc tgctaattct cggaaacccg 2940
tgaataaatt attatgaaat attttagccg ccccagtcag taatgactgg ggcgtttttt 3000
attgggagct cactagtcga tcgacattgc cataagtaaa ggcatcccct gcgtgataag 3060
attaccttca gtttatggag gactgaccat atgattaaag cctacgctgc cctggaagcc 3120
aacggaaaac tccaaccctt tgaatacgac cccggtgccc tgggtgctaa tgaggtggag 3180
attgaggtgc agtattgtgg ggtgtgccac agtgatttgt ccatgattaa taacgaatgg 3240
ggcatttcca attacccct agtgccgggt catgaggtgg tgggtactgt ggccgccatg 3300
ggcgaagggg tgaaccatgt tgaggtgggg gatttagtgg ggctgggttg gcattcgggc 3360
tactgcatga cctgccatag ttgtttatct ggctaccaca acctttgtgc cacggcggaa 3420
tcgaccattg tgggccacta cggtggcttt ggcgatcggg ttcgggccaa gggagtcagc 3480
gtggtgaaat tacctaaagg cattgaccta gccagtgccg ggcccctttt ctgtggagga 3540
attaccgttt tcagtcctat ggtggaactg agtttaaagc ccactgcaaa agtggcagtg 3600
atcggcattg gggcttggg ccatttagcg gtgcaatttc tccgggcctg gggctgtgaa 3660
gtgactgcct ttacctccag tgccaggaag caaacggaag tgttggaatt gggcgctcac 3720
cacatactag attccaccaa tccagaggcg atcgccagtg cggaaggcaa atttgactat 3780
attatctcca ctgtgaacct gaagcttgac tggaacttat acatcagcac cctggcgccc 3840
cagggacatt tccactttgt tggggtggtg ttggagcctt tggatctaaa tctttttccc 3900
cttttgatgg gacaacgctc cgtttctgcc tccccagtgg gtagtcccgc caccattgcc 3960
accatgttgg actttgctgt gcgccatgac attaaacccg tggtggaaca atttagcttt 4020
gatcagatca acgaggcgat cgcccatcta gaaagcggca aagcccatta tcgggtagtg 4080
ctcagccata gtaaaaatta gctctgcaaa ggttgcttct gggtccgtgg aacgctcggt 4140
tgccgccggg cgttttttat tcctgcagga tccacaggac gggtgtggtc gccatgatcg 4200
cgtagtcgat agtggctcca agtagcgaag cgagcaggac tgggcggcgg ccaaagcggt 4260
cggacagtgc tccgagaacg ggtgcgcata gaaattgcat caacgcatat agcgctagca 4320
gcacgccata gtgactggcg atgctgtcgg aatggacgat cgaattggcc gcggcgttgt 4380
gacaatttac cgaacaactc cgcggccggg aagccgatct cggcttgaac gaattgttag 4440
gtggcggtac ttgggtcgat atcaaagtgc atcacttctt cccgtatgcc caactttgta 4500
tagagagcca ctgcgggatc gtcaccgtaa tctgcttgca cgtagatcac ataagcacca 4560
agcgcgttgg cctcatgctt gaggagattg atgagcgcgg tggcaatgcc ctgcctccgg 4620
tgctcgccgg agactgcgag atcatagata tagatctcac tacgcggctg ctcaaacttg 4680
ggcagaacgt aagccgcgag agcgccaaca accgcttctt ggtcgaaggc agcaagcgcg 4740
atgaatgtct tactacggag caagttcccg aggtaatcgg agtccggctg atgttgggag 4800

-continued

```
taggtggcta cgtctccgaa ctcacgaccg aaaagatcaa gagcagcccg catggatttg   4860
acttggtcag ggccgagcct acatgtgcga atgatgccca tacttgagcc acctaacttt   4920
gttttagggc gactgccctg ctgcgtaaca tcgttgctgc tgcgtaacat cgttgctgct   4980
ccataacatc aaacatcgac ccacggcgta acgcgcttgc tgcttggatg cccgaggcat   5040
agactgtaca aaaaaacagt cataacaagc catgaaaacc gccactgcgc cgttaccacc   5100
gctgcgttcg gtcaaggttc tggaccagtt gcgtgagcgc atacgctact tgcattacag   5160
tttacgaacc gaacaggctt atgtcaattc gagcatcgat tgtatgggaa gcccgatgcg   5220
ccagagttgt ttctgaaaca tggcaaaggt agcgttgcca atgatgttac agatgagatg   5280
gtcagactaa actggctgac ggaatttatg cctcttccga ccatcaagca ttttatccgt   5340
actcctgatg atgcatggtt actcaccact gcgatccccg atcccccct cgatcaaggc    5400
aggcaacgcc cccggcgatc gccgtccttt tttatgccac atcttcggta tataaatccg   5460
cctgaaaatc tgcgaatact tgaccgatat cctgacccaa gatcactaaa ccttcattaa   5520
cggtttggta tttgatttcg atgagggtag gcagtttccc ccgatcaagt tcctccactc   5580
cttctcgaat gtattggtct aggacaaaat ctaaaaattc ttgctgcttt ccggtgtact   5640
tcgagaaaat cagatctcga tgcttaatta ctcgctcttc tctgctaatg ggtttggtgt   5700
tgtaggcaac ccaagtcagg acatcataga catcactttt ttccgcttcg gcaatgcgtg   5760
cgatcgcctt cagttgggtg tcaccgtagc ctttttccgc gagtccggtc aggaacgatt   5820
tacgggtatc gggtttcccc cagatggtgc gtagttcggc ttcatccttg aagaggtcgg   5880
gcaggtcgcc aaatagcttt tcgataaatt cttgggcgga aatgggttta ccatcagcat   5940
cccaaaaagt tgtggatgca tagcttgagt attctatagt gtcacctaaa tagcttggcg   6000
taatcatggt catagctgtt tcctgtgtga aattgttatc cgctcacaat tccacacaac   6060
atacgagccg gaagcataaa gtgtaaagcc tggggtgcct aatgagtgag ctaactcaca   6120
ttaattgcgt tgcgctcact gcccgctttc cagtcgggaa acctgtcgtg ccagctgcat   6180
taatgaatcg gccaacgcgc ggggagaggc ggtttgcgta ttgggcgctc ttccgcttcc   6240
tcgctcactg actcgctgcg ctcggtcgtt cggctgcggc gagcggtatc agctcactca   6300
aaggcggtaa tacggttatc cacagaatca ggggataacg caggaaagaa catgtgagca   6360
aaaggccagc aaaaggccag gaaccgtaaa aaggccgcgt tgctggcgtt tttccatagg   6420
ctccgccccc ctgacgagca tcacaaaaat cgacgctcaa gtcagaggtg gcgaaacccg   6480
acaggactat aaagatacca ggcgtttccc cctggaagct ccctcgtgcg ctctcctgtt   6540
ccgaccctgc cgcttaccgg atacctgtcc gcctttctcc cttcgggaag cgtggcgctt   6600
tctcatagct cacgctgtag gtatctcagt tcggtgtagg tcgttcgctc caagctgggc   6660
tgtgtgcacg aaccccccgt tcagcccgac cgctgcgcct tatccggtaa ctatcgtctt   6720
gagtccaacc cggtaagaca cgacttatcg ccactggcag cagccactgg taacaggatt   6780
agcagagcga ggtatgtagg cggtgctaca gagttcttga agtggtggcc taactacggc   6840
tacactagaa ggacagtatt tggtatctgc gctctgctga agccagttac cttcggaaaa   6900
agagttggta gctcttgatc cggcaaacaa accaccgctg gtagcggtgg tttttttgtt   6960
tgcaagcagc agattacgcg cagaaaaaaa ggatctcaag aagatccttt gatcttttct   7020
acggggtctg acgctcagtg gaacgaaaac tcacgttaag ggattttggt catgagatta   7080
tcaaaaagga tcttcaccta gatcctttta aattaaaaat gaagttttaa atcaatctaa   7140
```

-continued agtatatatg agtaaacttg gtctgacagt taccaatgct taatcagtga ggcacctatc 7200
tcagcgatct gtctatttcg ttcatccata gttgcctgac tccccgtcgt gtagataact 7260
acgatacggg agggcttacc atctggcccc agtgctgcaa tgataccgcg agacccacgc 7320
tcaccggctc cagatttatc agcaataaac cagccagccg gaagggccga gcgcagaagt 7380
ggtcctgcaa ctttatccgc ctccatccag tctattaatt gttgccggga agctagagta 7440
agtagttcgc cagttaatag tttgcgcaac gttgttggca ttgctacagg catcgtggtg 7500
tcacgctcgt cgtttggtat ggcttcattc agctccggtt cccaacgatc aaggcgagtt 7560
acatgatccc ccatgttgtg caaaaaagcg gttagctcct tcggtcctcc gatcgttgtc 7620
agaagtaagt tggccgcagt gttatcactc atggttatgg cagcactgca taattctctt 7680
actgtcatgc catccgtaag atgcttttct gtgactggtg agtactcaac caagtcattc 7740
tgagaatagt gtatgcggcg accgagttgc tcttgcccgg cgtcaatacg ggataatacc 7800
gcgccacata gcagaacttt aaaagtgctc atcattggaa aacgttcttc ggggcgaaaa 7860
ctctcaagga tcttaccgct gttgagatcc agttcgatgt aacccactcg tgcacccaac 7920
tgatcttcag catcttttac tttcaccagc gtttctgggt gagcaaaaac aggaaggcaa 7980
aatgccgcaa aaaagggaat aagggcgaca cggaaatgtt gaatactcat actcttcctt 8040
tttcaatatt attgaagcat ttatcagggt tattgtctca tgagcggata catatttgaa 8100
tgtatttaga aaaataaaca aataggggtt ccgcgcacat ttccccgaaa agtgccacct 8160
gtatgcggtg tgaaataccg cacagatgcg taaggagaaa ataccgcatc aggcgaaatt 8220
gtaaacgtta atattttgtt aaaattcgcg ttaaatattt gttaaatcag ctcatttttt 8280
aaccaatagg ccgaaatcgg caaaatccct tataaatcaa aagaatagac cgagataggg 8340
ttgagtgttg ttccagtttg gaacaagagt ccactattaa agaacgtgga ctccaacgtc 8400
aaagggcgaa aaaccgtcta tcagggcgat ggcccactac gtgaaccatc acccaaatca 8460
agttttttgc ggtcgaggtg ccgtaaagct ctaaatcgga accctaaagg gagcccccga 8520
tttagagctt gacggggaaa gccggcgaac gtggcgagaa aggaagggaa gaaagcgaaa 8580
ggagcgggcg ctagggcgct ggcaagtgta gcggtcacgc tgcgcgtaac caccacaccc 8640
gccgcgctta atgcgccgct acagggcgcg tccattcgcc attcaggctg cgcaactgtt 8700
gggaagggcg atcggtgcgg gcctcttcgc tattacgcca gctggcgaaa gggggatgtg 8760
ctgcaaggcg attaagttgg gtaacgccag ggttttccca gtcacgacgt tgtaaaacga 8820
cggccagtga attgtaatac gactcactat agggcgaatt gggcccgacg tcgcatgctc 8880
ccggccgcca tcactagttt ggagataatc gcctttgggc agttatctag aatgtacaca 8940
aatttattac catctaagac acgacaaaaa atacatactc atttccaatt acctaacaag 9000
ttttttatat cttggttacg gtctttgtcg catattagaa atatttgcgc tcatcattca 9060
aggctctgga atatacagct aggagaatca cctaaattgc ctgataggtt aaaaggaaaa 9120
tggctctcta gagaagtatt ggaggatatt aatcaaagaa acagccgtaa aattttcact 9180
ggcttatgtt gtattcagta tctcttagac agaattaaac cagagcataa ttttgcacag 9240
catttaaaaa gaacttttga gatgtatcca gaaatagaat ctaaaaactt aggctttccc 9300
aaagattggg aaaatcagcc tctctggaaa taatctaaga gtcagaattt taatttgtca 9360
taactctttc tcgttcaagg cagggcggcc tgcacatact gggaagcata ttcttcgatg 9420
cgcttaaagt tttgccgtgg tagtttagct tgatgctctt ccacgttgaa acctgctaag 9480
tagttacata cggctgacag cggcaaaaaa tgtttgagta taaggccata gttgatgctt 9540

-continued

```
gttggaatta aatttttaat aaaattcctg tctcagtttc ctgaagcttg ctctaaacct   9600

cgttcaaaaa aaatgcagaa taaagttggt caagaggaac atattgaata tttagctcgt   9660

agttttcatg agagtcgatt gccaagaaaa cccacgccac ctacaacggt tcctgatgag   9720

gtggttagca tagttcttaa tataagtttt aatatacagc ctgaaaatct tgagagaata   9780

aaagaagaac atcgattttc catggcagct gagaatattg taggagatct tctagaaaga   9840

tg                                                                   9842
```

<210> SEQ ID NO 84
<211> LENGTH: 79
<212> TYPE: DNA
<213> ORGANISM: Artificial
<220> FEATURE:
<223> OTHER INFORMATION: modified promoter PcorT*

<400> SEQUENCE: 84

```
ctttagttta ctcaaaacct tgacattgac actaatgtta aggtttaggc tgagaaggta     60

aaaatcgagg ataaaaagc                                                  79
```

<210> SEQ ID NO 85
<211> LENGTH: 13309
<212> TYPE: DNA
<213> ORGANISM: Artificial
<220> FEATURE:
<223> OTHER INFORMATION: #1353¶VZ325a-nrsRS-PnrsB-PDC_dsrA-Prbc*-
synADHdeg_oop standard

<400> SEQUENCE: 85

```
tcgaccctat atcgggcttt tctcaataaa atctttattt tttgaggtgc tttttagcca     60

taaataatca ctttagtata aaattttgac ggcgtaaagt tgataaaata gaattaagaa    120

tggactatcg gtacagaaaa aatgggtaac tggatggtga ataaacttcc cttacccaat    180

gcactctcca ccgttaaaga ccccctatgc ttaacggtga tcacctgggc aatggcgagt    240

cccaaccctg tcccccccgt tttgcgcgaa cgatctcgat taactcggta aaaacgctca    300

aaaatgtgtt cctgttggtc gggggcaatg ccgatgccgg tatcttgcac ggtgatgata    360

gccatctgtt catgggatgt cagggtaata tcaacacgtc ccccagcagt tgtgtattga    420

atggcgttgg caattaggtt tgagaccagt cgatagagtt gggattcatt accccaggcg    480

taaacttccc ctgaactcag atcactgctg agatcaatgt gggcggcgat cgctaattct    540

aaaaactctt cggtgaggtc actgactaaa tcatttaaac aacaaagccg ccaatcttcg    600

gcggtggttt cctgctctaa gcgacttagt agcaataaat ccgtaatcaa ttggcttaat    660

cgccttccct gtcgttcaac ggtatgtagc atggtgttaa tttctgggga atggcttgag    720

tcgatgcgta ataccgcttc caccgtggcc aacagactag ccaatggcga tcgtaattca    780

tgggctgcat tcgcggtgaa ttgttgttgt tgttggtagg actggtaaat gggacgcatg    840

gctaaccccg ctaagcccca actggagaag gcgaccaaac ccagggcaat gggaaaacta    900

agccctaaaa tccaaagaat acgtttattt tcggcatcaa aggctgccag gctccggcca    960

atttgtagat agccccagga agatttgtct gtattaccgg cgctatgcaa aatggtggtg   1020

aattgtcgat accgatcgcc ggttgggggg tgaatagtct gccaagtttc ctggttaaaa   1080

atggaggata gggaagccgg ttgattaggc gaaaaagcca gcaggttgcc ttgataatca   1140

aataaacgaa tgtaatataa actgcgatca ctaatgccca acgtgtgacg ttcaatcagg   1200

gtggggttga cctggcaggg ttggttgacc aaacacagat cgggcaacat tttttgtaat   1260
```

-continued

```
actccggtgg gactagcatt actcggcaac atcggctcta aactgtcatg caacgtcccg   1320
gcgatcgact ccacttctcg ctccaacgcc atccagttgg cctgcacaat ggcacgataa   1380
acccccaacc ccaacagggt aagaataccc cccattacta gggcatacca gaaagccaat   1440
tgcagacgac tacgggcaaa gaggcgacgg gtattcatgg cgatagggtg aaccgatagc   1500
cttgaccggg aactgtttta attgggcaag gacaattttg ttgagctagc ttgcgtcgta   1560
tcaaacgcat ttgggccgcc accacattac tcatgggctc ctcatcaaga tcccacagtt   1620
gttgccggat cttgctaccg gaaatgatcc gctctgggtt ttgcatcaga tattgaaaaa   1680
tttgaaattc tcttacggtt aaagcaattt cctgtctttc taggtttagt ggctccgaga   1740
tagttaccga taacagatta ttactgggat caaggctgaa gttgcccaaa gttaaaattt   1800
gcggttggaa ttgtggcgat cgccgttgta gtgcccgcag tcttgctaat agctctgcca   1860
tcacaaacgg ttttgttaga tagtcatctg ccccggcatc tagtccttcg acacggtttt   1920
ccggttctcc taacgctgtt aacatcaaca ccggcaagga attaccctgg gttctcagtt   1980
tttgacagag ttccaaaccc gataatcccg gcagtaacca atccacaatg gcaagggtgt   2040
attccgtcca ttgattttcc aaataatccc aagcttggga gccatccgtc acccaatcca   2100
ccacatactt ttcactaact agcactttct taatagccat tcccaaatcc gtctcatctt   2160
ccaccagcaa aattcgcatc gcctctgcct tttttataac ggtctgatct tagcggggga   2220
aggagatttt cacctgaatt tcataccccc tttggcagac tgggaaaatc ttggacaaat   2280
tcccaatttg aggtggtgtg atgaattctt atactgtcgg tacctattta gcggagcggc   2340
ttgtccagat tggtctcaag catcacttcg cagtcgcggg cgactacaac ctcgtccttc   2400
ttgacaacct gcttttgaac aaaaacatgg agcaggttta ttgctgtaac gaactgaact   2460
gcggtttcag tgcagaaggt tatgctcgtg ccaaaggcgc agcagcagcc gtcgttacct   2520
acagcgtcgg tgcgctttcc gcatttgatg ctatcggtgg cgcctatgca gaaaaccttc   2580
cggttatcct gatctccggt gctccgaaca acaatgatca cgctgctggt cacgtgttgc   2640
atcacgctct tggcaaaacc gactatcact atcagttgga aatggccaag aacatcacgg   2700
ccgcagctga agcgatttac accccagaag aagctccggc taaaatcgat cacgtgatta   2760
aaactgctct tcgtgagaag aagccggttt atctcgaaat cgcttgcaac attgcttcca   2820
tgccctgcgc cgctcctgga ccggcaagcg cattgttcaa tgacgaagcc agcgacgaag   2880
cttctttgaa tgcagcggtt gaagaaaccc tgaaattcat cgccaaccgc gacaaagttg   2940
ccgtcctcgt cggcagcaag ctgcgcgcag ctggtgctga agaagctgct gtcaaatttg   3000
ctgatgctct cggtggcgca gttgctacca tggctgctgc aaaaagcttc ttcccagaag   3060
aaaacccgca ttacatcggt acctcatggg gtgaagtcag ctatccgggc gttgaaaaga   3120
cgatgaaaga agccgatgcg gttatcgctc tggctcctgt cttcaacgac tactccacca   3180
ctggttggac ggatattcct gatcctaaga aactggttct cgctgaaccg cgttctgtcg   3240
tcgttaacgg cgttcgcttc cccagcgttc atctgaaaga ctatctgacc cgtttggctc   3300
agaaagtttc caagaaaacc ggtgctttgg acttcttcaa atccctcaat gcaggtgaac   3360
tgaagaaagc cgctccggct gatccgagtg ctccgttggt caacgcagaa atcgcccgtc   3420
aggtcgaagc tcttctgacc ccgaacacga cggttattgc tgaaaccggt gactcttggt   3480
tcaatgctca gcgcatgaag ctcccgaacg gtgctcgcgt tgaatatgaa atgcagtggg   3540
gtcacatcgg ttggtccgtt cctgccgcct tcggttatgc cgtcggtgct ccggaacgtc   3600
```

-continued

```
gcaacatcct catggttggt gatggttcct tccagctgac ggctcaggaa gtcgctcaga   3660
tggttcgcct gaaactgccg gttatcatct tcttgatcaa taactatggt tacaccatcg   3720
aagttatgat ccatgatggt ccgtacaaca acatcaagaa ctgggattat gccggtctga   3780
tggaagtgtt caacggtaac ggtggttatg acagcggtgc tggtaaaggc ctgaaggcta   3840
aaaccggtgg cgaactggca gaagctatca aggttgctct ggcaaacacc gacggcccaa   3900
ccctgatcga atgcttcatc ggtcgtgaag actgcactga agaattggtc aaatggggta   3960
agcgcgttgc tgccgccaac agccgtaagc ctgttaacaa gctcctctag tttttgggga   4020
tcaattcgag ctcagcaagt ttcatcccga ccccctcagg gtcgggattt ttttattgta   4080
ctagtaacgc ccggttgcca ccgggcgttt tttattccga cattgccata agtaaaggca   4140
tcccctgcgt gataagatta ccttcagttt atggaggact gaccatatga tcaaggctta   4200
tgccgcttta gaggctaatg gcaagttgca gccgttcgag tatgatccgg gcgctttagg   4260
cgccaacgaa gttgaaatcg aagttcaata ctgcggtgtt tgtcattccg acctcagtat   4320
gatcaacaat gagtggggta tcagtaacta tccgttggtt cccggccacg aagttgttgg   4380
caccgttgct gctatgggtg agggtgttaa tcacgtggaa gttggtgacc tggttggttt   4440
aggctggcac agtggttatt gtatgacttg tcactcctgc ctgagcggtt atcataattt   4500
gtgcgctacc gccgagagta ctatcgttgg tcattatggc ggtttcggtg accgtgtgcg   4560
tgctaaaggt gtgtccgttg ttaagctgcc caagggtatc gatttggctt ccgctggtcc   4620
gttgttttgc ggtggtatca ctgtgttttc cccccatggtt gagttatccc tgaaaccgac   4680
cgccaaggtt gccgttattg gtatcggtgg tctcggtcac ctggccgttc agttcttgcg   4740
tgcttggggt tgcgaggtta ccgctttcac tagctccgct cgtaaacaga ccgaggttct   4800
ggagctgggt gcccatcata ttttggacag tactaacccc gaagccattg cttccgccga   4860
gggtaagttc gattacatca ttagtaccgt taatttaaaa ttggattgga atctgtatat   4920
ttccacttta gccccgcaag gtcactttca tttcgtgggt gttgttctcg aacccctcga   4980
cttgaacttg ttcccgttgc tcatgggtca gcggagtgtg tccgctagtc cggttggctc   5040
cccggctact atcgctacta tgctcgattt cgccgttcgg cacgatatca agccggttgt   5100
tgagcagttc tccttcgacc aaattaatga agccattgct cacttggagt ccggtaaggc   5160
tcactaccgt gtggttttga gtcactccaa gaactgaaac gctcggttgc cgccgggcgt   5220
tttttattcc tgcaggagca gaagagcata catctggaag caaagccagg aaagcggcct   5280
atggagctgt gcggcagcgc tcagtaggca atttttcaaa atattgttaa gccttttctg   5340
agcatggtat ttttcatggt attaccaatt agcaggaaaa taagccattg aatataaaag   5400
ataaaaatgt cttgtttaca atagagtggg gggggtcagc ctgccgcctt gggccgggtg   5460
atgtcgtact tgcccgccgc gaactcggtt accgtccagc ccagcgcgac cagctccggc   5520
aacgcctcgc gcacccgctg gcggcgcttg cgcatggtcg aaccactggc ctctgacggc   5580
cagacatagc cgcacaaggt atctatggaa gccttgccgg ttttgccggg gtcgatccag   5640
ccacacagcc gctggtgcag caggcgggcg gtttcgctgt ccagcgcccg cacctcgtcc   5700
atgctgatgc gcacatgctg gccgccaccc atgacggcct gcgcgatcaa ggggttcagg   5760
gccacgtaca ggcgcccgtc cgcctcgtcg ctggcgtact ccgacagcag ccgaaacccc   5820
tgccgcttgc ggccattctg ggcgatgatg gataccttcc aaaggcgctc gatgcagtcc   5880
tgtatgtgct tgagcgcccc accactatcg acctctgccc cgatttcctt tgccagcgcc   5940
cgatagctac ctttgaccac atggcattca gcggtgacgg cctcccactt gggttccagg   6000
```

aacagccgga gctgccgtcc gccttcggtc ttgggttccg ggccaagcac taggccatta 6060
ggcccagcca tggccaccag cccttgcagg atgcgcagat catcagcgcc cagcggctcc 6120
gggccgctga actcgatccg cttgccgtcg ccgtagtcat acgtcacgtc cagcttgctg 6180
cgcttgcgct cgccccgctt gagggcacgg aacaggccgg gggccagaca gtgcgccggg 6240
tcgtgccgga cgtggctgag gctgtgcttg ttcttaggct tcaccacggg gcaccccctt 6300
gctcttgcgc tgcctctcca gcacggcggg cttgagcacc ccgccgtcat gccgcctgaa 6360
ccaccgatca gcgaacggtg cgccatagtt ggccttgctc acaccgaagc ggacgaagaa 6420
ccggcgctgg tcgtcgtcca caccccattc ctcggcctcg gcgctggtca tgctcgacag 6480
gtaggactgc cagcggatgt tatcgaccag taccgagctg ccccggctgg cctgctgctg 6540
gtcgcctgcg cccatcatgg ccgcgccctt gctggcatgg tgcaggaaca cgatagagca 6600
cccggtatcg gcggcgatgg cctccatgcg accgatgacc tgggccatgg ggccgctggc 6660
gttttcttcc tcgatgtgga accggcgcag cgtgtccagc accatcaggc ggcggccctc 6720
ggcggcgcgc ttgaggccgt cgaaccactc cggggccatg atgttgggca ggctgccgat 6780
cagcggctgg atcagcaggc cgtcagccac ggcttgccgt tcctcggcgc tgaggtgcgc 6840
cccaagggcg tgcaggcggt gatgaatggc ggtgggcggg tcttcggcgg gcaggtagat 6900
caccgggccg gtgggcagtt cgcccacctc cagcagatcc ggcccgcctg caatctgtgc 6960
ggccagttgc agggccagca tggatttacc ggcaccaccg ggcgacacca gcgccccgac 7020
cgtaccggcc accatgttgg gcaaaacgta gtccagcggt ggcggcgctg ctgcgaacgc 7080
ctccagaata ttgataggct tatgggtagc cattgattgc ctcctttgca ggcagttggt 7140
ggttaggcgc tggcggggtc actacccccg ccctgcgccg ctctgagttc ttccaggcac 7200
tcgcgcagcg cctcgtattc gtcgtcggtc agccagaact tgcgctgacg catccctttg 7260
gccttcatgc gctcggcata tcgcgcttgg cgtacagcgt cagggctggc cagcaggtcg 7320
ccggtctgct tgtccttttg gtctttcata tcagtcaccg agaaacttgc cggggccgaa 7380
aggcttgtct tcgcggaaca aggacaaggt gcagccgtca aggttaaggc tggccatatc 7440
agcgactgaa aagcggccag cctcggcctt gtttgacgta taaccaaagc caccgggcaa 7500
ccaatagccc ttgtcacttt tgatcaggta gaccgaccct gaagcgcttt tttcgtattc 7560
cataaaaccc ccttctgtgc gtgagtactc atagtataac aggcgtgagt accaacgcaa 7620
gcactacatg ctgaaatctg gcccgcccct gtccatgcct cgctggcggg gtgccggtgc 7680
ccgtgccagc tcggcccgcg caagctggac gctgggcaga cccatgacct tgctgacggt 7740
gcgctcgatg taatccgctt cgtggccggg cttgcgctct gccagcgctg ggctggcctc 7800
ggccatggcc ttgccgattt cctcggcact gcggccccgg ctggccagct tctgcgcggc 7860
gataaagtcg cacttgctga ggtcatcacc gaagcgcttg accagcccgg ccatctcgct 7920
gcggtactcg tccagcgccg tgcgccggtg gcggctaagc tgccgctcgg gcagttcgag 7980
gctggccagc ctgcgggcct tctcctgctg ccgctgggcc tgctcgatct gctggccagc 8040
ctgctgcacc agcgccgggc cagcggtggc ggtcttgccc ttggattcac gcagcagcac 8100
ccacggctga taaccggcgc gggtggtgtg cttgtccttg cggttggtga agcccgccaa 8160
gcggccatag tggcggctgt cggcgctggc cgggtcggcg tcgtactcgc tggccagcgt 8220
ccgggcaatc tgcccccgaa gttcaccgcc tgcggcgtcg gccaccttga cccatgcctg 8280
atagttcttc gggctggttt ccactaccag ggcaggctcc cggccctcgg ctttcatgtc 8340

-continued

```
atccaggtca aactcgctga ggtcgtccac cagcaccaga ccatgccgct cctgctcggc   8400
gggcctgata tacacgtcat tgccctgggc attcatccgc ttgagccatg gcgtgttctg   8460
gagcacttcg gcggctgacc attcccggtt catcatctgg ccggtggtgg cgtccctgac   8520
gccgatatcg aagcgctcac agcccatggc cttgagctgt cggcctatgg cctgcaaagt   8580
cctgtcgttc ttcatcgggc caccaagcgc agccagatcg agccgtcctc ggttgtcagt   8640
ggcgtcaggt cgagcaagag caacgatgcg atcagcagca ccaccgtagg catcatggaa   8700
gccagcatca cggttagcca tagcttccag tgccaccccc gcgacgcgct ccgggcgctc   8760
tgcgcggcgc tgctcacctc ggcggctacc tcccgcaact ctttggccag ctccacccat   8820
gccgcccctg tctggcgctg ggctttcagc cactccgccg cctgcgcctc gctggcctgc   8880
tgggtctggc tcatgacctg ccgggcttcg tcggccagtg tcgccatgct ctgggccagc   8940
ggttcgatct gctccgctaa ctcgttgatg cctctggatt tcttcactct gtcgattgcg   9000
ttcatggtct attgcctccc ggtattcctg taagtcgatg atctgggcgt tggcggtgtc   9060
gatgttcagg gccacgtctg cccggtcggt gcggatgccc cggccttcca tctccaccac   9120
gttcggcccc aggtgaacac cgggcaggcg ctcgatgccc tgcgcctcaa gtgttctgtg   9180
gtcaatgcgg gcgtcgtggc cagcccgctc taatgcccgg ttggcatggt cggcccatgc   9240
ctcgcgggtc tgctcaagcc atgccttggg cttgagcgct tcggtcttct gtgccccgcc   9300
cttctccggg gtcttgccgt tgtaccgctt gaaccactga gcggcgggcc gctcgatgcc   9360
gtcattgatc cgctcggaga tcatcaggtg gcagtgcggg ttctcgccgc caccggcatg   9420
gatggccagc gtatacggca ggcgctcggc accggtcagg tgctgggcga actcggacgc   9480
cagcgccttc tgctggtcga gggtcagctc gaccggcagg gcaaattcga cctccttgaa   9540
cagccgccca ttggcgcgtt catacaggtc ggcagcatcc cagtagtcgg cgggccgctc   9600
gacgaactcc ggcatgtgcc cggattcggc gtgcaagact tcatccatgt cgcgggcata   9660
cttgccttcg cgctggatgt agtcggcctt ggccctggcc gattggccgc ccgacctgct   9720
gccggttttc gccgtaaggt gataaatcgc catgctgcct cgctgttgct tttgcttttc   9780
ggctccatgc aatggccctc ggagagcgca ccgcccgaag ggtggccgtt aggccagttt   9840
ctcgaagaga aaccggtaag tgcgccctcc cctacaaagt agggtcggga ttgccgccgc   9900
tgtgcctcca tgatagccta cgagacagca cattaacaat ggggtgtcaa gatggttaag   9960
gggagcaaca aggcggcgga tcggctggcc aagctcgaag aacaacgagc gcgaatcaat  10020
gccgaaattc agcgggtgcg ggcaagggaa cagcagcaag agcgcaagaa cgaaacaagg  10080
cgcaaggtgc tggtgggggc catgattttg gccaaggtga acagcagcga gtggccggag  10140
gatcggctca tggcggcaat ggatgcgtac cttgaacgcg accacgaccg cgccttgttc  10200
ggtctgccgc cacgccagaa ggatgagccg ggctgaatga tcgaccgaga caggccctgc  10260
ggggctgcac acgcgccccc acccttcggg taggggggaaa ggccgctaaa gcggctaaaa  10320
gcgctccagc gtatttctgc ggggtttggt gtggggttta gcgggctttg cccgcctttc  10380
cccctgccgc gcagcggtgg ggcggtgtgt agcctagcgc agcgaataga ccagctatcc  10440
ggcctctggc cgggcatatt gggcaagggc agcagcgccc cacaagggcg ctgataaccg  10500
cgcctagtgg attattctta gataatcatg gatggatttt tccaacaccc cgccagcccc  10560
cgcccctgct gggtttgcag gtttgggggc gtgacagtta ttgcaggggt tcgtgacagt  10620
tattgcaggg gggcgtgaca gttattgcag gggttcgtga cagttagtac gggagtgacg  10680
ggcactggct ggcaatgtct agcaacggca ggcatttcgg ctgagggtaa aagaactttc  10740
```

-continued

```
cgctaagcga tagactgtat gtaaacacag tattgcaagg acgcggaaca tgcctcatgt  10800
ggcggccagg acggccagcc gggatcggga tactggtcgt taccagagcc accgacccga  10860
gcaaaccctt ctctatcaga tcgttgacga gtattacccg gcattcgctg cgcttatggc  10920
agagcaggga aaggaattgc cgggctatgt gcaacgggaa tttgaagaat ttctccaatg  10980
cgggcggctg gagcatggct ttctacgggt tcgctgcgag tcttgccacg ccgagcacct  11040
ggtcgctttc agctgtaatc cgggcagcgc aacggaacat tcatcagtgt aaaaatggaa  11100
tcaataaagc cctgcgcagc gcgcagggtc agcctgaata cgcgtgctcg aattgacata  11160
agcctgttcg gttcgtaaac tgtaatgcaa gtagcgtatg cgctcacgca actggtccag  11220
aaccttgacc gaacgcagcg gtggtaacgg cgcagtggcg gttttcatgg cttgttatga  11280
ctgttttttt gtacagtcta tgcctcgggc atccaagcag caagcgcgtt acgccgtggg  11340
tcgatgtttg atgttatgga gcagcaacga tgttacgcag cagcaacgat gttacgcagc  11400
agggcagtcg ccctaaaaca aagttaggtg gctcaagtat gggcatcatt cgcacatgta  11460
ggctcggccc tgaccaagtc aaatccatgc gggctgctct tgatcttttc ggtcgtgagt  11520
tcggagacgt agccacctac tcccaacatc agccggactc cgattacctc gggaacttgc  11580
tccgtagtaa gacattcatc gcgcttgctg ccttcgacca agaagcggtt gttggcgctc  11640
tcgcggctta cgttctgccc aggtttgagc agccgcgtag tgagatctat atctatgatc  11700
tcgcagtctc cggcgagcac cggaggcagg gcattgccac cgcgctcatc aatctcctca  11760
agcatgaggc caacgcgctt ggtgcttatg tgatctacgt gcaagcagat tacggtgacg  11820
atcccgcagt ggctctctat acaaagttgg gcatacggga agaagtgatg cactttgata  11880
tcgacccaag taccgccacc taacaattcg ttcaagccga gatcggcttc ccggccctag  11940
acgcgtattc aggctgaccc tgcgcgctgc gcagggcttt attgattcca tttttacact  12000
gatgaatgtt ccgttgcgct gcccggatta cagatcctct agaagaacag caaggccgcc  12060
aatgcctgac gatgcgtgga gaccgaaacc ttgcgctcgt tcgccagcca ggacagaaat  12120
gcctcgactt cgctgctgcc caaggttgcc gggtgacgca caccgtggaa acggatgaag  12180
gcacgaaccc agtggacata agcctgttcg gttcgtaagc tgtaatgcaa gtagcgtatg  12240
cgctcacgca actggtccag aaccttgacc gaacgcagcg gtggtaacgg cgcagtggcg  12300
gttttcatgg cttgttatga ctgttttttt ggggtacagt ctatgcctcg ggcatccaag  12360
cagcaagcgc gttacgccgt gggtcgatgt ttgatgttat ggagcagcaa cgatgttacg  12420
cagcagggca gtcgccctaa aacaaagtta aacatcatga gggaagcggt gatcgccgaa  12480
gtatcgactc aactatcaga ggtagttggc gtcatcgagc gccatctcga accgacgttg  12540
ctggccgtac atttgtacgg ctccgcagtg gatggcggcc tgaagccaca cagtgatatt  12600
gatttgctgg ttacggtgac cgtaaggctt gatgaaacaa cgcggcgagc tttgatcaac  12660
gaccttttgg aaacttcggc ttcccctgga gagagcgaga ttctccgcgc tgtagaagtc  12720
accattgttg tgcacgacga catcattccg tggcgttatc cagctaagcg cgaactgcaa  12780
tttggagaat ggcagcgcaa tgacattctt gcaggtatct tcgagccagc cacgatcgac  12840
attgatctgg ctatcttgct gacaaaagca agagaacata gcgttgcctt ggtaggtcca  12900
gcggcggagg aactctttga tccggttcct gaacaggatc tatttgaggc gctaaatgaa  12960
accttaacgc tatggaactc gccgcccgac tgggctggcg atgagcgaaa tgtagtgctt  13020
acgttgtccc gcatttggta cagcgcagta accggcaaaa tcgcgccgaa ggatgtcgct  13080
```

-continued gccgactggg caatggagcg cctgccggcc cagtatcagc ccgtcatact tgaagctaga 13140
caggcttatc ttggacaaga agaagatcgc ttggcctcgc gcgcagatca gttggaagaa 13200
tttgtccact acgtgaaagg cgagatcacc aaggtagtcg gcaaataatg tctaacaatt 13260
cgttcaagcc gacgccgctt cgcggcgcgg cttaactcaa gctctagag 13309

<210> SEQ ID NO 86
<211> LENGTH: 121
<212> TYPE: DNA
<213> ORGANISM: Artificial
<220> FEATURE:
<223> OTHER INFORMATION: modified promoter PnrsB*

<400> SEQUENCE: 86
cgcctctgcc ttttttataa cggtctgatc ttagcggggg aaggagattt tcacctgaat 60
ttcatacccc ctttggcaga ctgggaaaat cttggacaaa ttcccaattg gaggaggtgt 120
g 121

<210> SEQ ID NO 87
<211> LENGTH: 10630
<212> TYPE: DNA
<213> ORGANISM: Artificial
<220> FEATURE:
<223> OTHER INFORMATION: #1441¶AQ1-nrsRS-PnrsB*-zmPDC-Prbc*-synADH_oop
standard

<400> SEQUENCE: 87
tcgaccctat atcgggcttt tctcaataaa atctttattt tttgaggtgc tttttagcca 60
taaataatca ctttagtata aaattttgac ggcgtaaagt tgataaaata gaattaagaa 120
tggactatcg gtacagaaaa aatgggtaac tggatggtga ataaacttcc cttacccaat 180
gcactctcca ccgttaaaga ccccctatgc ttaacggtga tcacctgggc aatggcgagt 240
cccaaccctg tcccccccgt tttgcgcgaa cgatctcgat taactcggta aaaacgctca 300
aaaatgtgtt cctgttggtc gggggcaatg ccgatgccgg tatcttgcac ggtgatgata 360
gccatctgtt catgggatgt cagggtaata tcaacacgtc ccccagcagt tgtgtattga 420
atggcgttgg caattaggtt tgagaccagt cgatagagtt gggattcatt accccaggcg 480
taaacttccc ctgaactcag atcactgctg agatcaatgt gggcggcgat cgctaattct 540
aaaaactctt cggtgaggtc actgactaaa tcatttaaac aacaaagccg ccaatcttcg 600
gcggtggttt cctgctctaa gcgacttagt agcaataaat ccgtaatcaa ttggcttaat 660
cgccttccct gtcgttcaac ggtatgtagc atggtgttaa tttctgggga atggcttgag 720
tcgatgcgta ataccgcttc caccgtggcc aacagactag ccaatggcga tcgtaattca 780
tgggctgcat tcgcggtgaa ttgttgttgt tgttggtagg actggtaaat gggacgcatg 840
gctaaccccg ctaagcccca actggagaag gcgaccaaac ccagggcaat gggaaaacta 900
agccctaaaa tccaaagaat acgtttattt tcggcatcaa aggctgccag gctccggcca 960
atttgtagat agccccagga agatttgtct gtattaccgg cgctatgcaa aatggtggtg 1020
aattgtcgat accgatcgcc ggttgggggg tgaatagtct gccaagtttc ctggttaaaa 1080
atggaggata gggaagccgg ttgattaggc gaaaaagcca gcaggttgcc ttgataatca 1140
aataaacgaa tgtaatataa actgcgatca ctaatgccca acgtgtgacg ttcaatcagg 1200
gtggggttga cctggcaggg ttggttgacc aaacacagat cgggcaacat tttttgtaat 1260
actccggtgg gactagcatt actcggcaac atcggctcta aactgtcatg caacgtcccg 1320

-continued

```
gcgatcgact ccacttctcg ctccaacgcc atccagttgg cctgcacaat ggcacgataa   1380
acccccaacc ccaacagggt aagaataccc cccattacta gggcatacca gaaagccaat   1440
tgcagacgac tacgggcaaa gaggcgacgg gtattcatgg cgatagggtg aaccgatagc   1500
cttgaccggg aactgtttta attgggcaag gacaattttg ttgagctagc ttgcgtcgta   1560
tcaaacgcat ttgggccgcc accacattac tcatgggctc ctcatcaaga tcccacagtt   1620
gttgccggat cttgctaccg gaaatgatcc gctctgggtt ttgcatcaga tattgaaaaa   1680
tttgaaattc tcttacggtt aaagcaattt cctgtctttc taggtttagt ggctccgaga   1740
tagttaccga taacagatta ttactgggat caaggctgaa gttgcccaaa gttaaaattt   1800
gcggttggaa ttgtggcgat cgccgttgta gtgcccgcag tcttgctaat agctctgcca   1860
tcacaaacgg ttttgttaga tagtcatctg ccccggcatc tagtccttcg acacggtttt   1920
ccggttctcc taacgctgtt aacatcaaca ccggcaagga attaccctgg gttctcagtt   1980
tttgacagag ttccaaaccc gataatcccg gcagtaacca atccacaatg gcaagggtgt   2040
attccgtcca ttgattttcc aaataatccc aagcttggga gccatccgtc acccaatcca   2100
ccacatactt ttcactaact agcactttct taatagccat tcccaaatcc gtctcatctt   2160
ccaccagcaa aattcgcatc gcctctgcct tttttataac ggtctgatct tagcgggggga  2220
aggagatttt cacctgaatt tcatacccc tttggcagac tgggaaaatc ttggacaaat   2280
tcccaattgg aggaggtgtg atgaattctt atactgtcgg tacctattta gcggagcggc   2340
ttgtccagat tggtctcaag catcacttcg cagtcgcggg cgactacaac ctcgtccttc   2400
ttgacaacct gcttttgaac aaaaacatgg agcaggttta ttgctgtaac gaactgaact   2460
gcggtttcag tgcagaaggt tatgctcgtg ccaaaggcgc agcagcagcc gtcgttacct   2520
acagcgtcgg tgcgctttcc gcatttgatg ctatcggtgg cgcctatgca gaaaaccttc   2580
cggttatcct gatctccggt gctccgaaca acaatgatca cgctgctggt cacgtgttgc   2640
atcacgctct tggcaaaacc gactatcact atcagttgga aatggccaag aacatcacgg   2700
ccgcagctga agcgatttac accccagaag aagctccggc taaaatcgat cacgtgatta   2760
aaactgctct tcgtgagaag aagccggttt atctcgaaat cgcttgcaac attgcttcca   2820
tgccctgcgc cgctcctgga ccggcaagcg cattgttcaa tgacgaagcc agcgacgaag   2880
cttctttgaa tgcagcggtt gaagaaaccc tgaaattcat cgccaaccgc gacaaagttg   2940
ccgtcctcgt cggcagcaag ctgcgcgcag ctggtgctga agaagctgct gtcaaatttg   3000
ctgatgctct cggtggcgca gttgctacca tggctgctgc aaaaagcttc ttcccagaag   3060
aaaacccgca ttacatcggt acctcatggg gtgaagtcag ctatccgggc gttgaaaaga   3120
cgatgaaaga agccgatgcg gttatcgctc tggctcctgt cttcaacgac tactccacca   3180
ctggttggac ggatattcct gatcctaaga aactggttct cgctgaaccg cgttctgtcg   3240
tcgttaacgg cgttcgcttc cccagcgttc atctgaaaga ctatctgacc cgtttggctc   3300
agaaagtttc caagaaaacc ggtgctttgg acttcttcaa atccctcaat gcaggtgaac   3360
tgaagaaagc cgctccggct gatccgagtg ctccgttggt caacgcagaa atcgcccgtc   3420
aggtcgaagc tcttctgacc ccgaacacga cggttattgc tgaaaccggt gactcttggt   3480
tcaatgctca gcgcatgaag ctcccgaacg gtgctcgcgt tgaatatgaa atgcagtggg   3540
gtcacatcgg ttggtccgtt cctgccgcct tcggttatgc cgtcggtgct ccggaacgtc   3600
gcaacatcct catggttggt gatggttcct tccagctgac ggctcaggaa gtcgctcaga   3660
tggttcgcct gaaactgccg gttatcatct tcttgatcaa taactatggt tacaccatcg   3720
```

aagttatgat ccatgatggt ccgtacaaca acatcaagaa ctgggattat gccggtctga 3780
tggaagtgtt caacggtaac ggtggttatg acagcggtgc tggtaaaggc ctgaaggcta 3840
aaaccggtgg cgaactggca gaagctatca aggttgctct ggcaaacacc gacggcccaa 3900
ccctgatcga atgcttcatc ggtcgtgaag actgcactga agaattggtc aaatggggta 3960
agcgcgttgc tgccgccaac agccgtaagc ctgttaacaa gctcctctag tttttgggga 4020
tcaattcgag ctcactagtc gatcgacatt gccataagta aaggcatccc ctgcgtgata 4080
agattacctt cagtttatgg aggactgacc atatgattaa agcctacgct gccctggaag 4140
ccaacggaaa actccaaccc tttgaatacg accccggtgc cctgggtgct aatgaggtgg 4200
agattgaggt gcagtattgt ggggtgtgcc acagtgattt gtccatgatt aataacgaat 4260
ggggcatttc caattacccc ctagtgccgg gtcatgaggt ggtgggtact gtggccgcca 4320
tgggcgaagg ggtgaaccat gttgaggtgg gggatttagt ggggctgggt tggcattcgg 4380
gctactgcat gacctgccat agttgtttat ctggctacca caacctttgt gccacggcgg 4440
aatcgaccat tgtgggccac tacggtggct ttggcgatcg ggttcgggcc aagggagtca 4500
gcgtggtgaa attacctaaa ggcattgacc tagccagtgc cgggcccctt ttctgtggag 4560
gaattaccgt tttcagtcct atggtggaac tgagtttaaa gcccactgca aaagtggcag 4620
tgatcggcat tgggggcttg ggccatttag cggtgcaatt tctccgggcc tggggctgtg 4680
aagtgactgc ctttacctcc agtgccagga agcaaacgga agtgttggaa ttgggcgctc 4740
accacatact agattccacc aatccagagg cgatcgccag tgcggaaggc aaatttgact 4800
atattatctc cactgtgaac ctgaagcttg actggaactt atacatcagc accctggcgc 4860
cccagggaca tttccacttt gttggggtgg tgttggagcc tttggatcta aatcttttc 4920
cccttttgat gggacaacgc tccgtttctg cctccccagt gggtagtccc gccaccattg 4980
ccaccatgtt ggactttgct gtgcgccatg acattaaacc cgtggtggaa caatttagct 5040
ttgatcagat caacgaggcg atcgcccatc tagaaagcgg caaagcccat tatcgggtag 5100
tgctcagcca tagtaaaaat tagctctgca aaggttgctt ctgggtccgt ggaacgctcg 5160
gttgccgccg ggcgtttttt attcctgcag ccttgctcta gaagaacagc aaggccgcca 5220
atgcctgacg atgcgtggag accgaaacct tgcgctcgtt cgccagccag gacagaaatg 5280
cctcgacttc gctgctgccc aaggttgccg ggtgacgcac accgtggaaa cggatgaagg 5340
cacgaaccca gtggacataa gcctgttcgg ttcgtaagct gtaatgcaag tagcgtatgc 5400
gctcacgcaa ctggtccaga accttgaccg aacgcagcgg tggtaacggc gcagtggcgg 5460
ttttcatggc ttgttatgac tgttttttg gggtacagtc tatgcctcgg gcatccaagc 5520
agcaagcgcg ttacgccgtg ggtcgatgtt tgatgttatg gagcagcaac gatgttacgc 5580
agcagggcag tcgccctaaa acaaagttaa acatcatgag ggaagcggtg atcgccgaag 5640
tatcgactca actatcagag gtagttggcg tcatcgagcg ccatctcgaa ccgacgttgc 5700
tggccgtaca tttgtacggc tccgcagtgg atggcggcct gaagccacac agtgatattg 5760
atttgctggt tacggtgacc gtaaggcttg atgaaacaac gcggcgagct ttgatcaacg 5820
accttttgga aacttcggct tcccctggag agagcgagat tctccgcgct gtagaagtca 5880
ccattgttgt gcacgacgac atcattccgt ggcgttatcc agctaagcgc gaactgcaat 5940
ttggagaatg gcagcgcaat gacattcttg caggtatctt cgagccagcc acgatcgaca 6000
ttgatctggc tatcttgctg acaaaagcaa gagaacatag cgttgccttg gtaggtccag 6060

-continued

```
cggcggagga actctttgat ccggttcctg aacaggatct atttgaggcg ctaaatgaaa   6120
ccttaacgct atggaactcg ccgcccgact gggctggcga tgagcgaaat gtagtgctta   6180
cgttgtcccg catttggtac agcgcagtaa ccggcaaaat cgcgccgaag gatgtcgctg   6240
ccgactgggc aatggagcgc ctgccggccc agtatcagcc cgtcatactt gaagctagac   6300
aggcttatct tggacaagaa gaagatcgct tggcctcgcg cgcagatcag ttggaagaat   6360
ttgtccacta cgtgaaaggc gagatcacca aggtagtcgg caaataatgt ctaacaattc   6420
gttcaagccg acgccgcttc gcggcgcggc ttaactcaag cgttagatgc actaccggta   6480
tctttctaga agatcctcta gttctagagc ggccgctgga atttcccgat tctctgatgg   6540
gagatccaaa aattctcgca gtccctcaat cacgatatcg gtcttggatc gccctgtagc   6600
ttccgacaac tgctcaattt tttcgagcat ctctaccggg catcggaatg aaattaacgg   6660
tgttttagcc atgtgttata cagtgtttac aacttgacta acaaatacct gctagtgtat   6720
acatattgta ttgcaatgta tacgctattt tcactgctgt ctttaatggg gattatcgca   6780
agcaagtaaa aaagcctgaa aaccccaata ggtaagggat tccgagctta ctcgataatt   6840
atcacctttg agcgccccta ggaggaggcg aaaagctatg tctgacaagg ggtttgaccc   6900
ctgaagtcgt tgcgcgagca ttaaggtctg cggatagccc ataacatact tttgttgaac   6960
ttgtgcgctt ttatcaaccc cttaagggct tgggagcgtt ttatacgagt gcggggaact   7020
agtgatggcg gccgggagca tgcgacgtcg ggcccaattc gccctatagt gagtcgtatt   7080
acaattcact ggccgtcgtt ttacaacgtc gtgactggga aaaccctggc gttacccaac   7140
ttaatcgcct tgcagcacat ccccctttcg ccagctggcg taatagcgaa gaggcccgca   7200
ccgatcgccc ttcccaacag ttgcgcagcc tgaatggcga atggacgcgc cctgtagcgg   7260
cgcattaagc gcggcgggtg tggtggttac gcgcagcgtg accgctacac ttgccagcgc   7320
cctagcgccc gctcctttcg ctttcttccc ttcctttctc gccacgttcg ccggctttcc   7380
ccgtcaagct ctaaatcggg ggctcccttt agggttccga tttagagctt tacggcacct   7440
cgaccgcaaa aaacttgatt tgggtgatgg ttcacgtagt gggccatcgc cctgatagac   7500
ggtttttcgc cctttgacgt tggagtccac gttctttaat agtggactct tgttccaaac   7560
tggaacaaca ctcaacccta tctcggtcta ttcttttgat ttataaggga ttttgccgat   7620
ttcggcctat tggttaaaaa atgagctgat ttaacaaata tttaacgcga attttaacaa   7680
aatattaacg tttacaattt cgcctgatgc ggtattttct ccttacgcat ctgtgcggta   7740
tttcacaccg catacaggtg gcacttttcg gggaaatgtg cgcggaaccc ctatttgttt   7800
atttttctaa atacattcaa atatgtatcc gctcatgaga caataaccct gataaatgct   7860
tcaataatat tgaaaaagga agagtatgag tattcaacat ttccgtgtcg cccttattcc   7920
cttttttgcg gcattttgcc ttcctgtttt tgctcaccca gaaacgctgg tgaaagtaaa   7980
agatgctgaa gatcagttgg gtgcacgagt gggttacatc gaactggatc tcaacagcgg   8040
taagatcctt gagagttttc gccccgaaga acgttttcca atgatgagca cttttaaagt   8100
tctgctatgt ggcgcggtat tatcccgtat tgacgccggg caagagcaac tcggtcgccg   8160
catacactat tctcagaatg acttggttga gtactcacca gtcacagaaa agcatcttac   8220
ggatggcatg acagtaagag aattatgcag tgctgccata accatgagtg ataacactgc   8280
ggccaactta cttctgacaa cgatcggagg accgaaggag ctaaccgctt ttttgcacaa   8340
catgggggat catgtaactc gccttgatcg ttgggaaccg gagctgaatg aagccatacc   8400
aaacgacgag cgtgacacca cgatgcctgt agcaatgcca acaacgttgc gcaaactatt   8460
```

```
aactggcgaa ctacttactc tagcttcccg gcaacaatta atagactgga tggaggcgga   8520
taaagttgca ggaccacttc tgcgctcggc ccttccggct ggctggttta ttgctgataa   8580
atctggagcc ggtgagcgtg ggtctcgcgg tatcattgca gcactggggc cagatggtaa   8640
gccctcccgt atcgtagtta tctacacgac ggggagtcag gcaactatgg atgaacgaaa   8700
tagacagatc gctgagatag gtgcctcact gattaagcat tggtaactgt cagaccaagt   8760
ttactcatat atactttaga ttgatttaaa acttcatttt taatttaaaa ggatctaggt   8820
gaagatcctt tttgataatc tcatgaccaa aatcccttaa cgtgagtttt cgttccactg   8880
agcgtcagac cccgtagaaa agatcaaagg atcttcttga gatccttttt ttctgcgcgt   8940
aatctgctgc ttgcaaacaa aaaaaccacc gctaccagcg gtggtttgtt tgccggatca   9000
agagctacca actctttttc cgaaggtaac tggcttcagc agagcgcaga taccaaatac   9060
tgtccttcta gtgtagccgt agttaggcca ccacttcaag aactctgtag caccgcctac   9120
atacctcgct ctgctaatcc tgttaccagt ggctgctgcc agtggcgata agtcgtgtct   9180
taccgggttg gactcaagac gatagttacc ggataaggcg cagcggtcgg gctgaacggg   9240
gggttcgtgc acacagccca gcttggagcg aacgacctac accgaactga gatacctaca   9300
gcgtgagcta tgagaaagcg ccacgcttcc cgaagggaga aaggcggaca ggtatccggt   9360
aagcggcagg gtcggaacag gagagcgcac gagggagctt ccagggggaa acgcctggta   9420
tctttatagt cctgtcgggt ttcgccacct ctgacttgag cgtcgatttt tgtgatgctc   9480
gtcagggggg cggagcctat ggaaaaacgc cagcaacgcg gcctttttac ggttcctggc   9540
cttttgctgg ccttttgctc acatgttctt tcctgcgtta tcccctgatt ctgtggataa   9600
ccgtattacc gcctttgagt gagctgatac cgctcgccgc agccgaacga ccgagcgcag   9660
cgagtcagtg agcgaggaag cggaagagcg cccaatacgc aaaccgcctc tccccgcgcg   9720
ttggccgatt cattaatgca gctggcacga caggtttccc gactggaaag cgggcagtga   9780
gcgcaacgca attaatgtga gttagctcac tcattaggca ccccaggctt tacactttat   9840
gcttccggct cgtatgttgt gtggaattgt gagcggataa caatttcaca caggaaacag   9900
ctatgaccat gattacgcca agctatttag gtgacactat agaatactca agctatgcat   9960
ctccaacatg agggctttgt atttaagccg gatatcaaca ggcgatcgct ctcaccaaag  10020
attcacctgt tagagctact caacatccat cagttcttaa aaccaggggt gacattcacc  10080
ggggcgagcc ttgaagggtt caaggaaaat tgtttgcggt atgccaagcc gatcaagtgg  10140
attcttggca gaacgatcac cgacaaaatg agcccgctcg aaattgctca ggcgctccta  10200
ggcaagcttg accggaaatt ggaatacaag gggcgctttg gatcgcggga taaccgtcag  10260
cgggtctatg aggcgatcgc ccctaacgat cagcgcgaaa aggtctttgc tcattggtta  10320
cagcgtgacc aagcaaaatt aggggccgtg tccaacccct gtataaatag atttattcag  10380
gaggcttaga cccgtgatcg aaatactcgt tgtgcagctc tcccttggca atcccaaaca  10440
atctcaagat ttgctctgcg gtatcgggac gttttatgcc cttgcggaaa gcgcctttgc  10500
tcttctggta gcccctagac tgtgccagat cataagcctc actgagggtg agggcactac  10560
cgggggcatg agctcgccca agagattcag cgaccggggc gatcgccctt ggtaattctc  10620
tcaggcgctg                                                         10630
```

<210> SEQ ID NO 88
<211> LENGTH: 13291
<212> TYPE: DNA

-continued

<213> ORGANISM: Artificial
<220> FEATURE:
<223> OTHER INFORMATION: #1460¶VZ325a-nrsRS-PnrsB916-PDCdsrA-Prbc*-
synADHdeg standard

<400> SEQUENCE: 88
tcgacaaaat gaagtaccga agacaaccat cattggggtt gtcttttta ttggttaatt 60 ggcgaaagac tccaagggcg atcgcctttt aattaagttc tattcacctt ttctgagggg 120
taaacgcaga gtgaattggc taccttgatc cgcatcactc tggatttgga tagatccgtg 180
ataagcaagg gcgatcgcct gggcaatggc aagccctaaa cctgtccccc cggttttacg 240
ggaacggtca tcattaactc ggtaaaaccg tttaaaaatc tgttgttgtt gctctgggga 300
aatgcccata cctgtatccg taacggtaat tttggcatgg cgatcatccg tttttaaatt 360
tacattcacg ctgccacctt tgggggtata acgcagggca ttgtcgagga gattggacac 420
tagacgatag agttgggatt cgttcccttg cacataaatt tcctgtttgg ggagttcgtt 480
cgtgagggta ataccgacgg cgatcgccat ctctaaaaat tcttcggtga ggtcactgac 540
cagatcattc agacaacaat ccctccagtt ttctgaagtt tggggttgct ccaaacgact 600
gagcaacagc agatcattaa ttaattgact gagccgccgc ccctgccgtt cgacggtctg 660
gagcatggtt tggatgtcct gttgatcccc accattgagg cgcaaaatca cttcgacggt 720
tgccagcaaa ctcgcgaggg gcgatcgcag ttcgtgggcg gcatcagcgg taaattgttg 780
ctgctgttgg taagcgtcgt agatagggcg catggctaaa cctgctaacc accaactaga 840
gagggtaact acgccgagag caagaggtaa actgacccct aaaacccagc gaatccgttg 900
attttcctga tcaaaggcca tgaggctccg accaatctgg agataacccc atgaatcttg 960
aatatttgca gcgtcgtggg tgtaggcact atgaagaatc gtcgtaaatt gtcggtaacg 1020
gtcatcctcc tgtctaatgg tttgccatgt ctccggttgt aggttctggg ataagctctg 1080
cggttgattg ggggaaaagg caactaattg accttgatgg ttaaataggc ggatgtaata 1140
aaggcggcga tcgctaatgc ccatcgtgtg ccgttcaatt aaagttggtg tagtgtcaca 1200
gggctgatta acaaggcata gatctggaaa aatttgctgt aaagttcctg tggggttcgc 1260
attctccggc agtattggtt ctaggctatc gtgcagcgtt ccggcgattg actccacttc 1320
ccgttcaagg gcaacccaat tcgcttgcac aatggaacga taaacccccca gccctaaagc 1380 actcaaaatt ccccccatta cgagggcata ccagagagca agacggaggc gactgcgagc 1440
aaacagacga taactgttca tggttctacc gtaaaccgat aaccttggcc ggggacagtt 1500
tctatcgggc aaaaacaagc atatttcgct aattttcgcc gaattaaccg catttgcgcc 1560
gctacaacat tactaacggg ttcctcctcc aaatcccaaa gctgttgccg aattttactg 1620
ccggagagaa tgcgatctgg gttttgcatg aggtattgca gaatctgaaa ttccttgacc 1680
gtgagggtaa tggcttgggg ggcttgccct gtctgtctca ctactaattc ggtattgctg 1740
gggtcaaggc taaaattgcc cacccgaaga atttggggct gaaattgggg cgatcgccgt 1800
tggagagcgc gaacccgtgc gagtaattcc gccatcacaa aaggtttgac caaataatca 1860
tccgcccccg catccaagcc tctcactcga ttttctggtt ctcccaaggc agtcaacatc 1920
aatactggga gaggattatg ctgcgatcgc agtttttgac aaagctccaa gcctgacagt 1980
cctggcaaca accaatctag aattgccaca ccgtaatcag tccattgatt ttccagataa 2040
tgccaagcct gctgcccatc cgtcacccaa tccactacat acttctcgct gataagcacc 2100
ttcttaatca ccaagcctag atcttcttcg tcttctacca ataaaattcg catggtttaa 2160

-continued

```
gccagaatta ccacgaactt tatcctaatc acaaacagcc tatttcactt agatttcata   2220
ccccctctgg caaactggaa aaaattttcg tgccattttg tctctaaatg tgaggtgctg   2280
tgatgaattc ttatactgtc ggtacctatt tagcggagcg gcttgtccag attggtctca   2340
agcatcactt cgcagtcgcg ggcgactaca acctcgtcct tcttgacaac ctgcttttga   2400
acaaaaacat ggagcaggtt tattgctgta acgaactgaa ctgcggtttc agtgcagaag   2460
gttatgctcg tgccaaaggc gcagcagcag ccgtcgttac ctacagcgtc ggtgcgcttt   2520
ccgcatttga tgctatcggt ggcgcctatg cagaaaacct tccggttatc ctgatctccg   2580
gtgctccgaa caacaatgat cacgctgctg gtcacgtgtt gcatcacgct cttggcaaaa   2640
ccgactatca ctatcagttg gaaatggcca agaacatcac ggccgcagct gaagcgattt   2700
acaccccaga agaagctccg gctaaaatcg atcacgtgat taaaactgct cttcgtgaga   2760
agaagccggt ttatctcgaa atcgcttgca acattgcttc catgccctgc gccgctcctg   2820
gaccggcaag cgcattgttc aatgacgaag ccagcgacga agcttctttg aatgcagcgg   2880
ttgaagaaac cctgaaattc atcgccaacc gcgacaaagt tgccgtcctc gtcggcagca   2940
agctgcgcgc agctggtgct gaagaagctg ctgtcaaatt tgctgatgct ctcggtggcg   3000
cagttgctac catggctgct gcaaaaagct tcttcccaga agaaaacccg cattacatcg   3060
gtacctcatg gggtgaagtc agctatccgg gcgttgaaaa gacgatgaaa gaagccgatg   3120
cggttatcgc tctggctcct gtcttcaacg actactccac cactggttgg acggatattc   3180
ctgatcctaa gaaactggtt ctcgctgaac cgcgttctgt cgtcgttaac ggcgttcgct   3240
tccccagcgt tcatctgaaa gactatctga cccgtttggc tcagaaagtt tccaagaaaa   3300
ccggtgcttt ggacttcttc aaatccctca atgcaggtga actgaagaaa gccgctccgg   3360
ctgatccgag tgctccgttg gtcaacgcag aaatcgcccg tcaggtcgaa gctcttctga   3420
ccccgaacac gacggttatt gctgaaaccg gtgactcttg gttcaatgct cagcgcatga   3480
agctcccgaa cggtgctcgc gttgaatatg aaatgcagtg gggtcacatc ggttggtccg   3540
ttcctgccgc cttcggttat gccgtcggtg ctccggaacg tcgcaacatc ctcatggttg   3600
gtgatggttc cttccagctg acggctcagg aagtcgctca gatggttcgc ctgaaactgc   3660
cggttatcat cttcttgatc aataactatg gttacaccat cgaagttatg atccatgatg   3720
gtccgtacaa caacatcaag aactgggatt atgccggtct gatggaagtg ttcaacggta   3780
acggtggtta tgacagcggt gctggtaaag gcctgaaggc taaaaccggt ggcgaactgg   3840
cagaagctat caaggttgct ctggcaaaca ccgacggccc aaccctgatc gaatgcttca   3900
tcggtcgtga agactgcact gaagaattgg tcaaatgggg taagcgcgtt gctgccgcca   3960
acagccgtaa gcctgttaac aagctcctct agtttttggg gatcaattcg agctcagcaa   4020
gtttcatccc gacccctca gggtcgggat ttttttattg tactagtaac gcccggttgc   4080
caccgggcgt tttttattcc gacattgcca taagtaaagg catcccctgc gtgataagat   4140
taccttcagt ttatggagga ctgaccatat gatcaaggct tatgccgctt tagaggctaa   4200
tggcaagttg cagccgttcg agtatgatcc gggcgcttta ggcgccaacg aagttgaaat   4260
cgaagttcaa tactgcggtg tttgtcattc cgacctcagt atgatcaaca atgagtgggg   4320
tatcagtaac tatccgttgg ttcccggcca cgaagttgtt ggcaccgttg ctgctatggg   4380
tgagggtgtt aatcacgtgg aagttggtga cctggttggt ttaggctggc acagtggtta   4440
ttgtatgact tgtcactcct gcctgagcgg ttatcataat ttgtgcgcta ccgccgagag   4500
tactatcgtt ggtcattatg gcggtttcgg tgaccgtgtg cgtgctaaag gtgtgtccgt   4560
```

tgttaagctg cccaagggta tcgatttggc ttccgctggt ccgttgtttt gcggtggtat 4620
cactgtgttt tcccccatgg ttgagttatc cctgaaaccg accgccaagg ttgccgttat 4680
tggtatcggt ggtctcggtc acctggccgt tcagttcttg cgtgcttggg gttgcgaggt 4740
taccgctttc actagctccg ctcgtaaaca gaccgaggtt ctggagctgg gtgcccatca 4800
tattttggac agtactaacc ccgaagccat tgcttccgcc gagggtaagt tcgattacat 4860
cattagtacc gttaatttaa aattggattg gaatctgtat atttccactt tagccccgca 4920
aggtcacttt catttcgtgg gtgttgttct cgaacccctc gacttgaact tgttcccgtt 4980
gctcatgggt cagcggagtg tgtccgctag tccggttggc tccccggcta ctatcgctac 5040
tatgctcgat ttcgccgttc ggcacgatat caagccggtt gttgagcagt tctccttcga 5100
ccaaattaat gaagccattg ctcacttgga gtccggtaag gctcactacc gtgtggtttt 5160
gagtcactcc aagaactgaa acgctcggtt gccgccgggc gtttttttatt cctgcaggag 5220 cagaagagca tacatctgga agcaaagcca ggaaagcggc ctatggagct gtgcggcagc 5280
gctcagtagg caatttttca aaatattgtt aagccttttc tgagcatggt atttttcatg 5340
gtattaccaa ttagcaggaa aataagccat tgaatataaa agataaaaat gtcttgttta 5400
caatagagtg gggggggtca gcctgccgcc ttgggccggg tgatgtcgta cttgcccgcc 5460
gcgaactcgg ttaccgtcca gcccagcgcg accagctccg gcaacgcctc gcgcacccgc 5520
tggcggcgct tgcgcatggt cgaaccactg gcctctgacg gccagacata gccgcacaag 5580
gtatctatgg aagccttgcc ggttttgccg gggtcgatcc agccacacag ccgctggtgc 5640
agcaggcggg cggtttcgct gtccagcgcc cgcacctcgt ccatgctgat gcgcacatgc 5700
tggccgccac ccatgacggc ctgcgcgatc aaggggttca gggccacgta caggcgcccg 5760
tccgcctcgt cgctggcgta ctccgacagc agccgaaacc cctgccgctt gcggccattc 5820
tgggcgatga tggatacctt ccaaaggcgc tcgatgcagt cctgtatgtg cttgagcgcc 5880
ccaccactat cgacctctgc cccgatttcc tttgccagcg cccgatagct acctttgacc 5940
acatggcatt cagcggtgac ggcctcccac ttgggttcca ggaacagccg gagctgccgt 6000
ccgccttcgg tcttgggttc cgggccaagc actaggccat taggcccagc catggccacc 6060
agcccttgca ggatgcgcag atcatcagcg cccagcggct ccgggccgct gaactcgatc 6120
cgcttgccgt cgccgtagtc atacgtcacg tccagcttgc tgcgcttgcg ctcgccccgc 6180
ttgagggcac ggaacaggcc gggggccaga cagtgcgccg ggtcgtgccg gacgtggctg 6240
aggctgtgct tgttcttagg cttcaccacg gggcaccccc ttgctcttgc gctgcctctc 6300
cagcacggcg ggcttgagca ccccgccgtc atgccgcctg aaccaccgat cagcgaacgg 6360
tgcgccatag ttggccttgc tcacaccgaa gcggacgaag aaccggcgct ggtcgtcgtc 6420
cacaccccat tcctcggcct cggcgctggt catgctcgac aggtaggact gccagcggat 6480
gttatcgacc agtaccgagc tgccccggct ggcctgctgc tggtcgcctg cgcccatcat 6540
ggccgcgccc ttgctggcat ggtgcaggaa cacgatagag cacccggtat cggcggcgat 6600
ggcctccatg cgaccgatga cctgggccat ggggccgctg gcgttttctt cctcgatgtg 6660
gaaccggcgc agcgtgtcca gcaccatcag gcggcggccc tcggcggcgc gcttgaggcc 6720
gtcgaaccac tccggggcca tgatgttggg caggctgccg atcagcggct ggatcagcag 6780
gccgtcagcc acggcttgcc gttcctcggc gctgaggtgc gccccaaggg cgtgcaggcg 6840
gtgatgaatg gcggtgggcg ggtcttcggc gggcaggtag atcaccgggc cggtgggcag 6900

-continued

```
ttcgcccacc tccagcagat ccggcccgcc tgcaatctgt gcggccagtt gcagggccag   6960
catggattta ccggcaccac cgggcgacac cagcgccccg accgtaccgg ccaccatgtt   7020
gggcaaaacg tagtccagcg gtggcggcgc tgctgcgaac gcctccagaa tattgatagg   7080
cttatgggta gccattgatt gcctcctttg caggcagttg gtggttaggc gctggcgggg   7140
tcactacccc cgccctgcgc cgctctgagt tcttccaggc actcgcgcag cgcctcgtat   7200
tcgtcgtcgg tcagccagaa cttgcgctga cgcatccctt tggccttcat gcgctcggca   7260
tatcgcgctt ggcgtacagc gtcagggctg gccagcaggt cgccggtctg cttgtccttt   7320
tggtctttca tatcagtcac cgagaaactt gccggggccg aaaggcttgt cttcgcggaa   7380
caaggacaag gtgcagccgt caaggttaag gctggccata tcagcgactg aaaagcggcc   7440
agcctcggcc ttgtttgacg tataaccaaa gccaccgggc aaccaatagc ccttgtcact   7500
tttgatcagg tagaccgacc ctgaagcgct tttttcgtat tccataaaac ccccttctgt   7560
gcgtgagtac tcatagtata acaggcgtga gtaccaacgc aagcactaca tgctgaaatc   7620
tggcccgccc ctgtccatgc ctcgctggcg gggtgccggt gcccgtgcca gctcggcccg   7680
cgcaagctgg acgctgggca gacccatgac cttgctgacg gtgcgctcga tgtaatccgc   7740
ttcgtggccg ggcttgcgct ctgccagcgc tgggctggcc tcggccatgg ccttgccgat   7800
ttcctcggca ctgcggcccc ggctggccag cttctgcgcg gcgataaagt cgcacttgct   7860
gaggtcatca ccgaagcgct tgaccagccc ggccatctcg ctgcggtact cgtccagcgc   7920
cgtgcgccgg tggcggctaa gctgccgctc gggcagttcg aggctggcca gcctgcgggc   7980
cttctcctgc tgccgctggg cctgctcgat ctgctggcca gcctgctgca ccagcgccgg   8040
gccagcggtg gcggtcttgc ccttggattc acgcagcagc acccacggct gataaccggc   8100
gcgggtggtg tgcttgtcct tgcggttggt gaagcccgcc aagcggccat agtggcggct   8160
gtcggcgctg gccgggtcgg cgtcgtactc gctggccagc gtccgggcaa tctgcccccg   8220
aagttcaccg cctgcggcgt cggccacctt gacccatgcc tgatagttct tcgggctggt   8280
ttccactacc agggcaggct cccggccctc ggctttcatg tcatccaggt caaactcgct   8340
gaggtcgtcc accagcacca gaccatgccg ctcctgctcg gcgggcctga tatacacgtc   8400
attgccctgg gcattcatcc gcttgagcca tggcgtgttc tggagcactt cggcggctga   8460
ccattcccgg ttcatcatct ggccggtggt ggcgtccctg acgccgatat cgaagcgctc   8520
acagcccatg gccttgagct gtcggcctat ggcctgcaaa gtcctgtcgt tcttcatcgg   8580
gccaccaagc gcagccagat cgagccgtcc tcggttgtca gtggcgtcag gtcgagcaag   8640
agcaacgatg cgatcagcag caccaccgta ggcatcatgg aagccagcat cacggttagc   8700
catagcttcc agtgccaccc ccgcgacgcg ctccgggcgc tctgcgcggc gctgctcacc   8760
tcggcggcta cctcccgcaa ctctttggcc agctccaccc atgccgcccc tgtctggcgc   8820
tgggctttca gccactccgc cgcctgcgcc tcgctggcct gctgggtctg gctcatgacc   8880
tgccgggctt cgtcggccag tgtcgccatg ctctgggcca gcggttcgat ctgctccgct   8940
aactcgttga tgcctctgga tttcttcact ctgtcgattg cgttcatggt ctattgcctc   9000
ccggtattcc tgtaagtcga tgatctgggc gttggcggtg tcgatgttca gggccacgtc   9060
tgcccggtcg gtgcggatgc cccggccttc catctccacc acgttcggcc ccaggtgaac   9120
accgggcagg cgctcgatgc cctgcgcctc aagtgttctg tggtcaatgc gggcgtcgtg   9180
gccagcccgc tctaatgccc ggttggcatg gtcggcccat gcctcgcggg tctgctcaag   9240
ccatgccttg ggcttgagcg cttcggtctt ctgtgccccg cccttctccg ggtcttgcc    9300
```

-continued

```
gttgtaccgc ttgaaccact gagcggcggg ccgctcgatg ccgtcattga tccgctcgga   9360
gatcatcagg tggcagtgcg ggttctcgcc gccaccggca tggatggcca gcgtatacgg   9420
caggcgctcg gcaccggtca ggtgctgggc gaactcggac gccagcgcct tctgctggtc   9480
gagggtcagc tcgaccggca gggcaaattc gacctccttg aacagccgcc cattggcgcg   9540
ttcatacagg tcggcagcat cccagtagtc ggcgggccgc tcgacgaact ccggcatgtg   9600
cccggattcg gcgtgcaaga cttcatccat gtcgcgggca tacttgcctt cgcgctggat   9660
gtagtcggcc ttggccctgg ccgattggcc gcccgacctg ctgccggttt tcgccgtaag   9720
gtgataaatc gccatgctgc ctcgctgttg cttttgcttt tcggctccat gcaatggccc   9780
tcggagagcg caccgcccga agggtggccg ttaggccagt ttctcgaaga gaaaccggta   9840
agtgcgccct cccctacaaa gtagggtcgg gattgccgcc gctgtgcctc catgatagcc   9900
tacgagacag cacattaaca atggggtgtc aagatggtta aggggagcaa caaggcggcg   9960
gatcggctgg ccaagctcga agaacaacga gcgcgaatca atgccgaaat tcagcgggtg  10020
cgggcaaggg aacagcagca agagcgcaag aacgaaacaa ggcgcaaggt gctggtgggg  10080
gccatgattt tggccaaggt gaacagcagc gagtggccgg aggatcggct catggcggca  10140
atggatgcgt accttgaacg cgaccacgac cgcgccttgt tcggtctgcc gccacgccag  10200
aaggatgagc cgggctgaat gatcgaccga gacaggccct gcggggctgc acacgcgccc  10260
ccacccttcg ggtaggggga aaggccgcta aagcggctaa aagcgctcca gcgtatttct  10320
gcggggtttg gtgtggggtt tagcgggctt tgcccgcctt tccccctgcc gcgcagcggt  10380
ggggcggtgt gtagcctagc gcagcgaata gaccagctat ccggcctctg gccgggcata  10440
ttgggcaagg gcagcagcgc cccacaaggg cgctgataac cgcgcctagt ggattattct  10500
tagataatca tggatggatt tttccaacac cccgccagcc cccgcccctg ctgggtttgc  10560
aggtttgggg gcgtgacagt tattgcaggg gttcgtgaca gttattgcag gggggcgtga  10620
cagttattgc aggggttcgt gacagttagt acgggagtga cgggcactgg ctggcaatgt  10680
ctagcaacgg caggcatttc ggctgagggt aaaagaactt tccgctaagc gatagactgt  10740
atgtaaacac agtattgcaa ggacgcggaa catgcctcat gtggcggcca ggacggccag  10800
ccgggatcgg gatactggtc gttaccagag ccaccgaccc gagcaaaccc ttctctatca  10860
gatcgttgac gagtattacc cggcattcgc tgcgcttatg gcagagcagg gaaaggaatt  10920
gccgggctat gtgcaacggg aatttgaaga atttctccaa tgcgggcggc tggagcatgg  10980
ctttctacgg gttcgctgcg agtcttgcca cgccgagcac ctggtcgctt tcagctgtaa  11040
tccgggcagc gcaacggaac attcatcagt gtaaaaatgg aatcaataaa gccctgcgca  11100
gcgcgcaggg tcagcctgaa tacgcgtgct cgaattgaca taagcctgtt cggttcgtaa  11160
actgtaatgc aagtagcgta tgcgctcacg caactggtcc agaaccttga ccgaacgcag  11220
cggtggtaac ggcgcagtgg cggttttcat ggcttgttat gactgttttt ttgtacagtc  11280
tatgcctcgg gcatccaagc agcaagcgcg ttacgccgtg ggtcgatgtt tgatgttatg  11340
gagcagcaac gatgttacgc agcagcaacg atgttacgca gcagggcagt cgccctaaaa  11400
caaagttagg tggctcaagt atgggcatca ttcgcacatg taggctcggc cctgaccaag  11460
tcaaatccat gcgggctgct cttgatcttt tcggtcgtga gttcggagac gtagccacct  11520
actcccaaca tcagccggac tccgattacc tcgggaactt gctccgtagt aagacattca  11580
tcgcgcttgc tgccttcgac caagaagcgg ttgttggcgc tctcgcggct tacgttctgc  11640
```

```
ccaggtttga gcagccgcgt agtgagatct atatctatga tctcgcagtc tccggcgagc  11700

accggaggca gggcattgcc accgcgctca tcaatctcct caagcatgag gccaacgcgc  11760

ttggtgctta tgtgatctac gtgcaagcag attacggtga cgatcccgca gtggctctct  11820

atacaaagtt gggcatacgg gaagaagtga tgcactttga tatcgaccca agtaccgcca  11880

cctaacaatt cgttcaagcc gagatcggct tcccggccct agacgcgtat tcaggctgac  11940

cctgcgcgct gcgcagggct ttattgattc catttttaca ctgatgaatg ttccgttgcg  12000

ctgcccggat tacagatcct ctagaagaac agcaaggccg ccaatgcctg acgatgcgtg  12060

gagaccgaaa ccttgcgctc gttcgccagc caggacagaa atgcctcgac ttcgctgctg  12120

cccaaggttg ccgggtgacg cacaccgtgg aaacggatga aggcacgaac ccagtggaca  12180

taagcctgtt cggttcgtaa gctgtaatgc aagtagcgta tgcgctcacg caactggtcc  12240

agaaccttga ccgaacgcag cggtggtaac ggcgcagtgg cggttttcat ggcttgttat  12300

gactgttttt ttggggtaca gtctatgcct cgggcatcca agcagcaagc gcgttacgcc  12360

gtgggtcgat gtttgatgtt atggagcagc aacgatgtta cgcagcaggg cagtcgccct  12420

aaaacaaagt taaacatcat gagggaagcg gtgatcgccg aagtatcgac tcaactatca  12480

gaggtagttg gcgtcatcga gcgccatctc gaaccgacgt tgctggccgt acatttgtac  12540

ggctccgcag tggatggcgg cctgaagcca cacagtgata ttgatttgct ggttacggtg  12600

accgtaaggc ttgatgaaac aacgcggcga gctttgatca acgacctttt ggaaacttcg  12660

gcttcccctg gagagagcga gattctccgc gctgtagaag tcaccattgt tgtgcacgac  12720

gacatcattc cgtggcgtta tccagctaag cgcgaactgc aatttggaga atggcagcgc  12780

aatgacattc ttgcaggtat cttcgagcca gccacgatcg acattgatct ggctatcttg  12840

ctgacaaaag caagagaaca tagcgttgcc ttggtaggtc cagcggcgga ggaactcttt  12900

gatccggttc ctgaacagga tctatttgag gcgctaaatg aaaccttaac gctatggaac  12960

tcgccgcccg actgggctgg cgatgagcga aatgtagtgc ttacgttgtc ccgcatttgg  13020

tacagcgcag taaccggcaa aatcgcgccg aaggatgtcg ctgccgactg ggcaatggag  13080

cgcctgccgg cccagtatca gcccgtcata cttgaagcta gacaggctta tcttggacaa  13140

gaagaagatc gcttggcctc gcgcgcagat cagttggaag aatttgtcca ctacgtgaaa  13200

ggcgagatca ccaaggtagt cggcaaataa tgtctaacaa ttcgttcaag ccgacgccgc  13260

ttcgcggcgc ggcttaactc aagctctaga g                                 13291
```

<210> SEQ ID NO 89
<211> LENGTH: 10612
<212> TYPE: DNA
<213> ORGANISM: Artificial
<220> FEATURE:
<223> OTHER INFORMATION: #1473¶AQ1::nrsRS-PnrsB193-PDC-PrbcL*-synADH_oop-Sp standard

<400> SEQUENCE: 89

```
tcgacaaaat gaagtaccga agacaaccat cattggggtt gtctttttta ttggttaatt     60

ggcgaaagac tccaagggcg atcgcctttt aattaagttc tattcacctt ttctgagggg    120

taaacgcaga gtgaattggc taccttgatc cgcatcactc tggatttgga tagatccgtg    180

ataagcaagg gcgatcgcct gggcaatggc aagccctaaa cctgtccccc cggttttacg    240

ggaacggtca tcattaactc ggtaaaaccg tttaaaaatc tgttgttgtt gctctgggga    300

aatgcccata cctgtatccg taacggtaat tttggcatgg cgatcatccg tttttaaatt    360
```

-continued

```
tacattcacg ctgccacctt tgggggtata acgcagggca ttgtcgagga gattggacac    420

tagacgatag agttgggatt cgttcccttg cacataaatt tcctgtttgg ggagttcgtt    480

cgtgagggta ataccgacgg cgatcgccat ctctaaaaat tcttcggtga ggtcactgac    540

cagatcattc agacaacaat ccctccagtt ttctgaagtt tggggttgct ccaaacgact    600

gagcaacagc agatcattaa ttaattgact gagccgccgc ccctgccgtt cgacggtctg    660

gagcatggtt tggatgtcct gttgatcccc accattgagg cgcaaaatca cttcgacggt    720

tgccagcaaa ctcgcgaggg gcgatcgcag ttcgtgggcg gcatcagcgg taaattgttg    780

ctgctgttgg taagcgtcgt agatagggcg catggctaaa cctgctaacc accaactaga    840

gagggtaact acgccgagag caagaggtaa actgacccct aaaacccagc gaatccgttg    900

attttcctga tcaaaggcca tgaggctccg accaatctgg agataacccc atgaatcttg    960

aatatttgca gcgtcgtggg tgtaggcact atgaagaatc gtcgtaaatt gtcggtaacg   1020

gtcatcctcc tgtctaatgg tttgccatgt ctccggttgt aggttctggg ataagctctg   1080

cggttgattg ggggaaaagg caactaattg accttgatgg ttaaataggc ggatgtaata   1140

aaggcggcga tcgctaatgc ccatcgtgtg ccgttcaatt aaagttggtg tagtgtcaca   1200

gggctgatta acaaggcata gatctggaaa aatttgctgt aaagttcctg tggggttcgc   1260

attctccggc agtattggtt ctaggctatc gtgcagcgtt ccggcgattg actccacttc   1320

ccgttcaagg gcaacccaat tcgcttgcac aatggaacga taaacccccca gccctaaagc   1380

actcaaaatt ccccccatta cgagggcata ccagagagca agacggaggc gactgcgagc   1440

aaacagacga taactgttca tggttctacc gtaaaccgat aaccttggcc ggggacagtt   1500

tctatcgggc aaaaacaagc atatttcgct aattttcgcc gaattaaccg catttgcgcc   1560

gctacaacat tactaacggg ttcctcctcc aaatcccaaa gctgttgccg aattttactg   1620

ccggagagaa tgcgatctgg gttttgcatg aggtattgca gaatctgaaa ttccttgacc   1680

gtgagggtaa tggcttgggg ggcttgccct gtctgtctca ctactaattc ggtattgctg   1740

gggtcaaggc taaaattgcc cacccgaaga atttggggct gaaattgggg cgatcgccgt   1800

tggagagcgc gaacccgtgc gagtaattcc gccatcacaa aaggtttgac caaataatca   1860

tccgcccccg catccaagcc tctcactcga ttttctggtt ctcccaaggc agtcaacatc   1920

aatactggga gaggattatg ctgcgatcgc agtttttgac aaagctccaa gcctgacagt   1980

cctggcaaca accaatctag aattgccaca ccgtaatcag tccattgatt ttccagataa   2040

tgccaagcct gctgcccatc cgtcacccaa tccactacat acttctcgct gataagcacc   2100

ttcttaatca ccaagcctag atcttcttcg tcttctacca ataaaattcg catggtttaa   2160

gccagaatta ccacgaactt tatcctaatc acaaacagcc tatttcactt agatttcata   2220

ccccctctgg caaactggaa aaaattttcg tgccattttg tctctaaatg tgaggtgctg   2280

tgatgaattc ttatactgtc ggtacctatt tagcggagcg gcttgtccag attggtctca   2340

agcatcactt cgcagtcgcg ggcgactaca acctcgtcct tcttgacaac ctgcttttga   2400

acaaaaaacat ggagcaggtt tattgctgta acgaactgaa ctgcggtttc agtgcagaag   2460

gttatgctcg tgccaaaggc gcagcagcag ccgtcgttac ctacagcgtc ggtgcgcttt   2520

ccgcatttga tgctatcggt ggcgcctatg cagaaaacct tccggttatc ctgatctccg   2580

gtgctccgaa caacaatgat cacgctgctg gtcacgtgtt gcatcacgct cttggcaaaa   2640

ccgactatca ctatcagttg gaaatggcca agaacatcac ggccgcagct gaagcgattt   2700

acaccccaga agaagctccg gctaaaatcg atcacgtgat taaaactgct cttcgtgaga   2760
```

-continued agaagccggt ttatctcgaa atcgcttgca acattgcttc catgccctgc gccgctcctg 2820
gaccggcaag cgcattgttc aatgacgaag ccagcgacga agcttctttg aatgcagcgg 2880
ttgaagaaac cctgaaattc atcgccaacc gcgacaaagt tgccgtcctc gtcggcagca 2940
agctgcgcgc agctggtgct gaagaagctg ctgtcaaatt tgctgatgct ctcggtggcg 3000
cagttgctac catggctgct gcaaaaagct tcttcccaga agaaaacccg cattacatcg 3060
gtacctcatg ggtgaagtc agctatccgg gcgttgaaaa gacgatgaaa gaagccgatg 3120
cggttatcgc tctggctcct gtcttcaacg actactccac cactggttgg acggatattc 3180
ctgatcctaa gaaactggtt ctcgctgaac cgcgttctgt cgtcgttaac ggcgttcgct 3240
tccccagcgt tcatctgaaa gactatctga cccgtttggc tcagaaagtt tccaagaaaa 3300
ccggtgcttt ggacttcttc aaatccctca atgcaggtga actgaagaaa gccgctccgg 3360
ctgatccgag tgctccgttg gtcaacgcag aaatcgcccg tcaggtcgaa gctcttctga 3420
ccccgaacac gacggttatt gctgaaaccg gtgactcttg gttcaatgct cagcgcatga 3480
agctcccgaa cggtgctcgc gttgaatatg aaatgcagtg gggtcacatc ggttggtccg 3540
ttcctgccgc cttcggttat gccgtcggtg ctccggaacg tcgcaacatc ctcatggttg 3600
gtgatggttc cttccagctg acggctcagg aagtcgctca gatggttcgc ctgaaactgc 3660
cggttatcat cttcttgatc aataactatg gttacaccat cgaagttatg atccatgatg 3720
gtccgtacaa caacatcaag aactgggatt atgccggtct gatggaagtg ttcaacggta 3780
acggtggtta tgacagcggt gctggtaaag gcctgaaggc taaaaccggt ggcgaactgg 3840
cagaagctat caaggttgct ctggcaaaca ccgacggccc aaccctgatc gaatgcttca 3900
tcggtcgtga agactgcact gaagaattgg tcaaatgggg taagcgcgtt gctgccgcca 3960
acagccgtaa gcctgttaac aagctcctct agtttttggg gatcaattcg agctcactag 4020
tcgatcgaca ttgccataag taaaggcatc ccctgcgtga taagattacc ttcagtttat 4080
ggaggactga ccatatgatt aaagcctacg ctgccctgga agccaacgga aaactccaac 4140
cctttgaata cgaccccggt gccctgggtg ctaatgaggt ggagattgag gtgcagtatt 4200
gtggggtgtg ccacagtgat ttgtccatga ttaataacga atggggcatt tccaattacc 4260
ccctagtgcc gggtcatgag gtggtgggta ctgtggccgc catgggcgaa ggggtgaacc 4320
atgttgaggt gggggattta gtggggctgg gttggcattc gggctactgc atgacctgcc 4380
atagttgttt atctggctac cacaaccttt gtgccacggc ggaatcgacc attgtgggcc 4440
actacggtgg ctttggcgat cgggttcggg ccaagggagt cagcgtggtg aaattaccta 4500
aaggcattga cctagccagt gccgggcccc ttttctgtgg aggaattacc gttttcagtc 4560
ctatggtgga actgagttta aagcccactg caaaagtggc agtgatcggc attgggggct 4620
tgggccattt agcggtgcaa tttctccggg cctggggctg tgaagtgact gcctttacct 4680
ccagtgccag gaagcaaacg gaagtgttgg aattgggcgc tcaccacata ctagattcca 4740
ccaatccaga ggcgatcgcc agtgcggaag gcaaatttga ctatattatc tccactgtga 4800
acctgaagct tgactggaac ttatacatca gcaccctggc gccccaggga catttccact 4860
ttgttggggt ggtgttggag cctttggatc taaatctttt tccccttttg atgggacaac 4920
gctccgtttc tgcctcccca gtgggtagtc ccgccaccat tgccaccatg ttggactttg 4980
ctgtgcgcca tgacattaaa cccgtggtgg aacaatttag ctttgatcag atcaacgagg 5040
cgatcgccca tctagaaagc ggcaaagccc attatcgggt agtgctcagc catagtaaaa 5100

-continued

```
attagctctg caaaggttgc ttctgggtcc gtggaacgct cggttgccgc cgggcgtttt   5160
ttattcctgc agccttgctc tagaagaaca gcaaggccgc caatgcctga cgatgcgtgg   5220
agaccgaaac cttgcgctcg ttcgccagcc aggacagaaa tgcctcgact tcgctgctgc   5280
ccaaggttgc cgggtgacgc acaccgtgga aacggatgaa ggcacgaacc cagtggacat   5340
aagcctgttc ggttcgtaag ctgtaatgca agtagcgtat gcgctcacgc aactggtcca   5400
gaaccttgac cgaacgcagc ggtggtaacg gcgcagtggc ggttttcatg gcttgttatg   5460
actgtttttt tggggtacag tctatgcctc gggcatccaa gcagcaagcg cgttacgccg   5520
tgggtcgatg tttgatgtta tggagcagca acgatgttac gcagcagggc agtcgcccta   5580
aaacaaagtt aaacatcatg agggaagcgg tgatcgccga agtatcgact caactatcag   5640
aggtagttgg cgtcatcgag cgccatctcg aaccgacgtt gctggccgta catttgtacg   5700
gctccgcagt ggatggcggc ctgaagccac acagtgatat tgatttgctg gttacggtga   5760
ccgtaaggct tgatgaaaca acgcggcgag ctttgatcaa cgaccttttg gaaacttcgg   5820
cttcccctgg agagagcgag attctccgcg ctgtagaagt caccattgtt gtgcacgacg   5880
acatcattcc gtggcgttat ccagctaagc gcgaactgca atttggagaa tggcagcgca   5940
atgacattct tgcaggtatc ttcgagccag ccacgatcga cattgatctg gctatcttgc   6000
tgacaaaagc aagagaacat agcgttgcct tggtaggtcc agcggcggag gaactctttg   6060
atccggttcc tgaacaggat ctatttgagg cgctaaatga aaccttaacg ctatggaact   6120
cgccgcccga ctgggctggc gatgagcgaa atgtagtgct tacgttgtcc cgcatttggt   6180
acagcgcagt aaccggcaaa atcgcgccga aggatgtcgc tgccgactgg gcaatggagc   6240
gcctgccggc ccagtatcag cccgtcatac ttgaagctag acaggcttat cttggacaag   6300
aagaagatcg cttggcctcg cgcgcagatc agttggaaga atttgtccac tacgtgaaag   6360
gcgagatcac caaggtagtc ggcaaataat gtctaacaat tcgttcaagc cgacgccgct   6420
tcgcggcgcg gcttaactca agcgttagat gcactaccgg tatctttcta gaagatcctc   6480
tagttctaga gcggccgctg gaatttcccg attctctgat gggagatcca aaaattctcg   6540
cagtccctca atcacgatat cggtcttgga tcgccctgta gcttccgaca actgctcaat   6600
tttttcgagc atctctaccg ggcatcggaa tgaaattaac ggtgttttag ccatgtgtta   6660
tacagtgttt acaacttgac taacaaatac ctgctagtgt atacatattg tattgcaatg   6720
tatacgctat tttcactgct gtctttaatg gggattatcg caagcaagta aaaaagcctg   6780
aaaaccccaa taggtaaggg attccgagct tactcgataa ttatcacctt tgagcgcccc   6840
taggaggagg cgaaaagcta tgtctgacaa ggggtttgac ccctgaagtc gttgcgcgag   6900
cattaaggtc tgcggatagc ccataacata cttttgttga acttgtgcgc ttttatcaac   6960
cccttaaggg cttgggagcg ttttatacga gtgcggggaa ctagtgatgg cggccgggag   7020
catgcgacgt cgggcccaat tcgccctata gtgagtcgta ttacaattca ctggccgtcg   7080
ttttacaacg tcgtgactgg gaaaaccctg gcgttaccca acttaatcgc cttgcagcac   7140
atcccccttt cgccagctgg cgtaatagcg aagaggcccg caccgatcgc ccttcccaac   7200
agttgcgcag cctgaatggc gaatggacgc gccctgtagc ggcgcattaa gcgcggcggg   7260
tgtggtggtt acgcgcagcg tgaccgctac acttgccagc gccctagcgc ccgctccttt   7320
cgctttcttc ccttcctttc tcgccacgtt cgccggcttt ccccgtcaag ctctaaatcg   7380
ggggctccct ttagggttcc gatttagagc tttacggcac ctcgaccgca aaaaacttga   7440
tttgggtgat ggttcacgta gtgggccatc gccctgatag acggtttttc gccctttgac   7500
```

-continued

```
gttggagtcc acgttcttta atagtggact cttgttccaa actggaacaa cactcaaccc   7560
tatctcggtc tattcttttg atttataagg gattttgccg atttcggcct attggttaaa   7620
aaatgagctg atttaacaaa tatttaacgc gaattttaac aaaatattaa cgtttacaat   7680
ttcgcctgat gcggtatttt ctccttacgc atctgtgcgg tatttcacac cgcatacagg   7740
tggcactttt cggggaaatg tgcgcggaac ccctatttgt ttatttttct aaatacattc   7800
aaatatgtat ccgctcatga gacaataacc ctgataaatg cttcaataat attgaaaaag   7860
gaagagtatg agtattcaac atttccgtgt cgcccttatt cccttttttg cggcattttg   7920
ccttcctgtt tttgctcacc cagaaacgct ggtgaaagta aaagatgctg aagatcagtt   7980
gggtgcacga gtgggttaca tcgaactgga tctcaacagc ggtaagatcc ttgagagttt   8040
tcgccccgaa gaacgttttc caatgatgag cacttttaaa gttctgctat gtggcgcggt   8100
attatcccgt attgacgccg ggcaagagca actcggtcgc cgcatacact attctcagaa   8160
tgacttggtt gagtactcac cagtcacaga aaagcatctt acggatggca tgacagtaag   8220
agaattatgc agtgctgcca taaccatgag tgataacact gcggccaact tacttctgac   8280
aacgatcgga ggaccgaagg agctaaccgc ttttttgcac aacatggggg atcatgtaac   8340
tcgccttgat cgttgggaac cggagctgaa tgaagccata ccaaacgacg agcgtgacac   8400
cacgatgcct gtagcaatgc caacaacgtt gcgcaaacta ttaactggcg aactacttac   8460
tctagcttcc cggcaacaat taatagactg gatggaggcg gataaagttg caggaccact   8520
tctgcgctcg gcccttccgg ctggctggtt tattgctgat aaatctggag ccggtgagcg   8580
tgggtctcgc ggtatcattg cagcactggg gccagatggt aagccctccc gtatcgtagt   8640
tatctacacg acggggagtc aggcaactat ggatgaacga aatagacaga tcgctgagat   8700
aggtgcctca ctgattaagc attggtaact gtcagaccaa gtttactcat atatacttta   8760
gattgattta aaacttcatt tttaatttaa aaggatctag gtgaagatcc tttttgataa   8820
tctcatgacc aaaatccctt aacgtgagtt ttcgttccac tgagcgtcag accccgtaga   8880
aaagatcaaa ggatcttctt gagatccttt ttttctgcgc gtaatctgct gcttgcaaac   8940
aaaaaaacca ccgctaccag cggtggtttg tttgccggat caagagctac caactctttt   9000
tccgaaggta actggcttca gcagagcgca gataccaaat actgtccttc tagtgtagcc   9060
gtagttaggc caccacttca agaactctgt agcaccgcct acatacctcg ctctgctaat   9120
cctgttacca gtggctgctg ccagtggcga taagtcgtgt cttaccgggt tggactcaag   9180
acgatagtta ccggataagg cgcagcggtc gggctgaacg gggggttcgt gcacacagcc   9240
cagcttggag cgaacgacct acaccgaact gagataccta cagcgtgagc tatgagaaag   9300
cgccacgctt cccgaaggga gaaaggcgga caggtatccg gtaagcggca gggtcggaac   9360
aggagagcgc acgagggagc ttccaggggg aaacgcctgg tatctttata gtcctgtcgg   9420
gtttcgccac ctctgacttg agcgtcgatt tttgtgatgc tcgtcagggg ggcggagcct   9480
atggaaaaac gccagcaacg cggccttttt acggttcctg gccttttgct ggccttttgc   9540
tcacatgttc tttcctgcgt tatcccctga ttctgtggat aaccgtatta ccgcctttga   9600
gtgagctgat accgctcgcc gcagccgaac gaccgagcgc agcgagtcag tgagcgagga   9660
agcggaagag cgcccaatac gcaaaccgcc tctccccgcg cgttggccga ttcattaatg   9720
cagctggcac gacaggtttc ccgactggaa agcgggcagt gagcgcaacg caattaatgt   9780
gagttagctc actcattagg caccccaggc tttacacttt atgcttccgg ctcgtatgtt   9840
```

-continued

```
gtgtggaatt gtgagcggat aacaatttca cacaggaaac agctatgacc atgattacgc   9900

caagctattt aggtgacact atagaatact caagctatgc atctccaaca tgagggcttt   9960

gtatttaagc cggatatcaa caggcgatcg ctctcaccaa agattcacct gttagagcta  10020

ctcaacatcc atcagttctt aaaaccaggg gtgacattca ccggggcgag ccttgaaggg  10080

ttcaaggaaa attgtttgcg gtatgccaag ccgatcaagt ggattcttgg cagaacgatc  10140

accgacaaaa tgagcccgct cgaaattgct caggcgctcc taggcaagct tgaccggaaa  10200

ttggaataca aggggcgctt tggatcgcgg gataaccgtc agcgggtcta tgaggcgatc  10260

gcccctaacg atcagcgcga aaaggtcttt gctcattggt tacagcgtga ccaagcaaaa  10320

ttaggggccg tgtccaaccc ctgtataaat agatttattc aggaggctta gacccgtgat  10380

cgaaatactc gttgtgcagc tctcccttgg caatcccaaa caatctcaag atttgctctg  10440

cggtatcggg acgttttatg cccttgcgga aagcgccttt gctcttctgg tagcccctag  10500

actgtgccag atcataagcc tcactgaggg tgagggcact accgggggca tgagctcgcc  10560

caagagattc agcgaccggg gcgatcgccc ttggtaattc tctcaggcgc tg          10612


<210> SEQ ID NO 90
<211> LENGTH: 105
<212> TYPE: DNA
<213> ORGANISM: Artificial
<220> FEATURE:
<223> OTHER INFORMATION: generalized PziaA variant
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (38)..(50)
<223> OTHER INFORMATION: n is a, c, g, or t
<220> FEATURE:
<221> NAME/KEY: misc_feature
<222> LOCATION: (57)..(62)
<223> OTHER INFORMATION: n is a, c, g, or t
<220> FEATURE:
<221> NAME/KEY: misc_feature
<222> LOCATION: (64)..(79)
<223> OTHER INFORMATION: n is a, c, g, or t

<400> SEQUENCE: 90

nnnnnnnnnn naatatctga gcatatcttc aggtgttnnn nnnnnnnnnn tacggtnnnn     60

nnannnnnnn nnnnnnnnna aggagttaac attatgtctc atatg                    105


<210> SEQ ID NO 91
<211> LENGTH: 95
<212> TYPE: DNA
<213> ORGANISM: Synechocystis PCC6803
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (60)..(76)
<223> OTHER INFORMATION: n is a, c, g, or t

<400> SEQUENCE: 91

nnnnnnnnnn nnnngagatt ttcacctgaa tttcataccc cctttggcag actgggaaan     60

nnnnnnnnnn nnnnnnaatt tgaggtggtg tgatg                                95


<210> SEQ ID NO 92
<211> LENGTH: 103
```

<212> TYPE: DNA
<213> ORGANISM: Synechococcus PCC 7002
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (61)..(84)
<223> OTHER INFORMATION: n is a, c, g, or t

<400> SEQUENCE: 92
nnnnnnnnnn nnnngcctat ttcacttaga tttcataccc cctctggcaa actggaaaaa 60
nnnnnnnnnn nnnnnnnnnn nnnnaatgtg aggtgctgtg atg 103

<210> SEQ ID NO 93
<211> LENGTH: 26
<212> TYPE: DNA
<213> ORGANISM: Artificial
<220> FEATURE:
<223> OTHER INFORMATION: generalized nucleotide sequence of PziaA, operator region

<400> SEQUENCE: 93
aatatctgag catatcttca ggtgtt 26

<210> SEQ ID NO 94
<211> LENGTH: 30
<212> TYPE: DNA
<213> ORGANISM: Artificial
<220> FEATURE:
<223> OTHER INFORMATION: generalized nucleotide sequence of PcorT, operator region

<400> SEQUENCE: 94
aaccttgaca ttgacactaa tgttaaggtt 30

<210> SEQ ID NO 95
<211> LENGTH: 24
<212> TYPE: DNA
<213> ORGANISM: Artificial
<220> FEATURE:
<223> OTHER INFORMATION: generalized nucleotide sequence of the operator region of the aztA promoter

<400> SEQUENCE: 95
acaattgaat agttgttcaa ttgt 24

<210> SEQ ID NO 96
<211> LENGTH: 19
<212> TYPE: DNA
<213> ORGANISM: Artificial
<220> FEATURE:
<223> OTHER INFORMATION: generalized nucleotide sequence of the operator region of the nrsB promoter

<400> SEQUENCE: 96
gattttcacc tgaatttca 19

<210> SEQ ID NO 97
<211> LENGTH: 105
<212> TYPE: DNA
<213> ORGANISM: Artificial
<220> FEATURE:
<223> OTHER INFORMATION: ziaA promoter variant - construct #1133, PziaA*

<400> SEQUENCE: 97
gtcgacctaa catctttaat atctgagcat atcttcaggt gtttcaagat ttgtgctacg 60
gttcaaggag gtttttcttt aaatcacgtt ggccgccatg aattc 105

<210> SEQ ID NO 98
<211> LENGTH: 105
<212> TYPE: DNA
<213> ORGANISM: Artificial
<220> FEATURE:
<223> OTHER INFORMATION: ziaA promoter variant - construct #1134, PziaA*1

<400> SEQUENCE: 98
gtcgacctaa catctttaat atctgagcat atcttcaggt gtttcaagat ttgtgctata 60
attcaaggag gtttttcttt aaatcacgtt ggccgccatg aattc 105

<210> SEQ ID NO 99
<211> LENGTH: 105
<212> TYPE: DNA
<213> ORGANISM: Artificial
<220> FEATURE:
<223> OTHER INFORMATION: ziaA promoter variant - construct #1135, PziaA*2

<400> SEQUENCE: 99
gtcgacctaa catctttaat atctgagcat atcttcaggt gtttcaagat ttgtgctacg 60
gttcaaggag gtttttcttt aaatcaagga ggccgccatg aattc 105

<210> SEQ ID NO 100
<211> LENGTH: 105
<212> TYPE: DNA
<213> ORGANISM: Artificial
<220> FEATURE:
<223> OTHER INFORMATION: ziaA promoter variant - construct #1136, PziaA*3

<400> SEQUENCE: 100
gtcgacctaa catctttaat atctgagcat atcttcaggt gtttcaagat ttgtgctata 60
attcaaggag gtttttcttt aaatcaagga ggccgccatg aattc 105

<210> SEQ ID NO 101
<211> LENGTH: 105
<212> TYPE: DNA
<213> ORGANISM: Artificial
<220> FEATURE:
<223> OTHER INFORMATION: ziaA promoter variant - construct #1147, PziaA*4

<400> SEQUENCE: 101
gtcgacctaa catctttaac atctgaacat atcttcagat gtttcaagat ttgtgctacg 60
gttcaaggag gtttttcttt aaatcacgtt ggccgccatg aattc 105

<210> SEQ ID NO 102
<211> LENGTH: 105
<212> TYPE: DNA
<213> ORGANISM: Artificial
<220> FEATURE:
<223> OTHER INFORMATION: ziaA promoter variant - construct #1148, PziaA*5

<400> SEQUENCE: 102
gtcgacctaa catctttaac atctgaacat atcttcagat gtttcaagat ttgtgctata 60
attcaaggag gtttttcttt aaatcacgtt ggccgccatg aattc 105

<210> SEQ ID NO 103
<211> LENGTH: 105
<212> TYPE: DNA
<213> ORGANISM: Artificial
<220> FEATURE:
<223> OTHER INFORMATION: ziaA promoter variant - construct #1149, PziaA*6

<400> SEQUENCE: 103
gtcgacctaa catctttaac atctgaacat atcttcagat gtttcaagat ttgtgctacg 60
gttcaaggag gtttttcttt aaatcaagga ggccgccatg aattc 105

<210> SEQ ID NO 104
<211> LENGTH: 105
<212> TYPE: DNA
<213> ORGANISM: Artificial
<220> FEATURE:
<223> OTHER INFORMATION: ziaA promoter variant - construct #1150, PziaA*7

<400> SEQUENCE: 104
gtcgacctaa catctttaac atctgaacat atcttcagat gtttcaagat ttgtgctata 60
attcaaggag gtttttcttt aaatcaagga ggccgccatg aattc 105

<210> SEQ ID NO 105
<211> LENGTH: 96
<212> TYPE: DNA
<213> ORGANISM: Synechocystis PCC 6803

<400> SEQUENCE: 105
tcctaacatc tttaatatct gagcatatct tcaggtgttt caagatttgt gctacggttc 60
aaggaggttt ttctttaaat cacgttggcc gccatg 96

<210> SEQ ID NO 106
<211> LENGTH: 96
<212> TYPE: DNA
<213> ORGANISM: Anabaena PCC 7120

<400> SEQUENCE: 106
cctaaaatga taaccattgt acaattgaat agttgttcaa ttgttgtatt agaatattgg 60
cagttaactt tttgccttaa ttctaaagct gctatg 96

<210> SEQ ID NO 107
<211> LENGTH: 96
<212> TYPE: DNA
<213> ORGANISM: Synechococcus PCC 7002

<400> SEQUENCE: 107
atctaaacaa tacctgaata attgttcatg tgttaatcta aaaatgtgaa caatcgttca 60
actatttaag acaatacctt ggaggtttaa accatg 96

<210> SEQ ID NO 108
<211> LENGTH: 96
<212> TYPE: DNA
<213> ORGANISM: Synechococcus PCC 7942

<400> SEQUENCE: 108
tcacggtttg tccacccacc atacctgaat caagattcag atgttaggct aaacacatga 60
acagttattc agatattcaa aggagttgct gtcatg 96

-continued

<210> SEQ ID NO 109
<211> LENGTH: 87
<212> TYPE: DNA
<213> ORGANISM: Synechocystis PCC 6803

<400> SEQUENCE: 109
catcccttta gtttactcaa aaccttgaca ttgacactaa tgttaaggtt taggctgaga 60
aggtaaaaat ccaagttaaa aagcatg 87

<210> SEQ ID NO 110
<211> LENGTH: 93
<212> TYPE: DNA
<213> ORGANISM: Synechocystis PCC 6803

<400> SEQUENCE: 110 tagcgggggga aggagatttt cacctgaatt tcataccccc tttggcagac tgggaaaatc 60
ttggacaaat tcccaatttg aggtggtgtg atg 93

We claim:

1. An ethanologenic recombinant cyanobacterium comprising a recombinant alcohol dehydrogenase gene and a heterologous pyruvate decarboxylase gene wherein said alcohol dehydrogenase gene is operably linked to a first promoter and wherein said pyruvate decarboxylase gene is operably linked to a second promoter and wherein said second promoter is a Co2+ inducible promoter or a Zn2+ inducible promoter.

2. The ethanologenic recombinant cyanobacterium of claim 1 wherein said first promoter is a Co2+ inducible promoter or a Zn2+ inducible promoter.

3. The ethanologenic recombinant cyanobacterium of claim 1 wherein said first promoter is constitutive.

4. The ethanologenic recombinant cyanobacterium of claim 3 wherein said first promoter is PrbcL.

5. The ethanologenic recombinant cyanobacterium of claim 1 wherein said second promoter is selected from the group consisting of PziaA from *Synechocystis* 6803, PsmtA from *Synechococcus* 7942 and *Synechococcus* 7002, PcorT from *Synechocystis* 6803, PaztA from *Anabaena* 7120, PbmtA from *Oscillatoria brevis*, Pbxa1 from *Oscillatoria brevis*, PzntA from *Staphylococcus aureus*, PczrB from *Staphylococcus aureus* 912, and PnmtA from *Mycobacterium tuberculosis*.

6. The ethanologenic recombinant cyanobacterium of claim 1, further comprising an extrachromosomal plasmid either comprising a first promoter, recombinant alcohol dehydrogenase gene, second promoter, and heterologous pyruvate decarboxylase gene, or comprising a second promoter and a heterologous pyruvate decarboxylase gene.

7. The ethanologenic recombinant cyanobacterium of claim 1 wherein said second promoter is inducible by Zn2+.

8. The ethanologenic recombinant cyanobacterium of claim 7 wherein said second promoter has a sequence that is at least 70% identical to the sequence of a ziaA promoter having the sequence of:

(SEQ ID NO. 5)
(N)$_{11}$AATATCTGAGCATATCTTCAGGTGTT(N)$_{13}$TACGGT(N)$_{6}$A
(N)$_{16}$ACGTTGGCCGCCATG, wherein each of said N nucleotides is selected from a group consisting of A, T, C and G and wherein said 3'ATG is the start codon of said heterologous pyruvate decarboxylase gene.

9. The ethanologenic recombinant cyanobacterium of claim 7 wherein said second promoter has a sequence that is at least 70% identical to the sequence of a aztA promoter having the sequence of:

(SEQ ID NO. 44)
(N)$_{12}$TGTACAATTGAATAGTTGTTCAATTGTTGTATTAGAAT
(N)$_{5}$C(N)$_{17}$AATTCTAAAGCTGCTATG, wherein each of said N nucleotides is selected from a group consisting of A, T, C and G and wherein said 3'ATG is the start codon of said heterologous pyruvate decarboxylase gene.

10. The ethanologenic recombinant cyanobacterium of claim 1 wherein said second promoter is inducible by Co2+.

11. The ethanologenic recombinant cyanobacterium of claim 10 wherein said second promoter has a sequence that is at least 70% identical to the sequence of a corT promoter having the sequence of:

(SEQ IS NO. 31)
CAT(N)$_{7}$GTTTACTCAAAACCTTGACATTGACACTAATGTTAAGGTTTA
GGCT(N)$_{15}$CAAGTTAAAAAGCATG, wherein each of said N nucleotides is selected from a group consisting of A, T, C and G and wherein said 5' CAT is the start codon of a corR gene in the antisense orientation, and wherein said 3'ATG is the start codon of said heterologous pyruvate decarboxylase gene.

12. An ethanologenic recombinant cyanobacterium comprising a recombinant alcohol dehydrogenase gene and a heterologous pyruvate decarboxylase gene wherein said alcohol dehydrogenase gene is operably linked to a first promoter and wherein said pyruvate decarboxylase gene is operably linked to a second promoter and wherein said second promoter is a Ni2+ inducible promoter.

13. The ethanologenic recombinant cyanobacterium of claim 12 wherein said first promoter is a Ni2+ inducible promoter.

14. The ethanologenic recombinant cyanobacterium of claim 12 wherein said first promoter is constitutive.

15. The ethanologenic recombinant cyanobacterium of claim 14 wherein said first promoter is PrbcL.

16. The ethanologenic recombinant cyanobacterium of claim 12 wherein said second promoter is selected from the group consisting of nrsRS-PnrsB from *Synechocystis* PCC 6803 and nrsRS916-PnrsB916 from *Synechococcus* sp.

17. The ethanologenic recombinant cyanobacterium of claim 12 wherein said second promoter inducible by Ni2+ has a sequence that is at least 70% identical to the sequence of a nrsB promoter having the sequence of:

(SEQ ID NO. 91)
$(N)_{14}$GAGATTTTCACCTGAATTTCATACCCCCTTTGGCAGACTGGGAAA $(N)_{17}$AATTTGAGGTGGTGTGATG, wherein each of said N nucleotides is selected from a group consisting of A, T, C and G and wherein said 3'ATG is the start codon of said heterologous pyruvate decarboxylase gene.

18. The ethanologenic recombinant cyanobacterium of claim 11 wherein said second promoter inducible by Ni2+ has a sequence that is at least 70% identical to the sequence of a nrsB promoter having the sequence of:

(SEQ ID NO. 92)
$(N)_{14}$GCCTATTTCACTTAGATTTCATACCCCCTCTGGCAAACTGGAAA AA$(N)_{24}$AATGTGAGGTGCTGTGATG, wherein each of said N nucleotides is selected from a group consisting of A, T, C and G and wherein said 3'ATG is the start codon of said heterologous pyruvate decarboxylase gene.

* * * * *